US008785452B2

(12) United States Patent
Brodin et al.

(10) Patent No.: US 8,785,452 B2
(45) Date of Patent: Jul. 22, 2014

(54) ANTI-INFECTIVE COMPOUNDS

(75) Inventors: Priscille Brodin, Paris (FR); Thierry Christophe, Pontarlier (FR); Zaesung No, Seoul (KR); Jaeseung Kim, Seoul (KR); Auguste Genovesio, Seoul (KR); Denis Philippe Cedric Fenistein, Amsterdam (NL); Heekyoung Jeon, Gyeonggi-do (KR); Fanny Anne Ewann, Seoul (KR); Sunhee Kang, Gyeonggi-do (KR); Saeyeon Lee, Gyeonggi-do (KR); Min Jung Seo, Gyeonggi-do (KR); Eunjung Park, Seoul (KR); Monica Contreras Dominguez, Saint Louis (FR); Ji Youn Nam, Cheongju (KR); Eun Hye Kim, Kyoungki-do (KR)

(73) Assignees: Institut National de la Sante et de la Recherche Medicale, Paris (FR); Institut Pasteur Korea, Seongnam-si (KR)

(*) Notice: Subject to any disclaimer, the term of this patent is extended or adjusted under 35 U.S.C. 154(b) by 0 days.

(21) Appl. No.: 12/999,095

(22) PCT Filed: Jun. 17, 2009

(86) PCT No.: PCT/EP2009/004379
§ 371 (c)(1),
(2), (4) Date: Mar. 11, 2011

(87) PCT Pub. No.: WO2010/003533
PCT Pub. Date: Jan. 14, 2010

(65) Prior Publication Data
US 2011/0178077 A1   Jul. 21, 2011

Related U.S. Application Data

(60) Provisional application No. 61/132,285, filed on Jun. 17, 2008.

(51) Int. Cl.
*A01N 43/90* (2006.01)
*A61K 31/519* (2006.01)
*C07D 239/70* (2006.01)
*C07D 471/04* (2006.01)

(52) U.S. Cl.
CPC .................................. *C07D 471/04* (2013.01)
USPC .......................................... 514/259.1; 544/282

(58) Field of Classification Search
None
See application file for complete search history.

(56) References Cited

U.S. PATENT DOCUMENTS 4,219,649 A   8/1980   Knoll et al.
4,291,036 A   9/1981   Knoll et al.

FOREIGN PATENT DOCUMENTS

| EP | 0 218 423 | 4/1987 |
|----|-----------|--------|
| EP | 1 262 477 | 12/2002 |
| JP | S5448795 A | 4/1979 |
| JP | S63146884 A | 6/1988 |
| JP | H01265090 A | 10/1989 |
| WO | WO 93/23398 | 11/1993 |
| WO | WO93/23398 | * 11/1993 ........... C07D 471/04 |
| WO | WO 9323389 | * 11/1993 ........... C07D 471/04 |
| WO | WO 2004/037159 A2 | 5/2004 |
| WO | WO 2004/037159 A3 | 5/2004 |
| WO | WO 2005/030772 | 4/2005 |

OTHER PUBLICATIONS

Crippa, et. al., Gazzetta Chimica Italiana (1937), 67, 327-32.*
Roma, et. al., Journal of Heterocyclic Chemistry (1987), 24(2), 329-35.*
Ingalls, et. al., Journal of Heterocyclic Chemistry (1967), 4(4), 523-6.*
Snyder, et. al., Journal of the American Chemical Society (1952), 74, 4910-16.*
Oakes, et. al., Journal of the Chemical Society (1958) 209-11.*
Horvath, et. al., Acta Chimica Academiae Scientiarum Hungaricae (1974), 83(1), 15-24.*
Bogdanov et al., "A Novel Thermal Rearrangement in the Pyrido[1,2-a]pyrimidine Series: Transformation of 3-Acetyl-4-phenylaminopyrido[1,2-a]pyrimidin-2-one into 3-Acetyl-2-phenylaminopyrido[1,2-a]pyrimidin-4-one", *Mendeleev Communications*, Jan. 1995, vol. 5, No. 3, pp. 106-107.
Ferrarini et al., "Synthesis of Some 4H-Pyrido[1,2-a]pyrimidin-4-Ones Investigated as Antimicrobial Agents", *IL Farmaco, Societa Chimica Italiana*, Jan. 1995, vol. 50, No. 1, pp. 69-72.
Gotoh et al., "Intramolecular 1,3-Dipolar Cycloaddition at the Periphery of Heterocyclic Systems. Part 2.¹ A Mechanistic Proposal for the Facile Oxime-Nitrone Isomerization at the Periphery of Pyridine and Pyrido[1,2-a]pyrimidine Systems", *Tetrahedron*, Jan. 1996, vol. 52, No. 3, pp. 887-900.
Modha et al., "Synthesis and Biological Evaluation of Some New 3,4-Dihydropyrimidin-4-ones", *IL Farmaco*, 2001, vol. 56, No. 9, pp. 641-646.
Roma et al., "1,2-Fused Pyrimidines. III. Derivatives of 12H-Pyrido[1',2':1,2]pyrimido[4,5-b]quinoline, A Novel Heterocyclic System", *Journal of Heterocyclic Chemistry*, Mar.-Apr. 1987, vol. 24, No. 2, pp. 329-335.
Schantel, "Product class 19: azomethine imines", *Science of Synthesis*, Jan. 2004, vol. 27, No. 19, pp. 731-824.
Ingalls et al., "The Preparation, Structure and Reactions of Some 'Malonyl-α-aminopyridines'", *Journal of Heterocyclic Chemistry*, Dec. 1967, vol. 4, No. 4, pp. 523-526.
Hermecz et al., "Nitrogen Bridgehead Compounds. Part 83 [1]. Synthesis and Ring Transformation of 6-Methyl-4-oxo-4H-pyridol[1,2-α]pyrimidines-3-acrylates", *Journal of Heterocyclic Chemistry*, Mar.-Apr. 1992, vol. 29, No. 2, pp. 559-564.
Chinese Office Action, Application No. 200980128440.2, Date of Notification: Mar. 19, 2012.
Noguchi, Michihiko, et al., "A Facile and Stereoselective Azepine-Ring Formation at the Periphery of Pyridone and Pyrido[1,2-α]pryimidone Systems via Intramolecular Imine and Carbonyl Ene Reactions," *Tetrahedron*, 1996, vol. 52, No. 41, p. 13081-13096.

* cited by examiner

*Primary Examiner* — Jeffrey H Murray
(74) *Attorney, Agent, or Firm* — Saliwanchik, Lloyd & Eisenschenk

(57) ABSTRACT

The present invention relates to 4H-pyrido[1,2-a]pyrimidin-4-one compounds and their use in the treatment of bacterial infections, in particular Tuberculosis.

27 Claims, 52 Drawing Sheets

Figure 6

Figure 6

ANTI-INFECTIVE COMPOUNDS

CROSS REFERENCE TO A RELATED APPLICATION

Figure 1:
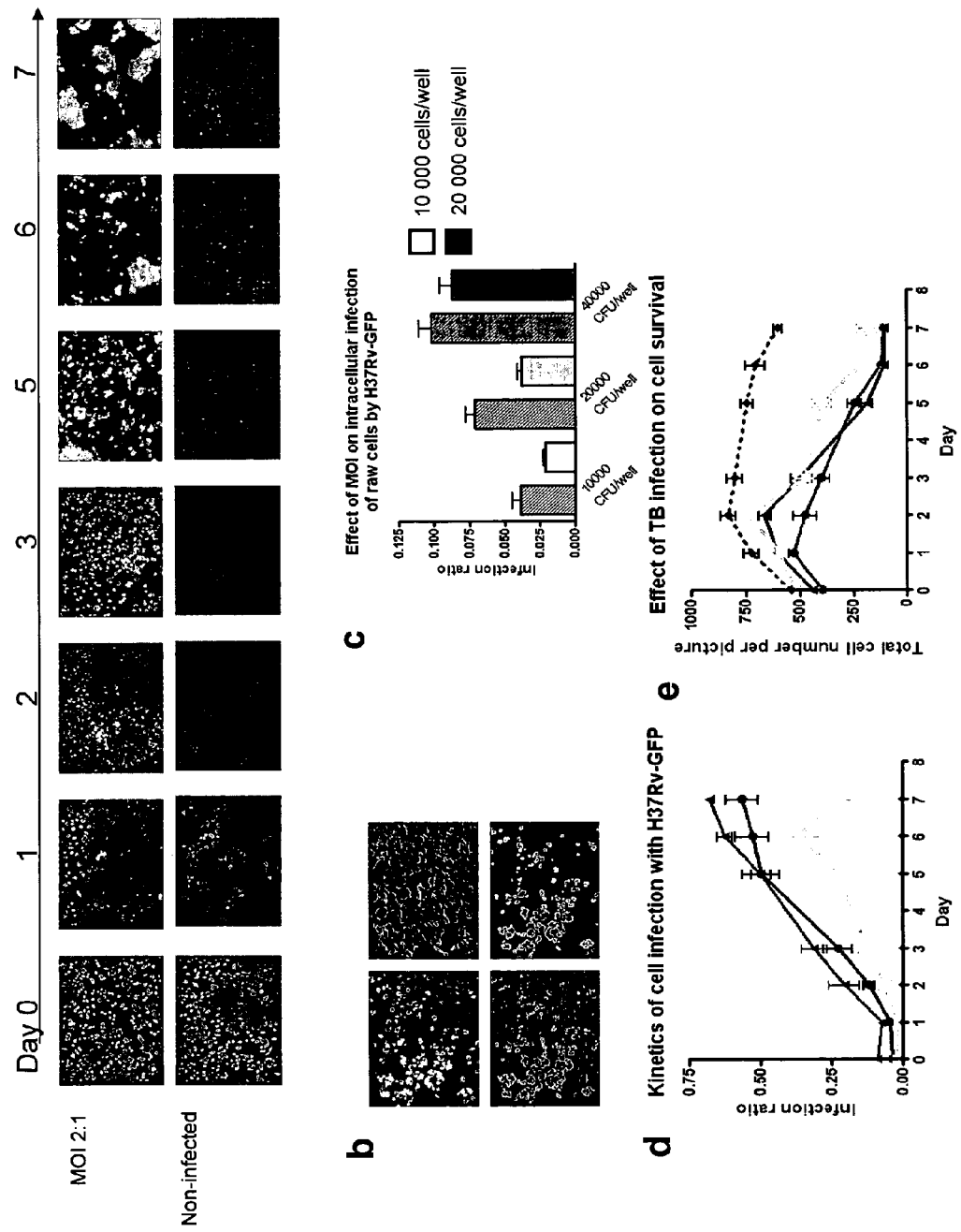

This application is a National Stage Application of International Application Number PCT/EP2009/004379, filed Jun. 17, 2009; which claims the benefit of U.S. Provisional Application Ser. No. 61/132,285, filed Jun. 17, 2008; which are incorporated herein by reference in their entirety.

The present invention relates to small molecule compounds and their use in the treatment of bacterial infections, in particular Tuberculosis.

BACKGROUND OF THE INVENTION

Tuberculosis (TB) as a disease continues to result in millions of deaths each year. Inadequate use of chemotherapy has led to an increasing number of drug resistant cases. This situation is likely to worsen with the emergence of extremely resistant strains to all currently known drugs (Van Rie and Enarson, 2006). The internationally recommended TB control strategy, also referred to as directly observed short-course chemotherapy (DOTS), relies on a combination of five antibacterial agents to be taken for a protracted period of more than six months (http://www.who.int/tb/dots/en/). With the use of a mathematical model, taking into consideration treatment duration and TB dynamics, benefits of reduced treatment length were predicted to be substantial and likely to greatly contribute to a reduced global TB burden (Salomon et al., 2006).

Current chemotherapy consists of compounds that directly target *Mycobacterium tuberculosis bacillus*, either by neutralizing general information pathways and critical processes such as RNA polymerization and protein synthesis inhibition or by interfering with mycobacterial specific cell envelope synthesis. The most widely used dedicated anti-tubercular drugs isoniazid, ethionamide and pyrazinamide are pro-drugs that first require activation. As active forms, they demonstrate inhibitory activity on a wide range of mycobacterial targets, which have not yet been fully characterized. As for other chronic infectious diseases like human immunodeficiency virus, a multi-therapy approach, including drugs that target a wide range of critical features of *M. tuberculosis*, proved to be the most successful strategy to date. It is, thus, likely that a combination of current drug inhibitors, having different mechanisms of action against *M. tuberculosis*, will be the solution for the control of the disease.

The most challenging approaches for discovering new anti-TB drugs rely on screening for active compounds that target critical features essential for the survival of the *bacillus*. Although there is still a lack of understanding of the biological mechanisms behind tubercle *bacillus* persistence, i.e. the location and state of latent bacteria, in humans, *M. tuberculosis* is thought to reside in primary granulomas under hypoxic conditions (Lenaerts et al., 2007) as well as to hide within various types of cells (Houben et al., 2006; Neyrolles et al., 2006). The *bacillus* mainly localizes inside phagocytic cells, such as macrophages and dendritic cells, and it has clearly been established that the tubercle *bacillus* adopts a different phenotype in the host macrophage's phagosome compared to growth in extracellular conditions (Rohde et al., 2007; Schnappinger et al., 2003). Upon infection, an inflammatory response is induced, thereby initiating recruitment of T lymphocytes that release interleukins and cytokines, which in turn activate the infected macrophages to enable the destruction of the pathogen. Upon the appropriate trigger, the host macrophage is, thus, able to eliminate the invading *bacillus*. This is further supported by the fact that of the people that inhale *M. tuberculosis*, more than 95% percent do not develop the disease, suggesting that the human host response is sufficient in most cases to thwart *M. tuberculosis* induced pathogenesis. This gives rise to the hypothesis that small molecular compounds could mimic the immune cell response signals and induce the host cells to clear the mycobacteria.

Accordingly, it was an object of the present invention to develop a phenotypic cell-based assay suitable for high throughput screening that allows for the search of compounds that would prevent *M. tuberculosis* multiplication inside the host macrophage.

Up to now, this type of investigation of the tubercle *bacillus* growth within host cells relied on colony forming units (CFUs) determination after host cell lysis followed by serial dilutions and a 3-week incubation period required for bacterial growth on agar plates. Luciferase-expressing mycobacteria have been shown to be efficient in reducing the experiment duration, although cell lysis and luciferin substrate addition steps are still required (Arain et al., 1996). Also, these types of experiments are not easily amenable to large scale screening.

It was another object of the present invention to identify compounds effective against bacterial infections, in particular compounds that would prevent *M. tuberculosis* multiplication inside the host macrophage.

DESCRIPTION OF THE INVENTION

In one aspect, the present invention relates to compounds having the general formula VIII:

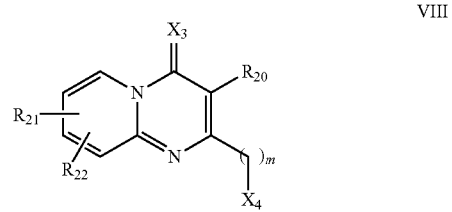

wherein
m is 0, 1, 2, or 3;
$X_3$ is selected from the group comprising $CH_2$, O, S and NH;
$X_4$ is selected from the group comprising halide, alkyl, $OR_{23}$, $SR_{24}$ and $NR_{25}R_{26}$;
$R_{20}$ is selected from the group comprising acyl, alkoxy, alkyl, alkylamino, alkylcarboxylic acid, arylcarboxylic acid, alkylcarboxylic alkylester, alkylene, alkylether, alkylhydroxy, alkylthio, alkynyl, amido, amino, aryl, arylalkoxy, arylamino, arylthio, carboxylic acid, cyano, cycloalkyl, carboxylic acid, ester, halo, haloalkoxy, haloalkyl, haloalkylether, heteroaryl, heteroarylamino, heterocycloalkyl and hydrogen, any of which is optionally substituted;
$R_{21}$ and $R_{22}$ are each independently selected from the group comprising alkoxy, alkyl, alkylamino, alkylene, alkylether, alkylthio, alkynyl, amido, amino, aryl, arylether, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thio, sulfonate, sulfonyl and sulfonylamino, any of which is optionally substituted;
$R_{23}$ is selected from the group comprising acyl, alkyl, alkylamino, alkylene, alkynyl, aryl, arylalkoxy, arylamino, arylthio, carboxy, cycloalkyl, ester, ether, haloalkyl, heteroaryl, heteroarylamino, heterocycloalkyl, hydrogen, thio, sulfonate, and sulfonylamino, any of which is optionally substituted;

$R_{24}$ is selected from the group comprising alkyl, alkylaryl, alkylene, alkynyl, aryl, cycloalkyl, ester, halo, haloalkyl, heteroaryl, heterocycloalkyl, and hydrogen, any of which is optionally substituted; and $R_{25}$ and $R_{26}$ are each independently selected from the group comprising acyl, alkyl, aminoalkyl, alkylene, alkylthio, alkynyl, aryl, arylalkoxy, arylamino, arylthio, carboxy, cycloalkyl, ester, ether, halo, haloalkoxy, haloalkyl, haloalkylether, heteroaryl, heteroarylamino, heterocycloalkyl and hydrogen, any of which is optionally substituted.

In general, the term "optionally substituted" as used herein is meant to indicate that a group, such as alkyl, alkylen, alkynyl, aryl, cycloalkyl, heterocycloalkyl, or heteroaryl, may be unsubstituted or substituted with one or more substituents. "Substituted" in reference to a group indicates that a hydrogen atom attached to a member atom within a group is replaced.

In another aspect, the present invention relates to compounds having the general formula VIIIa:

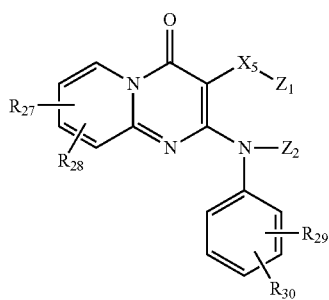

wherein
$X_5$ is selected from the group comprising $CH_2$, $C$=$O$ and $C$=$S$;

$Z_1$ and $Z_2$ are each independently selected from the group comprising alkoxy, alkyl, alkylamino, alkylene, alkylether, alkylthio, alkynyl, amido, amino, aryl, arylether, arylalkoxy, arylamino, arylthio, carboxy, cyano, cycloalkyl, ester, halo, haloalkoxy, haloalkyl, heteroaryl, heteroarylamino, heterocycloalkyl, hydroxyl, and hydrogen, or two groups are connected each other to make five or six membered cyclic, heterocyclic and heteroaryl rings, any of which is optionally substituted;

$R_{27}$ and $R_{28}$ are each independently selected from the group comprising alkoxy, alkyl, alkylamino, alkylene, alkylether, alkylthio, alkynyl, amido, amino, aryl, arylether, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thio, sulfonate, sulfonyl and sulfonylamino, any of which is optionally substituted;

$R_{29}$ and $R_{30}$ are each independently selected from the group comprising alkoxy, alkyl, alkylamino, alkylene, alkylether, alkylthio, alkynyl, amido, amino, aryl, arylether, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thio, sulfonate, sulfonyl and sulfonylamino, or two groups are connected each other to make five or six membered cyclic, heterocyclic, aryl, and heteroaryl rings, any of which is optionally substituted.

The term "alkyl" as used herein is meant to indicate that a group, such as substituted or non-substituted $C_1$-$C_{10}$ alkyl group which has the straight or branched chain.

The term "cycloalkyl" as used herein is meant to indicate that a group, such as substituted or non-substituted cyclic compound of $C_3$-$C_8$ ring structure.

The term "heteroaryl" as used herein is meant to indicate that a group, such as substituted or non-substituted 5- to 9-membered aromatic compounds which have more than one heteroatom of N, O, and S in the ring structure itself.

The term "optionally substituted" as used herein is meant to indicates that a hydrogen atom attached to a member atom within a group is possibly replaced by group, such as $C_1$-$C_{10}$ alkyl, halogen including fluorine, OH, $NO_2$, $OR_{31}$, CN, $NR_{31}R_{32}$, $COR_{31}$, $5OR_{32}$, $SO_2R_{31}$, $SO_2NR_{31}$, $CR_{31}$=$CR_{31}R_{32}$, $CR_{31}$=$NR_{32}$, aryl, aryloxy, $C_4$-$C_{10}$ heteroaryl group, or —$NR_{31}$—$COR_{32}$, —$O$—$COR_{31}$.

$R_{31}$ and $R_{32}$ are each independently selected from the group comprising hydrogen, alkyl, alkyloxy, alkylamino, alkylcarbonyl, alkylcarbonylamino, alkylcarbonyloxy, alkylaminocarbonyl, alkyloxycarbonyl, cycloalkyl, cycloalkyloxy, cycloalkylamino, cycloalkylcarbonyl, cycloalkylcarbonylamino, cycloalkylcarbonyloxy, cycloalkylaminocarbonyl, cycloalkyloxycarbonyl, heteroaryl, heteroaryloxy, heteroaryl amino, heteroaryl carbonyl, heteroaryl carbonylamino, heteroaryl carbonyloxy, heteroaryl aminocarbonyl, heteroaryl oxycarbonyl, heteroaryl alkyl, heteroaryl alkyloxy, heteroaryl alkylamino, heteroaryl alkylcarbonyl, heteroaryl alkylcarbonylamino, heteroaryl alkylcarbonyloxy, heteroaryl alkylaminocarbonyl, heteroaryl alkyloxycarbonyl, phenyl, phenyloxy, phenylamino, phenylcarbonyl, phenylcarbonylamino, phenylcarbonyloxy, phenylaminocarbonyl, and phenyloxycarbonyl, any of which is optionally substituted.

In another aspect, the present invention relates to compounds having one of the formulas 125-301 as shown in Example 7, preferably 132-135, 137, 139-140, 147, 151-152, 160, 163, 173, 180, 184-185, 193, 195, 199-201, 204, 206-222, 224, 226, 229, 231-243, 245-278, 280-286 and 290-301 as shown in Table 3. Particularly preferred compounds are compounds having one of the formulas 133, 232 and 264 as shown in Table 3.

In one aspect, the present invention relates to compounds having the general formula II:

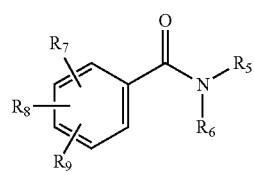

wherein
$R_5$ and $R_6$ are each independently selected from the group comprising acyl, alkyl, alkylamino, alkylene, alkylthio, alkynyl, aryl, arylalkoxy, arylamino, arylthio, carboxy, cycloalkyl, ester, haloalkoxy, haloalkyl, heteroaryl, heteroarylamino, heterocycloalkyl, hydroxyl, hydrogen, sulfonate and sulfonyl, any of which is optionally substituted and $R_7$, $R_8$ and $R_9$ are each independently selected from the group comprising alkoxy, alkyl, alkylamino, alkylene, alkylthio, alkynyl, amido, amino, aryl, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thio, sulfonate, sulfonyl and sulfonylamino, any of which is optionally substituted.

In another aspect, the present invention relates to compounds with the general formula II, wherein $R_5$ and $R_6$ are connected, having the general formula IIa:

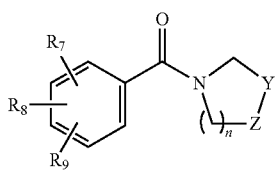

IIa wherein n is 0, 1, 2, or 3;

Y and Z are each independently selected from the group comprising $CH_2$, $CHOR_{10}$, $CHNR_{10}R_{11}$, $CR_{10}R_{11}$ and $NR_{10}$; and $R_{10}$ and $R_{11}$ are each independently selected from the group comprising acyl, alkyl, alkylamino, alkylene, alkylthio, alkynyl, aryl, arylalkoxy, arylamino, arylthio, carboxy, cycloalkyl, ester, haloalkoxy, haloalkyl, heteroaryl, heteroarylamino, heterocycloalkyl, hydrogen, sulfonate and sulfonyl, any of which is optionally substituted.

Figures 1, 9:
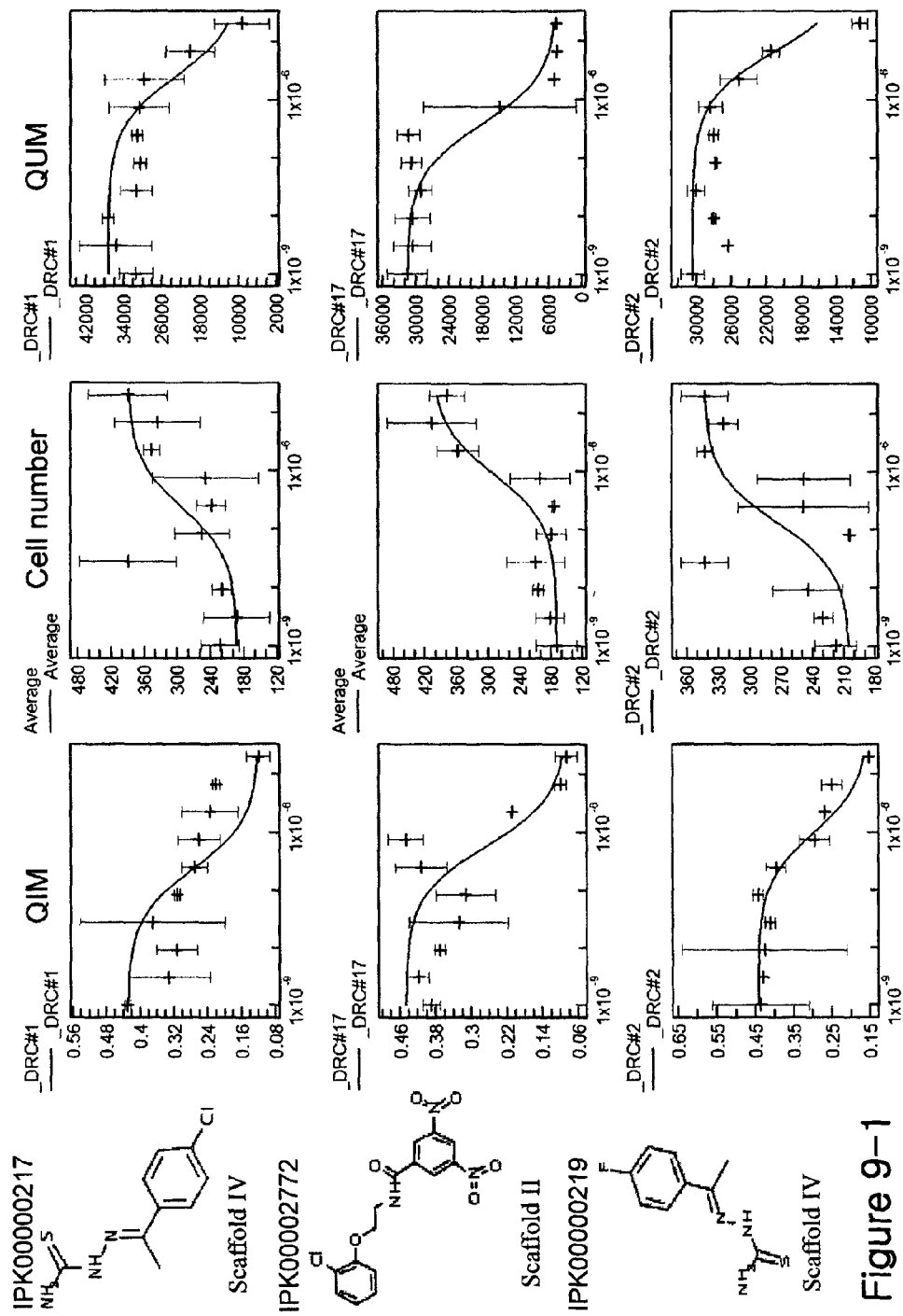
Figures 2, 9:
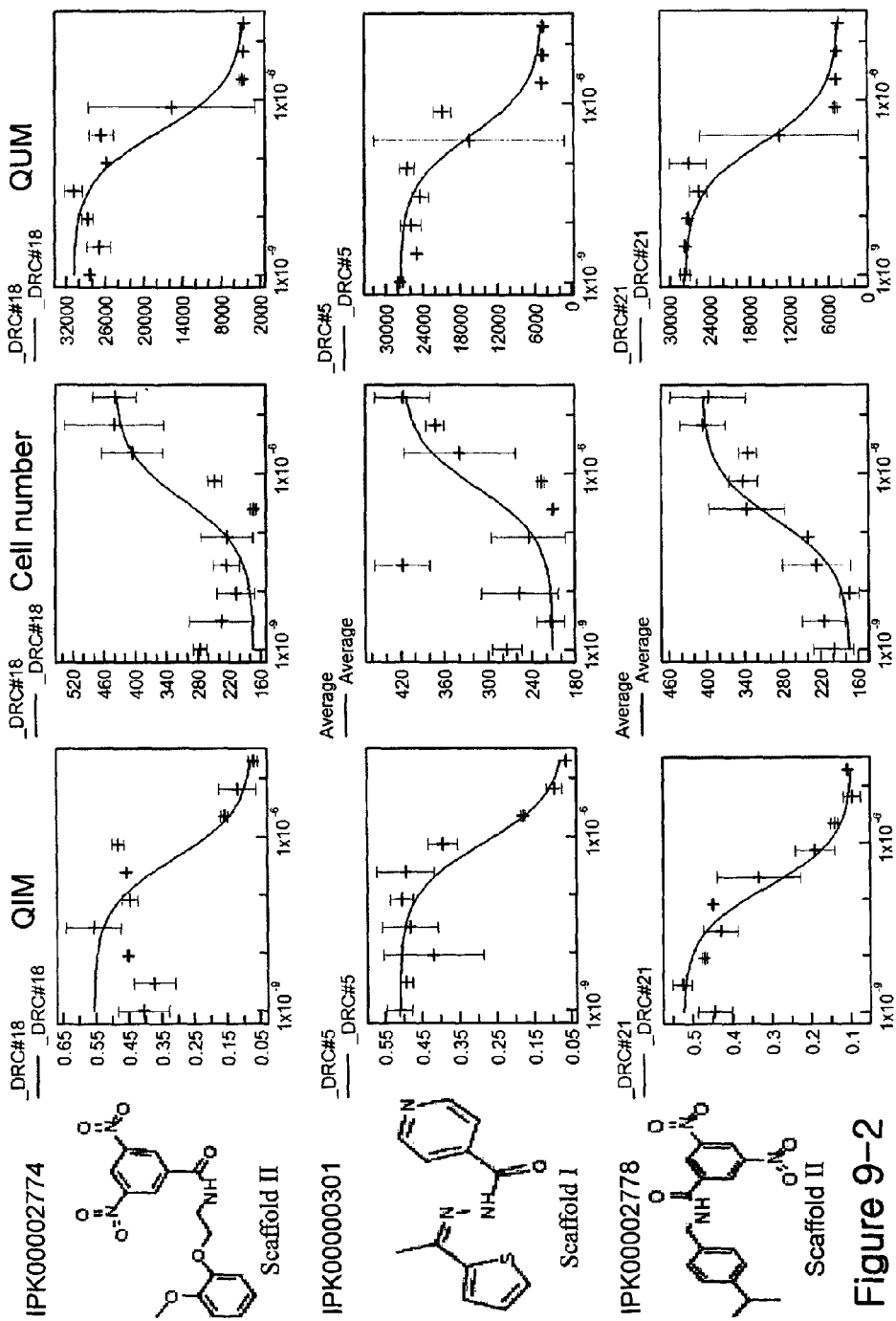
Figures 3, 9:
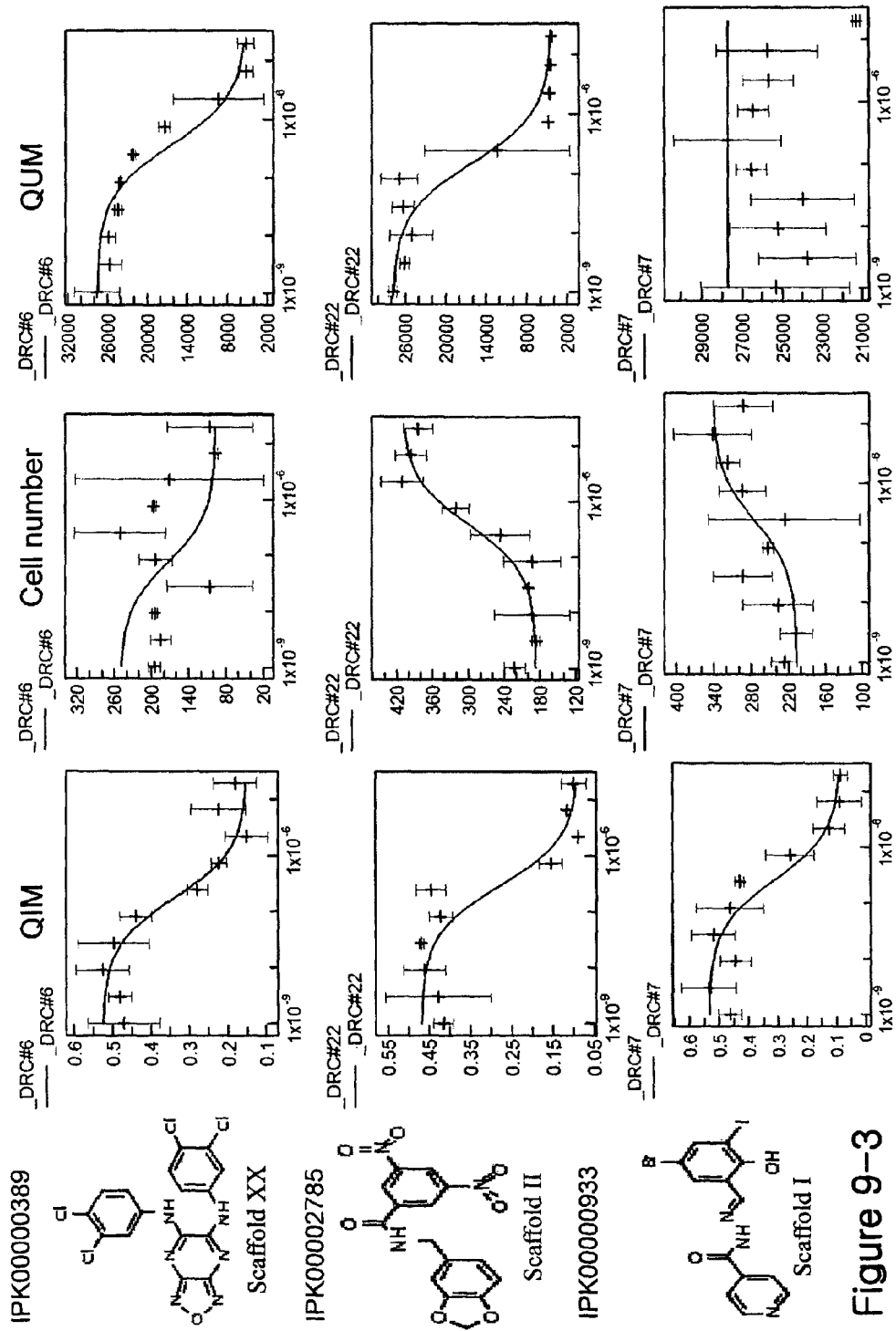
Figures 4, 9:
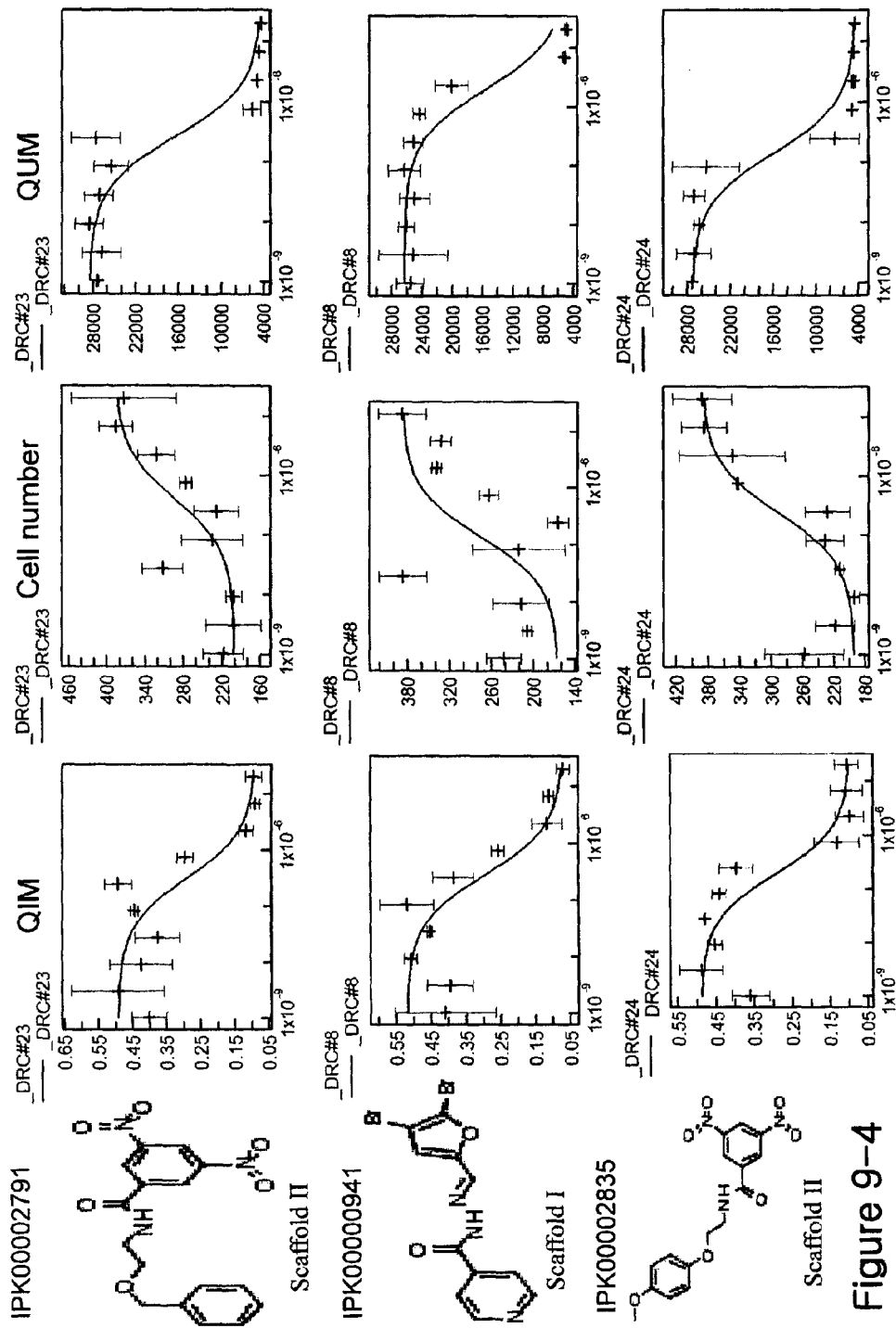
Figures 5, 9:
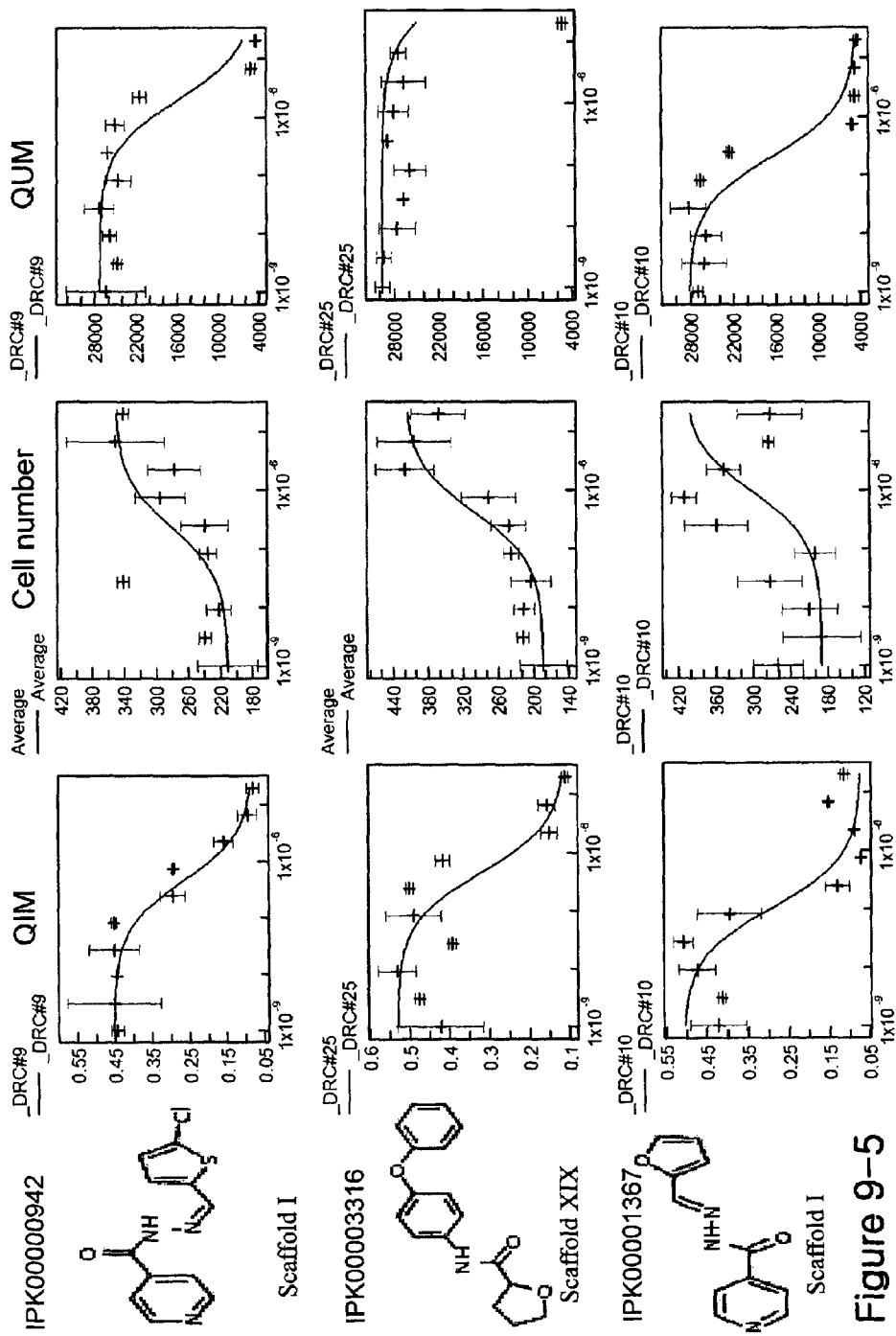
Figures 6, 9:
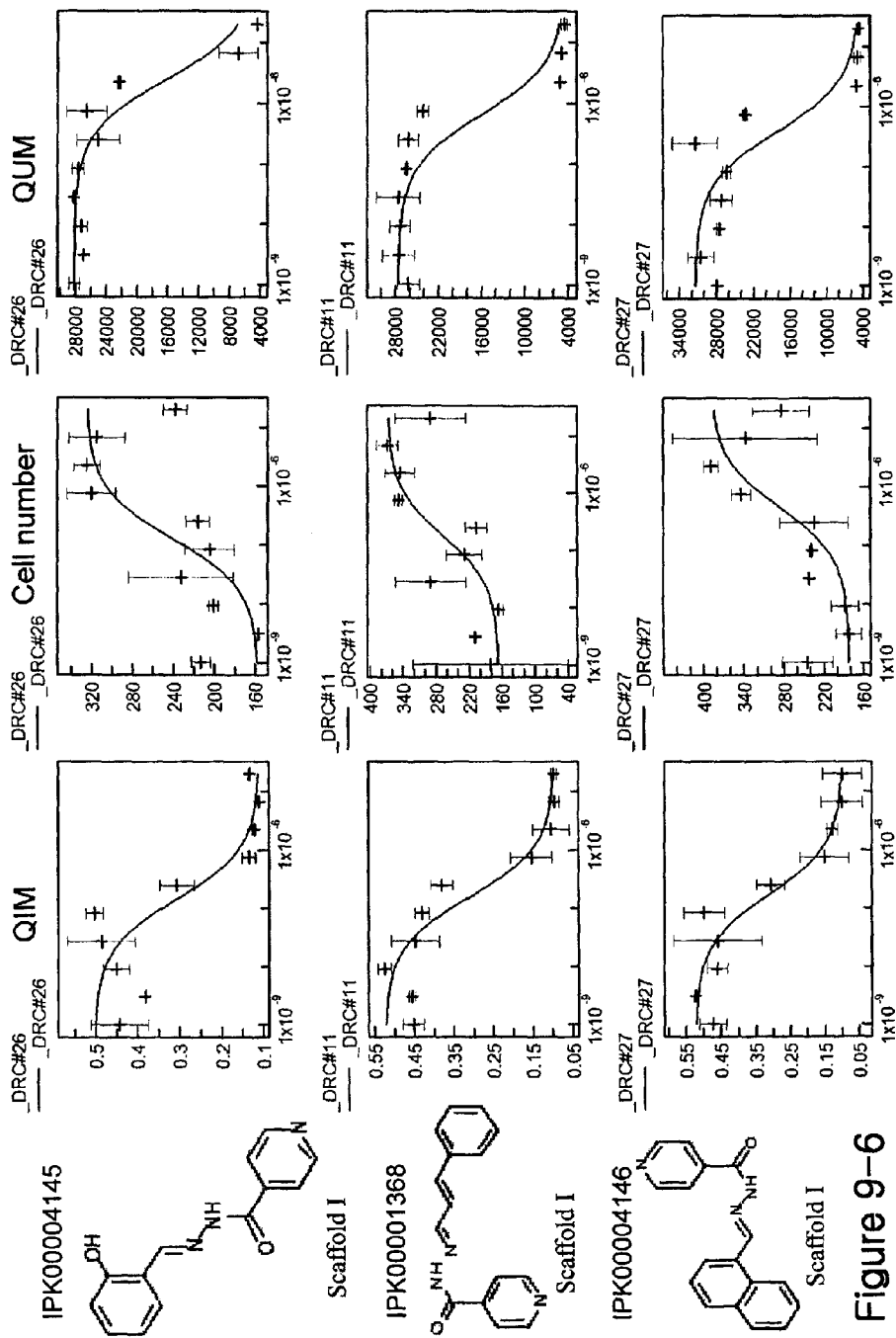
Figures 7, 9:
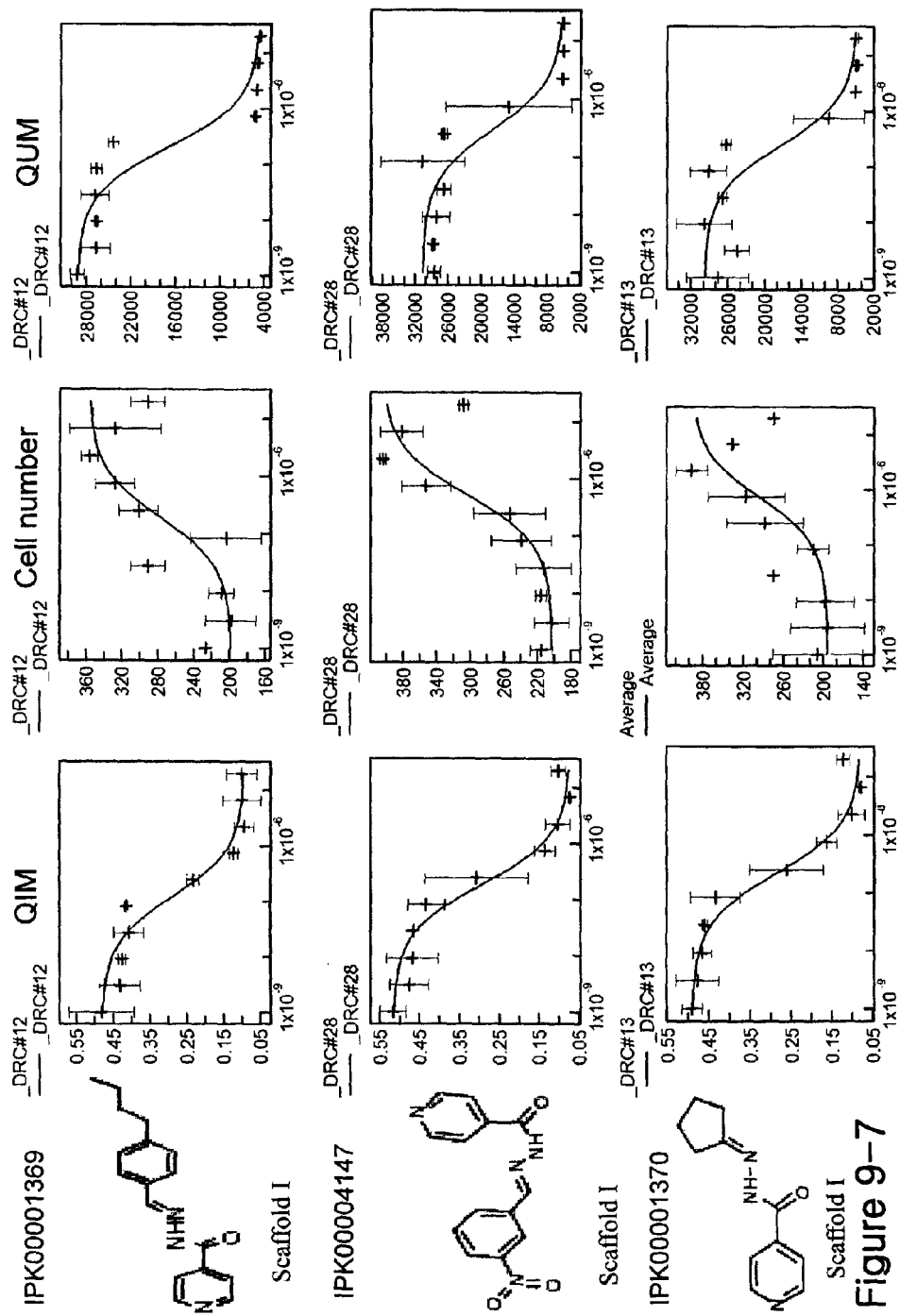
Figures 8, 9:
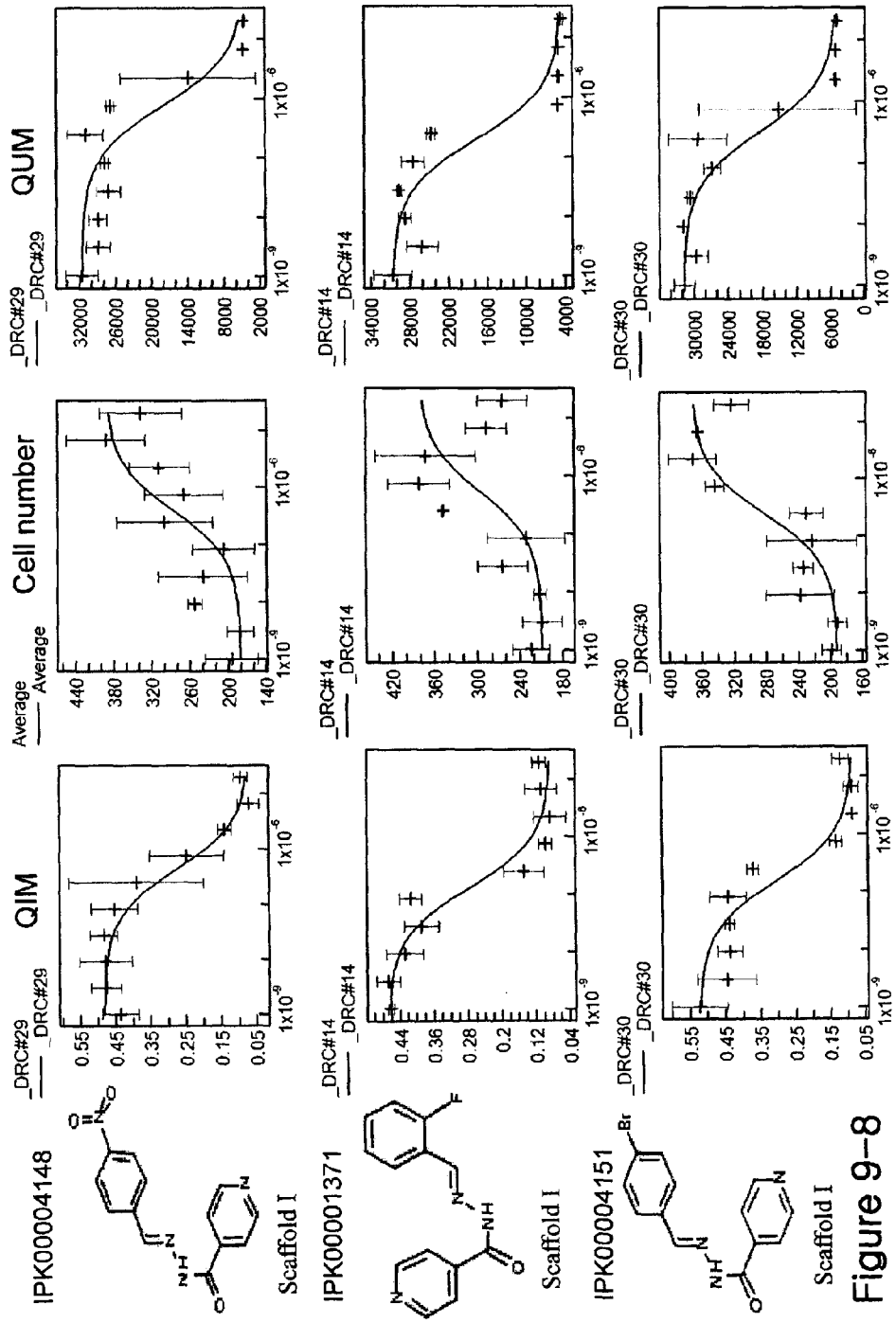
Figure 9:
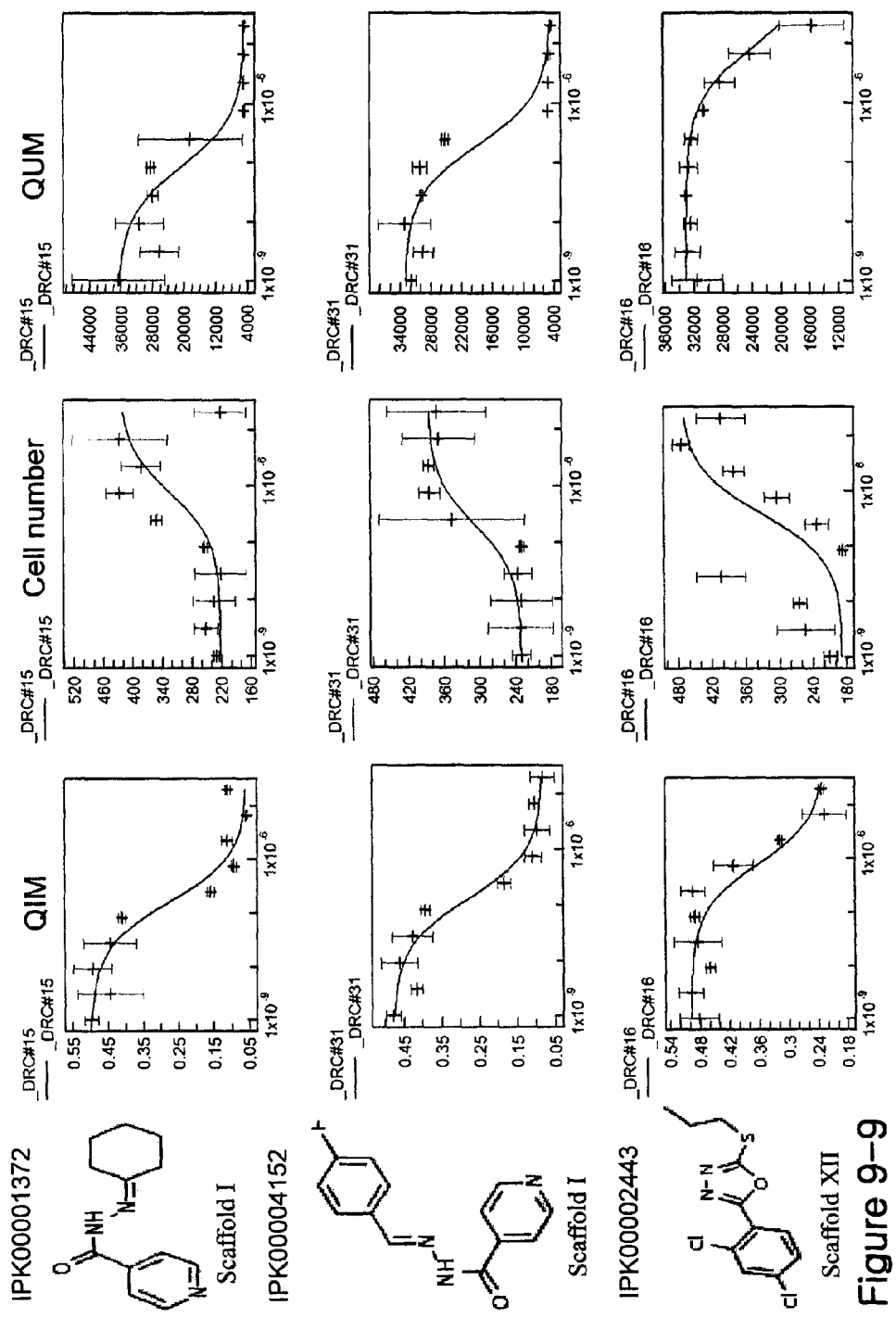
Figures 9, 10:
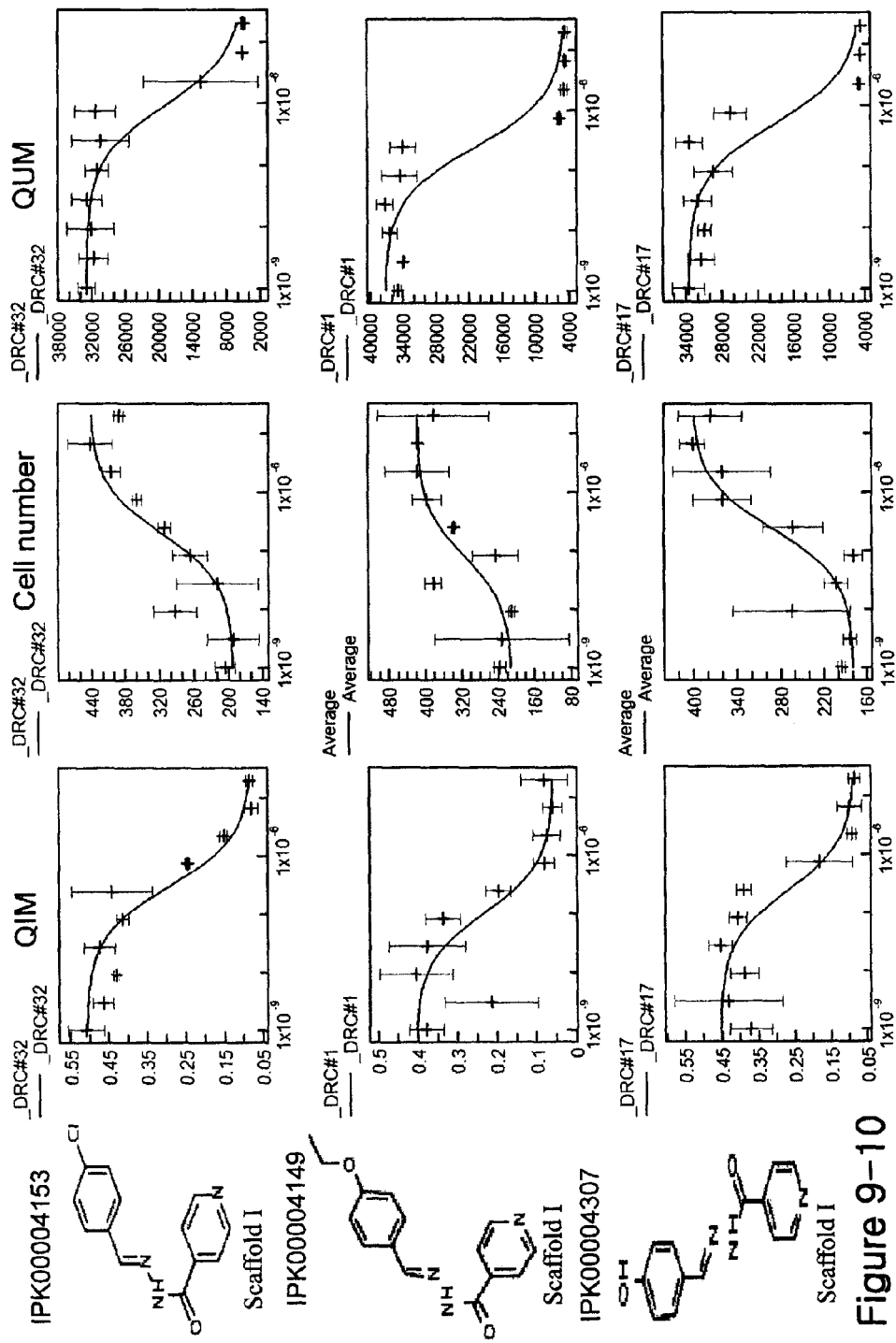
Figures 9, 10, 11:
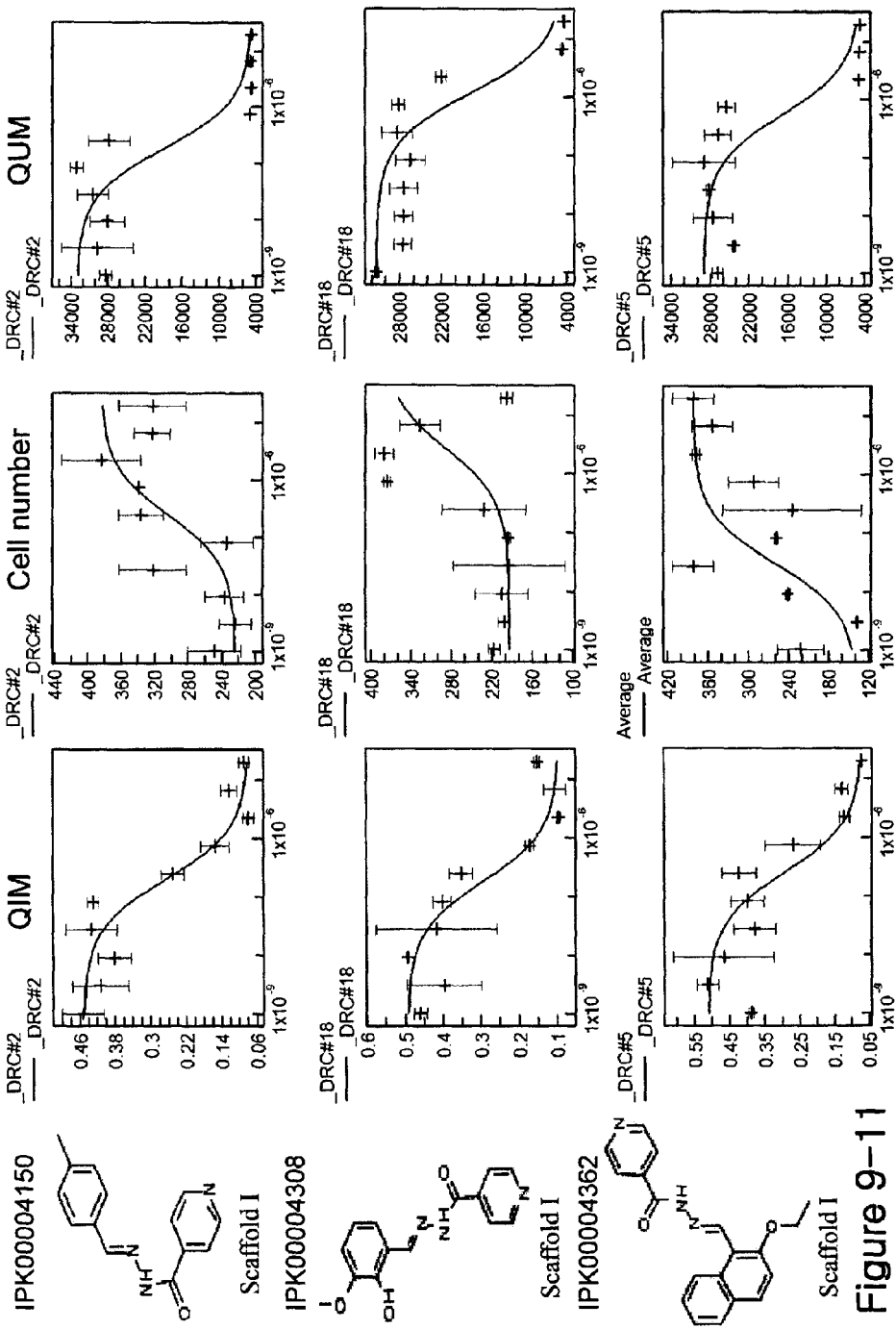
Figures 9, 10, 11, 12:
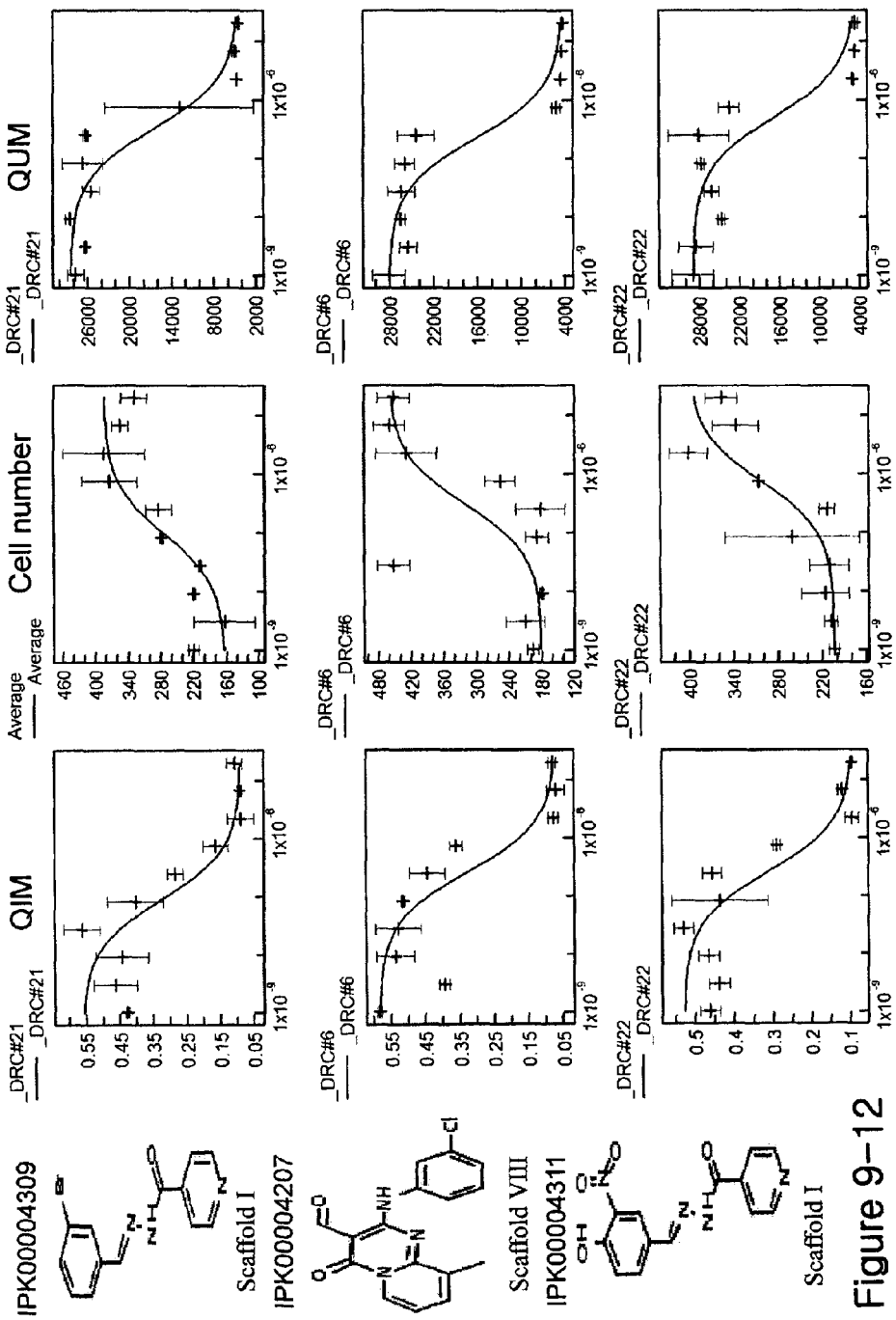
Figures 9, 10, 11, 12, 13:
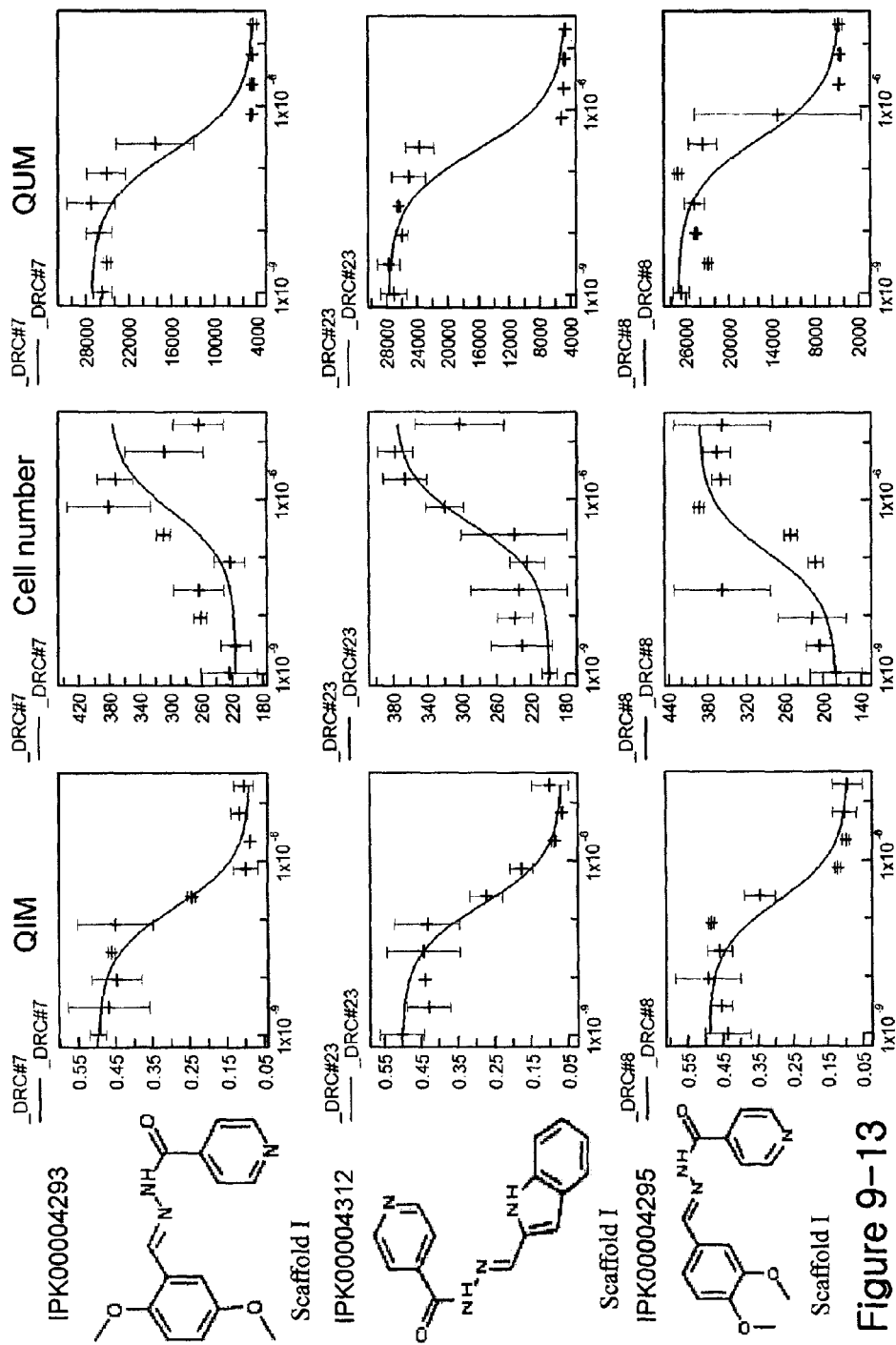
Figures 9, 10, 11, 12, 13, 14:
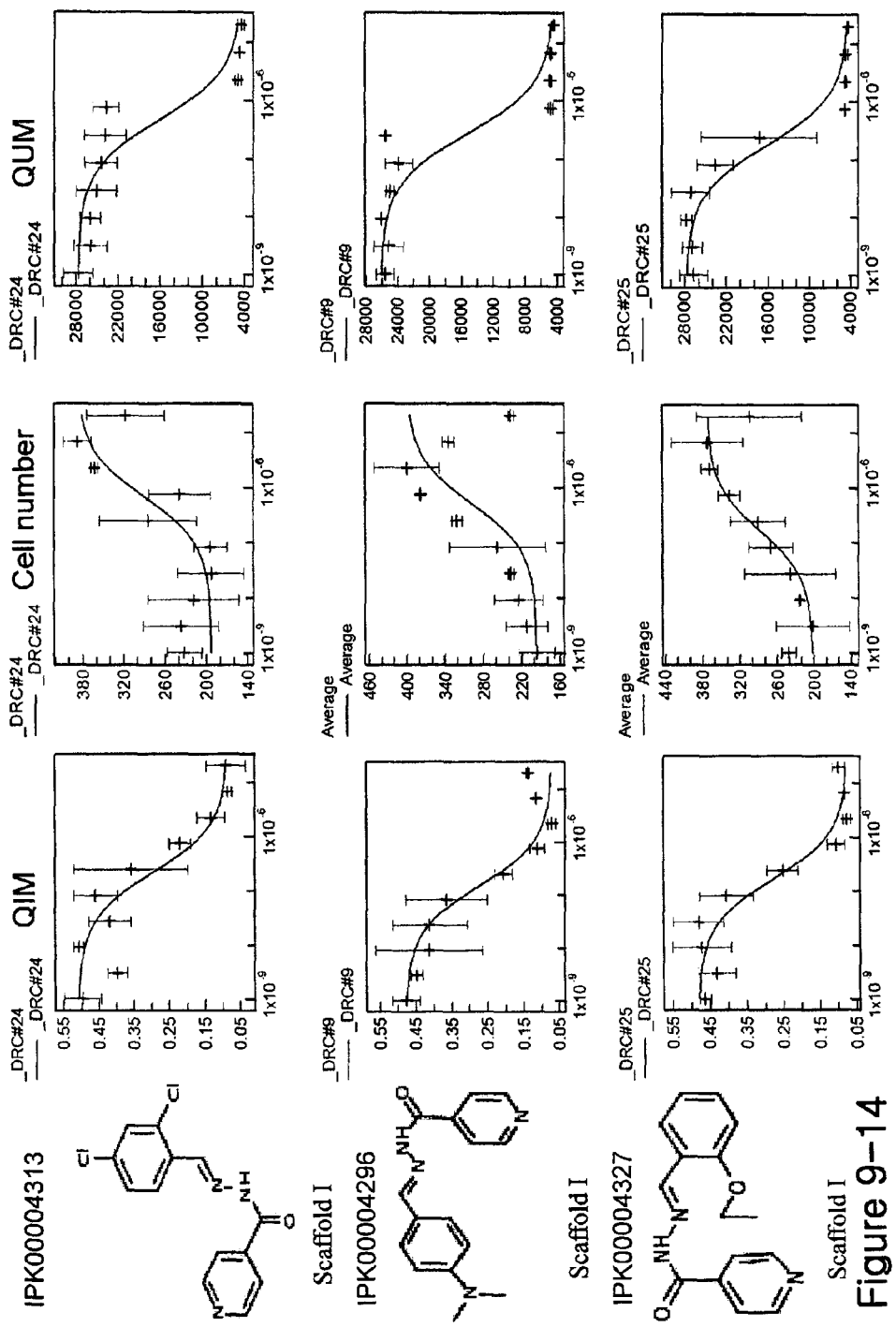
Figures 9, 10, 11, 12, 13, 14, 15:
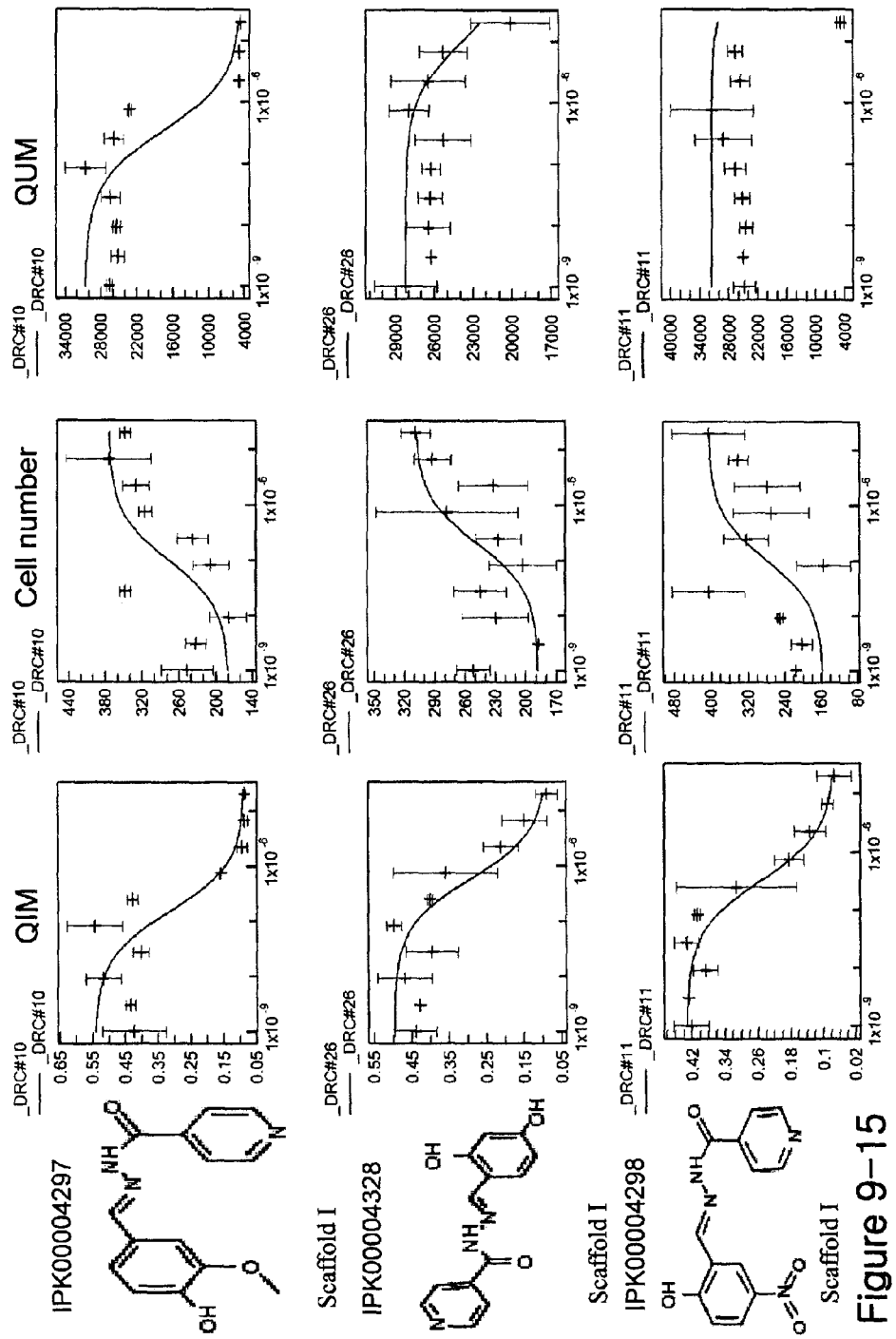
Figures 9, 10, 11, 12, 13, 14, 15, 16:
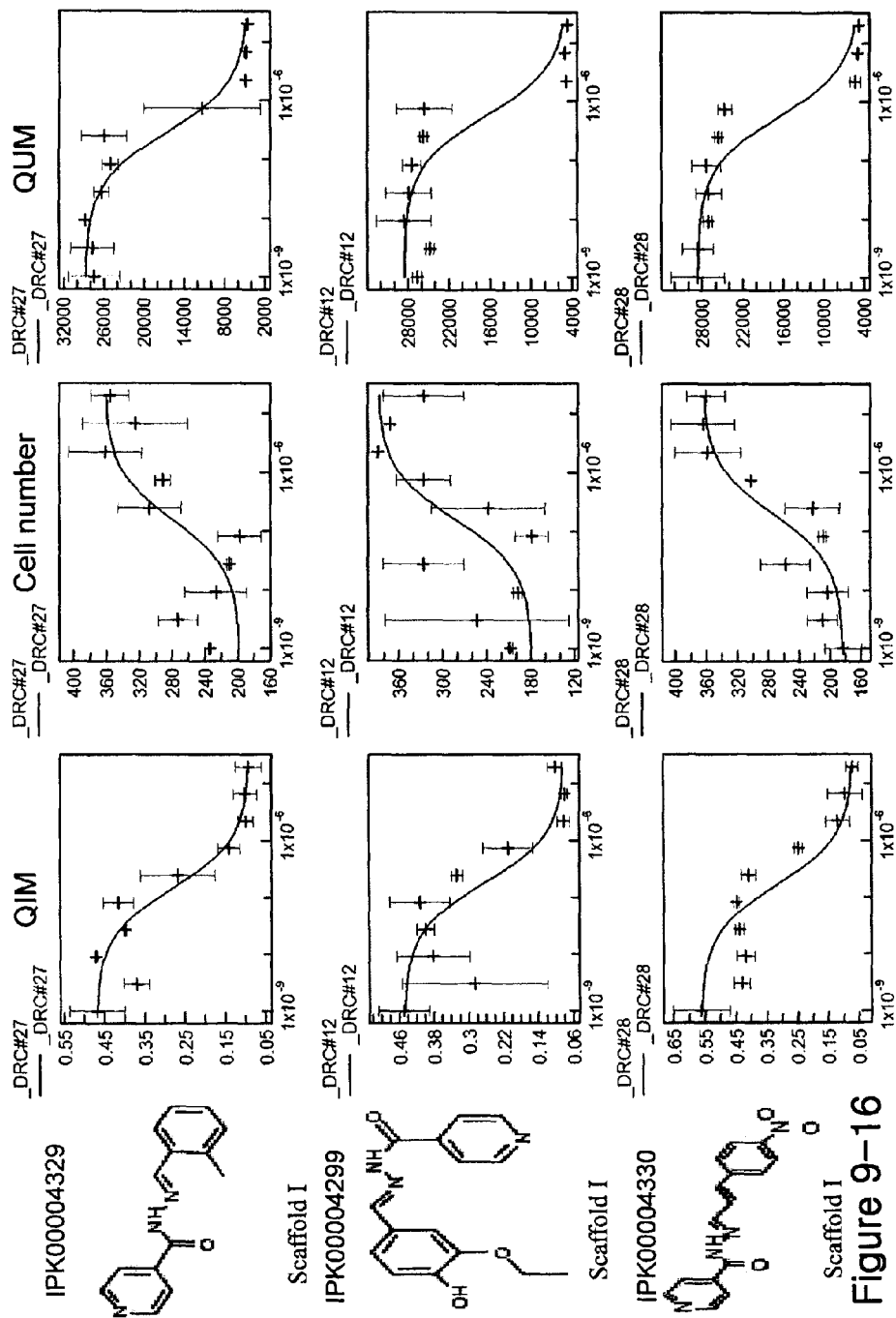
Figures 9, 10, 11, 12, 13, 14, 15, 16, 17:
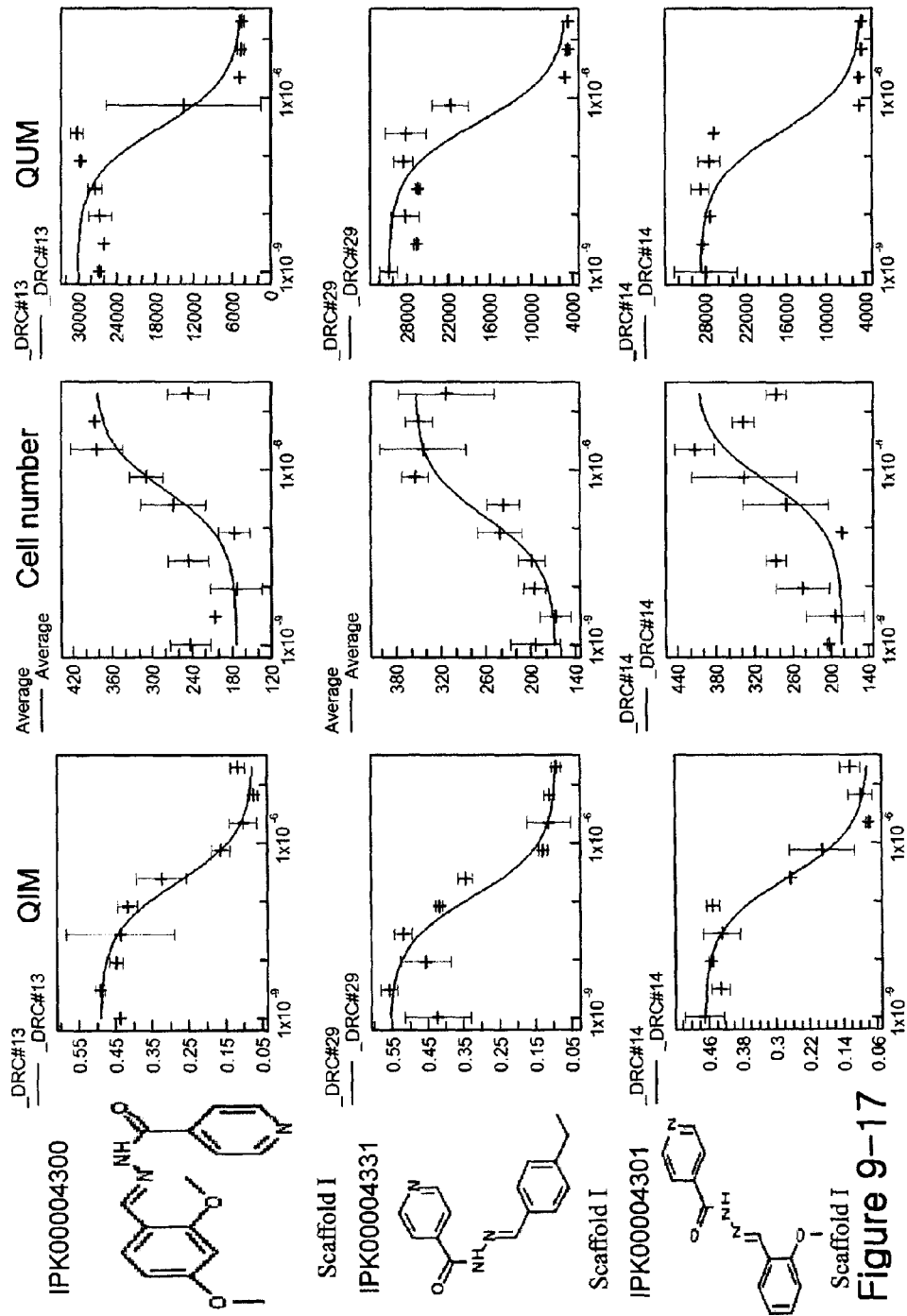
Figures 9, 10, 11, 12, 13, 14, 15, 16, 17, 18:
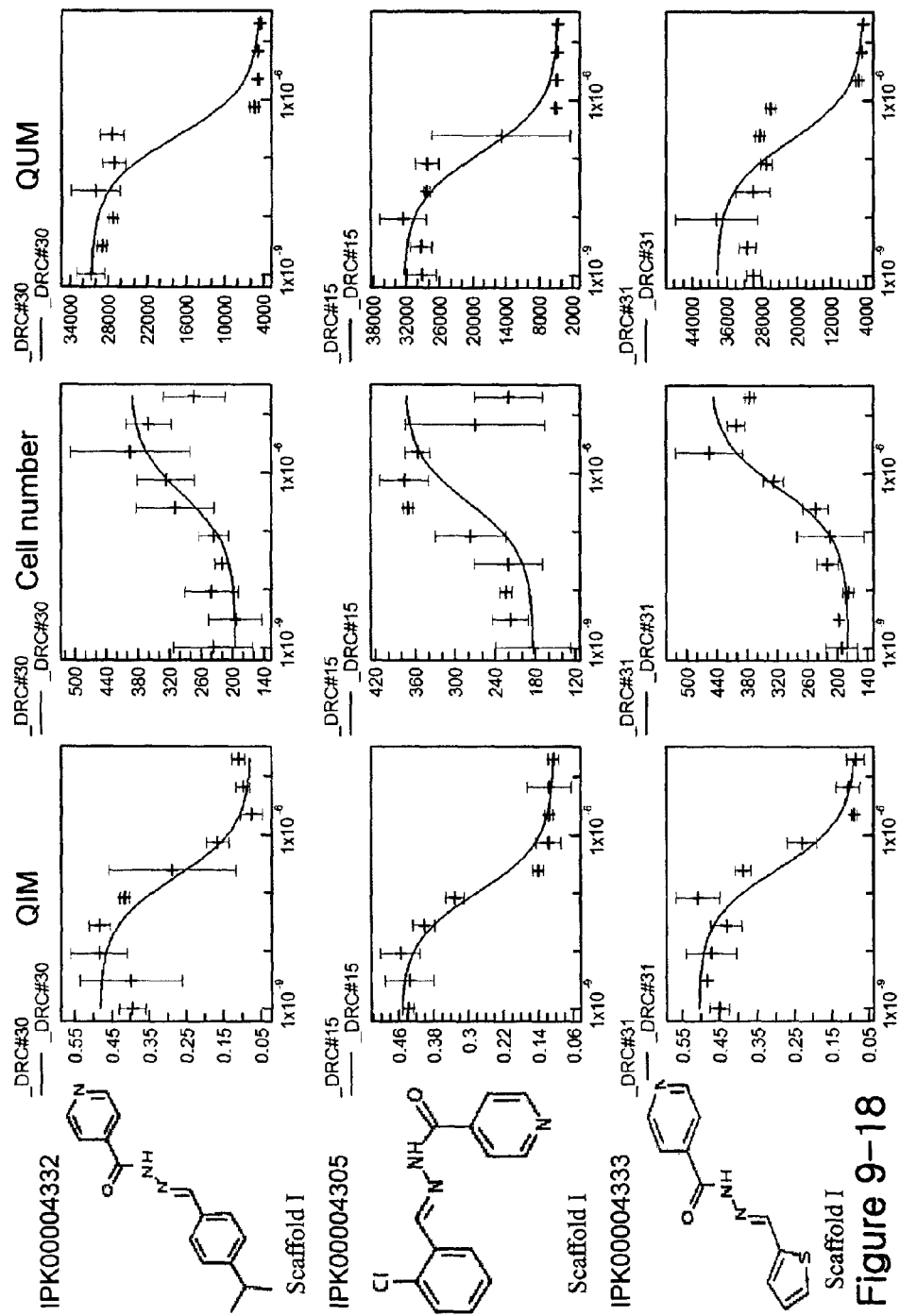
Figures 9, 10, 11, 12, 13, 14, 15, 16, 17, 18, 19:
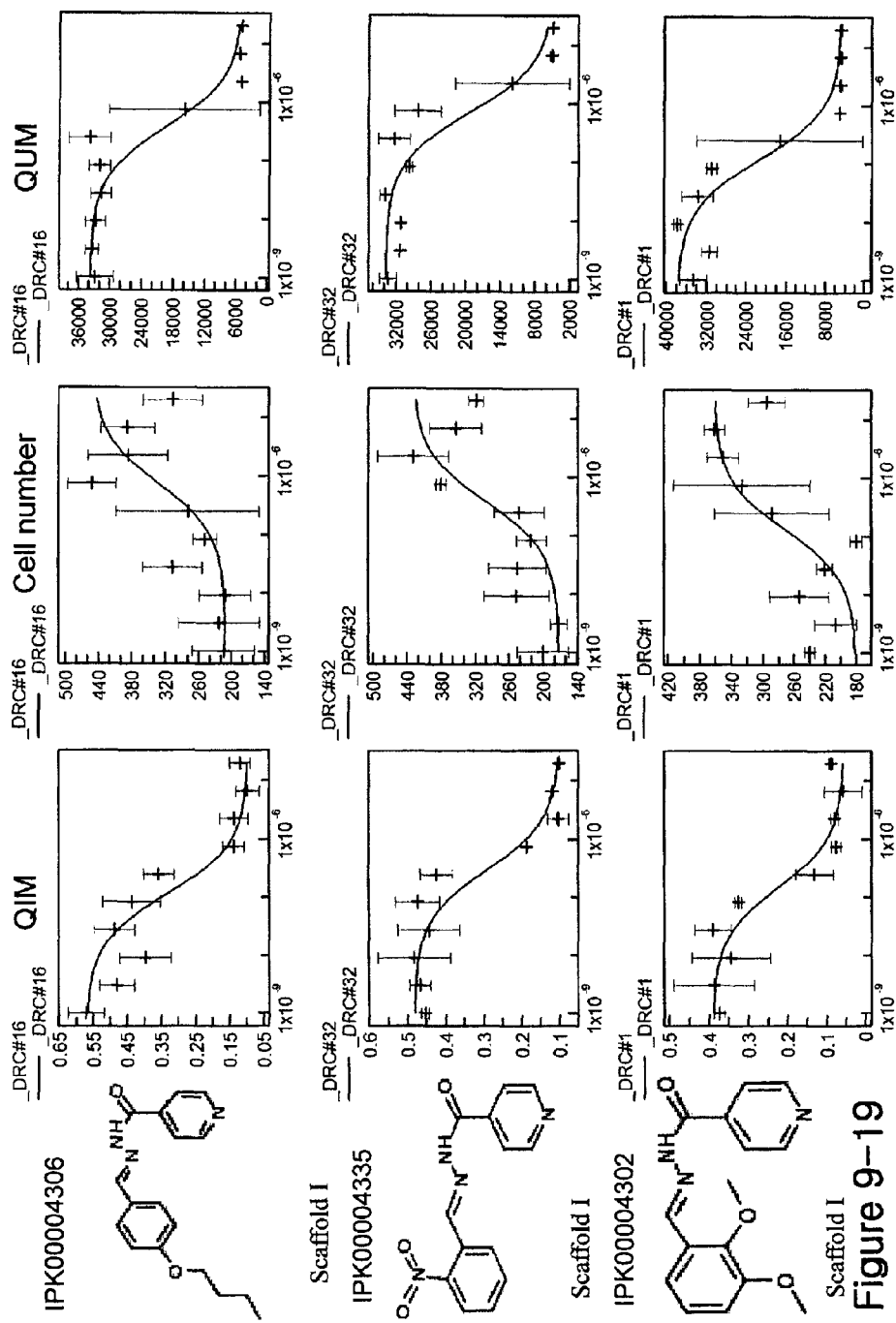
Figures 9, 10, 11, 12, 13, 14, 15, 16, 17, 18, 19, 20:
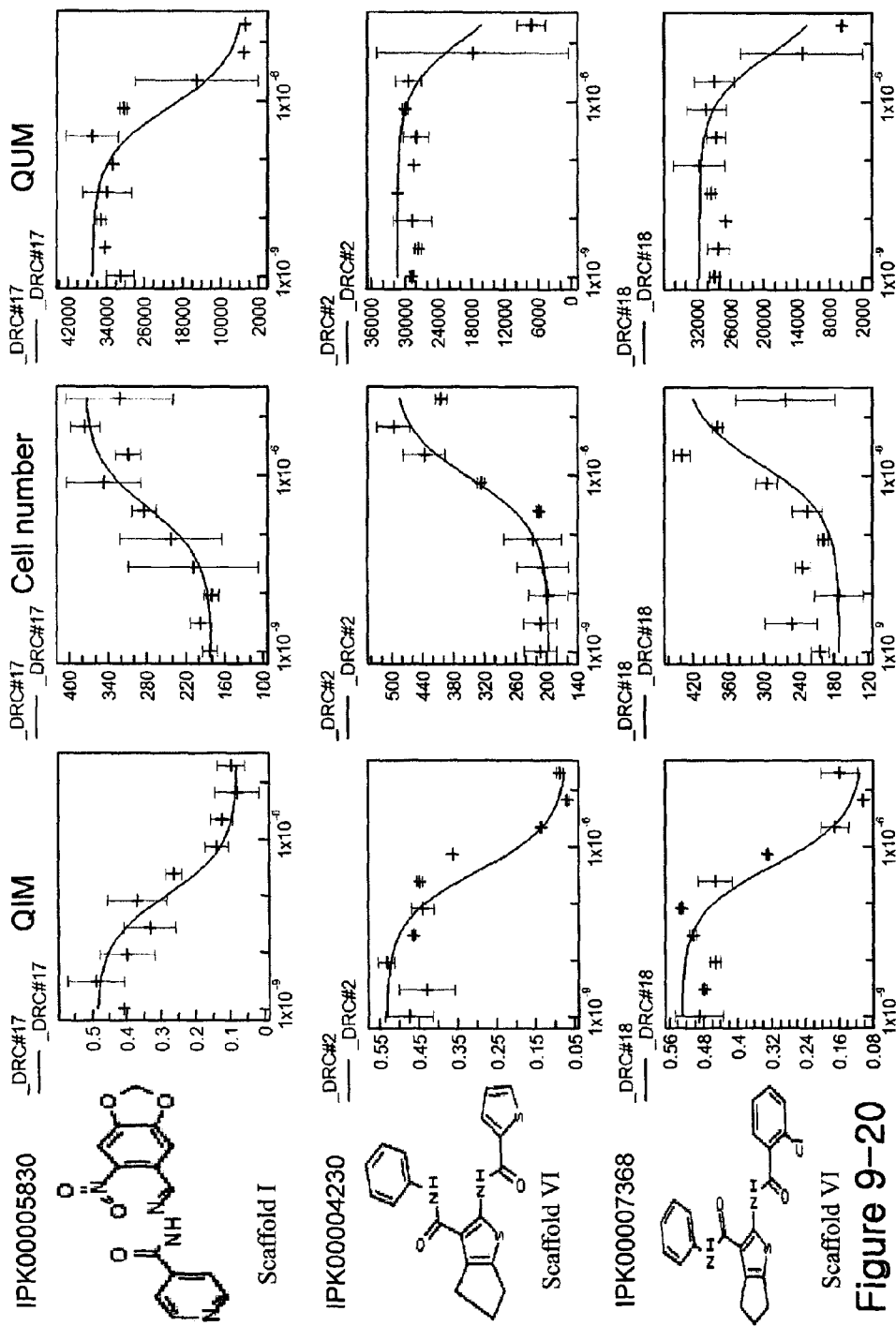
Figures 9, 10, 11, 12, 13, 14, 15, 16, 17, 18, 19, 20, 21:
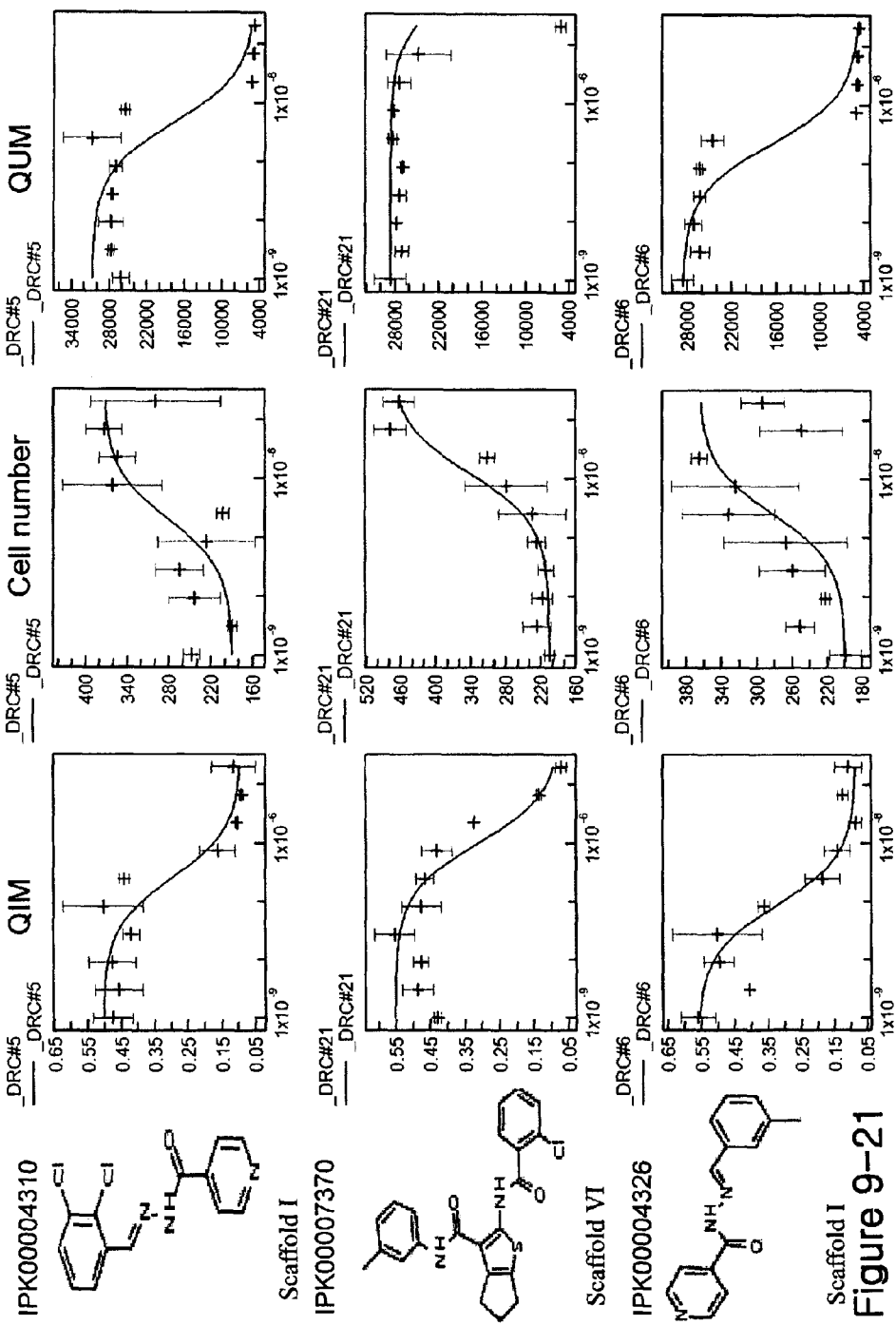
Figures 9, 10, 11, 12, 13, 14, 15, 16, 17, 18, 19, 20, 21, 22:
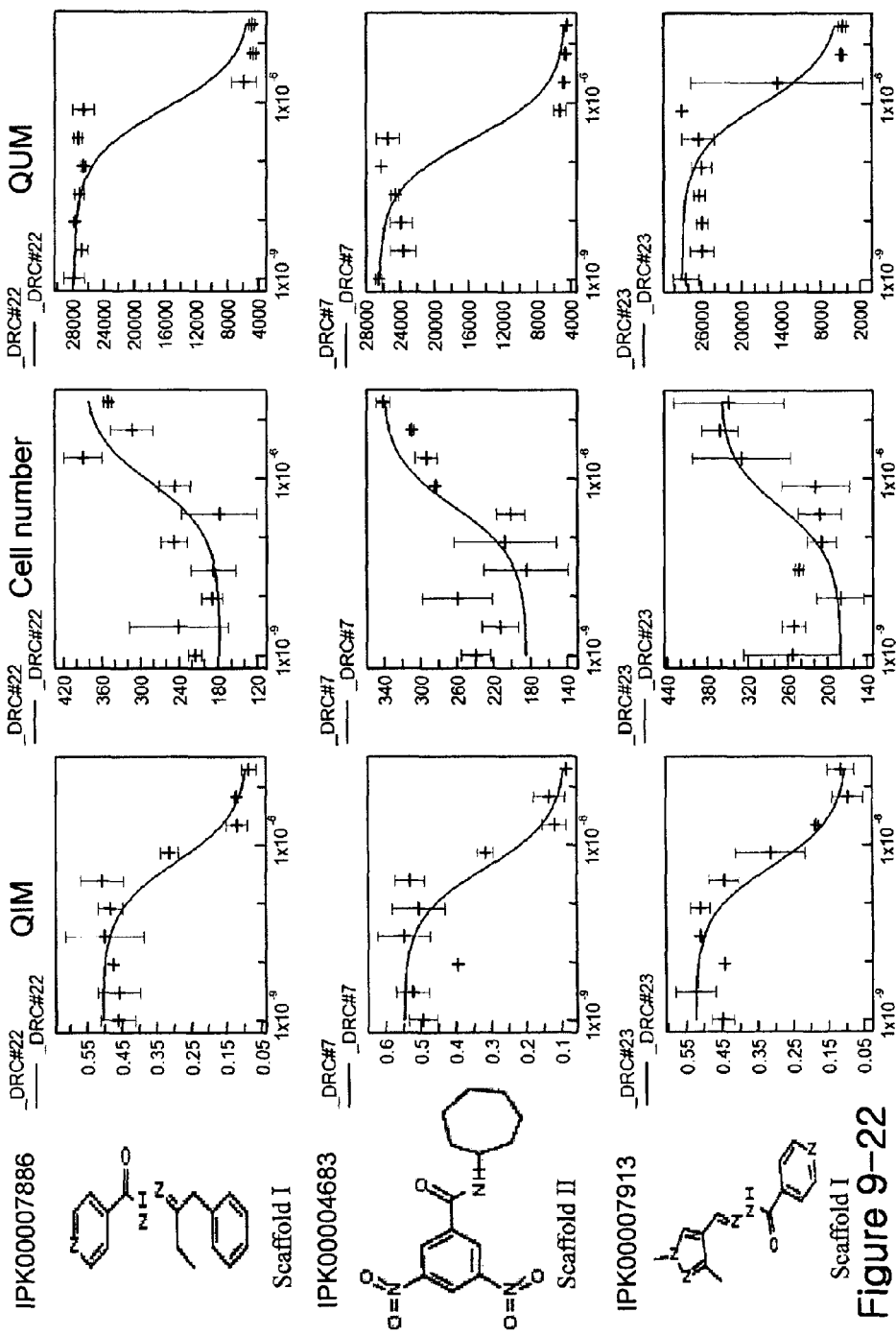
Figures 9, 10, 11, 12, 13, 14, 15, 16, 17, 18, 19, 20, 21, 22, 23:
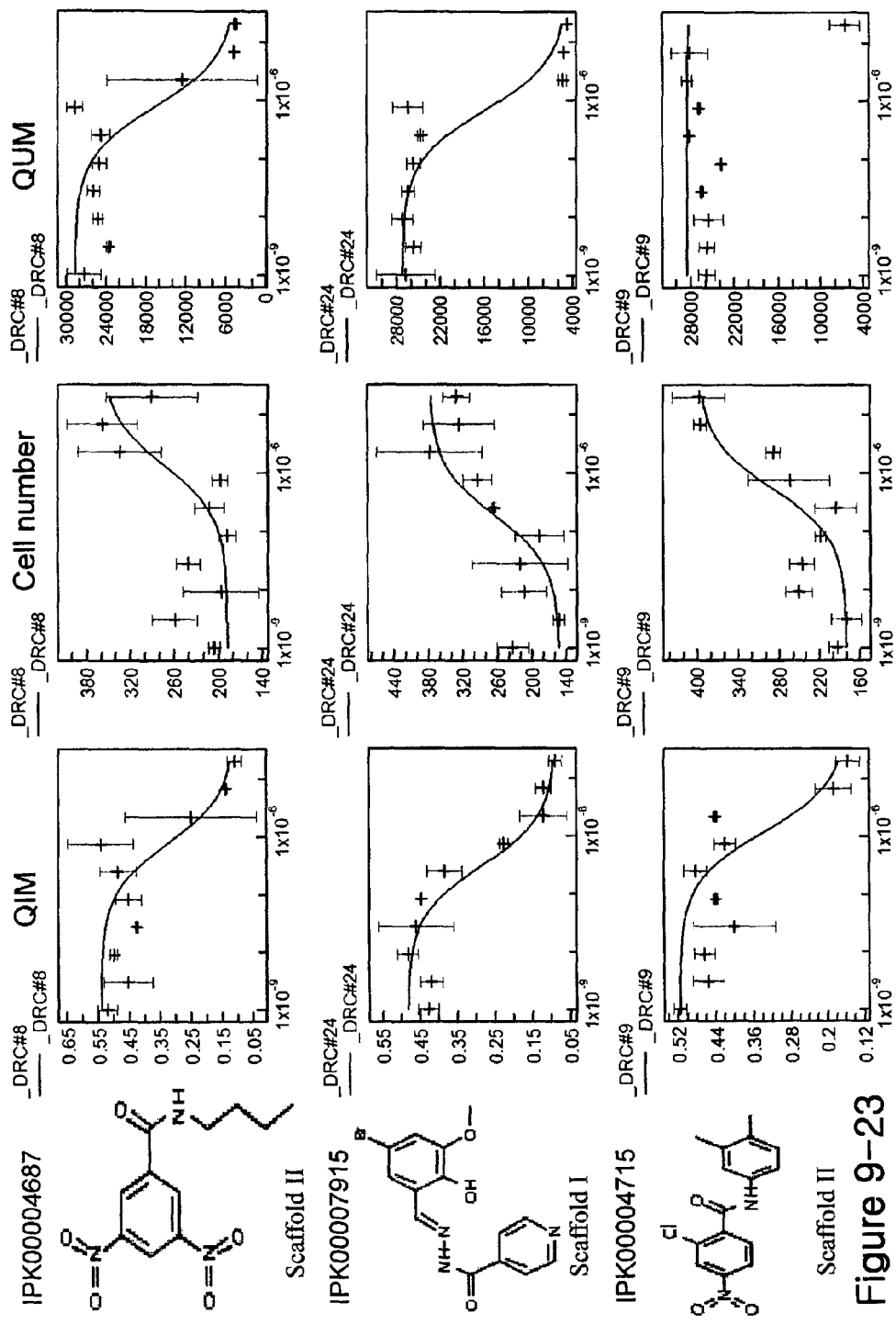
Figures 9, 10, 11, 12, 13, 14, 15, 16, 17, 18, 19, 20, 21, 22, 23, 24:
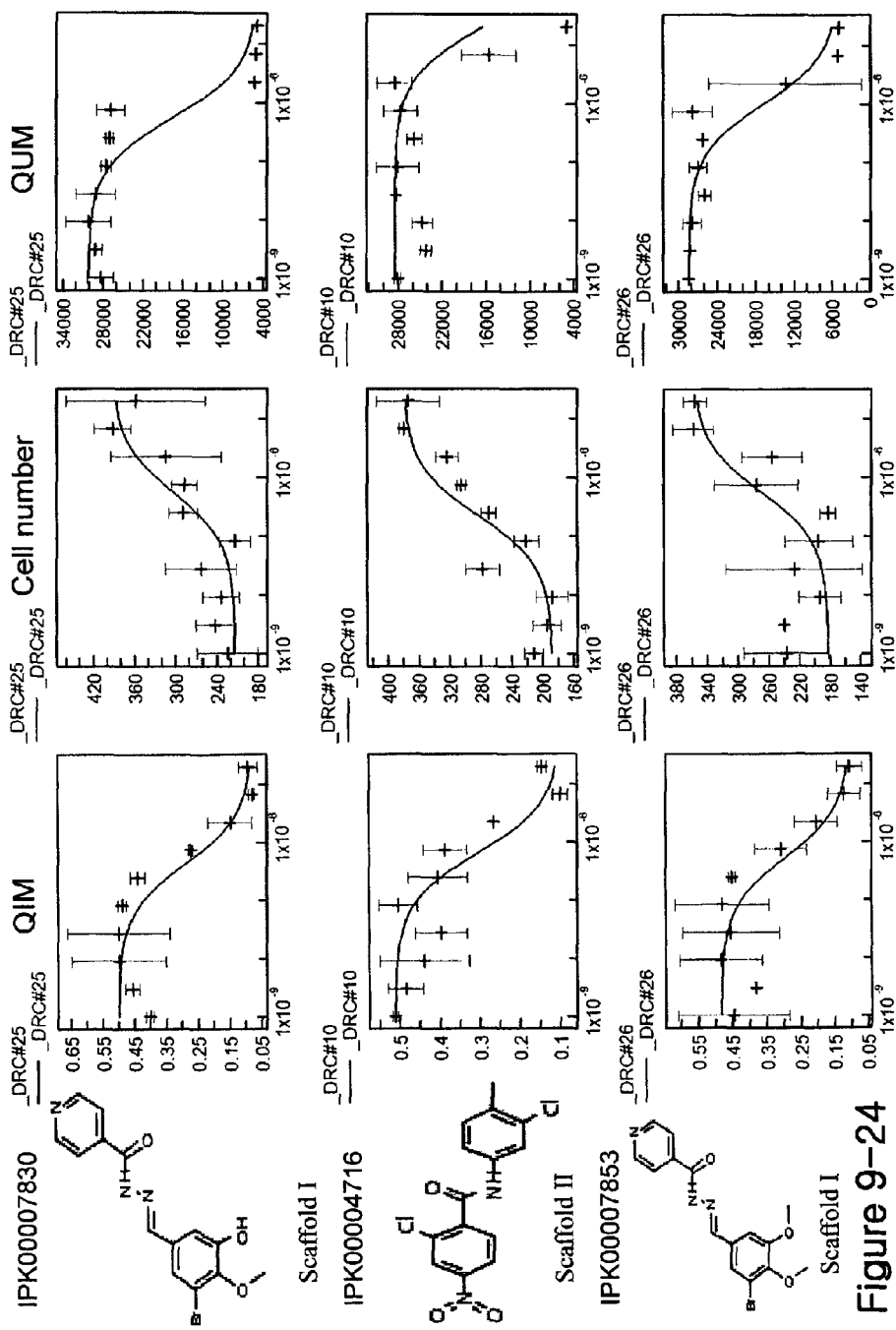
Figures 9, 10, 11, 12, 13, 14, 15, 16, 17, 18, 19, 20, 21, 22, 23, 24, 25:
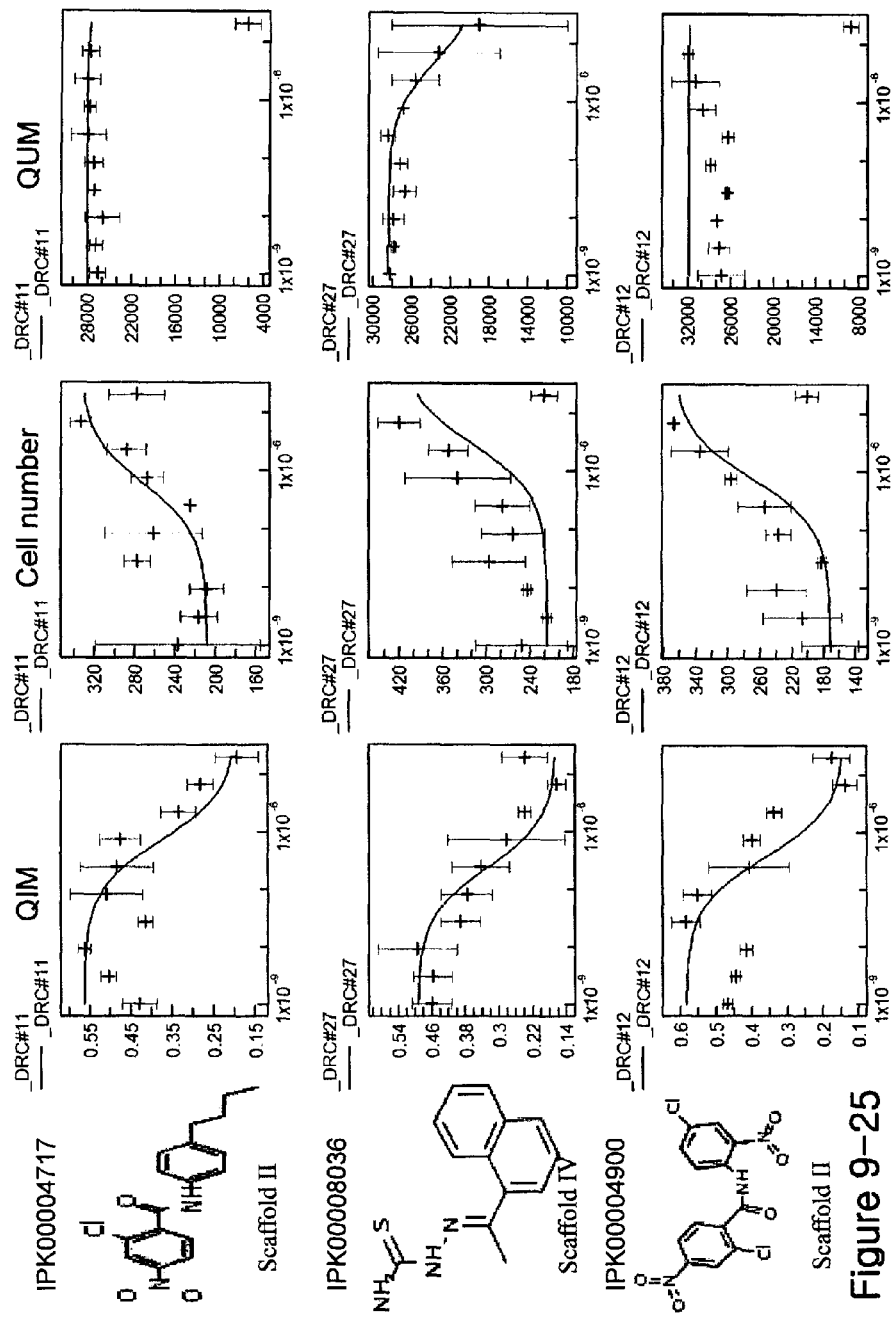
Figures 9, 10, 11, 12, 13, 14, 15, 16, 17, 18, 19, 20, 21, 22, 23, 24, 25, 26:
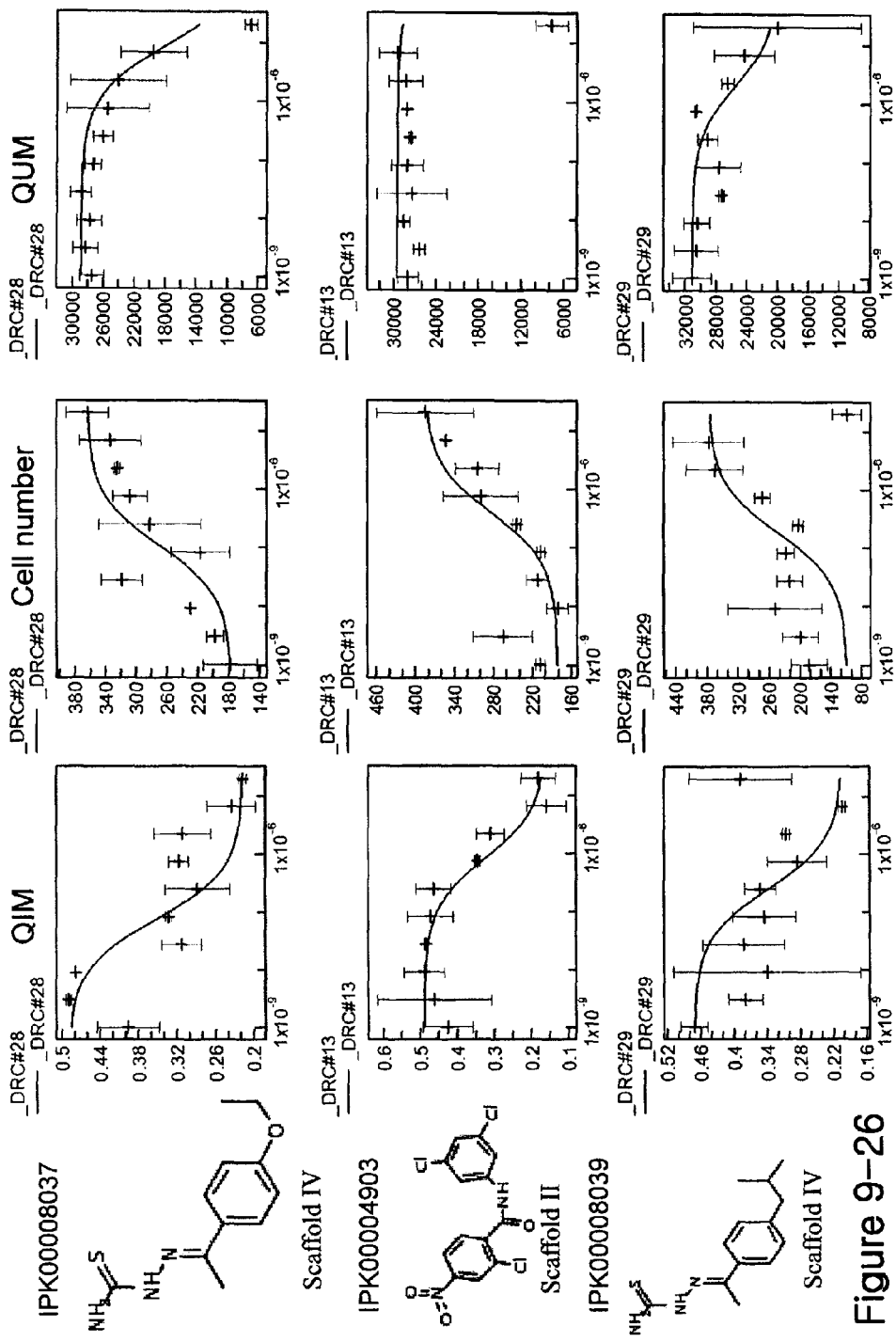
Figures 9, 10, 11, 12, 13, 14, 15, 16, 17, 18, 19, 20, 21, 22, 23, 24, 25, 26, 27:
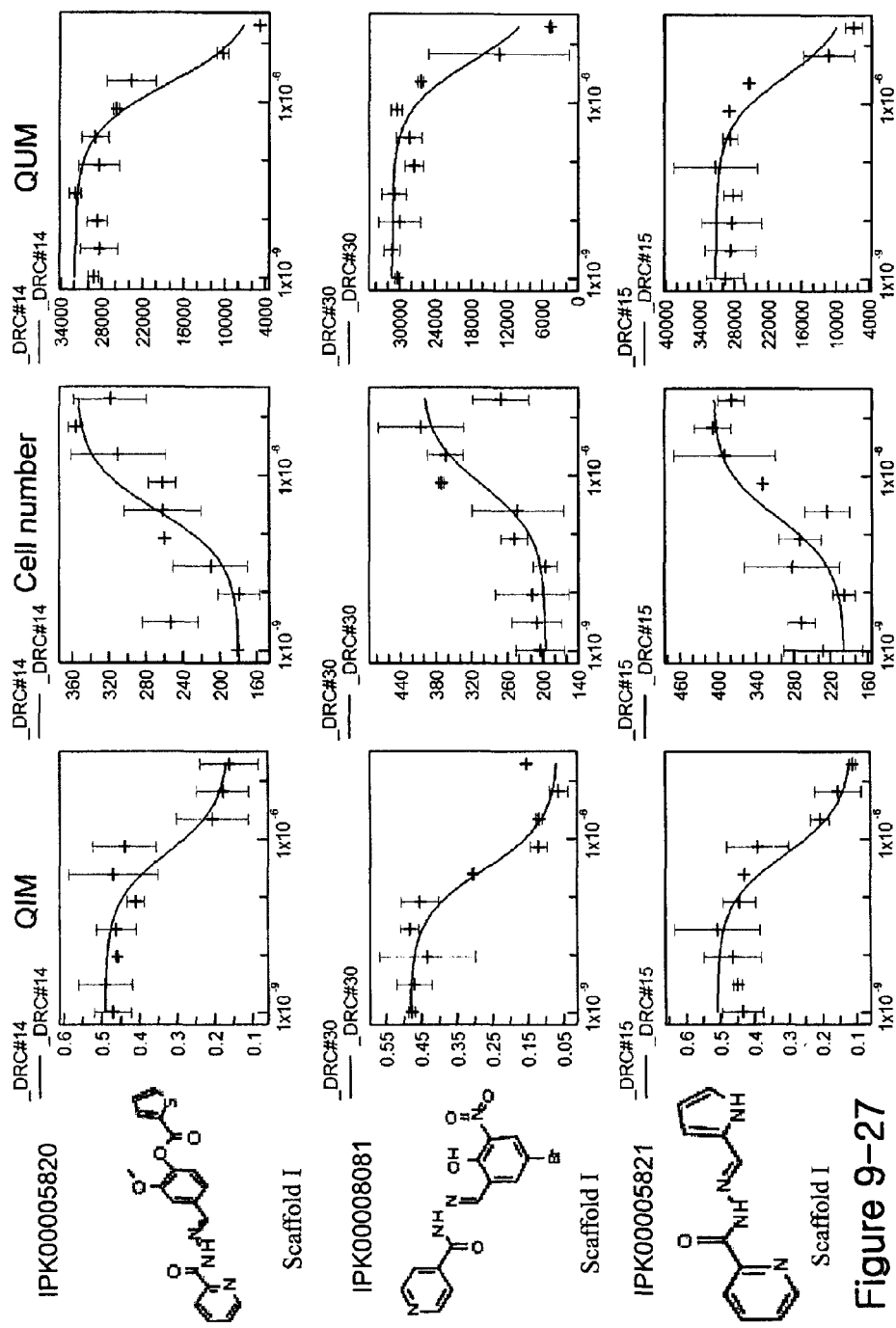
Figures 9, 10, 11, 12, 13, 14, 15, 16, 17, 18, 19, 20, 21, 22, 23, 24, 25, 26, 27, 28:
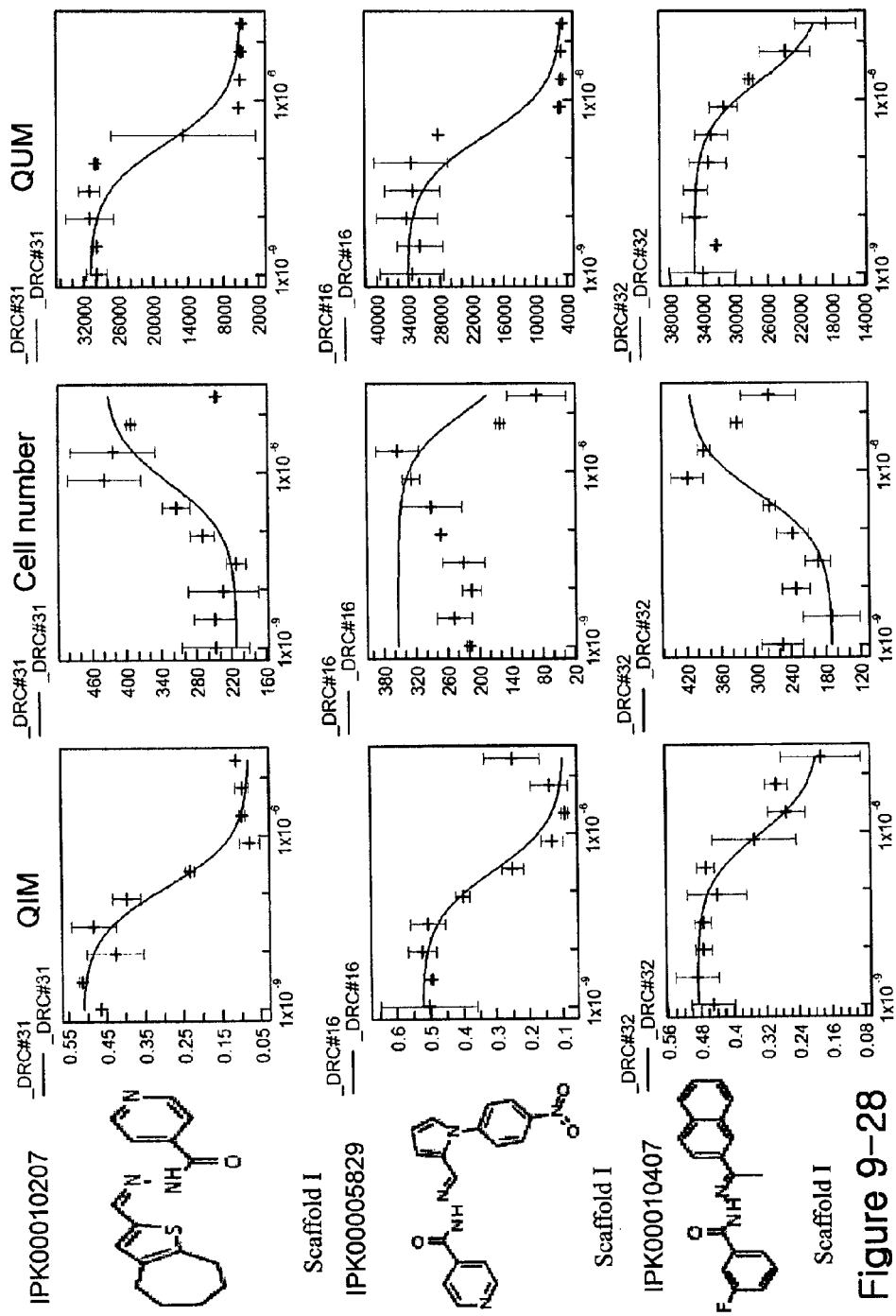
Figures 9, 10, 11, 12, 13, 14, 15, 16, 17, 18, 19, 20, 21, 22, 23, 24, 25, 26, 27, 28, 29:
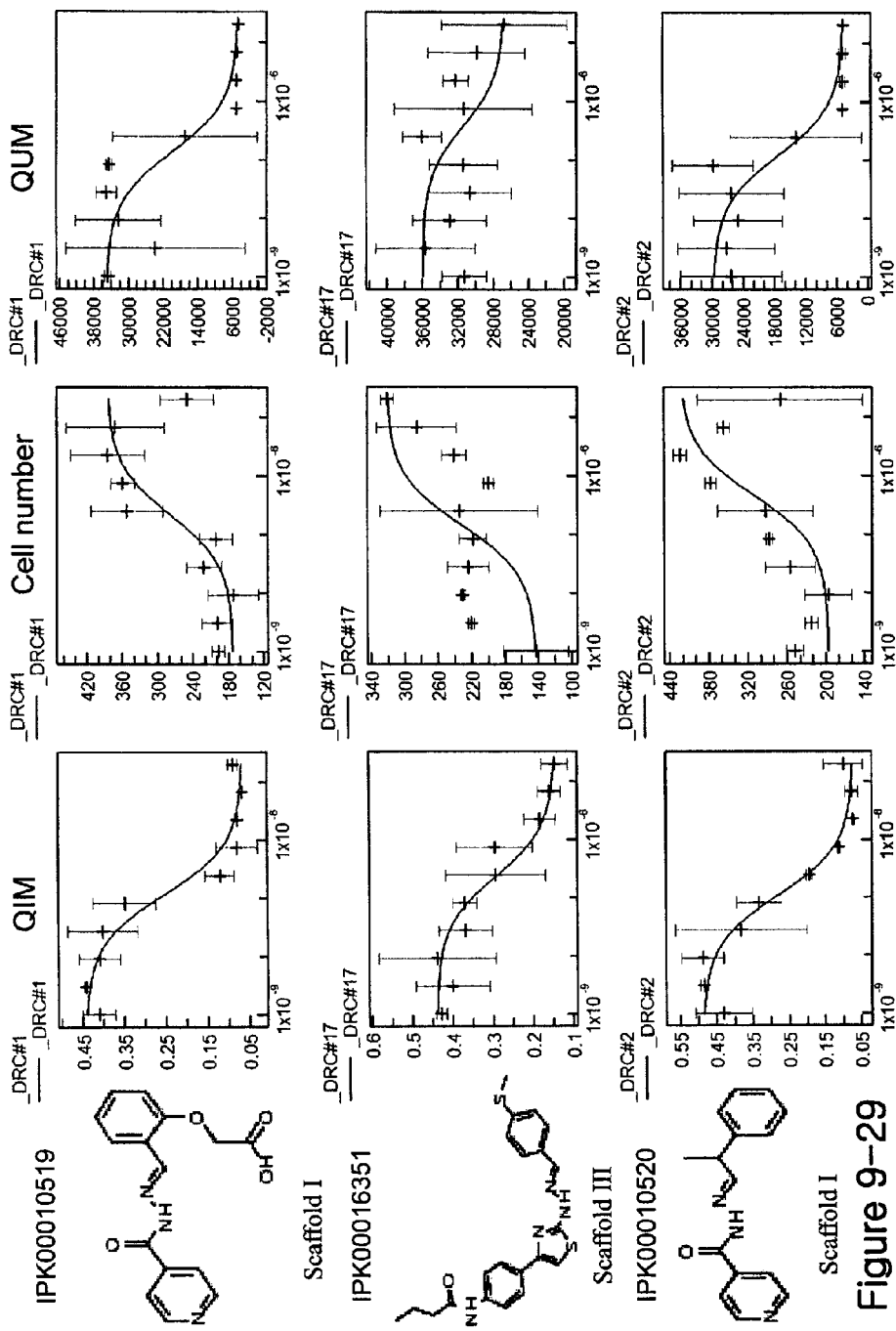
Figures 9, 10, 11, 12, 13, 14, 15, 16, 17, 18, 19, 20, 21, 22, 23, 24, 25, 26, 27, 28, 29, 30:
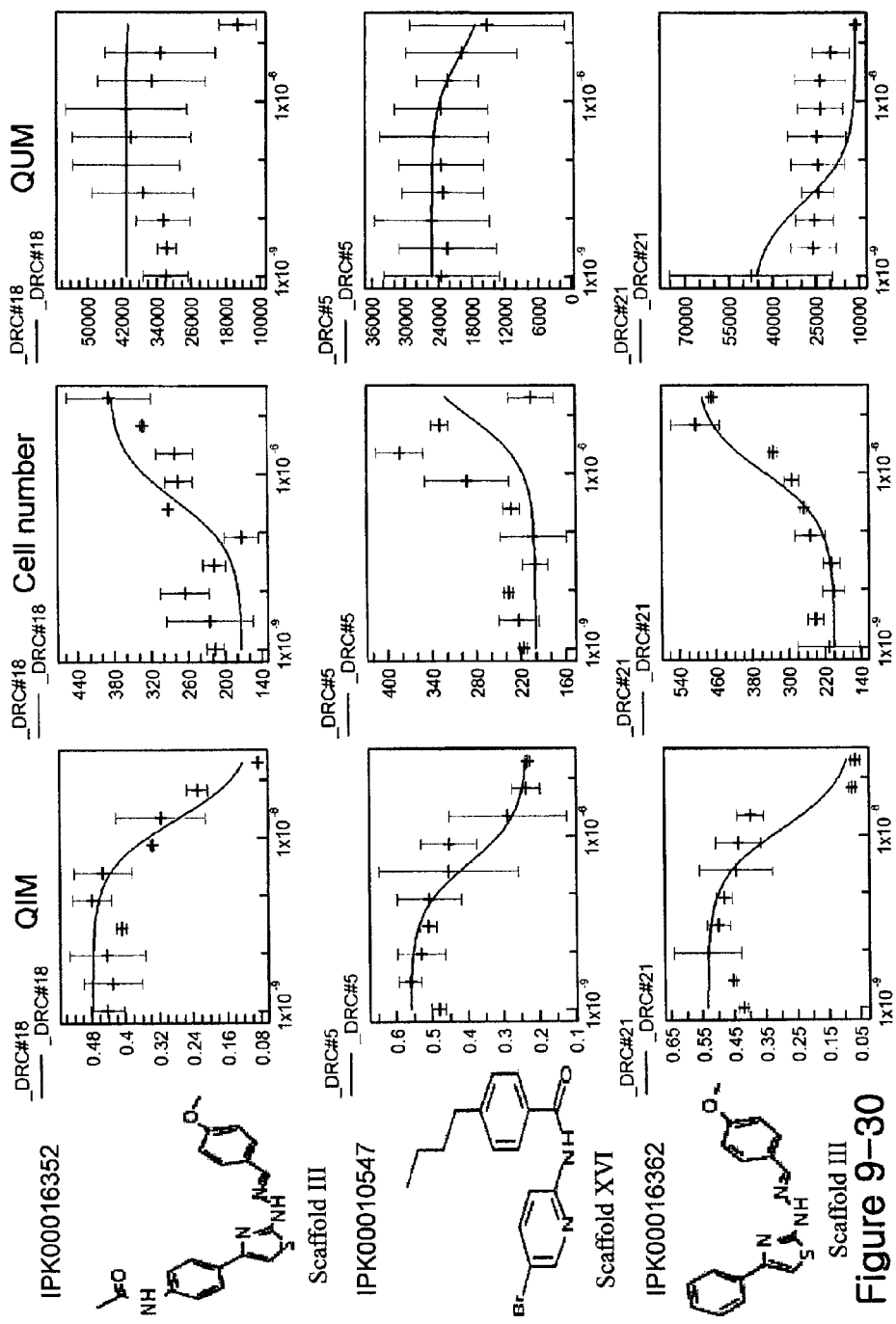
Figures 9, 10, 11, 12, 13, 14, 15, 16, 17, 18, 19, 20, 21, 22, 23, 24, 25, 26, 27, 28, 29, 30, 31:
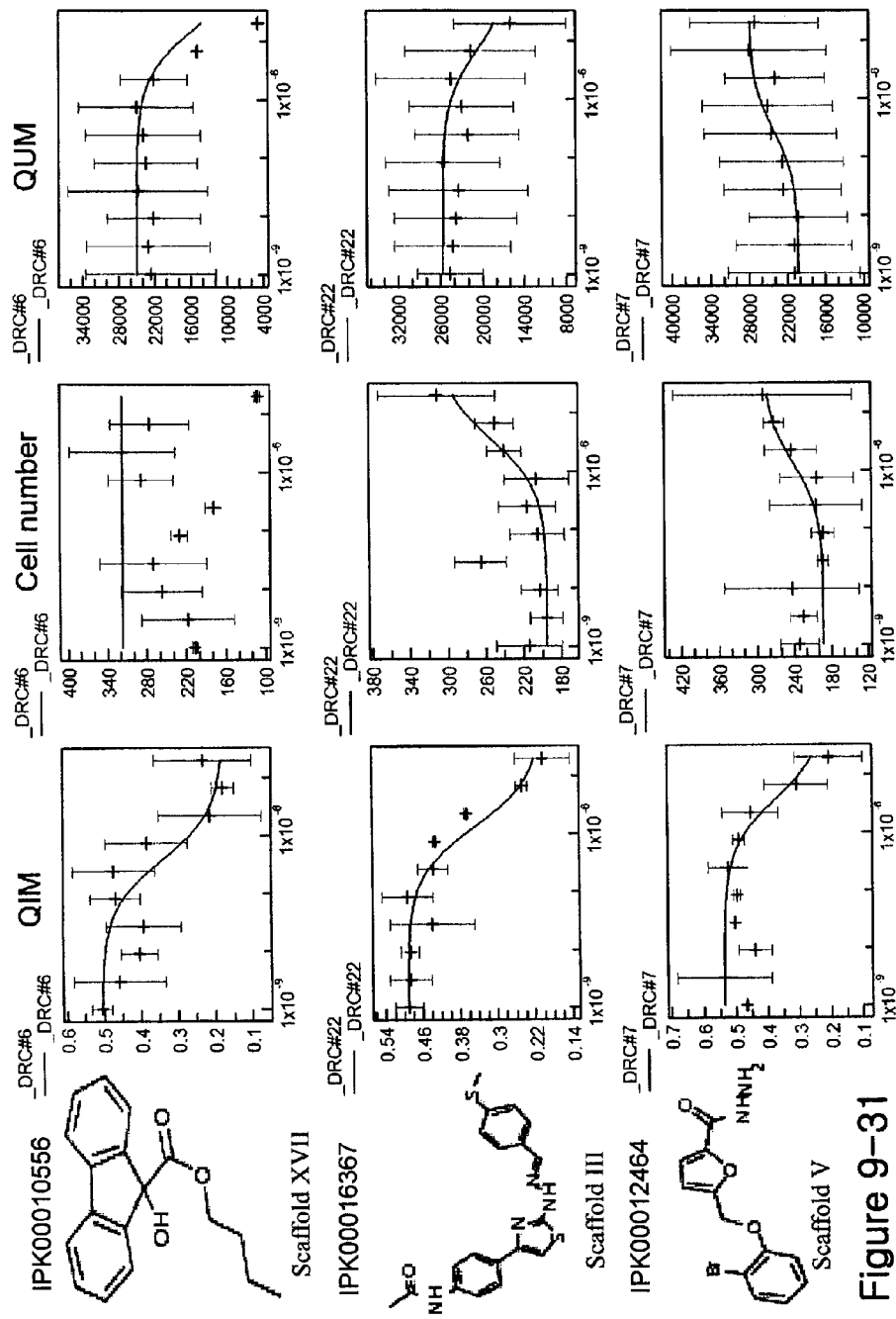
Figures 9, 10, 11, 12, 13, 14, 15, 16, 17, 18, 19, 20, 21, 22, 23, 24, 25, 26, 27, 28, 29, 30, 31, 32:
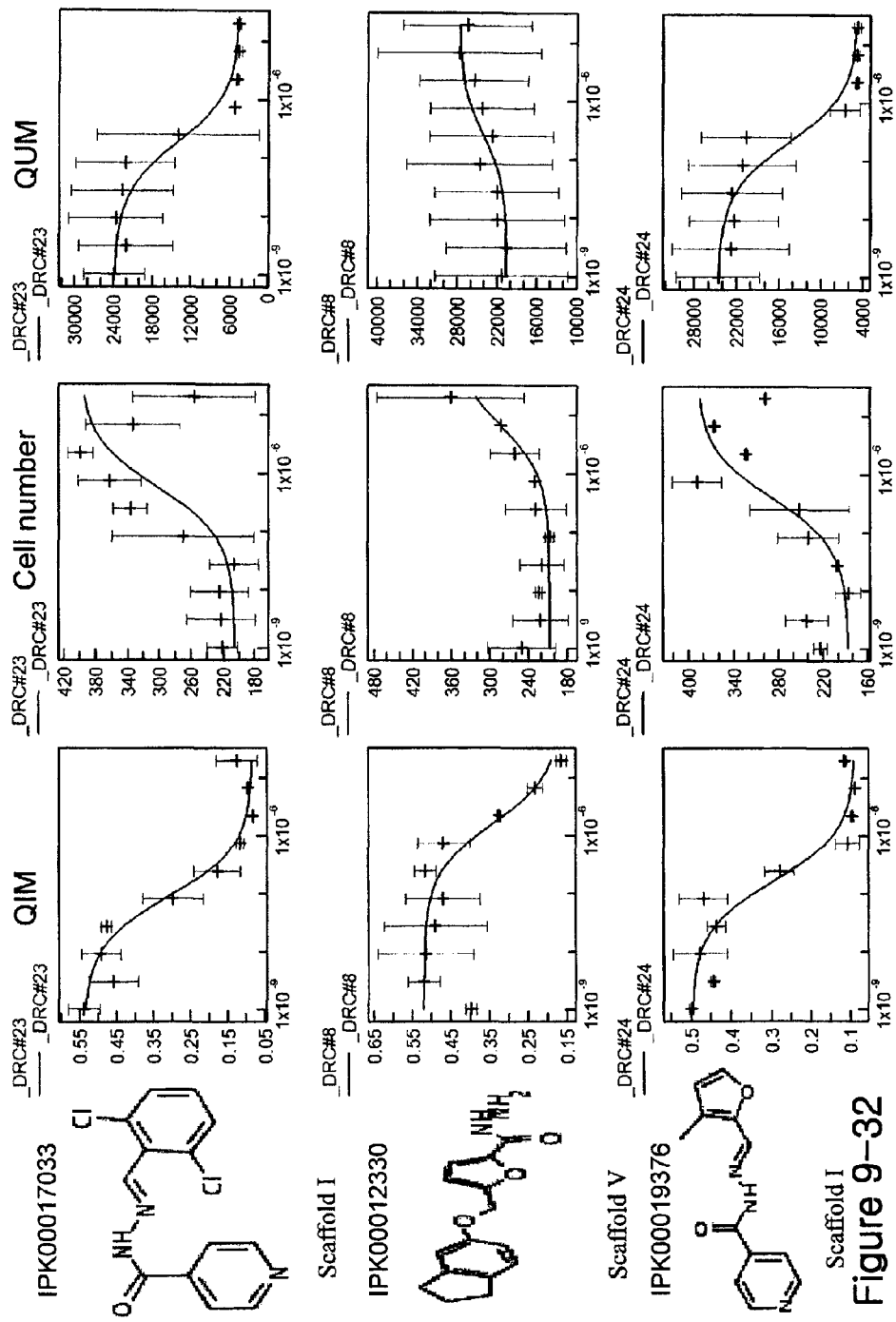
Figures 9, 10, 11, 12, 13, 14, 15, 16, 17, 18, 19, 20, 21, 22, 23, 24, 25, 26, 27, 28, 29, 30, 31, 32, 33:
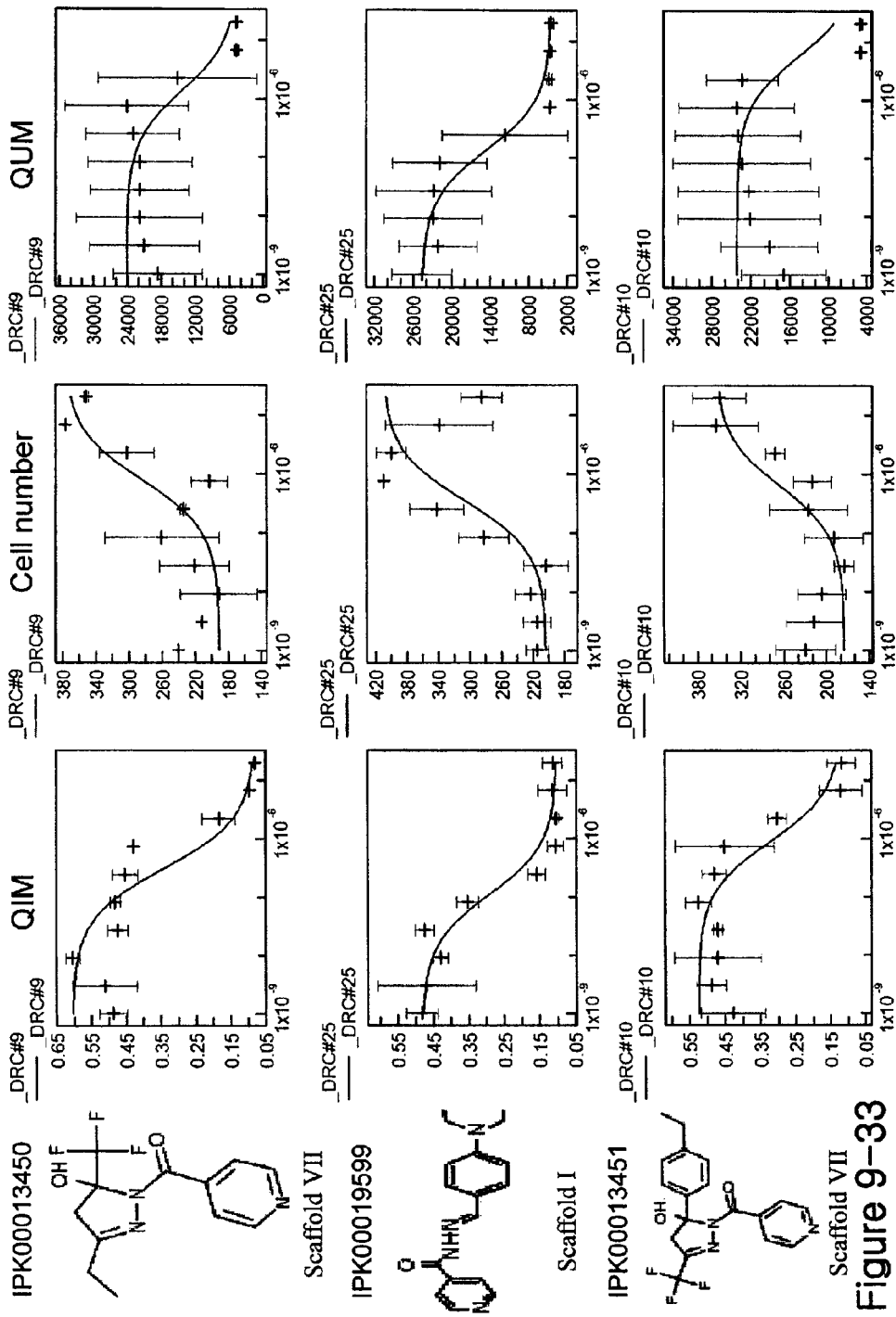
Figures 9, 10, 11, 12, 13, 14, 15, 16, 17, 18, 19, 20, 21, 22, 23, 24, 25, 26, 27, 28, 29, 30, 31, 32, 33, 34:
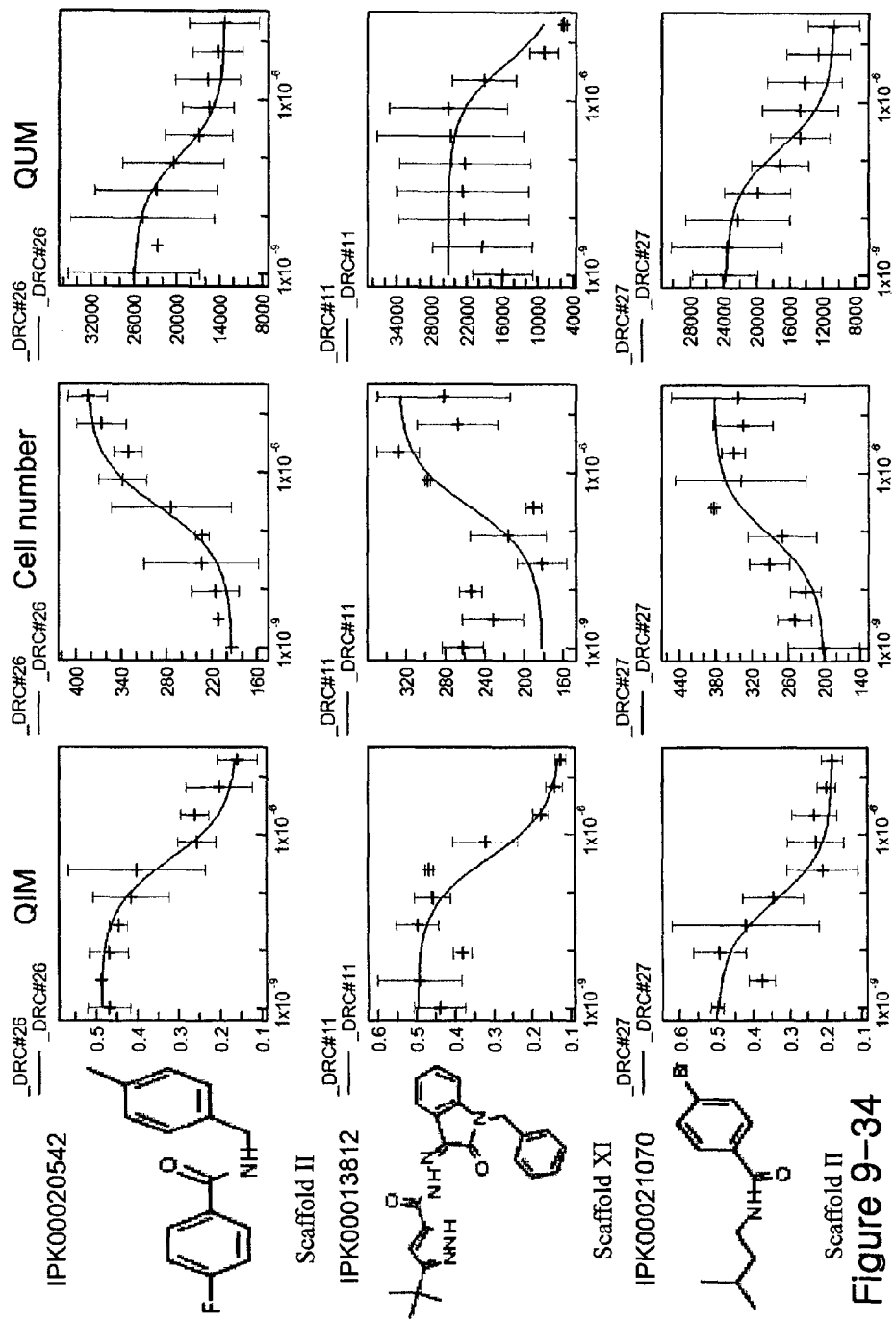
Figures 9, 10, 11, 12, 13, 14, 15, 16, 17, 18, 19, 20, 21, 22, 23, 24, 25, 26, 27, 28, 29, 30, 31, 32, 33, 34, 35:
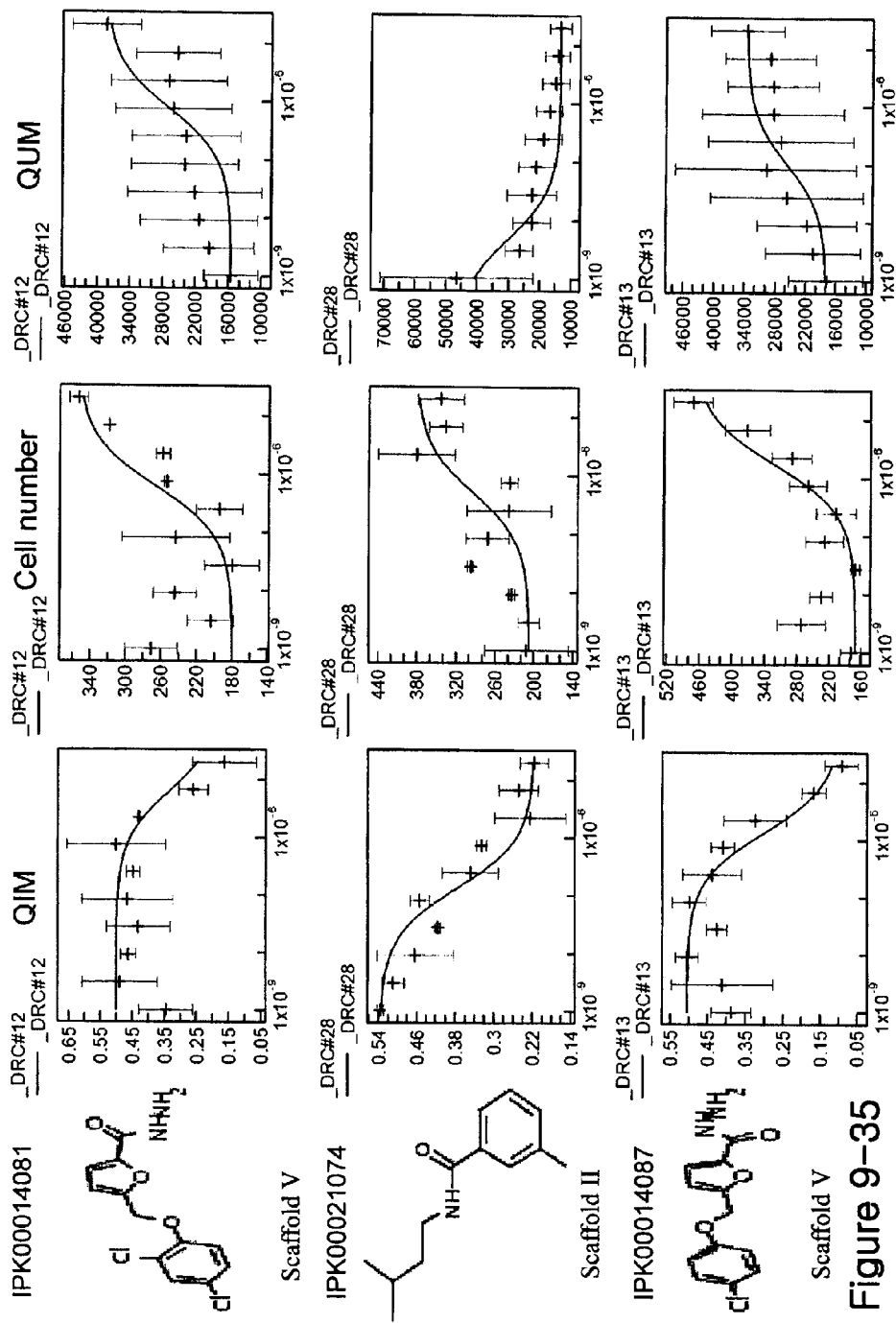
Figures 9, 10, 11, 12, 13, 14, 15, 16, 17, 18, 19, 20, 21, 22, 23, 24, 25, 26, 27, 28, 29, 30, 31, 32, 33, 34, 35, 36:
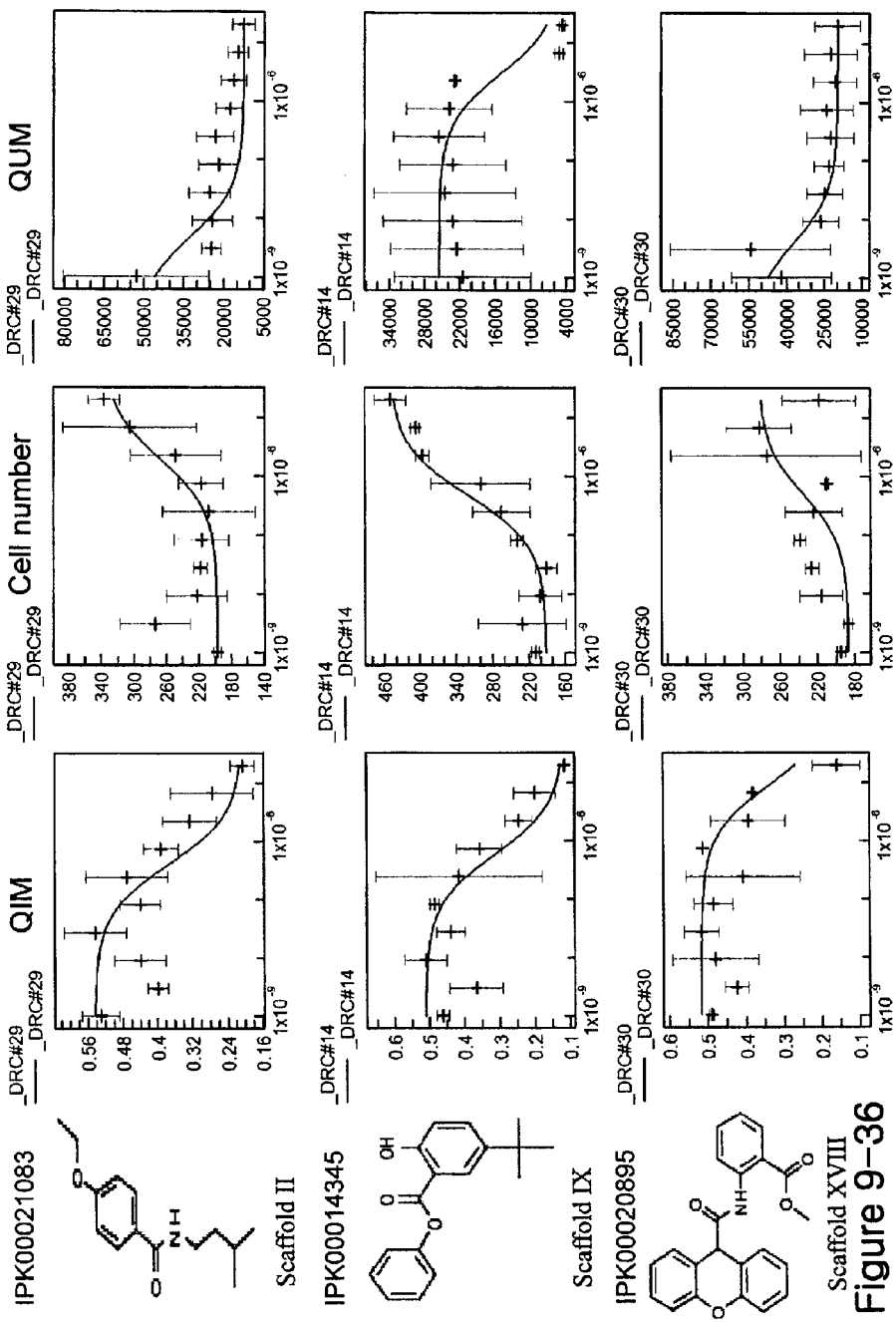
Figures 9, 10, 11, 12, 13, 14, 15, 16, 17, 18, 19, 20, 21, 22, 23, 24, 25, 26, 27, 28, 29, 30, 31, 32, 33, 34, 35, 36, 37:
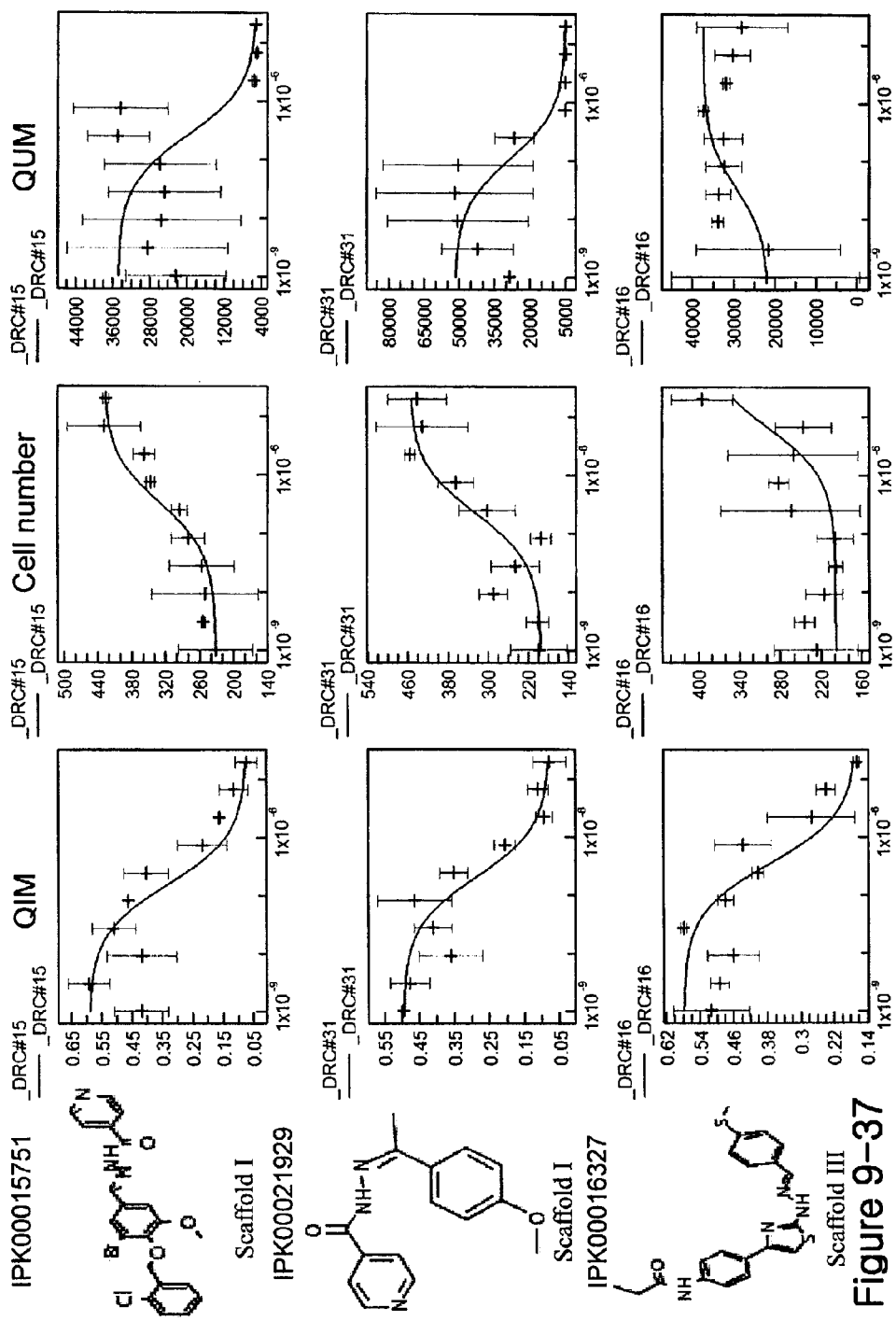
Figures 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
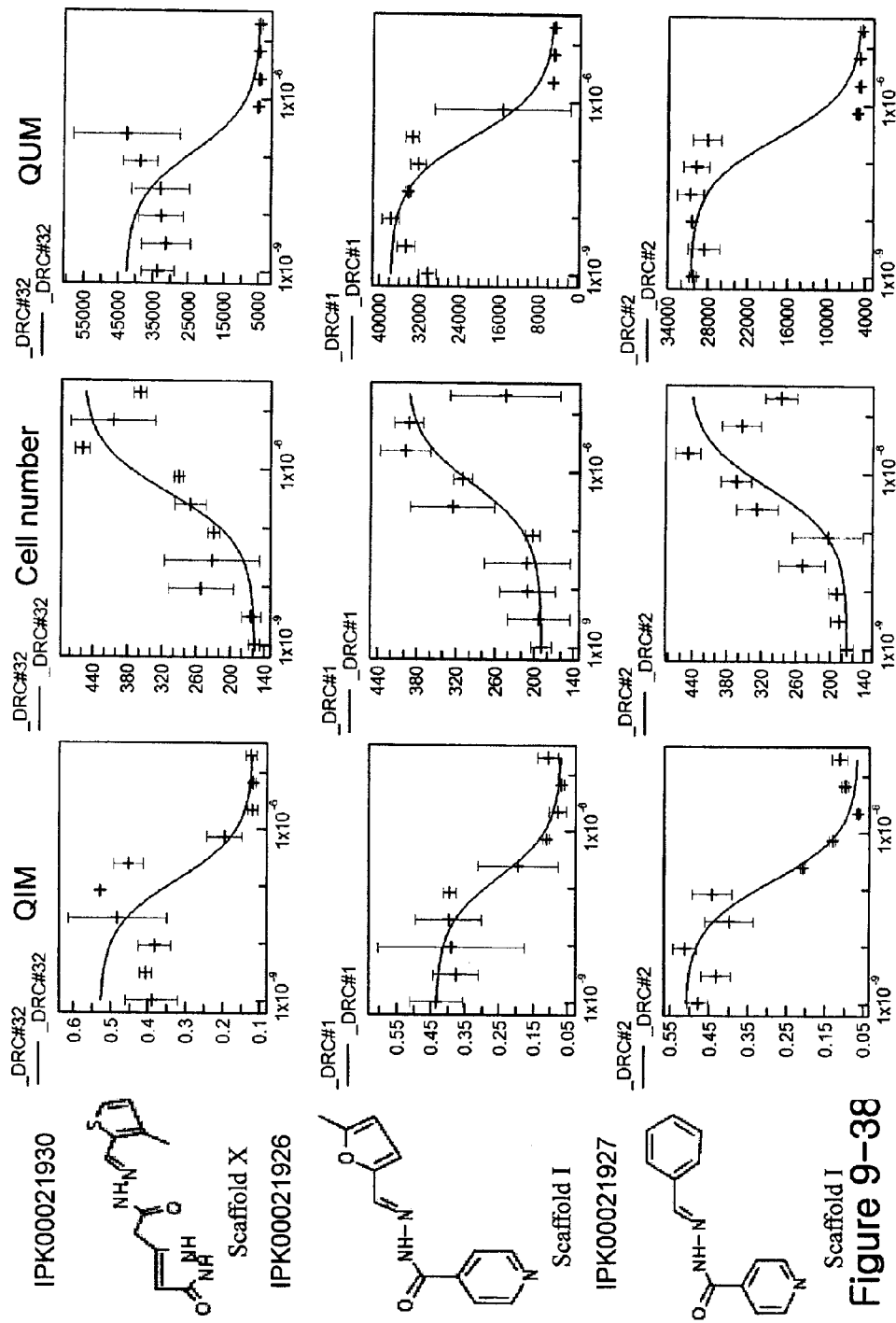
Figures 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
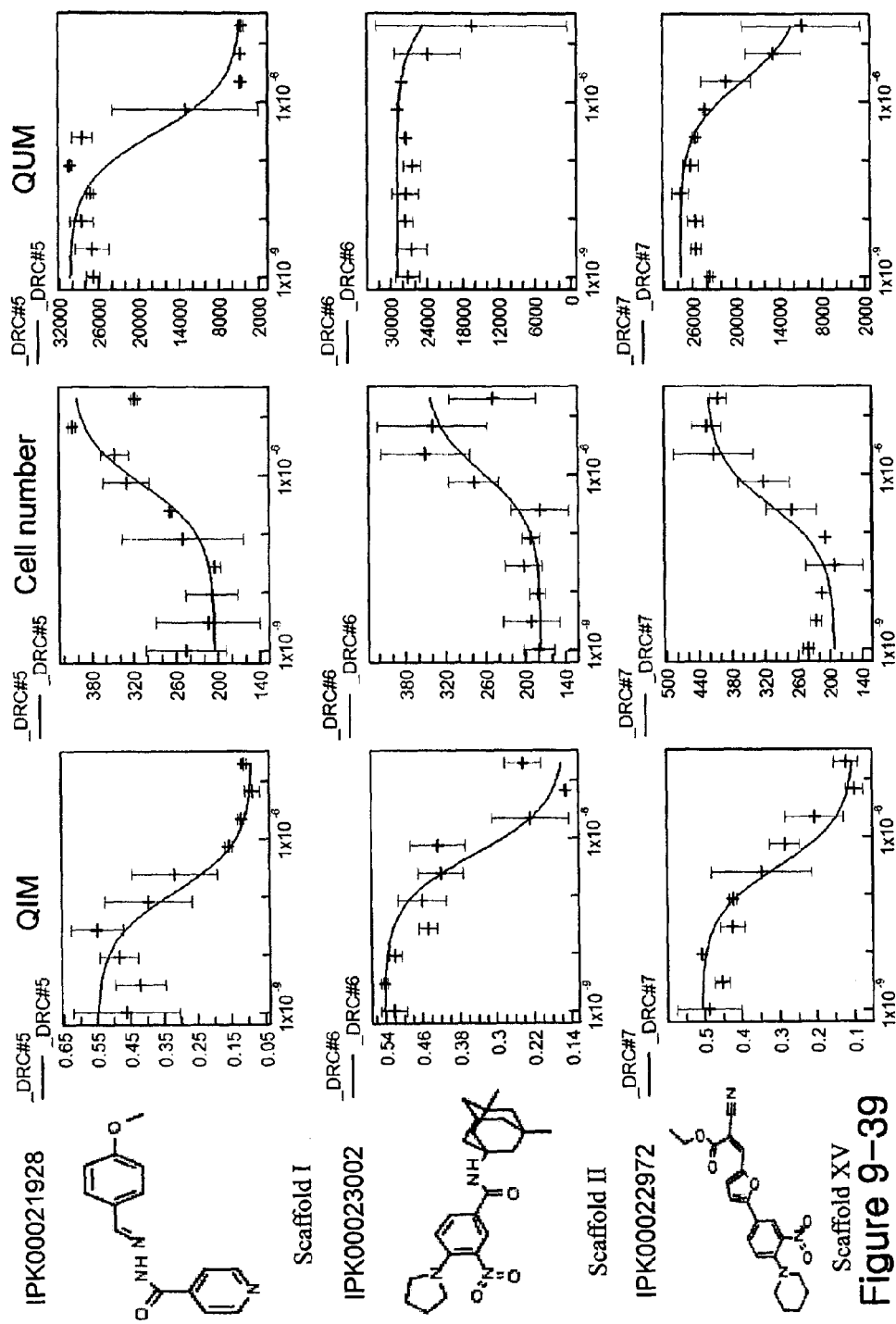
Figures 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
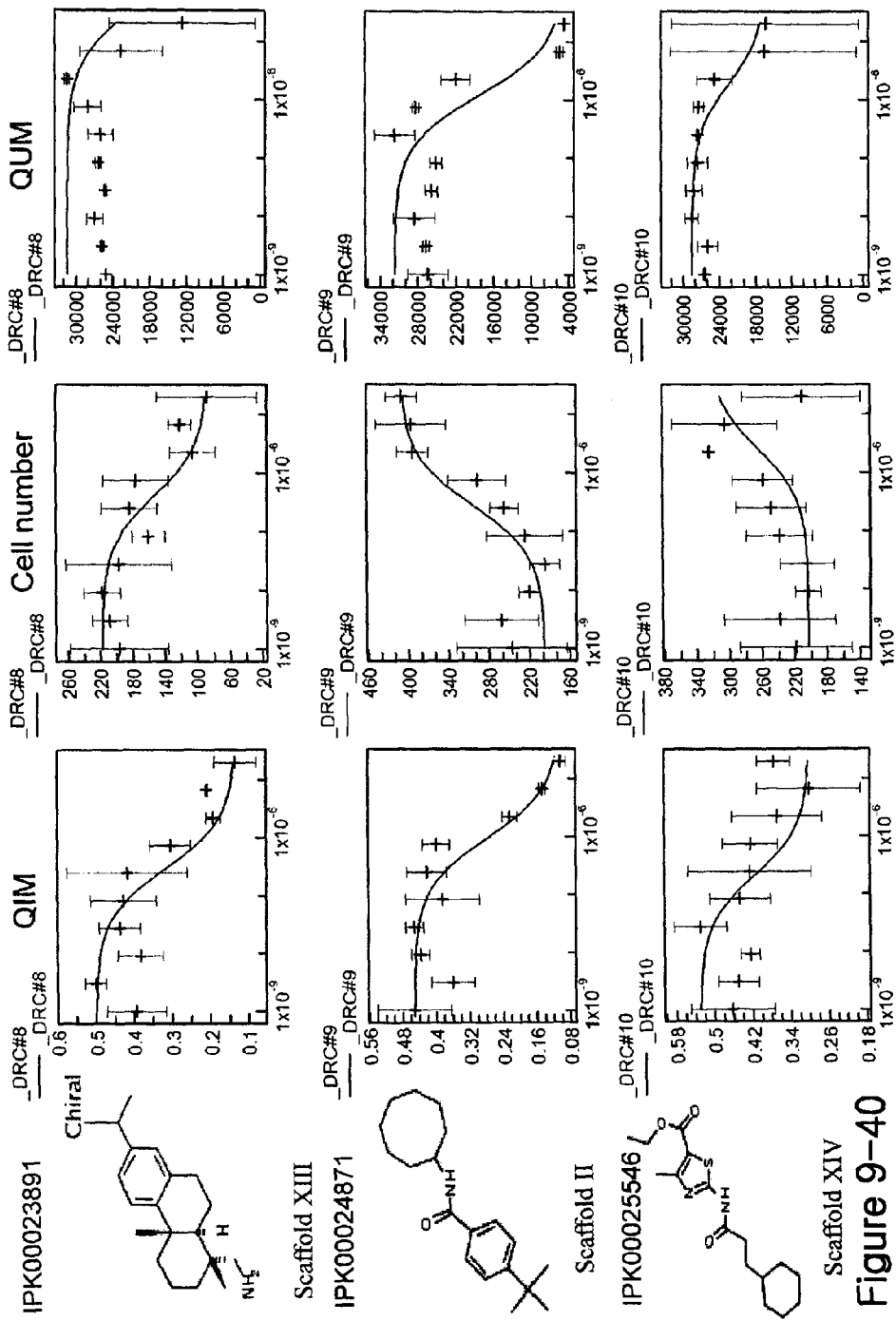
Figures 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
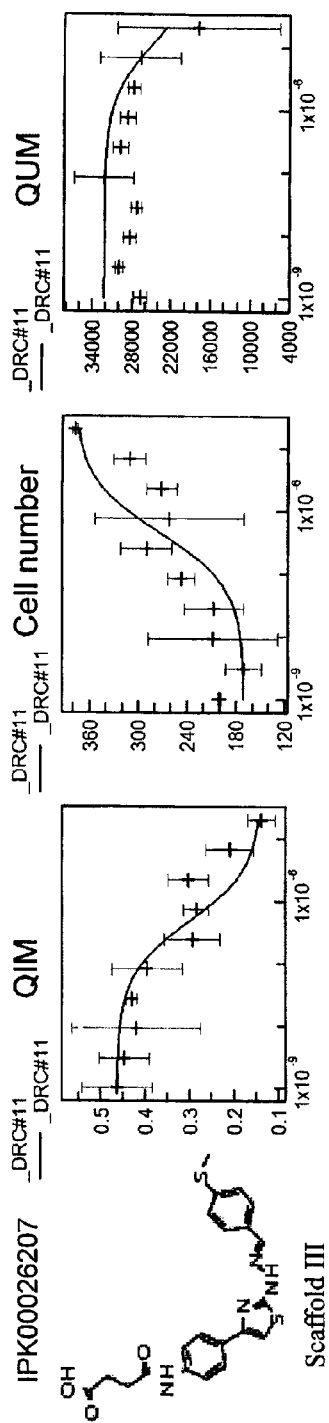

In another aspect, the present invention relates to compounds having one of the formulas with the general formula/scaffold II as shown in FIG. 9, as well as one of the formulas 1-123 as shown in Example 6, preferably 1-24, 26-34, 54, 56, 58-61, 63-64, 67, 90-101, 103-105, 107-109, 112, 114-116 and 118-121 as shown in Table 3. Particularly preferred compounds are compounds having one of the formulas 4 and 24 as shown in Table 3.

Preferably, the compounds as defined above have an inhibitory activity, preferably an inhibitory activity above 65%, on bacterial growth, preferably on the growth of *M. tuberculosis*, inside a host cell, preferably a macrophage, at a concentration between 5-20 µM, preferably less than 5 µM.

In one aspect, the present invention relates to compounds as defined above for use in the treatment of bacterial infections.

In one aspect, the present invention relates to compounds as defined above for use in the treatment of Tuberculosis.

In one aspect, the present invention relates to a pharmaceutical composition comprising a compound as defined above.

In one aspect, the present invention relates to a method of treatment of Tuberculosis, comprising the application of a suitable amount of a compound as defined above to a person in need thereof.

In another aspect, the present invention relates to compounds having one of the general formulas/scaffolds I, III-VII and IX-XX as shown in Table 2.

In one aspect, the present invention relates to compounds having the general formula I:

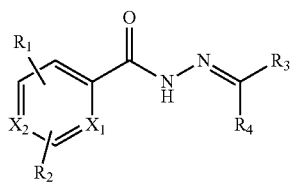

I wherein $X_1$ and $X_2$ are each independently selected from the group comprising CH and NH;

$R_1$ and $R_2$ are each independently selected from the group comprising alkoxy, alkyl, alkylamino, alkylene, alkylthio, alkynyl, amido, amino, aryl, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thio, sulfonate, sulfonyl and sulfonylamino, any of which is optionally substituted; and $R_3$ and $R_4$ are each independently selected from the group comprising alkoxy, alkyl, alkylamino, alkylene, alkylthio, alkynyl, aryl, arylalkoxy, arylamino, arylthio, cyano, cycloalkyl, haloalkoxy, haloalkyl, heteroaryl, heteroarylamino, heterocycloalkyl and hydrogen, any of which is optionally substituted.

In one aspect, the present invention relates to compounds having the general formula III:

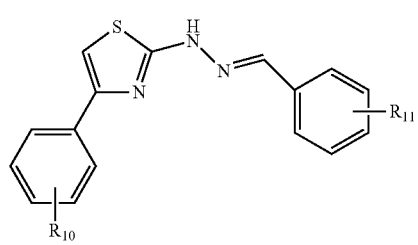

III wherein $R_{10}$ and $R_{11}$ are each independently selected from the group comprising alkoxy, alkyl, alkylamino, alkylene, alkylthio, alkynyl, amido, amino, aryl, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thio, sulfonate, sulfonyl and sulfonylamino, any of which is optionally substituted.

In another aspect, the present invention relates to compounds having the general formula IV:

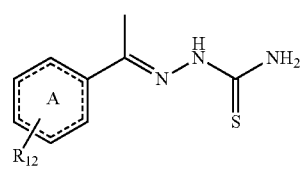

IV wherein

A is an optionally substituted heteroaryl, naphthyl and phenyl and $R_{12}$ is selected from the group comprising alkoxy, alkyl, alkylamino, alkylene, alkylthio, alkynyl, amido, amino, aryl, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thio, sulfonate, sulfonyl and sulfonylamino, any of which is optionally substituted.

In one aspect, the present invention relates to compounds having the general formula V:

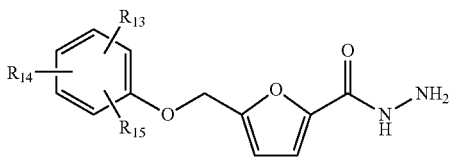

V wherein
$R_{13}$, $R_{14}$ and $R_{15}$ are each independently selected from the group comprising alkoxy, alkyl, alkylamino, alkylene, alkylthio, alkynyl, amido, amino, aryl, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thio, sulfonate, sulfonyl and sulfonylamino, any of which is optionally substituted.

In another aspect, the present invention relates to compounds having the general formula VI:

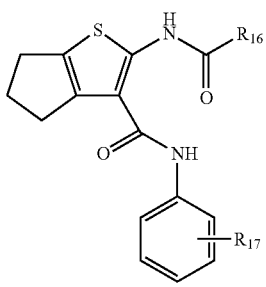

VI wherein
$R_{16}$ is selected from the group comprising alkoxy, alkyl, alkylamino, alkylene, alkynyl, amino, aryl, arylalkoxy, arylamino, arylthio, cycloalkyl, haloalkoxy, haloalkyl, heteroaryl, heteroarylamino, heterocycloalkyl, hydroxyl and hydrogen, any of which is optionally substituted and
$R_{17}$ is selected from the group comprising alkoxy, alkyl, alkylamino, alkylene, alkylthio, alkynyl, amido, amino, aryl, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thio, sulfonate, sulfonyl and sulfonylamino, any of which is optionally substituted.

In one aspect, the present invention relates to compounds having the general formula VII:

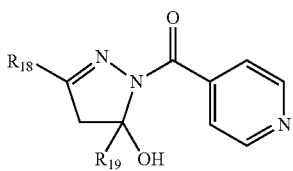

VII wherein
$R_{18}$ and $R_{19}$ are each independently selected from the group comprising alkoxy, alkyl, alkylamino, alkylene, alkylthio, alkynyl, amido, amino, aryl, arylalkoxy, arylamino, arylthio, carboxy, cyano, cycloalkyl, ester, halo, haloalkoxy, haloalkyl, heteroaryl, heteroarylamino, heterocycloalkyl and hydrogen, any of which is optionally substituted.

In another aspect, the present invention relates to compounds having one of the formulas with the general formulas I, III-VII and IX-XX as shown in FIG. 9.

In one aspect, the present invention relates to a compound listed in Table 1.

In one aspect, the present invention relates to compounds as defined above for use in the treatment of bacterial infections.

In one aspect, the present invention relates to compounds as defined above for use in the treatment of Tuberculosis.

In one aspect, the present invention relates to a pharmaceutical composition comprising a compound as defined above.

In one aspect, the present invention relates to a method of treatment of Tuberculosis, comprising the application of a suitable amount of a compound as defined above to a person in need thereof.

In another aspect, the present invention relates to a screening method comprising the steps of
(a) batch infection of host cells with fluorescently labeled *M. tuberculosis* mycobacteria;
(b) removing free unbound mycobacteria;
(c) adding compounds that are to be tested to a multi-well plate;
(d) seeding said host cells infected with fluorescently labeled *M. tuberculosis* mycobacteria into said multi-well plate containing said compounds;
(e) incubating said multi-well plate containing host cells infected with fluorescently labeled *M. tuberculosis* mycobacteria and said compounds;
(f) fluorescently labeling said host cells;
(g) analyzing said multi-well plate using automated confocal microscopy.

The screening method according to the present invention represents a phenotypic cell-based assay enabling the search for drugs that interfere with the multiplication of *M. tuberculosis* within host macrophages. The assay makes use of fluorescently labeled living macrophages infected with fluorescently labeled mycobacteria and uses automated confocal fluorescence microscopy to measure intracellular mycobacterial growth. The assay has been set-up for the high throughput screening (HTS) of large scale chemical libraries.

FIGURES AND TABLES

Figure 2:
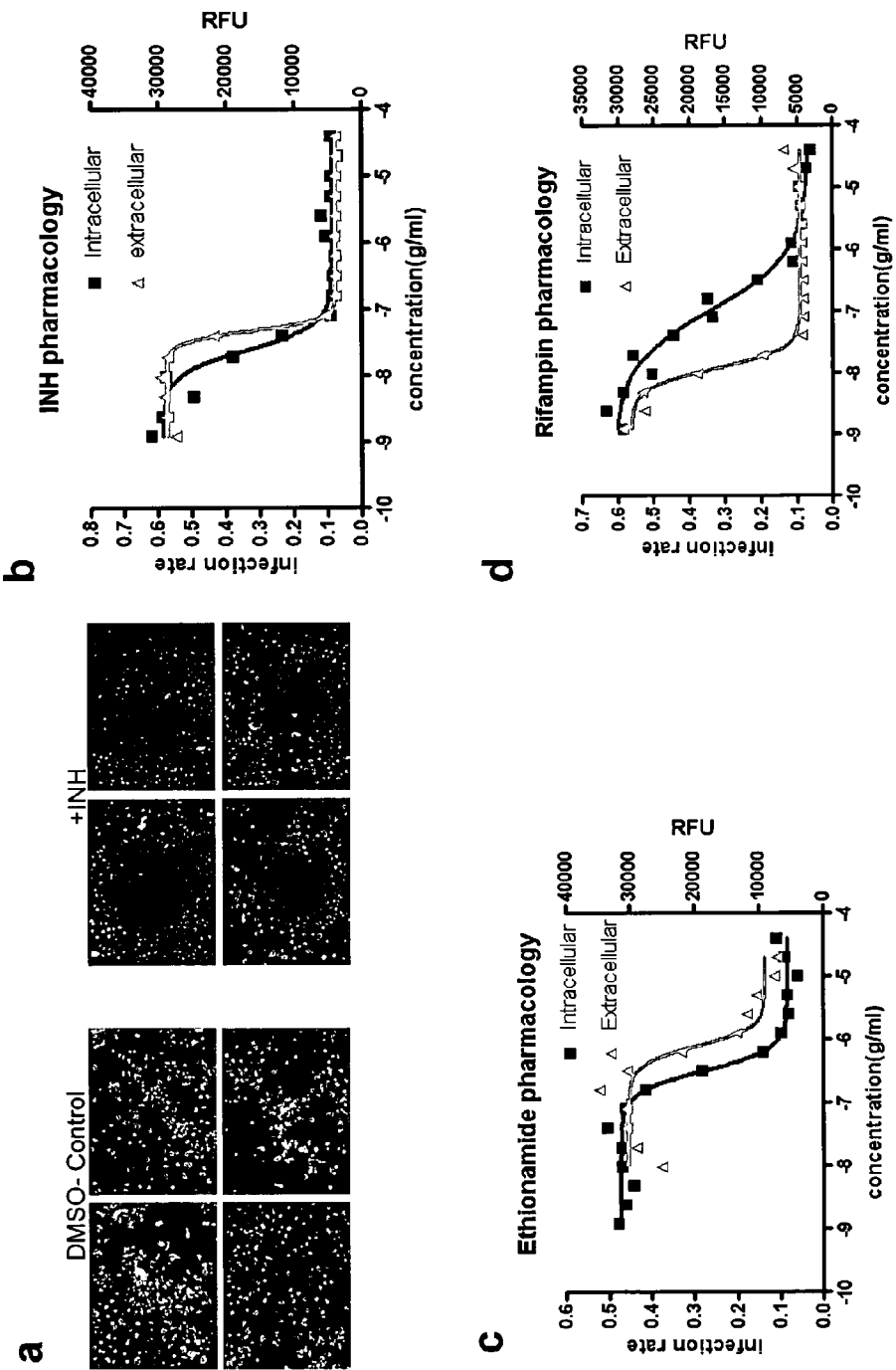
Figure 3:
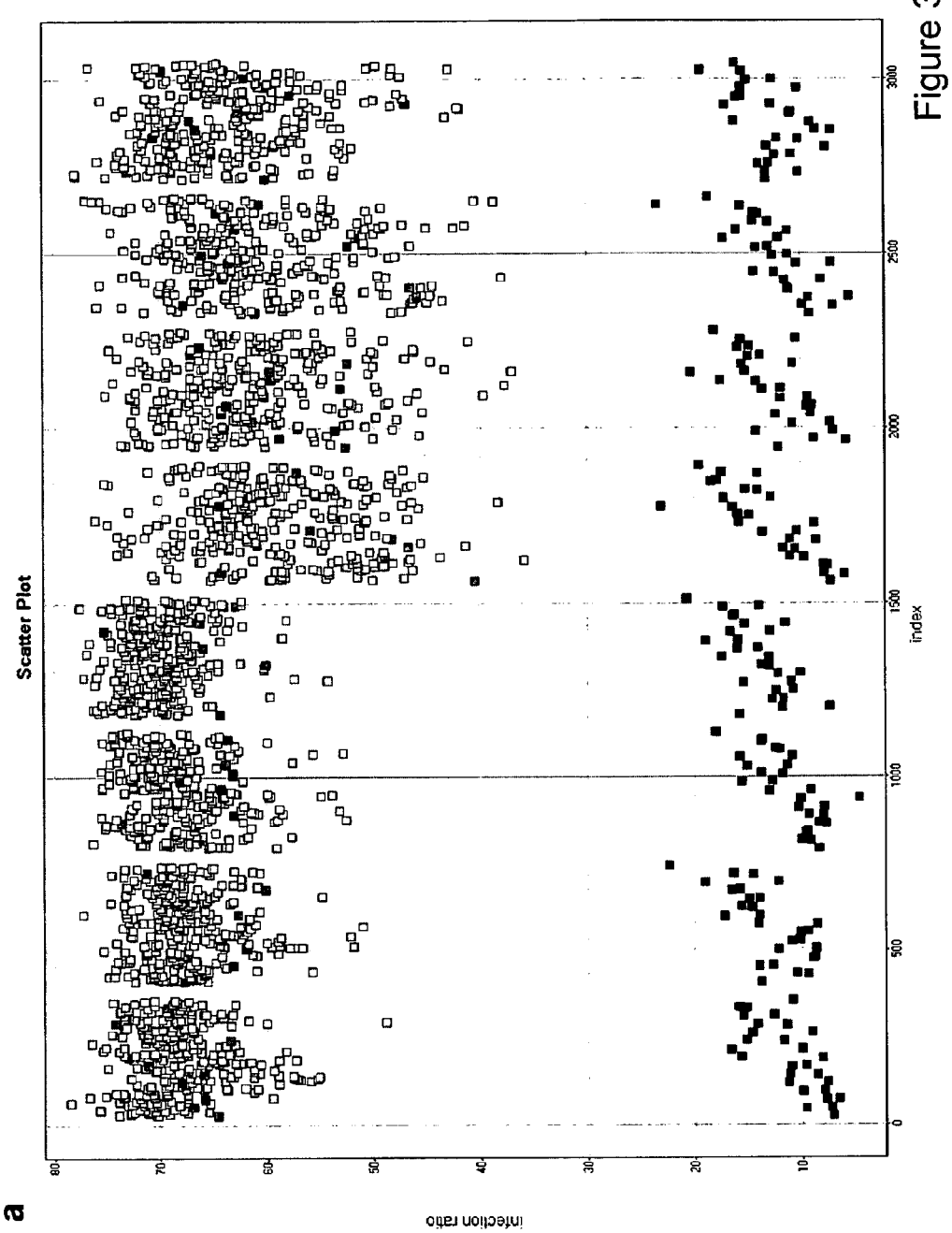
Figure 3:
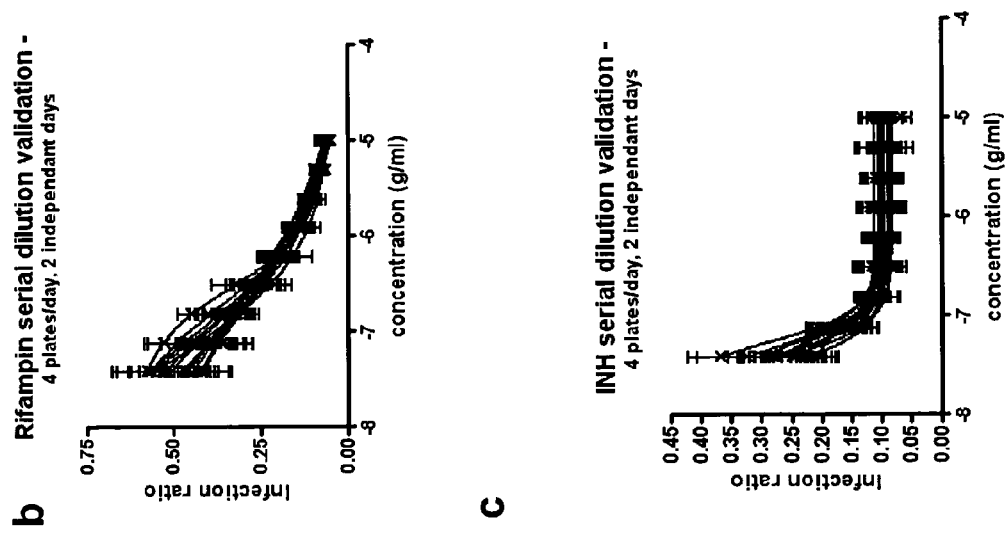
Figure 4:
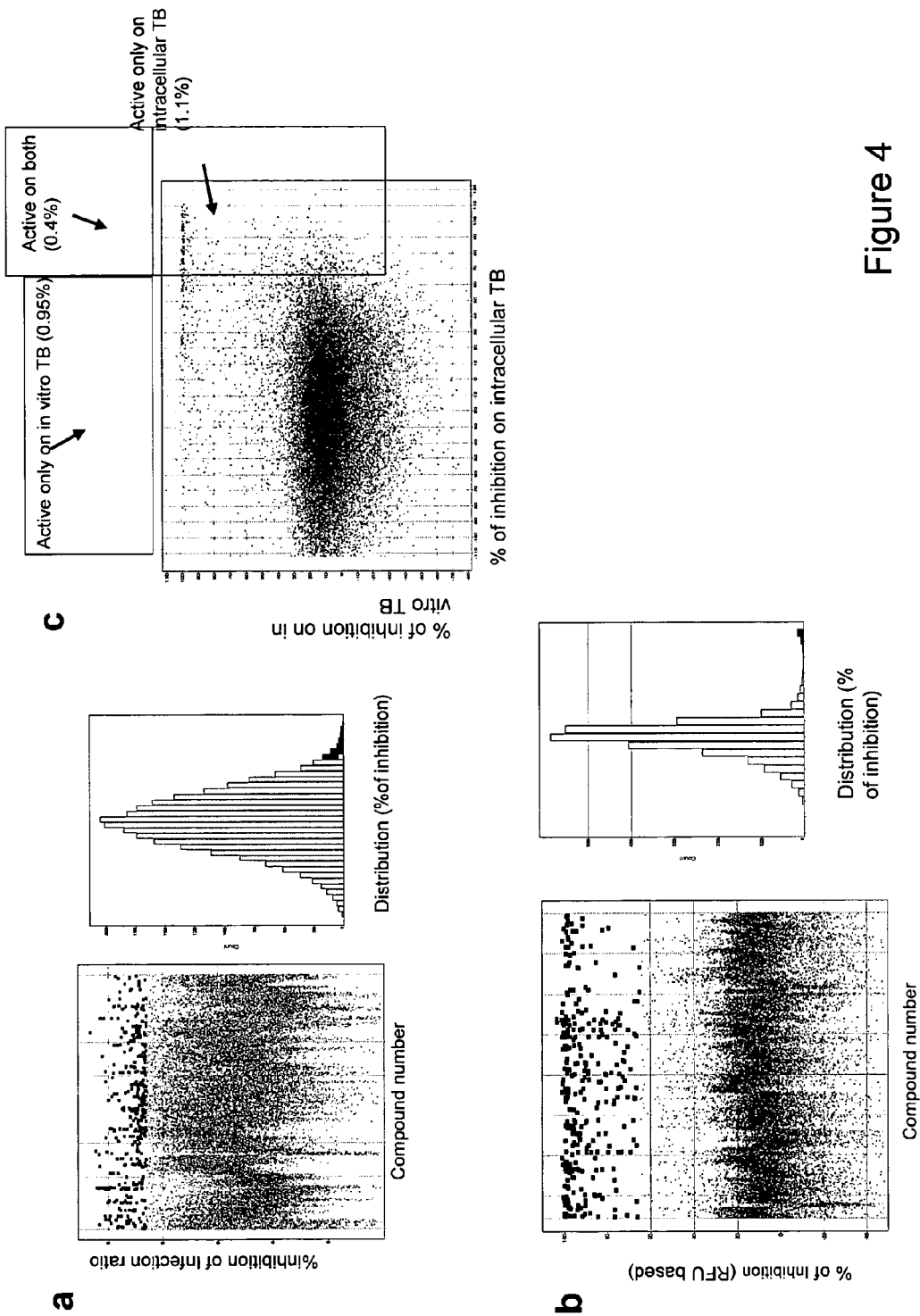
Figure 5:
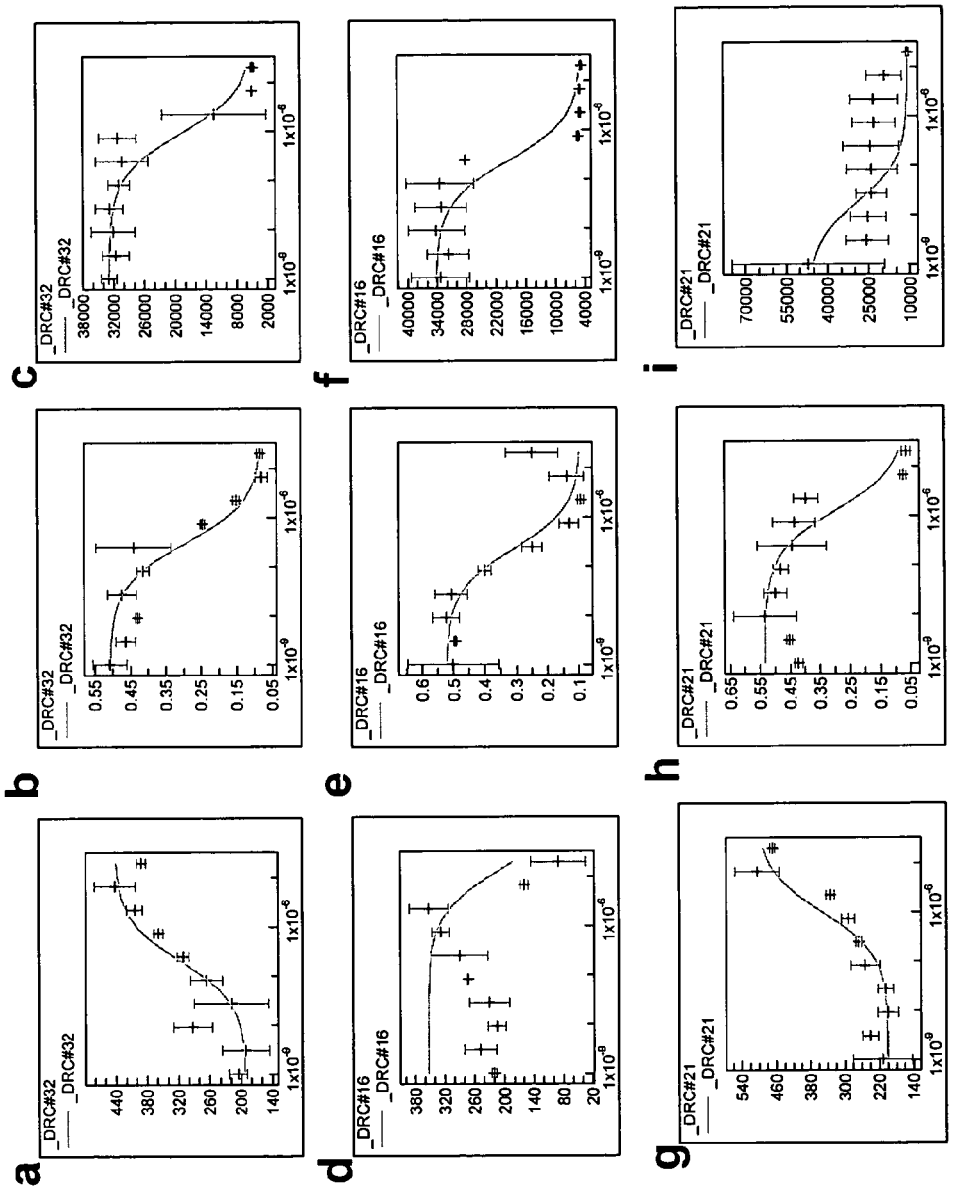
Figure 6:
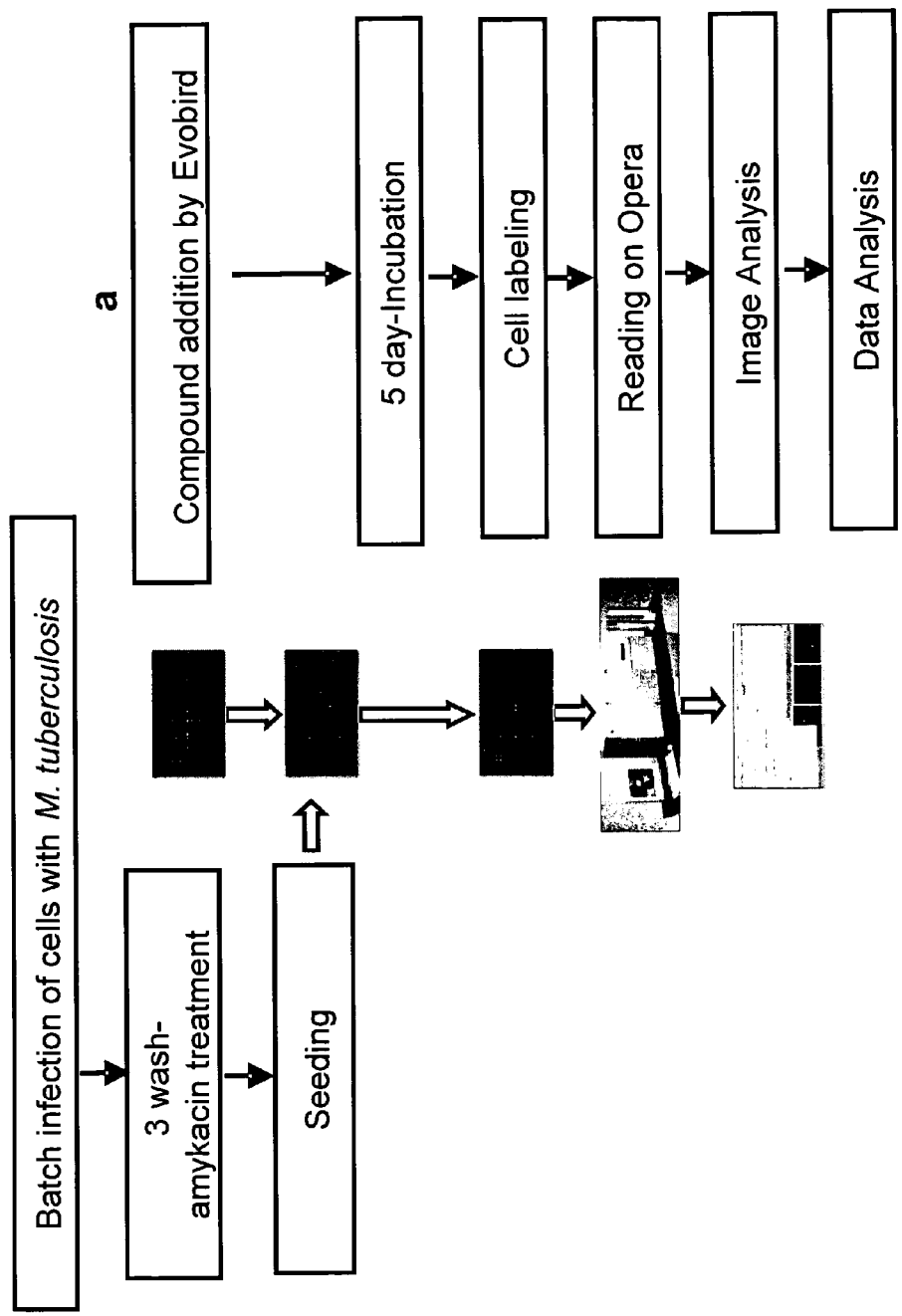
Figure 7:
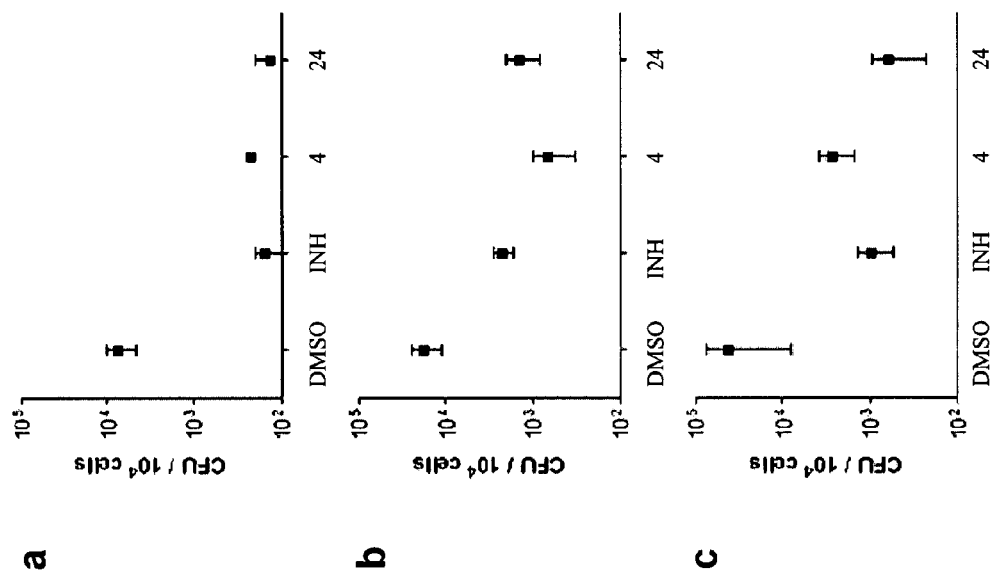
Figure 8:
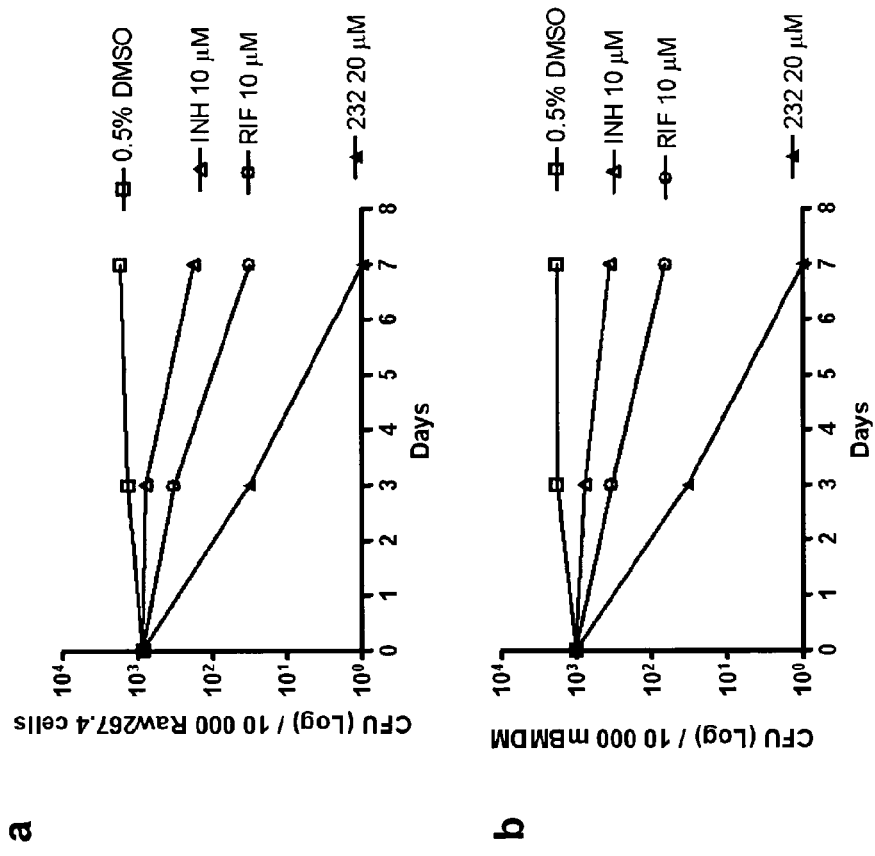

Reference is now made to the figures and tables, wherein
FIG. 1 shows the monitoring of tubercle *bacillus* intracellular growth inside macrophages by automated confocal microscopy: (a) Representative pictures of Raw264.7 cells infected with *M. tuberculosis* H37Rv-GFP at different time points after infection. (b) Image analysis: 1: Typical 2-color image; 2: Circled object corresponds to detected cells; 3: Circled object corresponds to bacterial aggregates; 4: Filled purple cells correspond to infected cells. (c,d,e) Image-based quantification of the percentage of infected cells and the mean number of cells from 2 hours to day 7 after infection with H37Rv-GFP at a multiplicity of infection of 0.5 (gray square), 1 (black circle) and 2 (dark gray triangle). Non-infected cells (black diamonds) were used as the negative control;

FIG. 2 shows the pharmacological validation and MIC (minimal inhibitory concentration) comparison of the reference drugs in the in vitro growth fluorescence assay and the phenotypic cell-based assay: (a) Representative pictures of infected cells in presence of INH at 1 µg/mL or DMSO control. (b,c,d) Dose-response of INH, rifampin and ethionamide; black square and line corresponds to growth inhibition in cell-based assay; gray circle and line correspond to in vitro growth inhibition; shown is a representative data set;

FIG. 3 shows assay automation validation of the phenotypic cell-based assay: (a) Percent of *M. tuberculosis* infected cells relative to 384-plate well-index. Black square, dark gray square, gray square and open square correspond to INH 1 μg/mL, rifampin 5 μg/mL, PBS and DMSO control respectively. (b,c) Percent of *M. tuberculosis* infected cells relative to INH and rifampin concentration. Experiments were performed on four different plates on two independent days;

FIG. 4 shows primary screening results for the phenotypic cell-based assay and the in vitro growth assay for 26500 compounds: (a) Percent inhibition based on infection ratio relative to each compound and distribution. (b) Percent inhibition based on RFU relative to each compound and distribution. (c) Comparison of inhibition percentage for the phenotypic cell-based assay and the in vitro growth assay for each compound;

FIG. 5 shows serial dilution results from the in vitro growth fluorescence assay and the phenotypic cell-based assay: Typical curves for compounds inhibiting (a,b,c) in vitro bacterial growth (d,e,f) both in vitro and intracellular growth and (g,h,i) intracellular growth only. (a,d,g) Infection ratio relative to compound concentration. (b,e,h) Cell number relative to compound concentration. (c,f,i) Relative fluorescence intensity relative to compound concentration. Compound concentration is given in M;

FIG. 6 shows (a) a scheme of assay automation. (b) a 384-plate format description; (c) a 384-plate dose-response curve description, A to P and a to b correspond to 2-fold serial dilution of INH and Rifampin respectively with a starting concentration of 20 mg/mL in well A or a; RIF: Rifampin 5 μg/mL, Cpd: compound, INH100 1 μg/mL, INH50 0.05 μg/mL;

FIG. 7 shows the anti-tuberculosis effect of compounds 4 and 24 (5 μM) on *M. tuberculosis* H37Rv-GFP in (a) Raw267.4 ($10^4$ cells), (b) mouse bone marrow-derived macrophages and (c) human primary macrophages differentiated with 50 ng/mL rhM-CSF ($1.5*10^4$) after 7 days of infection with MOI 2.5:1 (control INH at 5 μM);

FIG. 8 illustrates the colony forming units (CFUs) recovered from macrophages at different time points after infection with *M. tuberculosis* H37Rv. Either Raw264.7 cells (a) or murine BMDM (b) were infected at an MOI of 1:1 and treated with the indicated amount of pyridopyrimidione compound 232 (20 μM) with DMSO, INH (10 μM) and RIF (10 μM) as controls;

FIG. 9 lists 121 compounds which demonstrated an inhibitory activity above 65% at 2 μM without any apparent cell toxicity at 20 μM and consequently were selected for further confirmation by ten 3-fold serial dilutions;

Table 1 lists 340 hits whose inhibitory activity was confirmed in an intracellular (QIM) assay or an in vitro (QUM) assay, wherein the abbreviation "QIM" stands for Quantification of Intracellular *Mycobacteria*, the abbreviation "QUM" stands for Quantification of in vitro grown *Mycobacteria*, and the abbreviation "CellNb" stands for cell number;

Table 2 summarizes the independent/general molecular scaffolds/formulas of the 121 hits listed in FIG. 9;

Table 3 lists dinitrobenzamide and pyridopyrimidinone derivatives (general scaffold II and VIII, respectively, see Table 2) with their respective inhibitory activities, wherein the numbers in bold print refer to the compounds listed in Examples 6 and 7;

Table 4 shows the cytotoxicity and antibacterial spectrum of dinitrobenzamide compounds 4 and 24 (see Table 3);

Table 5 shows the cytotoxicity and antibacterial spectrum of pyridopyrimidinone compound 133 (see Table 3); and Table 6 shows the frequency of spontaneous resistance for representative dinitrobenzamide and pyridopyrimidinone compounds.

EXAMPLES

The invention is now further described by reference to the following examples which are intended to illustrate, not to limit the scope of the invention.

Materials and Methods

Genetic Constructs and Mycobacterial Strains

A recombinant strain of *M. tuberculosis* H37Rv expressing the green fluorescent protein (H37Rv-GFP) was obtained by transformation of an integrative plasmid (Abadie et al., 2005; Cremer et al., 2002). Within this plasmid, which is derived from the Ms6 mycobacteriophage, the gfp gene is cloned and constitutively expressed under the strong mycobacterial promoter pBlaF. Electrocompetent cells for *M. tuberculosis* H37Rv-GFP were prepared from 400 mL of a 15 days old Middlebrook 7H9 culture (Difco, Sparks Md., USA) supplemented with albumin-dextrose-catalase (ADC, Difco, Sparks Md., USA), glycerol and 0.05% Tween 80. Bacilli were harvested by centrifugation at 3000 g for 20 min, washed twice with $H_2O$ at room temperature, and resuspended in 1-2 mL of 10% glycerol at room temperature after recentrifugation. 250 μl of bacilli were mixed with green fluorescent protein encoding plasmid and electroporated using a Biorad Gene Pulser (Biorad). After electroporation, bacilli were resuspended in medium and left one day at 37° C. Transformants were selected on Middlebrook 7H11 medium (Difco, Sparks Md., USA) supplemented with oleic acid-albumin-dextrose-catalase (OADC, Difco, Sparks Md., USA) and 50 μg/mL hygromycin (Invitrogen, Carlsbad, Calif. USA). The selected hygromycin-resistant and green fluorescent colonies appeared after 3 weeks. A 100 mL culture of the H37Rv-GFP strain was grown in Middlebrook 7H9-ADC medium supplemented with 0.05% Tween 80 and 50 μg/mL of hygromycin. Bacteria were harvested, washed twice and suspended in 50 mM sodium phosphate buffer (pH 7.5). The bacteria were then sonicated and allowed to stand for 1 hour to allow residual aggregates to settle. The bacterial suspensions were then aliquoted and frozen at −80° C. A single defrosted aliquot was used to quantify the CFUs (colony forming units) prior to inoculation and typical stock concentrations were about 2 to $5\times10^8$ CFU/mL.

Host Cells

Mouse macrophage cell lines Raw 264.7 (ATCC # TIB-71), J774A.1 (ATCC # TIB-67) or human monocytes (ATCC # TIB-202) differentiated with 50 ng/mL PMA (Sigma) were grown in RPMI 1640 (Gibco) with 10% heat-inactivated fetal calf serum (Gibco).

Chemical Compounds

The small synthetic molecules from the screening libraries were suspended in pure DMSO (Sigma, D5879-500 mL) at a concentration of 10 mM (Master plates) in Corning 96 well clear V-bottom polypropylene plates (Corning, #3956). The compounds were then reformatted in Greiner 384 well V-shape polypropylene plates (Greiner, #781280) and diluted to a final concentration of 2 mM in pure DMSO. The compounds were kept frozen until use. For screening, compound plates were incubated at room temperature until thawed. The compounds were directly added into the assay plates from the DMSO stock using an EVObird liquid handler (Evotec Technologies), which transfers 250 nl of compound twice to reach a final dilution of 1:100. This one-step dilution reduces the risk of compound precipitation in intermediate plates and allows for a low final DMSO concentration (1%).

Positive control antibiotics (Isoniazid (Sigma, I3377-50G) and Rifampin (Euromedex, 1059-8, 5 g)) as well as negative controls (DMSO) were added manually in each plate in columns 1-2 and 23-24 (see FIG. 6 b for plate description).

A total of 26500 compounds were tested. These compounds came from commercial libraries from Timtec (25000 from the ActiProbe diverse library, 1000 from the Kinase inhibitors ActiTargK library and 500 from the Protease inhibitors ActitargP library). The screened compounds were selected based on high diversity and drug-like properties (using Lipinski rule-of-five (Lipinski et al., 2001)). They were first screened at one concentration (primary screen, concentration=20 µM). The "positive" compounds selected from the primary screen were then confirmed by testing at 3 concentrations (20, 2 and 0.2 µM) to identify the most active and/or by ten 3-fold ten dilutions (from 20 µM to 0.5 nM).

Macrophage Invasion Assay Set-Up

Cells were first seeded in 50 µl at a density of 20,000 cells per well of a 384-well plate (Evotec technologies #781058) for 16 hours and then infected with bacterial suspensions at a multiplicity of infection (MOI) varying from 10:1 to 1:1 (bacteria:host cells). After 2 hours, cells were washed three times with phosphate buffered saline (PBS) and the compounds diluted in fresh culture medium were added. Cells were incubated at 37° C., 5% $CO_2$ for up to seven days.

Macrophage Batch Infection Assay Scale-Up

Cells ($1.5 \times 10^8$ cells) were infected with H37Rv-GFP suspension at a MOI of 1:1 in 300 mL for 2 hours at 37° C. with shaking (100 rpm). After two washes by centrifugation at 1100 rpm (Beckman SX4250, 165 g) for 5 min., the remaining extracellular bacilli from the infected cells suspension were killed by a 1 hour amykacin (20 µM, Sigma, A2324-5G) treatment. After a final centrifugation step, cells were dispensed with the Wellmate (Matrix) into 384-well Evotec plates (#781058) preplated with 10 µl of the respective compound diluted in cell medium. Infected cells were then incubated in the presence of the compound for 5 days at 37° C., 5% $CO_2$. After five days, macrophages were stained with SYTO 60 (Invitrogen, S11342) followed by plate sealing and image acquisition. During screening, staining of the live cells was carried out on a set of three plates every two hours to limit cell death due to prolonged incubation with cell chemical stain.

Image Acquisition and Data Analysis

Confocal images were recorded on an automated fluorescent confocal microscope Opera™ (Evotec Technologies) using a 20×-water objective (NA 0.70), 488-nm and 635-nm lasers and a 488/635 primary dichroic mirror. Each image was then processed using dedicated in-house image analysis software (IM). Parameters determined were the total cell number and the number of infected cells. Briefly, the algorithm first segments the cells on the red channel using a sequence of processing steps as described elsewhere (Fenistein et al., manuscript in press). It is generally based on a succession of 1) thresholding the histogram of the original image (3 classes K-means) 2) gaussian filtering the original image with a standard deviation that is set equal to the cells' average radius, 3) searching for the local maxima of the filtered image that provides cell centers as seeds for 4) region growing that defines each cell's own surface and finally 5) removing extremely small cells as potential artifacts or noise. This step provides the total number of cells in the red channel. Infected cells are then defined as those having at least a given number of pixels (usually 3) whose intensity in the green channel is above a given intensity threshold. The ratio of infected cells to the total number of cells is the measure of interest (named infection ratio). For each well, 4 pictures were recorded and for each parameter, the mean of the four images was used.

Data obtained from either the intracellular assay image analysis or from the conventional antibacterial assay (see below) were then processed using ActivityBase (IDBS) to calculate the statistical data (% of inhibition, Z score for each compound, Z', CV etc. for the control plates) and to store the data in an Oracle database. Additional analyses with regards to both quality control of the screens and hit identification were performed with various software packages including Spotfire (Tibco) and Pipelinepilot (Accelrys).

In Vitro Aerobic Bacterial Growth Assay

A frozen aliquot of *M. tuberculosis* H37Rv-GFP was diluted at $1.5 \times 10^6$ CFU/mL in Middlebrook 7H9-ADC medium supplemented with 0.05% Tween 80. Greiner µclear-black 384-well plates (Greiner, #781091) were first preplated with 0.5 µl of compound dispensed by EVOBird (Evotec) in 10 µl of Middlebrook 7H9-ADC medium supplemented with 0.05% Tween 80. 40 µl of the diluted H37Rv-GFP bacterial suspension was then added on top of the diluted compound resulting in a final volume of 50 µl containing 1% DMSO. Plates were incubated at 37° C., 5% $CO_2$ for 10 days after which GFP-fluorescence was recorded using a Victor 3 reader (Perkin-Elmer Life Sciences).

Macrophage Infection Assay and Image Analysis

Raw 264.7 (ATCC # TIB-71) ($1.5 \times 10^8$ cells) were infected with H37Rv-GFP (Abadie et al., 2005, Cremer et al., 2002) in suspension at a MOI of 1:1 for 2 hours at 37° C. with shaking. After two washes by centrifugation, the remaining extracellular bacilli from the infected cell suspension were killed by a 1 hour Amikacin (20 µM, Sigma, A2324) treatment. After a final centrifugation step, cells were dispensed into 384-well Evotec plates (#781058) preplated with compounds and controls. Infected cells were then incubated for 5 days at 37° C., 5% $CO_2$. Murine Bone Marrow-Derived Macrophages (BMDM) were produced as described previously (Brodin et al., 2006). Briefly, cells were extracted from the femurs and tibia of 6 weeks old female mice (C57BL/6, Orientbio) and cultivated in RPMI 1640 media containing 10% heat-inactivated fetal calf serum (FCS) (both from Gibco® at Invitrogen, Carlsbad, Calif.) and 10% L-929 cell conditioned medium. Peripheral Blood Mononuclear Cells (PBMC) were isolated from Buffy coat from healthy volunteers. Buffy coat diluted in PBS supplemented with 1% FCS was treated with 15 ml of Ficoll-Paque Plus (Amersham Biosciences, Sweden) and centrifuged at 2500×g for 20 min. PBMC were obtained by $CD14^+$ bead separation (Miltenyi Biotec, Germany), washed 3-times with PBS (1% FCS) and transferred to 75 $cm^2$ culture flasks containing RPMI 1640 media, 10% FCS and 50 ng/ml of recombinant-human macrophage colony stimulating factor (R & D systems, Minneapolis). Six day old adherent murine BMDM and PBMC derived human macrophages were infected with H37Rv-GFP (Abadie et al., 2005) in suspension at a MOI of 1:1 for 2 hours at 37° C. and then extensively washed and finally incubated with compounds or controls. After several days, macrophages were stained with SYTO 60 (Invitrogen, S11342) and image acquisition was performed on an EVOscreen-MarkIII fully automated platform (PerkinElmer) integrated with an Opera™ (20×-water objective, NA 0.70) and located in a BSL-3 safety laboratory. *Mycobacteria*-GFP were detected using a 488-nm laser coupled with a 535/50 nm detection filter and cells labeled with a 635-nm laser coupled with a 690/40 nm detection filter. Four fields were recorded for each plate well and each image was then processed using dedicated in-house image analysis software (IM) as described elsewhere (Fenistein et al., in press).

Mycobacterial Strains and In Vitro Bacterial Growth Assay

*Mycobacterium tuberculosis* H37Rv, H37Ra and BCG Pasteur were used as reference strains. All strains were diluted at $1.5 \times 10^6$ CFU/mL in Middlebrook 7H9-ADC medium supplemented with 0.05% Tween 80. 384-well plates (Greiner, #781091) were first preplated with 0.5 µl of compound dispensed by EVOBird (Evotec) in 10 µl of Middlebrook 7H9-ADC medium supplemented with 0.05% Tween 80. Forty microliters of the diluted H37Rv-GFP bacterial suspension was then added to the diluted compound resulting in a final volume of 50 µl containing 1% DMSO. Plates were incubated at 37° C., 5% $CO_2$ for 10 days. Mycobacterial growth was determined by measuring GFP-fluorescence using a Victor 3 reader (Perkin-Elmer Life Sciences) for H37Rv-GFP or with resazurin method. Isoniazid at 0.05 µg/mL and 1 µg/mL (Sigma, I3377), Rifampin at 1 µg/mL (Euromedex) and DMSO were used as controls.

Cytotoxicity Assay

In order to address compound toxicity, seven cell lines originating from different body tissues were cultivated in the presence of 3-fold dilutions of compounds starting from 100 µM. After 5 days of culture, cell viability was assessed by the resazurin test. Briefly, cells were incubated with 10 µg/mL of resazurin (Sigma-Aldrich St. Louis, Mo.) for 4 h at 37° C. under 5% CO2. Resofurin fluorescence (RFU) was measured as indicated above. Percentage of toxicity on cells was calculated as follows: Cytotoxicity (%)=$(RFU_{DMSO}-RFU_{Blank})-(RFU_{compound}-RFU_{blank})/(RFU_{DMSO}-RFU_{Blank}) \times 100$. Percentage of cytotoxicity was plotted against compound concentration and the minimal toxic concentration ($MTC_{50}$) was determined by non-linear regression analysis as the lowest compound concentration where fifty percent toxicity was observed on the corresponding cell line.

Frequency of Spontaneous Resistance

The frequency of spontaneous mutations was determined on 7H10 plates containing increasing concentrations of dinitrobenzamide (0.2, 0.8, 1.6 and 3.2 µg/ml) or pyridopyrimidinone (0.4, 0.8, 1.6 and 3.2 µg/ml) compounds. $10^6$, $10^7$ and $10^8$ CFU containing bacterial suspensions were spread on compound containing agar plates. After 5-6 weeks at 37° C., colonies were counted and frequency of mutation was evaluated as the ratio of colonies relative to the original inoculum. DMSO and INH were used as negative and positive controls, respectively.

Example 1

Phenotypic Macrophage-Based Assay Set-Up and Automated Image Quantification

To set-up the optimal conditions of *M. tuberculosis* infection, Raw264.7 macrophages were first infected with mycobacteria that constitutively express green fluorescent protein (GFP) at different multiplicities of infection (MOI) followed by kinetic analysis. Up to 7 days post *bacillus* infection, the host live cells were daily labeled with the red chemical fluorescent dye Syto60, and confocal images of live samples were acquired using an automated confocal microscope. Typical images are displayed in FIG. 1*a*. During the first 24 hours, a few discrete weakly fluorescent bacteria localized within the cells. By day 2, the average number of cells had increased and mycobacteria had started to spread into neighboring cells leading to zones of strongly fluorescent bacteria. The localization of the green signal is always within a distance of 5 µm to that of the red cell signal and in most cases actually overlaps with the cell signal. This confirms the intracellular nature of the mycobacteria growth. By day 4, the cell number has significantly diminished and the bacteria have formed large, highly fluorescent aggregates, which cover almost the entire image from day 5 onwards. As a control, non-infected cells grew up to confluence at day 2 and remained alive until day 7.

In order to automatically quantify the intracellular bacterial load, an in-house image analysis script was developed. This script enables the automated quantification of the number of cells and the percentage of infected cells, whereby an infected cell is a cell containing at least three green pixels with an intensity above a defined threshold (FIG. 1*b*). 2 hours after infection, between 2 and 10% of Raw264.7 cells were found to harbor a low number of bacilli (FIG. 1*c*). The percentage of infected cells, hereafter named infection ratio, continued to increase from 72 hours post-infection reaching up to 70% at seven days post infection. This increase in infection ratio correlated with an increase in cell mortality (FIG. 1*d/e*).

Example 2

Comparative Minimal Inhibitory Concentration of Known Anti-Tubercular Drugs

To validate the assay set-up, the effect of current anti-tuberculosis drugs on *M. tuberculosis* intracellular growth was investigated. 2-fold serial dilutions of isoniazid (INH), rifampin and ethionamide were performed, followed by testing on macrophages that had previously been infected with *M. tuberculosis* H37Rv-GFP. After 5 days of incubation, macrophages were stained, and images acquired on an automated confocal microscope as described above. A larger number of cells and a fewer number of bacteria are clearly seen on pictures corresponding to samples that were incubated with INH compared to the DMSO negative control. This shows that INH prevents both intracellular *M. tuberculosis* growth and *bacillus* mediated cytotoxicity (FIG. 2*a*). A clear inhibition dose-response curve was obtained by image-extracted analysis (FIG. 2*b*). In parallel, inhibition of *M. tuberculosis* H37Rv-GFP in vitro growth by INH was monitored by recording green fluorescence intensity under the same conditions. In both experiments, the minimal inhibitory concentration (MIC) for INH was 0.1 µg/mL, which is in accordance with the MIC reported in the literature for extracellular *M. tuberculosis* growth (Andries et al., 2005). Similar results were obtained with the standard anti-tuberculosis drugs ethionamide (FIG. 2*c*) and ethambutol (data not shown), whereas for rifampin, there was a log-fold decrease in the MIC in the cell-based assay compared to the in vitro assay (FIG. 2*d*). The diminished efficacy of rifampin in the cell-based assay is likely due to impaired cell penetration and further demonstrates that it is the intracellular antibacterial activity that is being monitored in this assay. Thus, adaptation of both the intracellular and the in vitro *M. tuberculosis* growth assay for high throughput screening (HTS) was performed.

Example 3

Assay Scale-Up and Validation

To simplify the protocol for HTS purposes, macrophages were infected in batch with *M. tuberculosis* before being dispensed onto the compounds. The batch infection was carried out with macrophages in suspension at 37° C. under mild shaking. Free unbound mycobacteria were removed by washing three times with PBS and differential centrifugation, as well as by an additional one-hour incubation step with amykacin, an antibiotic known to selectively kill extracellular microbes (FIG. 6a). M. tuberculosis infected macrophages were then seeded in plates that had been previously dispensed with the compounds, DMSO or antibiotic controls. The day-to-day as well as plate-to plate reproducibility was first tested. To this end, either serial dilutions of INH or rifampin were dispensed into 8 plates along with the regular DMSO and positive control (INH at 1 µg/mL (MIC100) and at 0.05 µg/mL (MIC90) and rifampin at 1 µg/mL) wells that were subsequently seeded with infected cells. The same experiment was repeated over 2 consecutive days. After incubation for 5 days and macrophage staining, pictures from each plate were acquired. The mean infection ratio determined for the DMSO negative controls in each plate for the 2 days of experiments was between 50% and 70%, whereas for the INH and rifampin samples, the mean infection ratio fell to below 20% (FIG. 3a). Despite some variation in the mean infection ratio between the two experiments, the difference between the INH-positive and DMSO-negative controls was above five-fold for both days. P values calculated for each plate using a paired t-student test also confirmed a significant difference between the positive and negative controls (p<0.000001, data not shown). In addition, the inventors performed an experiment to determine if inhibitors of M. tuberculosis intracellular growth infection dispensed in any well on the plate could be detected by performing double-blind controls (spike of INH and rifampin at 3 different concentrations). Indeed, one hundred percent of the spikes were identified (data not shown). Taken together, these results prove that the assay is sensitive enough to be able to identify inhibitors under HTS conditions. Finally, the robustness of the assay was checked by monitoring the dose-response of reference compounds. Almost identical MICs for the antibiotic positive controls were determined independent of the plate or the day of the experiment (FIG. 3b/c). Calculated MICs from the image based quantification of the infection ratio were 0.16+/−0.05 µg/mL and 2.4+/−1.3 µg/mL for INH and rifampin, respectively, and were confirmed by CFU plating (data not shown). In parallel, the extracellular growth assay was validated with a similar approach (data not shown).

Example 4

Primary Screening of a Large Library of Small Synthetic Compounds Using the Phenotypic Cell-Based Assay A 26500 small molecule compound library, that was selected for its high chemical diversity and drug-like properties according to the Lipinski rules (Lipinski et al., 2001), was chosen as the first library to be screened using the validated phenotypic cell-based assay. The primary screen was carried out with compounds at 20 µM in singleton. The throughput was set to about 6000 compounds per working day encompassing 25 plates. The screening was performed with Raw264.7 cells that had been expanded from frozen stocks for ten days before infection with M. tuberculosis H37Rv-GFP. To accept the screening results, the MICs obtained from 2 serial dilutions of INH and Rifampin processed at the beginning and at the end of the screening day should show similar results compared to the values obtained during the validation (see above). Each screened plate is then accepted by the quality control procedure if the window between DMSO and INH (1 µg/ml) is higher than 3 and the CV calculated for the 320 compounds present in each plate is lower than 25. Such quality control criteria allow the identification of hits with an activity higher than 75%. Subsequently, the percent inhibition for each compound was determined relative to the corresponding mean infection ratio between 1 µg/mL INH (100%) and DMSO (0%) in the same 384-well plate. The percent inhibition distribution is centered around −20% of inhibition (FIG. 4a). It was decided to select compounds that have an inhibitory effect greater than 65% which corresponds to a little less than 1.5% of the total compounds.

In parallel, the same compounds were only tested for their inhibitory activity on the M. tuberculosis H37Rv-GFP bacterial growth. The results from this assay, which are based on classical fluorescence intensity, showed a higher degree of reproducibility and the criteria for plate validation was set to a Z' value (DMSO/INH) greater than 0.35. The throughput for this fluorescence based assay was approximately 20,000 compounds per day. Compounds that prevented M. tuberculosis growth in vitro with an inhibitory effect above 65% were then selected as hits (1.4%) as they belong to a clear independent population compared to the inactive population centered to 0% (FIG. 4b).

The results gathered from the two different screenings were then compiled and compared (FIG. 4c). Four different populations could be identified: compounds that are i) active only on extracellular bacteria, ii) active only on intracellular bacteria, iii) active in both settings or iv) not active. 657 compounds (2.5%) belonged to one of the first three categories and, thus, were selected for further investigation.

An important parameter that can be measured during image analysis is the total cell number, also referred to as cell cytotoxicity. A low cell number can be the result of two independent phenomena, the compound toxicity and M. tuberculosis growth mediated cell toxicity. Indeed, at day 5 after infection with M. tuberculosis, the cell number decreased to less than 100 cells per image compared to more than 500 cells per image for uninfected cells (FIG. 1e). In contrast, a high cell number is obtained only when the compound is not toxic and prevents mycobacterial growth. This turns out to be a second relevant measurement of a compound's anti-mycobacterial activity. However, this criterion was not applied for the selection of hits from the primary screen as a low cell number was found for only a few compounds and the inventors wanted to avoid failing to select highly active compounds that would later on prove to be active at much lower concentrations despite a cell toxicity at 20 µM. An additional validation criterion of a Z' (DMSO/INH) value of the total cell number greater than 0.2 was added for the following screening steps.

Example 5

Confirmation of Screening Results, Dose-Response Analysis and Hit Classification The 657 selected hits were first confirmed at 3 different concentrations, 20 µM, 2 µM and 0.2 µM. For 340 hits the activity was confirmed either at 20 µM or 2 µM, on the intracellular or the in vitro assay (see Table 1). From this latter list, 121 compounds demonstrated an inhibitory activity above 65% at 2 µM without any apparent cell toxicity at 20 µM and consequently were selected for further confirmation by ten 3-fold serial dilutions (see FIG. 9). All 121 compounds were confirmed by serial dilution with a MIC ranging between 250 nM and 20 µM. The results shown in FIG. 5 are representative of the three types of behavior observed: most of the compounds exhibited a clear dose response curve when activity was measured as infection ratio (FIG. 5b/e/h). Compounds active on the bacilli level present a similar activity in the extracellular assay (FIG. 5c/f) even if the MIC is different from one assay to the other. A few compounds don't present clear activity on the in vitro bacilli (FIG. 5i) and may represent drugs acting through a cellular target or on a bacilli target involved only during the infection process. Furthermore, toxic compounds can be identified thanks to a dramatic decrease in the cell number when the compound concentration increases (FIG. 5d) and activity of non-toxic compounds are validated by a dose response protective effect on the cell number (FIG. 5a). Consequently cell number detection represents an independent secondary assay in the same well as the primary assay. The serial dilution results from all 121 compounds are presented in FIG. 9.

The 121 confirmed hits can be clustered as 20 independent/general scaffolds (Table 2). The number of compounds for each scaffold varied, ranging from 1 to 69 molecules. The molecules from the 69-compound scaffold share a common structure which is similar to INH thereby validating the screening results. One scaffold contains molecules that were only active in the intracellular assay and its mechanism of action will be the focus of further investigation.

Example 6

Derivatization of the Benzamide Compounds

The benzamide compounds (scaffold II; see Table 2) underwent derivatization according to the methods outlined below (Schemes 1-7). Formation of the amide can be performed under general conditions using EDC or DCC coupling reagents with acids instead of acyl chloride. Resulting derivatives were examined for inhibitory activity using the assay described above and the results are summarized in Table 3.

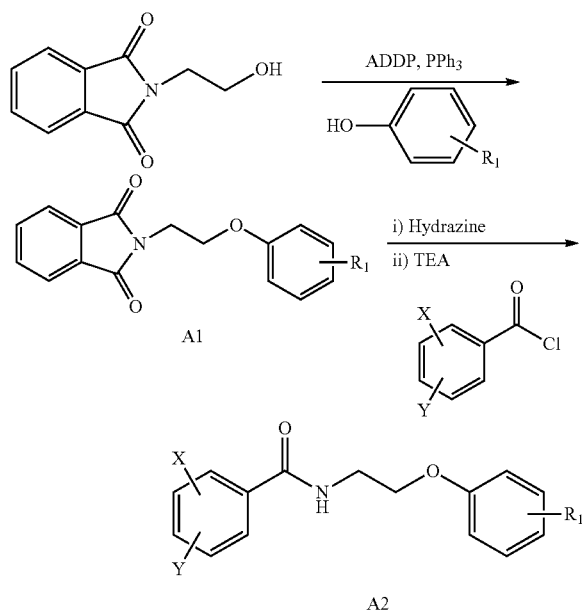

Scheme 1

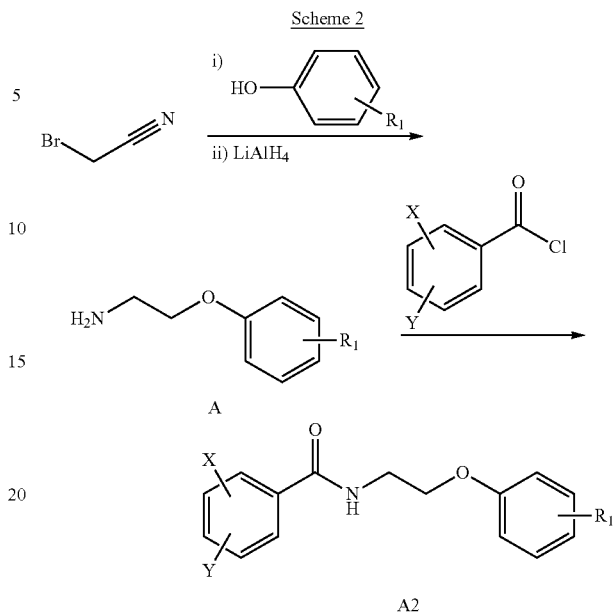

Scheme 2

General Procedure for the Synthesis of 2-phenoxyethyl isoindoline-1,3-dione (A1)

To a solution of 2-(2-hydroxyethyl)isoindoline-1,3-dione (1.68 mmol) in methylene chloride (10 mL) was added ADDP (1.68 mmol), triphenylphosphine (1.68 mmol) and phenol (3.18 mmol) and stirred at room temperature. After stirring overnight, the reaction mixture was diluted with methylene chloride (30 mL) and washed with 1 M NaOH aqueous solution (50 mL), and brine (50 mL). The organic layer was dried over anhydrous MgSO$_4$ and concentrated in vacuo. The crude product was purified by silica gel flash column chromatography (4:1 hexanes/ethyl acetate) and recrystallized from a mixture of hexanes and ethyl acetate to give A1.

General Procedure for the Synthesis of N-(2-phenoxyethyl)-benzamide (A2)

To a solution of A1 (1.14 mmol) in methanol (10 mL) was added hydrazine monohydrate (1.42 mmol) and the resulting mixture was refluxed under a nitrogen atmosphere. After 3 h, the reaction mixture was allowed to cool to room temperature and concentrated in vacuo. The residue was precipitated with methylene chloride (10 mL). The resulting precipitate was filtered through Celite and the filtrate was concentrated in vacuo to afford an amine intermediate. To a solution of the amine in methylene chloride (10 mL) was added triethylamine (0.45 mmol) and a benzoylchloride (0.45 mmol) at 0° C. and the resulting mixture was stirred at room temperature. After 3 h, the reaction mixture was diluted with methylene chloride (10 mL) and washed with 1 M HCl aqueous solution (30 mL), saturated Na$_2$CO$_3$ aqueous solution (30 mL) and brine (30 mL). The organic layer was dried over anhydrous MgSO$_4$ and concentrated in vacuo. The crude product was purified by silica gel flash column chromatography (3:1 hexanes/ethyl acetate) and recrystallized from a mixture of hexanes and ethyl acetate to give A2.

3,5-Dinitro-N-(2-phenoxyethyl)benzamide (1)

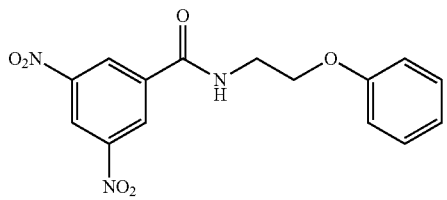

¹H NMR (400 MHz, Acetone-d₆) δ 3.88 (t, J=4.4 Hz, 2H), 4.21 (t, J=5.2 Hz, 2H), 6.89 (d, J=8.4 Hz, 3H), 7.24 (t, J=8.0 Hz, 2H), 8.78 (brs, 1H), 9.02 (d, J=2.0 Hz, 1H), 9.07 (d, J=2.0 Hz, 2H); ¹³C NMR (100 MHz, Acetone-d₆) δ 40.1, 66.0, 114.5, 120.8, 127.6, 129.6, 137.8, 148.8, 158.9, 163.0.

N-(2-(2-Methoxyphenoxy)ethyl)-3,5-dinitrobenzamide (2)

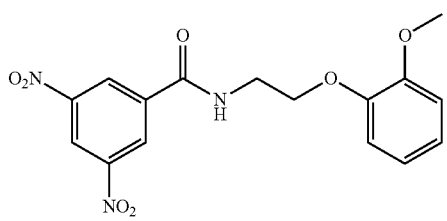 [SMILES: COc1ccccc1OCCNC(=O)c1cc([N+](=O)[O-])cc([N+](=O)[O-])c1]

¹H NMR (400 MHz, CDCl₃) δ 3.89 (s, 3H), 3.92 (dd, J=5.2, 10.4 Hz, 2H), 4.23 (t, J=4.8 Hz, 2H), 6.91-7.02 (m, 4H), 7.63 (brs, 1H), 9.02 (d, J=1.6 Hz, 2H), 9.14 (t, J=2.0 Hz, 1H);

¹³C NMR (100 MHz, CDCl₃) δ 40.0, 56.1, 68.8, 112.2, 115.8, 121.0, 121.5, 122.9, 127.3, 137.8, 147.5, 148.6, 149.8, 162.6.

N-(2-(3-Methoxyphenoxy)ethyl)-3,5-dinitrobenzamide (3)

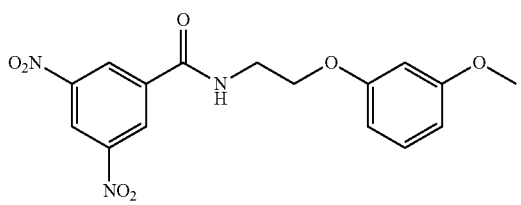 [SMILES: COc1cccc(OCCNC(=O)c2cc([N+](=O)[O-])cc([N+](=O)[O-])c2)c1]

¹H NMR (400 MHz, Acetone-d₆) δ 3.74 (s, 3H), 3.85 (dd, J=5.6 Hz, 4.8 Hz, 2H), 4.21 (t, J=5.2 Hz, 2H), 6.50 (m, 3H), 7.14 (t, J=8.4 Hz, 1H), 8.75 (brs, 1H), 9.04 (s, 1H), 9.08 (s, 2H); ¹³C NMR (100 MHz, Acetone-d₆) δ 40.1, 54.8, 66.1, 100.9, 106.5, 106.8, 120.9, 127.5, 130.0, 137.9, 148.8, 160.2, 161.2, 163.0.

N-(2-(4-Methoxyphenoxy)ethyl)-3,5-dinitrobenzamide (4)

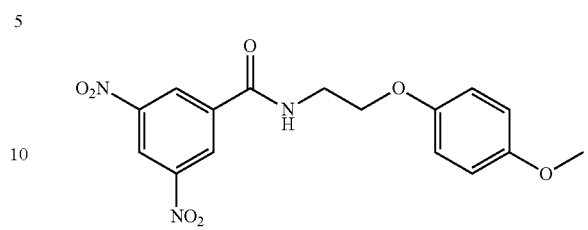

¹H NMR (400 MHz, CDCl₃) δ 3.72 (s, 3H), 3.91 (dd, J=5.2, 10.8 Hz, 2H), 4.12 (t, J=4.8 Hz, 2H), 6.74-6.80 (m, 4H), 7.21 (brs, 1H), 8.95 (d, J=2.0 Hz, 2H), 9.07 (t, J=2.0 Hz, 1H); ¹³C NMR (100 MHz, CDCl₃) δ 40.4, 55.6, 66.8, 114.7, 115.4, 121.0, 127.2, 137.6, 148.5, 152.2, 154.3, 163.1; LC-MS (ESI, m/z): 361 [M+H]⁺.

N-(2-(2-Chlorophenoxy)ethyl)-3,5-dinitrobenzamide (5)

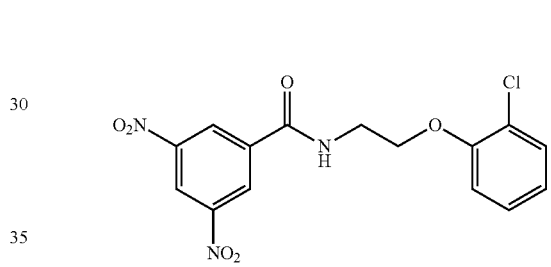

¹H NMR (400 MHz, CDCl₃) δ 3.97 (dd, J=5.2, 10.4 Hz, 2H), 4.25 (t, J=5.2 Hz, 2H), 6.93-6.95 (m, 2H), 7.19-7.24 (m, 2H), 7.35 (dd, J=1.2, 8.0 Hz, 1H), 8.98 (d, J=2.0 Hz, 2H), 9.12 (t, J=2.0 Hz, 1H); ¹³C NMR (100 MHz, CDCl₃) δ 34.9, 63.0, 109.7, 116.2, 117.7, 118.2, 122.3, 123.1, 125.5, 132.6, 143.7, 148.7, 157.9.

N-(2-(3-Chlorophenoxy)ethyl)-3,5-dinitrobenzamide (6)

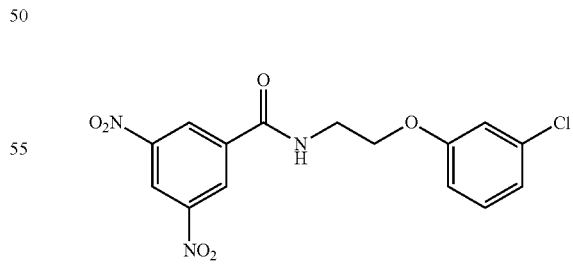

¹H NMR (400 MHz, CDCl₃) δ 3.97 (dd, J=5.6, 10.8 Hz, 2H), 4.19 (t, J=4.8 Hz, 2H), 6.80-6.98 (m, 4H), 7.24 (t, J=8.0 Hz, 1H), 8.96 (d, J=2.0 Hz, 2H), 9.17 (t, J=2.0 Hz, 1H); ¹³C NMR (100 MHz, CDCl₃) δ 40.1, 66.4, 110.7, 115.0, 121.2, 121.7, 127.2, 130.4, 135.1, 137.6, 148.7, 158.8, 163.0.

N-(2-(4-Chlorophenoxy)ethyl)-3,5-dinitrobenzamide (7)

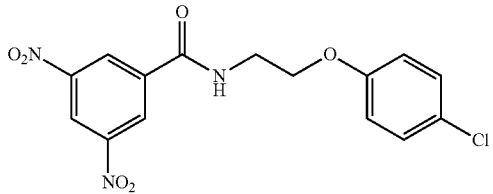

$^1$H NMR (400 MHz, CDCl$_3$) δ 3.96 (dd, J=5.6, 10.4 Hz, 2H), 4.17 (t, J=4.8 Hz, 2H), 6.78 (brs, 1H), 6.86 (dd, J=2.4, 6.8 Hz, 2H), 7.23 (dd, J=2.0, 6.8 Hz, 2H), 8.96 (d, J=2.4 Hz, 2H), 9.17 (t, J=2.0 Hz, 1H); $^{13}$C NMR (100 MHz, CDCl$_3$) δ 40.1, 66.5, 115.7, 121.2, 126.5, 127.2, 129.6, 137.6, 148.9, 156.8, 163.0.

N-(2-(2-Fluorophenoxy)ethyl)-3,5-dinitrobenzamide (8)

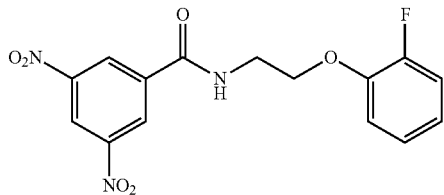 [SMILES: O=C(NCCOc1ccccc1Cl)c1cc([N+](=O)[O-])cc([N+](=O)[O-])c1]

$^1$H NMR (400 MHz, CDCl$_3$) δ 3.97 (dd, J=5.2, 10.8 Hz, 2H), 4.25 (t, J=5.2 Hz, 2H), 6.91-7.06 (m, 4H), 7.39 (brs, 1H), 8.97 (d, J=2.0 Hz, 2H), 9.15 (t, J=2.0 Hz, 1H); $^{13}$C NMR (100 MHz, CDCl$_3$) δ 40.1, 68.3, 115.7, 116.3 (d, J=20 Hz, due to F), 121.1, 122.3 (d, J=7 Hz, due to F), 124.6 (d, J=5 Hz, due to F), 127.3, 137.6, 146.2, 148.6, 152.8 (d, J=250 Hz, due to F), 163.1; LC-MS (ESI, m/z): 350 [M+H]$^+$.

N-(2-(4-Fluorophenoxy)ethyl)-3,5-dinitrobenzamide (9)

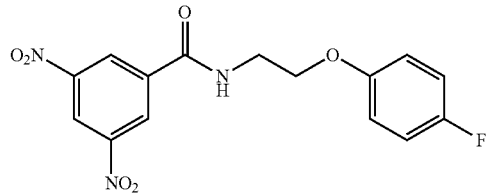 [SMILES: O=C(NCCOc1ccc(F)cc1)c1cc([N+](=O)[O-])cc([N+](=O)[O-])c1]

$^1$H NMR (400 MHz, Acetone-d$_6$) δ 3.88 (dd, J=5.2, 10.8 Hz, 2H), 4.23 (t, J=5.2 Hz, 2H), 6.95-7.07 (m, 4H), 8.79 (brs, 1H), 9.07 (t, J=2.4 Hz, 1H), 9.11 (d, J=2.0 Hz, 2H).

N-(2-(4-Hydroxyphenoxy)ethyl)-3,5-dinitrobenzamide (10)

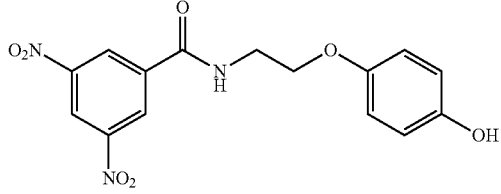 [SMILES: O=C(NCCOc1ccc(O)cc1)c1cc([N+](=O)[O-])cc([N+](=O)[O-])c1]

$^1$H NMR (400 MHz, DMSO-d$_6$) δ 3.66 (dd, J=5.6, 11.2 Hz, 2H), 4.06 (t, J=5.2 Hz, 2H), 6.65-6.68 (m, 2H), 6.76-6.80 (m, 2H), 8.91 (brs, 1H), 8.98 (t, J=2.0 Hz, 1H), 9.08 (d, J=2.4 Hz, 2H), 9.42 (brs, 1H); $^{13}$C NMR (100 MHz DMSO-d$_6$) δ 40.1, 66.9, 116.2, 116.4, 121.5, 128.2, 137.4, 148.8, 151.8, 152.0, 163.1.

N-(2-(3-(Trifluoromethoxy)phenoxy)ethyl)-3,5-dinitrobenzamide (11)

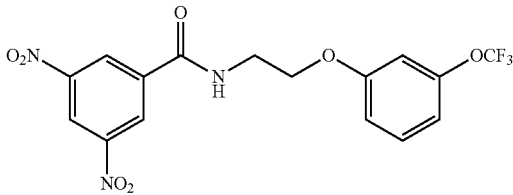 [SMILES: O=C(NCCOc1cccc(OC(F)(F)F)c1)c1cc([N+](=O)[O-])cc([N+](=O)[O-])c1]

$^1$H NMR (400 MHz, Acetone-d$_6$) δ 3.89 (dd, J=5.6, 11.2 Hz, 2H), 4.29 (t, J=5.6 Hz, 2H), 6.88 (d, J=6.0 Hz, 2H), 6.99 (d, J=8.0 Hz, 1H), 7.38 (t, J=8.4 Hz, 1H), 8.79 (brs, 1H), 9.05 (d, J=1.2 Hz, 1H), 9.08 (d, J=1.2 Hz, 2H); $^{13}$C NMR (100 MHz, Acetone-d$_6$) δ 39.9, 66.7, 107.8, 113.1, 113.6, 120.9, 127.6, 130.9, 137.8, 148.9, 150.1, 160.2, 163.0.

N-(2-(4-(Trifluoromethoxy)phenoxy)ethyl)-3,5-dinitrobenzamide (12)

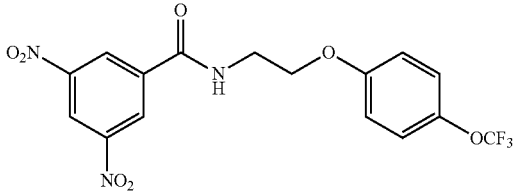 [SMILES: O=C(NCCOc1ccc(OC(F)(F)F)cc1)c1cc([N+](=O)[O-])cc([N+](=O)[O-])c1]

$^1$H NMR (400 MHz, Acetone-d$_6$) δ 3.88 (dd, J=10.8 Hz, 5.2 Hz, 2H), 4.27 (t, J=5.6 Hz, 2H), 7.03 (dd, J=7.2, 2.0 Hz, 2H), 7.23 (d, J=8.8 Hz, 2H), 8.78 (brs, 1H), 9.04 (d, J=2.0 Hz, 1H), 9.08 (d, J=2.0 Hz, 2H); $^{13}$C NMR (100 MHz, Acetone-d$_6$) δ 40.0, 66.8, 115.7, 120.9, 122.7, 127.6, 137.8, 142.7, 142.8, 148.9, 157.9, 163.1.

Methyl 4-(2-(3,5-dinitrobenzamido)ethoxy)benzoate (13)

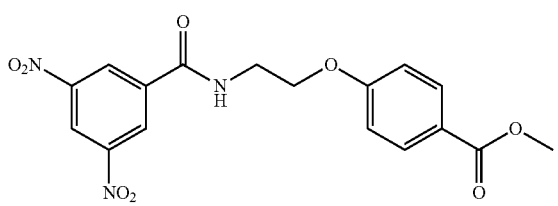 [SMILES: COC(=O)c1ccc(OCCNC(=O)c2cc([N+](=O)[O-])cc([N+](=O)[O-])c2)cc1]

$^1$H NMR (400 MHz, Acetone-d$_6$) δ 3.81 (s, 3H), 3.91 (t, J=5.6 Hz, 2H), 4.33 (t, J=5.6 Hz, 2H), 7.00 (t, J=2.8 Hz, 1H), 7.03 (t, J=2.8 Hz, 1H), 7.90 (t, J=2.8 Hz, 1H), 7.92 (t, J=2.8 Hz, 1H), 8.78 (brs, 1H), 9.03 (t, J=2.4 Hz, 1H), 9.07 (d, J=2.4 Hz, 2H); $^{13}$C NMR (100 MHz, Acetone-d$_6$) δ 39.9, 51.3, 66.5, 114.4, 120.9, 123.0, 127.6, 131.5, 137.8, 148.9, 162.8, 163.0, 166.1.

N-(2-(4-Aminophenoxy)ethyl)-3,5-dinitrobenzamidehydrochloride (14)

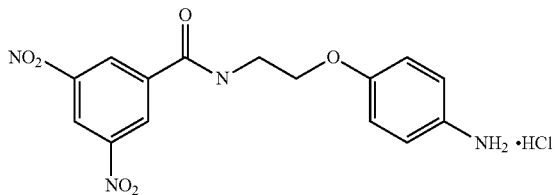 [SMILES: Nc1ccc(OCCNC(=O)c2cc([N+](=O)[O-])cc([N+](=O)[O-])c2)cc1 ; Cl]

$^1$H NMR (400 MHz, DMSO-$d_6$) δ 3.67 (d, J=5.2 Hz, 2H), 4.15 (t, J=5.2 Hz, 2H), 7.03 (d, J=1.6 Hz, 2H), 7.29 (d, J=1.6 Hz, 2H), 8.91 (d, J=2.0 Hz, 1H), 9.04 (d, J=2.0 Hz, 2H), 9.52 (brs, 1H), 10.28 (brs, 3H); $^{13}$C NMR (100 MHz, DMSO-$d_6$) δ 40.1, 66.1, 115.4, 120.8, 124.3, 124.5, 127.5, 136.7, 148.1, 157.8, 162.4.

N-(2-(4-(t-Butoxycarbonylamino)phenoxy)ethyl)-3,5-dinitrobenzamide (15)

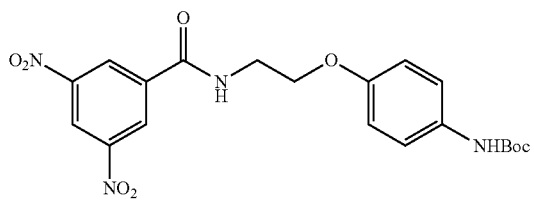 [SMILES: CC(C)(C)OC(=O)Nc1ccc(OCCNC(=O)c2cc([N+](=O)[O-])cc([N+](=O)[O-])c2)cc1]

$^1$H NMR (400 MHz, Acetone-$d_6$) δ 1.44 (s, 9H), 3.83 (m, 2H), 4.18 (m, 2H), 6.84 (dd, J=3.2, 9.2 Hz, 2H), 7.40 (d, J=7.6 Hz, 2H), 8.15 (brs, 1H), 8.73 (brs, 1H), 9.03 (t, J=2.0 Hz, 1H), 9.08 (d, J=2.0 Hz, 2H); $^{13}$C NMR (100 MHz, Acetone-$d_6$) δ 27.8, 40.1, 66.4, 78.9, 114.8, 119.9, 120.9, 127.6, 133.3, 137.9, 148.8, 153.2, 154.4, 163.0; LC-MS (ESI, m/z): 469 [M+Na]$^+$.

N-(2-(4-Methoxyphenoxy)ethyl)-3-nitrobenzamide (16)

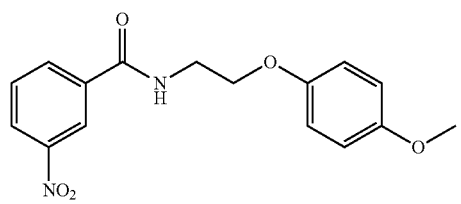 [SMILES: COc1ccc(OCCNC(=O)c2cccc([N+](=O)[O-])c2)cc1]

$^1$H NMR (400 MHz, CDCl$_3$) δ 3.69 (s, 3H), 3.81 (dd, J=5.2, 10.4 Hz, 2H), 4.06 (t, J=5.6 Hz, 2H), 6.73-6.78 (m, 4H), 7.48 (brs, 1H), 7.53 (t, J=8.0 Hz, 1H), 8.13 (d, J=7.6 Hz, 1H), 8.24 (d, J=10.4 Hz, 1H), 8.56 (t, J=2.0 Hz, 1H); $^{13}$C NMR (100 MHz, CDCl$_3$) δ 39.8, 55.4, 66.7, 114.4, 115.2, 121.9, 125.8, 129.5, 133.1, 135.7, 147.8, 152.3, 153.9, 165.2.

N-(2-(2-Fluorophenoxy)ethyl)-3-nitrobenzamide (17)

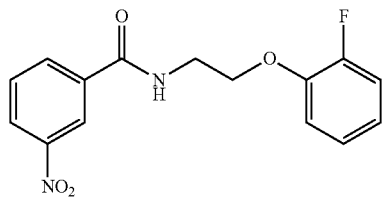 [SMILES: O=C(NCCOc1ccccc1F)c1cccc([N+](=O)[O-])c1]

$^1$H NMR (400 MHz, CDCl$_3$) δ 3.92 (dd, J=5.6, 10.8 Hz, 2H), 4.23 (t, J=4.8 Hz, 2H), 6.90-7.09 (m, 4H and brs, 1H), 7.62 (t, J=8.0 Hz, 1H), 8.14 (d, J=8.0 Hz, 1H), 8.33 (d, J=8.0 Hz, 1H), 8.63 (t, J=2.0 Hz, 1H); $^{13}$C NMR (100 MHz, CDCl$_3$) δ 39.8, 68.3, 115.6, 116.6 (d, J=18.6 Hz, due to F), 122.3 (d, J=5.3 Hz, due to F), 124.7 (d, J=4.5 Hz, due to F), 126.0, 129.7, 133.0, 135.8, 146.3 (d, J=10.4 Hz, due to F), 148.1, 152.6 (d, J=245 Hz, due to F), 165.2.

N-(2-(4-Methoxyphenoxy)ethyl)benzamide (18)

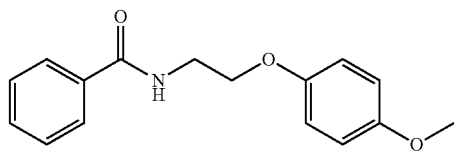 [SMILES: COc1ccc(OCCNC(=O)c2ccccc2)cc1]

$^1$H NMR (400 MHz, CDCl$_3$) δ 3.72 (s, 3H), 3.80 (dd, J=5.2, 10.8 Hz, 2H), 4.05 (t, J=5.6 Hz, 2H), 6.78-6.83 (m, 4H), 7.03 (brs, 1H), 7.35-7.45 (m, 4H), 7.74 (d, J=11.2 Hz, 1H); $^{13}$C NMR (100 MHz, CDCl$_3$) δ 39.4, 55.4, 67.1, 114.5, 115.2, 126.8, 128.3, 131.3, 134.1, 152.4, 153.9, 167.6.

N-(2-(4-Methoxyphenoxy)ethyl)-N-methyl-3,5-dinitrobenzamide (19)

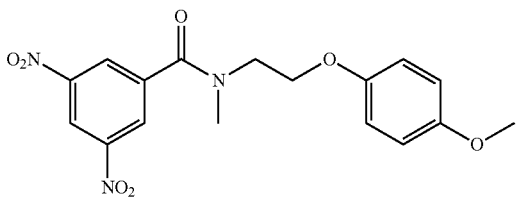 [SMILES: COc1ccc(OCCN(C)C(=O)c2cc([N+](=O)[O-])cc([N+](=O)[O-])c2)cc1]

(Two rotamers, 1:1) $^1$H NMR (400 MHz, CDCl$_3$) δ 3.18 (brs, 3H), 3.65 (brs, 1H), 3.75 (s, 3H), 3.94 (brs, 1H), 4.03 (brs, 1H), 4.27 (brs, 1H), 6.79-6.84 (brd, 4H), 8.55 (brs, 1H), 8.72 (brs, 1H), 9.04 (br s, 1H).

N-Ethyl-N-(2-(4-methoxyphenoxy)ethyl)-3,5-dinitrobenzamide (20)

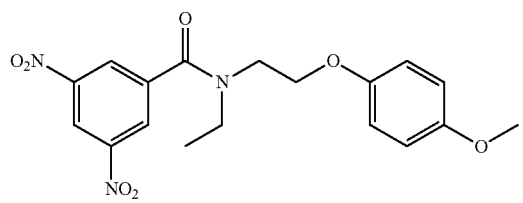 [SMILES: CCN(CCOc1ccc(OC)cc1)C(=O)c1cc([N+](=O)[O-])cc([N+](=O)[O-])c1]

(Two rotamers, 1:1) $^1$H NMR (400 MHz, CDCl$_3$) δ 1.22-1.30 (m, 3H), 3.42 (brs, 1H), 3.63 (brs, 2H), 3.75 (s, 3H), 3.89 (brs, 1H), 4.01 (brs, 1H), 4.26 (brs, 1H), 6.80 (br, 4H), 8.53 (brs, 1H), 8.72 (brs, 1H), 9.04 (brs, 1H).

N-(3-(4-Methoxyphenoxy)propyl)-3,5-dinitrobenzamide (21)

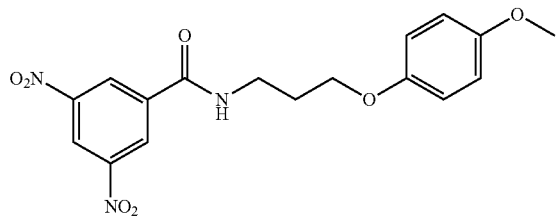 [SMILES: COc1ccc(OCCCNC(=O)c2cc([N+](=O)[O-])cc([N+](=O)[O-])c2)cc1]

$^1$H NMR (400 MHz, CDCl$_3$) δ 2.04-2.20 (m, 2H), 3.76 (t, J=6.0 Hz, 2H), 3.77 (s, 3H), 4.17 (t, J=5.2 Hz, 2H), 6.85-6.91 (m, 4H), 7.24 (brs, 1H), 8.96 (d, J=2.0 Hz, 2H), 9.16 (t, J=2.0 Hz, 1H).

Methyl 4-(3-(3,5-dinitrobenzamido)propoxy)benzoate (22)

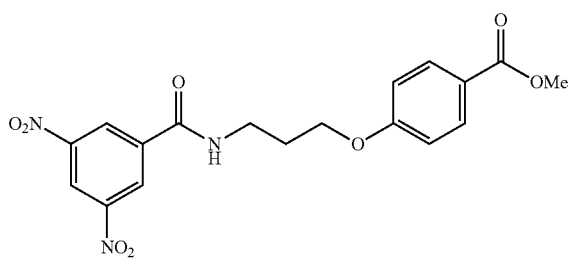 [SMILES: COC(=O)c1ccc(OCCCNC(=O)c2cc([N+](=O)[O-])cc([N+](=O)[O-])c2)cc1]

$^1$H NMR (400 MHz, CDCl$_3$) δ 2.21-2.24 (m, 2H), 3.77 (dd, J=6.0, 12.0 Hz, 2H), 3.89 (s, 3H), 4.24 (t, J=5.6 Hz, 2H), 6.95 (d, J=8.8 Hz, 2H), 7.04 (brs, 1H), 8.00 (d, J=8.8 Hz, 2H), 8.96 (d, J=2.0 Hz, 2H), 9.16 (s, 1H); $^{13}$C NMR (100 MHz, CDCl$_3$) δ 28.4, 39.3, 52.0, 67.2, 113.9, 121.1, 123.3, 127.0, 131.8, 137.8, 148.6, 161.9, 162.5, 166.6.

N-(3-(2-Fluorophenoxy)propyl)-3,5-dinitrobenzamide (23)

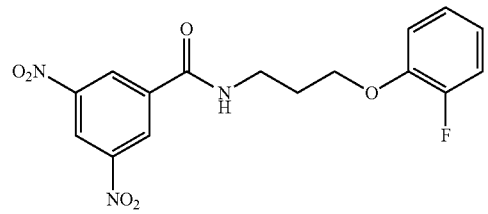 [SMILES: O=C(NCCCOc1ccccc1F)c1cc([N+](=O)[O-])cc([N+](=O)[O-])c1]

$^1$H NMR (400 MHz, CDCl$_3$) δ 2.19-2.25 (m, 2H), 3.83 (dd, J=5.2, 11.2 Hz, 2H), 4.27 (t, J=5.2 Hz, 2H), 6.90-7.11 (m, 4H), 7.50 (brs, 1H), 8.99 (d, J=2.0 Hz, 2H), 9.16 (t, J=2.0 Hz, 1H); $^{13}$C NMR (100 MHz, CDCl$_3$) δ 28.2, 40.0, 69.5, 114.0, 116.3 (d, J=18 Hz, due to F), 120.9, 121.8 (d, J=7.4 Hz, due to F), 124.7 (d, J=3.7 Hz, due to F), 127.2, 127.3, 138.1, 147.3 (d, J=245 Hz, due to F), 153.5, 162.7.

Scheme 3

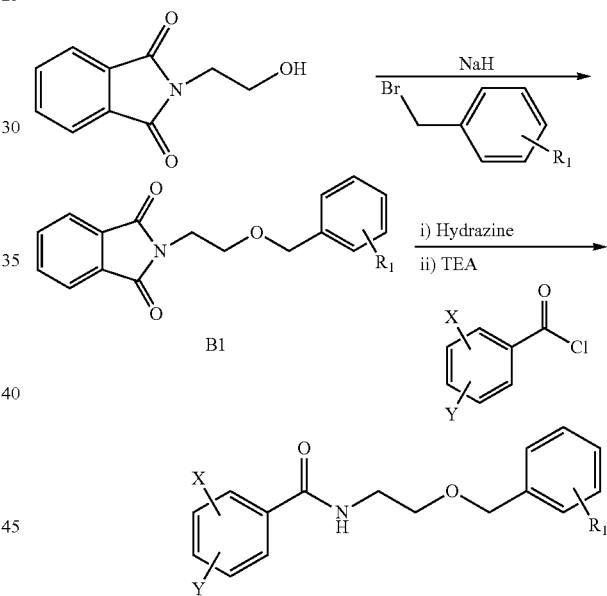

General Procedure for the Synthesis of N-(2-(benzyloxy)ethyl)-dinitrobenzamide (B2)

To a solution of 2-(2-hydroxyethyl)isoindoline-1,3-dione (1.17 mmol) in dimethyl formamide (10 mL) was added sodium hydride (2.34 mmol) and a benzyl bromide (1.40 mmol) at 0° C. and the resulting mixture stirred at room temperature. After stirring overnight, distilled water (50 mL) was added and the resulting precipitate was collected by filtration to afford B1.

To a solution of B1 (0.85 mmol) in methanol (10 mL) was added hydrazine monohydrate (0.85 mmol) and the resulting mixture was refluxed under a nitrogen atmosphere. After 3 h, the reaction mixture was allowed to cool to room temperature and concentrated in vacuo. The residue was precipitated with methylene chloride (10 mL). The resulting precipitate was filtered off through Celite, and the filtrate was concentrated in vacuo to afford an amine.

To a solution of the amine in methylene chloride (10 mL) was added triethylamine (113 μl, 0.81 mmol) and a benzoyl-chloride (0.81 mmol) at 0° C. and the resulting mixture was stirred at room temperature. After 3 h, the reaction mixture was diluted with methylene chloride (30 mL) and washed with 1 M HCl aqueous solution (50 mL), saturated $Na_2CO_3$ aqueous solution (50 mL) and brine (50 mL). The organic layer was dried over anhydrous $MgSO_4$ and concentrated in vacuo. The crude product was purified by silica gel flash column chromatography (3:1 hexanes/ethyl acetate) and recrystallized from a mixture of hexanes and ethyl acetate to give B2.

N-(2-(Benzyloxy)ethyl)-3,5-dinitrobenzamide (24)

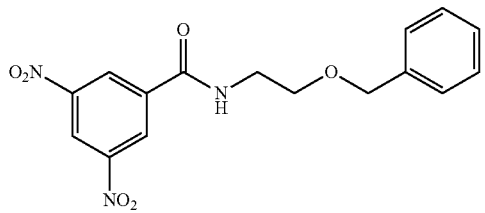 [SMILES: O=C(NCCOCc1ccccc1)c1cc([N+](=O)[O-])cc([N+](=O)[O-])c1]

$^1$H NMR (400 MHz, $CDCl_3$) δ 3.68-3.72 (m, 4H), 4.55 (s, 2H), 6.75 (brs, 1H), 7.24-7.33 (m, 5H), 8.91 (d, J=2.0 Hz, 2H), 9.13 (t, J=2.0 Hz, 1H); $^{13}$C NMR (100 MHz, $CDCl_3$) δ 40.4, 68.1, 73.4, 121.0, 127.2, 128.0, 128.2, 128.7, 137.5, 138.0, 148.6, 162.7; LC-MS (ESI, m/z): 346 [M+H]$^+$.

N-(2-(3-Methoxybenzyloxy)ethyl)-3,5-dinitrobenzamide (25)

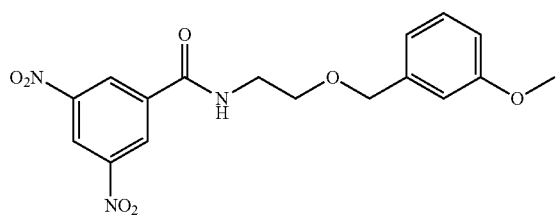 [SMILES: COc1cccc(COCCNC(=O)c2cc([N+](=O)[O-])cc([N+](=O)[O-])c2)c1]

$^1$H NMR (400 MHz, $CDCl_3$) δ 3.71-3.74 (m, 4H), 3.76 (s, 3H), 4.52 (s, 2H), 6.77-6.90 (m, 3H), 6.97 (brs, 1H), 7.23 (t, J=8.0 Hz, 1H), 8.91 (d, J=2.0 Hz, 2H), 9.12 (t, J=2.0 Hz, 1H); $^{13}$C NMR (100 MHz, $CDCl_3$) δ 40.5, 55.2, 68.2, 73.1, 113.1, 113.6, 120.0, 120.9, 127.2, 129.6, 137.8, 139.1, 148.5, 159.7, 162.8.

N-(2-(4-Methoxybenzyloxy)ethyl)-3,5-dinitrobenzamide (26)

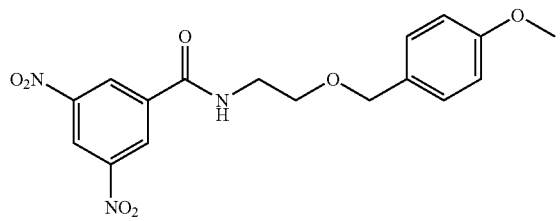 [SMILES: COc1ccc(COCCNC(=O)c2cc([N+](=O)[O-])cc([N+](=O)[O-])c2)cc1]

$^1$H NMR (400 MHz, $CDCl_3$) δ 3.65-3.71 (m, 4H), 3.75 (s, 3H), 4.47 (s, 2H), 6.71 (brs, 1H), 6.84 (dd, J=6.8, 2.0 Hz, 2H), 7.23 (d, J=8.4 Hz, 2H), 8.87 (d, J=2.4 Hz, 2H), 9.13 (t, J=2.0 Hz, 1H); $^{13}$C NMR (100 MHz, $CDCl_3$) δ 40.5, 55.3, 67.8, 73.1, 114.0, 121.0, 127.1, 129.6, 130.0, 137.9, 148.6, 159.5, 162.7.

N-(2-(4-Chlorobenzyloxy)ethyl)-3,5-dinitrobenzamide (27)

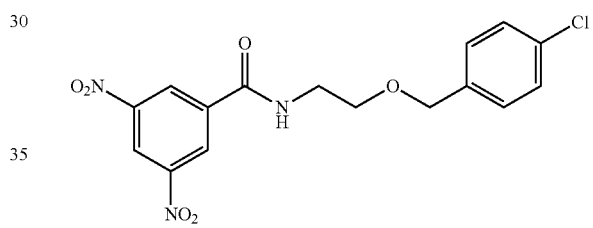

$^1$H NMR (400 MHz, $CDCl_3$) δ 3.68-3.76 (m, 4H), 4.53 (s, 2H), 6.77 (brs, 1H), 7.25-7.32 (m, 4H), 8.91 (d, J=2.0 Hz, 2H), 9.15 (t, J=2.0 Hz, 1H); $^{13}$C NMR (100 MHz, $CDCl_3$) δ 40.4, 68.3, 72.6, 121.1, 127.2, 128.8, 129.2, 134.0, 136.0, 137.8, 148.6, 162.7.

N-(2-(3-chlorobenzyloxy)ethyl)-3,5-dinitrobenzamide (28)

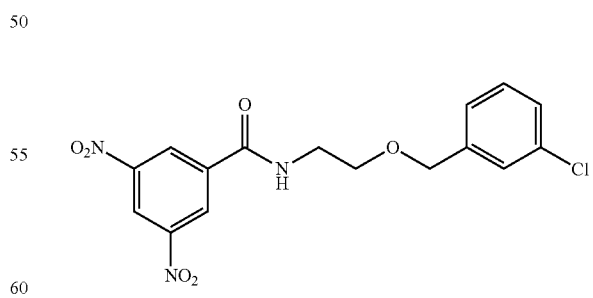

$^1$H NMR (400 MHz, $CDCl_3$) δ 3.68-3.76 (m, 4H), 4.52 (s, 2H), 6.79 (brs, 1H), 7.17-7.29 (m, 4H), 8.91 (d, J=2.0 Hz, 2H), 9.13 (t, J=2.0 Hz, 1H); $^{13}$C NMR (100 MHz, $CDCl_3$) δ 40.4, 68.4, 72.5, 121.1, 125.8, 127.2, 127.8, 128.1, 129.2, 134.5, 137.8, 139.6, 148.6, 162.8.

N-(2-(4-Fluorobenzyloxy)ethyl)-3,5-dinitrobenzamide (29)

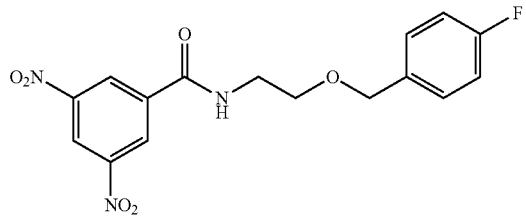 [SMILES: O=C(NCCOCc1ccc(F)cc1)c1cc([N+](=O)[O-])cc([N+](=O)[O-])c1]

¹H NMR (400 MHz, CDCl₃) δ 3.68-3.76 (m, 4H), 4.53 (s, 2H), 6.74 (brs, 1H), 7.02-7.06 (m, 2H), 7.30-7.33 (m, 2H), 8.92 (d, J=2.0 Hz, 2H), 9.16 (t, J=2.0 Hz, 1H); ¹³C NMR (100 MHz, CDCl₃) δ 40.4, 68.1, 72.6, 115.5 (d, J=22 Hz, due to F), 121.1, 127.1, 130.0 (d, J=8.2 Hz, due to F), 133.5 (d, J=3.0 Hz, due to F), 137.8, 148.6, 162.5 (d, J=245 Hz, due to F), 162.7.

N-(2-(2-Fluorobenzyloxy)ethyl)-3,5-dinitrobenzamide (30)

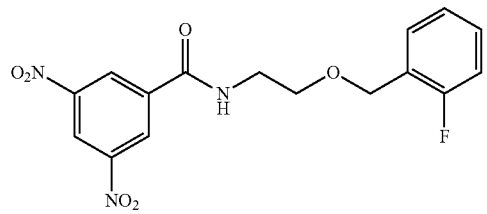 [SMILES: O=C(NCCOCc1ccccc1F)c1cc([N+](=O)[O-])cc([N+](=O)[O-])c1]

¹H NMR (400 MHz, CDCl₃) δ 3.75 (s, 4H), 4.64 (s, 2H), 7.07-7.17 (m, 3H), 7.29-7.39 (m, 1H and brs. 1H), 8.94 (d, J=2.0 Hz, 2H), 9.17 (t, J=2.0 Hz, 1H).

3,5-Dinitro-N-(2-(4-(trifluoromethoxy)benzyloxy)ethyl)benzamide (31)

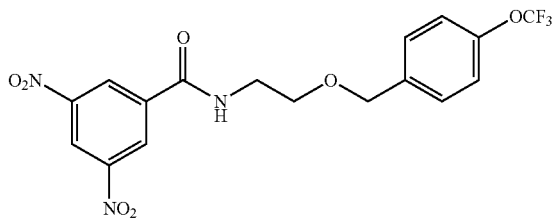 [SMILES: O=C(NCCOCc1ccc(OC(F)(F)F)cc1)c1cc([N+](=O)[O-])cc([N+](=O)[O-])c1]

¹H NMR (400 MHz, CDCl₃) δ 3.72-3.76 (m, 4H), 4.54 (s, 2H), 7.13 (d, J=8.0 Hz, 2H), 7.31-7.35 (m, 2H and brs, 1H), 8.94 (d, J=2.0 Hz, 2H), 9.08 (t, J=2.0 Hz, 1H); ¹³C NMR (100 MHz, CDCl₃) δ 40.4, 68.4, 72.2, 120.9, 121.0, 127.2, 129.1, 136.3, 137.7, 148.4, 148.7, 148.9, 162.9.

3,5-Dinitro-N-(2-(3-(trifluoromethyl)benzyloxy)ethyl)benzamide (32)

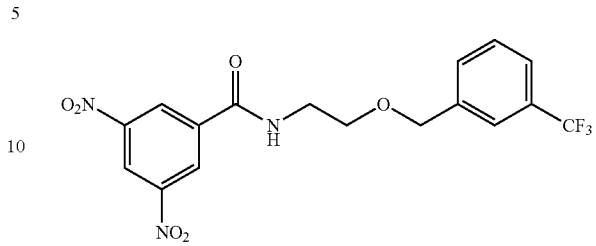

¹H NMR (400 MHz, CDCl₃) δ 3.72-3.79 (m, 4H), 4.61 (s, 2H), 7.06 (brs, 1H), 7.45-7.55 (m, 4H), 8.93 (d, J=2.0 Hz, 2H), 9.10 (t, J=2.0 Hz, 1H); ¹³C NMR (100 MHz, CDCl₃) δ 40.4, 68.7, 72.4, 121.0, 124.1, 124.6, 124.7, 127.2, 129.0, 130.6 (q, J=32 Hz, due to F), 130.8, 137.7, 138.6, 148.6, 162.9.

Methyl 4-((2-(3,5-dinitrobenzamido)ethoxy)methyl)benzoate (33)

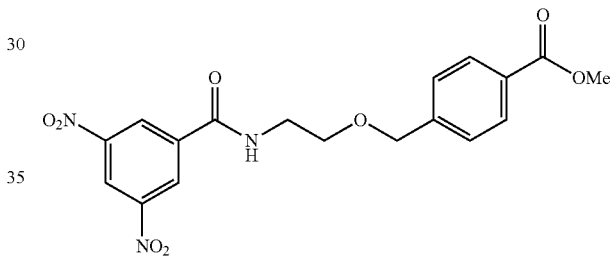

¹H NMR (400 MHz, CDCl₃) δ 3.71-3.74 (m, 4H), 3.84 (s, 3H), 4.55 (s, 2H), 7.29 (d, J=8.0 Hz, 2H and brs, 1H), 7.85 (d, J=8.0 Hz, 2H), 8.90 (d, J=2.0 Hz, 2H), 9.01 (t, J=2.0 Hz, 1H); ¹³C NMR (100 MHz, CDCl₃) δ 40.6, 52.2, 68.8, 72.6, 120.9, 127.3, 129.5, 129.7, 137.8, 142.9, 148.5, 163.0, 166.8.

4-((2-(3,5-Dinitrobenzamido)ethoxy)methyl)benzoic acid (34)

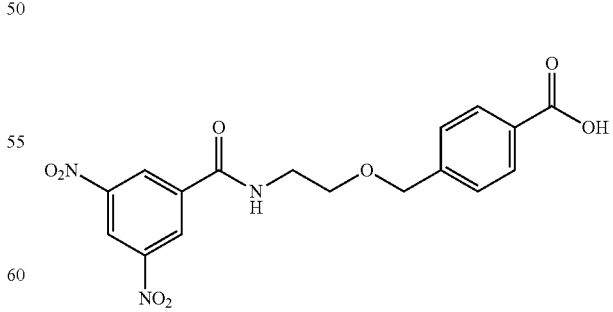

¹H NMR (400 MHz, Acetone-d₆) δ 3.74 (t, J=5.2 Hz, 2H), 3.81 (t, J=5.2 Hz, 2H), 4.72 (s, 2H), 7.56 (d, J=8.4 Hz, 2H) 7.72 (brs, 1H), 8.03 (d, J=8.4 Hz, 2H), 9.02 (d, J=2.0 Hz, 2H), 9.13 (t, J=2.0 Hz, 1H).

N-(2-(Benzyloxy)ethyl)benzamide (35)

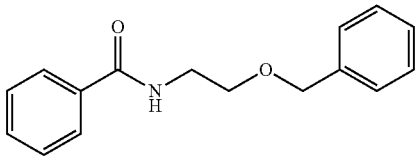 [SMILES: O=C(NCCOCc1ccccc1)c1ccccc1]

$^1$H NMR (400 MHz, CDCl$_3$) δ 3.62-3.68 (m, 4H), 4.52 (s, 2H), 6.71 (brs, 1H), 7.24-7.49 (m, 8H), 7.73-7.76 (m, 2H); $^{13}$C NMR (100 MHz, CDCl$_3$) δ 39.7, 68.8, 73.1, 126.9, 127.8, 128.4, 131.3, 134.5, 137.8, 167.5.

N-(2-(3-(Trifluoromethyl)benzyloxy)ethyl)benzamide (36)

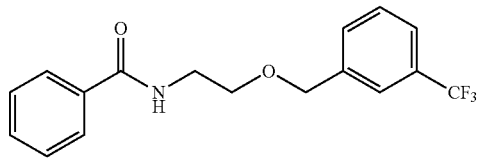 [SMILES: O=C(NCCOCc1cccc(C(F)(F)F)c1)c1ccccc1]

$^1$H NMR (400 MHz, CDCl$_3$) δ 3.63-3.70 (m, 4H), 4.56 (s, 2H), 6.72 (brs, 1H), 7.37-7.53 (m, 6H), 7.58 (s, 1H), 7.74-7.76 (m, 2H); $^{13}$C NMR (100 MHz, CDCl$_3$) δ 39.7, 69.3, 72.3, 124.2, 124.3, 124.6, 126.9, 128.5, 128.9, 130.8, 131.5, 134.4, 139.0, 148.6, 167.6.

N-(2-(3-Chlorobenzyloxy)ethyl)benzamide (37)

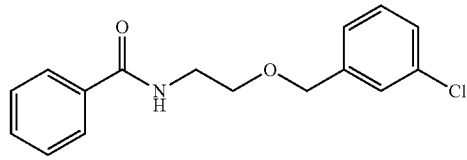 [SMILES: O=C(NCCOCc1cccc(Cl)c1)c1ccccc1]

$^1$H NMR (400 MHz, CDCl$_3$) δ 3.62-3.69 (m, 4H), 4.49 (s, 2H), 6.71 (brs, 1H), 7.17-7.50 (m, 7H), 7.75-7.77 (m, 2H); $^{13}$C NMR (100 MHz, CDCl$_3$) δ 39.7, 69.0, 72.2, 125.6, 126.8, 127.6, 127.8, 128.4, 129.7, 131.3, 134.3, 139.9, 167.4.

N-(2-(3-Chlorobenzyloxy)ethyl)-3,5-difluorobenzamide (38)

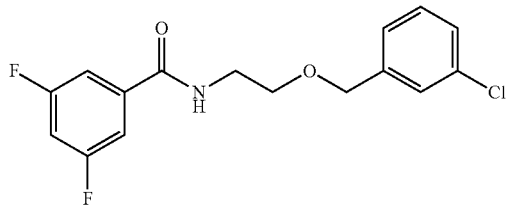 [SMILES: O=C(NCCOCc1cccc(Cl)c1)c1cc(F)cc(F)c1]

$^1$H NMR (400 MHz, CDCl$_3$) δ 3.64-3.69 (m, 4H), 4.52 (s, 2H), 6.54 (brs, 1H), 6.95 (tt, J=2.4, 11.2 Hz, 1H), 7.19-7.33 (m, 6H).

N-(2-(3-Chlorobenzyloxy)ethyl)-3,5-dichlorobenzamide (39)

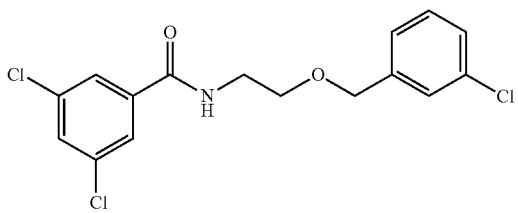 [SMILES: O=C(NCCOCc1cccc(Cl)c1)c1cc(Cl)cc(Cl)c1]

$^1$H NMR (400 MHz, CD$_3$OD) δ 3.13 (t, J=5.2 Hz, 2H), 3.67 (t, J=5.2 Hz, 2H), 4.55 (s, 2H), 7.27-7.29 (m, 3H), 7.42 (s, 1H), 7.46, (s, 1H), 7.81 (s, 2H); $^{13}$C NMR (100 MHz, CDCl$_3$) δ 40.6, 67.2, 73.2, 127.0, 128.7, 128.8, 128.9, 130.7, 131.0, 135.4, 135.5, 141.4, 142.7, 171.5.

N-(2-(3-Chlorobenzyloxy)ethyl)-3,5-bis(trifluoromethyl)benzamide (40)

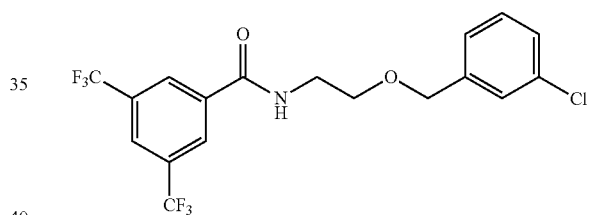

$^1$H NMR (400 MHz, CDCl$_3$) δ 3.64-3.68 (m, 4H), 4.49 (s, 2H), 6.89 (brs, 1H), 7.15 (d, J=3.6 Hz, 1H), 7.21-7.24 (m, 2H), 7.27 (s, 1H), 7.95 (s, 1H), 8.18 (s, 2H); $^{13}$C NMR (100 MHz, CDCl$_3$) δ 40.3, 68.37, 72.5, 121.6, 125.0, 125.1, 125.7, 127.8, 128.1, 129.9, 132.0, 134.5, 136.6, 139.8, 164.8.

N-(2-(3-Chlorobenzyloxy)ethyl)-3-methoxybenzamide (41)

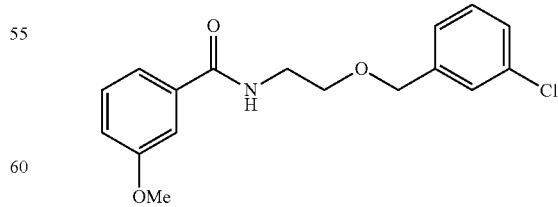

$^1$H NMR (400 MHz, CDCl$_3$) δ 3.63 (d, J=3.6 Hz, 2H), 3.65 (d, J=3.6 Hz, 2H), 3.81 (s, 3H), 4.49 (s, 2H), 6.51 (brs, 1H), 7.01 (dd, J=8.0 Hz, 2.4 Hz, 1H), 7.16 (d, J=4.4 Hz, 1H), 7.28 (m, 3H), 7.25-7.34 (m, 3H); $^{13}$C NMR (100 MHz, CDCl$_3$) δ

39.9, 55.5, 69.2, 72.5, 112.4, 117.8, 118.7, 125.8, 127.8, 128.0, 129.6, 129.9, 134.5, 136.0, 140.0, 159.9, 167.5.

N-(2-(3-Chlorobenzyloxy)ethyl)-4-methoxybenzamide (42)

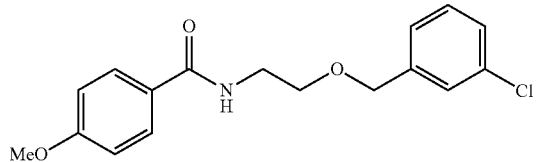 [SMILES: COc1ccc(C(=O)NCCOCc2cccc(Cl)c2)cc1]

$^1$H NMR (400 MHz, CDCl$_3$) δ 3.62-3.66 (m, 4H), 3.82 (s, 3H), 4.49 (S, 2H), 6.48 (brs, 1H), 6.89 (d, J=8.8 hz, 2H), 7.17 (t, J=4.4 Hz, 2H), 7.24 (m, 1H), 7.32 (s, 1H), 7.71 (d, J=8.8 Hz, 2H) $^{13}$C NMR (100 MHz, CDCl$_3$) δ 39.8, 55.5, 69.4, 72.4, 113.8, 125.7, 126.8, 127.8, 128.0, 128.8, 129.8, 134.5, 140.1, 162.2, 167.1.

N-(2-(3-Chlorobenzyloxy)ethyl)-3-(trifluoromethoxy)benzamide (43)

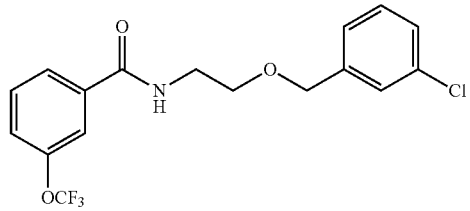

$^1$H NMR (400 MHz, CDCl$_3$) δ 3.62-3.68 (m, 4H), 4.49 (s, 2H), 6.62 (brs, 1H), 7.15 (dd, J=1.2, 8.8 Hz, 1H), 7.22-7.23 (m, 2H), 7.36 (t, J=1.2 Hz, 2H), 7.43 (t, J=8.4 Hz, 1H), 7.63 (dd, J=1.2, 4.4 Hz, 2H); $^{13}$C NMR (100 MHz, CDCl$_3$) δ 40.0, 69.0, 72.4, 119.3, 120.1, 123.8, 125.1, 125.7, 127.8, 128.0, 129.9, 130.1, 134.5, 136.6, 140.0, 149.4, 166.1.

N-(2-(3-Chlorobenzyloxy)ethyl)-4-(trifluoromethyl)benzamide (44)

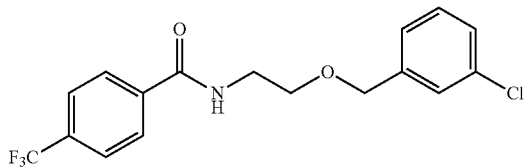 [SMILES: O=C(NCCOCc1cccc(Cl)c1)c1ccc(C(F)(F)F)cc1]

$^1$H NMR (400 MHz, CDCl$_3$) δ 3.62-3.68 (m, 4H), 4.49 (s, 2H), 6.71 (brs, 1H), 7.14-7.17 (m, 1H), 7.23-7.24 (m, 2H), 7.3 (s, 1H), 7.64 (d, J=8.0 Hz, 2H), 7.83 (d, J=8.0 Hz, 2H); $^{13}$C NMR (100 MHz, CDCl$_3$) δ 40.0, 68.9, 72.4, 125.6 (q, J=3.7 Hz), 125.8, 127.5, 127.8, 128.1, 129.9, 138.1, 133.4, 134.5, 137.7, 140.0, 166.4.

N-(2-(3-Chlorobenzyloxy)ethyl)-3-(trifluoromethyl)benzamide (45)

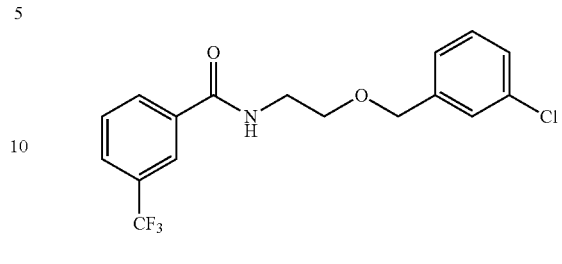

$^1$H NMR (400 MHz, CDCl$_3$) δ 3.62 (m, 4H), 4.46 (s, 2H), 6.96 (brs, 1H), 7.14-7.27 (m, 4H), 7.47 (t, J=7.2 Hz, 1H), 7.68 (d, J=3.2 Hz, 1H), 7.89 (d, J=3.2 Hz, 1H), 8.01 (s, 1H); $^{13}$C NMR (100 MHz, CDCl$_3$) δ 40.0, 68.9, 72.3, 122.4, 124.1, 125.7, 127.7, 127.9, 128.0, 129.1, 129.8, 130.3, 130.8, 134.4, 135.2, 140.0, 166.3.

Methyl 3-(2-(3-chlorobenzyloxy)ethylcarbamoyl)benzoate (46)

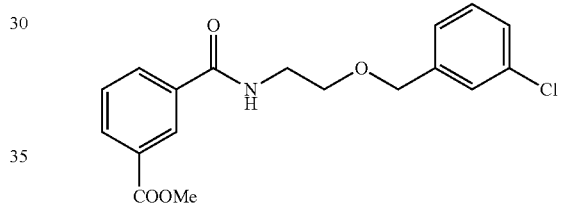

$^1$H NMR (400 MHz, CDCl$_3$) δ 3.62-3.69 (m, 4H), 3.89 (s, 3H), 4.48 (s, 2H), 6.71 (brs, 1H), 7.15-7.16 (m, 1H), 7.21-7.24 (m, 2H), 7.28 (s, 1H), 7.47 (t, J=4.0 Hz, 1H), 7.97 (d, J=4.8 Hz, 1H), 8.11 (d, J=4.8 Hz, 1H), 8.35 (t, J=1.6 Hz, 1H); $^{13}$C NMR (100 MHz, CDCl$_3$) δ 40.0, 52.4, 69.0, 72.4, 125.7, 127.7, 127.8, 128.0, 128.9, 129.8, 130.5, 131.8, 132.4, 134.4, 134.8, 140.0, 166.3, 166.6.

Methyl 4-(2-(3-chlorobenzyloxy)ethylcarbamoyl)benzoate (47)

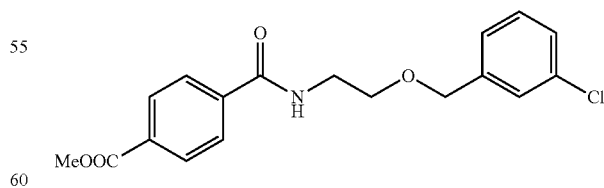

$^1$H NMR (400 MHz, CDCl$_3$) δ 3.62-3.66 (m, 4H), 3.90 (s, 3H), 4.48 (s, 2H), 6.65 (brs, 1H), 7.14-7.17 (m, 1H), 7.22 (d, J=5.2 Hz, 2H), 7.30 (s, 1H), 7.78 (d, J=8.0 Hz, 2H), 8.04 (d, J=8.0 Hz, 2H); $^{13}$C NMR (100 MHz, CDCl$_3$) δ 40.0, 52.4, 69.0, 72.4, 125.7, 127.1, 127.8, 128.1, 129.9, 132.7, 134.5, 138.4, 140.0, 160.3, 166.7.

35

N-(2-(3-Chlorobenzyloxy)ethyl)-3-nitrobenzamide (48)

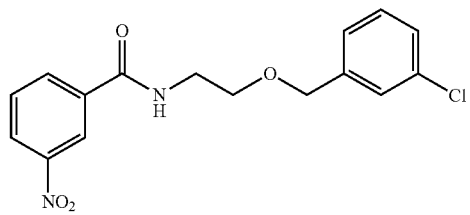

¹H NMR (400 MHz, CDCl₃) δ 3.64 (m, 4H), 4.45 (s, 2H), 7.13-7.23 (m, 5H), 7.53 (m, 1H), 8.08 (d, J=6.8 Hz, 1H) 8.22 (d, J=6.8 Hz, 1H), 8.54 (s, 1H); ¹³C NMR (100 MHz, CDCl₃) δ 40.1, 68.7, 72.2, 122.0, 125.6, 125.9, 127.5, 127.8, 129.7, 129.8, 133.1, 134.2, 136.0, 139.9, 148.0, 165.3.

N-(2-(3-Chlorobenzyloxy)ethyl)-4-nitrobenzamide (49)

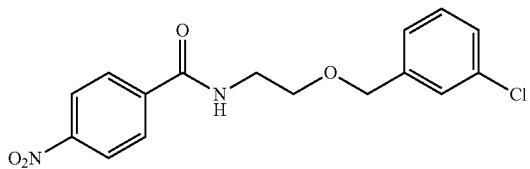 [SMILES: O=C(NCCOCc1cccc(Cl)c1)c1ccc([N+](=O)[O-])cc1]

¹H NMR (400 MHz, CDCl₃) δ 3.63 (m, 4H), 4.45 (s, 2H), 6.97 (brs, 1H), 7.12-7.25 (m, 4H), 7.87 (d, J=6.4 Hz, 2H), 8.15 (d, J=6.4 Hz, 2H); ¹³C NMR (100 MHz, CDCl₃) δ 40.1, 68.7, 72.2, 123.6, 125.6, 127.5, 127.9, 128.2, 129.7, 134.3, 139.9, 140.0, 149.4, 165.6.

N-(2-(3-Chlorobenzyloxy)ethyl)-3-fluorobenzamide (50)

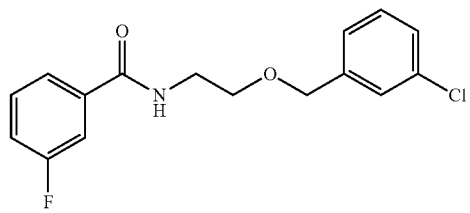 [SMILES: O=C(NCCOCc1cccc(Cl)c1)c1cccc(F)c1]

¹H NMR (400 MHz, CDCl₃) δ 3.56-3.61 (m, 41-1), 4.43 (s, 2H), 6.66 (brs, 1H), 7.10-7.12 (m, 2H), 7.18-7.19 (m, 2H), 7.25 (s, 1H), 7.30-7.31 (m, 1H), 7.41-7.45 (m, 2H); ¹³C NMR (100 MHz, CDCl₃) δ 39.9, 69.0, 72.4, 114.3 (d, J=23.0 Hz, due to F), 118.4 (d, J=20.8 Hz, due to F), 122.4 (d, J=3.0 Hz, due to F), 125.7, 127.7, 128.0, 129.8, 130.2 (d, J=8.2 Hz, due to F), 134.5, 136.7 (d, J=6.7 Hz, due to F), 140.0, 163.0 (d, J=245 Hz, due to F), 166.3 (d, J=3.0 Hz, due to F).

36

N-(2-(3-Chlorobenzyloxy)ethyl)-3-chlorobenzamide (51)

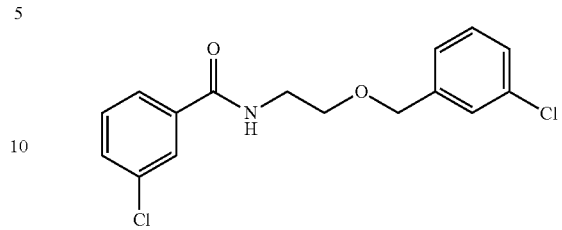

¹H NMR (400 MHz, CDCl₃) δ 3.64 (m, 4H), 4.49 (s, 2H), 6.52 (brs, 1H), 7.17 (d, J=3.2 Hz, 1H), 7.24 (s, 2H), 7.31-7.36 (m, 2H), 7.44 (d, J=3.6 Hz, 1H), 7.59 (d, J=7.6 Hz, 1H), 7.73 (s, 1H); ¹³C NMR (100 MHz, CDCl₃) δ 40.0, 69.1, 72.5, 125.1, 125.8, 127.5, 127.8, 128.1, 129.9, 130.0, 131.6, 134.6, 134.9, 136.3, 140.0, 166.3.

N-(2-(3-Chlorobenzyloxy)ethyl)-4-hydroxybenzamide (52)

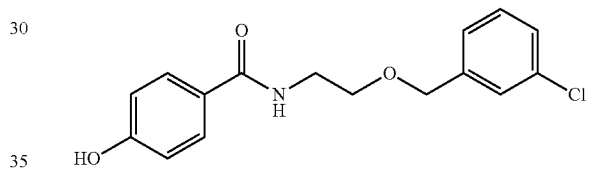

¹H NMR (400 MHz, CDCl₃) δ 3.64 (s, 4H), 4.48 (s, 2H), 6.57 (brs, 1H), 6.84 (dd, J=2.0, 8.8 Hz, 2H), 7.17 (d, J=3.2 Hz, 1H), 7.23 (d, J=3.2 Hz, 2H), 7.31 (s, 1H), 7.60 (dd, J=2.0, 8.8 Hz, 2H), 8.22 (brs, 1H); ¹³C NMR (100 MHz, CDCl₃) δ 40.0, 69.1, 72.5, 115.7, 125.4, 125.8, 127.8, 128.1, 129.0, 129.9, 134.5, 140.0, 160.2, 168.2.

N-(2-(3-Chlorobenzyloxy)ethyl)-3-hydroxybenzamide (53)

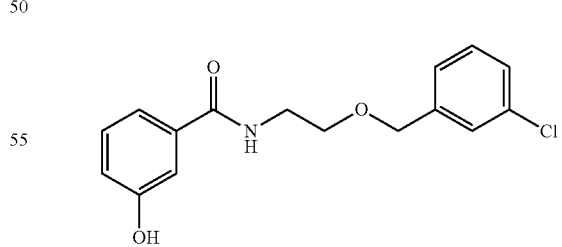

¹H NMR (400 MHz, CDCl₃) δ 3.65 (m, 4H), 4.49 (s, 2H), 6.64 (brs, 1H), 6.98 (d, J=8.0 Hz, 1H), 7.13 (d, J=8.0 Hz, 1H), 7.17-7.26 (m, 5H), 7.30 (s, 1H), 7.50 (s, 1H); ¹³C NMR (100 MHz, CDCl₃) δ 40.0, 69.1, 72.5, 115.1, 117.8, 119.3, 125.9, 127.3, 128.1, 129.9, 130.0, 134.6, 135.4, 139.9, 157.2, 168.0.

Scheme 4

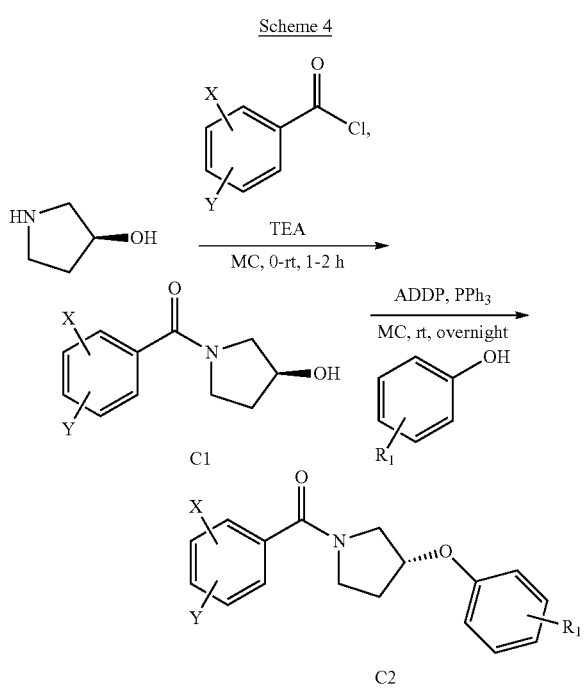

General Procedure for the Synthesis of phenoxy-pyrrolidin-1-yl-methanone (C2)

To a solution of (S)-3-pyrrolidinol (10 mmol) and triethylamine (11 mmol) in methylene chloride (50 mL) was added benzoyl chloride (8.67 mmol) at 0° C. The reaction temperature was brought up to room temperature. After 2 h, the reaction mixture was diluted with methylene chloride (50 mL) and then washed with 0.5 M HCl aqueous solution (100 mL) and brine (100 mL). The organic layer was dried over anhydrous MgSO$_4$ and concentrated in vacuo. The crude product was purified by silica gel flash column chromatography (2:1 hexanes/ethyl acetate) to give C1.

To a solution of C1 (1.07 mmol) in methylene chloride (10 mL) was added ADDP (1.28 mmol), triphenylphosphine (1.28 mmol) and a phenol (1.28 mmol) at room temperature. After stirring overnight, the reaction mixture was diluted with methylene chloride (30 mL) and washed with 1 M HCl aqueous solution (50 mL), saturated Na$_2$CO$_3$ aqueous solution (50 mL) and brine (50 mL). The organic layer was dried over anhydrous MgSO$_4$ and concentrated in vacuo. The crude was purified by silica gel flash column chromatography (2:1 hexanes/ethyl acetate) and recrystallized from a mixture of hexanes and ethyl acetate to give C2.

(R)-(3,5-Dinitrophenyl)(3-(4-methoxyphenoxy)pyrrolidin-1-yl)methanone (54)

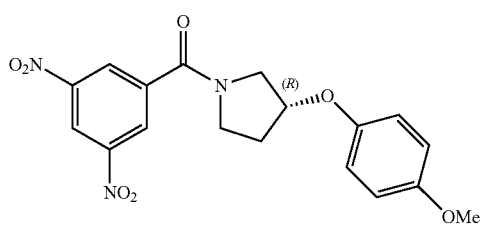

(Two rotamers, 1:1 ratio), m.p. 124-125° C.; $^1$H NMR (400 MHz, CDCl$_3$) δ 2.11-2.19 (m, 1H), 2.30-2.34 (m, 1H), 3.54-3.64 (m, 1H), 3.72 & 3.76 (s, 3H), 3.81-3.99 (m, 3H), 4.86-4.94 (m, 1H), 6.74-6.84 (m, 4H), 8.68 & 8.75 (d, J=1.6 Hz, 2H), 9.05 & 9.08 (brs, 1H); $^{13}$C NMR (100 MHz, CDCl$_3$) δ 30.6, 32.4, 45.2, 47.7, 52.8, 54.8, 55.8, 55.9, 75.7, 115.0, 117.1, 117.3, 120.1, 120.2, 127.7, 127.9, 139.9, 140.0, 148.6, 150.4, 150.8, 154.8, 154.8, 164.7, 165.1; LC-MS (ESI, m/z): 388 [M+H]$^+$.

(R)-(3,5-Dinitrophenyl)(3-(4-fluorophenoxy)pyrrolidin-1-yl)methanone (55)

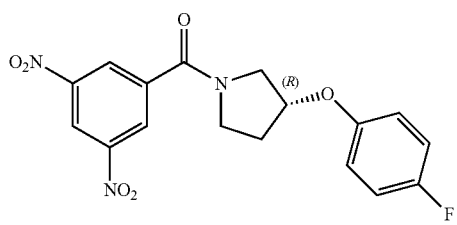

(Two rotamers, 1:1 ratio, 75%), a pale yellow solid; $^1$H NMR (400 MHz, CDCl$_3$) δ 2.15-2.37 (m, 2H), 3.56-3.63 (m, 1H), 3.79-3.97 (m, 3H), 4.91-4.99 (m, 1H), 6.76-7.03 (m, 4H), 8.71 & 8.76 (d, J=1.6 Hz, 2H), 9.08 & 9.10 (brs, 1H); $^{13}$C NMR (100 MHz, CDCl$_3$) δ 29.9, 32.3, 45.1, 47.7, 52.7, 54.8, 75.5, 77.0, 116.2, 116.5, 116.9, 117.0, 117.1, 120.1, 120.2, 127.7, 127.8, 139.8, 139.9, 148.6, 152.6, 152.9, 157.9 (d, J=245 Hz, due to F), 164.7, 165.0.

(R)—N-(4-(1-(3,5-Dinitrobenzoyl)pyrrolidin-3-yloxy)phenyl)acetamide (56)

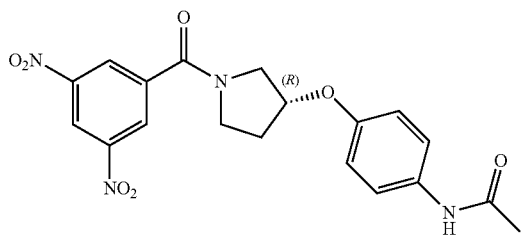

(Two rotamers, 1:1 ratio, 63%), a yellow solid; $^1$H NMR (400 MHz, CDCl$_3$+CD$_3$OD) δ 1.96 & 1.99 (s, 3H), 2.03-2.27 (m, 2H), 3.45-3.50 (m, 1H), 3.69-3.83 (m, 3H), 4.83-4.91 (m, 1H), 6.64 & 6.74 (d, J=8.8 Hz, 2H), 7.26 & 7.33 (d, J=8.8 Hz, 2H), 8.58 & 8.65 (d, J=2.0 Hz, 2H), 8.95-8.99 (m, 1H); $^{13}$C NMR (100 MHz, CDCl$_3$+CD$_3$OD) δ 23.3, 23.4, 29.7, 32.0, 45.0, 47.6, 52.6, 54.6, 75.0, 76.4, 115.8, 115.9, 120.0, 121.9, 127.4, 127.5, 127.6, 127.7, 132.4, 132.5, 139.4, 148.4, 152.8, 153.1, 165.0, 165.3, 169.7.

(R)-(3,5-Dinitrophenyl)(3-(4-(trifluoromethoxy)phenoxy)pyrrolidin-1-yl)methanone (57)

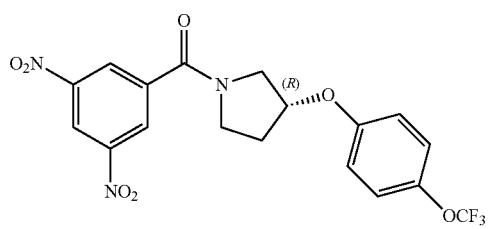

(Two rotamers, δ:4 ratio, 67%), a white solid; ¹H NMR (400 MHz, CDCl₃) δ 2.20-2.40 (m, 2H), 3.59-3.66 (m, 1H), 3.84-4.00 (m, 3H), 4.97-5.05 (m, 1H), 6.83 & 6.92 (d, J=8.8 Hz, 2H), 7.12 & 7.18 (d, J=8.8 Hz, 2H), 8.73 & 8.77 (d, J=2.0 Hz, 2H), 9.09 & 9.11 (d, J=2.0 Hz, 1H); ¹³C NMR (100 MHz, CDCl₃) δ 29.8, 32.2, 45.1, 47.6, 52.6, 54.7, 75.2, 76.7, 116.4, 120.1, 122.8, 127.7, 127.8, 139.6, 139.7, 143.4, 148.5, 155.0, 155.2, 164.7, 164.9.

(R)-Methyl-4-(1-(3,5-dinitrobenzoyl)pyrrolidin-3-yloxy)benzoate (58)

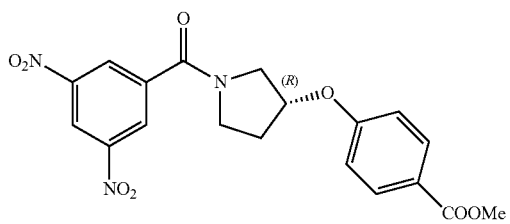

(Two rotamers 1:1 ratio), ¹H NMR (400 MHz, CDCl₃) δ 2.21-2.37 (m, 2H), 3.57-3.65 (m, 1H), 3.85 & 3.87 (s, 3H), 3.89-3.99 (m, 3H), 5.03-5.11 (m, 1H), 6.82 & 6.91 (d, J=7.2 Hz, 2H), 7.93 & 7.99 (d, J=7.2 Hz, 2H), 8.70 & 8.75 (s, 2H), 9.07 & 9.09 (s, 1H); ¹³C NMR (100 MHz, CDCl₃) 5 22.1, 30.0, 32.4, 45.2, 47.7, 52.2, 52.8, 54.8, 74.9, 76.3, 115.0, 120.36, 123.7, 123.8, 127.8, 127.9, 132.0, 139.7, 148.6, 160.2, 160.5, 164.7, 166.7.

(R)-(3,5-Dinitrophenyl)(3-(2-fluorophenoxy)pyrrolidin-1-yl)methanone (59)

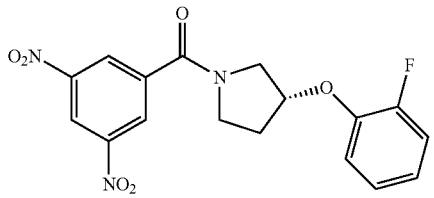 [SMILES: O=C(c1cc([N+](=O)[O-])cc([N+](=O)[O-])c1)N1CC[C@@H](Oc2ccccc2F)C1]

(Two rotamers 1:1 ratio), ¹H NMR (400 MHz, CD₃OD) δ 2.26-2.33 (m, 2H), 3.62-3.97 (m, 3H), 4.00 & 4.36 (s, 1H), 5.06 & 5.21 (s, 1H), 7.11 & 7.27 (m, 4H), 8.78 & 8.83 (d, J=2.0 Hz, 2H), 9.01 & 9.04 (d, J=2.0 Hz, 1H); ¹³C NMR (100 MHz, CD₃OD) δ 29.9, 31.9, 44.9, 52.3, 54.4, 77.2, 78.7, 116.62, 116.67, 116.80, 116.85, 117.8 (d, J=20 Hz, due to F), 120.04 (d, J=3.7 Hz, due to F), 122.5, 122.6, 122.70, 122.77, 125.1, 125.15 (d, J=3.7 Hz, due to F), 127.80 (d, J=7.4 Hz due to F), 127.9, 139.8, 153.6 (d, J=244 Hz, due to F), 165.4, 165.5.

(S)-Methyl-4-(1-(3,5-dinitrobenzoyl)pyrrolidin-3-yloxy)benzoate (60)

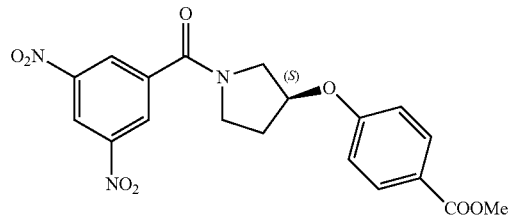

(Two rotamers 1:1 ratio), ¹H NMR (400 MHz, Acetone-d₆) δ 2.21-2.29 (m, 2H), 3.58 & 3.61 (s, 1H), 3.69 & 3.71 (s, 3H), 3.73-4.02 (m, 3H), 4.99 & 5.06 (s, 1H), 6.77-6.94 (m, 4H), 8.73 & 8.77 (s, 2H), 8.96 & 8.99 (s, 1H); ¹³C NMR (100 MHz, CDCl₃) δ 29.9, 31.9, 44.1, 44.7, 52.2, 54.2, 55.1, 55.2, 76.0, 77.5, 114.82, 114.88, 117.2, 119.6, 127.7, 127.8, 140.5, 148.7, 151.1, 151.3, 154.7, 164.6, 164.7.

(S)-(3,5-dinitrophenyl)(3-(4-methoxyphenoxy)pyrrolidin-1-yl)methanone (61)

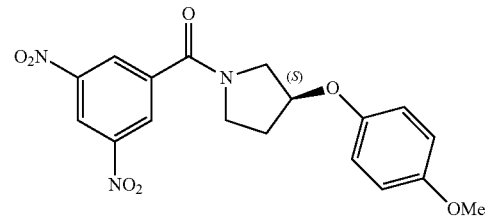

(Two rotamers 1:1 ratio), ¹H NMR (400 MHz, Acetone-d₆) δ 2.19-2.28 (m, 2H) 3.60-4.01 (m, 4H), 4.98 & 5.06 (s, 1H), 6.76-6.94 (m, 4H), 8.73 & 8.76 (s, 2H), 8.95 & 8.99 (s, 1H); ¹³C NMR (100 MHz, Acetone-d₆) δ 31.9, 44.7, 52.2, 54.2, 55.0, 55.1, 65.8, 75.9, 77.5, 114.81, 114.87, 117.2, 119.6, 127.7, 127.8, 128.6, 129.8, 140.4, 148.7, 151.3, 154.7, 164.6, 164.7.

(S)—N-(4-(1-(3,5-Dinitrobenzoyl)pyrrolidin-3-yloxy)phenyl)acetamide (62)

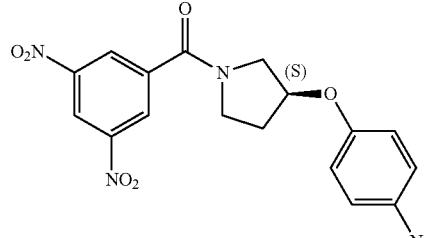

(Two rotamers 1:1 ratio), ¹H NMR (400 MHz, Acetone-d₆) δ 1.99 (s, 3H), 2.22-2.28 (m, 2H), 3.54-4.06 (m, 3H), 5.04 & 5.11 (s, 1H), 6.80 & 6.90 (d, J=8.8 Hz, 1H), 7.46-7.70 (m, 4H, brs, 1H), 8.73 & 8.76 (s, 2H), 8.95 & 8.99 (s, 1H); ¹³C NMR (100 MHz, Acetone-d₆) δ 24.1, 24.2, 30.0, 32.2, 45.2, 47.7, 52.7, 54.7, 75.1, 76.6, 115.9, 120.0, 120.1, 127.7, 127.8, 128.7, 128.8, 131.6, 132.0, 132.4, 132.6, 132.7, 132.8, 139.7, 148.4, 153.1, 165.0, 169.1.

(S)-4-(1-(3,5-Dinitrobenzoyl)pyrrolidin-3-yloxy) benzoic acid (63)

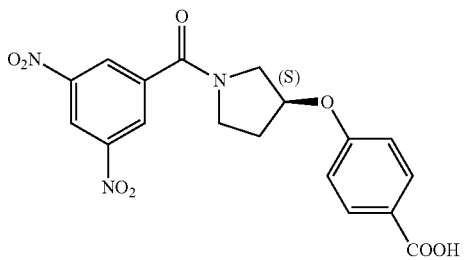

(Two rotamers 1:1 ratio), $^1$H NMR (400 MHz, Acetone-d$_6$) δ 2.31-2.42 (m, 2H), 3.61-3.65 (m, 1H), 3.75-4.06 (m, 3H), 5.19 & 5.28 (s, 1H), 7.02 & 7.13 (d, J=8.8 Hz, 2H), 7.98 & 8.06 (d, J=8.8 Hz, 2H), 8.72 & 8.78 (d, J=2.0 Hz, 2H), 9.02 & 9.05 (s, 1H).

(S)-(3,5-Dinitrophenyl)(3-(2-fluorophenoxy)pyrrolidin-1-yl)methanone (64)

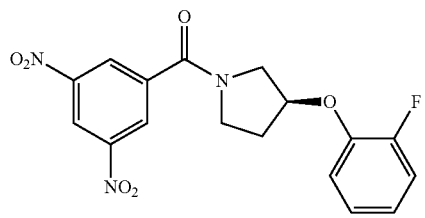 [SMILES: O=C(c1cc([N+](=O)[O-])cc([N+](=O)[O-])c1)N1CC[C@H](Oc2ccccc2F)C1]

(Two rotamers, 1:1 ratio), $^1$H NMR (400 MHz, DMSO-d$_6$) δ 2.14-2.24 (m, 2H), 3.50-3.88 (m, 4H), 4.98 & 5.08 (s, 1H), 6.86-7.15 (m, 4H), 8.65 & 8.69 (s, 2H), 8.88 & 8.92 (s, 1H); $^{13}$C NMR (100 MHz, DMSO-d$_6$) δ 29.1, 31.1, 44.1, 51.5, 53.6, 76.4, 77.9, 115.7, 115.8, 115.9, 116.0, 117.1 (d, J=22.3 Hz, due to F), 119.2 (d, J=3.7 Hz, due to F), 121.7, 121.83, 121.88, 121.9, 124.2 (d, J=3.7 Hz, due to F), 127.0, 139.0, 144.1, 144.4, 148.0, 152.8 (d, J=242.6 Hz, due to F), 164.6, 164.7.

(R)-(3-(2-Fluorophenoxy)pyrrolidin-1-yl)(phenyl)methanone (65)

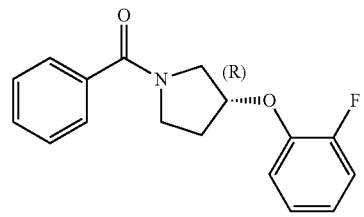

(Two rotamers 1:1 ratio), $^1$H NMR (400 MHz, CDCl$_3$) δ 2.02-2.24 (m, 2H), 3.51-3.91 (m, 4H), 4.85 & 4.98 (s, 1H), 6.86-7.09 (m, 4H), 7.36-7.48 (m, 3H), 7.52 (d, J=5.2 Hz, 1H), 7.53 (d, J=5.2 Hz, 1H); $^{13}$C NMR (100 MHz, CDCl$_3$) δ 30.3, 32.4, 44.3, 47.5, 52.1, 54.8, 78.0, 79.0, 116.8, 117.0, 117.9, 118.6, 122.6, 122.7, 122.9, 123.0, 124.6 (d, J=3.7 Hz due to F), 127.2, 127.4, 128.5, (d, J=3.7 Hz, due to F), 130.1, 130.3, 136.7, 136.9, 144.7 (d, J=20.1 Hz due to F), 153.8 (d, J=245.6 Hz, due to F), 155.2, 170.0, 170.2.

(R)-(3-(4-Methoxyphenoxy)pyrrolidin-1-yl)(phenyl)methanone (66)

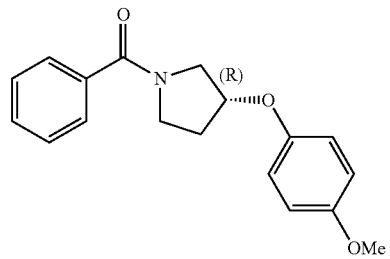

(Two rotamers, 1:1 ratio), $^1$H NMR (400 MHz, CDCl$_3$) δ 1.99-2.21 (m, 2H), 3.48-3.66 (m, 2H), 3.68 & 3.73 (s, 3H), 3.79-3.89 (m, 2H), 4.74 & 4.96 (s, 1H), 6.71 (s, 2H), 6.76 (s, 2H), 7.34 & 7.36 (d, J=5.6 Hz, 3H), 7.46 & 7.52 (d, J=5.2 Hz, 2H); $^{13}$C NMR (100 MHz, CDCl$_3$) δ 30.2, 32.3, 44.4, 47.6, 52.1, 54.8, 55.8, 55.9, 76.0, 114.9, 115.0, 117.1, 117.3, 127.3, 127.4, 128.50, 128.54, 130.1, 130.2, 136.8, 137.0, 150.9, 151.1, 154.5, 154.6, 169.9, 170.2; LC-MS (ESI, m/z): 298.1 [M+H]$^+$.

(R)-(3,5-Dinitrophenyl)(3-hydroxypyrrolidin-1-yl)methanone (67)

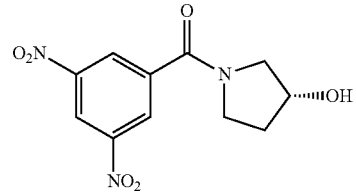 [SMILES: O=C(c1cc([N+](=O)[O-])cc([N+](=O)[O-])c1)N1CC[C@@H](O)C1]

(Two rotamers, 1:1 ratio), $^1$H NMR (400 MHz, CDCl$_3$) δ 1.98-2.11 (m, 2H), 3.23 (brs, 1H), 3.37-3.48 (m, 1H), 3.61-3.79 (m, 3H), 4.47 & 4.56 (s, 1H), 8.62 & 8.67 (s, 2H), 8.99-9.00 (m, 1H); $^{13}$C NMR (100 MHz, CDCl$_3$) δ 33.0, 34.9, 45.1, 47.6, 55.5, 57.5, 69.4, 70.9, 120.1, 120.2, 127.8, 139.8, 139.9, 148.5, 165.1, 165.3.

(R)-(3-(3-Methoxyphenoxy)pyrrolidin-1-yl)(3-methoxyphenyl)methanone (68)

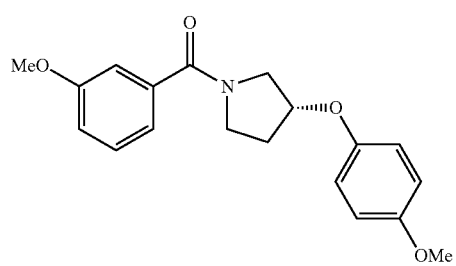 [SMILES: COc1ccc(O[C@@H]2CCN(C(=O)c3cccc(OC)c3)C2)cc1]

(Two rotamers, 1:1 ratio, 85%), a pale yellow liquid; $^1$H NMR (400 MHz, CDCl$_3$) δ 1.97-2.22 (m, 2H), 3.48-3.65 (m, 2H), 3.68 & 3.71 (s, 3H), 3.73 & 3.76 (s, 3H), 3.79-3.89 (m, 2H), 4.74-4.84 (m, 1H), 6.70-6.80 (m, 4H), 6.86-6.92 (m, 1H), 6.99 & 7.01 (s, 1H), 7.04 & 7.08 (s, 1H), 7.21-7.28 (m, 1H); $^{13}$C NMR (100 MHz, CDCl$_3$) δ 30.2, 32.3, 44.5, 47.7, 52.2, 54.8, 55.6, 55.8, 76.0, 112.6, 112.8, 114.9, 115.0, 116.1, 116.6, 117.1, 117.2, 119.4, 119.6, 129.27, 129.32, 138.1, 150.9, 151.1, 154.5, 159.7, 169.8.

(R)-(3-(4-Methoxyphenoxy)pyrrolidin-1-yl)(3-methoxyphenyl)methanone (69)

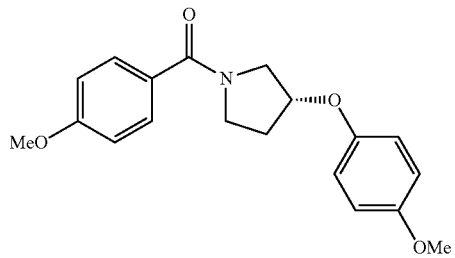 [SMILES: COc1ccc(O[C@@H]2CCN(C(=O)c3ccc(OC)cc3)C2)cc1]

(Two rotamers, 1:1 ratio, 83%), a pale yellow liquid; $^1$H NMR (400 MHz, CDCl$_3$) δ 1.97-2.22 (m, 2H), 3.48-3.65 (m, 2H), 3.68 & 3.71 (s, 3H), 3.73 & 3.76 (s, 3H), 3.79-3.89 (m, 2H), 4.72-4.84 (m, 1H), 6.70-6.80 (m, 4H), 6.86-6.92 (m, 1H), 6.99-7.08 (m, 2H), 7.21-7.28 (m, 1H); $^{13}$C NMR (100 MHz, CDCl$_3$) δ 29.2, 32.1, 44.4, 47.6, 52.1, 54.4, 55.33, 55.62, 75.8, 113.4, 114.7, 116.9, 128.63, 128.75, 129.16, 129.32, 131.9, 150.9, 154.3, 160.9, 169.48, 169.79.

(R)-Methyl 3-(3-(4-methoxyphenoxy)pyrrolidine-1-carbonyl)benzoate (70)

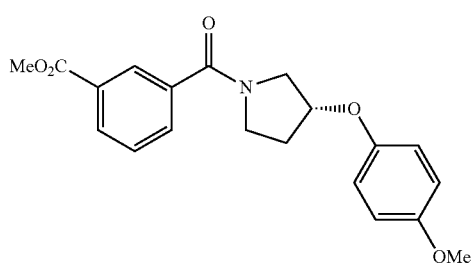 [SMILES: COC(=O)c1cccc(C(=O)N2CC[C@@H](Oc3ccc(OC)cc3)C2)c1]

(Two rotamers, 1:1 ratio, 87%), a pale yellow liquid; $^1$H NMR (400 MHz, CDCl$_3$) δ 1.99-2.24 (m, 2H), 3.45-3.65 (m, 2H), 3.67 & 3.71 (s, 3H), 3.75-3.82 (m, 2H), 3.86 & 3.87 (s, 3H), 4.74-4.86 (m, 1H), 6.72 & 6.80 (m, 4H), 7.40-7.67 (m, 1H), 7.66 & 7.71 (d, J=7.6 Hz, 1H), 8.04 (t, J=9.0 Hz, 1H), 8.13 & 8.19 (s, 1H); $^{13}$C NMR (100 MHz, CDCl$_3$) δ 29.9, 32.0, 44.3, 47.3, 52.2, 54.5, 55.5, 55.6, 75.7, 114.7, 114.8, 116.9, 117.0, 128.1, 128.2, 128.5, 128.6, 130.9, 134.0, 131.5, 131.6, 136.8, 136.9, 150.5, 150.7, 154.33, 154.38, 166.6, 168.6, 168.9.

(R)-Methyl 4-(3-(4-methoxyphenoxy)pyrrolidine-1-carbonyl)benzoate (71)

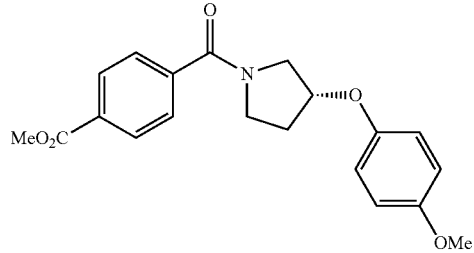 [SMILES: COC(=O)c1ccc(C(=O)N2CC[C@@H](Oc3ccc(OC)cc3)C2)cc1]

(Two rotamers, 1:1 ratio, 85%), a pale yellow liquid; $^1$H NMR (400 MHz, CDCl$_3$) δ 1.98-2.11 (m, 1H), 2.15-2.25 (m, 1H), 3.42-3.67 (m, 2H), 3.68 & 3.71 (s, 3H), 3.77-3.81 (m, 1H), 3.83-3.88 (m, 1H), 3.86 & 3.88 (s, 3H), 4.73-4.86 (m, 1H), 6.69-6.75 (m, 2H), 6.80 (s, 2H), 7.51 (d, J=8.0 Hz, 1H), 7.57 (d, J=8.4 Hz, 1H), 8.00 (d, J=8.4 Hz, 1H), 8.03 (d, J=8.4 Hz, 1H); $^{13}$C NMR (100 MHz, CDCl$_3$) δ 29.9, 32.0, 44.2, 47.2, 51.9, 52.2, 54.3, 55.5, 55.6, 75.6, 114.7, 114.8, 116.8, 117.0, 127.0, 127.1, 129.5, 129.6, 131.2, 131.3, 140.7, 140.8, 150.5, 150.7, 154.3, 154.4, 168.7, 168.9.

(R)-(3-(4-Methoxyphenoxy)pyrrolidin-1-yl)(3-(trifluoromethyl)phenyl)methanone (72)

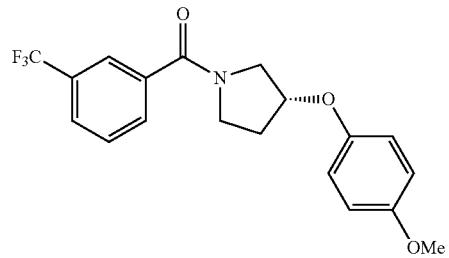 [SMILES: COc1ccc(O[C@@H]2CCN(C(=O)c3cccc(C(F)(F)F)c3)C2)cc1]

(Two rotamers, 1:1 ratio, 82%), a pale yellow liquid; $^1$H NMR (400 MHz, CDCl$_3$) δ 2.04-2.15 (m, 1H), 2.21-2.30 (m, 1H), 3.48-3.67 (m, 2H), 3.72 & 3.75 (s, 3H), 3.78-3.90 (m, 2H), 4.79-4.90 (m, 1H), 6.74-6.83 (m, 4H), 7.48-7.55 (m, 1H), 7.64-7.82 (m, 3H); $^{13}$C NMR (100 MHz, CDCl$_3$) δ 30.0, 32.1, 44.5, 47.5, 52.2, 54.6, 55.7, 55.8, 75.8, 114.8, 114.9, 117.0, 117.2, 124.2, 124.3, 129.0, 129.1, 130.4, 130.6, 137.3, 137.4, 150.6, 150.8, 154.5, 154.6, 168.3, 168.6.

(R)-(3-(4-Methoxyphenoxy)pyrrolidin-1-yl)(4-(trifluoromethyl)phenyl)methanone (73)

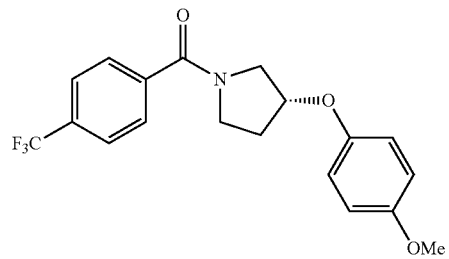

(Two rotamers, 1:1 ratio, 55%), a pale yellow solid; $^1$H NMR (400 MHz, CDCl$_3$) δ 2.03-2.06 (m, 1H), 2.20-2.25 (m, 1H), 3.49-3.70 (m, 2H), 3.72 & 3.75 (s, 3H), 3.81-3.88 (m, 2H), 4.72 & 8.89 (m, 1H), 6.74-6.83 (m, 4H), 7.23-7.50 (m, 4H); $^{13}$C NMR (100 MHz, CDCl$_3$) δ 30.0, 32.2, 44.5, 47.5, 52.2, 54.6, 55.7, 55.8, 75.8, 76.8, 114.9, 117.0, 117.2, 119.8, 120.1, 122.5, 122.6, 125.6, 125.8, 130.0, 130.1, 138.5, 149.1, 150.6, 150.9, 154.5, 168.2.

(R)-(3-(4-Methoxyphenoxy)pyrrolidin-1-yl)(3-(trifluoromethoxy)phenyl)methanone (74)

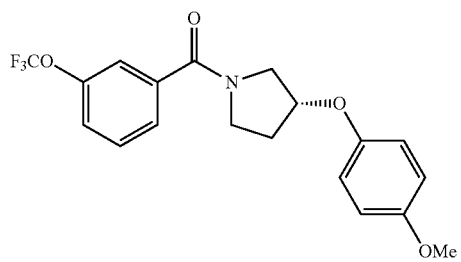 [SMILES: COc1ccc(O[C@@H]2CCN(C(=O)c3cccc(OC(F)(F)F)c3)C2)cc1]

(Two rotamers, 1:1 ratio, 67%), a yellow liquid; $^1$H NMR (400 MHz, CDCl$_3$) δ 2.01-2.23 (m, 2H), 3.43-3.68 (m, 2H), 3.69 & 3.72 (s, 3H), 3.72-3.83 (m, 2H), 4.75-4.88 (m, 1H), 6.72-6.82 (m, 4H), 7.58-7.66 (m, 4H); $^{13}$C NMR (100 MHz, CDCl$_3$) δ 29.1, 30.1, 32.2, 38.9, 44.6, 47.6, 52.2, 54.7, 55.8, 75.9, 114.9, 115.0, 117.1, 117.3, 125.5, 125.6, 127.7, 128.8, 150.8, 151.0, 154.6, 154.7, 168.5, 168.6.

(R)-(3-(4-Methoxyphenoxy)pyrrolidin-1-yl)(3-nitrophenyl)methanone (75)

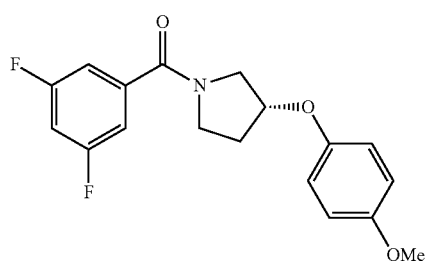 [SMILES: COc1ccc(O[C@@H]2CCN(C(=O)c3cc(F)cc(F)c3)C2)cc1]

(Two rotamers, 1:1 ratio, 84%), a yellow liquid; $^1$H NMR (400 MHz, CDCl$_3$) δ 2.00-2.24 (m, 2H), 3.48-3.56 (m, 1H), 3.68 & 3.72 (s, 3H), 3.73-3.88 (m, 3H), 4.79-4.89 (m, 1H), 6.71-6.83 (m, 4H), 7.52-7.59 (m, 1H), 7.81 & 7.87 (d, J=7.6H, 1H), 8.22 (t, J=9.8 Hz, 1H), 8.32 & 8.38 (s, 1H); $^{13}$C NMR (100 MHz, CDCl$_3$) δ 29.8, 32.0, 44.5, 47.4, 52.2, 54.5, 55.5, 55.6, 75.6, 77.0, 114.7, 114.8, 116.9, 117.0, 122.2, 122.3, 124.6, 124.7, 129.6, 133.1, 133.2, 138.0, 138.1, 147.8, 150.4, 150.6, 154.3, 154.4, 166.9, 167.2.

(R)-(3-(4-Methoxyphenoxy)pyrrolidin-1-yl)(4-nitrophenyl)methanone (76)

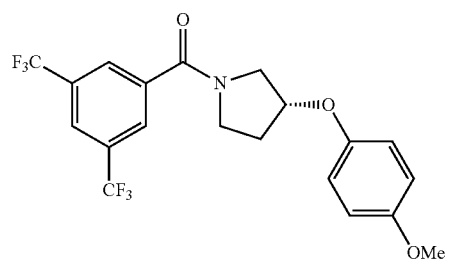 [SMILES: COc1ccc(O[C@@H]2CCN(C(=O)c3cc(C(F)(F)F)cc(C(F)(F)F)c3)C2)cc1]

(Two rotamers, 1:1 ratio, 73%), a yellow solid; $^1$H NMR (400 MHz, CDCl$_3$) δ 2.01-2.31 (m, 2H), 3.44-3.69 (m, 2H), 3.72 & 3.75 (s, 3H), 3.80-3.90 (m, 2H), 4.79-4.90 (m, 1H), 6.72-6.82 (m, 4H), 7.63 & 7.70 (d, J=8.0 Hz, 2H), 8.22 & 8.24 (d, J=8.2 Hz, 2H); $^{13}$C NMR (100 MHz, CDCl$_3$) δ 30.2, 31.9, 44.3, 47.2, 52.0, 55.5, 75.5, 76.7, 114.7, 114.8, 116.8, 116.9, 123.5, 128.0, 128.2, 128.6, 142.4, 142.5, 148.4, 150.3, 150.6, 154.3, 154.4, 167.3, 167.6.

(R)-(3-Fluorophenyl)(3-(4-methoxyphenoxy)pyrrolidin-1-yl)methanone (77)

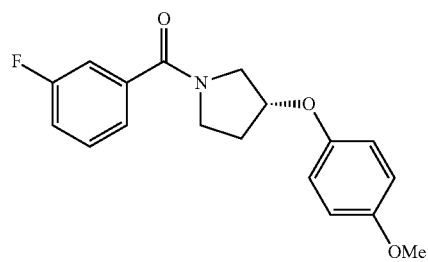 [SMILES: COc1ccc(O[C@@H]2CCN(C(=O)c3cccc(F)c3)C2)cc1]

(Two rotamers, 1:1 ratio, 78%), a pale yellow liquid; $^1$H NMR (400 MHz, CDCl$_3$) δ 2.01-2.11 (m, 1H), 2.12-2.42 (m, 1H), 3.48-3.69 (m, 2H), 3.71 & 3.74 (s, 3H), 3.78-3.87 (m, 2H), 4.76-4.88 (m, 1H), 6.72-6.82 (m, 4H), 7.05-7.36 (m, 4H); $^{13}$C NMR (100 MHz, CDCl$_3$) δ 29.9, 32.0, 44.3, 47.4, 52.0, 54.5, 55.6, 75.7, 114.4, 114.8, 116.9, 117.1, 122.8, 122.9, 130.1, 130.2, 138.6, 138.7, 150.6, 150.8, 154.4, 154.5, 162.4 (d, J=245 Hz, due to F), 168.3, 168.5.

(R)-(3-Chlorophenyl)(3-(4-methoxyphenoxy)pyrrolidin-1-yl)methanone (78)

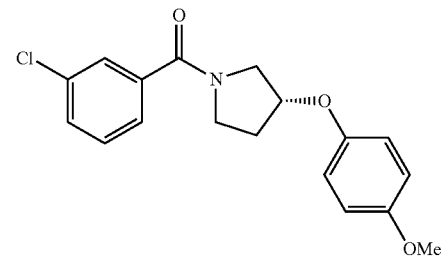 [SMILES: COc1ccc(O[C@@H]2CCN(C(=O)c3cccc(Cl)c3)C2)cc1]

(Two rotamers, 1:1 ratio, 87%), a pale yellow liquid; $^1$H NMR (400 MHz, CDCl$_3$) δ 2.01-2.24 (m, 2H), 3.47-3.69 (m, 2H), 3.71 & 3.74 (s, 3H), 3.78-3.86 (m, 2H), 4.75-4.88 (m, 1H), 6.73-6.82 (m, 4H), 7.26-7.42 (m, 3H), 7.46 & 7.52 (s, 1H); $^{13}$C NMR (100 MHz, CDCl$_3$) δ 29.9, 32.0, 44.3, 47.4, 52.0, 54.5, 55.6, 55.7, 75.7, 76.7, 114.7, 114.8, 116.6, 117.1, 125.1, 125.3, 127.3, 127.4, 129.7, 129.8, 130.0, 130.1, 134.3, 138.2, 138.3, 150.5, 150.7, 154.4, 168.1, 168.4

(R)-(3-Hydroxyphenyl)(3-(4-methoxyphenoxy)pyrrolidin-1-yl)methanone (79)

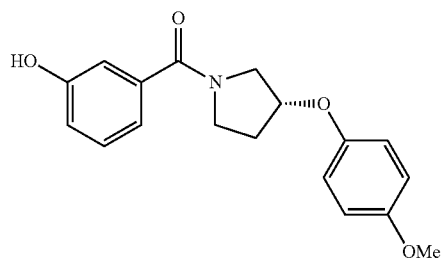 [SMILES: COc1ccc(O[C@@H]2CCN(C(=O)c3cccc(O)c3)C2)cc1]

(Two rotamers, 1:1 ratio, 53%), a white liquid; $^1$H NMR (400 MHz, CDCl$_3$) δ 1.96-2.25 (m, 2H), 3.53-3.74 (m, 2H), 3.77 & 3.81 (s, 3H), 3.83-3.94 (m, 2H), 4.73 & 4.87 (m, 1H), 6.72-6.82 (m, 4H), 6.85-6.98 (m, 2H), 7.08-7.20 (m, 2H), 8.21 (brs, 1H);

(R)-(4-Hydroxyphenyl)(3-(4-methoxyphenoxy)pyrrolidin-1-yl)methanone (80)

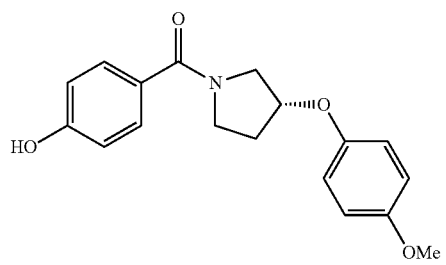 [SMILES: COc1ccc(O[C@@H]2CCN(C(=O)c3ccc(O)cc3)C2)cc1]

(Two rotamers, 1:1 ratio, 37%), a white solid; $^1$H NMR (400 MHz, CDCl$_3$) δ 2.03-2.32 (m, 2H), 3.59-3.71 (m, 2H), 3.74 & 3.76 (s, 3H), 3.79-3.93 (m, 2H), 4.80-4.91 (m, 1H), 6.75-6.84 (m, 4H), 7.21-7.24 (m, 2H), 7.56 & 7.62 (d, J=8.0 Hz, 2H), 8.01 & 8.03 (brs, 1H).

(R)-(4-Hydroxy-3-nitrophenyl)(3-(4-methoxyphenoxy)pyrrolidin-1-yl)methanone (81)

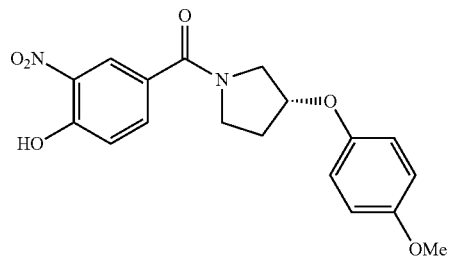 [SMILES: COc1ccc(O[C@@H]2CCN(C(=O)c3ccc(O)c([N+](=O)[O-])c3)C2)cc1]

(Two rotamers, 1:1 ratio, 63%), a yellow liquid; $^1$H NMR (400 MHz, CDCl$_3$) δ 2.01-2.14 (m, 1H), 2.25-2.27 (m, 1H), 3.56-3.65 (m, 2H), 3.72 & 3.74 (s, 3H), 3.81-3.91 (m, 2H), 4.81-4.89 (m, 1H), 6.76 (m, 4H), 7.16 (t, J=9.4 Hz, 1H), 7.78 & 7.84 (d, J=8.4 Hz, 1H), 8.29 & 8.37 (s, 1H); $^{13}$C NMR (100 MHz, CDCl$_3$) δ 29.9, 31.8, 45.0, 47.6, 52.6, 54.9, 55.9, 115.1, 117.2, 117.3, 120.4, 124.7, 125.0, 128.8, 133.1, 136.9, 137.0, 151.0, 154.7, 156.4, 166.9, 167.3.

(R)-(3,5-Dichlorophenyl)(3-(4-methoxyphenoxy)pyrrolidin-1-yl)methanone (82)

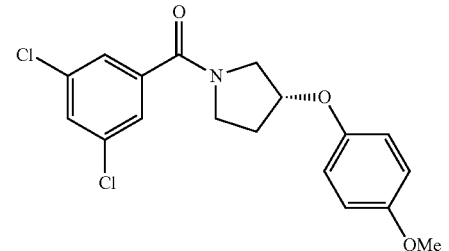 [SMILES: COc1ccc(O[C@@H]2CCN(C(=O)c3cc(Cl)cc(Cl)c3)C2)cc1]

(Two rotamers, 1:1 ratio, 85%), a pale yellow liquid; $^1$H NMR (400 MHz, CDCl$_3$) δ 2.02-2.10 (m, 1H), 2.20-2.25 (m, 1H), 3.47-3.70 (m, 2H), 3.72 & 3.74 (s, 3H), 3.75-3.85 (m, 2H), 4.78-4.87 (m, 1H), 6.74-6.82 (m, 4H), 7.34-7.41 (m, 3H); $^{13}$C NMR (100 MHz, CDCl$_3$) δ 29.9, 32.0, 44.4, 47.4, 52.1, 54.4, 55.6, 55.7, 75.5, 114.8, 116.9, 125.6, 125.7, 130.0, 135.1, 139.2, 139.3, 150.4, 150.7, 154.4, 154.5, 166.7, 167.0.

(R)-(3,5-Difluorophenyl)(3-(4-methoxyphenoxy)pyrrolidin-1-yl)methanone (83)

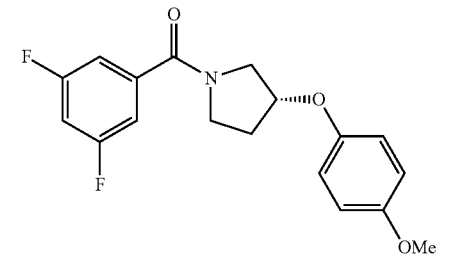 [SMILES: COc1ccc(O[C@@H]2CCN(C(=O)c3cc(F)cc(F)c3)C2)cc1]

(Two rotamers, 1:1 ratio, 75%), a yellow liquid; $^1$H NMR (400 MHz, CDCl$_3$) δ 2.01-2.27 (m, 2H), 3.48-3.67 (m, 2H), 3.71 & 3.74 (s, 3H), 3.77-3.85 (m, 2H), 4.78-4.88 (m, 1H), 6.73-6.87 (m, 5H), 6.99 & 7.06 (d, J=5.6 Hz, 2H); $^{13}$C NMR (100 MHz, CDCl$_3$) δ 29.8, 32.0, 44.4, 47.3, 52.1, 54.9, 55.6, 75.6, 105.3, 105.4, 110.3, 110.4, 110.5, 110.7, 114.8, 116.9, 117.1, 150.2, 154.9, 162.4 (d, J=250 Hz, due to F), 162.5 (d, J=250 Hz, due to F), 167.0, 167.3.

(R)-(3,5-Bis(trifluoromethyl)phenyl)(3-(4-methoxyphenoxy)pyrrolidin-1-yl)methanone (84)

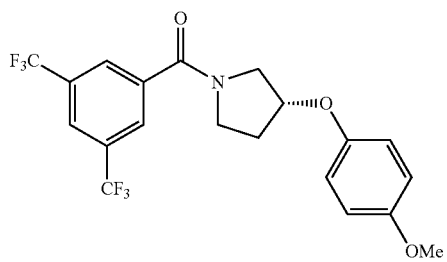 [SMILES: COc1ccc(O[C@@H]2CCN(C(=O)c3cc(C(F)(F)F)cc(C(F)(F)F)c3)C2)cc1]

(Two rotamers, 1:1 ratio, 65%), a yellow liquid; $^1$H NMR (400 MHz, CDCl$_3$) δ 2.08-2.14 (m, 1H), 2.24-2.29 (m, 1H), 3.47-3.67 (m, 2H), 3.71 & 3.74 (s, 3H), 3.76-3.91 (m, 2H), 4.81-4.91 (m, 1H), 6.74-6.83 (m, 4H), 7.90-8.12 (m, 3H); $^{13}$C NMR (100 MHz, CDCl$_3$) δ 29.8, 32.1, 44.6, 47.4, 52.3, 54.5, 55.6, 75.6, 114.8, 114.9, 116, 9, 117.2, 123.7, 124.3, 127.5, 127.7, 131.1, 132.1, 138.5, 138.6, 150.4, 150.7, 154.5, 154.7, 166.5, 166.8.

(R)-(3-(4-Methoxyphenoxy)pyrrolidin-1-yl)(pyridin-3-yl)methanone (85)

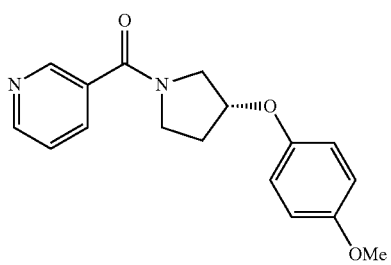 [SMILES: COc1ccc(O[C@@H]2CCN(C(=O)c3cccnc3)C2)cc1]

(Two rotamers, 1:1 ratio, 82%), a yellow solid; $^1$H NMR (400 MHz, CDCl$_3$) δ 2.00-2.10 (m, 1H), 2.16-2.24 (m, 1H), 3.48-3.58 (m, 1H), 3.64-3.73 (m, 1H), 3.67 & 3.69 (s, 3H), 3.73-3.85 (m, 2H), 4.75-4.85 (m, 1H), 6.69-6.78 (m, 4H), 7.25-7.31 (m, 1H), 7.78 & 7.83 (d, J=7.6 Hz, 1H), 8.57-8.61 (m, 1H), 8.71 & 8.77 (s, 1H); $^{13}$C NMR (100 MHz, CDCl$_3$) δ 29.7, 31.9, 44.3, 47.2, 51.9, 54.4, 55.49, 55.53, 75.5, 114.66, 114.69, 116.8, 116.9, 123.1, 123.2, 132.3, 134.8, 134.9, 147.9, 148.1, 150.39, 150.63, 150.83, 150.89, 154.2, 154.3, 167.0, 167.3.

(R)-(3-(4-Methoxyphenoxy)pyrrolidin-1-yl)(pyridin-4-yl)methanone (86)

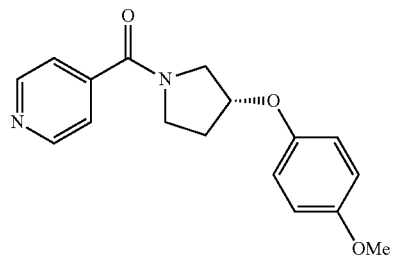 [SMILES: COc1ccc(O[C@@H]2CCN(C(=O)c3ccncc3)C2)cc1]

(Two rotamers, 1:1 ratio, 79%), a yellow solid; $^1$H NMR (400 MHz, CDCl$_3$) δ 2.04-2.23 (m, 2H), 3.46-3.67 (m, 2H), 3.70 & 3.72 (s, 3H), 3.73-3.90 (m, 2H), 4.78-4.88 (m, 1H), 6.76-6.82 (m, 4H), 7.34 (s, 1H), 7.40 (s, 1H), 8.66 (d, J=13.2 Hz, 2H); $^{13}$C NMR (100 MHz, CDCl$_3$) δ 29.6, 31.7, 44.0, 46.8, 51.7, 53.9, 55.3, 55.4, 75.3, 114.5, 114.6, 116.7, 116.8, 120.9, 121.0, 143.6, 143.7, 149.7, 150.2, 154.1, 154.2, 166.9, 167.1.

(R)-4-(3-(4-Methoxyphenoxy)pyrrolidine-1-carbonyl)pyridine 1-oxide (87)

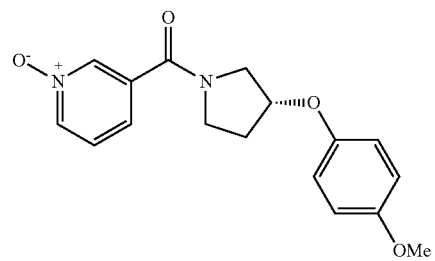

(Two rotamers, 1:1 ratio, 97%), a yellow solid; $^1$H NMR (400 MHz, CDCl$_3$) δ 2.03-2.11 (m, 1H), 2.21-2.26 (m, 1H), 3.50-3.68 (m, 2H), 3.70 & 3.72 (s, 3H), 3.74-3.88 (m, 2H), 4.79-4.87 (m, 1H), 6.70-6.81 (m, 4H), 7.25-7.41 (m, 2H), 8.17-8.20 (m, 1H), 8.29 & 8.35 (brs, 1H); $^{13}$C NMR (100 MHz, CDCl$_3$) δ 29.8, 32.0, 44, 7, 47.3, 52.3, 54.4, 55.7, 75.4, 114.8, 116.9, 117.0, 124.5, 126.0, 126.1, 135.7, 135.8, 137.9, 138.1, 140.1, 150.3, 154.5, 154.5, 164.1, 164.3.

(R)-4-(3-(4-Methoxyphenoxy)pyrrolidine-1-carbonyl)pyridine-1-oxide (88)

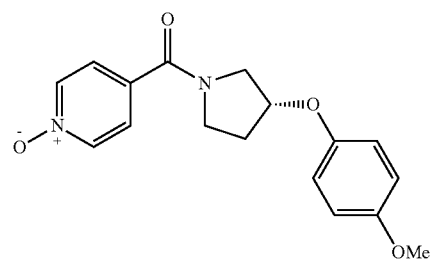

(Two rotamers, 1:1 ratio, 95%), a yellow solid; $^1$H NMR (400 MHz, CDCl$_3$) δ 2.03-2.10 (m, 1H), 2.22-2.27 (m, 1H), 3.52-3.68 (m, 2H), 3.70 & 3.72 (s, 3H), 3.76-3.83 (m, 2H), 4.80-4.87 (m, 1H), 6.70-6.79 (m, 4H), 7.40 (d, J=6.4 Hz, 1H), 7.47 (d, J=6.8 Hz, 1H), 8.13-8.18 (m, 2H); $^{13}$C NMR (100 MHz, CDCl$_3$) δ 29.7, 32.1, 44.7, 47.3, 52.4, 54.4, 55.6, 75.4, 114.8, 116.9, 125.0, 125.1, 132.9, 133.0, 139.1, 150.3, 150.6, 154.4, 154.6, 165.3.

(R)-(3-(4-Methoxyphenoxy)pyrrolidin-1-yl)(pyrimidin-5-yl)methanone (89)

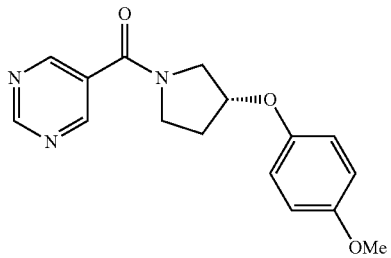 [SMILES: COc1ccc(O[C@@H]2CCN(C(=O)c3cncnc3)C2)cc1]

(Two rotamers, 1:1 ratio, 84%), a pale yellow solid; $^1$H NMR (400 MHz, CDCl$_3$) δ 2.03-2.13 (m, 1H), 2.23-2.28 (m, 1H), 3.52-3.67 (m, 2H), 3.69 & 3.72 (s, 3H), 3.78-3.88 (m, 2H), 4.79-4.89 (m, 1H), 6.70-6.80 (m, 4H), 8.56 & 8.91 (s, 2H), 9.20 & 9.22 (s, 1H); $^{13}$C NMR (100 MHz, CDCl$_3$) δ 29.8, 32.1, 44.7, 52.3, 54.4, 55.6, 55.7, 75.5, 114.8, 116.9, 117.0 130.2, 130.3, 150.3, 150.6, 154.5, 154.6, 155.5, 155.6, 159.4, 159.5, 164.5.

(3,5-Dinitrophenyl)(4-hydroxypiperidin-1-yl)methanone (90)

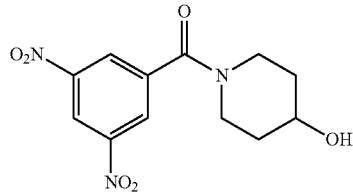 [SMILES: O=C(c1cc([N+](=O)[O-])cc([N+](=O)[O-])c1)N1CCC(O)CC1]

$^1$H NMR (400 MHz, Acetone-d$_6$) δ 1.50-1.56 (m, 2H), 1.80-1.90 (m, 2H), 3.30-3.42 (m, 2H), 3.63 (brs, 1H), 3.94-4.05 (m, 3H), 8.61 (d, J=2.0 Hz, 2H), 8.95 (d, J=2.0 Hz, 1H); $^{13}$C NMR (100 MHz, Acetone-d$_6$) δ 33.7, 34.5, 39.5, 44.9, 66.0, 119.1, 127.4, 140.2, 148.8, 165.1.

Methyl 4-(1-(3,5-dinitrobenzoyl)piperidin-4-yloxy)benzoate (91)

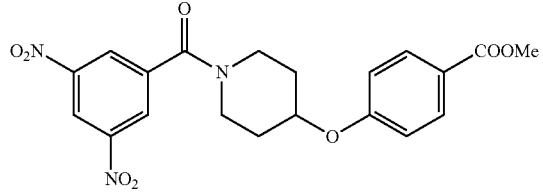 [SMILES: COC(=O)c1ccc(OC2CCN(C(=O)c3cc([N+](=O)[O-])cc([N+](=O)[O-])c3)CC2)cc1]

$^1$H NMR (400 MHz, Acetone-d$_6$) δ 1.84 (brs, 2H), 1.96 (brs, 2H), 3.31 (brs, 1H), 3.59-3.74 (m, 2H), 3.77 (s, 3H), 3.84-3.96 (m, 1H), 4.63-4.66 (m, 1H), 6.81-6.85 (m, 2H), 7.87-7.90 (m, 2H), 8.50 (d, J=2.0 Hz, 2H), 8.97 (d, J=2.0 Hz, 1H).

(3,5-Dinitrophenyl)(4-(4-methoxyphenoxy)piperidin-1-yl)methanone (92)

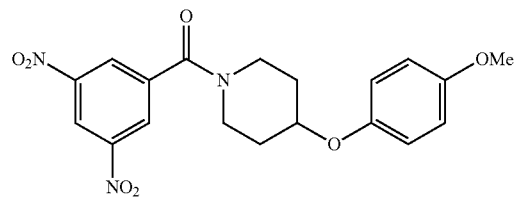 [SMILES: COc1ccc(OC2CCN(C(=O)c3cc([N+](=O)[O-])cc([N+](=O)[O-])c3)CC2)cc1]

$^1$H NMR (400 MHz, CDCl$_3$) δ 1.85-1.98 (m, 4H), 3.35 (brs, 1H), 3.68-3.80 (m, 2H), 3.73 (s, 3H), 3.93 (brs, 1H), 4.49 (brs, 1H), 6.79 (d, J=8.4 Hz, 2H), 6.84 (d, J=8.4 Hz, 2H), 8.57 (s, 2H), 9.03 (s, 1H); $^{13}$C NMR (100 MHz, CDCl$_3$) δ 30.0, 31.2, 39.3, 44.6, 55.8, 71.9, 115.0, 117.9, 119.8, 127.5, 139.6, 148.7, 150.8, 154.6, 165.4.

N-(4-(1-(3,5-Dinitrobenzoyl)piperidin-4-yloxy)phenyl)acetamide (93)

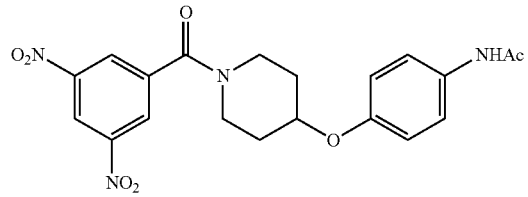 [SMILES: CC(=O)Nc1ccc(OC2CCN(C(=O)c3cc([N+](=O)[O-])cc([N+](=O)[O-])c3)CC2)cc1]

$^1$H NMR (400 MHz, DMSO-d$_6$) δ 1.62-1.96 (m, 4H), 1.97 (s, 3H), 3.48 (m, 3H), 3.93 (brs, 1H), 4.56 (s, 1H), 6.89 (d, J=8.4 Hz, 2H), 7.44 (d, J=8.4 Hz, 2H), 8.64 (s, 2H), 8.33 (s, 1H), 9.74 (s, 1H);

(3,5-Dinitrophenyl)(4-(2-fluorophenoxy)piperidin-1-yl)methanone (94)

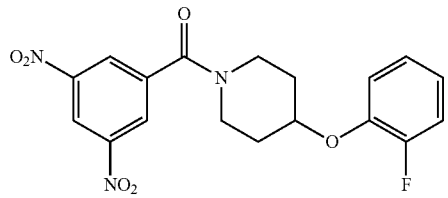

$^1$H NMR (400 MHz, DMSO-d$_6$) δ 1.70-2.10 (m, 4H), 3.39-4.11 (m, 4H), 4.59 (m, 1H), 6.86-6.92 (m, 1H), 7.01-7.15 (m, 3H), 8.60 (d, J=2.0 Hz, 2H), 8.89 (d, J=2.0 Hz, 1H); $^{13}$C NMR (100 MHz, DMSO-d$_6$) δ 31.1, 31.9, 45.5, 49.6, 75.0, 117.6 (d, J=18.6 Hz, due to F), 119.5, 120.5, 123.3 (d, J=6.7 Hz, due to F), 126.0 (d, J=3.7 Hz, due to F), 128.6, 140.6, 146.1, 149.8, 154.8 (d, J=242.6 Hz, due to F), 166.9.

(3,5-Dinitrophenyl)(4-(2-methoxyphenyl)piperazin-1-yl)methanone (95)

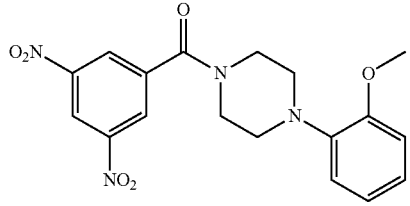 [SMILES: COc1ccccc1N1CCN(C(=O)c2cc([N+](=O)[O-])cc([N+](=O)[O-])c2)CC1]

¹H NMR (400 MHz, Acetone-d₆) δ 3.02-3.12 (m, 4H), 3.62 (brs, 2H), 3.82 (s, 3H), 3.87 (brs, 2H), 6.85-6.95 (m, 4H), 8.68 (d, J=2.0 Hz, 2H), 8.96 (d, J=2.4 Hz, 1H); LC-MS (ESI, m/z): 387 [M+H]⁺.

(3,5-Dinitrophenyl)(4-(4-methoxyphenyl)piperazin-1-yl)methanone (96)

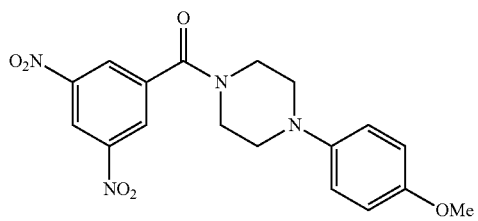 [SMILES: COc1ccc(N2CCN(C(=O)c3cc([N+](=O)[O-])cc([N+](=O)[O-])c3)CC2)cc1]

¹H NMR (400 MHz, Acetone-d₆) δ 3.08-3.17 (m, 4H), 3.68 (brs, 2H), 3.71 (s, 3H), 3.88 (brs, 2H), 6.82 (d, J=8.8 Hz, 2H), 6.93, (d, J=8.8 Hz, 2H), 8.69 (d, J=2.0 Hz, 2H), 8.98 (d, J=2.0 Hz, 1H); ¹³C NMR (100 MHz, Acetone-d₆) δ 42.4, 47.7, 50.5, 50.9, 54.9, 114.4, 118.8, 119.3, 127.7, 139.9, 145.6, 148.8, 154.5, 165.2; LC-MS (ESI, m/z): 387 [M+H]⁺.

(4-(2-chlorophenyl)piperazin-1-yl)(3,5-dinitrophenyl)methanone (97)

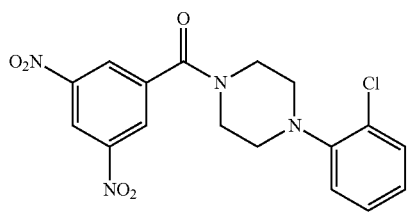 [SMILES: O=C(c1cc([N+](=O)[O-])cc([N+](=O)[O-])c1)N1CCN(c2ccccc2Cl)CC1]

¹H NMR (400 MHz, Acetone-d₆) δ 3.09-3.17 (m, 4H), 3.70 (brs, 2H), 3.94 (brs, 2H), 7.07 (t, J=7.6 Hz, 1H), 7.18 (d, J=8 Hz, 1H), 7.30 (t, J=8 Hz, 1H), 7.41 (d, J=8 Hz, 1H), 8.72 (s, 1H), 9.00 (s, 1H); ¹³C NMR (100 MHz, Acetone-d₆) δ 43.3, 48.7, 51.6, 52.1, 120.0, 122.0, 125.3, 128.5, 128.9, 129.4, 131.4, 140.6, 149.6, 149.8, 166.1; LC-MS (ESI, m/z): 391 [M+H]⁺.

Scheme 5

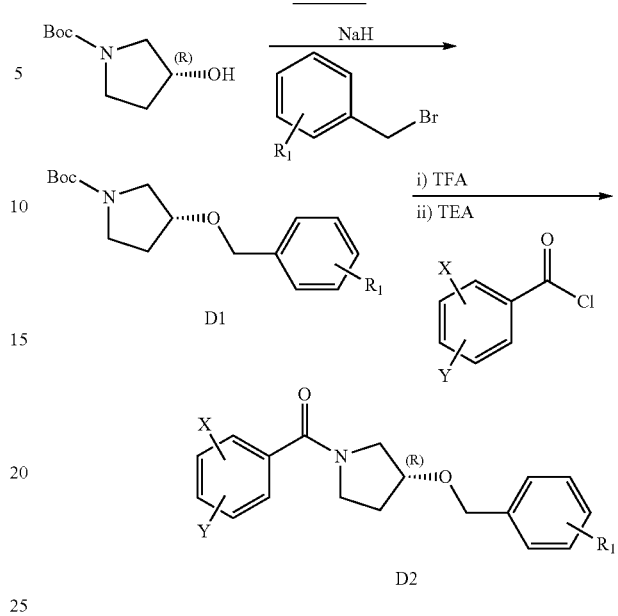

General Procedure for the Synthesis of t-butyl-benzyloxypyrrolidine-1-carboxylate (D1)

To a solution of (R)-tert-butyl 3-hydroxypyrrolidine-1-carboxylate (3.2 mmol) in dimethyl formamide (10 mL) was added sodium hydride (3.2 mmol) and benzyl bromide (3.2 mmol) at 0° C. and the resulting mixture was stirred at room temperature. After stirring overnight, distilled water (50 mL) was added and the resulting precipitate was collected by filtration to afford D1.

General Procedure for the Synthesis of benzyloxy-pyrrolidinyl-phenylmethanone (D2)

D1 (0.43 mmol) was dissolved in trifluoro acetic acid (5 mL) and stirred at room temperature. After 1 h, the reaction mixture was concentrated in vacuo to afford an amine. To a solution of the amine in methylene chloride (5 mL) was added triethylamine (0.51 mmol) and a benzoylchloride (0.51 mmol) at 0° C. and the resulting mixture was stirred at room temperature. After 3 h, the reaction mixture was diluted with methylene chloride (30 mL) and washed with 1 M HCl aqueous solution (30 mL), saturated Na₂CO₃ aqueous solution (30 mL) and brine (30 mL). The organic layer was dried over anhydrous MgSO₄ and concentrated in vacuo. The crude product was purified by silica gel flash column chromatography (3:1 hexanes/ethyl acetate) and recrystallized from a mixture of hexanes and ethyl acetate to give D2.

(R)-(3-(Benzyloxy)pyrrolidin-1-yl)(3,5-dinitrophenyl)methanone (98)

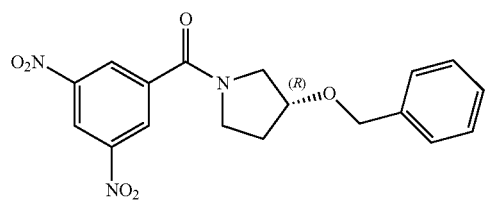

(Two rotamers, 1:1 ratio, 23%), a white solid; ¹H NMR (400 MHz, CDCl₃) δ 2.18-2.29 (m, 2H), 3.53-3.58 (m, 1H), 3.76-3.93 (m, 3H), 5.12-5.37 (m, 3H), 7.34-7.44 (m, 5H), 8.67 & 8.73 (d, J=1.6 Hz, 2H), 9.08 & 9.09 (d, J=1.6 Hz, 1H).

((R)-3-(3-Chlorobenzyloxy)pyrrolidin-1-yl)(3,5-dinitrophenyl)methanone (99)

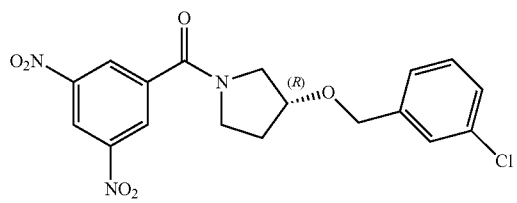

(Two rotamers 3:1 ratio, 75%); ¹H NMR (400 MHz, CDCl₃) δ 1.93-2.21 (m, 2H), 3.38-3.83 (m, 4H), 4.13-4.47 (m, 1H), 4.99 & 5.07 (s, 1H), 5.17 & 5.29 (s, 1H), 7.07-7.29 (m, 4H), 8.64 & 8.69 (s, 2H), 8.98 (s, 1H); ¹³C NMR (100 MHz, CDCl₃) δ 29.8, 32.2, 45.1, 47.6, 52.3, 54.8, 70.3, 70.4, 76.4, 78.0, 120.0, 120.1, 125.5, 125.6, 127.5, 127.7, 127.8, 127.9, 128.1, 129.9, 134.5, 134.6, 139.7, 139.8, 139.9, 148.5, 164.7, 164.8.

((R)-3-(2-Fluorobenzyloxy)pyrrolidin-1-yl)(3,5-dinitrophenyl)methanone (100)

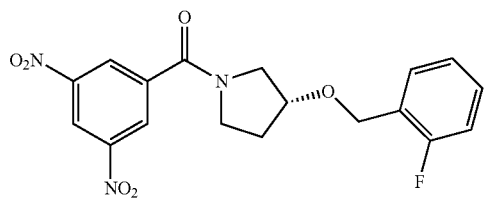 [SMILES: O=C(c1cc([N+](=O)[O-])cc([N+](=O)[O-])c1)N1CC[C@@H](OCc2ccccc2F)C1]

(Two rotamers 1:1 ratio), ¹H NMR (400 MHz, CDCl₃) δ 2.02-2.30 (m, 2H), 3.50 & 3.52 (s, 1H), 3.63-3.94 (m, 3H), 4.24 & 4.33 (s, 1H), 4.48 & 4.56 (d, J=12.0 Hz, 1H), 4.65 (s, 1H), 6.99-7.44 (m, 4H), 8.69 & 8.75 (s, 2H), 9.10 (s, 1H).

((R)-3-(3-(Trifluoromethyl)benzyloxy)pyrrolidin-1-yl)(3,5-dinitrophenyl)methanone (101)

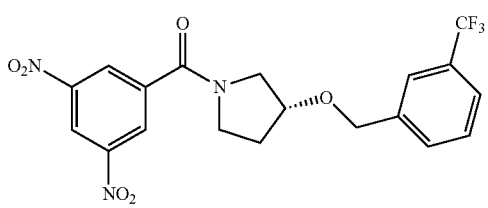 [SMILES: O=C(c1cc([N+](=O)[O-])cc([N+](=O)[O-])c1)N1CC[C@@H](OCc2cccc(C(F)(F)F)c2)C1]

(Two rotamers 2:1 ratio), ¹H NMR (400 MHz, CDCl₃) δ 2.06-2.29 (m, 2H), 3.53 & 3.55 (s, 1H), 3.78-3.96 (m, 3H), 4.27 & 4.35 (s, 1H), 4.51 & 4.62 (d, J=12.4 Hz, 1H), 4.65 (s, 1H), 7.47-7.62 (m, 4H), 8.69 & 8.74 (s, 2H), 9.07 (s, 1H); ¹³C NMR (100 MHz, CDCl₃) δ 29.7, 32.1, 45.1, 47.7, 52.4, 54.9, 70.4, 70.5, 76.7, 78.2, 120.1, 124.1, 124.3, 124.83, 124.87, 127.7, 127.8, 129.2, 130.8, 130.9, 138.7, 138.8, 139.7, 139.8, 148.5, 165.0.

(R)-(3,5-Dinitrophenyl)(3-(pyridin-4-ylmethoxy)pyrrolidin-1-yl)methanone (102)

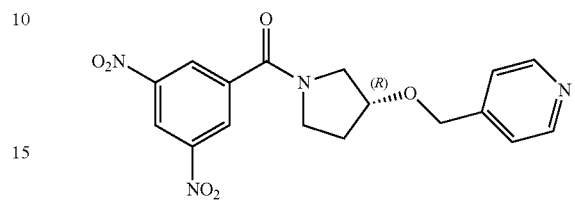

(Two rotamers, 1:1 ratio, 75%), a brown oil; ¹H NMR (400 MHz, CDCl₃) δ 1.99-2.24 (m, 2H), 3.49-3.92 (m, 4H), 4.20-4.28 (m, 1H), 4.41-4.61 (m, 2H), 7.14-7.24 (m, 2H), 8.49-8.56 (m, 2H), 8.67 & 8.70 (d, J=1.6 Hz, 2H), 9.04 (d, J=1.6 Hz, 1H); ¹³C NMR (100 MHz, CDCl₃) δ 29.7, 32.3, 45.1, 47.6, 52.3, 54.8, 69.4, 69.5, 76.9, 78.5, 120.1, 121.6, 121.7, 121.8, 127.7, 127.8, 139.8, 139.9, 146.6, 146.8, 148.5, 150.1, 150.2, 164.7.

Scheme 6

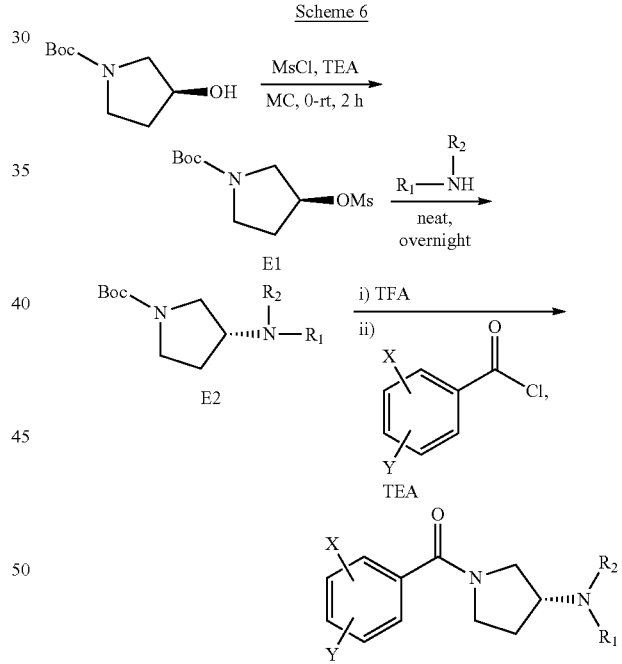

General Procedure for the Synthesis of aminopyrrolidinyl-phenyl-methanone (E3)

To a solution of (S)-(+)-N-Boc-3-pyrrolidinol (2.67 mmol) and triethylamine (4.01 mmol) in methylene chloride (50 mL) was added methansulfonyl chloride (4.01 mmol) under ice-bath and the resulting mixture was further stirred at 4° C. After 2 h, the residue was diluted with methylene chloride (50 mL) and washed with water (100 mL) and brine (100 mL). The organic layer was dried over anhydrous MgSO₄ and concentrated in vacuo. The crude product was purified by silica gel flash column chromatography (2:1 hexanes/ethyl acetate) to give E1.

A solution of E1 (0.75 mmol) and an amine (3.75 mmol) was stirred at 100° C. After stirring overnight, the residue was dissolved in methylene chloride (30 mL) and washed with water (30 mL) and brine (30 mL). The organic layer was dried over anhydrous MgSO$_4$ and concentrated in vacuo. The crude product was purified by silica gel flash column chromatography (1:1 hexanes/ethyl acetate) to give E2.

To a solution of E2 (0.96 mmol) in methylene chloride (20 mL) was added trifluoroacetic acid (0.5 mL). After 3 h, the solvent was removed in vacuo. The reaction mixture was dissolved in methylene chloride (20 mL) and cooled to 0° C. Triethylamine (4.83 mmol) and a benzoyl chloride (1.05 mmol) was added. After 2 h, the residue was diluted with methylene chloride (20 mL) and washed with water (40 mL) and brine (40 mL). The organic layer was dried over anhydrous MgSO$_4$ and concentrated in vacuo. The crude was purified by silica gel flash column chromatography (1:1 hexanes/ethyl acetate) to give E3.

(R)-(3,5-Dinitrophenyl)(3-(4-methoxyphenylamino) pyrrolidin-1-yl)methanone (103)

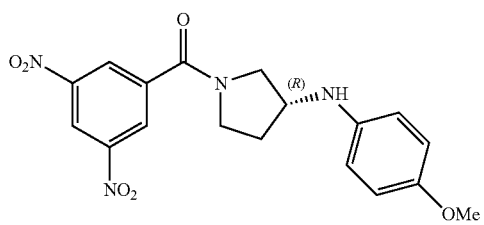

(Two rotamers, 1:1 ratio, 63%), a brown solid; $^1$H NMR (400 MHz, CDCl$_3$+CD$_3$OD) δ 1.93-2.01 (m, 1H), 2.14-2.30 (m, 1H), 3.26-3.30 & 3.44-3.50 (m, 1H), 3.54-3.72 (m, 2H), 3.61 & 3.68 (s, 3H), 3.80-3.91 (m, 1H), 3.95-4.05 (m, 1H), 6.43 & 6.55 (d, J=8.8 Hz, 2H), 6.62 & 6.70 (d, J=8.8 Hz, 2H), 8.58 & 8.67 (d, J=2.4 Hz, 2H), 8.95-8.99 (m, 1H); $^{13}$C NMR (100 MHz, CDCl$_3$+CD$_3$OD) δ 30.4, 32.4, 45.2, 47.9, 52.6, 53.0, 54.4, 55.0, 55.8, 55.9, 115.0, 115.1, 115.2, 115.3, 120.1, 127.6, 127.7, 139.6, 140.5, 140.7, 148.5, 148.6, 152.8, 152.9, 165.2, 165.4.

(R)-(3-(4-Butoxyphenylamino)pyrrolidin-1-yl)(3,5-dinitrophenyl)methanone (104)

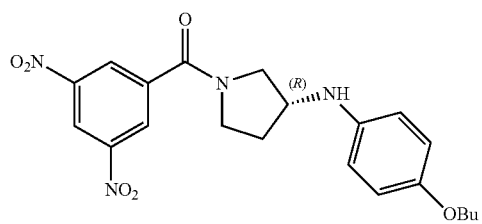

(Two rotamers, 1:1 ratio, 54%), a brown solid; m.p. 118-120 D; $^1$H NMR (400 MHz, CDCl$_3$) δ 0.83-0.98 (m, 3H), 1.39-1.52 (m, 2H), 1.61-1.76 (m, 2H), 2.02-2.05 (m, 1H), 2.24-2.41 (m, 1H), 3.33-3.37 & 3.50-3.63 (m, 2H), 3.66-4.13 (m, 6H), 6.47 & 6.60 (d, J=8.4 Hz, 2H), 6.70 & 6.78 (d, J=8.4 Hz, 2H), 8.66 & 8.74 (s, 2H), 9.05 & 9.08 (s, 1H); $^{13}$C NMR (100 MHz, CDCl$_3$) δ 14.0, 14.1, 19.4, 19.5, 30.9, 31.6, 31.7, 32.9, 45.3, 47.9, 52.8, 53.4, 54.6, 55.2, 68.5, 68.6, 115.0, 115.2, 116.0, 116.2, 120.2, 127.8, 127.9, 139.9, 140.1, 140.4, 148.6, 152.7, 164.9, 165.1.

(R)-(3,5-Dinitrophenyl)(3-(4-phenoxyphenylamino) pyrrolidin-1-yl)methanone (105)

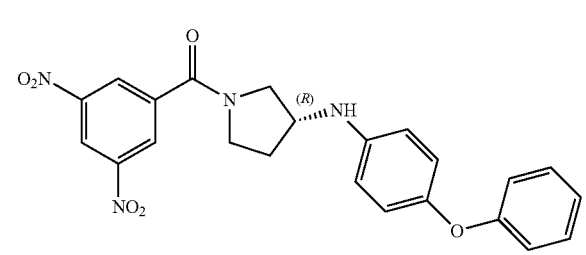

(Two rotamers, 1:1 ratio, 60%), a brown solid; $^1$H NMR (400 MHz, CDCl$_3$+CD$_3$OD) δ 2.00-2.06 (m, 1H), 2.18-2.35 (m, 1H), 3.32-3.35 & 3.48-3.54 (m, 1H), 3.61-3.78 (m, 2H), 3.82-4.12 (m, 2H), 6.47 & 6.60 (d, J=8.8 Hz, 2H), 6.77-6.97 (m, 5H), 7.17, 7.24 (m, 2H), 8.63 & 8.69 (d, J=1.6 Hz, 2H), 9.01 & 9.04 (s, 1H); $^{13}$C NMR (100 MHz, CDCl$_3$+CD$_3$OD) δ 30.6, 32.5, 45.3, 47.9, 52.3, 53.0, 54.0, 55.1, 114.5, 114.8, 117.4, 117.5, 120.2, 121.3, 121.4, 122.4, 122.5, 127.7, 127.8, 129.7, 139.6, 142.8, 143.0, 148.6, 148.8, 165.2, 165.3.

(R)-(3,5-Dinitrophenyl)(3-(4-hydroxyphenylamino) pyrrolidin-1-yl)methanone (106)

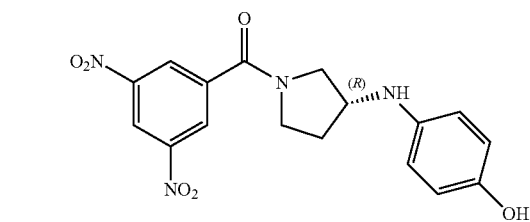

(Two rotamers, 1:1 ratio, 83%), a yellow solid; $^1$H NMR (400 MHz, DMSO-d$_6$) δ 1.78-1.89 (m, 1H), 2.03-2.15 (m, 1H), 3.12-3.17 (m, 1H), 3.37-3.45 (m, 1H), 3.52-3.95 (m, 3H), 5.15-5.23 (m, 1H), 6.36-6.56 (m, 4H), 8.38 & 8.44 (brs, 1H), 8.64 & 8.67 (s, 2H), 8.81 & 8.84 (s, 1H); $^{13}$C NMR (100 MHz, DMSO-d$_6$) δ 29.6, 31.3, 44.6, 46.9, 51.6, 51.9, 53.3, 54.1, 113.8, 114.2, 115.6, 115.7, 119.4, 127.4, 127.5, 139.6, 139.7, 140.3, 140.4, 148.0, 148.1, 148.5, 148.7, 164.2.

(R)-(3,5-Dinitrophenyl)(3-(phenylamino)pyrrolidin-1-yl)methanone (107)

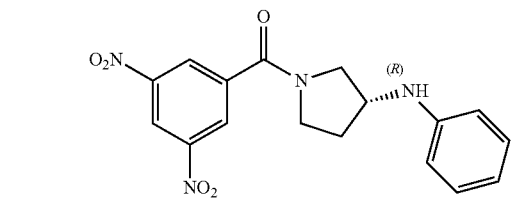

(Two rotamers, 1:1 ratio, 80%), a red solid; $^1$H NMR (400 MHz, CDCl$_3$+CD$_3$OD) δ 1.99-2.04 (m, 1H), 2.17-2.33 (m, 1H), 3.28-3.31 & 3.57-3.95 (m, 4H), 4.04-4.11 (m, 1H), 6.46-6.48 (m, 1H), 6.59-6.70 (m, 2H), 7.02-7.14 (m, 2H), 8.60 & 8.67 (s, 2H), 8.98 & 9.01 (s, 1H); $^{13}$C NMR (100 MHz, CDCl$_3$+CD$_3$OD) δ 30.3, 32.2, 45.1, 47.8, 51.7, 52.8, 53.3, 54.9, 113.2, 113.5, 118.3, 118.4, 120.0, 127.6, 127.7, 129.4, 139.5, 146.3, 146.4, 148.4, 148.5, 165.1, 165.3.

(R)-(3,5-Dinitrophenyl)(3-(pyridin-2-ylamino)pyrrolidin-1-yl)methanone (108)

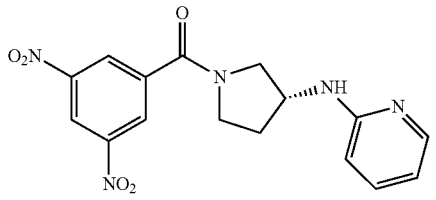

(Two rotamers, 1:1 ratio, 70%), a yellow solid; $^1$H NMR (400 MHz, CDCl$_3$) δ 2.00-2.44 (m, 2H), 3.38-4.11 (m, 4H), 4.38 & 4.50 (m, 1H), 6.36 & 6.44 (d, J=8.4 Hz, 1H), 6.57 & 6.64 (t, J=6.0 Hz, 1H), 7.37 & 7.44 (t, J=7.8 Hz, 1H), 7.98 & 8.11 (d, J=5.2 Hz, 1H), 8.67 & 8.73 (s, 2H), 9.05 & 9.09 (s, 1H); $^{13}$C NMR (100 MHz, CDCl$_3$) δ 30.4, 32.6, 45.1, 47.7, 51.7, 52.9, 55.3, 76.7, 101.8, 108.3, 113.7, 119.9, 127.7, 137.5, 137.7, 147.8, 147.9, 148.3, 148.4, 157.2, 157.4, 164.8, 164.9.

(R)-3-(Cyclohexylamino)pyrrolidin-1-yl)(3,5-dinitrophenyl)methanone (109)

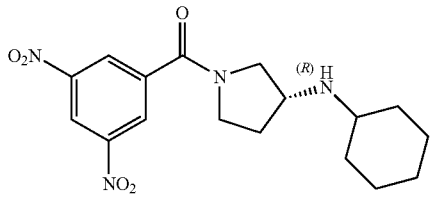

(Two rotamers, 1:1 ratio, 69%), a pale yellow solid; $^1$H NMR (400 MHz, CDCl$_3$+CD$_3$OD) 0.99-1.35 (m, 6H), 1.60-1.98 (m, 5H), 2.15-2.32 (m, 1H), 2.39-2.57 (m, 1H), 3.24-3.60 (m, 2H), 3.63-3.73 (m, 2H), 3.81-3.91 (m, 2H), 8.73 & 8.78 (s, 2H), 9.10 (s, 1H); $^{13}$C NMR (100 MHz, CDCl$_3$+CD$_3$OD) δ 24.7, 24.8, 24.9, 25.6, 25.7, 30.6, 32.4, 33.3, 33.4, 45.2, 47.7, 52.6, 54.5, 54.8, 54.9, 55.1, 119.7, 127.4, 127.5, 139.5, 148.3, 164.9, 165.0.

(R)—N-Cyclohexyl-N-(1-(3,5-dinitrobenzoyl)pyrrolidin-3-yl)-3,5-dinitrobenzamide (110)

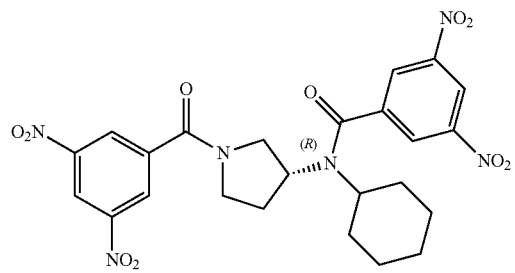

(Two rotamers, 1:1 ratio, 15%), a white solid; $^1$H NMR (400 MHz, CDCl$_3$) δ 1.01-1.22 (m, 3H), 1.62-1.86 (m, 6H), 2.18-2.26 (m, 1H), 2.74-2.89 (m, 1H), 3.30-3.35 (m, 1H), 3.50-3.78 (m, 2H), 3.97-4.19 (m, 4H), 8.51 & 8.56 (s, 2H), 8.74 (s, 2H), 9.09-9.10 (m, 2H); $^{13}$C NMR (100 MHz, CDCl$_3$) δ 24.8, 24.9, 25.3, 25.5, 27.3, 30.0, 31.8, 45.6, 48.7, 48.9, 50.0, 53.6, 54.8, 60.5, 119.8, 120.0, 126.7, 127.8, 139.8, 140.1, 140.2, 140.4, 148.6, 148.2, 164.4, 164.7, 166.6, 166.7.

(R)-(3-(4-Methoxyphenylamino)pyrrolidin-1-yl)(phenyl)methanone (111)

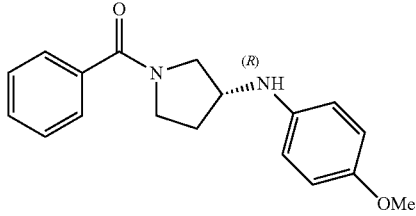

(Two rotamers, 1:1 ratio, 75%), a pale yellow solid; $^1$H NMR (400 MHz, CDCl$_3$) δ 1.84-1.88 (m, 1H), 2.08-2.32 (m, 1H), 3.26-3.34 & 3.49-4.03 (m, 5H), 3.69 & 3.72 (s, 3H), 6.48 & 6.50 (d, J=6.4 Hz, 2H), 6.71 & 6.76 (d, J=6.4 Hz, 2H), 7.36-7.51 (m, 5H); $^{13}$C NMR (100 MHz, CDCl$_3$) δ 30.7, 32.5, 44.5, 47.7, 52.6, 52.7, 54.2, 55.2, 55.8, 55.9, 114.7, 114.9, 115.0, 127.2, 128.3, 130.1, 136.7, 140.8, 141.0, 152.6, 170.0.

(R)-(3-(3-Chlorobenzylamino)pyrrolidin-1-yl)(3,5-dinitrophenyl)methanone (112)

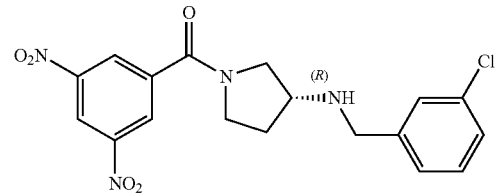

(Two rotamers, 1:1 ratio, 32%) as a pale yellow solid; $^1$H NMR (400 MHz, CDCl$_3$+CD$_3$OD) δ 1.83-1.89 (m, 1H), 2.01-2.08 & 2.14-2.19 (m, 1H), 2.75 (brs, 1H), 3.15-3.19 & 3.35-3.83 (m, 7H), 7.05-7.23 (m, 4H), 8.58 & 8.67 (d, J=2.0 Hz, 2H), 8.97-8.99 (m, 1H); $^{13}$C NMR (100 MHz, CDCl$_3$+CD$_3$OD) δ 30.4, 32.1, 45.2, 47.7, 51.2, 51.4, 52.4, 54.9, 55.2, 57.5, 119.8, 126.0, 126.2, 127.2, 127.3, 127.5, 127.6, 127.8, 128.0, 129.7, 129.8, 134.1, 134.2, 139.5, 139.6, 141.3, 141.7, 148.2, 148.3, 164.7, 164.8.

(R)—N-(3-Chlorobenzyl)-N-(1-(3,5-dinitrobenzoyl)pyrrolidin-3-yl)-3,5-dinitrobenzamide (113)

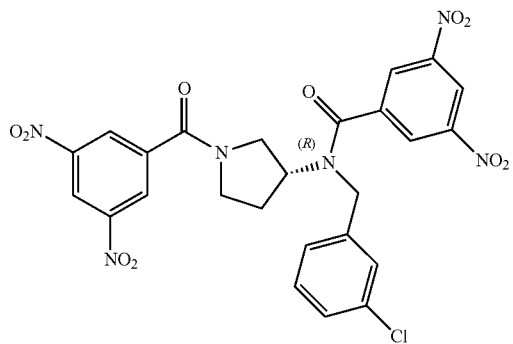

(Two rotamers, 1:1 ratio, 44%), a white solid; $^1$H NMR (400 MHz, CDCl$_3$) δ 2.26-2.35 (m, 2H), 3.56-4.05 (m, 4H), 4.57-4.65 (m, 3H), 7.06-7.15 (m, 2H), 7.24-7.35 (m, 2H), 8.50-8.62 (m, 4H), 8.97-9.02 (m, 2H); LC-MS (ESI, m/z): 599 [M+H]$^+$.

(R)-(3-(Benzylamino)pyrrolidin-1-yl)(3,5-dinitrophenyl)methanone (114)

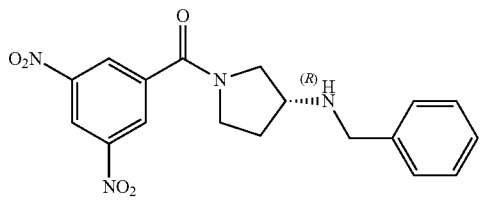

$^1$H NMR (400 MHz, CDCl$_3$) δ 1.59 (brs, 1H), 1.87-1.94 (m, 1H), 2.06-2.24 (m, 1H), 3.20 (dd, J=4.8, 10.4 Hz, 0.5H), 3.46-3.89 (m, 6.5H), 7.15-7.36 (m, 5H), 8.63 (d, J=2.0 Hz, 1H), 8.71 (d, J=2.0 Hz, 1H), 9.03 (t, J=2.0 Hz, 0.5H), 9.06 (t, J=2.0 Hz, 0.5H).

(R)-(3,5-Dinitrophenyl)(3-(3-(trifluoromethyl)benzylamino)pyrrolidin-1-yl)methanone (115)

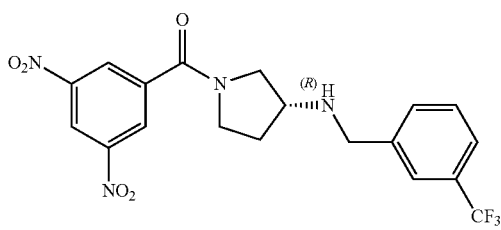

$^1$H NMR (400 MHz, CDCl$_3$) δ 1.51 (brs, 1H), 1.89-1.94 (m, 1H), 2.10-2.28 (m, 1H), 3.24 (dd, J=5.2, 10.0 Hz, 0.5H), 3.45-3.92 (m, 6.5H), 7.40-7.61 (m, 4H), 8.65 (d, J=2.0 Hz, 1H), 8.72 (d, J=2.0 Hz, 1H), 9.06 (t, J=2.0 Hz, 0.5H), 9.08 (t, J=2.0 Hz, 0.5H).

(R)-(3,5-Dinitrophenyl)(3-(2-fluorobenzylamino)pyrrolidin-1-yl)methanone (116)

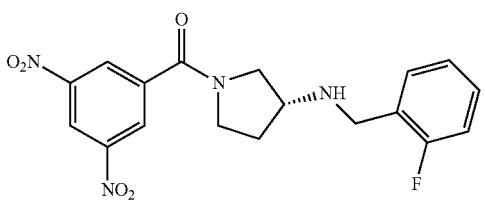 [SMILES: O=C(c1cc([N+](=O)[O-])cc([N+](=O)[O-])c1)N1CC[C@@H](NCc2ccccc2F)C1]

(Two rotamers, 1:1 ratio, 75%), a yellow solid; $^1$H NMR (400 MHz, CDCl$_3$) δ 1.89-1.94 (m, 1H), 2.11-2.25 (m, 1H), 3.22-3.89 (m, 7H), 6.93 & 7.02 (t, J=8.6 Hz, 2H), 7.20 & 7.33 (m, 2H), 8.66 & 8.72 (d, J=2.0 Hz, 2H), 9.06 (s, 1H); $^{13}$C NMR (100 MHz, CDCl$_3$) δ 30.7, 32.5, 45.3, 47.8, 51.3, 51.5, 52.7, 55.1, 55.4, 57.7, 115.1, 115.3, 119.8, 119.9, 127.6, 127.7, 129.4, 129.6, 135.4, 135.5, 139.8, 148.3, 148.4, 162.0 (d, J=245 Hz, due to F), 162.1 (d, J=245 Hz, due to F), 164.5, 164.6.

(R)-(3,5-Dinitrophenyl)(3-(2-fluorobenzylamino)pyrrolidin-1-yl)methanone hydrochloride (117)

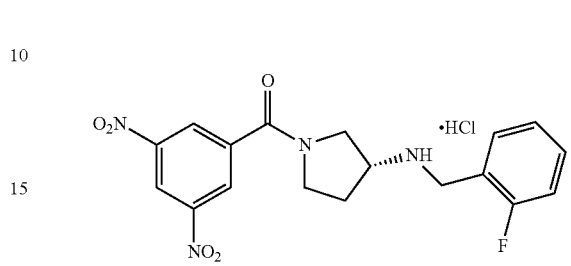

(Two rotamers, 1:1 ratio, 92%), a white solid; $^1$H NMR (400 MHz, CD$_3$OD+D$_2$O) δ 2.24-2.35 (m, 1H), 2.48-2.63 (m, 1H), 3.48-4.34 (m, 7H), 7.13 & 7.24 (t, J=8.6 Hz, 2H), 7.47 & 7.58 (q, J=7.0 Hz, 2H), 8.73 & 8.8 (d, J=2.0 Hz, 2H), 9.16 (brs, 1H); $^{13}$C NMR (100 MHz, CD$_3$OD+D$_2$O) δ 28.1, 29.7, 45.5, 50.6, 50.7, 51.9, 56.6, 57.7, 81.1, 117.0, 117.1, 127.7, 128.6, 128.7, 133.2, 133.3, 139.0, 147.1, 149.7, 167.5, 167.6.

(R)-(3,5-Dinitrophenyl)(3-(pyridin-4-ylmethylamino)pyrrolidin-1-yl)methanone (118)

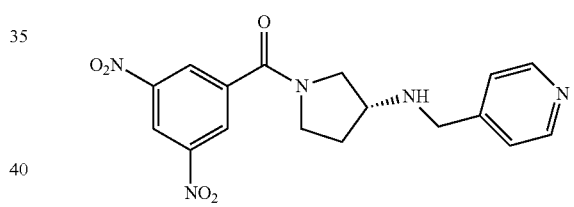

(Two rotamers, 1:1 ratio, 69%), a yellow solid; $^1$H NMR (400 MHz, CDCl$_3$) δ 1.80 (br, 1H), 1.88-2.23 (m, 2H), 3.23-3.89 (m, 7H), 7.17 & 7.26 (d, J=5.2 Hz, 2H), 8.45 & 8.52 (d, J=5.6 Hz, 2H), 8.65 & 8.69 (d, J=2.0 Hz, 2H), 9.04 (t, J=2.0 Hz, 1H); $^{13}$C NMR (100 MHz, CDCl$_3$) δ 30.2, 32.4, 44.7, 47.7, 52.4, 54.8, 55.9, 76.0, 115.0, 115.1, 117.2, 117.4, 124.4, 124.5, 127.0, 129.1, 130.6, 130.8, 137.5, 137.7, 150.8, 151.0, 154.7, 154.8, 168.5, 168.8.

Scheme 7

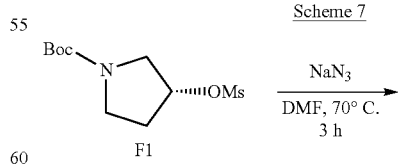

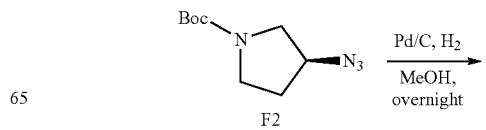

-continued

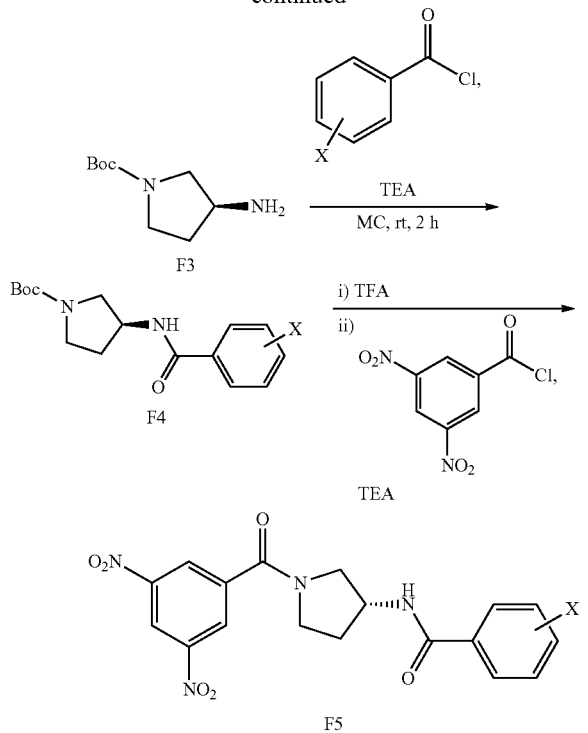

General Procedure for the Synthesis of (R)—N-benzoylpyrrolidinyl-benzamide (F5)

To a solution of F1 (3.77 mmol) in DMF (15 mL) was added sodium azide (11.00 mmol) and the resulting mixture was warmed to 70° C. After 3 h, the solvent was removed in vacuo, dissolved in ethylacetate (50 mL) and washed with water (50 mL) and brine (50 mL). The organic layer was dried over anhydrous $MgSO_4$ and concentrated in vacuo. The crude product was purified by silica gel flash column chromatography (1:1 hexanes/ethyl acetate) to give F2.

To a solution of F2 (2.68 mmol) was added 10% palladium on activated carbon and stirred overnight under hydrogen atmosphere. The reaction mixture was filtered using cellite 545 and the resulting filtrate was concentrated in vacuo to give F3.

To a solution of F3 (0.77 mmol) and triethylamine (1.16 mmol) in methylene chloride (10 mL) was added benzoyl chloride (1.00 mmol) under ice bath. The reaction mixture was brought up to room temperature. After 2 h, the reaction mixture was diluted with methylene chloride (20 mL) and washed with water (30 mL) and brine (30 mL). The organic layer was dried over anhydrous $MgSO_4$ and concentrated in vacuo. The crude product was purified by silica gel flash column chromatography (2:1 hexanes/ethyl acetate) to give F4.

To a solution of F4 (0.59 mmol) in methylene chloride (10 mL) was added trifluoroacetic acid (0.5 mL) and stirred at room temperature. After 3 h, the solvent was removed in vacuo. The crude product was dissolved in methylene chloride (10 mL) and triethylamine (0.41 mL, 2.96 mmol) was added. The reaction mixture was cooled to 0° C. and then 3,5-dichlorobenzoyl chloride (0.65 mmol) was added. The resulting mixture was brought up to room temperature. After 2 h, the solvent was removed in vacuo and the crude residue was purified by silica gel flash column chromatography (1:1 hexanes/ethyl acetate) to give F5.

(R)—N-(1-(3,5-Dinitrobenzoyl)pyrrolidin-3-yl)-3-(trifluoromethoxy)benzamide (119)

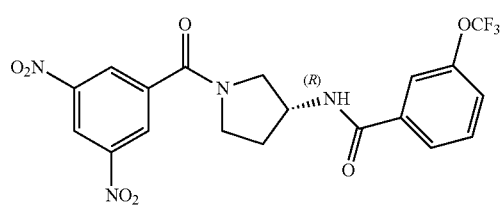

(Two rotamers, 1:1 ratio, 67%), a pale yellow solid; $^1$H NMR (400 MHz, $CDCl_3$) δ 2.07-2.18 (m, 1H), 2.29-2.40 (m, 1H), 3.49-3.60 (m, 1H), 3.68-3.76 (m, 1H), 3.87-3.98 (m, 2H), 4.60-4.74 (m, 1H), 7.19-7.60 (m, 5H), 8.51 & 8.59 (s, 2H), 8.91 & 8.96 (s, 1H); $^{13}$C NMR (100 MHz, $CDCl_3$) δ 29.9, 32.5, 45.3, 48.0, 49.2, 50.8, 51.9, 54.8, 119.9, 120.0, 120.2, 124.3, 125.7, 127.6, 130.2, 135.7, 136.0, 139.4, 148.4, 148.5, 149.2, 164.9, 165.0, 166.5, 166.6.

(R)—N-(1-(3,5-Dinitrobenzoyl)pyrrolidin-3-yl)-4-methoxybenzamide (120)

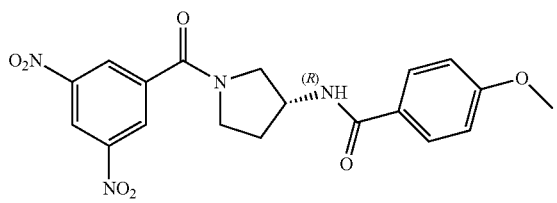

(Two rotamers, 1:1 ratio, 0.19 g, 76%), a white solid; $^1$H NMR (400 MHz, $CDCl_3$) δ 2.08-2.15 (m, 1H), 2.35-2.47 (m, 1H), 3.47-4.08 (m, 4H), 3.81 & 3.84 (s, 3H), 4.62-4.64 & 4.77-4.78 (m, 1H), 6.45 & 6.50 (brs, 1H), 6.82 & 6.88 (d, J=8.4 Hz, 2H), 7.62 & 7.72 (d, J=8.4 Hz, 2H), 8.62 & 8.71 (s, 2H), 9.04 & 9.08 (s, 1H); $^{13}$C NMR (100 MHz, $CDCl_3$) δ 30.0, 32.8, 45.2, 48.0, 48.9, 50.5, 52.2, 55.2, 55.6, 60.6, 113.9, 120.2, 125.6, 126.1, 127.7, 127.8, 129.0, 139.5, 148.5, 162.7, 164.9, 165.0, 167.4.

(R)-3-Chloro-N-(1-(3,5-dinitrobenzoyl)pyrrolidin-3-yl)benzamide (121)

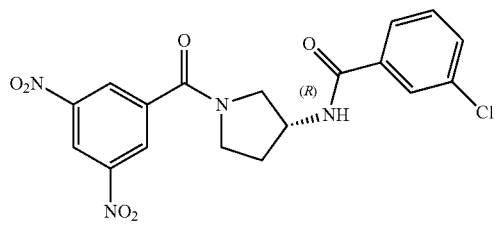

(Two rotamers, 1:1 ratio, 66%), a pale yellow solid; $^1$H NMR (400 MHz, DMSO-$d_6$) δ 1.94-2.20 (m, 2H), 3.33-3.83

(m, 4H), 4.42-4.55 (m, 1H), 7.43-7.60 (m, 2H), 7.71-7.90 (m, 2H), 8.66 & 8.69 (d, J=2.0 Hz, 2H, brs, 1H), 8.83-8.86 (m, 1H); $^{13}$C NMR (100 MHz, DMSO-$d_6$) δ 29.3, 31.5, 44.6, 47.0, 48.4, 49.9, 51.1, 53.3, 119.4, 119.5, 126.2, 126.3, 127.0, 127.1, 127.5, 130.2, 130.3, 131.1, 133.0, 133.1, 136.1, 136.3, 139.5, 139.6, 148.0, 164.0, 164.1, 165.0, 165.1.

(S)-1-(3,5-Dinitrobenzoyl)pyrrolidin-3-yl methanesulfonate (122)

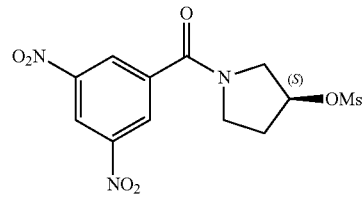

(Two rotamers, 1:1 ratio, 92%), a white solid; m.p. 138-140 µl; $^1$H NMR (400 MHz, CDCl$_3$) δ 2.25-2.46 (m, 2H), 3.03 & 3.10 (s, 3H), 3.59-3.67 & 3.75-4.03 (m, 4H), 5.28-5.40 (m, 1H), 8.68 & 8.73 (s, 2H), 9.08 (s, 1H); $^{13}$C NMR (100 MHz, CDCl$_3$) δ 31.1, 33.6, 38.9, 39.0, 44.7, 47.2, 53.3, 55.3, 78.2, 78.6, 120.5, 127.8, 127.9, 139.3, 148.7, 164.8, 165.0; LC-MS (ESI, m/z): 360 [M+H]$^+$.

(R)-1-(3,5-Dinitrobenzoyl)pyrrolidin-3-yl methanesulfonate (123)

(Two rotamers, 1:1 ratio, 89%), a white solid; $^1$H NMR (400 MHz, CDCl$_3$+CD$_3$OD) δ 2.16-2.32 (m, 2H), 2.94 & 3.02 (s, 3H), 3.50-3.91 (m, 4H), 5.19-5.30 (m, 1H), 8.58 & 8.63 (s, 2H), 8.97 (s, 1H); $^{13}$C NMR (100 MHz, CDCl$_3$+CD$_3$OD) δ 30.7, 33.1, 38.3, 38.4, 44.5, 46.9, 53.0, 55.0, 78.5, 79.0, 120.1, 127.6, 139.0, 148.4, 164.9, 165.0.

Example 7

Derivatization of the Pyridopyrimidinone Compounds

The pyridopyrimidinone compounds (scaffold VIII; see Table 2) underwent derivatization according to the methods outlined below (Schemes 8-10). Resulting derivatives were examined for inhibitory activity using the assay described above and the results are summarized in Table 3.

Scheme 8
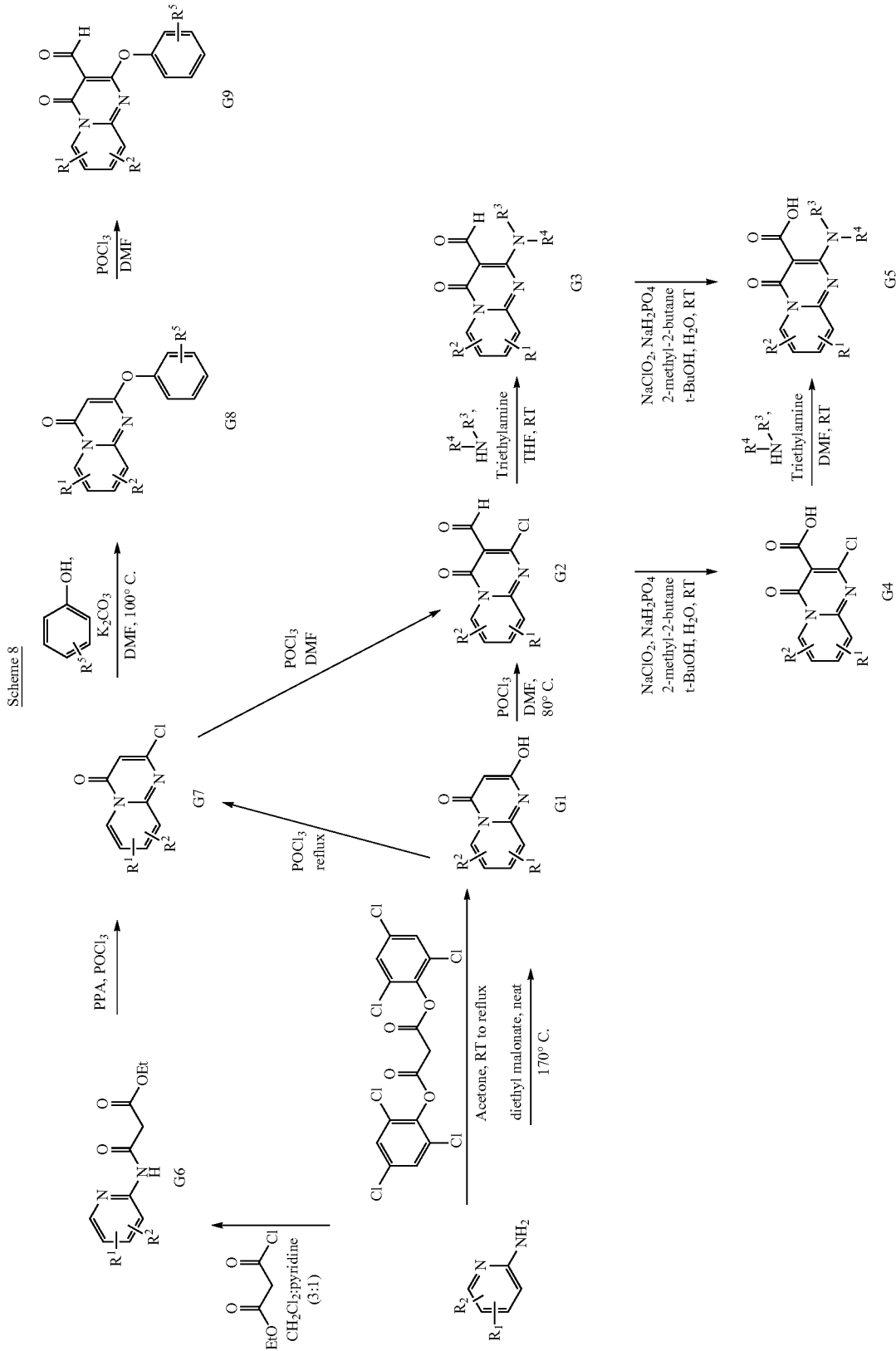

General Procedure for the Synthesis of G1

2-Amino-3-picoline (1.0 mmol) was dissolved in diethyl malonate (1.0 mmol). The solution was heated to 170° C. for 12 h. After cooling, the dark residue was triturated with $CH_2Cl_2$ (10 mL). The residual pale solid was collected by filtration and washed with $CH_2Cl_2$ to give G1.

General Procedure for the Synthesis of G2

To a DMF (2.0 mL) was added $POCl_3$ (3.0 mmol) at 0° C. After the mixture was stirred at 0° C. for 40 min, a solution of G1 (1.0 mmol) in DMF (2.0 mL) was added and stirred at 80° C. for 1 h. The mixture was cooled and concentrated in vacuo. The residue was diluted with water and extracted with $CH_2Cl_2$ (10 mL×3). The combined organic layers were washed with brine, dried over $MgSO_4$ and concentrated. The residue was purified by flash column chromatography to give G2.

General Procedure for the Synthesis of G3

To a stirred solution of G2 (1.0 mmol) in THF (2.0 mL) was added $Et_3N$ (2.0 mmol). The mixture was cooled to 0° C. After 5 min, an amine (1.0 mmol) was added dropwise and the mixture was stirred at room temperature overnight. The reaction mixture was diluted with $CH_2Cl_2$ (10 mL) and washed with brine (10 mL). The organic layer was dried over anhydrous $MgSO_4$ and concentrated in vacuo. The crude product was purified by flash column chromatography to give G3.

General Procedure for the Synthesis of G4

G2 (0.5 mmol) was dissolved in 10.4 mL of tert-butyl alcohol and 2.5 mL of 2-methyl-2-butene. A solution of sodium chlorite (4.59 mmol) and sodium dihydrogenphosphate (3.46 mmol) in 4.2 mL of water was added dropwise. The reaction mixture was stirred at room temperature overnight. Volatile components were then removed under vacuum, and the residue was dissolved in 10 ml of water and extracted with two 10 ml portions of hexane. The aqueous layer was acidified to pH=3 with HCl(aq) and extracted with 10 mL portions of methylene chloride. The combined organic layers were washed with 20 mL of cold water, dried and concentrated to give G4.

General Procedure for the Synthesis of G5 from G3

G3 (36.6 μmol) was dissolved in 760 μl of tert-butyl alcohol and 180 μl of 2-methyl-2-butene. A solution of sodium chlorite (335 μmol) and sodium dihydrogenphosphate (253 μmol) in 300 μl of water was added dropwise. The reaction mixture was stirred at room temperature overnight. Volatile components were then removed under vacuum and the residue was dissolved in 10 ml of water and extracted with two 10 ml portions of hexane. The aqueous layer was acidified to pH=3 with HCl(aq) and extracted with 10 ml portions of methylene chloride. The combined organic layers were washed with 20 ml of cold water, dried and concentrated to give G5.

General Procedure for the Synthesis of G5 from G4

To a stirred solution of G4 (1.0 mmol) in DMF (2.0 mL) was added $Et_3N$ (2.0 mmol) and amine (1.5 mmol) and the mixture was stirred at 60° C. overnight. The reaction mixture was diluted with $CH_2Cl_2$ (10 mL) and washed with brine (10 ml). The organic layer was dried over anhydrous $MgSO_4$ and concentrated in vacuo. The crude product was purified by recrystallization from a mixture of hexanes and methylene chloride to give G5.

General Procedure for the Synthesis of G6

The solution of 2-amino-3-picoline (4.0 mmol) in a solution of $CH_2Cl_2$ (3 mL) and dried pyridine (1 mL) was added dropwise at room temperature to a stirred solution of ethyl 3-chloro-3-oxo-propionate (5.3 mmol) in $CH_2Cl_2$ (3 mL) (an exothermic reaction with emission of white fume occurred during the addition). The resulting warm mixture was stirred at room temperature for 30 min and then poured into 30 mL of cold water; an excess of sodium carbonate was carefully added with stirring and the mixture was further stirred at room temperature for 1 h. The organic layer was then collected and the aqueous phase was extracted several times with $CH_2Cl_2$. The combined organic layers were washed with water, dried over anhydrous $Na_2SO_4$, and concentrated in vacuo. The crude product was purified by flash column chromatography to give G6.

General Procedure for the Synthesis of G7

A mixture of G6 (1.83 mmol), $POCl_3$ (0.5 mL) and polyphosphoric acid (137 mg) was heated with stirring at 130° C. for 3 h. After cooling, anhydrous ethanol was added and the mixture was refluxed for 30 min, then allowed to cool. The mixture was treated with aqueous sodium carbonate and exhaustively extracted with $CH_2Cl_2$ (10 mL×3). The combined layers were washed with water (10 mL), brine (10 mL), dried over $MgSO_4$, filtered and concentrated in vacuo. The crude product was purified by flash column chromatography to give G7.

General Procedure for the Synthesis of G8

To a solution of G6 (1 mmol) in DMF (0.96 mL) was added potassium carbonate (5.0 mmol) followed by phenol (1.94 mmol). After 12 h at 100° C., the solution was allowed to cool to 23° C. The reaction mixture was washed with $H_2O$ (50 mL), and the aqueous layer was extracted with $CH_2Cl_2$ (20 mL×3). The combined organic layers were washed with 1 N HCl (20 mL×2), filtered, and concentrated in vacuo. The crude product was purified by flash column chromatography to give G8.

General Procedure for the Synthesis of G9

To DMF (2.0 mL) was added $POCl_3$ (3.0 mmol) at 0° C. After the mixture was stirred at 0° C. for 40 min, a solution of G8 (1.0 mmol) in DMF (2.0 mL) was added and stirred at 80° C. for 1 h. The mixture was cooled and concentrated in vacuo. The residue was diluted with water and extracted with $CH_2Cl_2$ (10 mL×3). The combined organic layers were washed with brine, dried over $MgSO_4$ and concentrated. The residue was purified by flash column chromatography to give G9.

Ethyl 3-(3-methylpyridin-2-ylamino)-3-oxopropanoate (124)

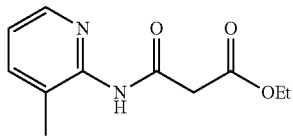 [SMILES: CCOC(=O)CC(=O)Nc1ncccc1C]

$^1$H NMR (400 MHz, $CDCl_3$) δ 1.25 (t, J=7.0 Hz, 3H), 2.25 (s, 3H), 3.45 (s, 2H), 4.20 (q, J=7.2 Hz, 2H), 7.47 (d, J=8.4 Hz, 1H), 8.03 (d, J=8.4 Hz, 1H), 8.07 (s, 1H), 9.67 (brs, 1H); $^{13}$C NMR (100 MHz, $CDCl_3$) δ 13.9, 17.7, 42.6, 61.7, 113.8, 129.3, 138.8, 147.6, 148.8, 163.5, 168.4.

2-Hydroxy-9-methyl-4H-pyrido[1,2-a]pyrimidin-4-one (125)

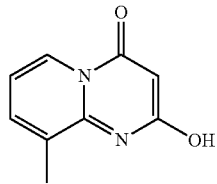

¹H NMR (400 MHz, DMSO-d₆) δ 2.48 (s, 3H), 5.44 (s, 1H), 7.20 (t, J=7.0 Hz, 1H), 7.87 (d, J=6.8 Hz, 1H), 8.84 (d, J=6.8 Hz, 1H), 11.52 (brs, 1H).

2-Hydroxy-8-methyl-4H-pyrido[1,2-a]pyrimidin-4-one (126)

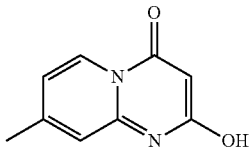

¹H NMR (400 MHz, DMSO-d₆) δ 2.50 (s, 3H), 4.88 (s, 1H), 7.20-7.24 (m, 2H), 8.85 (d, J=6.8 Hz, 1H), 11.98 (br s, 1H); ¹³C NMR (100 MHz, DMSO-d₆) δ 20.6, 80.3, 114.4, 117.1, 127.7, 146.7, 153.5, 155.3, 162.3.

2-Chloro-9-methyl-4H-pyrido[1,2-a]pyrimidin-4-one (127)

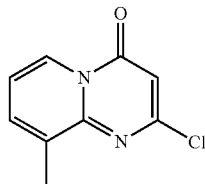

¹H NMR (400 MHz, CDCl₃) δ 2.57 (s, 3H), 6.45 (s, 1H), 7.12 (t, J=7.0 Hz, 1H), 7.68 (d, J=6.8 Hz, 1H), 8.93 (d, J=6.8 Hz, 1H); ¹³C NMR (100 MHz, CDCl₃) δ 18.0, 102.3, 115.8, 125.7, 134.7, 136.9, 150.0, 157.6, 157.9.

2-Chloro-9-methyl-4-oxo-4H-pyrido[1,2-a]pyrimidine-3-carbaldehyde (128)

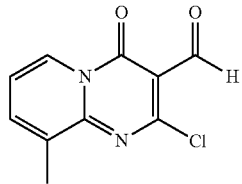

¹H NMR (400 MHz, CDCl₃) δ 2.64 (s, 3H), 7.30 (t, J=7.0 Hz, 1H), 7.92 (d, J=7.2 Hz, 1H), 9.10 (d, J=6.4 Hz, 1H), 10.42 (s, 1H); ¹³C NMR (100 MHz, CDCl₃) δ 17.7, 107.3, 117.7, 127.0, 135.6, 140.6, 150.0, 156.4, 160.2, 187.1.

2-Chloro-8-methyl-4-oxo-4H-pyrido[1,2-a]pyrimidine-3-carbaldehyde (129)

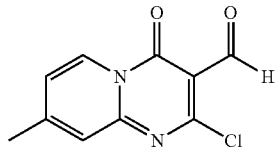

¹H NMR (400 MHz, CDCl₃) δ 2.59 (s, 3H), 7.24 (d, J=7.2 Hz, 1H), 7.52 (s, 1H), 9.09 (d, J=7.2 Hz, 1H), 10.40 (s, 1H).

2-Chloro-7-methyl-4-oxo-4H-pyrido[1,2-a]pyrimidine-3-carbaldehyde (130)

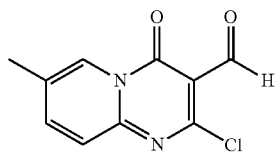

¹H NMR (400 MHz, DMSO-d₆) δ 2.32 (s, 3H), 7.49 (d, J=8.8 Hz, 1H), 7.78 (d, J=8.8 Hz, 1H), 8.79 (s, 1H), 10.16 (s, 1H).

2-Chloro-6-methyl-4-oxo-4H-pyrido[1,2-a]pyrimidine-3-carbaldehyde (131)

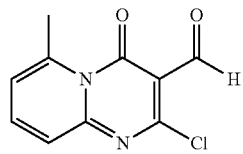

¹H NMR (400 MHz, CDCl₃) δ 3.11 (s, 3H), 6.98 (d, J=7.2 Hz, 1H), 7.51 (d, J=8.8 Hz, 1H), 7.79 (t, J=8.0 Hz, 1H), 10.29 (s, 1H).

9-Methyl-4-oxo-2-(phenylamino)-4H-pyrido[1,2-a]pyrimidine-3-carbaldehyde (132)

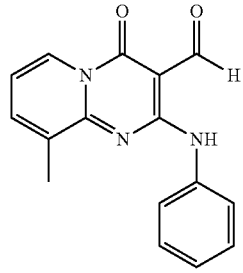 [SMILES: Cc1cccn2c(=O)c(C=O)c(Nc3ccccc3)nc12]

¹H NMR (400 MHz, CDCl₃) δ 2.44 (s, 3H), 6.89 (t, J=6.8 Hz, 1H), 7.11 (t, J=7.2 Hz, 1H), 7.34 (t, J=7.6 Hz, 2H), 7.62 (d, J=6.4 Hz, 1H), 7.76 (d, J=8.0 Hz, 2H), 8.80 (d, J=6.8 Hz, 1H), 10.27 (s, 1H), 11.67 (brs, 1H); ¹³C NMR (100 MHz, CDCl₃) δ 18.1, 94.6, 113.6, 121.8, 124.2, 125.9, 128.7, 133.6, 138.1, 138.9, 152.5, 153.8, 160.2, 190.2.

2-(3-Chlorophenylamino)-9-methyl-4-oxo-4H-pyrido[1,2-a]pyrimidine-3-carbaldehyde (133)

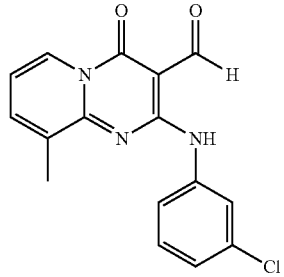 [SMILES: Cc1cccn2c(=O)c(C=O)c(Nc3cccc(Cl)c3)nc12]

¹H NMR (400 MHz, CDCl₃) δ 2.50 (s, 3H), 6.97 (t, J=6.8 Hz, 1H), 7.08 (d, J=8.0 Hz, 1H), 7.25 (t, J=8.0 Hz, 1H), 7.42 (d, J=8.0H, 1H), 7.69 (d, J=6.8 Hz, 1H), 8.18 (s, 1H), 8.84 (d, J=6.8 Hz, 1H), 10.27 (s, 1H), 11.72 (brs, 1H).

9-Methyl-4-oxo-2-(3-(trifluoromethoxy)phenylamino)-4H-pyrido[1,2-a]pyrimidine-3-carbaldehyde (134)

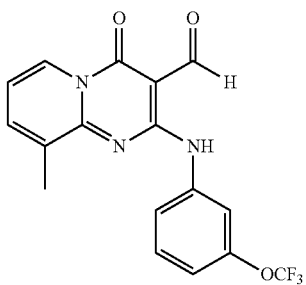 [SMILES: Cc1cccn2c(=O)c(C=O)c(Nc3cccc(OC(F)(F)F)c3)nc12]

¹H NMR (400 MHz, CDCl₃) δ 2.50 (s, 3H), 6.99 (t, J=7.0 Hz, 1H), 7.36 (t, J=8.0 Hz, 1H), 7.42 (d, J=8.0 Hz, 1H), 7.70 (d, J=6.8 Hz, 1H), 8.16 (s, 1H), 8.88 (d, J=8.0 Hz, 1H), 10.32 (s, 1H), 11.86 (brs, 1H); ¹³C NMR (100 MHz, CDCl₃) δ 18.0, 94.7, 114.2, 114.7, 116.5, 119.7, 126.1, 129.7, 133.8, 139.4, 139.7, 149.4, 152.6, 157.0, 160.1, 190.4.

9-Methyl-4-oxo-2-(3-(trifluoromethyl)phenylamino)-4H-pyrido[1,2-a]pyrimidine-3-carbaldehyde (135)

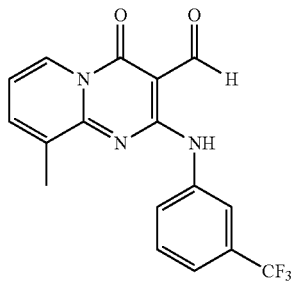

¹H NMR (400 MHz, CDCl₃) δ 2.49 (s, 1H), 6.98 (t, J=6.8 Hz, 1H), 7.37 (d, J=7.6 Hz, 1H), 7.45 (d, J=7.6 Hz, 1H), 7.61 (d, J=8.0 Hz, 1H), 7.70 (d, J=6.0 Hz, 1H), 8.61 (s, 1H), 8.87 (d, J=6.8 Hz, 1H), 10.30 (s, 1H), 11.85 (brs, 1H).

2-(4-tert-Butylphenylamino)-9-methyl-4-oxo-4H-pyrido[1,2-a]pyrimidine-3-carbaldehyde (136)

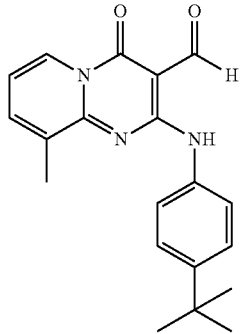 [SMILES: Cc1cccn2c(=O)c(C=O)c(Nc3ccc(C(C)(C)C)cc3)nc12]

¹H NMR (400 MHz, CDCl₃) δ 1.32 (s, 9H), 2.48 (s, 3H), 6.89 (t, J=7.0 Hz, 1H), 7.37 (d, J=8.4 Hz, 1H), 7.62 (d, J=6.8 Hz, 1H), 7.73 (d, J=8.8 Hz, 1H), 8.81 (d, J=7.2 Hz, 1H), 10.30 (s, 1H), 11.68 (br s, 1H); ¹³C NMR (100 MHz, CDCl₃) δ 18.2, 31.3, 34.3, 94.6, 113.5, 121.4, 125.6, 125.9, 133.6, 135.6, 138.8, 147.2, 152.6, 156.7, 160.4, 190.2.

2-(3-Chlorobenzylamino)-9-methyl-4-oxo-4H-pyrido[1,2-a]pyrimidine-3-carbaldehyde (137)

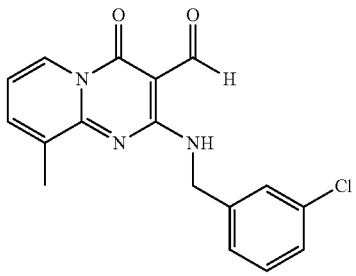 [SMILES: Cc1cccn2c(=O)c(C=O)c(NCc3cccc(Cl)c3)nc12]

¹H NMR (400 MHz, CDCl₃) δ 2.40 (s, 3H), 4.80 (d, J=6.0 Hz, 2H), 6.87 (t, J=7.0 Hz, 1H), 7.24-7.26 (m, 3H), 7.37 (s, 1H), 7.59 (d, J=6.8 Hz, 1H), 8.79 (d, J=7.2 Hz, 1H), 10.34 (brs, 1H), 10.30 (s, 1H).

9-Methyl-2-morpholino-4-oxo-4H-pyrido[1,2-a]pyrimidine-3-carbaldehyde (138)

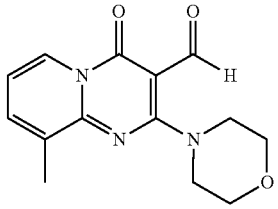 [SMILES: Cc1cccn2c(=O)c(C=O)c(N3CCOCC3)nc12]

¹H NMR (400 MHz, CDCl₃) δ 2.30 (s, 3H), 3.65 (d, J=2.4 Hz, 4H), 3.72 (d, J=3.2 Hz, 4H), 6.74-6.77 (m, 1H), 7.49 (d, J=6.8 Hz, 1H), 8.62 (d, J=7.2 Hz, 1H), 10.01 (s, 1H); ¹³C

NMR (100 MHz, CDCl$_3$) δ 17.6, 49.5, 67.0, 95.9, 112.9, 125.7, 133.0, 138.1, 150.5, 158.4, 162.3, 186.2

2-(4-(2-Chlorophenyl)piperazin-1-yl)-9-methyl-4-oxo-4H-pyrido[1,2-a]pyrimidine-3-carbaldehyde (139)

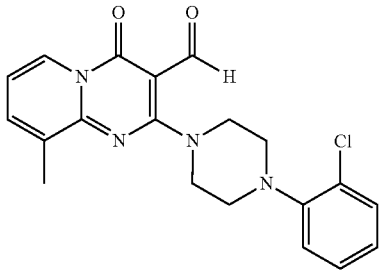 [SMILES: Cc1cccn2c(=O)c(C=O)c(N3CCN(c4ccccc4Cl)CC3)nc12]

$^1$H NMR (400 MHz, CDCl$_3$) δ 2.41 (s, 3H), 3.19 (t, J=4.8 Hz, 4H), 3.92 (t, J=4.6 Hz, 4H), 6.82 (t, J=7.0 Hz, 1H), 6.98 (t, J=7.6 Hz, 1H), 7.04 (d, J=7.2 Hz, 1H), 7.21 (t, J=7.6 Hz, 1H), 7.36 (d, J=7.6 Hz, 1H), 7.55 (d, J=6.4 Hz, 1H), 8.73 (d, J=6.8 Hz, 1H), 10.15 (s, 1H); $^{13}$C NMR (100 MHz, CDCl$_3$) δ 17.6, 49.3, 51.4, 96.1, 112.7, 120.5, 124.0, 125.8, 127.6, 128.8, 130.6, 133.0, 137.8, 148.7, 150.5, 158.6, 162.5, 186.4.

2-(3,4-Dihydroisoquinolin-2(1H)-yl)-9-methyl-4-oxo-4H-pyrido[1,2-a]pyrimidine-3-carbaldehyde (140)

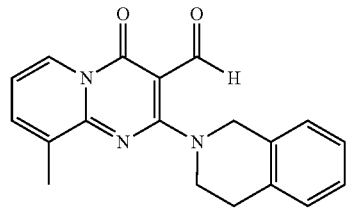 [SMILES: Cc1cccn2c(=O)c(C=O)c(N3CCc4ccccc4C3)nc12]

$^1$H NMR (400 MHz, CDCl$_3$) δ 2.43 (s, 3H), 3.05 (t, J=5.8 Hz, 2H), 4.03 (t, J=5.8 Hz, 2H), 4.73 (s, 2H), 6.78 (t, J=7.0 Hz, 1H), 7.06-7.17 (m, 4H), 7.52 (d, J=6.8 Hz, 1H), 8.70 (d, J=7.6 Hz, 1H), 10.21 (s, 1H); $^{13}$C NMR (100 MHz, CDCl$_3$) δ 17.6, 28.7, 46.3, 52.0, 96.1, 112.5, 125.8, 126.2, 126.6, 128.4, 133.0, 133.9, 134.6, 137.5, 150.3, 158.6, 162.3, 186.7.

2-(Isobutylamino)-9-methyl-4-oxo-4H-pyrido[1,2-a]pyrimidine-3-carbaldehyde (141)

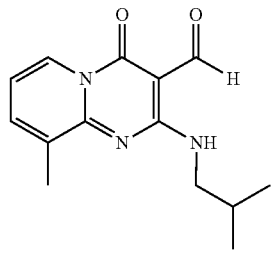 [SMILES: Cc1cccn2c(=O)c(C=O)c(NCC(C)C)nc12]

$^1$H NMR (400 MHz, CDCl$_3$) δ 0.95 (d, J=4 Hz, 6H), 1.90 (m, 1H), 2.37 (s, 3H), 3.41 (t, J=6.8 Hz, 2H), 6.76 (t, J=6.8 Hz, 1H), 7.24-7.52 (m, 1H), 8.69 (dd, J=0.8, 7.2 Hz, 1H), 9.67 (brs, 1H), 10.22 (s, 1H); $^{13}$C NMR (100 MHz, CDCl$_3$) δ 17.9, 20.4, 28.7, 48.1, 94.4, 112.5, 125.9, 133.2, 138.1, 152.8, 159.5, 160.7, 190.2.

2-(Diethylamino)-9-methyl-4-oxo-4H-pyrido[1,2-a]pyrimidine-3-carbaldehyde (142)

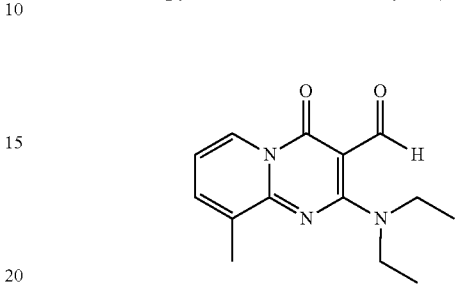

$^1$H NMR (400 MHz, CDCl$_3$) δ 1.25 (t, J=6.8 Hz, 6H), 2.36 (s, 3H), 3.65 (q, J=6.8 Hz, 4H), 6.72 (t, J=6.8 Hz, 1H), 7.47 (d, J=6.8 Hz, 1H), 8.65 (d, J=6.4 Hz, 1H), 10.12 (s, 1H); $^{13}$C NMR (100 MHz, CDCl$_3$) δ 13.2, 17.7, 45.3, 96.2, 112.2, 125.8, 133.0, 137.3, 150.2, 158.5, 162.6, 186.9.

2-(Cyclohexylmethylamino)-9-methyl-4-oxo-4H-pyrido[1,2-a]pyrimidine-3-carbaldehyde (143)

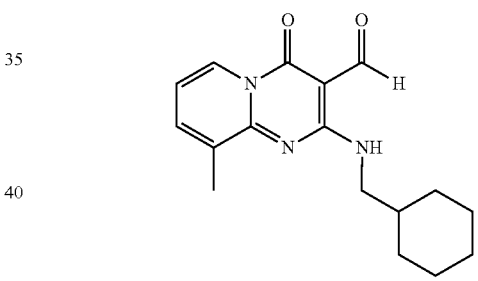

$^1$H NMR (400 MHz, CDCl$_3$) δ 0.93-1.02 (m, 2H), 1.11-1.25 (m, 3H), 1.57-1.77 (m, 6H), 2.36 (s, 3H), 3.43 (t, J=6.0 Hz, 2H), 6.75 (t, J=7.2 Hz, 1H), 7.50 (d, J=7.2 Hz, 1H), 8.67 (d, J=6.8 Hz, 1H), 9.65 (brs, 1H), 10.21 (s, 1H); $^{13}$C NMR (100 MHz, CDCl$_3$) δ 17.9, 26.0, 26.5, 31.1, 38.2, 47.0, 94.4, 112.5, 125.8, 133.2, 138.0, 152.8, 159.4, 160.6, 190.2

2-Chloro-9-methyl-4-oxo-4H-pyrido[1,2-a]pyrimidine-3-carboxylic acid (144)

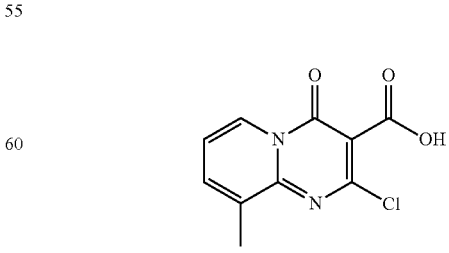

$^1$H NMR (400 MHz, DMSO-d$_6$) δ 2.58 (s, 3H), 7.53 (t, J=7.0 Hz, 1H), 8.14 (d, J=7.2 Hz, 1H), 8.97 (d. J=6.8 Hz, 1H), 13.53 (brs, 1H); ¹³C NMR (100 MHz, DMSO-d₆) δ 16.7, 108.1, 117.1, 125.6, 133.3, 138.7, 148.2, 152.0, 154.6, 163.9.

2-Chloro-7-methyl-4-oxo-4H-pyrido[1,2-a]pyrimidine-3-carboxylic acid (145)

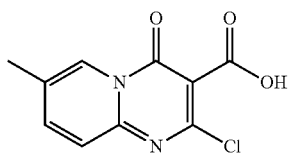 [SMILES: Cc1ccc2nc(Cl)c(C(=O)O)c(=O)n2c1]

¹H NMR (400 MHz, DMSO-d₆) δ 2.49 (s, 3H), 7.76 (d, J=8.8 Hz, 1H), 8.11 (d, J=8.8 Hz, 1H), 8.89 (s, 1H), 13.46 (br s, 1H).

2-Chloro-6-methyl-4-oxo-4H-pyrido[1,2-a]pyrimidine-3-carboxylic acid (146)

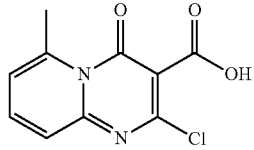 [SMILES: Cc1cccc2nc(Cl)c(C(=O)O)c(=O)n12]

¹H NMR (400 MHz, DMSO-d₆) δ 3.00 (s, 3H), 7.19 (d, J=7.6 Hz, 1H), 7.52 (d, J=8.0 Hz, 1H), 7.92 (t, J=8.0 Hz, 1H), 13.35 (br s, 1H).

9-Methyl-4-oxo-2-(phenylamino)-4H-pyrido[1,2-a]pyrimidine-3-carboxylic acid (147)

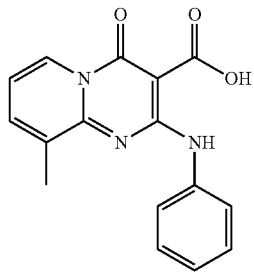 [SMILES: Cc1cccn2c(=O)c(C(=O)O)c(Nc3ccccc3)nc12]

¹H NMR (400 MHz, CDCl₃) δ 2.50 (s, 3H), 6.70 (dd, J=6.8, 7.2 Hz, 1H), 7.15 (dd, J=7.2, 7.2 Hz, 1H), 7.37 (dd, J=7.2, 7.6 Hz, 2H), 7.65 (d, J=6.8 Hz, 1H), 7.76 (d, J=8.4 Hz, 2H), 8.76 (d, J=7.2 Hz, 1H), 11.70 (brs, 1H), 14.31 (s, 1H).

2-(3-Chlorophenylamino)-9-methyl-4-oxo-4H-pyrido[1,2-a]pyrimidine-3-carboxylic acid (148)

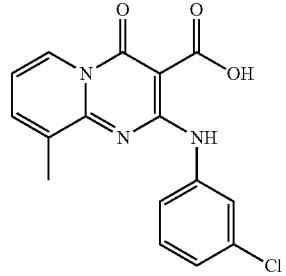 [SMILES: Cc1cccn2c(=O)c(C(=O)O)c(Nc3cccc(Cl)c3)nc12]

¹H NMR (400 MHz, DMSO-d₆) δ 2.55 (s, 3H), 7.04 (t, J=7.0 Hz, 1H), 7.12 (d, J=8.0 Hz, 1H), 7.28 (J=8.0 Hz, 1H), 7.71 (d, J=8.0 Hz, 1H), 8.17 (s, 1H), 8.79 (d, J=7.6 Hz, 1H), 11.78 (brs, 1H).

2-(3-Chlorophenylamino-8-methyl-4-oxo-4H-pyrido[1,2-a]pyrimidine-3-carboxylic acid (149)

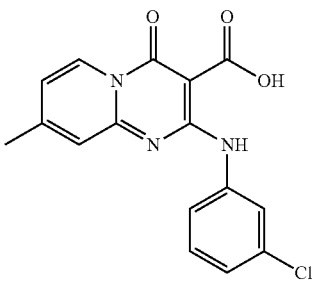 [SMILES: Cc1ccn2c(=O)c(C(=O)O)c(Nc3cccc(Cl)c3)nc2c1]

¹H NMR (400 MHz, CDCl₃) δ 2.49 (s, 3H), 6.93 (d, J=7.6 Hz, 1H), 7.12 (d, J=7.6 Hz, 1H), 7.25-7.29 (m, 2H), 7.46 (d, J=7.2 Hz, 1H), 7.96 (s, 1H), 8.76 (d, J=7.2 Hz, 1H), 11.72 (br s, 1H), 14.19 (s, 1H).

2-(3-Chlorophenylamino)-7-methyl-4-oxo-4H-pyrido[1,2-a]pyrimidine-3-carboxylic acid (150)

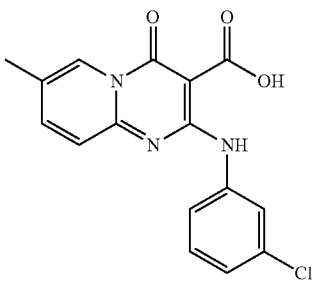 [SMILES: Cc1ccc2nc(Nc3cccc(Cl)c3)c(C(=O)O)c(=O)n2c1]

¹H NMR (400 MHz, CDCl₃) δ 2.41 (s, 3H), 7.12 (d, J=8.0 Hz, 1H), 7.27 (t, J=8.6 Hz, 1H), 7.41 (d, J=8.8 Hz, 1H), 7.47 (d, J=7.6 Hz, 1H), 7.96 (s, 1H), 8.68 (s, 1H), 11.70 (br s, 1H), 14.28 (s, 1H).

2-(3-Chlorophenylamino)-6-methyl-4-oxo-4H-pyrido[1,2-a]pyrimidine-3-carboxylic acid (151)

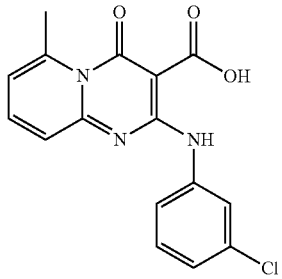 [SMILES: Cc1cccc2nc(Nc3cccc(Cl)c3)c(C(=O)O)c(=O)n12]

¹H NMR (400 MHz, CDCl₃) δ 3.03 (s, 3H), 6.70 (d, J=6.8 Hz, 1H), 7.10 (d, J=8.0 Hz, 1H), 7.23-7.27 (m, 2H), 7.44 (d, J=8.0 Hz, 1H), 7.56 (t, J=8.0 Hz, 1H), 7.91 (s, 1H), 11.76 (br s, 1H), 14.37 (s, 1H).

2-(3-Fluorophenylamino)-9-methyl-4-oxo-4H-pyrido[1,2-a]pyrimidine-3-carboxylic acid (152)

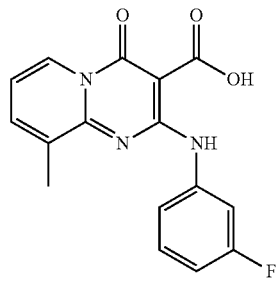 [SMILES: Cc1cccn2c(=O)c(C(=O)O)c(Nc3cccc(F)c3)nc12]

¹H NMR (400 MHz, CDCl₃) δ 2.54 (s, 3H), 6.81-6.87 (m, 1H), 7.03 (t, J=7.2 Hz, 1H), 7.28-7.31 (m, 2H), 7.71 (d, J=6.8 Hz, 1H), 7.89 (d, J=10.4 Hz, 1H), 8.79 (d, J=7.2 Hz, 1H), 11.83 (b s, 1H), 14.26 (br s, 1H).

9-Methyl-4-oxo-2-(3-(trifluoromethyl)phenylamino)-4H-pyrido[1,2-a]pyrimidine-3-carboxylic acid (153)

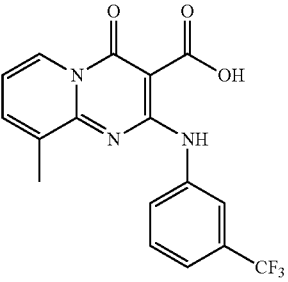 [SMILES: Cc1cccn2c(=O)c(C(=O)O)c(Nc3cccc(C(F)(F)F)c3)nc12]

¹H NMR (400 MHz, CDCl₃) δ 2.54 (s, 3H), 7.05 (t, J=7.0 Hz, 1H), 7.40 (d, J=7.6 Hz, 1H), 7.47 (t, J=8.0 Hz, 1H), 7.61 (d, J=8.0 Hz, 1H), 7.73 (d, J=6.8 Hz, 1H), 8.58 (s 1H), 8.81 (d, J=6.8 Hz, 1H), 11.91 (br s, 1H).

9-Methyl-4-oxo-2-(3-(trifluoromethoxy)phenylamino)-4H-pyrido[1,2-a]pyrimidine-3-carboxylic acid (154)

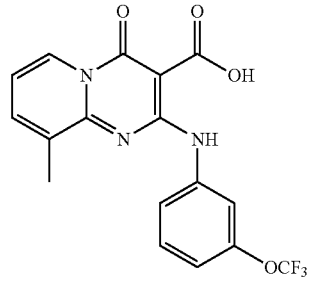 [SMILES: Cc1cccn2c(=O)c(C(=O)O)c(Nc3cccc(OC(F)(F)F)c3)nc12]

¹H NMR (400 MHz, CDCl₃) δ 2.58 (s, 3H), 7.00 (d, J=8.0 Hz, 1H), 7.05 (t, J=7.0 Hz, 1H), 7.36 (t, J=8.0 Hz, 1H), 7.42 (d, J=8.0 Hz, 1H), 7.72 (d, J=6.8 Hz, 1H), 8.09 (s, 1H), 8.81 (d, J=7.2 Hz, 1H), 11.89 (br s, 1H), 14.26 (br s, 1H).

9-Methyl-2-(3-nitrophenylamino)-4-oxo-4H-pyrido[1,2-a]pyrimidine-3-carboxylic acid (155)

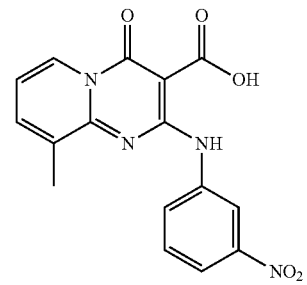

¹H NMR (400 MHz, DMSO-d₆) δ 2.60 (s, 3H), 7.40 (t, J=7.0 Hz, 1H), 7.73 (t, J=8.2 Hz, 1H), 7.96 (d, J=7.6 Hz, 1H), 8.02 (d, J=7.6 Hz, 1H), 8.13 (d, J=6.8 Hz, 1H), 8.90 (d, J=7.2 Hz, 1H), 9.33 (s, 1H), 11.84 (br s, 1H), 14.43 (br s, 1H).

2-(3-(Methoxycarbonyl)phenylamino)-9-methyl-4-oxo-4H-pyrido[1,2-a]pyrimidine-3-carboxylic acid (156)

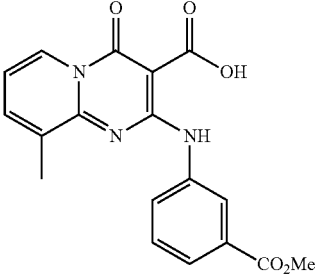 [SMILES: COC(=O)c1cccc(Nc2nc3c(C)cccn3c(=O)c2C(=O)O)c1]

¹H NMR (400 MHz, CDCl₃) δ 2.57 (s, 3H), 3.92 (s, 3H), 7.052 (t, J=6.8 Hz, 1H), 7.43 (t, J=8.0 Hz, 1H), 7.71 (t, J=7.0

Hz, 2H), 7.82 (d, J=8.0 Hz, 1H), 8.79 (d, J=6.8 Hz, 1H), 8.83 (s, 1H), 11.83 (br s, 1H), 14.28 (br s, 1H).

2-(3-Hydroxyphenylamino)-9-methyl-4-oxo-4H-pyrido[1,2-a]pyrimidine-3-carboxylic acid (157)

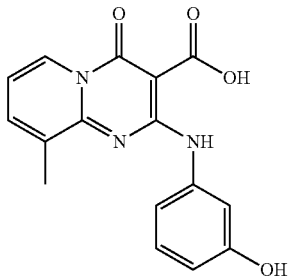 [SMILES: Cc1cccn2c(=O)c(C(=O)O)c(Nc3cccc(O)c3)nc12]

$^1$H NMR (400 MHz, CD$_3$OD) δ 2.55 (s, 3H), 6.61 (d, J=8.0 Hz, 1H), 7.15-7.24 (m, 3H), 7.34 (s, 1H), 7.88 (d, J=6.8 Hz, 1H), 8.82 (d, J=7.2 Hz, 1H).

2-(4-Hydroxyphenylamino)-9-methyl-4-oxo-4H-pyrido[1,2-a]pyrimidine-3-carboxylic acid (158)

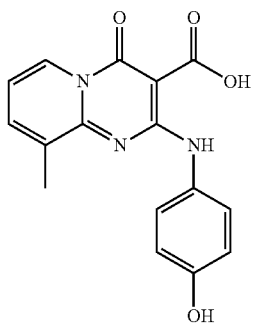 [SMILES: Cc1cccn2c(=O)c(C(=O)O)c(Nc3ccc(O)cc3)nc12]

$^1$H NMR (400 MHz, CD$_3$OD) δ 2.45 (s, 3H), 6.81 (d, J=8.8 Hz, 2H), 7.10 (t, J=7.0 Hz, 1H), 7.57 (d, J=8.8 Hz, 1H), 7.81 (d, J=6.8 Hz, 1H), 8.78 (d, J=7.2 Hz, 1H), 11.26 (br s, 1H).

2-(4-tert-Butylphenylamino)-9-methyl-4-oxo-4H-pyrido[1,2-a]pyrimidine-3-carboxylic acid (159)

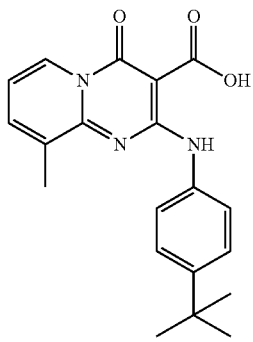 [SMILES: Cc1cccn2c(=O)c(C(=O)O)c(Nc3ccc(C(C)(C)C)cc3)nc12]

$^1$H NMR (400 MHz, CDCl$_3$) δ 1.33 (s, 9H), 2.49 (s, 3H), 6.95 (t, J=7.0 Hz, 1H), 7.37 (d, J=7.2 Hz, 2H), 7.63 (d, J=5.6 Hz, 1H), 7.69 (d, J=6.8 Hz, 2H), 8.71 (d, J=6.8 Hz, 1H), 11.64 (br s, 1H) 14.31 (br s, 1H); $^{13}$C NMR (100 MHz, CDCl$_3$) δ 18.2, 31.3, 34.4, 85.3, 114.1, 121.3, 125.5, 125.7, 133.6, 135.4, 138.2, 147.4, 150.2, 157.0, 161.8, 169.7.

2-(3-Chlorobenzylamino)-9-methyl-4-oxo-4H-pyrido[1,2-a]pyrimidine-3-carboxylic acid (160)

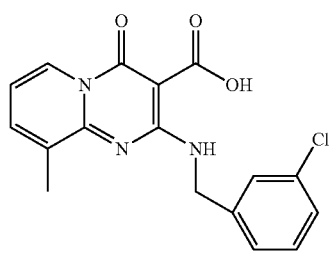 [SMILES: Cc1cccn2c(=O)c(C(=O)O)c(NCc3cccc(Cl)c3)nc12]

$^1$H NMR (400 MHz, CDCl$_3$) δ 2.38 (s, 3H), 4.83 (d, J=6.0 Hz, 2H), 7.17 (t, J=7.0 Hz, 1H), 7.32-7.40 (m, 3H), 7.50 (s, 1H), 7.89 (d, J=6.8 Hz, 1H), 8.68 (d, J=7.2 Hz, 1H), 9.82 (d, J=6.2 Hz, 1H), 14.25 (br s, 1H).

2-(Diethylamino)-9-methyl-4-oxo-4H-pyrido[1,2-a]pyrimidine-3-carboxylic acid (161)

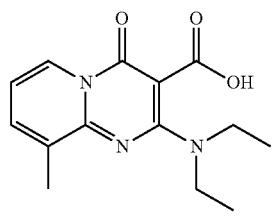 [SMILES: CCN(CC)c1nc2c(C)cccn2c(=O)c1C(=O)O]

$^1$H NMR (400 MHz, CDCl$_3$) δ 1.32 (t, J=6.8 Hz, 6H), 2.41 (s, 3H), 3.68 (q, J=6.8 Hz, 4H), 6.67 (t, J=7.2 Hz, 1H), 7.38 (d, J=6.8 Hz, 1H), 8.71 (d, J=7.2 Hz, 1H), 14.08 (s, 1H); $^{13}$C NMR (100 MHz, CDCl$_3$) δ 13.8, 17.8, 45.4, 96.2, 112.2, 125.8, 133.0, 137.3, 150.2, 158.5, 162.6, 171.6.

2-(Isobutylamino)-9-methyl-4-oxo-4H-pyrido[1,2-a]pyrimidine-3-carboxylic acid (162)

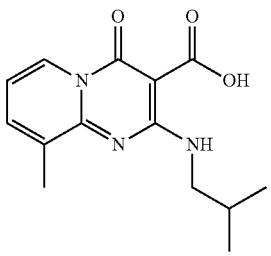 [SMILES: Cc1cccn2c(=O)c(C(=O)O)c(NCC(C)C)nc12]

$^1$H NMR (400 MHz, CDCl$_3$) δ 0.97 (d, J=6.8 Hz, 6H), 1.93-1.99 (m, 1H), 2.40 (s, 3H), 3.43 (t, J=6.4 Hz, 2H), 6.84 (t, J=7.2 Hz, 1H), 7.53 (d, J=6.4 Hz, 1H), 8.62 (d, J=7.6 Hz, 1H), 9.52 (brs, 1H), 14.12 (s, 1H); $^{13}$C NMR (100 MHz, CDCl₃) δ 17.9, 20.4, 28.7, 48.6, 84.8, 113.2, 125.7, 133.2, 137.5, 150.5, 159.7, 162.0, 169.9.

2-(Cyclohexylmethylamino)-9-methyl-4-oxo-4H-pyrido[1,2-a]pyrimidine-3-carboxylic acid (163)

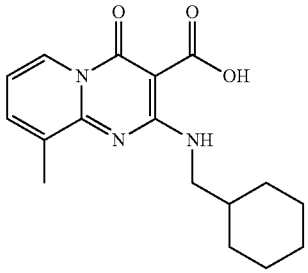 [SMILES: Cc1cccn2c(=O)c(C(=O)O)c(NCC3CCCCC3)nc12]

¹H NMR (400 MHz, CDCl₃) δ 0.98-1.05 (m, 2H), 1.13-1.24 (m, 3H), 1.60-1.79 (m, 6H), 2.42 (s, 3H), 3.45 (t, J=6.4 Hz, 2H), 6.83 (t, J=7.2 Hz, 1H), 7.54 (d, J=6.8 Hz, 1H), 8.62 (d, J=7.2 Hz, 1H), 9.57 (brs, 1H), 14.13 (s, 1H); ¹³C NMR (100 MHz, CDCl₃) δ 18.0, 26.0, 26.2, 31.2, 38.2, 47.4, 84.8, 113.2, 125.7, 133.2, 137.5, 150.5, 159.6, 162.0, 170.0.

2-(Cyclohexylamino)-9-methyl-4-oxo-4H-pyrido[1,2-a]pyrimidine-3-carboxylic acid (164)

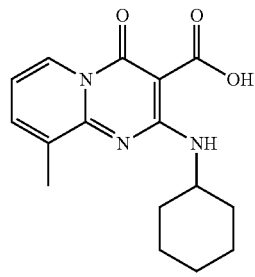 [SMILES: Cc1cccn2c(=O)c(C(=O)O)c(NC3CCCCC3)nc12]

¹H NMR (400 MHz, CDCl₃) δ 1.19-1.42 (m, 5H), 1.56-1.60 (m, 2H), 1.70-1.76 (m, 2H), 1.94-1.98 (m, 2H), 2.38 (s, 3H), 6.79 (t, J=6.8 Hz, 1H), 7.51 (d, J=6.8 Hz, 1H), 8.56 (d, J=6.8 Hz, 1H), 9.42 (d, J=6.8 Hz, 1H), 14.14 (s, 1H); ¹³C NMR (100 MHz, CDCl₃) δ 17.8, 24.7, 25.7, 32.6, 50.0, 84.7, 113.1, 125.6, 133.1, 137.4, 150.5, 158.5, 162.0, 169.9.

2-(Cyclopentylamino)-9-methyl-4-oxo-4H-pyrido[1,2-a]pyrimidine-3-carboxylic acid (165)

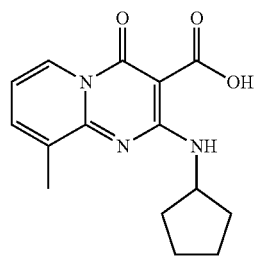 [SMILES: Cc1cccn2c(=O)c(C(=O)O)c(NC3CCCC3)nc12]

¹H NMR (400 MHz, CDCl₃) δ 1.54-1.67 (m, 4H), 1.73-1.78 (m, 2H), 2.04-2.10 (m, 2H), 2.42 (s, 3H), 4.51 (q, J=6.8 Hz, 1H), 6.83 (t, J=6.8 Hz, 1H), 7.53 (d, J=6.8 Hz, 1H), 8.59 (d, J=6.8 Hz, 1H), 9.47 (d, J=6.8 Hz, 1H), 14.15 (s, 1H); ¹³C NMR (100 MHz, CDCl₃) δ 18.0, 24.1, 33.3, 53.0, 84.8, 113.3, 125.7, 133.3, 137.5, 150.5, 158.9, 162.0, 169.9.

2-(Cycloheptylamino)-9-methyl-4-oxo-4H-pyrido[1,2-a]pyrimidine-3-carboxylic acid (166)

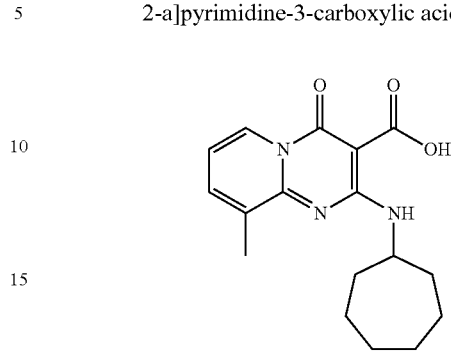

¹H NMR (400 MHz, CDCl₃) δ 1.23-1.57 (m, 4H), 1.59-1.68 (m, 4H), 1.69-1.74 (m, 2H), 1.98-2.04 (m, 2H), 2.43 (s, 3H), 4.30-4.36 (m, 1H), 6.83 (t, J=6.8 Hz, 1H), 7.53 (d, J=6.8 Hz, 1H), 8.64 (d, J=6.8 Hz, 1H), 9.53 (d, J=6.8 Hz, 1H), 14.19 (s, 1H); ¹³C NMR (100 MHz, CDCl₃) δ 18.0, 24.6, 28.1, 34.7, 52.3, 84.8, 113.1, 125.8, 133.2, 137.4, 150.4, 158.3, 162.1, 170.0.

2-(1-(tert-Butoxycarbonyl)piperidin-4-ylamino)-9-methyl-4-oxo-4H-pyrido[1,2-a]pyrimidine-3-carboxylic acid (167)

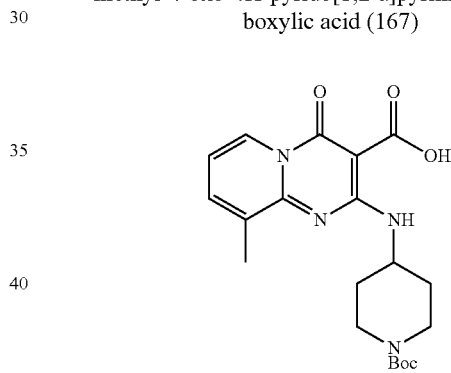

¹H NMR (400 MHz, CDCl₃) δ 1.51 (s, 9H), 1.61-1.65 (m, 2H), 2.01-2.03 (m, 2H), 2.42 (s, 3H), 2.99-3.05 (m, 2H), 3.98-4.00 (m, 2H), 4.26-4.33 (m, 1H), 6.88 (t, J=7.2 Hz, 1H), 7.58 (d, J=6.8 Hz, 1H), 8.67 (d, J=7.2 Hz, 1H), 9.56 (d, J=6.8 Hz, 1H), 14.12 (s, 1H); ¹³C NMR (100 MHz, CDCl₃) δ 17.9, 28.6, 31.6, 48.5, 66.4, 79.9, 85.0, 113.5, 125.9, 133.2, 137.8, 150.6, 154.9, 158.9, 162.0, 169.9.

2-(2-(4-Fluorophenoxy)ethylamino)-9-methyl-4-oxo-4H-pyrido[1,2-a]pyrimidine-3-carboxylic acid (168)

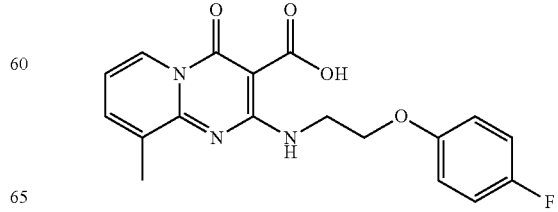

¹H NMR (400 MHz, CDCl₃) δ 2.44 (s, 3H), 4.01 (t, J=5.6 Hz, 2H), 4.15 (t, J=5.6 Hz, 2H), 6.83-6.96 (m, 5H), 7.59 (d, J=6.8 Hz, 1H), 8.68 (d, J=7.2 Hz, 1H), 9.81 (brs, 1H), 14.01 (s, 1H); ¹³C NMR (100 MHz, CDCl₃) δ 18.0, 40.5, 67.1, 85.3, 113.6, 115.8, 115.9, 116.0, 116.1, 125.9, 133.2, 137.9, 150.6, 154.8, 159.8, 161.9, 169.7.

9-Methyl-4-oxo-2-(2-(4-(trifluoromethoxy)phenoxy)ethylamino)-4H-pyrido[1,2-a]pyrimidine-3-carboxylic acid (169)

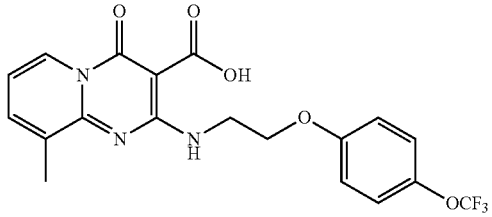 [SMILES: Cc1cccn2c(=O)c(C(=O)O)c(NCCOc3ccc(OC(F)(F)F)cc3)nc12]

¹H NMR (400 MHz, CDCl₃) δ 2.44 (s, 3H), 4.03 (t, J=5.6 Hz, 2H), 4.18 (t, J=5.6 Hz, 2H), 6.90 (d, J=9.2 Hz, 2H), 6.91 (t, J=6.8 Hz, 1H), 7.11 (d, J=9.2 Hz, 2H), 7.60 (d, J=6.8 Hz, 1H), 9.70 (d, J=7.2 Hz, 1H), 9.82 (brs, 1H), 14.08 (s, 1H); ¹³C NMR (100 MHz, CDCl₃) δ 18.0, 40.5, 66.9, 77.4, 85.4, 113.7, 115.7, 122.6, 126.0, 133.2, 138.0, 155.8, 157.6, 159.9, 162.0, 169.0, 170.4.

9-Methyl-2-morpholino-4-oxo-4H-pyrido[1,2-a]pyrimidine-3-carboxylic acid (170)

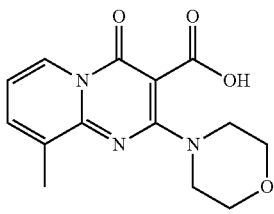 [SMILES: Cc1cccn2c(=O)c(C(=O)O)c(N3CCOCC3)nc12]

¹H NMR (400 MHz, CDCl₃) δ 2.42 (s, 3H), 3.65 (t, J=4.8 Hz, 4H), 3.74 (t, J=4.8 Hz, 4H), 6.86 (t, J=6.8 Hz, 1H), 7.51 (d, J=6.8 Hz, 1H), 8.67 (d, J=6.8 Hz, 1H), 13.98 (s, 1H); ¹³C NMR (100 MHz, CDCl₃) δ 18.1, 58.4, 64.8, 97.5, 113.6, 124.6, 132.6, 136.0, 148.1, 160.5, 161.7, 171.3.

2-(3,4-Dihydroisoquinolin-2(1H)-yl)-9-methyl-4-oxo-4H-pyrido[1,2-a]pyrimidine-3-carboxylic acid (171)

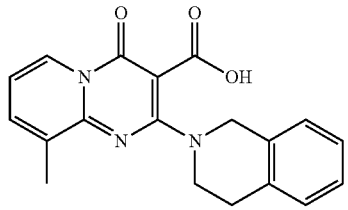 [SMILES: Cc1cccn2c(=O)c(C(=O)O)c(N3CCc4ccccc4C3)nc12]

¹H NMR (400 MHz, CDCl₃) δ 2.45 (s, 3H), 3.03 (t, J=5.8 Hz, 2H), 4.08 (m, 2H), 4.73 (m, 2H), 6.83 (t, J=7.0 Hz, 1H), 7.06-7.18 (m, 4H), 7.52 (d, J=6.8 Hz, 1H), 8.60 (d, J=7.2 Hz, 1H), 13.73 (br s, 1H); ¹³C NMR (100 MHz, CDCl₃) δ 17.6, 28.5, 46.1, 52.4, 86.4, 113.0, 125.5, 126.1, 126.2, 126.6, 128.4, 132.9, 133.7, 134.4, 136.8, 148.1, 159.9, 163.2, 165.3.

2-(4-(2-Chlorophenyl)piperazin-1-yl)-9-methyl-4-oxo-4H-pyrido[1,2-a]pyrimidine-3-carboxylic acid (172)

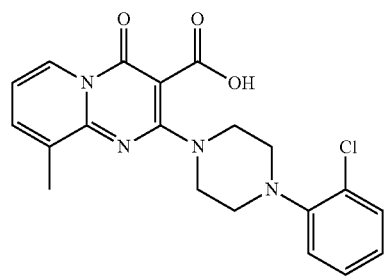

¹H NMR (400 MHz, CDCl₃) δ 2.44 (s, 3H), 3.19 (t, J=4.8 Hz, 4H), 3.96 (m, 4H), 6.87 (t, J=7.0 Hz, 1H), 6.98 (t, J=7.6 Hz, 1H), 7.02 (d, J=8.4 Hz, 1H), 7.20 (t, J=7.8 Hz, 1H), 7.36 (d, J=8.0 Hz, 1H), 7.55 (d, J=6.8 Hz, 1H), 8.66 (d, J=7.2 Hz, 1H), 13.74 (br s, 1H).

2-(3-Chlorophenylamino)-8-(4-methylpiperazin-1-yl)-4-oxo-4H-pyrido[1,2-a]pyrimidine-3-carboxylic acid (173)

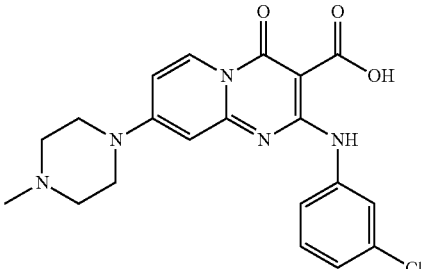

¹H NMR (400 MHz, CDCl₃) δ 2.34 (s, 3H), 2.53 (t, J=4.8 Hz, 4H), 3.54 (t, J=4.8 Hz, 4H), 6.34 (d, J=2.8 Hz, 1H), 6.55 (dd, J=2.8, 8.4 Hz, 1H), 7.04 (d, J=7.2 Hz, 1H), 7.22 (t, J=8.0 Hz, 1H), 7.49 (dd, J=1.6, 8.0 Hz, 1H), 7.86 (t, J=2.0 Hz, 1H), 8.53 (d, J=8.4 Hz, 1H), 11.5 (s, 1H), 14.18 (s, 1H); ¹³C NMR (100 MHz, CDCl₃) δ 46.1, 46.4, 54.4, 83.6, 98.8, 105.1, 120.0, 121.9, 124.0, 128.8, 129.9, 134.4, 139.9, 151.4, 155.6, 158.2, 161.8, 170.2.

87
88
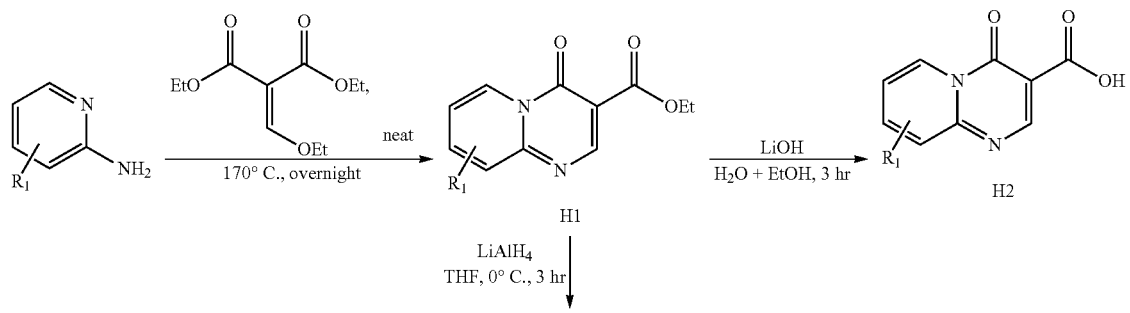
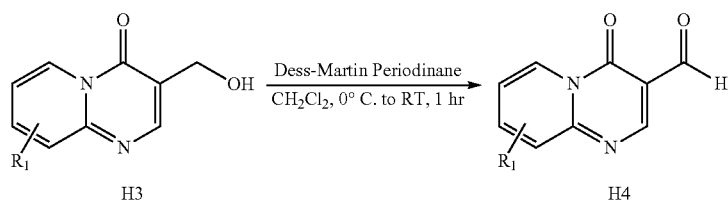
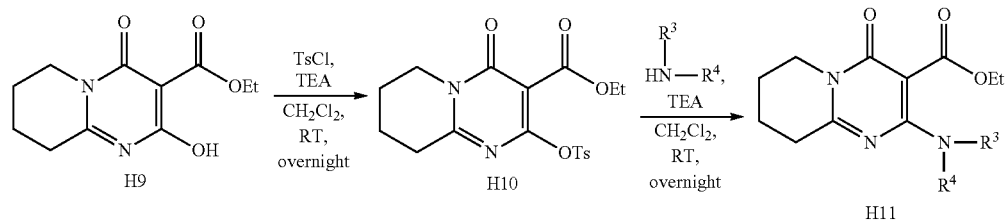
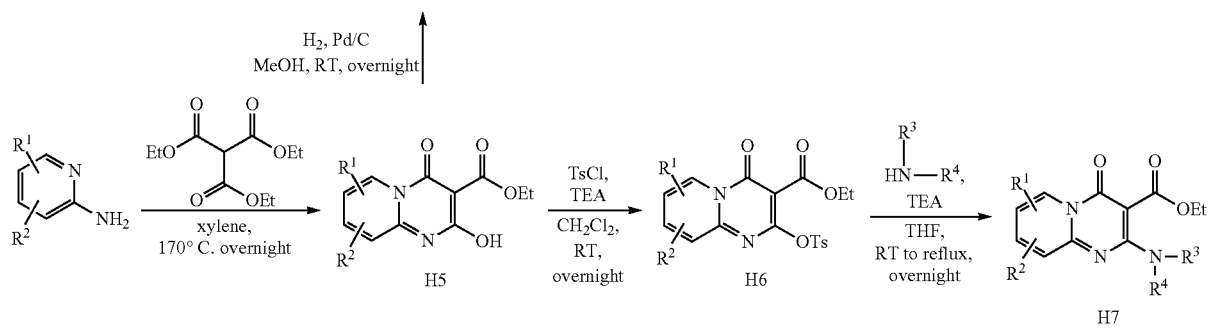
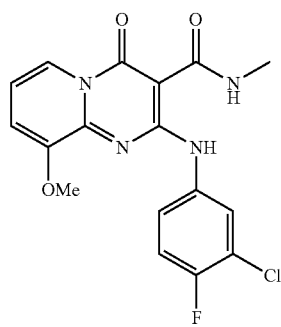

-continued

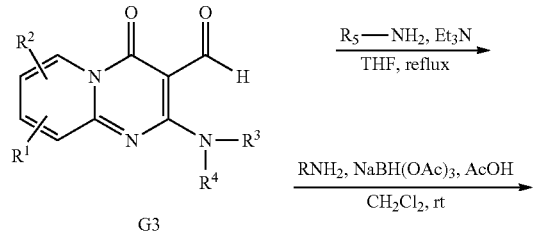 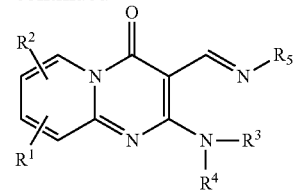

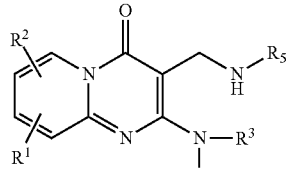

General Procedure for the Synthesis of H1

2-Amino-3-picoline (1.0 mmol) was dissolved in diethyl ethoxymethylenemalonate (1.0 mmol). The solution was heated to 170° C. for 12 h. After cooling, the dark residue was triturated with EtOAc (10 mL). The residual pale solid was collected by filtration and washed with EtOAc to give H1.

General Procedure for the Synthesis of H2

To a stirred solution of H1 (0.43 mmol) in $H_2O$ (3.0 mL) and EtOH (1.0 mL) was added LiOH (0.86 mmol). The mixture was stirred at room temperature for 3 h. The reaction mixture was diluted with $CH_2Cl_2$ (10 mL) and washed with 1 N HCl (10 ml). The organic layer was dried over anhydrous $MgSO_4$ and concentrated in vacuo. The crude product was purified by flash column chromatography to give H2.

General Procedure for the Synthesis of H3

To a stirred solution of H1 (0.38 mmol) in THF (2.0 mL) was added $LiAlH_4$ (0.57 mmol) at 0° C. The reaction mixture was stirred at 0° C. for 3 h. After reaction was completed, 1N NaOH (2 mL) was added dropwise. The mixture was diluted with $CH_2Cl_2$ (10 mL) and washed with $H_2O$ (10 ml). The organic layer was dried over anhydrous $MgSO_4$ and concentrated in vacuo. The crude product was purified by flash column chromatography to give H3.

General Procedure for the Synthesis of H4

To a stirred solution of H3 (95 μmol) in $CH_2Cl_2$ (1.0 mL) was added $NaHCO_3$ (285 μmol) and Dess-Martin Periodinane (114 μmol) at 0° C. The mixture was stirred at 0° C. for 1 h. The reaction mixture was filtered off and concentrated in vacuo. The crude product was purified by flash column chromatography to give H4.

General Procedure for the Synthesis of H5

To a stirred solution of 2-Amino-pyridine (10.6 mmol) in xylene (10.0 mL) was added diethyl ethoxymethylenemalonate (21.2 mmol). The mixture was stirred at 140° C. for 3 hr. After reaction was completed, the residual pale solid was collected by filtration and washed with diethyl ether to give H5.

General Procedure for the Synthesis of H6

To a stirred solution of H5 (0.42 mmol) in THF (5.0 mL) was added triethylamine (0.63 mmol) and p-toluenesulfonylchloride (0.46 mmol) at 0° C. The reaction mixture was stirred at room temperature for overnight. After reaction was completed, the mixture was diluted with $CH_2Cl_2$ (40 mL) and washed with 1N HCl (50 ml), saturated $NaHCO_3$ (50 ml) and brine (50 ml). The organic layer was dried over anhydrous $MgSO_4$ and concentrated in vacuo. The crude product was purified by flash column chromatography to give H6.

General Procedure for the Synthesis of H7

To a stirred solution of H6 (0.25 mmol) in THF (1.2 mL) was added triethylamine (0.5 mmol) and an amine (0.26 mmol) at 0° C. The reaction mixture was stirred at room temperature for overnight. After reaction was completed, the mixture was diluted with $CH_2Cl_2$ (10 mL) and washed with 1N HCl (10 ml), saturated $NaHCO_3$ (10 ml) and brine (10 ml). The organic layer was dried over anhydrous $MgSO_4$ and concentrated in vacuo. The crude product was purified by flash column chromatography to give H7.

General Procedure for the Synthesis of H8

To a stirred solution of H7 (0.27 mmol) in ethylene glycol (3.0 mL) was added methylamine (2 N solution in THF 1.3 mL). The mixture was stirred at 150° C. for 3 hr. The reaction mixture was added with ethylacetate (10 mL) and the residual pale solid was collected by filtration and washed with EtOAc. The crude product was purified by flash column chromatography to give H8.

General Procedure for the Synthesis of H9

To a stirred solution of H5 (2.13 mmol) in MeOH (8.0 mL) was added Pd/C (113 mg). The mixture was stirred at room temperature under $H_2$ for 3 h. After reaction was completed, the reaction mixture was filtered off and concentrated in vacuo. The crude product was recrystallized with EtOAc and hexane (1:4) to give H9.

General Procedure for the Synthesis of H10

To a stirred solution of H9 (0.42 mmol) in $CH_2Cl_2$ (5.0 mL) was added triethylamine (0.63 mmol) and p-toluenesulfonylchloride (0.46 mmol) at 0° C. The reaction mixture was stirred at room temperature for overnight. After reaction was completed, the mixture was diluted with $CH_2Cl_2$ (40 mL) and washed with 1N HCl (50 ml), saturated $NaHCO_3$ (50 ml) and brine (50 ml). The organic layer was dried over anhydrous $MgSO_4$ and concentrated in vacuo. The crude product was purified by flash column chromatography (Hexane: EtOAc=1:2) to give H10.

General Procedure for the Synthesis of H11

To a stirred solution of H10 (0.25 mmol) in THF (2.0 mL) was added triethylamine (0.5 mmol) and an amine (0.37 mmol) at 0° C. The reaction mixture was stirred at room temperature for overnight. After reaction was completed, the mixture was diluted with $CH_2Cl_2$ (10 mL) and washed with 1N HCl (10 ml), saturated $NaHCO_3$ (10 ml) and brine (10 ml). The organic layer was dried over anhydrous $MgSO_4$ and concentrated in vacuo. The crude product was purified by flash column chromatography (Hexane: EtOAc=1:1) to give H11.

General Procedure for the Synthesis of H12

A solution of G3 (1.0 mmol), an amine (1.1 mmol) and triethylamine (2.0 mmol) in THF (2 mL) was refluxed for 1 h and cooled to room temperature. The solvent was evaporated to dryness, which was extracted with CH₂Cl₂ (20 mL×3).

The reaction mixture was washed with 5% sodium bicarbonate. The organic layer was dried (MgSO₄), filtered, and concentrated in vacuo. The crude product was purified by flash column chromatography to give H12.

General Procedure for the Synthesis of H13

To a solution of G3 (1.1 mmol), an amine (1.0 mmol) in CH₂Cl₂ (5 mL) were added sodium triacetoxyborohydride (2.0 mmol) and glacial acetic acid (2.0 mmol) at room temperature for 20 h. The reaction mixture was added saturated ammonium chloride solution and stirred for 10 min. The reaction mixture was extracted with CH₂Cl₂ (20 mL). The organic layer was dried (MgSO₄), filtered, and concentrated in vacuo. The crude product was purified by flash column chromatography to give H13.

Ethyl 9-methyl-4-oxo-4H-pyrido[1,2-a]pyrimidine-3-carboxylate (174)

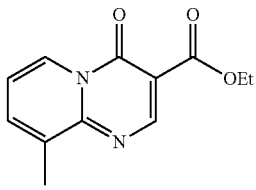 [SMILES: CCOC(=O)c1cnc2c(C)cccn2c1=O]

¹H NMR (400 MHz, CDCl₃) δ 1.39 (t, J=7.2 Hz, 3H), 2.62 (s, 3H), 4.39 (q, J=7.2 Hz, 2H), 7.20 (t, J=7.2 Hz, 1H), 7.77 (d, J=7.2 Hz, 1H), 9.05 (s, 1H), 9.16 (d, J=7.2 Hz, 1H); ¹³C NMR (100 MHz, CDCl₃) 14.6, 18.2, 61.2, 105.3, 116.8, 127.0, 135.9, 138.2, 155.3, 158.4, 165.0, 189.1.

9-Methyl-4-oxo-4H-pyrido[1,2-a]pyrimidine-3-carboxylic acid (175)

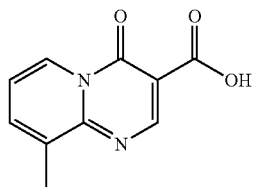

¹H NMR (400 MHz, CDCl₃) δ 2.56 (s, 3H), 7.12 (t, J=6.8 Hz, 1H), 7.79 (d, J=6.8 Hz, 1H), 8.87 (s, 1H), 9.21 (d, J=7.2 Hz), 14.13 (s, 1H); ¹³C NMR (100 MHz, CDCl₃) δ18.3, 110.9, 117.1, 128.1, 137.6, 141.1, 155.0, 157.1, 158.3, 171.3.

3-(Hydroxymethyl)-9-methyl-4H-pyrido[1,2-a]pyrimidin-4-one (176)

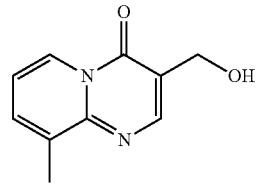

¹H NMR (400 MHz, CDCl₃) δ 2.51 (s, 3H), 3.27 (brs, 1H), 4.66 (s, 2H), 7.01 (t, J=6.8 Hz, 1H), 7.51 (d, J=6.8 Hz, 1H), 8.32 (s, 1H), 8.87 (s, 1H); ¹³C NMR (100 MHz, CDCl₃) 18.2, 44.1, 111.2, 117.9, 127.1, 135.7, 139.8, 153.9, 155.6, 158.2.

9-Methyl-4-oxo-4H-pyrido[1,2-a]pyrimidine-3-carbaldehyde (177)

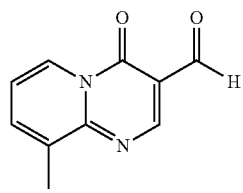

¹H NMR (400 MHz, CDCl₃) δ 2.63 (s, 3H), 7.29 (t, J=7.2 Hz, 1H), 7.86 (d, J=7.2 Hz, 1H), 8.85 (s, 1H), 9.14 (d, J=7.2 Hz, 1H), 10.33 (s, 1H); ¹³C NMR (100 MHz, CDCl₃) δ 18.2, 110.9, 117.5, 126.7, 136.5, 139.5, 153.1, 155.6, 158.1, 188.5.

Ethyl 2-hydroxy-4-oxo-4H-pyrido[1,2-a]pyrimidine-3-carboxylate (178)

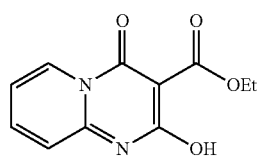 [SMILES: CCOC(=O)c1c(O)nc2ccccn2c1=O]

¹H NMR (400 MHz, CDCl₃) δ 1.42 (t, J=7.2 Hz, 3H), 4.45 (q, J=7.2 Hz, 2H), 7.13 (ddd, J=1.2, 6.8, 7.2 Hz, 1H), 7.49 (d, J=8.8 Hz, 1H), 7.82-7.86 (m, 1H), 9.00 (d, J=7.2 Hz, 1H), 13.64 (brs, 1H, NH); ¹³C NMR (100 MHz, CDCl₃) δ 14.2, 62.3, 87.1, 115.3, 125.1, 128.7, 140.3, 148.4, 152.6, 155.5, 171.7.

2-Hydroxy-4-oxo-4H-pyrido[1,2-a]pyrimidine-3-carboxylic acid (179)

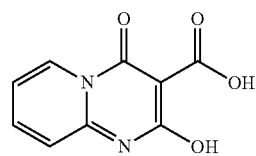 [SMILES: O=C(O)c1c(O)nc2ccccn2c1=O]

¹H NMR (400 MHz, CDCl₃) δ 2.50 (s, 3H), 6.70 (dd, J=6.8, 7.2 Hz, 1H), 7.15 (dd, J=7.2, 7.2 Hz, 1H), 7.37, (dd, J=7.2, 7.6 Hz, 1H), 7.65 (d, J=6.8 Hz, 1H), 7.76 (d, J=8.4 Hz, 1H), 8.76 (d, J=7.2 Hz, 1H), 11.70 (brs, 1H), 14.31 (s, 1H).

Ethyl 4-oxo-2-(phenylamino)-4H-pyrido[1,2-a]pyrimidine-3-carboxylate (180)

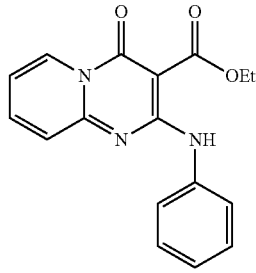 [SMILES: CCOC(=O)c1c(Nc2ccccc2)nc2ccccn2c1=O]

¹H NMR (400 MHz, CDCl₃) δ 1.45 (t, J=7.2 Hz, 3H), 4.44 (q, J=7.2 Hz, 2H), 6.93 (dd, J=6.8, 6.8 Hz, 1H), 7.29-7.36 (m, 3H), 7.65-7.68 (m, 3H), 8.97 (d, J=7.2 Hz, 1H), 11.39 (brs, 1H); ¹³C NMR (100 MHz, CDCl₃) δ 14.4, 61.0, 85.5, 113.6, 122.5, 124.2, 124.5, 128.4, 128.6, 138.4, 139.0, 151.6, 155.9, 159.5, 169.6.

Ethyl 2-(3-hydroxyphenylamino)-4-oxo-4H-pyrido[1,2-a]pyrimidine-3-carboxylate (181)

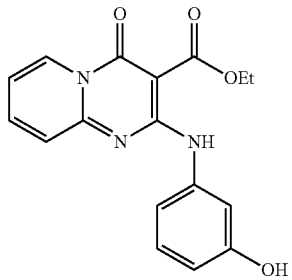 [SMILES: CCOC(=O)c1c(Nc2cccc(O)c2)nc2ccccn2c1=O]

¹H NMR (400 MHz, CDCl₃+CD₃OD) δ 1.38 (t, J=7.0 Hz, 3H), 4.37 (q, J=7.2 Hz, 2H), 6.56-6.58 (m, 1H), 6.92 (dd, J=6.8, 7.2 Hz, 1H0, 7.05 (d, J=8.4 Hz, 1h0, 7.12 (dd, J=8.0, 8.0 Hz, 1H), 7.26 (m, 1H), 7.31 (d, J=8.8 Hz, 1H), 7.66 (dd, J=7.2, 7.6 Hz, 1H), 8.90 (d, J=7.2 Hz, 1H), 11.22 (brs, 1H).

Ethyl 2-(2-hydroxyphenylamino)-4-oxo-4H-pyrido[1,2-a]pyrimidine-3-carboxylate (182)


¹H NMR (400 MHz, CDCl₃) δ 1.45 (t, J=7.2 Hz, 3H), 4.45 (q, J=6.8 Hz, 2H), 6.90 (dd, J=7.2, 8.0 Hz, 1H), 7.05-7.08 (m, 2H), 7.13 (dd, J=7.6, 8.4 Hz, 2H), 7.37 (d, J=8.4 Hz, 1H), 7.81 (dd, J=7.6, 8.0 Hz, 1H), 9.03 (d, J=6.8 Hz, 1H), 11.52 (brs, 1H); ¹³C NMR (100 MHz, CDCl₃) 14.4, 61.3, 114.7, 120.1, 120.5, 122.9, 124.4, 127.0, 127.1, 129.0, 140.8, 149.3, 151.1, 158.6, 169.5.

Ethyl 2-(3-nitrophenylamino)-4-oxo-4H-pyrido[1,2-a]pyrimidine-3-carboxylate (183)

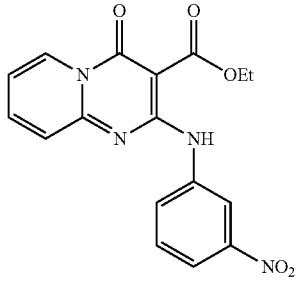 [SMILES: CCOC(=O)c1c(Nc2cccc([N+](=O)[O-])c2)nc2ccccn2c1=O]

¹H NMR (400 MHz, CDCl₃) δ 1.46 (t, J=6.4 Hz, 3H), 4.45 (q, J=7.2 Hz, 2H), 7.05 (ddd, J=1.2, 6.8, 6.8 Hz, 1H), 7.43 (d, J=8.8 Hz, 1H), 7.47 (dd, J=8.0, 8.4 Hz, 2H), 7.77-7.82 (m, 2H), 7.93-7.96 (m, 1H), 8.97-8.98 (m, 1H), 9.04 (dd, J=0.8, 7.2 Hz, 1H), 11.74 (brs, 1H); ¹³C NMR (100 MHz, CDCl₃) 14.4, 61.3, 86.1, 114.5, 116.9, 118.4, 124.7, 127.4, 128.6, 129.2, 139.8, 148.5, 151.5, 155.7, 159.5, 169.6.

Ethyl 4-oxo-2-phenoxy-4H-pyrido[1,2-a]pyrimidine-3-carboxylate (184)

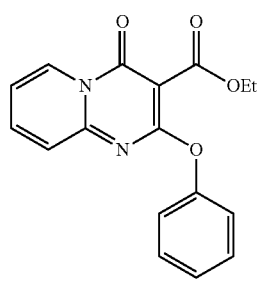 [SMILES: CCOC(=O)c1c(Oc2ccccc2)nc2ccccn2c1=O]

¹H NMR (400 MHz, CDCl₃) δ 1.38 (t, J=7.2 Hz, 3H), 4.42 (q, J=7.2 Hz, 2H), 7.15-7.17 (m, 3H), 7.24 (d, J=6.4 Hz, 1H), 7.36-7.41 (m, 3H), 7.77 (ddd, J=1.6, 6.8, 6.8 Hz, 1H), 9.10 (dd, J=0.8, 6.8 Hz, 1H); ¹³C NMR (100 MHz, CDCl₃) δ 14.2, 61.3, 115.7, 121.8, 125.3, 128.5, 129.2, 128.7, 150.3, 152.5, 156.7, 164.1, 165.0.

Ethyl 2-(3-fluorophenoxy)-4-oxo-4H-pyrido[1,2-a]pyrimidine-3-carboxylate (185)

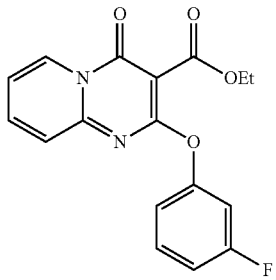 [SMILES: CCOC(=O)c1c(Oc2cccc(F)c2)nc2ccccn2c1=O]

¹H NMR (400 MHz, CDCl₃) δ 1.37 (t, J=7.0 Hz, 3H), 4.40 (q, J=6.8 Hz, 2H), 6.91-6.98 m, 3H), 7.19 (ddd, J=1.2, 7.2, 7.2 Hz, 1H), 7.32-7.36 (m, 1H), 7.39 (d, J=8.8 Hz, 1H), 7.78-7.82 (m, 1H), 9.10 (d, J=6.8 Hz, 1H); ¹³C NMR (100 MHz, CDCl₃) δ 14.2, 61.4, 94.6, 109.8, 110.0, 112.2, 112.4, 115.9, 117.5, 117.6, 125.3, 128.5, 129.8, 129.9, 139.9, 150.3, 153.3, 156.6, 161.6, 163.8, 164.0, 164.5.

Ethyl 4-oxo-2-(3-(trifluoromethyl)phenoxy)-4H-pyrido[1,2-a]pyrimidine-3-carboxylate (186)

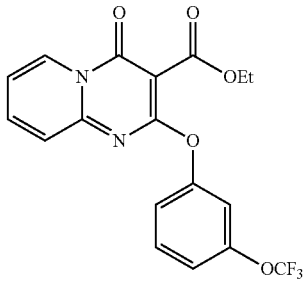 [SMILES: CCOC(=O)c1c(Oc2cccc(OC(F)(F)F)c2)nc2ccccn2c1=O]

¹H NMR (400 MHz, CDCl₃) δ 1.39 (t, J=7.2 Hz, 3H), 4.43 (q, J=7.0 Hz, 2H), 7.21 (dd, J=6.8, 6.8 Hz, 1H), 7.38 (d, J=8.0 Hz, 2H), 7.47-7.52 (m, 2H), 7.81 (dd, J=7.2, 8.4 Hz, 1H), 9.12 (d, J=6.8 Hz, 1H).

Methyl 2-chloro-9-methyl-4-oxo-4H-pyrido[1,2-a]pyrimidine-3-carboxylate (187)

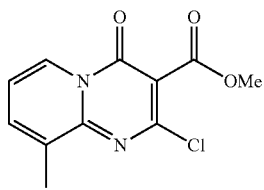 [SMILES: COC(=O)c1c(Cl)nc2c(C)cccn2c1=O]

¹H NMR (400 MHz, CDCl₃) δ 2.56 (s, 3H), 3.93 (s, 3H), 7.19 (t, J=7.2 Hz, 1H), 7.75 (d, J=6.8 Hz, 1H), 8.91 (d, J=7.2 Hz, 1H); ¹³C NMR (100 MHz, CDCl₃) δ 17.1, 52.8, 108.0, 116.7, 126.1, 134.9, 138.3, 149.1, 155.1, 155.2, 164.2.

Methyl 2-(3-chlorophenylamino)-9-methyl-4-oxo-4H-pyrido[1,2-a]pyrimidine-3-carboxylate (188)

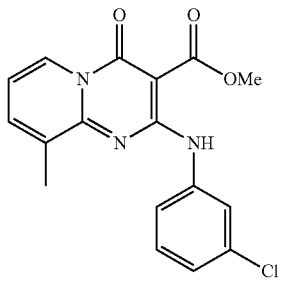 [SMILES: COC(=O)c1c(Nc2cccc(Cl)c2)nc2c(C)cccn2c1=O]

¹H NMR (400 MHz, CDCl₃) δ 2.51 (s, 3H), 3.99 (s, 3H), 6.94 (t, J=7.0 Hz, 1H), 7.09 (d, J=7.6 Hz, 1H), 7.27 (d, J=8.4 Hz, 1H), 7.41 (d, J=8.0 Hz, 1H), 7.64 (d, J=6.8 Hz, 1H), 8.18 (s, 1H), 8.91 (d, J=7.2 Hz, 1H), 11.52 (br s, 1H); ¹³C NMR (100 MHz, CDCl₃) δ 18.0, 52.1, 85.3, 113.7, 119.6, 121.9, 123.5, 126.4, 129.4, 133.2, 134.1, 138.4, 139.9, 151.0, 156.2, 158.6, 170.1.

Methyl 2-(3-chlorobenzylamino)-9-methyl-4-oxo-4H-pyrido[1,2-a]pyrimidine-3-carboxylate (189)

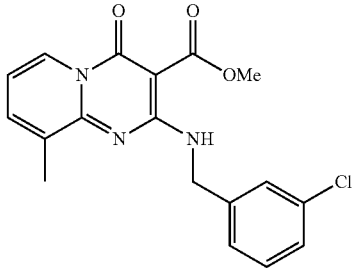 [SMILES: COC(=O)c1c(NCc2cccc(Cl)c2)nc2c(C)cccn2c1=O]

¹H NMR (400 MHz, CDCl₃) δ 2.35 (s, 3H), 3.92 (s, 3H), 4.77 (d, J=6.0 Hz, 2H), 6.80 (t, J=6.8 Hz, 1H), 7.20-7.24 (m, 3H), 7.34 (s, 3H), 7.50 (d, J=6.8 Hz, 1H), 8.82 (d, J=7.2 Hz, 1H), 9.69 (br s, 1H); ¹³C NMR (100 MHz, CDCl₃) δ 17.8, 44.4, 51.8, 84.6, 112.6, 125.5, 126.4, 127.2, 127.7, 129.7, 132.7, 134.3, 137.6, 141.1, 151.3, 156.4, 160.8, 170.1.

Ethyl 2-hydroxy-4-oxo-6,7,8,9-tetrahydro-4H-pyrido[1,2-a]pyrimidine-3-carboxylate (190)

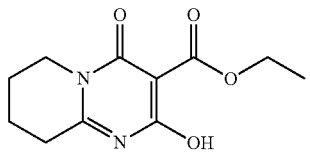 [SMILES: CCOC(=O)c1c(O)nc2n(c1=O)CCCC2]

¹H NMR (400 MHz, CDCl₃) δ 1.36 (t, J=7.2 Hz, 3H), 1.82-1.93 (m, 4H), 2.86 (t, J=6.8 Hz, 2H), 3.84 (t, J=6.0 Hz, 2H), 4.39 (q, J=7.2 Hz, 2H); ¹³C NMR (100 MHz, CDCl₃) δ 14.4, 18.9, 21.9, 32.2, 43.0, 62.4, 90.9, 159.8, 165.1, 171.7, 173.5.

Ethyl 4-oxo-2-(tosyloxy)-6,7,8,9-tetrahydro-4H-pyrido[1,2-a]pyrimidine-3-carboxylate (191)

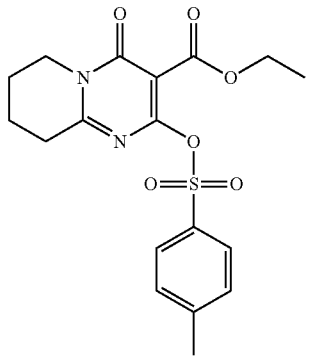 [SMILES: CCOC(=O)c1c(OS(=O)(=O)c2ccc(C)cc2)nc2n(c1=O)CCCC2]

¹H NMR (400 MHz, CDCl₃) δ 1.25 (t, J=7.2 Hz, 3H), 1.79-1.91 (m, 4H), 2.41 (s, 3H), 2.79 (t, J=6.4 Hz, 2H), 3.84 (t, J=6.4 Hz, 2H), 4.25 (q, J=7.2 Hz, 2H), 7.31 (d, J=8.0 Hz, 2H), 7.89 (d, J=8.0 Hz, 2H); ¹³C NMR (100 MHz, CDCl₃) δ

14.2, 18.8, 21.6, 21.9, 31.8, 43.6, 61.9, 104.2, 129.1, 129.7, 134.2, 145.8, 159.4, 160.8, 162.0, 162.2.

Ethyl 4-oxo-2-(phenylamino)-6,7,8,9-tetrahydro-4H-pyrido[1,2-a]pyrimidine-3-carboxylate (192)

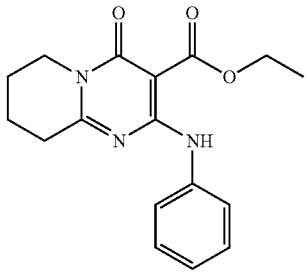 [SMILES: CCOC(=O)c1c(Nc2ccccc2)nc2n(c1=O)CCCC2]

$^1$H NMR (400 MHz, CDCl$_3$) δ 1.40 (t, J=7.2 Hz, 3H), 1.80-1.92 (m, 4H), 2.80 (t, J=6.8 Hz, 2H), 3.87 (t, J=6.0 Hz, 2H), 4.36 (q, J=7.2 Hz, 2H), 7.08 (t, J=7.2 Hz, 1H), 7.29 (t, J=7.2 Hz, 2H), 7.53 (d, J=7.6 Hz, 2H), 11.2 (s, 1H); $^{13}$C NMR (100 MHz, CDCl$_3$) δ 14.6, 19.2, 22.2, 32.2, 42.4, 61.0, 88.4, 122.9, 124.4, 128.8, 138.4, 160.5, 160.8, 162.2, 169.8.

Ethyl 2-(3-chlorophenylamino)-4-oxo-6,7,8,9-tetrahydro-4H-pyrido[1,2-a]pyrimidine-3-carboxylate (193)

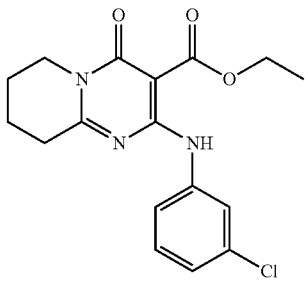 [SMILES: CCOC(=O)c1c(Nc2cccc(Cl)c2)nc2n(c1=O)CCCC2]

$^1$H NMR (400 MHz, CDCl$_3$) δ 1.32 (t, J=7.2 Hz, 3H), 1.76-1.88 (m, 4H), 2.76 (t, J=6.8 Hz, 2H), 3.78 (t, J=6.0 Hz, 2H), 4.29 (q, J=7.06 (dd, J=7.2 Hz, 2H), J=1.2, 8.0 Hz, 1H), 7.27 (t, J=8.0 Hz, 1H), 7.51 (dd, J=1.2, 8.0 Hz, 1H), 7.58 (d, J=2.0 Hz, 1H); $^{13}$C NMR (100 MHz, CDCl$_3$) δ 14.3, 18.6, 22.1, 32.1, 42.6, 61.1, 81.4, 111.2, 111.7, 113.0, 128.4, 140.4, 149.6, 158.7, 161.12, 163.2, 170.4

Ethyl 4-oxo-2-(3-(trifluoromethyl)phenylamino)-6,7,8,9-tetrahydro-4H-pyrido[1,2-a]pyrimidine-3-carboxylate (194)

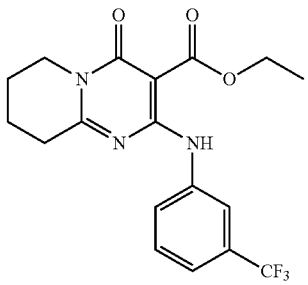 [SMILES: CCOC(=O)c1c(Nc2cccc(C(F)(F)F)c2)nc2n(c1=O)CCCC2]

$^1$H NMR (400 MHz, CDCl$_3$) δ 1.45 (t, J=7.2 Hz, 3H), 1.88-1.97 (m, 4H), 2.87 (t, J=6.4 Hz, 2H), 3.93 (t, J=5.6 Hz, 2H), 4.41 (q, J=7.2 Hz, 2H), 7.35 (t, J=7.2 Hz, 1H), 7.35 (d, J=7.6 Hz, 1H), 7.67 (d, J=7.6 Hz, 1H), 8.05 (s, 1H), 11.2 (s, 1H);

Ethyl 2-(2-hydroxyphenylamino)-4-oxo-6,7,8,9-tetrahydro-4H-pyrido[1,2-a]pyrimidine-3-carboxylate (195)

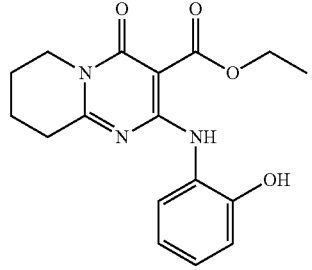 [SMILES: CCOC(=O)c1c(Nc2ccccc2O)nc2n(c1=O)CCCC2]

$^1$H NMR (400 MHz, CDCl$_3$) δ 1.40 (t, J=7.2 Hz, 3H), 1.81-1.94 (m, 4H), 2.65 (t, J=6.8 Hz, 2H), 3.65 (t, J=6.0 Hz, 2H), 4.18 (q, J=6.8 Hz, 2H), 6.85 (t, J=7.2 Hz, 1H), 7.00 (d, J=7.2 Hz, 1H), 7.06-7.12 (m, 2H), 9.98 (s, 1H), 11.3 (s, 1H); $^{13}$C NMR (100 MHz, CDCl$_3$) δ 14.6, 18.8, 21.9, 31.6, 42.6, 61.3, 88.4, 120.2, 120.7, 124.5, 127.1, 127.2, 149.1, 159.4, 159.5, 163.0, 169.6.

Ethyl 2-(3-hydroxyphenylamino)-4-oxo-6,7,8,9-tetrahydro-4H-pyrido[1,2-a]pyrimidine-3-carboxylate (196)

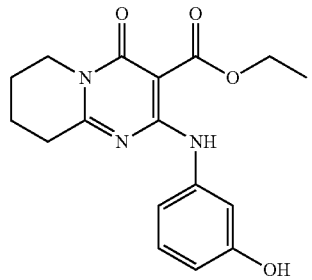 [SMILES: CCOC(=O)c1c(Nc2cccc(O)c2)nc2n(c1=O)CCCC2]

$^1$H NMR (400 MHz, CDCl$_3$+MeOD-d$_4$) δ 1.26 (t, J=7.2 Hz, 3H), 1.71-1.81 (m, 4H), 2.72 (t, J=6.4 Hz, 2H), 3.74 (t, J=6.4 Hz, 2H), 4.23 (q, J=7.2 Hz, 2H), 6.47 (d, J=7.6 Hz, 1H), 6.88 (d, J=8.0 Hz, 1H), 6.99 (d, J=8.0 Hz, 1H), 7.02 (t, J=2.0 Hz, 1H); $^{13}$C NMR (100 MHz, CDCl$_3$+MeOD-d$_4$) δ 14.2, 18.8, 21.9, 31.8, 42.4, 60.9, 79.8, 109.8, 111.6, 114.0, 129.4, 139.4, 149.7, 159.3, 160.2, 163.1, 169.6

Ethyl 2-(4-hydroxyphenylamino)-4-oxo-6,7,8,9-tetrahydro-4H-pyrido[1,2-a]pyrimidine-3-carboxylate (197)

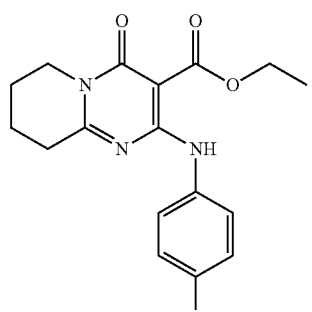

¹H NMR (400 MHz, DMSO-d₆) δ 1.21 (t, J=7.2 Hz, 3H), 1.67-1.80 (m, 4H), 2.65 (t, J=6.8 Hz, 2H), 3.65 (t, J=6.0 Hz, 2H), 4.18 (q, J=7.2 Hz, 2H), 6.68 (d, J=8.8 Hz, 2H), 7.25 (d, J=8.8 Hz, 2H), 9.29 (s, 1H), 10.7 (s, 1H); ¹³C NMR (100 MHz, CDCl₃) δ 14.9, 18.9, 21.9, 32.1, 42.3, 60.4, 87.2, 115.7, 125.0, 130.1, 154.9, 159.4, 160.6, 163.3, 169.6.

2-(3-Chloro-4-fluorophenylamino)-9-methoxy-N-methyl-4-oxo-4H-pyrido[1,2-a]pyrimidine-3-carboxamide (198)

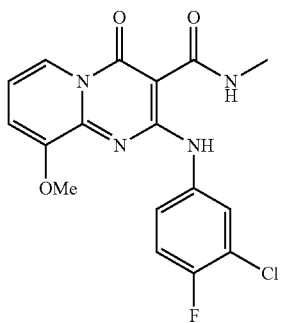 [SMILES: CNC(=O)c1c(Nc2ccc(F)c(Cl)c2)nc2c(OC)cccn2c1=O]

mp=218° C. (decomp.); ¹H NMR (400 MHz, CDCl₃) δ 2.97 (d, J=4.8 Hz, 3H), 4.41 (s, 3H), 6.89 (dd, J=7.2 Hz, 7.2 Hz, 1H), 6.97 (dd, J=1.2 Hz, 8.0 Hz, 1H), 7.05 (dd, J=8.8 Hz, 8.8 Hz, 1H), 7.40-7.44 (m, 1H), 8.46-8.51 (m, 2H), 8.82 (d, J=2.0 Hz, 1H), 12.98 (s, 1H);

(E)-2-(3-Chlorophenylamino)-3-((cyclohexylimino)methyl)-4H-pyrido[1,2-a]pyrimidin-4-one (199)

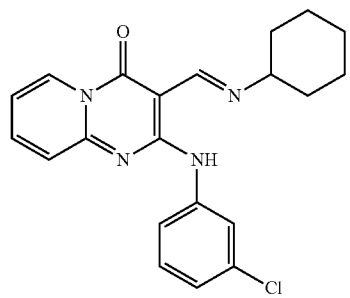 [SMILES: O=c1c(/C=N/C2CCCCC2)c(Nc2cccc(Cl)c2)nc2ccccn12]

¹H NMR (400 MHz, CDCl₃) δ 1.23-1.37 (m, 3H), 1.41-1.50 (m, 2H), 1.56-1.59 (m, 1H), 1.73-1.76 (m, 4H), 3.16-3.22 (m, 1H), 6.85 (ddd, J=1.2, 6.8, 6.8 Hz, 1H), 6.94 (ddd, J=0.8, 1.2, 8.0 Hz, 1H), 7.14 (dd, J=8.0, 8.0 Hz, 1H), 7.38 (ddd, J=0.8, 1.2, 8.0 Hz, 1H), 7.54-7.58 (m, 1H), 7.90-7.91 (m, 1H), 8.83 (s, 1H), 8.85 (dd, J=0.8, 1.2 Hz, 1H), 13.40 (brs, 1H); ¹³C NMR (100 MHz, CDCl₃) δ 24.4, 25.6, 34.9, 68.4, 91.6, 113.4, 119.2, 121.2, 123.0, 124.7, 127.6, 129.5, 134.2, 137.6, 140.8, 150.6, 156.3, 157.0, 158.3.

(E)-2-(3-Chlorophenylamino)-3-((3-chlorophenylimino)methyl)-4H-pyrido[1,2-a]pyrimidin-4-one (200)

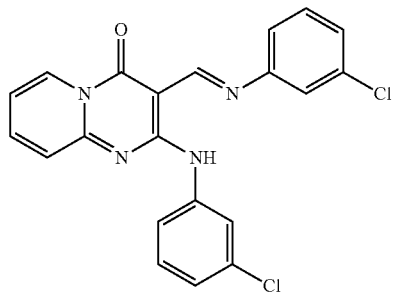 [SMILES: O=c1c(/C=N/c2cccc(Cl)c2)c(Nc2cccc(Cl)c2)nc2ccccn12]

¹H NMR (400 MHz, CDCl₃) δ 7.01 (dd, J=0.8, 1.2, 8.0 Hz, 1H), 7.28 (d, J=8.4 Hz, 1H), 7.29 (dd, J=2.0, 4.0 Hz, 1H), 7.33 (d, J=8.0 Hz, 1H), 7.44 (d, J=8.8 Hz, 1H), 7.52 (ddd, J=0.8, 1.2, 8.0 Hz, 1H), 7.17-7.76 (m, 1H), 8.02-8.04 (m, 1H), 8.98 (dd, J=0.8, 6.8 Hz, 1H), 9.17 (s, 1H), 12.94 (brs, 1H); ¹³C NMR (100 MHz, CDCl₃) δ 92.6, 114.0, 119.5, 119.8, 121.8, 123.9, 125.0, 125.7, 128.0, 129.7, 130.2, 134.4, 134.8, 138.7, 140.1, 151.3, 151.8, 157.0, 158.0, 158.9.

2-(3-Chlorophenylamino)-3-((cyclopentylamino)methyl)-4H-pyrido[1,2-a]pyrimidin-4-one (201)

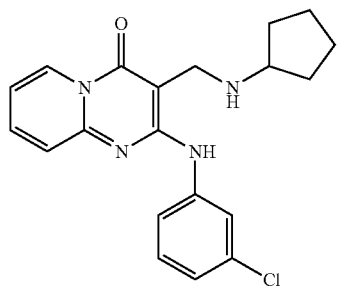 [SMILES: O=c1c(CNC2CCCC2)c(Nc2cccc(Cl)c2)nc2ccccn12]

¹H NMR (400 MHz, CDCl₃) δ 1.54-1.57 (m, 2H), 1.74-1.83 (m, 4H), 2.05-2.08 (m, 2H), 3.23-3.24 (m, 1H), 4.19 (s, 2H), 6.93-6.98 (m, 2H), 7.11-7.15 (m, 1H), 7.32 (d, J=8.4 Hz, 1H), 7.51 (dd, J=2.0, 8.4 Hz, 1H), 7.61-7.65 (m, 1H), 7.74-7.75 (m, 1H), 8.73 (d, J=7.2 Hz, 1H).

101

2-(3-Chlorophenylamino)-3-((cyclohexylamino)methyl)-4H-pyrido[1,2-a]pyrimidin-4-one (202)

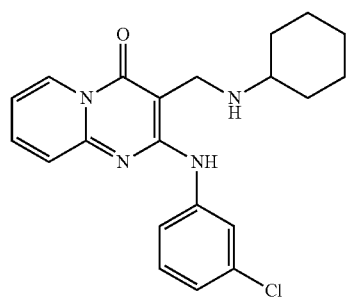 [SMILES: O=c1c(CNC2CCCCC2)c(Nc2cccc(Cl)c2)nc2ccccn12]

$^1$H NMR (400 MHz, CDCl$_3$) δ 1.20-1.35 (m, 4H), 1.66-1.72 (m, 2H), 1.86-1.89 (m, 2H), 2.23-2.39 (m, 2H), 3.12-3.18 (m, 1H), 6.93 (ddd, J=1.2, 6.8, 7.2 Hz, 1H), 6.99 (ddd, J=0.8, 1.2, 7.6 Hz, 1H), 7.20 (dd, J=8.0, 8.0 Hz, 1H), 7.25 (d, J=8.8 Hz, 1H), 7.52-7.57 (m, 1H), 7.61 (dd, J=1.2, 8.0 Hz, 1H), 7.84-7.85 (m, 1H), 8.76 (d, J=6.4 Hz, 1H), 9.77 (brs, 1H); $^{13}$C NMR (100 MHz, CDCl$_3$) δ 24.6, 25.0, 41.2, 57.9, 88.9, 114.6, 119.2, 121.1, 122.8, 124.6, 127.3, 129.4, 133.7, 137.3, 140.8, 149.6, 157.2, 158.8.

2-(3-Chlorophenylamino)-3-((cycloheptylamino)methyl)-4H-pyrido[1,2-a]pyrimidin-4-one (203)

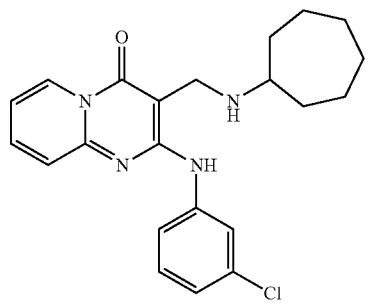 [SMILES: O=c1c(CNC2CCCCCC2)c(Nc2cccc(Cl)c2)nc2ccccn12]

$^1$H NMR (400 MHz, CDCl$_3$) δ 1.40-1.59 (m, 6H), 1.72-1.81 (m, 4H), 2.18-2.23 (m, 2H), 3.07-3.12 (m, 1H), 4.05 (m, 2H), 6.82 (ddd, J=1.2, 6.8, 6.8 Hz, 1H), 6.91 (dd, J=1.2, 8.0 Hz, 1H), 7.14 (dd, J=8.0, 8.0 Hz, 1H), 7.44-7.49 (m, 2H), 7.78-7.80 (m, 1H), 8.70 (d, J=6.8 Hz, 1H), 10.00 (brs, 1H); $^{13}$C NMR (100 MHz, CDCl$_3$) δ 23.8, 32.3, 41.5, 59.7, 89.7, 114.2, 118.7, 120.6, 122.4, 124.4, 127.2, 129.3, 133.7, 136.8, 140.9, 149.4, 157.2, 158.2.

102

2-(3-Chlorophenylamino)-3-((isopropylamino)methyl)-4H-pyrido[1,2-a]pyrimidin-4-one (204)

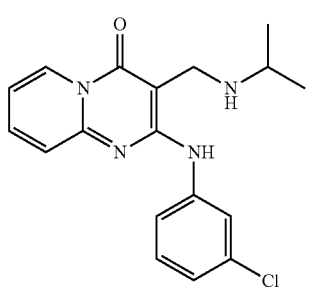 [SMILES: CC(C)NCc1c(Nc2cccc(Cl)c2)nc2ccccn2c1=O]

$^1$H NMR (400 MHz, CDCl$_3$) δ 1.25 (s, 3H), 1.26 (s, 3H), 2.30-3.06 (m, 1H), 4.05 (s, 2H), 6.87 (dd, J=6.4, 7.2 Hz, 1H), 6.95 (d, J=7.2 Hz, 1H), 7.17 (dd, J=8.0, 8.0 Hz, 1H), 7.32 (d, J=8.8 Hz, 1H), 7.41 (d, J=8.0 Hz, 1H), 7.54 (dd, J=7.2, 7.2 Hz, 1H), 7.81 (s, 1H), 8.83 (d, J=6.8 Hz, 1H); $^{13}$C NMR (100 MHz, CDCl$_3$) δ 22.1, 41.7, 48.9, 91.5, 113.7, 118.2, 120.1, 122.2, 124.6, 127.5, 129.5, 134.1, 136.2, 141.2, 149.5, 157.4, 157.8.

2-(3-Chlorophenylamino)-3-((cyclohexylamino)methyl)-8-(4-methylpiperazin-1-yl)-4H-pyrido[1,2-a]pyrimidin-4-one (205)

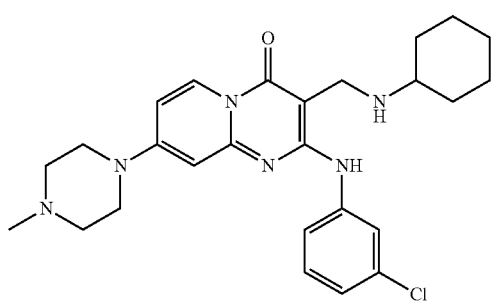 [SMILES: CN1CCN(c2ccn3c(=O)c(CNC4CCCCC4)c(Nc4cccc(Cl)c4)nc3c2)CC1]

$^1$H NMR (400 MHz, CDCl$_3$) δ 1.20-1.34 (m, 3H), 1.71-1.91 (m, 3H), 1.92-2.04 (m, 2H), 2.20 (s, 3H), 2.23-2.36 (m, 6H), 3.04-3.10 (m, 5H), 4.01 (s, 2H), 5.87 (s, 1H), 6.55 (s, J=8.0 hz, 1H), 6.90 (d, J=8.0 Hz, 1H), 7.14 (t, J=8.0 Hz, 1H), 7.62 (d, J=7.6 Hz, 1H), 7.84 (s, 1H), 8.46 (d, J=7.6 Hz, 1H), 9.59 (s, 1H); $^{13}$C NMR (100 MHz, CDCl$_3$) δ 24.9, 25.3, 30.2, 41.2, 46.1, 46.3, 54.2, 58.4, 86.2, 98.9, 106.5, 119.3, 121.0, 122.3, 128.3, 129.5, 133.9, 141.9, 150.8, 154.8, 157.7, 158.9.

Scheme 10

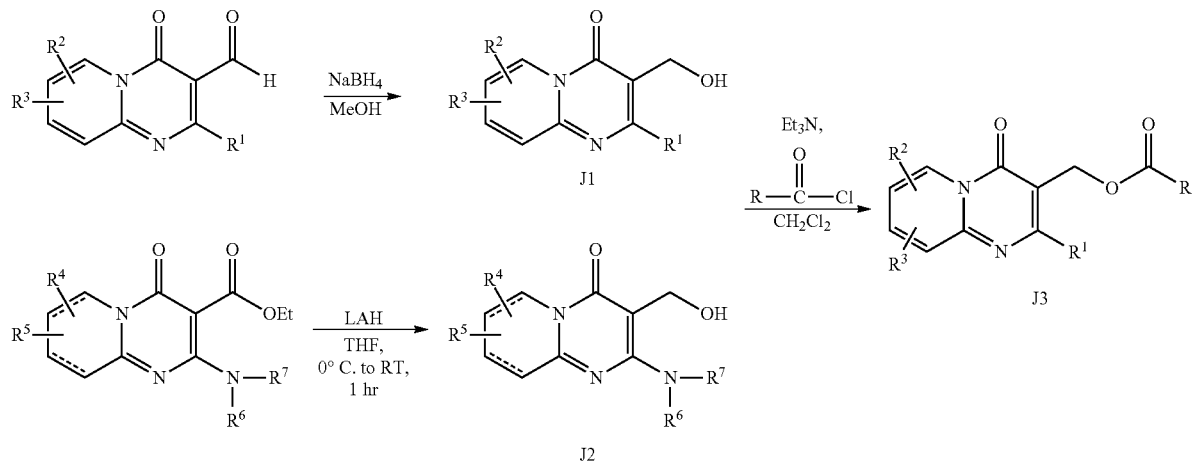

General Procedure for the Synthesis of J1

To a solution of an aldehyde (0.9 mmol) in methanol (0.5 mL) was added NaBH$_4$ (1.35 mmol) at room temperature. After stirring 1 h, the reaction mixture was diluted with methylene chloride (10 mL) and washed with brine (10 ml). The organic layer was dried over MgSO$_4$ and concentrated in vacuo. The crude product was purified by recrystallization from a mixture of hexanes and ethyl acetate to give J1.

General Procedure for the Synthesis of J2

To a stirred solution of an ester (0.06 mmol) in THF (1.0 mL) was added LiAlH$_4$ (0.09 mmol). The reaction mixture was stirred at room temperature for 1 hr. After reaction was completed, H$_2$O (0.1 mL) was added dropwise. The reaction mixture was filtered off and concentrated in vacuo. The crude product was purified by flash column chromatography to give J2.

General Procedure for the Synthesis of J3

To a stirred solution of J1 or J2 (0.19 mmol) in CH$_2$Cl$_2$ (0.6 mL) was added triethylamine (0.38 mmol) and a benzoyl chloride (0.28 mmol) at 0° C. The reaction mixture was stirred at room temperature for 1 h. After reaction was completed, the mixture was diluted with CH$_2$Cl$_2$ (10 mL) and washed with brine (10 ml). The organic layer was dried over anhydrous MgSO$_4$ and concentrated in vacuo. The crude product was purified by flash column chromatography (Hexane: EtOAc=2:1) to give J3.

3-(Hydroxymethyl)-2-(phenylamino)-4H-pyrido[1,2-a]pyrimidin-4-one (206)

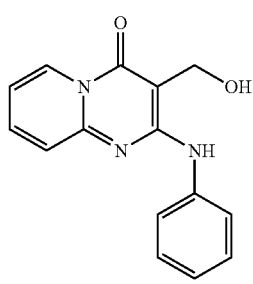 [SMILES: O=c1c(CO)c(Nc2ccccc2)nc2ccccn12]

$^1$H NMR (400 MHz, CDCl$_3$+CD$_3$OD) δ 4.80 (s, 2H), 6.87-6.90 (m, 1H), 8.03 (dd, J=7.2, 7.6 Hz, 1H), 7.27 (dd, J=7.6, 8.0 Hz, 2H), 7.53-7.58 (m, 3H), 8.36 (brs, 1H), 8.82 (d, J=6.8 Hz, 1H); $^{13}$C NMR (100 MHz, CDCl$_3$+CD$_3$OD) δ 56.0, 94.80, 94.85, 113.8, 121.1, 121.2, 123.2, 123.3, 124.5, 127.5, 128.6, 136.4, 138.9, 139.0, 149.7, 157.1, 158.0, 158.1.

2-(3-Chlorophenylamino)-3-(hydroxy methyl)-4H-pyrido[1,2-a]pyrimidin-4-one (207)

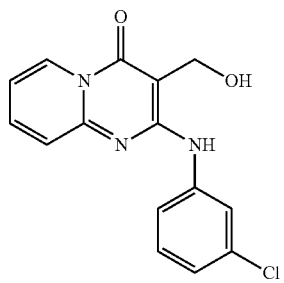 [SMILES: O=c1c(CO)c(Nc2cccc(Cl)c2)nc2ccccn12]

$^1$H NMR (400 MHz, CDCl$_3$) δ 4.95 (d, J=6.4 Hz, 2H), 6.93 (t, J=6.8 Hz, 1H), 7.05 (d, J=8.0 Hz, 1H), 7.38 (t, J=4.4 Hz, 2H), 7.42 (s, 1H), 7.63 (t, J=6.8 Hz, 1H), 7.81 (t, J=1.6 Hz, 1H), 8.20 (s, 1H), 8.92 (d, J=7.2 Hz, 1H), 2-(3-Fluorophenylamino)-3-(hydroxymethyl)-4H-pyrido[1,2-a]pyrimidine-3-carbaldehyde (208)

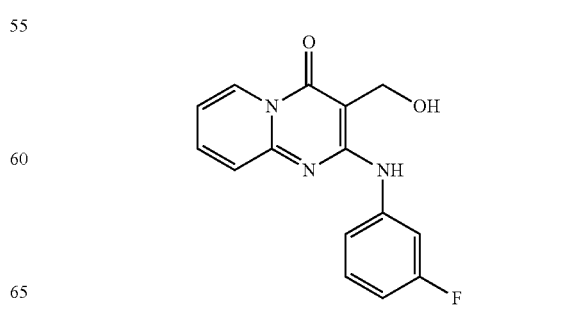

¹H NMR (400 MHz, CDCl₃) δ 4.94 (s, 2H), 6.94 (t, J=6.0 Hz, 2H), 7.17 (d, J=8.0 Hz, 1H), 7.43 (d, J=8.8 Hz, 2H), 7.63 (t, J=7.2 Hz, 2H), 7.70 (d, J=9.2 Hz, 1H), 8.26 (s, 1H), 8.93 (d, J=7.2 Hz, 1H).

3-(Hydroxymethyl)-2-(3-(trifluoromethyl)phenylamino)-4H-pyrido[1,2-a]pyrimidin-4-one (209)

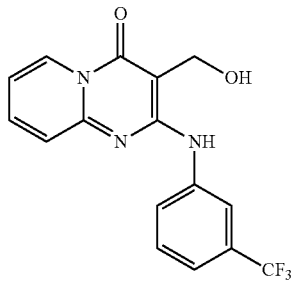

¹H NMR (400 MHz, CDCl₃) δ 4.99 (s, 2H), 6.99 (d, J=6.0 Hz, 2H), 7.32 (d, J=8.0 Hz, 1H), 7.43 (d, J=7.6 Hz, 2H), 7.69 (brs, 2H), 8.06 (s, 1H), 8.27 (s, 1H), 8.96 (d, J=7.6 Hz, 1H).

3-(Hydroxymethyl)-2-(3-(trifluoromethoxy)phenylamino)-4H-pyrido[1,2-a]pyrimidin-4-one (210)

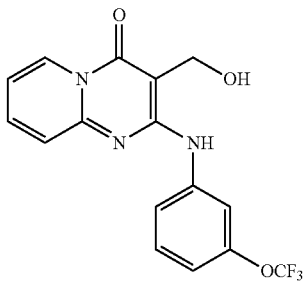

¹H NMR (400 MHz, CDCl₃) δ 4.95 (d, J=6.4 Hz, 2H), 6.84 (t, J=6.8 Hz, 1H), 6.92 (d, J=6.8 Hz, 1H), 7.30-7.34 (m, 3H), 7.59 (t, J=7.2 Hz, 1H), 7.86 (s, 1H), 8.36 (s, 1H), 8.87 (d, J=6.4 Hz, 1H),

Methyl 3-(3-(hydroxymethyl)-4-oxo-4H-pyrido[1,2-a]pyrimidin-2-ylamino)benzoate (211)

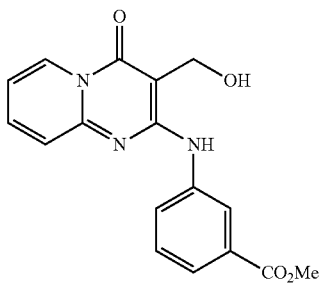 [SMILES: COC(=O)c1cccc(Nc2nc3ccccn3c(=O)c2CO)c1]

¹H NMR (400 MHz, CDCl₃) δ 3.92 (s, 3H), 4.99 (d, J=6.4 Hz, 2H), 6.96 (t, J=7.2 Hz, 1H), 7.38-7.42 (m, 2H), 7.63 (t, J=7.8 Hz, 1H), 7.75 (d, J=7.6 Hz, 1H), 7.88 (d, J=8.0 Hz, 1H), 8.21 (s, 1H), 8.25 (brs, 1H), 8.96 (d, J=7.6 Hz, 1H).

3-(3-(hydroxymethyl)-4-oxo-4H-pyrido[1,2-a]pyrimidin-2-ylamino)benzoic acid (212)

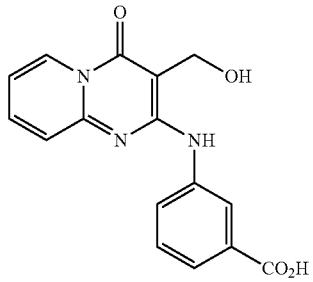 [SMILES: O=C(O)c1cccc(Nc2nc3ccccn3c(=O)c2CO)c1]

¹H NMR (400 MHz, CDCl₃) δ 4.73 (s, 1H), 5.74 (s, 2H), 7.19 (t, J=7.2 Hz, 1H), 7.38-7.42 (m, 2H), 7.45 (d, J=7.6 Hz, 1H), 7.86 (t, J=8.4 Hz, 1H), 8.00 (d, J=8.0 Hz, 1H), 8.19 (s, 1H), 8.82 (s, 1H), 8.89 (d, J=6.8 Hz, 1H).

2-(4-Chlorophenylamino)-3-(hydroxymethyl)-4H-pyrido[1,2-a]pyrimidin-4-one (213)

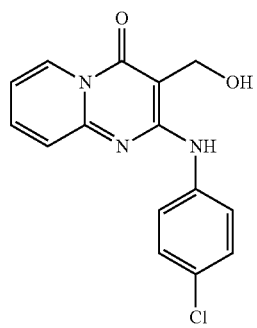 [SMILES: O=c1c(CO)c(Nc2ccc(Cl)cc2)nc2ccccn12]

¹H NMR (400 MHz, DMSO) δ 4.05 (d, J=7.2 Hz, 2H), 7.37 (d, J=8.8 Hz, 2H), 7.44 (d, J=8.8 Hz, 1H), 7.75 (d, J=6.8 Hz, 2H), 7.88 (t, J=8.8 Hz, 1H), 8.81 (s, 1H), 8.88 (d, J=6.4 Hz, 1H).

2-(2-Chlorophenylamino)-3-(hydroxymethyl)-4H-pyrido[1,2-a]pyrimidin-4-one (214)

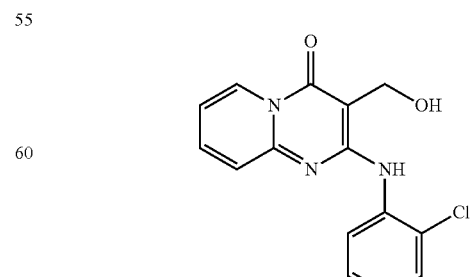

¹H NMR (400 MHz, CDCl₃) δ 5.01 (d, J=5.6 Hz, 2H), 6.97-7.01 (m, 3H), 7.26-7.29 (m, 1H), 7.42 (t, J=8.8 Hz, 2H), 7.66 (t, J=7.2 Hz, 1H), 8.41 (t, J=5.2 Hz, 1H), 8.53 (s, 1H), 8.99 (d, J=6.8 Hz, 1H).

3-(Hydroxymethyl)-2-(3-hydroxyphenylamino)-4H-pyrido[1,2-a]pyrimidin-4-one (215)

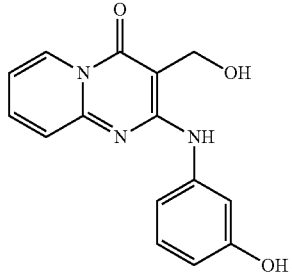 [SMILES: O=c1c(CO)c(Nc2cccc(O)c2)nc2ccccn12]

¹H NMR (400 MHz, CDCl₃+CD₃OD) δ 4.81 (s, 2H), 6.53 (d, J=8.0 Hz, 1H), 6.99 (dd, J=6.8, 6.8 Hz, 1H), 7.04 (d, J=8.0 Hz, 1H), 7.12 (dd, J=6.8, 6.8 Hz, 1H), 7.18 (s, 1H), 7.42 (d, J=9.6 Hz, 1H), 7.64 (dd, J=6.8, 8.8 Hz, 1H), 8.88 (d, J=7.2 Hz, 1H).

3-(Hydroxymethyl)-2-(4-hydroxyphenylamino)-4H-pyrido[1,2-a]pyrimidin-4-one (216)

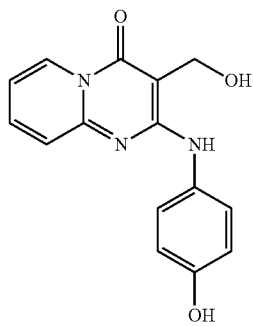 [SMILES: O=c1c(CO)c(Nc2ccc(O)cc2)nc2ccccn12]

¹H NMR (400 MHz, CD₃OD) δ 4.83 (s, 2H), 6.77 (dd, J=2.0, 8.8 Hz, 2H), 7.04 (dd, J=6.8, 6.8 Hz, 1H), 7.32 (d, J=8.8 Hz, 1H), 7.34-7.67 (m, 2H), 7.67-7.73 (m, 1H), 8.84 (d, J=6.8 Hz, 1H).

3-(Hydroxymethyl)-2-(2-hydroxyphenylamino)-4H-pyrido[1,2-a]pyrimidin-4-one (217)

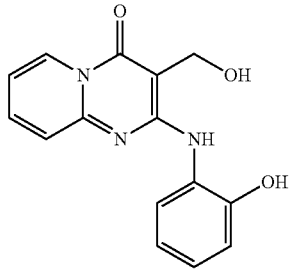 [SMILES: O=c1c(CO)c(Nc2ccccc2O)nc2ccccn12]

¹H NMR (400 MHz, CDCl₃+CD₃OD) δ 3.71 (s, 1H), 4.86 (s, 2H), 6.88 (ddd, J=1.6, 7.6, 8.0 Hz, 1H), 6.93 (dd, J=1.6, 8.0 Hz, 1H), 6.98 (ddd, J=1.6, 7.2, 8.0 Hz, 1H), 7.05 (ddd, J=1.2, 6.8, 6.8 Hz, 1H), 7.43 (d, J=8.8 Hz, 1H), 7.69-7.73 (m, 2H), 8.91 (dd, J=0.8, 6.8 Hz, 1H).

2-(2,6-Dichlorophenylamino)-3-(hydroxymethyl)-4H-pyrido[1,2-a]pyrimidin-4-one (218)

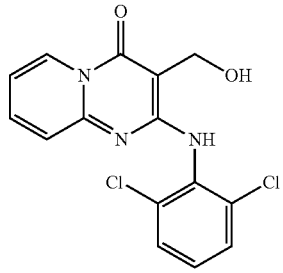 [SMILES: O=c1c(CO)c(Nc2c(Cl)cccc2Cl)nc2ccccn12]

¹H NMR (400 MHz, CDCl₃) δ 5.03 (d, J=6.0 Hz, 2H), 6.96 (t, J=7.2 Hz, 1H), 7.16 (t, J=7.6 Hz, 2H), 7.2 (s, 1H), 7.39 (d, J=8.0 Hz, 2H), 7.56 (t, J=7.6 Hz, 1H), 7.77 (s, 1H), 8.96 (d, J=7.2 Hz, 1H).

2-(3,5-Dichlorophenylamino)-3-(hydroxymethyl)-4H-pyrido[1,2-a]pyrimidin-4-one (219)

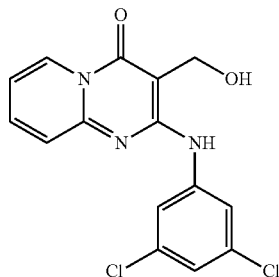 [SMILES: O=c1c(CO)c(Nc2cc(Cl)cc(Cl)c2)nc2ccccn12]

¹H NMR (400 MHz, CDCl₃) δ 4.97 (d, J=6.0 Hz, 2H), 7.01-7.04 (m, 2H), 7.50 (t, J=6.8 Hz, 1H), 7.60 (s, 2H), 7.71 (t, J=8.4 Hz, 2H), 8.24 (s, 1H), 8.98 (d, J=7.2 Hz, 1H).

2-(3,5-Difluorophenylamino)-3-(hydroxymethyl)-4H-pyrido[1,2-a]pyrimidin-4-one (220)

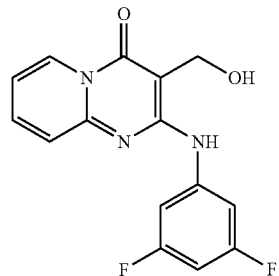 [SMILES: O=c1c(CO)c(Nc2cc(F)cc(F)c2)nc2ccccn12]

¹H NMR (400 MHz, CDCl₃) δ 4.99 (d, J=6.0 Hz, 2H), 6.52 (t, J=8.8 Hz, 1H), 7.05 (t, J=5.6 Hz, 2H), 7.29 (d, J=2.0 Hz, 2H), 7.51 (s, 1H), 7.72 (t, J=7.6 Hz, 1H), 8.30 (s, 1H), 8.99 (d, J=6.4 Hz, 1H).

2-(2,6-Dimethylphenylamino)-3-(hydroxymethyl)-
4H-pyrido[1,2-a]pyrimidin-4-one (221)

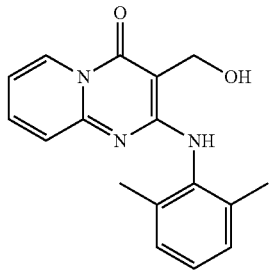 [SMILES: Cc1cccc(C)c1Nc1nc2ccccn2c(=O)c1CO]

$^1$H NMR (400 MHz, CDCl$_3$) δ 2.23 (s, 6H), 5.02 (d, J=6.4 Hz, 2H), 6.92 (t, J=6.8 Hz, 1H), 7.12 (s, 3H), 7.20 (d, J=8.8 Hz, 1H), 7.33 (s, 1H), 7.53 (t, J=6.8 Hz, 1H), 8.94 (d, J=6.4 Hz, 1H).

3-(Hydroxymethyl)-2-phenoxy-4H-pyrido[1,2-a]pyrimidin-4-one (222)

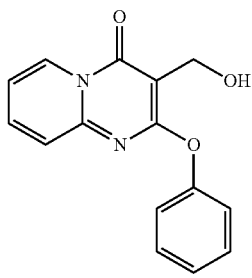 [SMILES: O=c1c(CO)c(Oc2ccccc2)nc2ccccn12]

$^1$H NMR (400 MHz, CDCl$_3$) δ 3.31 (brs, 1H), 4.86 (s, 2H), 7.03-7.09 (m, 3H), 7.13-7.18 (m, 1H), 7.28-7.34 (m, 3H), 7.58-7.62 (m, 1H), 8.94-8.96 (m, 1H); $^{13}$C NMR (100 MHz, CDCl$_3$) δ 56.0, 99.7, 115.2, 121.7, 125.1, 125.3, 127.4, 129.3, 136.8, 149.2, 152.8, 159.6, 164.0.

2-(3-Fluorophenoxy)-3-(hydroxymethyl)-4H-pyrido[1,2-a]pyrimidin-4-one (223)

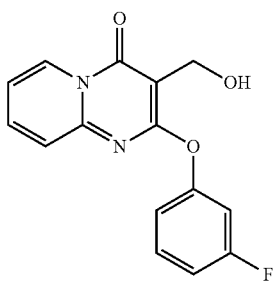 [SMILES: O=c1c(CO)c(Oc2cccc(F)c2)nc2ccccn12]

$^1$H NMR (400 MHz, CDCl$_3$) δ 3.62 (brs, 1H), 4.78 (s, 2H), 6.78-6.85 (m, 3H), 7.02 (ddd, J=1.2, 6.8, 7.2 Hz, 1H), 7.18-7.23 (m, 1H), 7.25 (d, J=9.2 Hz, 1H), 7.57-7.62 (m, 1H), 8.89 (d, J=6.8 Hz, 1H); $^{13}$C NMR (100 MHz, CDCl$_3$) δ 55.3, 99.7, 109.4, 109.6, 111.7, 111.9, 115.2, 117.2, 117.3, 125.0, 127.3, 129.7, 129.8, 137.0, 149.0, 153.5, 153.6, 159.4, 161.4, 163.6, 163.8.

2-(3-Chlorophenoxy)-3-(hydroxymethyl)-4H-pyrido[1,2-a]pyrimidin-4-one (224)

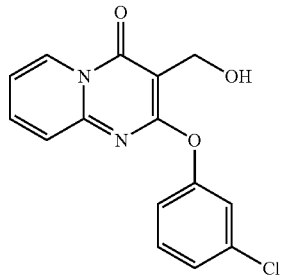 [SMILES: O=c1c(CO)c(Oc2cccc(Cl)c2)nc2ccccn12]

$^1$H NMR (400 MHz, CDCl$_3$) δ 3.51 (t, J=6.4 Hz, 1H), 4.79 (d, J=6.4 Hz, 2H), 6.95-6.98 (m, 1H), 7.04 (dd, J=6.8, 7.2 Hz, 1H), 7.08-7.10 (m, 1H), 7.20 (dd, J=8.4, 8.8 Hz, 1H), 7.27 (d, J=8.8 Hz, 1H), 7.59-7.63 (m, 1H), 8.91 9dd, J=0.4, 7.2 Hz, 1H); $^{13}$C NMR (100 MHz, CDCl$_3$) δ 53.3, 55.4, 99.7, 115.3, 120.1, 122.2, 125.1, 127.4, 129.8, 134.3, 137.0, 153.2, 159.2, 163.6.

3-(Hydroxymethyl)-2-(phenylamino)-6,7,8,9-tetrahydro-4H-pyrido[1,2-a]pyrimidin-4-one (225)

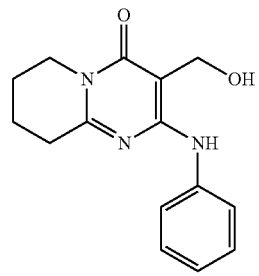 [SMILES: O=c1c(CO)c(Nc2ccccc2)nc2n1CCCC2]

$^1$H NMR (400 MHz, CDCl$_3$) δ 1.85-1.93 (m, 4H), 2.15 (s, 2H), 2.84 (t, J=6.8 Hz, 2H), 3.87 (t, J=6.2 Hz, 2H), 7.06 (t, J=7.0 Hz, 1H), 7.26 (t, J=7.0 Hz, 2H), 7.51 (d, J=7.4 Hz, 2H), 11.2 (s, 1H); $^{13}$C NMR (100 MHz, CDCl$_3$) δ 14.6, 19.2, 22.2, 32.2, 42.4, 88.4, 122.9, 124.4, 128.8, 138.4, 160.5, 160.8, 162.2.

2-(3-Chlorophenylamino)-3-(hydroxymethyl)-6,7,8,9-tetrahydro-4H-pyrido[1,2-a]pyrimidin-4-one (226)

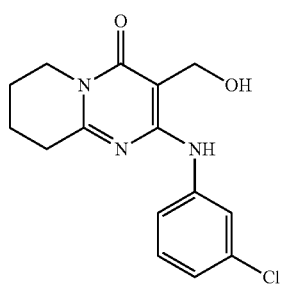 [SMILES: O=c1c(CO)c(Nc2cccc(Cl)c2)nc2n1CCCC2]

¹H NMR (400 MHz, DMSO-d₆) δ 1.23-1.34 (m, 2H), 1.38-1.51 (m, 4H), 2.35-2.41 (m, 2H), 3.98-4.05 (m, 2H), 4.12 (s, 2H), 7.17-7.22 (m, 2H), 7.31 (t, J=2.0 Hz, 1H), 7.36 (t, J=8.0 Hz, 1H), 7.77 (s, 1H); ¹³C NMR (100 MHz, DMSO-d₆) δ 15.1, 23.1, 31.4, 42.4, 59.2, 61.4, 65.7, 122.8, 123.9, 125.6, 131.6, 134.3, 139.4, 157.9, 164.3

3-(Hydroxymethyl)-2-(3-(trifluoromethyl phenylamino)-6,7,8,9-tetrahydro-4H-pyrido[1,2-a]pyrimidin-4-one (227)

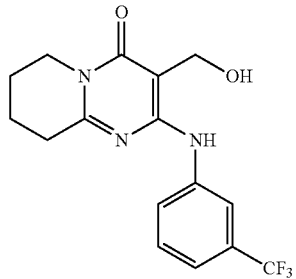 [SMILES: O=c1c(CO)c(Nc2cccc(C(F)(F)F)c2)nc2n1CCCC2]

¹H NMR (400 MHz, DMSO-d₆) δ 1.19-1.38 (m, 2H), 1.48-1.54 (m, 2H), 1.70-1.73 (m, 2H), 2.38 (t, J=12.8 Hz, 1H), 3.98-4.06 (m, 2H), 4.13 (s, 2H), 7.47 (d, J=7.6 Hz, 1H), 7.52 (d, J=8.8 Hz, 1H), 7.55-7.59 (m, 2H), 7.83 (s, 1H); ¹³C NMR (100 MHz, DMSO-d₆) 614.3, 22.2, 30.5, 41.5, 58.4, 77.9, 119.8, 121.2, 127.0, 129.8, 130.1, (d, J=26.8 due to CF₃), 138.2, 146.1, 157.1, 163.6, 169.1.

3-Hydroxymethyl)-2-(2-hydroxyphenylamino)-6,7,8,9-tetrahydro-4H-pyrido[1,2-a]pyrimidin-4-one (228)

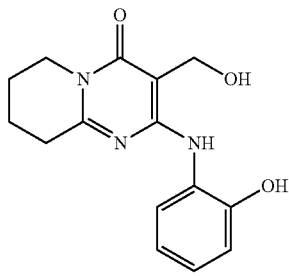 [SMILES: O=c1c(CO)c(Nc2ccccc2O)nc2n1CCCC2]

¹H NMR (400 MHz, CDCl₃) δ 1.78-1.94 (m, 4H), 2.13-2.23 (m, 2H), 2.61 (t, J=6.0 Hz, 1H), 3.98-4.05 (m, 2H), 4.12 (s, 2H), 6.81 (t, J=7.2 Hz, 1H), 6.89 (d, J=7.2 Hz, 1H), 6.98-7.12 (m, 2H), 10.11 (s, 1H), 11.3 (s, 1H); ¹³C NMR (100 MHz, CDCl₃) δ 14.3, 21.4, 31.3, 42.1, 61.1, 87.7, 121.2, 126.4, 128.3, 128.6, 151.1, 161.3, 162.5, 163.7, 169.4.

3-(Hydroxymethyl)-2-(3-hydroxyphenylamino)-6,7,8,9-tetrahydro-4H-pyrido[1,2-a]pyrimidin-4-one (229)

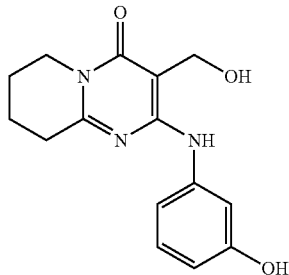 [SMILES: O=c1c(CO)c(Nc2cccc(O)c2)nc2n1CCCC2]

¹H NMR (400 MHz, CDCl₃) δ 1.41-1.61 (m, 4H), 1.62-1.77 (m, 2H), 2.72 (t, J=10.0 Hz, 1H), 3.78-3.95 (m, 2H), 4.17 (s, 2H), 6.43 (d, J=7.6 Hz, 1H), 6.81 (d, J=8.0 Hz, 1H), 6.87 (d, J=8.0 Hz, 1H), 6.98 (t, J=2.0 Hz, 1H); ¹³C NMR (100 MHz, CDCl₃) δ 14.2, 21.8, 31.9, 42.4, 60.1, 79.8, 109.8, 111.6, 114.0, 129.4, 139.4, 149.7, 159.3, 160.2, 163.1.

3-(Hydroxymethyl)-2-(4-hydroxyphenylamino)-6,7,8,9-tetrahydro-4H-pyrido[1,2-a]pyrimidin-4-one (230)

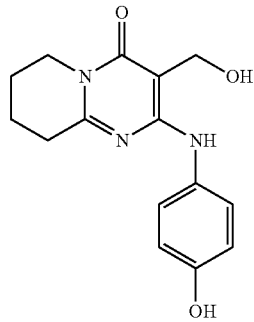 [SMILES: O=c1c(CO)c(Nc2ccc(O)cc2)nc2n1CCCC2]

¹H NMR (400 MHz, DMSO-d₆) δ 1.21-1.45 (m, 4H), 1.63-1.71 (m, 2H), 2.34 (t, J=12.8 Hz, 1H), 3.98-4.05 (m, 2H), 4.19 (s, 2H), 6.75 (d, J=8.8 Hz, 2H), 7.00 (d, J=8.8 Hz, 2H); ¹³C NMR (100 MHz, DMSO-d₆) δ 14.9, 21.9, 32.1, 42.3, 60.4, 87.2, 115.7, 125.0, 130.1, 154.9, 159.4, 160.6, 163.3.

3-(Hydroxymethyl)-9-methyl-2-(phenylamino)-4H-pyrido[1,2-a]pyrimidin-4-one (231)

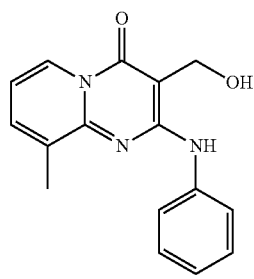 [SMILES: Cc1cccn2c(=O)c(CO)c(Nc3ccccc3)nc12]

¹H NMR (400 MHz, CDCl₃) δ 2.40 (s, 3H), 2.97 (brs, 1H), 4.93 (s, 2H), 6.89 (t, J=6.8 Hz, 1H), 7.11 (t, J=7.2 Hz, 1H), 7.34 (t, J=7.6 Hz, 2H), 7.62 (d, J=6.4 Hz, 1H), 8.02 (d, J=8.0 Hz, 2H), 8.73 (d, J=6.8 Hz, 1H).

2-(3-Chlorophenylamino)-3-(hydroxymethyl)-9-methyl-4H-pyrido[1,2-a]pyrimidin-4-one (232)

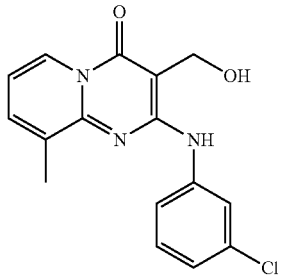 [SMILES: Cc1cccn2c(=O)c(CO)c(Nc3cccc(Cl)c3)nc12]

¹H NMR (400 MHz, CDCl₃) δ 2.43 (s, 3H), 3.06 (t, J=6.4 Hz, 1H), 4.92 (d, J=6.4 Hz, 2H), 6.69 (d, J=7.0 Hz, 1H), 7.03 (d, J=7.6 Hz, 1H), 7.23 (t, J=8.0 Hz, 1H), 7.29 (d, J=8.0 Hz, 1H), 7.44 (d, J=6.8 Hz, 1H), 8.03 (s, 1H), 8.38 (s, 1H), 8.71 (d, J=7.2 Hz, 1H).

2-((3-Chlorophenyl)(methyl)amino)-3-(hydroxymethyl)-9-methyl-4H-pyrido[1,2-a]pyrimidin-4-one (233)

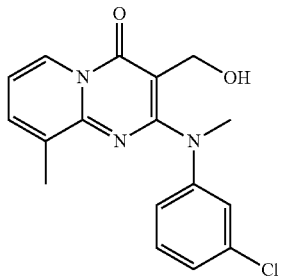 [SMILES: Cc1cccn2c(=O)c(CO)c(N(C)c3cccc(Cl)c3)nc12]

¹H NMR (400 MHz, CDCl₃) δ 2.51 (s, 3H), 4.09 (t, J=6.8 Hz, 1H), 4.12 (d, J=7.2 Hz, 2H), 6.95 (t, J=7.0 Hz, 1H), 7.04-7.06 (m, 2H), 7.20 (t, J=8.4 Hz, 1H), 7.54 (d, J=6.8 Hz, 1H), 8.84 (d, J=7.2 Hz, 1H).

2-((3-Chlorophenyl)(methyl)amino)-3-(methoxymethyl)-9-methyl-4H-pyrido[1,2-a]pyrimidin-4-one (234)

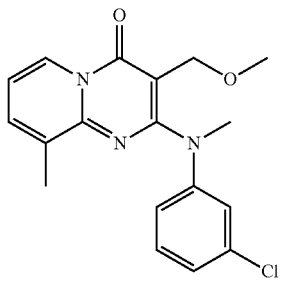 [SMILES: COCc1c(N(C)c2cccc(Cl)c2)nc2c(C)cccn2c1=O]

¹H NMR (400 MHz, CDCl₃) δ 2.49 (s, 3H), 3.01 (s, 3H), 4.04 (s, 3H), 6.91 (t, J=7.0 Hz, 1H), 7.08 (d, J=8.4 Hz, 1H), 7.12 (d, J=7.2 Hz, 1H), 7.20 (s, 1H), 7.26 (t, J=8.0 Hz, 1H), 7.52 (d, J=6.8 Hz, 1H), 8.86 (d, J=7.2 Hz, 1H).

3-(Hydroxymethyl)-9-methyl-2-(3-(trifluoromethoxy)phenylamino)-4H-pyrido[1,2-a]pyrimidin-4-one (235)

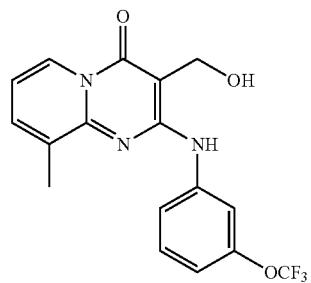 [SMILES: Cc1cccn2c(=O)c(CO)c(Nc3cccc(OC(F)(F)F)c3)nc12]

¹H NMR (400 MHz, CDCl₃) δ 2.40 (s, 3H), 3.15 (t, J=6.2 Hz, 1H), 4.93 (d, J=6.4 Hz, 2H), 6.67 (t, J=7.0 Hz, 1H), 6.91 (d, J=8.0 Hz, 1H), 7.25-7.27 (m, 1H), 7.32 (t, J=8.2 Hz, 1H), 7.43 (d, J=6.8 Hz, 1H), 7.98 (s, 1H), 8.51 (s, 1H), 8.72 (d, J=6.8 Hz, 1H).

3-(Hydroxymethyl)-2-(3-hydroxyphenylamino)-9-methyl-4H-pyrido[1,2-a]pyrimidin-4-one (236)

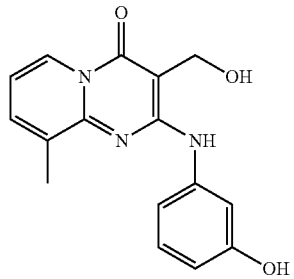 [SMILES: Cc1cccn2c(=O)c(CO)c(Nc3cccc(O)c3)nc12]

¹H NMR (400 MHz, CDCl₃+CD₃OD) δ 2.44 (s, 3H), 4.75 (s, 2H), 6.45 (dd, J=2.4, 8.0 Hz, 1 h), 6.84 (dd, J=6.8, 6.8 Hz, 1H), 7.06 (dd, J=8.0, 8.4 Hz, 1H), 7.11 (dd, J=2.0, 2.4 Hz, 1H), 7.17 (dd, H=2.0, 8.0 Hz, 1H), 7.45 (d, J=6.8 Hzm 1H), 8.72 (d, J=7.2 Hz, 1H).

3-(Hydroxymethyl)-2-(4-hydroxyphenylamino)-9-methyl-4H-pyrido[1,2-a]pyrimidin-4-one (237)

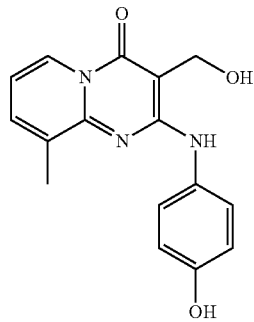 [SMILES: Cc1cccn2c(=O)c(CO)c(Nc3ccc(O)cc3)nc12]

¹H NMR (400 MHz, CDCl₃) δ 2.40 (s, 3H), 4.94 (d, J=4.8 Hz, 1H), 6.81-6.84 (m, 3H), 7.46 (d, J=7.2 Hz, 1H), 7.50 (d, J=8.8 Hz, 2H), 7.84 (s, 1H), 8.82 (d, J=7.2 Hz, 1H).

2-(4-tert-Butylphenylamino)-3-(hydroxymethyl)-9-methyl-4H-pyrido[1,2-a]pyrimidin-4-one (238)

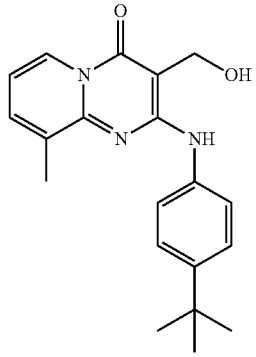 [SMILES: Cc1cccn2c(=O)c(CO)c(Nc3ccc(C(C)(C)C)cc3)nc12]

¹H NMR (400 MHz, CDCl₃) δ 1.34 (s, 9H), 2.40 (s, 3H), 3.07 (t, J=6.2 Hz, 1H), 4.91 (d, J=6.4 Hz, 2H), 6.61 (t, J=6.8 Hz, 1H), 7.34 (d, J=7.2 Hz, 2H), 7.38 (d, J=6.8 Hz, 1H), 8.21 (br s, 1H), 8.69 (d, J=7.2 Hz, H).

2-(3-Chlorobenzylamino)-3-(hydroxymethyl)-9-methyl-4H-pyrido[1,2-a]pyrimidin-4-one (239)

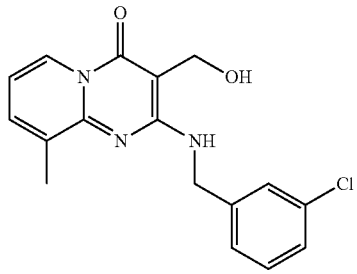 [SMILES: Cc1cccn2c(=O)c(CO)c(NCc3cccc(Cl)c3)nc12]

¹H NMR (400 MHz, CDCl₃+CD₃OD) δ 2.31 (s, 3H), 3.02 (s, 1H), 4.68 (d, J=5.6 Hz, 2H), 4.70 (s, 2H), 6.70 (dd, J=5.6, 6.0 Hz, 1H), 6.74 (dd, J=6.8, 7.2 Hz, 1H), 7.11-7.20 (m, 3H), 7.31 (s, 1H), 7.38 (d, J=6.8 Hz, 1H), 8.66 (d, J=6.8 Hz, 1H); ¹³C NMR (100 MHz, CDCl₃+CD₃OD) δ 17.7, 44.2, 44.3, 55.8, 93.1, 93.2, 112.6, 125.4, 125.5, 126.9, 127.5, 129.5, 132.6, 134.0, 134.9, 141.7, 149.45, 149.47, 157.4, 159.10, 159.16.

3-(Hydroxymethyl)-2-(isobutylamino)-9-methyl-4H-pyrido[1,2-a]pyrimidin-4-one (240)

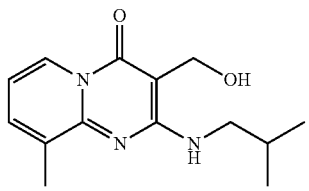 [SMILES: Cc1cccn2c(=O)c(CO)c(NCC(C)C)nc12]

¹H NMR (400 MHz, CDCl₃) δ 0.96 (d, J=6.8 Hz, 6H), 1.88-1.95 (m, 1H), 2.34 (s, 3H), 3.13 (brs, 1H), 3.32 (t, J=6.0 Hz, 2H), 4.78 (d, J=6.0 Hz, 2H), 6.08 (brs, 1H), 6.72 (t, J=6.8 Hz, 1H), 7.37 (d, J=6.8 Hz, 1H), 8.66 (d, J=6.8 Hz, 1H); ¹³C NMR (100 MHz, CDCl₃) δ 17.9, 20.5, 28.9, 48.6, 57.1, 92.5, 112.1, 126.0, 132.5, 134.6, 149.6, 157.1, 159.5.

2-(Diethylamino)-3-(hydroxymethyl)-9-methyl-4H-pyrido[1,2-a]pyrimidin-4-one (241)

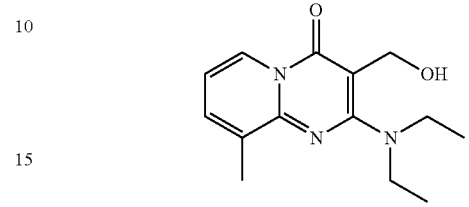

¹H NMR (400 MHz, CDCl₃) δ 1.22 (t, J=6.8 Hz, 6H), 2.35 (s, 3H), 3.41 (s, 1H), 3.63 (q, J=6.8 Hz, 4H), 4.44 (s, 2H), 6.65 (t, J=7.2 Hz, 1H), 7.31 (d, J=6.8 Hz, 1H), 8.68 (d, J=7.2 Hz, 1H) ¹³C NMR (100 MHz, CDCl₃) δ 13.9, 17.7, 44.0, 67.0, 92.2, 111.7, 125.8, 132.5, 134.4, 148.1, 160.7, 160.8.

2-(Cyclohexylmethylamino)-3-(hydroxymethyl)-9-methyl-4H-pyrido[1,2-a]pyrimidin-4-one (242)

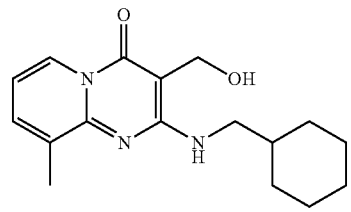 [SMILES: Cc1cccn2c(=O)c(CO)c(NCC3CCCCC3)nc12]

¹H NMR (400 MHz, CDCl₃) δ 0.95-0.98 (m, 2H), 1.18-1.23 (m, 3H), 1.58-1.79 (m, 6H), 2.42 (s, 3H), 3.27 (t, J=6.4 Hz, 2H), 3.85 (brs, 1H), 4.74 (m, 2H), 6.21 (t, J=7.2 Hz, 1H), 6.68 (d, J=6.8 Hz, 1H), 7.33 (d, J=7.2 Hz, 1H), 8.57 (d, J=7.2 Hz, 1H); ¹³C NMR (100 MHz, CDCl₃) δ 17.9, 26.2, 26.7, 31.3, 38.4, 47.5, 56.9, 92.8, 112.0, 126.0, 132.3, 134.5, 149.4, 156.9, 159.5.

3-(Hydroxymethyl)-9-methyl-2-morpholino-4H-pyrido[1,2-a]pyrimidin-4-one (243)

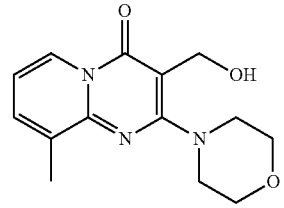 [SMILES: Cc1cccn2c(=O)c(CO)c(N3CCOCC3)nc12]

¹H NMR (400 MHz, CDCl₃) δ 2.01 (brs, 1H), 2.43 (s, 3H), 3.62 (t, J=4.8 Hz, 4H), 3.78 (t, J=4.8 Hz, 4H), 4.62 (s, 2H), 6.85 (t, J=6.8 Hz, 1H), 7.46 (d, J=6.8 Hz, 1H), 8.76 (d, J=6.8 Hz, 1H); ¹³C NMR (100 MHz, CDCl₃) δ 17.9, 49.7, 58.9, 67.1, 95.5, 113.3, 125.2, 133.4, 135.0, 148.2, 160.6, 161.7.

117

3-(Hydroxymethyl)-9-methyl-2-morpholino-4H-pyrido[1,2-a]pyrimidin-4-one hydrochloride (244)

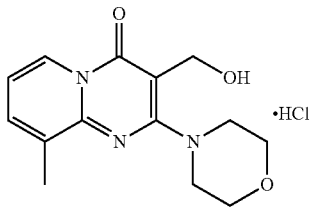 [SMILES: Cc1cccn2c(=O)c(CO)c(N3CCOCC3)nc12 ; Cl]

¹H NMR (400 MHz, CDCl₃) δ 2.43 (s, 3H), 3.42 (s, 1H), 3.62 (t, J=4.8 Hz, 4H), 3.78 (t, J=4.8 Hz, 4H), 4.62 (s, 2H), 6.85 (t, J=6.8 Hz, 1H), 7.46 (d, J=6.8 Hz, 1H), 8.76 (d, J=6.8 Hz, 1H); ¹³C NMR (100 MHz, CDCl₃) δ 17.9, 49.7, 58.9, 67.1, 98.5, 113.3, 125.2, 133.4, 135.0, 148.2, 160.6, 161.7.

7-Bromo-2-(3-chlorophenylamino)-3-(hydroxymethyl)-4H-pyrido[1,2-a]pyrimidin-4-one (245)

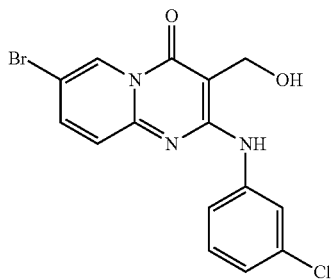

¹H NMR (400 MHz, DMSO-d₆) δ 4.78 (s, 2H), 5.37 (s, 1H), 7.12 (dd, J=1.6 Hz, 8.4 Hz, 1H), 7.32 (d, J=8.0 Hz, 1H), 7.42 (dd, J=1.6 Hz, 8.4 Hz, 1H), 7.54 (dd, J=0.8 Hz, 8.0 Hz, 1H), 7.64 (d, J=8.0 Hz, 1H), 7.91 (d, J=2.0 Hz, 1H), 8.47 (s, 1H), 8.71 (s, 1H);

2-(3-Chlorophenylamino)-3-(hydroxymethyl)-7-methoxy-4H-pyrido[1,2-a]pyrimidin-4-one (246)

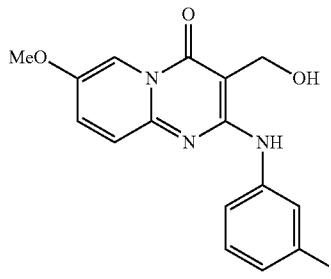

¹H NMR (400 MHz, DMSO-d₆) δ 3.86 (s, 3H), 4.70 (s, 2H), 5.22 (s, 1H), 7.02 (dd, J=0.8 Hz, 8.0 Hz, 1H), 7.28-7.32 (m, 1H), 7.41 (dd, J=1.2 Hz, 9.6 Hz, 1H), 7.58 (dd, J=0.8 Hz, 8.0 Hz, 1H), 7.64-7.68 (m, 1H), 7.87 (d, J=2.0 Hz, 1H), 8.36 (s, 1H), 8.69 (s, 1H)

118

2-(3-Chlorophenylamino)-3-(hydroxymethyl)-8-methoxy-4H-pyrido[1,2-a]pyrimidin-4-one (247)

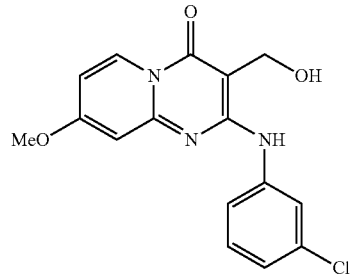 [SMILES: COc1ccn2c(=O)c(CO)c(Nc3cccc(Cl)c3)nc2c1]

¹H NMR (400 MHz, DMSO-d₆) δ 3.92 (s, 3H), 4.62 (s, 2H), 5.07 (s, 1H), 6.71 (d, J=2.8 Hz, 1H), 6.83 (dd, J=2.8 Hz, 8.0 Hz, 1H), 7.01 (d, J=8.0 Hz, 1H), 7.28 (dd, J=8.0 Hz, J=8.0 Hz, 1H), 7.62 (d, J=8.0 Hz, 1H), 7.76 (d, J=2.0 Hz, 1H), 8.62 (s, 1H), 8.71 (d, J=8.0 Hz, 1H); ¹³C NMR (100 MHz, DMSO-d₆) 54.8, 57.3, 93.8, 101.5, 109.3, 120.0, 120.9, 122.5, 129.5, 130.7, 133.4, 142.2, 151.9, 156.9, 157.8, 166.2.

8-Chloro-2-(3-chlorophenylamino)-3-(hydroxymethyl)-4H-pyrido[1,2-a]pyrimidin-4-one (248)

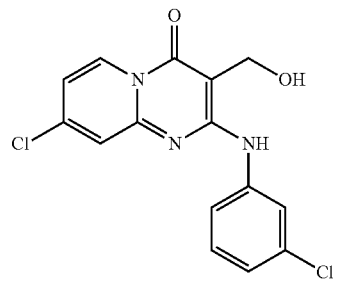 [SMILES: O=c1c(CO)c(Nc2cccc(Cl)c2)nc2cc(Cl)ccn12]

¹H NMR (400 MHz, CDCl₃) δ 4.68 (s, 2H), 5.14 (brs, 1H), 7.03 (dd, J=1.2, 8.0 Hz, 1H), 7.19 (dd, J=2.4, 7.6 Hz, 1H), 7.28 (t, J=8.0 Hz, 1H), 7.54, (d, J=2.0 Hz, 1H), 7.58 (dd, J=1.2, 8.4 Hz, 1H), 7.57 (t, J=2.0 Hz, 1H), 8.78 (d, J=8.0 Hz, 1H).

2-(3-Chlorophenylamino)-3-(hydroxymethyl)-8-(methylamino)-4H-pyrido[1,2-a]pyrimidin-4-one (249)

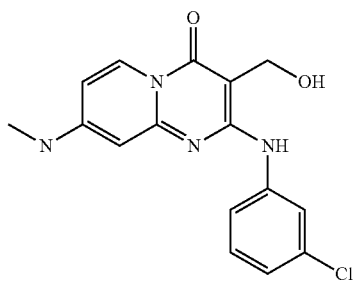 [SMILES: CNc1ccn2c(=O)c(CO)c(Nc3cccc(Cl)c3)nc2c1]

¹H NMR (400 MHz, CDCl₃) δ 2.81 (s, 3H), 3.85 (s, 2H), 6.02 (s, 1H), 6.32 (d, J=7.6 Hz, 1H), 6.93 (d, J=2 Hz, 1H), 7.12 (t, J=8.0 Hz, 1H), 7.38 (d, J=8.0 Hz, 1H), 7.81 (s, 1H), 8.42 (s, 1H), 9.93 (s, 1H).

2-(3-Chlorophenylamino)-8-(diethylamino)-3-(hydroxymethyl)-4H-pyrido[1,2-a]pyrimidin-4-one (250)

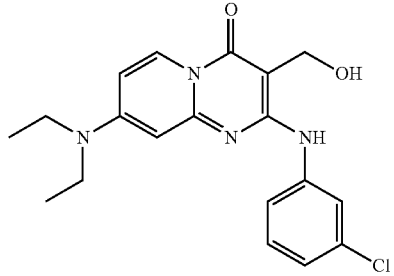 [SMILES: CCN(CC)c1ccn2c(=O)c(CO)c(Nc3cccc(Cl)c3)nc2c1]

¹H NMR (400 MHz, CDCl₃) δ 1.23 (t, J=6.8 Hz, 6H), 3.44 (q, J=6.8 Hz, 4H), 3.99 (s, 2H), 4.82 (t, J=2.1 Hz, 1H), 6.29 (d, J=2.1 Hz, 1H), 6.54 (dd, J=2.4, 8.4 Hz, 1H), 6.92 (d, J=2 Hz, 1H), 7.21 (t, J=8.0 Hz, 1H), 7.81 (d, J=2.4 Hz, 1H), 8.06 (t, J=2.0 Hz, 1H), 8.85 (d, J=8.4 Hz, 1H), 9.71 (s, 1H); ¹³C NMR (100 MHz, CDCl₃) δ 12.7, 20.0, 44.7, 92.8, 97.1, 104.0, 118.9, 120.7, 121.9, 128.5, 129.5, 134.1, 142.8, 150.6, 151.9, 158.3, 159.2.

3-(Hydroxymethyl)-8-morpholino-2-(phenylamino)-4H-pyrido[1,2-a]pyrimidin-4-one (251)

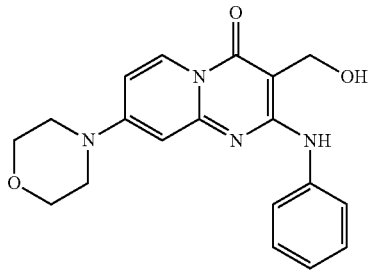 [SMILES: O=c1c(CO)c(Nc2ccccc2)nc2cc(N3CCOCC3)ccn12]

¹H NMR (400 MHz, DMSO-d₆) δ 3.43 (s, 4H), 3.67 (s, 4H), 4.59 (d, J=5.2 Hz, 2H), 5.05, (t, J=4.8 Hz, 1H), 6.41 (d, J=2.0 Hz, 1H), 6.95 (t, J=7.2 Hz, 1H), 7.00 (dd, J=2.8, 8.4 Hz, 1H), 7.25 (t, J=8.0 Hz, 2H), 7.64 (d, J=7.6 Hz, 2H), 8.38 (s, 1H), 8.69 (d, J=8.0 Hz, 1H); ¹³C NMR (100 MHz, DMSO-d₆) δ 46.5, 55.1, 66.3, 91.5, 99.1, 105.4, 121.3, 122.6, 128.5, 129.1, 140.9, 151.4, 155.0, 156.7, 158.5.

2-(3-Fluorophenylamino)-3-(hydroxymethyl)-8-morpholino-4H-pyrido[1,2-a]pyrimidin-4-one (252)

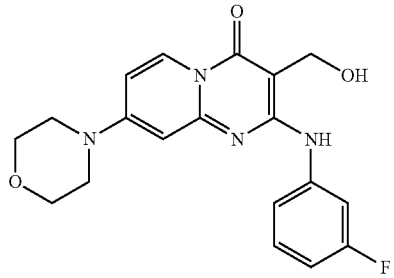 [SMILES: O=c1c(CO)c(Nc2cccc(F)c2)nc2cc(N3CCOCC3)ccn12]

¹H NMR (400 MHz, DMSO-d₆) δ 3.46 (s, 4H), 3.68 (s, 4H), 4.59 (d, J=5.2 Hz, 2H), 5.06, (t, J=5.2 Hz, 1H), 6.47 (d, J=2.4 Hz, 1H), 6.74 (t, J=7.2 Hz, 1H), 7.03 (dd, J=2.8, 8.0 Hz, 1H), 7.26 (t, J=7.2 Hz, 1H), 7.64 (d, J=8.0 Hz, 1H), 7.79 (d, J=12.4 Hz, 1H), 8.52 (s, 1H), 8.60 (d, J=8.0 Hz, 1H); ¹³C NMR (100 MHz, DMSO-d₆) δ 45.8, 54.2, 65.6, 91.3, 98.4, 105.0, 108.0 (d, J=20 Hz, due to F), 116.0, 128.0, 129.8 (d, J=10 Hz, due to F), 142.1 (d, J=11 Hz, due to F), 150.6, 154.4, 156.1, 157.4, 161.0, 163.3.

2-(3-Chlorophenylamino)-3-(hydroxymethyl)-8-morpholino-4H-pyrido[1,2-a]pyrimidin-4-one (253)

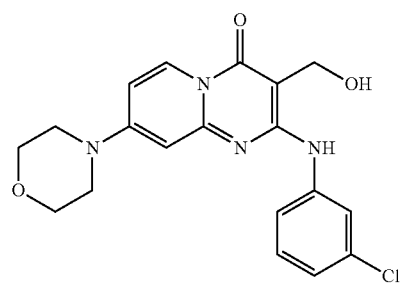 [SMILES: O=c1c(CO)c(Nc2cccc(Cl)c2)nc2cc(N3CCOCC3)ccn12]

¹H NMR (400 MHz, DMSO-d₆) δ 3.45 (t, J=5.6 Hz, 4H), 3.69 (t, J=5.6 Hz, 4H), 4.58 (d, J=5.2 Hz, 2H), 5.01 (t, J=5.2 Hz, 1H), 6.42 (d, J=2.8 Hz, 1H), 6.98 (d, J=8.0 Hz, 1H), 7.05 (dd, J=2.8, 8.0 Hz, 1H), 7.26 (t, J=8.0 Hz, 1H), 7.64 (d, J=8.0 Hz, 1H), 7.80 (t, J=2.0 Hz, 1H), 8.48 (s, 1H), 8.60 (d, J=8.0 Hz, 1H); ¹³C NMR (100 MHz, DMSO-d₆) δ 45.4, 53.6, 65.7, 84.7, 98.6, 105.3, 117.8, 118.7, 119.8, 127.1, 130.2, 129.2, 141.8, 149.7, 153.0, 155.3, 157.4; LC-MS (ESI, m/z): 386 [M+H]⁺.

3-(Hydroxymethyl)-8-(4-methylpiperazin-1-yl)-2-(phenylamino)-4H-pyrido[1,2-a]pyrimidin-4-one (254)

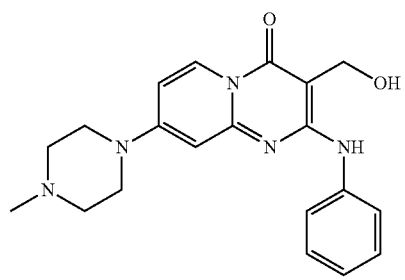 [SMILES: CN1CCN(c2ccn3c(=O)c(CO)c(Nc4ccccc4)nc3c2)CC1]

¹H NMR (400 MHz, CDCl₃) δ 2.34 (s, 3H), 2.52 (t, J=5.2 Hz, 4H), 3.43 (t, J=5.2 Hz, 4H), 4.88 (s, 2H), 5.28 (s, 1H), 6.37 (s, 1H), 6.55 (d, J=8.0 Hz, 1H), 7.05 (t, J=7.2 Hz, 1H), 7.33 (t, J=7.6 Hz, 2H), 7.60 (d, J=7.6 Hz, 2H), 7.91 (s, 1H), 8.64 (d, J=8.0 Hz, 1H).

121

2-(3-Chlorophenylamino)-3-(hydroxymethyl)-8-(4-methylpiperazin-1-yl)-4H-pyrido[1,2-a]pyrimidin-4-one (255)

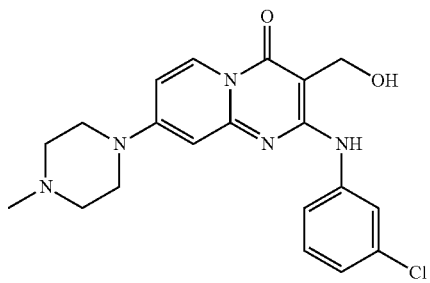 [SMILES: CN1CCN(c2ccn3c(=O)c(CO)c(Nc4cccc(Cl)c4)nc3c2)CC1]

$^1$H NMR (400 MHz, CDCl$_3$) δ 2.14 (s, 3H), 2.38 (t, J=4.4 Hz, 4H), 3.45 (t, J=4.4 Hz, 4H), 3.56 (s, 2H), 6.41 (d, J=2.4 Hz, 1H), 6.95 (dd, J=1.6, 8.0 Hz, 1H), 7.01 (dd, J=2.4, 8.0 Hz, 1H), 7.27 (t, J=8.0 Hz, 1H), 7.50 (d, J=1.6 Hz, 1H), 8.0 (d, J=8.0 Hz, 1H), 10.4 (s, 1H), 14.18 (s, 1H); $^{13}$C NMR (100 MHz, CDCl$_3$) δ 45.6, 51.6, 54.0, 55.0, 85.3, 98.3, 105.1, 117.7, 118.5, 121.0, 127.9, 130.3, 133.0, 142.1, 150.8, 154.1, 156.4, 157.8; LC-MS (ESI, m/z): 400 [M+H]$^+$.

2-(3-Fluorophenylamino)-3-(hydroxymethyl)-8-(4-methylpiperazin-1-yl)-4H-pyrido[1,2-a]pyrimidin-4-one (256)

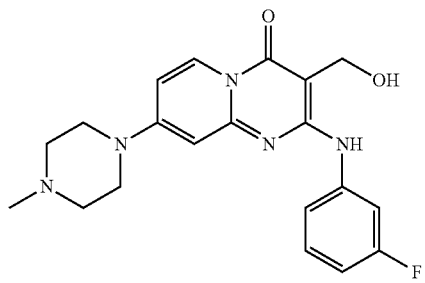 [SMILES: CN1CCN(c2ccn3c(=O)c(CO)c(Nc4cccc(F)c4)nc3c2)CC1]

$^1$H NMR H (400 MHz, CDCl$_3$) δ 2.35 (s, 3H), 2.54 (t, J=4.4 Hz, 4H), 3.48 (t, J=4.8 Hz, 4H), 4.87 (s, 2H), 5.23 (s, 1H), 6.42 (s, 1H), 6.60 (d, J=8.4 Hz, 1H), 6.73 (t, J=8.4 Hz, 1H), 7.12 (d, J=8.4 Hz, 1H), 7.19 (d, J=8.4 Hz, 1H), 7.71-7.75 (m, 1H), 8.04 (s, 1H), 8.71 (d, J=8.0 Hz, 1H).

2-(3-Chlorophenylamino)-3-(hydroxymethyl)-8-methyl-4H-pyrido[1,2-a]pyrimidin-4-one (257)

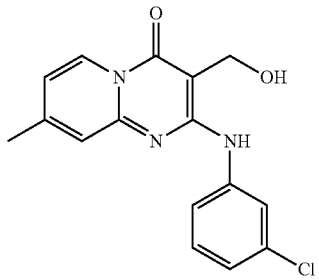 [SMILES: Cc1ccn2c(=O)c(CO)c(Nc3cccc(Cl)c3)nc2c1]

Colorless solid, mp 235° C. (decomp.); $^1$H NMR (400 MHz, CDCl$_3$) δ 2.42 (s, 3H), 4.07 (q, J=7.2 Hz, 2H), 7.03 (d, J=8.8 Hz, 2H), 7.26 (t, J=8.0 Hz, 2H), 7.46 (d, J=8.4 Hz, 1H), 7.84 (t, J=2.0 Hz, 1H), 8.79 (d, J=7.2 Hz, 2H).

122

2-(4-Chlorophenylamino)-3-(hydroxymethyl)-8-methyl-4H-pyrido[1,2-a]pyrimidin-4-one (258)

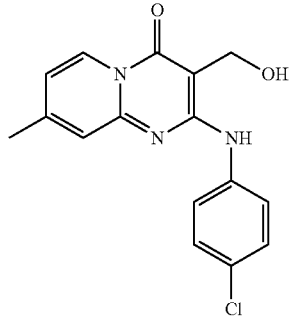 [SMILES: Cc1ccn2c(=O)c(CO)c(Nc3ccc(Cl)cc3)nc2c1]

Colorless solid, mp 227° C. (decomp.); $^1$H NMR (400 MHz, CDCl$_3$) δ 2.42 (s, 3H), 4.10 (s, 2H), 6.85 (d, J=7.2 Hz, 1H), 7.23-7.28 (m, 4H), 7.87 (d, J=6.8 Hz, 2H), 8.94 (d, J=7.6 Hz, 1H).

2-(4-Fluorophenylamino)-3-(hydroxymethyl)-8-methyl-4H-pyrido[1,2-a]pyrimidin-4-one (259)

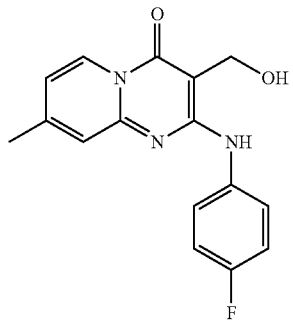 [SMILES: Cc1ccn2c(=O)c(CO)c(Nc3ccc(F)cc3)nc2c1]

Colorless solid, mp 232° C. (decomp.); $^1$H NMR (400 MHz, CDCl$_3$) δ 2.42 (s, 3H), 4.12 (s, 2H), 6.85 (d, J=6.8 Hz, 1H), 7.05 (t, J=8.4 Hz, 2H), 7.21 (s, 1H), 7.31-7.38 (m, 2H), 7.85 (q, J=4.8 Hz, 2H), 8.94 (d, J=7.2 Hz, 1H).

2-(3,4-Dichlorophenylamino)-3-(hydroxymethyl)-8-methyl-4H-pyrido[1,2-a]pyrimidin-4-one (260)

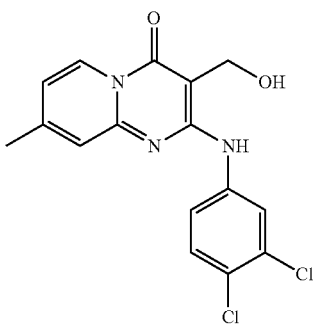 [SMILES: Cc1ccn2c(=O)c(CO)c(Nc3ccc(Cl)c(Cl)c3)nc2c1]

Colorless solid, mp 230° C. (decomp.); $^1$H NMR (400 MHz, CDCl$_3$) δ 2.44 (s, 3H), 4.09 (s, 2H), 6.89 (d, J=7.2 Hz, 1H), 7.26 (s, 1H), 7.36 (d, J=8.8 Hz, 1H), 7.76 (d, J=8.4 Hz, 1H), 8.24 (d, J=2.4 Hz, 1H), 8.95 (d, J=7.2 Hz, 1H), 9.71 (s, 1H).

2-(3-Chloro-4-fluorophenylamino)-3-(hydroxymethyl)-8-methyl-4H-pyrido[1,2-a]pyrimidin-4-one (261)

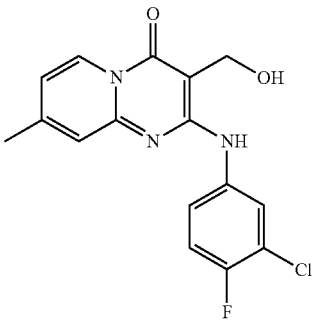 [SMILES: Cc1ccn2c(=O)c(CO)c(Nc3ccc(F)c(Cl)c3)nc2c1]

Colorless solid, mp 225° C. (decomp.); $^1$H NMR (400 MHz, CDCl$_3$) δ 2.43 (s, 3H), 4.09 (s, 2H), 6.88 (d, J=7.2 Hz, 1H), 7.11 (t, J=8.8 Hz, 1H), 7.27 (s, 1H), 7.69-7.73 (m, 1H), 8.12 (d, J=6.8 Hz, 1H), 8.95 (d, J=7.2 Hz, 1H), 9.71 (s, 1H).

9-Chloro-2-(3-chlorophenylamino)-3-(hydroxymethyl)-4H-pyrido[1,2-a]pyrimidin-4-one (262)

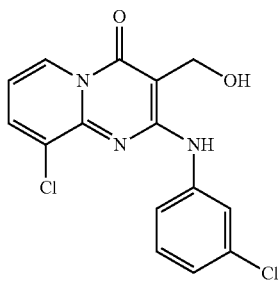

Colorless solid, mp 230° C. (decomp.); $^1$H NMR (400 MHz, CDCl$_3$) δ 4.95 (d, J=6.0 Hz, 2H), 6.80 (t, J=7.2 Hz, 1H), 7.06 (d, J=8.0 Hz, 1H), 7.27 (d, J=8.4 Hz, 1H), 7.46 (d, J=8.0 Hz, 1H), 7.78 (d, J=7.2 Hz, 1H), 8.18 (t, J=2.4 Hz, 1H), 8.43 (s, 1H), 8.81 (d, J=7.2 Hz, 1H).

2-(3-Chlorophenylamino)-3-(hydroxymethyl)-9-(trifluoromethyl)-4H-pyrido[1,2-a]pyrimidin-4-one (263)

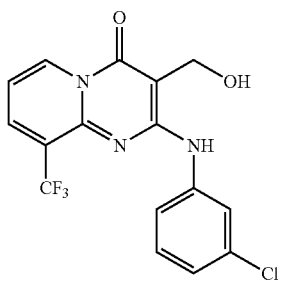

$^1$H NMR (400 MHz, DMSO-d$_6$) δ 4.77 (s, 2H), 7.11-7.13 (m, 1H), 7.32 (dd, J=7.2, 7.2 Hz, 1H), 7.35 (dd, J=8.0, 8.0 Hz, 1H), 7.48-7.50 (m, 1H), 8.13-8.14 (m, 1H), 8.41 (d, J=7.2 Hz, 1H), 9.12 (dd, J=1.2, 7.2 Hz, 1H).

2-(3-Chlorophenylamino)-9-fluoro-3-(hydroxymethyl)-4H-pyrido[1,2-a]pyrimidin-4-one (264)

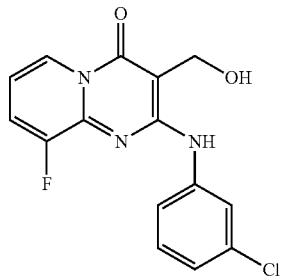

$^1$H NMR (400 MHz, DMSO-d$_6$) δ 4.76 (s, 1H), 5.31 (brs, 1H), 7.11-7.13 (m, 1H), 7.18-7.23 (m, 1H), 7.38 (dd, J=8.0, 8.0 Hz, 1H), 7.63-7.65 (m, 1H), 7.86 (dd, J=8.4, 8.8 Hz, 1H), 8.12-8.13 (m, 1H), 8.73 (d, J=7.2 Hz, 1H), 8.96 (brs, 1H).

2-(4-Chlorophenylamino)-9-fluoro-3-(hydroxymethyl)-4H-pyrido[1,2-a]pyrimidin-4-one (265)

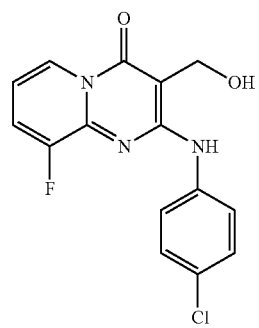 [SMILES: O=c1c(CO)c(Nc2ccc(Cl)cc2)nc2c(F)cccn12]

$^1$H NMR (400 MHz, DMSO-d$_6$) δ 4.72 (s, 2H), 5.30 (brs, 1H), 7.15-7.20 (m, 1H), 7.41-7.44 (m, 2H), 7.79-7.82 (m, 2H), 7.84-7.86 (m, 1H), 8.72 (d, J=7.2 Hz, 1H), 8.92 (brs, 1H).

9-Fluoro-2-(4-fluorophenylamino)-3-(hydroxymethyl)-4H-pyrido[1,2-a]pyrimidin-4-one (266)

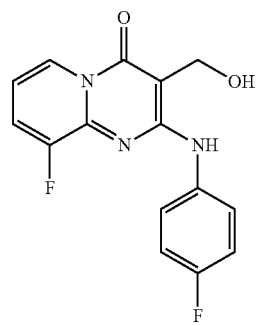 [SMILES: O=c1c(CO)c(Nc2ccc(F)cc2)nc2c(F)cccn12]

¹H NMR (400 MHz, DMSO-d₆) δ 4.75 (s, 2H), 5.25 (brs, 1H), 7.13-7.25 (m, 3H), 7.73-7.77 (m, 2H), 7.80-7.85 (m, 1H), 8.72 (d, J=7.2 Hz, 1H), 8.84 (brs, 1H).

2-((3-Chloro-4-fluorophenylamino)-9-fluoro-3-(hydroxymethyl)-4H-pyrido[1,2-a]pyrimidin-4-one (267)

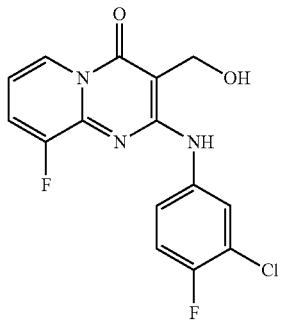

¹H NMR (400 MHz, DMSO-d₆) δ 4.74 (s, 2H), 5.24 (brs, 1H), 7.18-7.22 (m, 1H), 7.39-7.44 (m, 1H), 7.65-7.69 (m, 1H), 7.83-7.87 (m, 1H), 8.20-8.22 (m, 1H), 8.72 (d, J=7.2 Hz, 1H), 8.91 (brs, 1H).

2-(3,4-Difluorophenylamino)-9-fluoro-3-(hydroxymethyl)-4H-pyrido[1,2-a]pyrimidin-4-one (268)

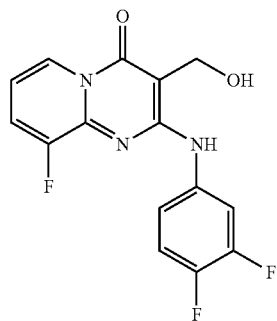 [SMILES: O=c1c(CO)c(Nc2ccc(F)c(F)c2)nc2c(F)cccn12]

¹H NMR (400 MHz, DMSO-d₆) δ 4.75 (s, 2H), 5.26 (brs, 1H), 7.17-7.22 (m, 1H), 7.39-7.49 (m, 1H), 7.84-7.88 (m, 1H), 8.08-8.14 (m, 1H), 8.73 (m, J=7.2 Hz, 1H), 8.93 (brs, 1H).

2-(3,4-Dichlorophenylamino)-9-fluoro-3-(hydroxymethyl)-4H-pyrido[1,2-a]pyrimidin-4-one (269)

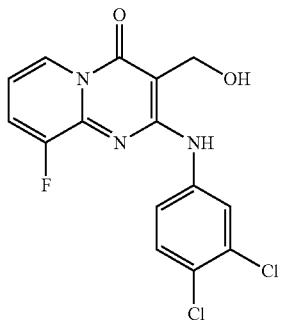 [SMILES: O=c1c(CO)c(Nc2ccc(Cl)c(Cl)c2)nc2c(F)cccn12]

¹H NMR (400 MHz, DMSO-d₆) δ 4.75 (s, 2H), 5.27 (brs, 1H), 7.19-7.23 (m, 1H), 7.60 (d, J=8.8 Hz, 1H), 7.7 (dd, J=2.8, 8.8 Hz, 1H), 7.85-7.89 (m, 1H), 8.83 (d, J=2.8 Hz, 1H), 8.73 (d, J=8.8 Hz, 1H), 9.00 (brs, 1H).

2-(1H-Indol-5-ylamino)-9-fluoro-3-(hydroxymethyl)-4H-pyrido[1,2-a]pyrimidin-4-one (270)

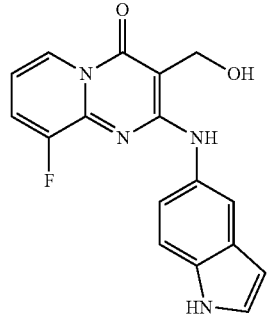 [SMILES: O=c1c(CO)c(Nc2ccc3[nH]ccc3c2)nc2c(F)cccn12]

m.p=184-185° C.; ¹H NMR (400 MHz, DMSO-d₆) δ 4.70 (d, J=5.2 Hz, 2H), 5.18 (t, J=5.2 Hz, 1H), 6.35 (s, 1H), 7.00-7.04 (m, 1H), 7.23 (dd, J=2 Hz, 8.8 Hz, 1H), 7.28-7.32 (m, 2H), 7.68 (dd, J=8 Hz, J=8 Hz, 1H), 7.82 (s, 1H), 8.61 (s, 1H), 8.64 (d, J=6 Hz, 1H), 10.98 (s, 1H); ¹³C NMR (100 MHz, DMSO-d₆) 55.2, 94.6, 101.7 (d, J=5.2 Hz, due to F), 111.6, 112.1 (d, J=7.4 Hz, due to F), 113.7, 118.0, 119.8 (d, J=17.1 Hz, due to F), 124.2 (d, J=4.4 Hz, due to F), 126.5, 128.2, 131.9, 133.5, 151.6, 154.1, 156.3, 157.6.

3-(Hydroxymethyl)-9-methoxy-2-(phenylamino)-4H-pyrido[1,2-a]pyrimidin-4-one (271)

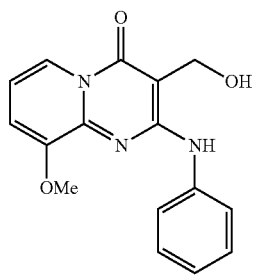 [SMILES: COc1cccn2c(=O)c(CO)c(Nc3ccccc3)nc12]

¹H NMR (400 MHz, DMSO-d₆) δ 3.93 (s, 3H), 4.71 (d, J=5.2 Hz, 2H), 5.29 (t, J=5.2 Hz, 1H), 6.97-7.01 (m, 1H), 7.06-7.10 (m, 1H), 7.27-7.32 (m, 3H), 7.83 (d, J=8.4 Hz, 2H), 8.47 (d, J=7.2 Hz, 1H), 8.68 (s, 1H).

3-(Hydroxymethyl)-9-methoxy-2-(phenylamino)-4H-pyrido[1,2-a]pyrimidine-4-thione (272)

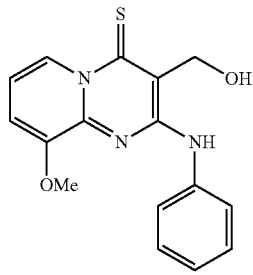

¹H NMR (400 MHz, CDCl₃) δ 3.98 (s, 3H), 4.11 (d, J=7.2 Hz, 2H), 6.88 (t, J=8.0 Hz, 2H), 7.04 (t, J=7.2 Hz, 1H), 7.31 (t, J=7.2 Hz, 2H), 7.82 (d, J=7.6 Hz, 2H), 7.98 (s, 1H), 8.59 (d, J=5.6 Hz, 1H); ¹³C NMR (100 MHz, CDCl₃) 26.9, 57.1, 94.2, 111.8, 112.7, 119.9, 121.1, 123.3, 128.9, 139.8, 143.7, 151.3, 155.6, 158.6.

2-(3-Chlorophenylamino)-3-(hydroxymethyl)-9-methoxy-4H-pyrido[1,2-a]pyrimidin-4-one (273)

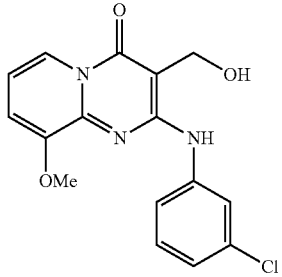 [SMILES: COc1cccn2c(=O)c(CO)c(Nc3cccc(Cl)c3)nc12]

¹H NMR (400 MHz, DMSO-d₆) δ 3.94 (s, 3H), 4.68 (s, 2H), 6.99 (d, J=7.6 Hz, 1H), 7.09 (dd, J=7.2 Hz, J=7.2 Hz, 1H), 7.25-7.29 (m, 2H), 7.56 (d, J=8.0 Hz, 1H), 8.42 (s, 1H), 8.45 (d, J=6.8 Hz, 1H), 8.77 (s, 1H).

2-(4-Chlorophenylamino)-3-(hydroxymethyl)-9-methoxy-4H-pyrido[1,2-a]pyrimidin-4-one (274)

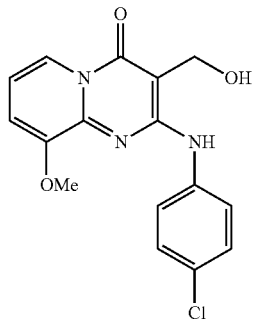 [SMILES: COc1cccn2c(=O)c(CO)c(Nc3ccc(Cl)cc3)nc12]

¹H NMR (400 MHz, DMSO-d₆) δ 3.90 (s, 3H), 4.65 (d, J=5.2 Hz, 2H), 5.19 (t, J=5.2 Hz, 1H), 7.03 (dd, J=7.2 Hz, 7.6 Hz, 1H), 7.23 (d, J=7.6 Hz, 1H), 7.29 (d, J=8.8 Hz, 2H), 7.85 (d, J=9.2 Hz, 2H), 8.42 (d, J=7.2 Hz, 1H), 8.72 (s, 1H).

2-(4-Fluorophenylamino)-3-(hydroxymethyl)-9-methoxy-4H-pyrido[1,2-a]pyrimidin-4-one (275)

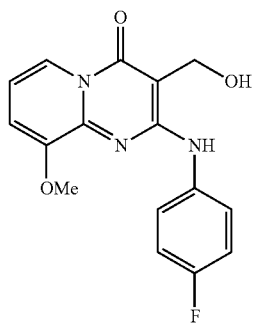 [SMILES: COc1cccn2c(=O)c(CO)c(Nc3ccc(F)cc3)nc12]

¹H NMR (400 MHz, DMSO-d₆) δ 3.91 (s, 3H), 4.69 (d, J=5.2 Hz, 2H), 5.19 (t, J=5.2 Hz, 1H), 7.06 (t, J=6.8 Hz, 1H), 7.13 (t, J=8.8 Hz, 1H), 7.25 (d, J=7.6 Hz, 1H), 7.83-7.86 (m, 1H), 8.45 (dd, J=1.2 Hz, 7.2 Hz, 1H), 8.66 (s, 1H).

3-(Hydroxymethyl)-9-methoxy-2-(4-(trifluoromethoxy)phenylamino)-4H-pyrido[1,2-a]pyrimidin-4-one (276)

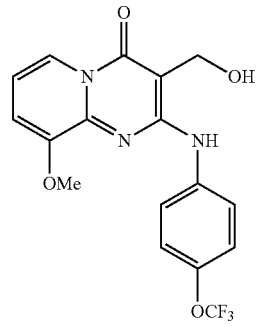 [SMILES: COc1cccn2c(=O)c(CO)c(Nc3ccc(OC(F)(F)F)cc3)nc12]

¹H NMR (400 MHz, DMSO-d₆) δ 3.96 (s, 3H), 4.67 (d, J=4.0 Hz, 2H), 5.20 (s, 1H), 7.07 (dd, J=7.2 Hz, J=7.2 Hz, 1H), 7.23 (s, 1H), 7.27 (d, J=8.0 Hz, 2H), 7.95 (dd, J=8.8 Hz, J=8.8 Hz, 2H), 8.45 (d, J=7.6 Hz, 1H), 8.78 (s, 1H).

3-(Hydroxymethyl)-9-methoxy-2-(4-(trifluoromethyl)phenylamino)-4H-pyrido[1,2-a]pyrimidin-4-one (277)

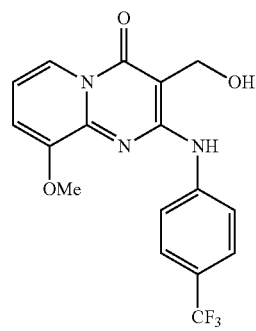 [SMILES: COc1cccn2c(=O)c(CO)c(Nc3ccc(C(F)(F)F)cc3)nc12]

¹H NMR (400 MHz, DMSO-d₆) δ 3.97 (s, 3H), 4.72 (s, 2H), 5.32 (s, 1H), 7.14, (dd, J=7.2 Hz, 7.2 Hz, 1H), 7.33 (d, J=7.6 Hz, 1H), 7.64 (d, J=8.8 Hz, 2H), 8.11 (d, J=8.8 Hz, 2H), 8.49 (d, J=7.2 Hz, 1H), 9.09 (s, 1H).

2-(3-Chloro-4-fluorophenylamino)-3-(hydroxymethyl)-9-methoxy-4H-pyrido[1,2-a]pyrimidin-4-one (278)

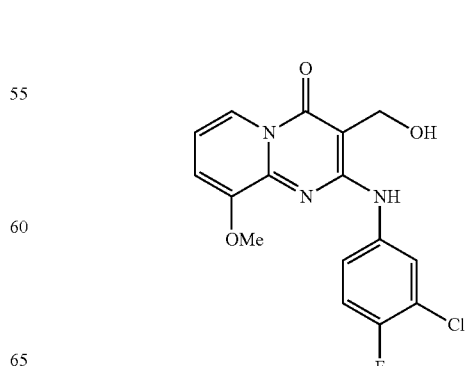

¹H NMR (400 MHz, DMSO-d₆) δ 3.95 (s, 3H), 4.69 (d, J=4.8 Hz, 2H), 5.16 (t, J=4.8 Hz, 1H), 7.10 (dd, J=7.2 Hz, 7.2 Hz, 1H), 7.30 (dd, J=0.8 Hz, 8.0 Hz, 1H), 7.32 (dd, J=9.2 Hz, 9.2 Hz, 1H), 7.61-7.65 (m, 1H), 8.46 (dd, J=0.8 Hz, 7.2 Hz, 1H), 8.59 (dd, J=2.8 Hz, 7.2 Hz, 1H), 8.76 (s, 1H).

2-(3,4-Difluorophenylamino)-3-(hydroxymethyl)-9-methoxy-4H-pyrido[1,2-a]pyrimidin-4-one (279)

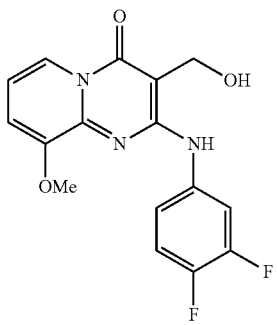 [SMILES: COc1cccn2c(=O)c(CO)c(Nc3ccc(F)c(F)c3)nc12]

m.p=231° C. (decomp.); ¹H NMR (400 MHz, CDCl₃) δ 3.92 (s, 3H), 4.66 (s, 2H), 5.17 (brs, 1H), 7.07 (dd, J=7.2 Hz, 7.2 Hz, 1H), 7.26-7.33 (m, 2H), 7.39-7.41 (m, 1H), 8.34-8.40 (m, 1H), 8.44 (d, J=7.2 Hz, 1H), 8.74 (s, 1H); ¹³C NMR (100 MHz, DMSO) δ 54.1, 56.8, 95.2, 109.1, 113.4, 116.0 (d, J=3.8 Hz, due to F), 116.8, 118.7, 137.5 (d, J=9.7 Hz, due to F), 143.2 (d, J=11.9 Hz, due to F), 145.6, 147.5 (d, J=13.4 Hz, due to F), 149.9 (d, J=13.4 Hz, due to F), 150.6, 155.5.

2-(3-Chloro-4-hydroxyphenylamino)-3-(hydroxymethyl)-9-methoxy-4H-pyrido[1,2-a]pyrimidin-4-one (280)

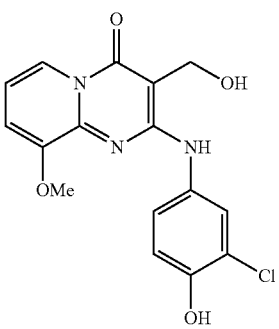 [SMILES: COc1cccn2c(=O)c(CO)c(Nc3ccc(O)c(Cl)c3)nc12]

¹H NMR (400 MHz, DMSO-d₆) δ 3.93 (s, 3H), 4.68 (s, 2H), 5.14 (s, 1H), 6.99 (d, J=8.4 Hz, 1H), 7.06 (dd, J=7.2 Hz, 7.2 Hz, 1H), 7.26 (dd, J=1.2 Hz, 8.0 Hz, 1H), 7.38 (dd, J=1.2 Hz, 8.0 Hz, 1H), 8.25 (d, J=2.8 Hz, 1H), 8.45 (dd, J=1.2 Hz, 7.2 Hz, 1H), 8.52 (s, 1H), 9.79 (s, 1H).

2-(3,4-Dichlorophenylamino)-3-(hydroxymethyl)-9-methoxy-4H-pyrido[1,2-a]pyrimidin-4-one (281)

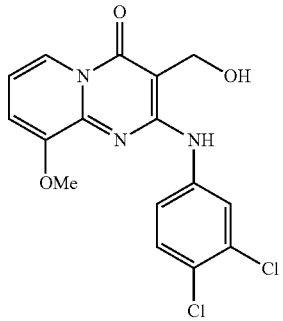 [SMILES: COc1cccn2c(=O)c(CO)c(Nc3ccc(Cl)c(Cl)c3)nc12]

¹H NMR (400 MHz, DMSO-d₆) δ 3.93 (s, 3H), 4.66 (d, J=5.2 Hz, 2H), 5.16 (d, J=5.2 Hz, 1H), 7.09 (t, J=7.2 Hz, 1H), 7.29 (d, J=6.8 Hz, 1H), 7.48 (d, J=8.8 Hz, 1H), 7.64 (dd, J=2.8 Hz, 8.8 Hz, 1H), 8.44 (d, J=7.2 Hz, 1H), 8.67 (d, J=2.8 Hz, 1H), 8.82 (s, 1H).

3-(Hydroxymethyl)-9-methoxy-2-(4-methyl-3-(trifluoromethyl)phenylamino)-4H-pyrido[1,2-a]pyrimidin-4-one (282)

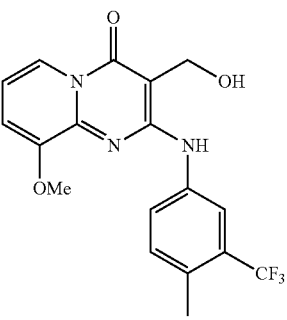 [SMILES: COc1cccn2c(=O)c(CO)c(Nc3ccc(C)c(C(F)(F)F)c3)nc12]

¹H NMR (400 MHz, DMSO-d₆) δ 2.49 (t, J=2.0 Hz, 3H due to CF₃), 3.93 (s, 3H), 4.70 (d, J=4.8 Hz, 2H), 5.19 (t, J=4.8 Hz, 1H), 7.10 (t, J=7.2 Hz, 1H), 7.29 (dd, J=1.2 Hz, 8.0 Hz, 1H), 7.32 (d, J=8.4 Hz, 1H), 7.74 (dd, J=1.6 Hz, 8.0 Hz, 1H), 8.46 (dd, J=1.2 Hz, 6.8 Hz, 1H), 8.81 (s, 1H), 8.85 (d, J=2.0 Hz, 1H).

2-(4-Fluoro-3-(trifluoromethyl)phenylamino)-3-(hydroxymethyl)-9-methoxy-4H-pyrido[1,2-a]pyrimidin-4-one (283)

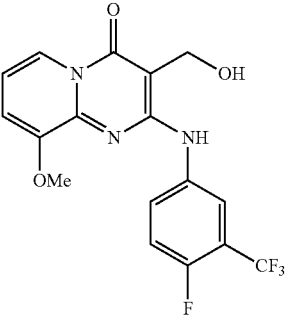 [SMILES: COc1cccn2c(=O)c(CO)c(Nc3ccc(F)c(C(F)(F)F)c3)nc12]

¹H NMR (400 MHz, DMSO-d₆) δ 3.92 (s, 3H), 4.68 (d, J=5.2 Hz, 2H), 5.12 (t, J=5.2 Hz, 1H), 7.07 (dd, J=7.2 Hz, 7.2 Hz, 1H), 7.27 (d, J=7.2 Hz, 1H), 7.37-7.42 (m, 1H), 7.86-7.88 (m, 1H), 8.43 (d, J=7.2 Hz, 1H), 8.87 (s, 1H), 8.99-9.00 (m, 1H).

2-(2,3-Dihydro-1H-inden-5-ylamino)-3-(hydroxymethyl)-9-methoxy-4H-pyrido[1,2-a]pyrimidin-4-one (284)

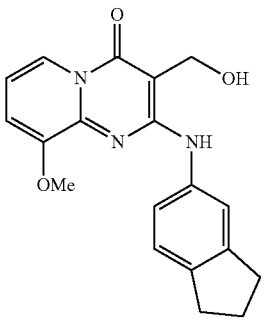 [SMILES: COc1cccn2c(=O)c(CO)c(Nc3ccc4c(c3)CCC4)nc12]

¹H NMR (400 MHz, DMSO-d₆) δ 1.97-2.05 (m, 2H), 2.79 (t, J=7.6 Hz, 2H), 2.85 (t, J=7.6 Hz, 2H), 3.92 (s, 3H), 4.69 (d, J=5.6 Hz, 2H), 5.26 (t, J=5.6 Hz, 1H), 7.04 (dd, J=7.2 Hz, 1H), 7.12 (d, J=8.4 Hz, 1H), 7.24 (dd, J=0.8 Hz, 7.6 Hz, 1H), 7.46 (dd, J=2.0 Hz, 8.0 Hz, 1H), 7.82 (s, 1H), 8.45 (dd, J=1.2 Hz, 7.2 Hz, 1H), 8.59 (s, 1H).

2-(Benzo[d][1,3]dioxol-5-ylamino)-3-(hydroxymethyl)-9-methoxy-4H-pyrido[1,2-a]pyrimidin-4-one (285)

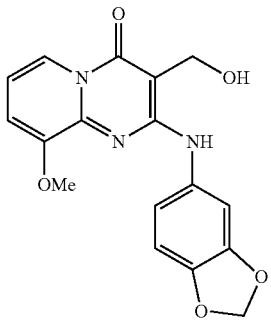

¹H NMR (400 MHz, DMSO-d₆) δ 3.91 (s, 3H), 4.68 (d, J=5.2 Hz, 2H), 5.21 (t, J=5.2 Hz, 1H), 5.98 (s, 2H), 6.84 (d, J=8.4 Hz, 1H), 7.05-7.07 (m, 1H), 7.26 (dd, J=1.2 Hz, 8.0 Hz, 1H), 7.82 (d, J=2.0 Hz, 1H), 8.46 (d, J=2.0 Hz, 1H), 8.45 (dd, J=1.2 Hz, 7.2 Hz, 1H), 8.56 (s, 1H).

2-(2,3-Dihydrobenzo[b][1,4]dioxin-6-ylamino)-3-(hydroxymethyl)-9-methoxy-4H-pyrido[1,2-a]pyrimidin-4-one (286)

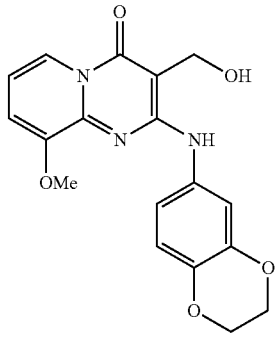 [SMILES: COc1cccn2c(=O)c(CO)c(Nc3ccc4c(c3)OCCO4)nc12]

¹H NMR (400 MHz, DMSO-d₆) δ 3.92 (s, 3H), 4.19-4.24 (m, 4H), 4.67 (d, J=5.2 Hz, 2H), 5.19 (t, J=5.2 Hz, 1H), 6.77 (d, J=8.8 Hz, 1H), 7.05 (dd, J=7.2 Hz, 7.2 Hz, 1H), 7.12 (dd, J=2.4 Hz, 8.4 Hz, 1H), 7.26 (d, J=6.8 Hz, 1H), 7.64 (d, J=2.4 Hz, 1H), 8.46 (dd, J=2.0 Hz, 7.2 Hz, 1H), 8.47 (s, 1H).

3-(Hydroxymethyl)-9-methoxy-2-(1-methyl-1H-indol-5-ylamino)-4H-pyrido[1,2-a]pyrimidin-4-one (287)

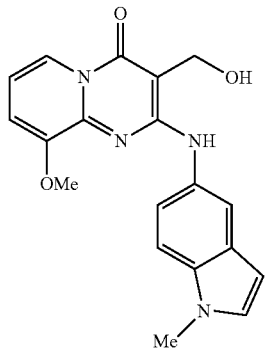

m.p=195-197° C.; ¹H NMR (400 MHz, DMSO-d₆) δ 3.82 (s, 3H), 3.97 (s, 3H), 4.77 (d, J=5.2 Hz, 2H), 5.28 (t, J=5.2 Hz, 1H), 6.42 (d, J=3.0 Hz, 1H), 7.09 (dd, J=7.2, 7.6 Hz, 1H), 7.28-7.30 (m, 1H), 7.33 (d, J=3.0 Hz, 1H), 7.41 (d, J=8.8 Hz, 1H), 7.46 (dd, J=2.0, 8.8 Hz, 1H), 8.18 (d, J=2.0 Hz, 1H), 8.52 (dd, J=1.2, 6.8 Hz, 1H), 8.62 (br s, 1H).

3-(Hydroxymethyl)-9-methoxy-2-(1-methyl-1H-benzo[d]imidazol-5-ylamino)-4H-pyrido[1,2-a]pyrimidin-4-one (288)

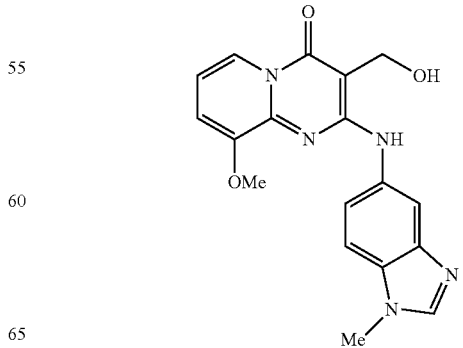

m.p=186° C. (decomp.); $^1$H NMR (400 MHz, DMSO-$d_6$) δ 3.87 (s, 3H), 3.98 (s, 3H), 4.79 (d, J=5.6 Hz, 2H), 5.31 (t, J=5.6 Hz, 1H), 7.08 (dd, J=7.2, 7.2 Hz, 1H), 7.28 (dd, J=0.8, 7.6 Hz, 1H), 7.50 (d, J=8.8 Hz, 1H), 7.56 (dd, J=2.0, 8.8 Hz, 1H), 8.13 (s, 1H), 8.34 (d, J=1.6 Hz, 1H), 8.53 (dd, J=0.8, 7.2 Hz, 1H), 8.73 (br s, 1H).

3-(Hydroxymethyl)-9-methoxy-2-(1-methyl-1H-indazol-5-ylamino)-4H-pyrido[1,2-a]pyrimidin-4-one (289)

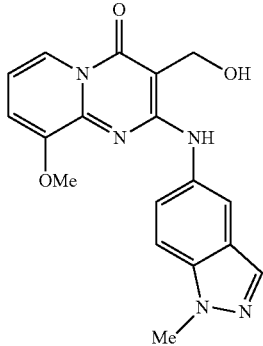 [SMILES: COc1cccn2c(=O)c(CO)c(Nc3ccc4c(ccn4C)c3)nc12]

m.p=205° C. (decomp.); $^1$H NMR (400 MHz, DMSO-$d_6$) δ 3.40 (s, 3H), 4.08 (s, 3H), 4.78 (d, J=4.8 Hz, 2H), 5.28 (t, J=5.0 Hz, 1H), 7.12 (dd, J=7.2, 7.6 Hz, 1H), 7.32 (1H, J=1.2, 7.6 Hz, 1H), 7.62 (d, J=9.0 Hz, 1H), 7.68 (dd, J=2.0, 9.0 Hz, 1H), 8.04 (m, 1H), 8.07 (d, J=1.2 Hz, 1H), 8.53 (dd, J=1.2, 6.8 Hz, 1H), 8.75 (br s, 1H).

9-(Difluoromethoxy)-2-(4-fluorophenylamino)-3-(hydroxymethyl)-4H-pyrido[1,2-a]pyrimidin-4-one (290)

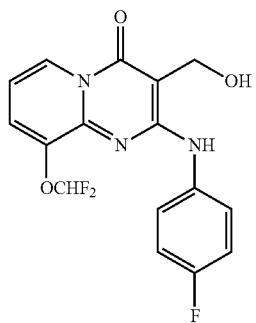 [SMILES: O=c1c(CO)c(Nc2ccc(F)cc2)nc2c(OC(F)F)cccn12]

$^1$H NMR (400 MHz, DMSO-$d_6$) δ 4.67 (d, J=5.2 Hz, 2H), 5.14 (t, J=5.2 Hz, 1H), 7.07-7.11 (m, 3H), 7.17 (t, J=74 Hz due to F$_2$, 1H), 7.63-7.69 (m, 3H), 8.71 (d, J=7.2 Hz, 1H), 8.75 (s, 1H).

2-(4-Chlorophenylamino)-9-(difluoromethoxy)-3-(hydroxymethyl)-4H-pyrido[1,2-a]pyrimidin-4-one (291)

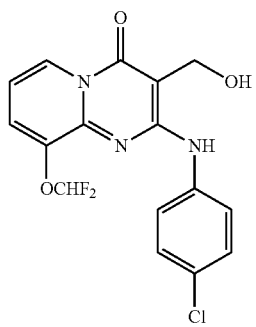 [SMILES: O=c1c(CO)c(Nc2ccc(Cl)cc2)nc2c(OC(F)F)cccn12]

$^1$H NMR (400 MHz, DMSO-$d_6$) δ 4.69 (d, J=5.6 Hz, 2H), 5.23 (t, J=5.2 Hz, 1H), 7.13 (dd, J=7.2 Hz, 7.2 Hz, 1H), 7.23 (t, J=74 Hz, 1H, due to F$_2$), 7.30-7.33 (m, 2H), 7.72-7.75 (m, 3H), 8.75 (dd, J=1.2 Hz, 7.2 Hz, 1H), 8.86 (s, 1H);

9-(Difluoromethoxy)-2-(3,4-difluorophenylamino)-3-(hydroxymethyl)-4H-pyrido[1,2-a]pyrimidin-4-one (292)

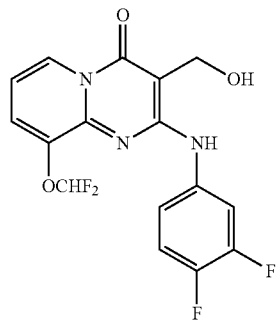

$^1$H NMR (400 MHz, DMSO-$d_6$) δ 4.70 (d, J=5.2 Hz, 2H), 5.22 (s, 1H), 7.16 (dd, J=7.2 Hz, J=7.2 Hz, 1H), 7.26 (t, J=74 Hz, due to F2, 1H), 7.33-7.38 (m, 2H), 7.75 (d, J=7.2 Hz, 1H), 8.12 (dd, J=7.6 Hz, 12.8 Hz, 1H), 8.76 (d, J=6.8 Hz, 1H), 8.90 (s, 1H); LC-MS (ESI, m/z): 370 [M+H]$^+$.

2-(3,4-Dichlorophenylamino)-9-(difluoromethoxy)-3-(hydroxymethyl)-4H-pyrido[1,2-a]pyrimidin-4-one (293)

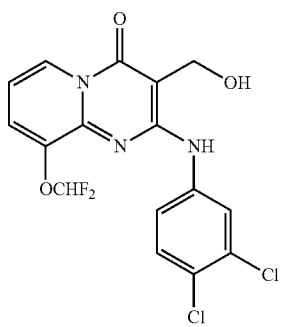

$^1$H NMR (400 MHz, DMSO-$d_6$) δ 4.68 (s, 2H), 5.19 (s, 1H), 7.15 (t, J=7.2 Hz, 1H), 7.24 (t, J=74 Hz, due to F$_2$, 1H), 7.47-7.57 (m, 2H), 7.72 (d, J=7.2 Hz, 1H), 8.32 (d, J=2.4 Hz, 1H), 8.73 (dd, J=1.6 Hz, 7.2 Hz, 1H), 8.92 (s, 1H).

2-(3-Chloro-4-fluorophenylamino)-9-(difluoromethoxy)-3-(hydroxymethyl)-4H-pyrido[1,2-a]pyrimidin-4-one (294)

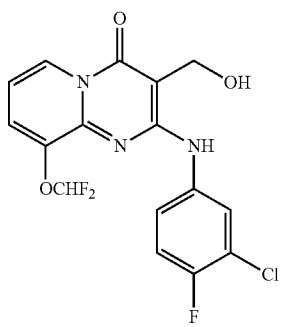

¹H NMR (400 MHz, DMSO-d₆) δ 4.68 (d, J=4.0 Hz, 2H), 5.18 (s, 1H), 7.15 (dd, J=7.2 Hz, 7.2 Hz, 1H), 7.24 (t, J=74 Hz, 1H, due to F₂), 7.32 (dd, J=9.2 Hz, 9.2 Hz, 1H), 7.50-7.54 (m, 1H), 7.73 (d, J=7.6 Hz, 1H), 8.22 (dd, J=2.8 Hz, 6.8 Hz, 1H), 8.74 (dd, J=1.2 Hz, 7.2 Hz, 1H), 8.86 (s, 1H).

2-(1H-Indol-5-ylamino)-9-(difluoromethoxy)-3-(hydroxymethyl)-4H-pyrido[1,2-a]pyrimidin-4-one (295)

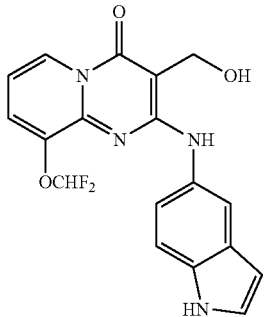 [SMILES: O=c1c(CO)c(Nc2ccc3[nH]ccc3c2)nc2c(OC(F)F)cccn12]

¹H NMR (400 MHz, DMSO-d₆) δ 4.72 (d, J=4.8 Hz, 2H), 5.23 (t, J=4.8 Hz, 1H), 6.34 (s, 1H), 7.05-7.09 (m, 1H), 7.23 (dd, J=8.8 Hz, 8.8 Hz, 1H), 7.25 (t, J=74.4 Hz, 1H due to F₂), 7.31-7.33 (m, 2H), 7.68 (d, J=7.2 Hz, 1H), 7.93 (s, 1H), 8.70 (s, 1H), 8.73 (d, J=1.2 Hz, 1H), 10.99 (s, 1H).

2-(3-chlorophenylamino)-3-(hydroxymethyl)-6,8-dimethyl-4H-pyrido[1,2-a]pyrimidin-4-one (296)

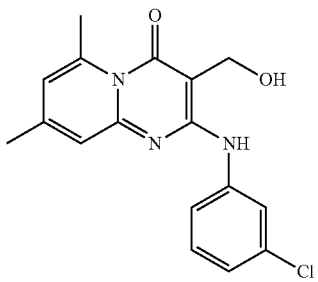 [SMILES: Cc1cc(C)n2c(=O)c(CO)c(Nc3cccc(Cl)c3)nc2c1]

¹H NMR (400 MHz, CDCl₃) δ 2.32 (s, 3H), 2.40 (s, 3H), 3.55 (s, 2H), 6.78 (s, 1H), 7.06 (d, J=2.0 Hz, 1H), 7.21 (dd, J=8.0 Hz, J=8.0 Hz, 1H), 7.39 (d, J=8.4 Hz, 1H), 7.69 (d, J=2.0 Hz, 1H), 7.71 (s, 1H), 9.60 (s, 1H); LC-MS (ESI, m/z): 330 [M+H].

7,9-Dichloro-2-(3-chlorophenylamino)-3-(hydroxymethyl)-4H-pyrido[1,2-a]pyrimidin-4-one (297)

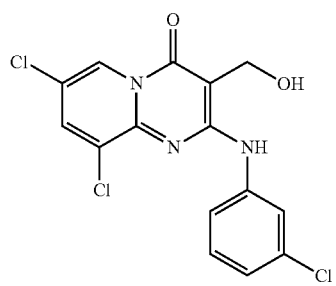 [SMILES: O=c1c(CO)c(Nc2cccc(Cl)c2)nc2c(Cl)cc(Cl)cn12]

¹H NMR (400 MHz, DMSO-d₆) δ 4.65 (s, 2H), 5.70 (d, J=7.6 Hz, 1H), 7.29 (dd, J=8.0 Hz, J=8.0 Hz, 1H), 7.57 (dd, J=8.0 Hz, J=8.0 Hz, 1H), 8.25 (s, 1H), 8.32 (d, J=2.0 Hz, 1H), 8.76 (d, J=2.0 Hz, 1H).

2-(3-Chlorophenylamino)-7,9-difluoro-3-(hydroxymethyl)-4H-pyrido[1,2-a]pyrimidin-4-one (298)

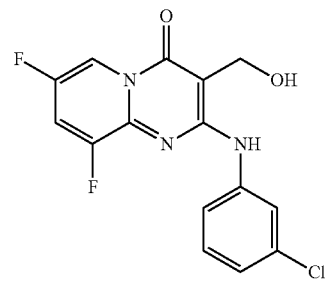 [SMILES: O=c1c(CO)c(Nc2cccc(Cl)c2)nc2c(F)cc(F)cn12]

¹H NMR (400 MHz, CDCl₃) δ 4.69 (d, J=4.8 Hz, 2H), 5.31 (t, J=4.8 Hz, 1H), 7.06 (dd, J=1.2 Hz, 8.0 Hz, 1H), 7.32 (t, J=8.0 Hz, 1H), 7.56 (dd, J=1.2 Hz, 8.0 Hz, 1H), 8.02 (s, 1H), 8.18-8.23 (m, 1H), 8.68 (t, J=2.0 Hz, 1H), 8.90 (s, 1H).

(4-Oxo-2-(phenylamino)-4H-pyrido[1,2-a]pyrimidin-3-yl)methyl benzoate (299)

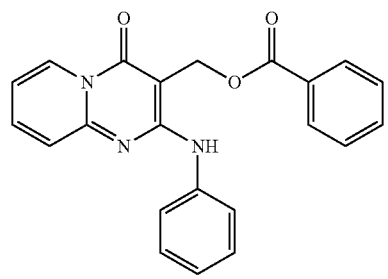 [SMILES: O=C(OCc1c(Nc2ccccc2)nc2ccccn2c1=O)c1ccccc1]

m.p=178-179° C.; ¹H NMR (400 MHz, DMSO-d₆) δ 5.66 (s, 2H), 6.96 (ddd, J=1.2, 1.2, 6.8 Hz, 1H), 7.06-7.10 (m, 1H), 7.33-7.44 (m, 5H), 7.53-7.56 (m, 1H), 7.61-7.65 (m, 1H), 7.72 (m, 2H), 8.12 (dd, J=1.2, 8.4 Hz, 1H), 9.14 (brs, 1H).

(4-Oxo-2-(phenylamino)-4H-pyrido[1,2-a]pyrimidin-3-yl)methyl acetate (300)

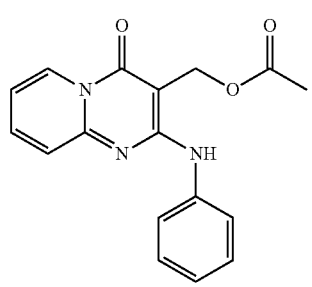 [SMILES: CC(=O)OCc1c(Nc2ccccc2)nc2ccccn2c1=O]

m.p=160-161° C.; $^1$H NMR (400 MHz, CDCl$_3$) δ 2.13 (s, 3H), 6.92 (dd, J=6.8, 7.2 Hz, 1H), 7.04-7.08 (m, 1H), 7.30-7.37 (m, 3H), 7.59-7.66 (m, 3H), 8.91 (brs, 1H), 8.94 (d, J=7.2 Hz, 1H).

(4-Oxo-2-phenylamino-4H-pyrido[1,2-a]pyrimidin-3-yl)methyl isobutyrate (301)

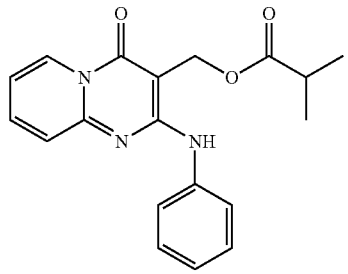 [SMILES: CC(C)C(=O)OCc1c(Nc2ccccc2)nc2ccccn2c1=O]

m.p=161-163° C.; $^1$H NMR (400 MHz, CDCl$_3$) δ 1.17 (d, J=7.2 Hz, 6H), 2.62-2.65 (m, 1H), 6.94 (dd, J=6.8, 7.2 Hz, 1H), 7.04-7.08 (m, 1H), 7.31-7.38 (m, 3H), 7.60-7.67 (m, 3H), 8.95 (brs, 1H), 8.95 (d, J=6.8 Hz, 1H).

Example 8

Additional Studies on Dinitrobenzamide Compounds

Two representative molecules, compounds 4 and 24, were re-synthesized in-house and subjected to conventional CFU-based activity testing in primary macrophages (FIG. 7). A ten-fold decrease in the number of CFUs, similar to that seen with INH, was observed for both compounds five days after infection on three different cell lines. This confirms the potency of this series of compounds.

To address the issue of toxicity, compounds 4 and 24 were tested on a panel of five cell lines derived from different body tissue. Cells were incubated with increasing amounts of compound and cell viability was assessed with resazurin after 5 days of co-incubation. Percentage cytotoxicity was determined by taking as a reference the resofurin fluorescence measured by DMSO containing wells. The concentration where fifty percent of the cells died was defined as the Minimal Toxic Concentration (MTC$_{50}$). Both compounds 4 and 24 showed no cytotoxicity against the panel of cell lines suggesting this series of compounds to be promising new anti-tuberculosis drugs (Table 4).

To gain insight into the possible specificity of activity of compounds 4 and 24, analysis of the broad antimicrobial spectrum was undertaken and showed that the effect of these dinitrobenzamide derivatives was mainly restricted to actinomycetes with the most potent activity observed against *Mycobacterium* (Table 4). Of particular importance, the tested DNB were also highly active against multidrug-resistant (MDR) and extensively drug-resistant (XDR) clinical isolates, suggesting that they might act on different targets than current antituberculosis compounds.

Mutation frequency of *M. tuberculosis* H37Rv was determined for compounds 4 and 24. Increasing numbers of bacteria grew on 7H10 agar medium supplemented with different concentrations of compounds. After a 6-week growth, colonies were counted in order to evaluate the proportion of spontaneous mutational frequency (Table 6). For compound 4, $1 \times 10^{-6}$ and $1 \times 10^{-8}$ frequencies of resistance were found at 0.2 µg/ml and 3.2 µg/ml, respectively. Spontaneous mutational rate was therefore calculated to be $1 \times 10^{-7}$. For compound 24, at 0.2 µg/ml and 3.2 µg/ml, frequency of mutation was $7 \times 10^{-7}$ and $1 \times 10^{-8}$, respectively which corresponds to a mean frequency of $3.5 \times 10^{-7}$. Overall, these values were superior to frequency of mutation observed for INH-resistant mutants ($3 \times 10^{-6}$). These results, thus, demonstrate that this class of compounds result in a low frequency of mutation.

Example 9

Additional Studies on Pyridopyrimidinone Compounds

Table 5 shows the minimal inhibitory concentration (MIC) of one representative compound, 133, on different Mycobacterial species. While it has no effect on the fast growing *Mycobacterium smegmatis* mc$^2$, it was able to inhibit typical laboratory strains such as H37Rv, H137Ra and BCG Pasteur with an MIC of 2 µM. More importantly, the antimicrobial activity of 133 was also tested against clinical isolates strains of mycobacteria. The MIC values for multi-drug-resistant (MDR-TB) and extensive-drug-resistant (XDR-TB) isolates strains were within the micromolar range.

To address the issue of toxicity, compound 133 was tested on a panel of seven cell lines derived from different body tissue. Cells were incubated with increasing amounts of compound and cell viability was assessed with resazurin after 5 days of co-incubation. Percentage of cytotoxicity was determined by taking as a reference the resofurin fluorescence measured by DMSO containing wells. The concentration where fifty percent of the cells died was defined as the Minimal Toxic Concentration (MTC$_{50}$). Compound 133 showed no cytotoxicity for all tested cell lines up to 100 µM (Table 5). The selectivity index, which consists of the ratio between antitubercular activity and cytotoxicity was therefore above 50 for both extracellular and intracellular mycobacteria suggesting this series of compounds to be promising new antituberculosis drugs.

The effect of this series of compounds on primary macrophages was further determined. Host cells that had priory been incubated with compound 232 harbored fewer bacteria compared to DMSO control and were more abundant at day 5 after infection as shown in FIG. 8. Similar data were obtained for compound 133 (data not shown). Conventional CFU determination was then performed seven days after infection to quantify the remaining bacterial load. A ten-fold decrease in the number of CFUs, similar to that seen with INH, was observed for both compounds on both human and mouse cells (FIG. 8). This confirms the potency of this series of compounds.

Mutation frequency of *M. tuberculosis* H37Rv was determined for compound 264. Increasing numbers of bacteria grew on 7H10 agar medium supplemented with different concentrations of compound. After a 6-week growth, colonies were counted in order to evaluate the proportion of spontaneous mutational frequency (Table 6). Compound 264 gave frequencies of resistance of $3.4 \times 10^{-6}$ and $8 \times 10^{-6}$ at 0.4 and 0.8 µg/ml, respectively, and $2 \times 10^{-8}$ at both 1.6 µg/ml and 3.2 µg/ml. Accordingly, spontaneous mutational rate was calculated to be $7 \times 10^{-7}$. Overall, these values are better than the frequency of mutation observed for INH ($2.9 \times 10^{-6}$). These results, therefore, demonstrate that this class of compounds result in a low frequency of mutation.

One of the current challenges for TB drug discovery is the identification of compounds that are active against persistent bacteria. Although the location and state of latent bacteria remains a matter of debate, one commonly shared hypothesis for mycobacterial persistence is that *M. tuberculosis* bacilli are able to survive in macrophages for prolonged periods of time and, unlike other bacteria, are able to actively replicate. The intraphagosomal profile of *M. tuberculosis* is complex; a large variety of genes are over-expressed and timely regulated and are also dependent on environmental factors. Altogether, this makes the identification of one specific tubercle factor that could be selected as the ideal target difficult. Consequently, non-target cell-based assays are a critical tool in the search of intracellular *M. tuberculosis* inhibitors.

Investigation of *bacillus* growth inhibitors within macrophages has long been limited due to cumbersome CFU plating, slow *bacillus* growth, safety requirements and difficulties in setting-up appropriate infection conditions. As a consequence, this approach was always used as a secondary assay after the initial selection of compounds that are active on in vitro extracellular growth. With the advent of automated confocal microscopy, the above mentioned limitations could be readdressed and the inventors show the feasibility of large scale compound screening. It was decided to perform suspension macrophage batch infection in order to minimize the steps and to meet safety requirements. To this end, careful attention was paid to the removal of the extracellular non-phagocytosed mycobacteria. The centrifugation conditions used during the wash steps were set up in order to recover only the infected cells and discard most of the extracellular bacteria. By microscopy the inventors confirmed that unbound mycobacteria represented less than 10% of the total bacterial load (data not shown). *Mycobacteria* are able to grow independently of host cells and consequently any remaining extracellular bacilli would greatly compromise the validity of the inventors' model. To this end, an additional amikacin treatment step was added to the protocol to further eliminate any remaining mycobacteria. Thus with the optimized protocol, there is almost no non-phagocytosed mycobacteria left by the time compound is added. The obtained results also demonstrate that it is specifically the effect on the intracellular mycobacteria that is being measured with compound treatment. Indeed, the inventors observed a weak inhibition with rifampin, an antibiotic that is known to poorly penetrate cells. The 50-fold reproducible decrease in MIC for rifampin in the intracellular assay compared to the in vitro growth assay proved that the targeted bacteria are not extracellular. Otherwise no difference would have been seen in MIC between the two assays. Similarly, compounds able to inhibit mycobacterial growth in the phenotypic cell-based assay, but not the in vitro growth assay were also identified. In addition, the fact that the compounds are mixed with previously infected cells should decrease the chance for the identification of primary infection inhibitors. However, such compounds may still be identified as blockers of neighboring cell infection.

Compared to a conventional CFU-plating method, the microscopy based detection of fluorescent bacteria is not sufficiently sensitive to distinguish between dead and live bacilli as the GFP signal is stable for several days. Indeed, at a high concentration of INH, rifampin or active compound, there is always 10% of the cells that appear to be infected, which is similar to the initial infection ratio. Surprisingly, no CFU could be recovered after plating such samples. Owing to the fact that latent bacilli are able to recover growth (Cho et al., 2007), the microscopy-detected bacilli must be dead bacilli rather than latent bacilli. Thus, the inventors' assay detects compounds that interfere with bacilli growth within macrophages.

As it is well established and confirmed (FIG. 1a), macrophages are able to support high bacterial loads which end up encompassing a large part of the cell cytoplasm and eventually lead to macrophage cell death. It is obvious when *M. tuberculosis* is the infectious agent compared to BCG (Bacille Calmette-Guerin), which even at high MOI fails to induce much cytotoxicity (data not shown). Taking this into account, it was decided to set the data acquisition at day 5 post-infection when the cell number in the DMSO samples had significantly decreased relative to the antibiotically protected controls. Thus, monitoring cell number was an additional parameter enabling the inventors to confirm the compound's antibacterial activity.

Unlike direct fluorescence based assays, analysis for image-based assays proved to be much more variable. Several parameters that are inherent to the biology of the assay partially explain the lower Z'-values that are usually accepted for HTS validation. The remaining fluorescent dead bacilli do not have much of an impact on the Z'-value, rather the variability in the infection ratio for the DMSO controls seems to account for the discrepancy. Also of importance is the fact that, upon infection, the macrophages had a tendency to migrate which in turn led to a heterogeneous set of images (FIG. 2a). However, the aim of the primary screen was to identify compounds fully active at a concentration of 20 µM. Thus, for this purpose, a positive Z' for the infection ratio (INH/DMSO) was considered an acceptable value. The best proof of the validity of the hit selection according to the present invention comes from the subsequent serial dilution analysis, whereby almost 100% of the hits were confirmed. For each of the hits, a nicely fitted dose-response curve for the infection ratio was obtained as well as for the non-toxic compound in terms of cell number. Again, cell number brought an additional confirmation of the results that is totally independent of green fluorescence emission and GFP expression.

Obviously compounds found to be active against both intracellular and in vitro *M. tuberculosis* growth are the most promising. The best inhibitors isolated from this library have an inhibitory activity within the same range as INH. Further structure activity relationship studies will contribute to determine if their activity could be improved. In the course of another study using this phenotypic cell-based model, MIC down to the ng/mL scale was obtained for compounds with known in vitro antibacterial efficacy showing that compounds with a lower MIC than INH can be identified by the assay according to the present invention (data not shown). Of utmost interest are the compounds that are active only in the intracellular bacteria assay as they are likely to have a new mechanism of action independent of the infecting strain suggesting that they may also be active on the non-curable multi-drug-resistant (MDR)-strains.

Taken together, the above results show that monitoring *M. tuberculosis* growth with automated fluorescence microscopy is highly robust and reliable and that this method enables fast selection of potent anti-TB compounds.

REFERENCES

Abadie, V., Badell, E., Douillard, P., Ensergueix, D., Leenen, P. J., Tanguy, M., Fiette, L., Saeland, S., Gicquel, B., and Winter, N. (2005). Neutrophils rapidly migrate via lymphatics after *Mycobacterium bovis* BCG intradermal vaccination and shuttle live bacilli to the draining lymph nodes. Blood 106, 1843-1850.

Andries, K., Verhasselt, P., Guillemont, J., Gohlmann, H. W., Neefs, J. M., Winkler, H., Van Gestel, J., Timmerman, P., Zhu, M., Lee, E., et al. (2005). A diarylquinoline drug active on the ATP synthase of *Mycobacterium tuberculosis*. Science 307, 223-227.

Arain, T. M., Resconi, A. E., Singh, D. C., and Stover, C. K. (1996). Reporter gene technology to assess activity of antimycobacterial agents in macrophages. Antimicrob Agents Chemother 40, 1542-1544.

Brodin, P., Majlessi, L., Marsollier, L., de Jonge, M. I., Bottai, D., Demangel, Cl., Hinds, J., Neyrolles, O., Butcher, P. D., Leclerc, C., Coles, S. T., Brosch, R., (2006). Dissection of ESAT-6 system 1 of *Mycobacterium tuberculosis* and impact on immunogenicity and virulence. Infect Immun 74, 88-98.

Cho, S. H., Warit, S., Wan, B., Hwang, C. H., Pauli, G. F., and Franzblau, S. G. (2007). Low-oxygen-recovery assay for high-throughput screening of compounds against nonreplicating *Mycobacterium tuberculosis*. Antimicrob Agents Chemother 51, 1380-1385.

Cremer, I., Dieu-Nosjean, M. C., Marechal, S., Dezutter-Dambuyant, C., Goddard, S., Adams, D., Winter, N., Menetrier-Caux, C., Sautes-Fridman, C., Fridman, W. H., and Mueller, C. G. (2002). Long-lived immature dendritic cells mediated by TRANCE-RANK interaction. Blood 100, 3646-3655.

Fenistein, D., Lenseigne, B., Christophe, T., Brodin, P., and Genovesio, A. (2008). A fast fully automated cell segmentation algorithm for high throughput and high content screening. Cytometry part A, in press.

Houben, E. N., Nguyen, L., and Pieters, J. (2006). Interaction of pathogenic mycobacteria with the host immune system. Curr Opin Microbiol 9, 76-85.

Lenaerts, A. J., Hoff, D., Aly, S., Ehlers, S., Andries, K., Cantarero, L., Orme, I. M., and Basaraba, R. J. (2007). Location of persisting mycobacteria in a Guinea pig model of tuberculosis revealed by r207910. Antimicrob Agents Chemother 51, 3338-3345.

Lipinski, C. A., Lombardo, F., Dominy, B. W., and Feeney, P. J. (2001). Experimental and computational approaches to estimate solubility and permeability in drug discovery and development settings. Advanced Drug Delivery Reviews 46, 3-26.

Neyrolles, O., Hernandez-Pando, R., Pietri-Rouxel, F., Fornes, P., Tailleux, L., Barrios Payan, J. A., Pivert, E., Bordat, Y., Aguilar, D., Prevost, M. C., et al. (2006). Is adipose tissue a place for *Mycobacterium tuberculosis* persistence? PLoS ONE 1, e43.

Rohde, K. H., Abramovitch, R. B., and Russell, D. G. (2007). *Mycobacterium tuberculosis* invasion of macrophages: linking bacterial gene expression to environmental cues. Cell Host Microbe 2, 352-364.

Salomon, J. A., Lloyd-Smith, J. O., Getz, W. M., Resch, S., Sanchez, M. S., Porco, T. C., and Borgdorff, M. W. (2006). Prospects for advancing tuberculosis control efforts through novel therapies. PLoS Med 3, e273.

Schnappinger, D., Ehrt, S., Voskuil, M. I., Liu, Y., Mangan, J. A., Monahan, I. M., Dolganov, G., Efron, B., Butcher, P. D., Nathan, C., and Schoolnik, G. K. (2003). Transcriptional Adaptation of *Mycobacterium tuberculosis* within Macrophages: Insights into the Phagosomal Environment. J Exp Med 198, 693-704.

Van Rie, A., and Enarson, D. (2006). XDR tuberculosis: an indicator of public-health negligence. Lancet 368, 1554-1556.

TABLE 1

| ID | Structure | Primary QIM CellNb | QIM Confirm CellNb 20 uM | QIM Confirm CellNb 2 uM | QIM Confirm CellNb 0.2 uM | Primary QIM % Inhibition | QIM Confirm % Inhibition 20 uM |
|---|---|---|---|---|---|---|---|
| IPK000 00132 | 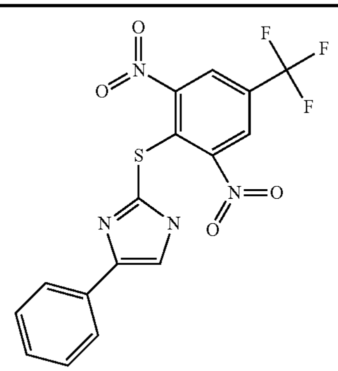 | 88.3 | 113.8 | 208.5 | 241.4 | 25.4 | 50.7 |
| IPK000 00190 | 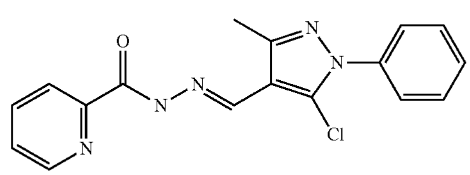 [SMILES: Cc1nn(-c2ccccc2)c(Cl)c1/C=N/NC(=O)c1ccccn1] | 435.5 | 317.6 | 173.6 | 190.0 | 91.9 | 96.5 |
| IPK000 00203 | 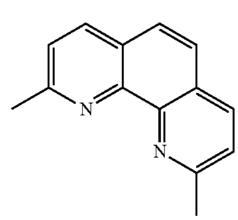 [SMILES: Cc1ccc2ccc3ccc(C)nc3c2n1] | 77.0 | 148.0 | 92.0 | 241.4 | −28.5 | −12.3 |

TABLE 1-continued

| ID | Structure | | | | | | |
|---|---|---|---|---|---|---|---|
| IPK 000 000 217 | (thiosemicarbazone of 4-chloroacetophenone) | 235.5 | 249.8 | 541.6 | 472.3 | 26.6 | 24.5 |
| IPK 000 000 287 | (N-(thiazol-2-yl)-2-(thiophen-2-ylthio)acetamide) | 350.3 | 412.9 | 246.1 | 315.9 | 65.9 | 66.0 |
| IPK 000 000 301 | (isonicotinoyl hydrazone of 2-acetylthiophene) | 373.5 | 248.3 | 457.3 | 232.6 | 88.2 | 40.4 |
| IPK 000 000 389 | (5,6-bis(3,4-dichlorophenylamino)-[1,2,5]oxadiazolo[3,4-b]pyrazine) | 72.5 | 103.0 | 200.6 | 265.3 | 27.7 | 84.6 |
| IPK 000 000 390 | (5,6-bis(4-chlorophenylamino)-[1,2,5]oxadiazolo[3,4-b]pyrazine) | 78.0 | 133.4 | 75.6 | 142.3 | 15.7 | 67.9 |
| IPK 000 000 391 | (5,6-bis(4-fluorophenylamino)-[1,2,5]oxadiazolo[3,4-b]pyrazine) | 63.0 | 128.8 | 148.9 | 220.9 | 31.6 | 76.4 |

TABLE 1-continued

| ID | Structure | | | | | | |
|---|---|---|---|---|---|---|---|
| IPK 000 000 635 | (isatin-3-ylidene isonicotinohydrazide) | 424.3 | 328.8 | 320.9 | 262.8 | 97.6 | 65.2 |
| IPK 000 000 731 | (2-(2-(4-iodophenyl)hydrazono)malononitrile) | 61.3 | 166.5 | 308.8 | 393.1 | −28.2 | 25.8 |
| IPK 000 000 802 | (5-bromo-2-(isonicotinamido)isoindoline-1,3-dione) | 305.8 | 484.5 | 218.8 | 306.6 | 83.2 | 98.0 |
| IPK 000 000 812 | (triazine derivative with OCF$_3$-phenyl, N-methylpiperazine and OCH$_2$CF$_3$) | 396.3 | 248.0 | 225.6 | 292.9 | 64.1 | 78.4 |
| IPK 000 000 933 | (N'-(3,5-dibromo-2-hydroxybenzylidene)isonicotinohydrazide) | 314.5 | 333.6 | 475.9 | 264.8 | 79.9 | 56.9 |
| IPK 000 000 941 | (N'-((4,5-dibromofuran-2-yl)methylene)isonicotinohydrazide) | 345.8 | 446.5 | 488.3 | 257.8 | 92.9 | 99.6 |
| IPK 000 000 942 | (N'-((5-chlorothiophen-2-yl)methylene)isonicotinohydrazide) | 376.5 | 255.0 | 473.5 | 326.3 | 93.1 | 97.9 |
| IPK 000 000 978 | (pyrazoline derivative with CF$_3$, OH and isonicotinoyl) | 454.5 | 376.1 | 414.4 | 325.5 | 102.6 | 88.6 |

TABLE 1-continued

| ID | Structure | | | | | | |
|---|---|---|---|---|---|---|---|
| IPK 000 010 06 | (bicyclononene cyclopropane carbohydrazide with 3-bromobenzaldehyde) | 322.8 | 380.9 | 344.9 | 412.0 | 81.0 | 81.8 |
| IPK 000 011 19 | (furazano-indeno-pyrazinone) | 190.8 | 279.1 | 80.0 | 248.8 | 60.0 | 47.6 |
| IPK 000 011 65 | (bis-morpholino triazine with 5-bromofurfurylidene hydrazine) | 145.5 | 201.1 | 336.5 | 259.6 | 6.5 | 41.9 |
| IPK 000 013 67 | (isonicotinohydrazide furfurylidene) | 358.0 | 457.3 | 545.1 | 452.5 | 98.7 | 66.7 |
| IPK 000 013 68 | (isonicotinohydrazide cinnamylidene) | 276.3 | 438.8 | 528.8 | 400.1 | 65.0 | 67.2 |
| IPK 000 013 69 | (isonicotinohydrazide 4-butylbenzylidene) | 327.5 | 443.3 | 532.1 | 405.8 | 91.3 | 58.6 |
| IPK 000 013 70 | (pyridazine carbohydrazide cyclopentylidene) | 309.3 | 518.5 | 510.9 | 412.6 | 88.3 | 103.0 |
| IPK 000 013 71 | (isonicotinohydrazide 2-fluorobenzylidene) | 358.8 | 377.4 | 544.3 | 476.5 | 102.9 | 97.5 |

TABLE 1-continued

| ID | Structure | | | | | | |
|---|---|---|---|---|---|---|---|
| IPK 000 013 72 | (N-cyclohexylidene isonicotinohydrazide) | 355.5 | 457.3 | 541.6 | 448.5 | 82.2 | 100.6 |
| IPK 000 015 36 | (chlorinated chalcone) | 146.5 | 168.0 | 286.0 | 331.0 | 38.1 | 36.1 |
| IPK 000 016 00 | (benzyloxyphenyl-pyridinylethylamine) | 93.0 | 300.3 | 265.4 | 278.8 | −19.0 | 37.9 |
| IPK 000 016 05 | (indole derivative) | 192.0 | 282.0 | 148.9 | 206.8 | 67.9 | 43.4 |
| IPK 000 018 65 | (quinolinyl 2-fluorobenzoate) | 218.0 | 256.4 | 218.3 | 256.6 | 23.1 | 39.2 |
| IPK 000 018 66 | (quinolin-8-yl 3-nitrobenzoate) | 63.3 | 130.4 | 296.6 | 258.1 | −26.8 | 16.7 |

TABLE 1-continued

| ID | Structure | | | | | | |
|---|---|---|---|---|---|---|---|
| IPK 000 018 82 | 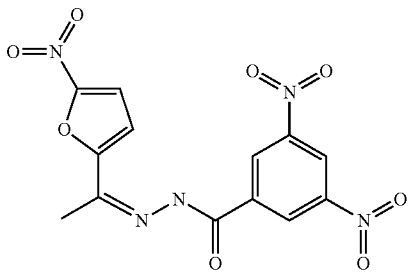 [SMILES: C/C(=N/NC(=O)c1cc([N+](=O)[O-])cc([N+](=O)[O-])c1)c1ccc([N+](=O)[O-])o1] | 106.8 | 184.1 | 209.0 | 443.0 | −57.3 | 4.1 |
| IPK 000 018 97 | 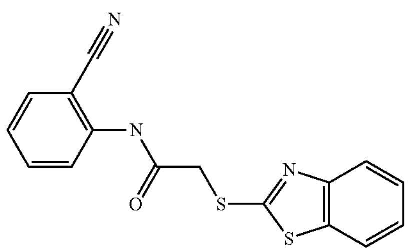 [SMILES: N#Cc1ccccc1NC(=O)CSc1nc2ccccc2s1] | 314.0 | 553.9 | 299.8 | 288.5 | 76.7 | 83.8 |
| IPK 000 019 84 | 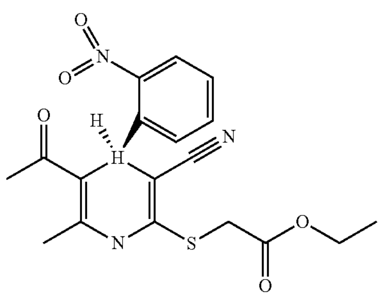 | 402.0 | 610.5 | 329.0 | 287.9 | 88.8 | 94.6 |
| IPK 000 021 87 | 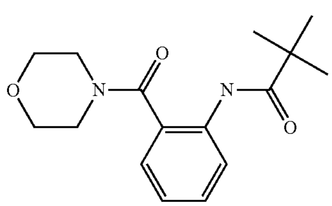 [SMILES: CC(C)(C)C(=O)Nc1ccccc1C(=O)N1CCOCC1] | 405.0 | 609.0 | 403.4 | 305.3 | 90.2 | 96.5 |
| IPK 000 022 33 | 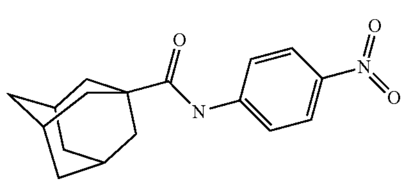 [SMILES: O=C(Nc1ccc([N+](=O)[O-])cc1)C12CC3CC(CC(C3)C1)C2] | 372.0 | 517.1 | 472.3 | 315.6 | 66.0 | 90.0 |
| IPK 000 024 43 | 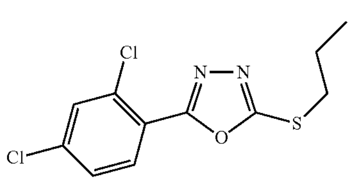 [SMILES: CCCSc1nnc(-c2ccc(Cl)cc2Cl)o1] | 203.8 | 205.0 | 349.0 | 352.1 | 5.8 | 59.1 |

TABLE 1-continued

| ID | Structure | | | | | | |
|---|---|---|---|---|---|---|---|
| IPK 000 0027 72 | (2-chlorophenoxy)ethyl 3,5-dinitrobenzamide | 333.3 | 238.1 | 440.4 | 267.0 | 82.6 | 100.0 |
| IPK 000 0027 74 | (2-methoxyphenoxy)ethyl 3,5-dinitrobenzamide | 366.0 | 435.8 | 478.8 | 268.5 | 87.2 | 96.9 |
| IPK 000 0027 77 | (3-methoxyphenoxy)ethyl 3,5-dinitrobenzamide | 378.0 | 322.3 | 315.3 | 218.1 | 89.1 | 86.3 |
| IPK 000 0027 78 | (4-isopropylbenzyl) 3,5-dinitrobenzamide | 332.0 | 499.4 | 543.5 | 366.0 | 79.6 | 96.3 |
| IPK 000 0027 85 | (benzo[d][1,3]dioxol-5-ylmethyl) 3,5-dinitrobenzamide | 315.0 | 224.8 | 487.4 | 429.3 | 100.3 | 40.1 |
| IPK 000 0027 91 | (2-(benzyloxy)ethyl) 3,5-dinitrobenzamide | 410.8 | 325.6 | 434.1 | 295.3 | 89.0 | 46.1 |

TABLE 1-continued

| | | | | | | | |
|---|---|---|---|---|---|---|---|
| IPK 000 028 35 | (structure) | 315.3 | 308.9 | 478.6 | 489.8 | 94.5 | 17.8 |
| IPK 000 033 16 | (structure) | 283.0 | 303.9 | 573.9 | 296.1 | 81.9 | 92.3 |
| IPK 000 033 61 | (structure) | 188.3 | 111.8 | 434.1 | 210.8 | 31.6 | 62.9 |
| IPK 000 035 56 | (structure) | 266.0 | 524.3 | 313.1 | 247.1 | 83.3 | 89.0 |
| IPK 000 035 58 | (structure) | 104.0 | 279.9 | 330.0 | 292.3 | −51.3 | 2.8 |
| IPK 000 036 07 | (structure) | 142.3 | 164.4 | 293.9 | 267.4 | 27.7 | 59.5 |
| IPK 000 040 14 | (structure) | 95.5 | 330.0 | 262.3 | 321.4 | −38.6 | 18.1 |

TABLE 1-continued
| | | | | | | | |
|---|---|---|---|---|---|---|---|
| IPK 000 041 45 | 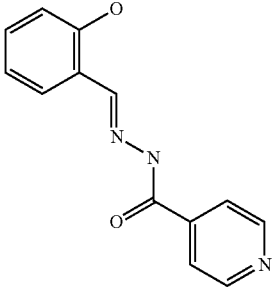 [SMILES: O=C(N/N=C/c1ccccc1O)c1ccncc1] | 324.5 | 243.8 | 527.9 | 437.4 | 88.6 | 87.2 |
| IPK 000 041 46 | 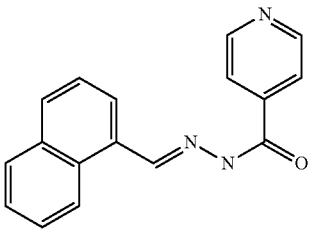 [SMILES: O=C(N/N=C/c1cccc2ccccc12)c1ccncc1] | 320.0 | 347.1 | 542.6 | 386.9 | 81.2 | 93.3 |
| IPK 000 041 47 | 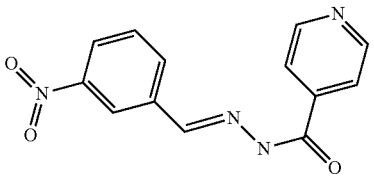 [SMILES: O=C(N/N=C/c1cccc([N+](=O)[O-])c1)c1ccncc1] | 362.8 | 345.8 | 516.1 | 479.8 | 102.4 | 95.5 |
| IPK 000 041 48 | 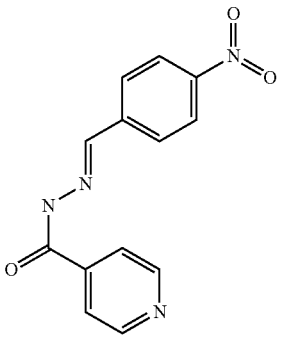 [SMILES: O=C(N/N=C/c1ccc([N+](=O)[O-])cc1)c1ccncc1] | 315.3 | 347.6 | 508.4 | 414.6 | 84.5 | 88.4 |
| IPK 000 041 49 | 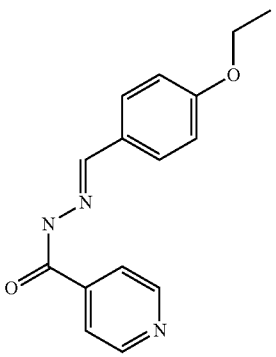 [SMILES: CCOc1ccc(/C=N/NC(=O)c2ccncc2)cc1] | 336.5 | 338.1 | 535.4 | 394.6 | 83.8 | 94.5 |

TABLE 1-continued
| | | | | | | | |
|---|---|---|---|---|---|---|---|
| IPK 000 041 50 | 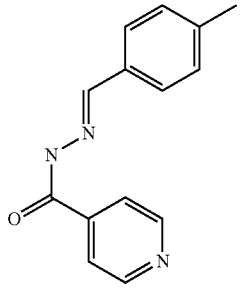 [SMILES: Cc1ccc(/C=N/NC(=O)c2ccncc2)cc1] | 296.3 | 315.9 | 515.5 | 396.3 | 81.6 | 90.8 |
| IPK 000 041 51 | 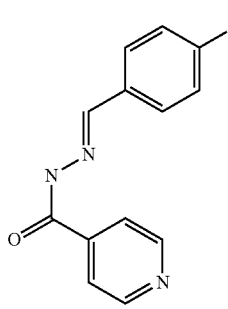 | 351.3 | 350.6 | 505.6 | 368.0 | 89.0 | 94.0 |
| IPK 000 041 52 | 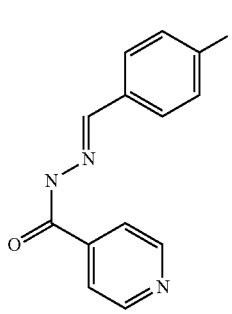 | 262.5 | 362.8 | 523.5 | 451.8 | 75.6 | 93.7 |
| IPK 000 041 53 | 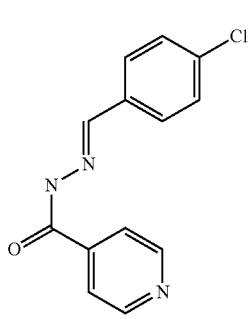 [SMILES: O=C(N/N=C/c1ccc(Cl)cc1)c1ccncc1] | 426.8 | 431.1 | 523.3 | 197.8 | 100.2 | 97.0 |
| IPK 000 042 07 | 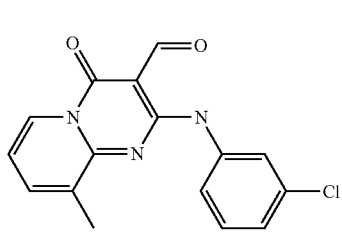 [SMILES: Cc1cccn2c(=O)c(C=O)c(Nc3cccc(Cl)c3)nc12] | 198.0 | 596.4 | 616.9 | 259.4 | 34.7 | 107.1 |

TABLE 1-continued

| ID | Structure | | | | | | |
|---|---|---|---|---|---|---|---|
| IPK000 04230 | 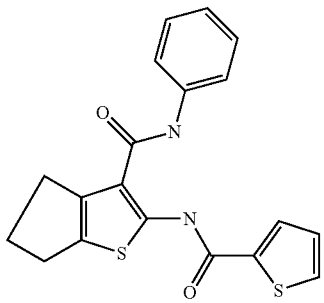 [SMILES: O=C(Nc1sc2c(c1C(=O)Nc1ccccc1)CCC2)c1cccs1] | 193.8 | 376.8 | 658.0 | 384.8 | 73.7 | 95.9 |
| IPK000 04272 | 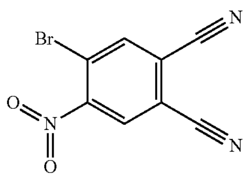 [SMILES: N#Cc1cc(Br)c([N+](=O)[O-])cc1C#N] | 152.0 | 199.9 | 96.1 | 227.8 | 11.9 | 57.6 |
| IPK000 04277 | 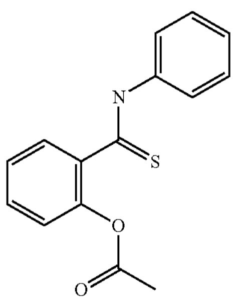 [SMILES: CC(=O)Oc1ccccc1C(=S)Nc1ccccc1] | 367.0 | 425.5 | 255.3 | 352.6 | 104.9 | 48.9 |
| IPK000 04278 | 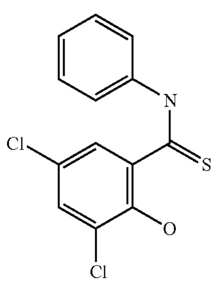 [SMILES: Oc1c(Cl)cc(Cl)cc1C(=S)Nc1ccccc1] | 194.5 | 341.9 | 311.5 | 322.6 | 73.9 | 91.7 |
| IPK000 04293 | 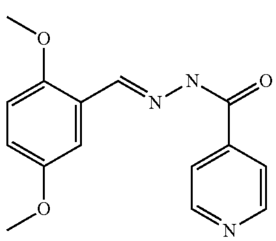 [SMILES: COc1ccc(OC)c(/C=N/NC(=O)c2ccncc2)c1] | 321.8 | 451.8 | 532.9 | 387.9 | 108.6 | 105.5 |
| IPK000 04295 | 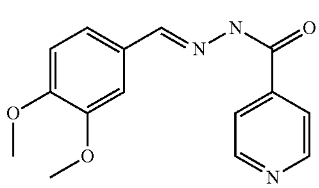 | 143.5 | 433.9 | 494.6 | 493.0 | 64.7 | 98.8 |

TABLE 1-continued
| | | | | | | | |
|---|---|---|---|---|---|---|---|
| IPK 000 042 96 | 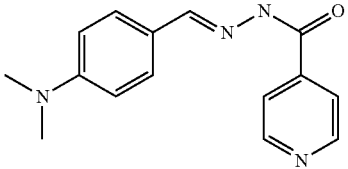 [SMILES: CN(C)c1ccc(/C=N/NC(=O)c2ccncc2)cc1] | 216.3 | 477.0 | 472.5 | 491.4 | 84.3 | 105.4 |
| IPK 000 042 97 | 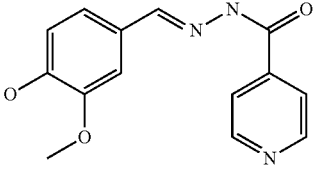 [SMILES: COc1cc(/C=N/NC(=O)c2ccncc2)ccc1O] | 307.8 | 483.0 | 502.4 | 312.9 | 99.7 | 103.4 |
| IPK 000 042 98 | 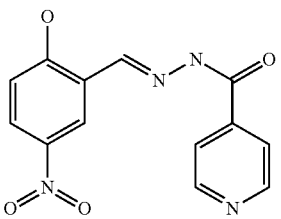 [SMILES: O=C(N/N=C/c1cc([N+](=O)[O-])ccc1O)c1ccncc1] | 350.0 | 554.9 | 494.5 | 279.6 | 102.3 | 105.4 |
| IPK 000 042 99 | 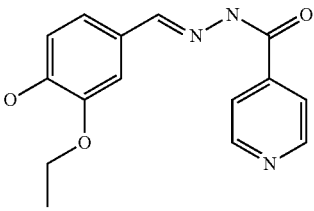 [SMILES: CCOc1cc(/C=N/NC(=O)c2ccncc2)ccc1O] | 364.0 | 488.3 | 567.3 | 378.4 | 102.7 | 106.3 |
| IPK 000 043 00 | 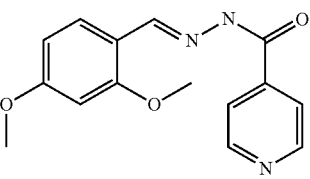 [SMILES: COc1ccc(/C=N/NC(=O)c2ccncc2)c(OC)c1] | 333.3 | 413.1 | 537.9 | 371.0 | 104.4 | 101.8 |
| IPK 000 043 01 | 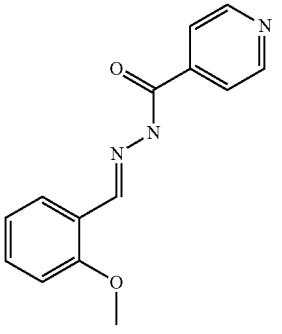 [SMILES: COc1ccccc1/C=N/NC(=O)c1ccncc1] | 287.8 | 448.5 | 584.3 | 385.1 | 86.6 | 102.6 |
| IPK 000 043 02 | 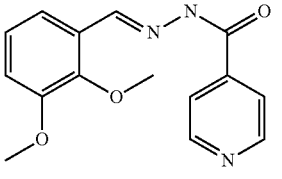 | 229.5 | 422.1 | 483.0 | 476.3 | 81.1 | 99.8 |

TABLE 1-continued

| ID | Structure | | | | | | |
|---|---|---|---|---|---|---|---|
| IPK 00004305 | (2-chlorobenzylidene)isonicotinohydrazide | 228.8 | 494.4 | 502.8 | 469.0 | 97.1 | 103.8 |
| IPK 00004306 | (4-butoxybenzylidene)isonicotinohydrazide | 200.3 | 436.0 | 520.1 | 213.5 | 81.4 | 98.0 |
| IPK 00004307 | (4-hydroxybenzylidene)isonicotinohydrazide | 303.5 | 416.6 | 541.6 | 392.0 | 104.3 | 98.6 |
| IPK 00004308 | (2-hydroxy-3-methoxybenzylidene)isonicotinohydrazide | 255.5 | 367.6 | 486.8 | 397.6 | 87.3 | 95.1 |
| IPK 00004309 | (3-bromobenzylidene)isonicotinohydrazide | 258.5 | 459.3 | 516.8 | 420.0 | 95.8 | 102.4 |

TABLE 1-continued

| ID | Structure | | | | | | |
|---|---|---|---|---|---|---|---|
| IPK 000 043 10 | (2,3-dichlorobenzylidene isonicotinohydrazide) | 176.8 | 441.6 | 509.8 | 367.0 | 14.3 | 98.3 |
| IPK 000 043 11 | (4-hydroxy-3-nitrobenzylidene isonicotinohydrazide) | 366.0 | 514.6 | 532.3 | 350.4 | 104.4 | 104.5 |
| IPK 000 043 12 | (indol-2-ylmethylene isonicotinohydrazide) | 195.0 | 406.3 | 500.3 | 432.0 | 69.9 | 100.0 |
| IPK 000 043 13 | (2,4-dichlorobenzylidene isonicotinohydrazide) | 177.8 | 468.8 | 469.0 | 269.9 | 49.2 | 104.2 |
| IPK 000 043 26 | (3-methylbenzylidene isonicotinohydrazide) | 347.3 | 430.3 | 523.3 | 413.6 | 109.4 | 102.1 |

TABLE 1-continued

| ID | Structure | | | | | | |
|---|---|---|---|---|---|---|---|
| IPK 000 043 27 | 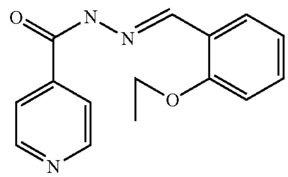 [SMILES: CCOc1ccccc1/C=N/NC(=O)c1ccncc1] | 125.8 | 438.6 | 549.8 | 459.1 | 47.6 | 102.0 |
| IPK 000 043 28 | 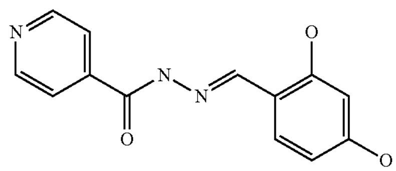 [SMILES: O=C(N/N=C/c1ccc(O)cc1O)c1ccncc1] | 326.5 | 408.3 | 482.8 | 332.6 | 94.9 | 95.9 |
| IPK 000 043 29 | 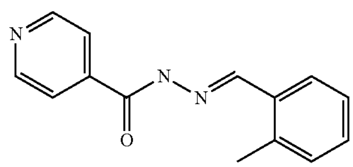 [SMILES: Cc1ccccc1/C=N/NC(=O)c1ccncc1] | 415.5 | 454.4 | 567.1 | 489.3 | 111.0 | 100.2 |
| IPK 000 043 30 | 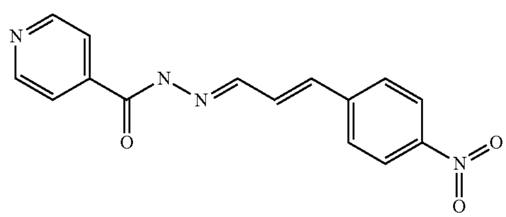 [SMILES: O=C(N/N=C/C=C/c1ccc([N+](=O)[O-])cc1)c1ccncc1] | 305.0 | 503.3 | 575.8 | 251.1 | 107.2 | 102.5 |
| IPK 000 043 31 | 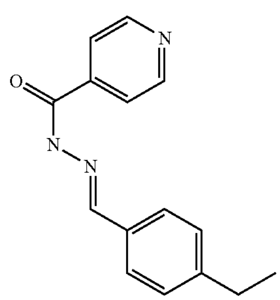 [SMILES: CCc1ccc(/C=N/NC(=O)c2ccncc2)cc1] | 334.0 | 442.5 | 526.9 | 321.1 | 94.6 | 100.4 |
| IPK 000 043 32 | 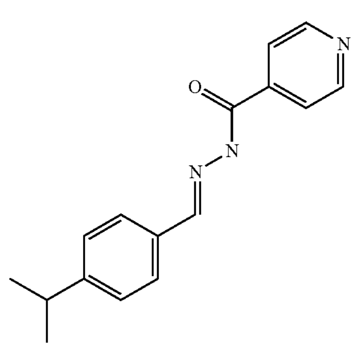 [SMILES: CC(C)c1ccc(/C=N/NC(=O)c2ccncc2)cc1] | 164.0 | 452.4 | 425.4 | 481.6 | 60.5 | 102.5 |

TABLE 1-continued

| ID | Structure | | | | | | |
|---|---|---|---|---|---|---|---|
| IPK 000 043 33 | (pyridine-4-carbohydrazide, thiophene-2-carbaldehyde hydrazone) | 270.8 | 522.8 | 515.1 | 362.8 | 83.0 | 104.4 |
| IPK 000 043 35 | (2-nitrobenzaldehyde isonicotinoyl hydrazone) | 245.5 | 461.5 | 484.3 | 335.4 | 104.0 | 100.9 |
| IPK 000 043 62 | (2-ethoxy-1-naphthaldehyde isonicotinoyl hydrazone) | 393.8 | 523.9 | 561.9 | 502.1 | 98.2 | 104.5 |
| IPK 000 043 83 | (5-bromo-2-hydroxybenzaldehyde 2-hydroxyaniline Schiff base) | 89.0 | 252.3 | 303.8 | 296.4 | −80.9 | 31.3 |
| IPK 000 044 20 | (2-hydroxy-5-nitrobenzaldehyde 2-hydroxyaniline Schiff base) | 135.0 | 219.0 | 278.5 | 303.0 | −67.5 | 30.7 |
| IPK 000 044 41 | (3,5-dibromo-2-hydroxybenzaldehyde 2-hydroxyaniline Schiff base) | 126.8 | 307.0 | 377.5 | 260.0 | −120.3 | 29.9 |

TABLE 1-continued

| ID | Structure | | | | | | |
|---|---|---|---|---|---|---|---|
| IPK000 04501 | (3,5-dichloro-2-hydroxybenzylidene)(2-hydroxyphenyl)amine | 145.0 | 273.8 | 328.5 | 305.8 | −9.3 | 30.6 |
| IPK000 04678 | 3,5-dinitro-N-isobutylbenzamide | 193.3 | 284.4 | 388.9 | 335.3 | 73.3 | 88.9 |
| IPK000 04680 | 3,5-dinitro-N-(1-phenylethyl)benzamide | 238.8 | 389.1 | 277.8 | 353.3 | 76.9 | 64.6 |
| IPK000 04683 | N-cycloheptyl-3,5-dinitrobenzamide | 204.0 | 379.6 | 437.5 | 355.0 | 75.8 | 61.7 |
| IPK000 04686 | 2-(3,5-dinitrobenzoyl)-1,2,3,4-tetrahydroisoquinoline | 129.3 | 285.6 | 305.0 | 300.1 | 26.6 | 40.8 |
| IPK000 04687 | N-butyl-3,5-dinitrobenzamide | 239.0 | 343.3 | 411.1 | 328.6 | 74.4 | 56.3 |

TABLE 1-continued

| ID | Structure | | | | | | |
|---|---|---|---|---|---|---|---|
| IPK 000 046 92 | 3,5-dinitro-N-(4-bromophenyl)benzamide | 303.5 | 309.6 | 325.4 | 304.1 | 90.2 | 93.4 |
| IPK 000 047 06 | 3-nitro-4-methyl-N-cycloheptylbenzamide | 290.8 | 440.0 | 365.8 | 300.0 | 57.3 | 69.9 |
| IPK 000 047 15 | 2-chloro-4-nitro-N-(3,4-dimethylphenyl)benzamide | 281.8 | 432.3 | 482.3 | 298.0 | 69.7 | 85.8 |
| IPK 000 047 16 | 2-chloro-4-nitro-N-(3-chloro-4-methylphenyl)benzamide | 280.5 | 309.1 | 549.8 | 297.5 | 69.4 | 85.1 |
| IPK 000 047 17 | 2-chloro-4-nitro-N-(4-butylphenyl)benzamide | 152.3 | 196.3 | 536.1 | 328.1 | 57.6 | 88.5 |
| IPK 000 048 49 | N-(3,4-dichlorophenyl)furan-2-carboxamide | 253.8 | 281.3 | 457.3 | 354.8 | 84.5 | 92.9 |
| IPK 000 048 71 | 4-chloro-3-nitro-N-(4-sec-butylphenyl)benzamide | 56.5 | 98.1 | 331.5 | 255.1 | 62.1 | 70.0 |

| | | | | | | | |
|---|---|---|---|---|---|---|---|
| IPK 000 048 99 | (structure) | 217.8 | 211.4 | 494.5 | 311.4 | 76.8 | 73.5 |
| IPK 000 049 00 | (structure) | 108.0 | 212.4 | 503.6 | 349.5 | 32.1 | 74.2 |
| IPK 000 049 03 | (structure) | 205.3 | 481.3 | 525.4 | 370.8 | 62.6 | 48.6 |
| IPK 000 049 20 | (structure) | 155.5 | 157.0 | 405.8 | 296.1 | 71.5 | 88.6 |
| IPK 000 052 50 | (structure) | 44.0 | 117.6 | 289.6 | 339.1 | 45.0 | 76.4 |
| IPK 000 052 75 | (structure) | 48.8 | 290.3 | 265.9 | 256.8 | −77.4 | 10.1 |

TABLE 1-continued

| ID | Structure | | | | | | |
|---|---|---|---|---|---|---|---|
| IPK 000 057 78 | (structure) | 177.0 | 292.4 | 203.8 | 252.1 | −10.9 | 35.5 |
| IPK 000 057 92 | (structure) | 165.3 | 197.4 | 225.8 | 237.3 | −30.7 | 27.2 |
| IPK 000 058 20 | (structure) | 344.8 | 278.0 | 458.8 | 295.1 | 98.1 | 44.3 |
| IPK 000 058 21 | (structure) | 452.5 | 453.1 | 525.3 | 341.6 | 90.9 | 56.0 |
| IPK 000 058 29 | (structure) | 75.5 | 224.8 | 432.0 | 499.8 | 63.0 | 31.5 |
| IPK 000 058 30 | (structure) | 315.8 | 435.3 | 483.4 | 325.6 | 95.5 | 70.8 |

TABLE 1-continued
| | | | | | | | |
|---|---|---|---|---|---|---|---|
| IPK 000 063 24 | 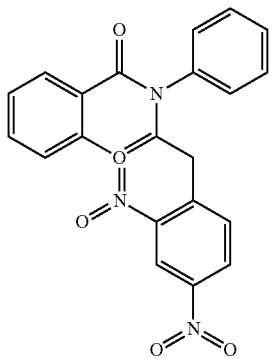 | 188.3 | 183.6 | 232.5 | 327.4 | 49.6 | 68.7 |
| IPK 000 065 03 | 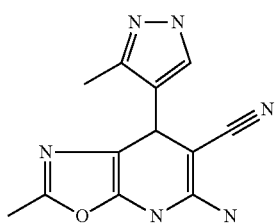 [SMILES: Cc1nc2c(o1)NC(N)=C(C#N)C2c1c[nH]nc1C] | 197.8 | 172.1 | 227.0 | 299.3 | 68.2 | 73.2 |
| IPK 000 067 51 | 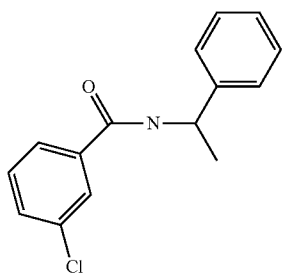 [SMILES: CC(NC(=O)c1cccc(Cl)c1)c1ccccc1] | 142.3 | 164.5 | 301.5 | 367.1 | 75.2 | 73.2 |
| IPK 000 067 60 | 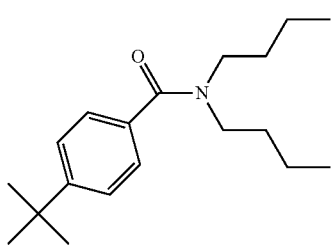 [SMILES: CCCCN(CCCC)C(=O)c1ccc(C(C)(C)C)cc1] | 164.3 | 278.3 | 179.1 | 326.4 | 63.4 | 46.6 |
| IPK 000 067 61 | 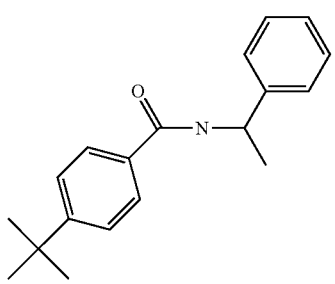 [SMILES: CC(NC(=O)c1ccc(C(C)(C)C)cc1)c1ccccc1] | 182.0 | 478.4 | 340.5 | 305.0 | 84.3 | 68.5 |

TABLE 1-continued
| | | | | | | | |
|---|---|---|---|---|---|---|---|
| IPK 000 068 87 | 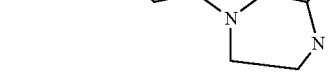 | 156.8 | 183.6 | 221.4 | 295.9 | 73.1 | 71.4 |
| IPK 000 073 11 | 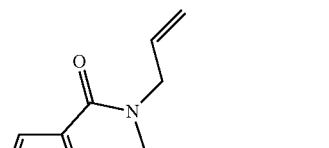 | 147.8 | 224.4 | 168.9 | 256.1 | 49.1 | 56.1 |
| IPK 000 073 29 | 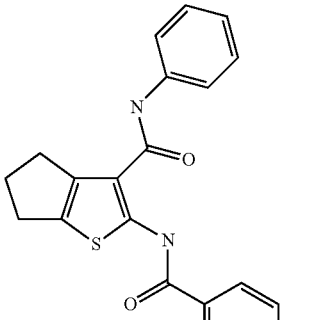 | 230.5 | 193.1 | 551.9 | 315.5 | 78.6 | 86.6 |
| IPK 000 073 68 | 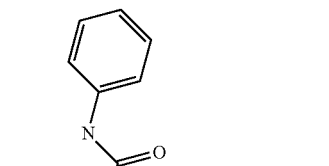 | 202.3 | 242.6 | 557.3 | 378.6 | 88.2 | 92.6 |

TABLE 1-continued

| | | | | | | | |
|---|---|---|---|---|---|---|---|
| IPK 000 073 69 | [structure] | 246.5 | 465.9 | 375.5 | 335.9 | 87.0 | 32.3 |
| IPK 000 073 70 | [structure] | 234.0 | 539.8 | 523.0 | 348.3 | 88.6 | 103.0 |
| IPK 000 073 71 | [structure] | 218.3 | 534.3 | 467.8 | 244.5 | 87.5 | 65.2 |
| IPK 000 077 22 | [structure] | 84.5 | 253.9 | 380.5 | 314.1 | −33.0 | 46.6 |

TABLE 1-continued
| | | | | | | | |
|---|---|---|---|---|---|---|---|
| IPK 000 078 30 | 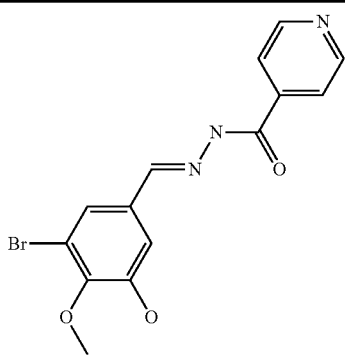 | 388.3 | 540.5 | 495.6 | 250.6 | 108.5 | 105.0 |
| IPK 000 078 53 | 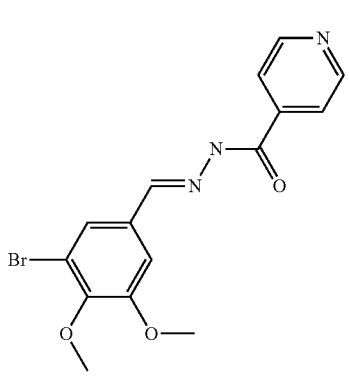 [SMILES: COc1cc(/C=N/NC(=O)c2ccncc2)cc(Br)c1OC] | 386.0 | 523.3 | 489.9 | 298.6 | 84.0 | 106.6 |
| IPK 000 078 86 | 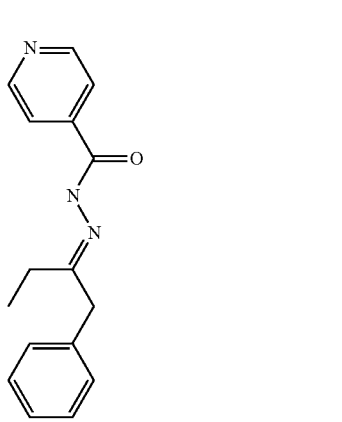 [SMILES: CC/C(Cc1ccccc1)=N\NC(=O)c1ccncc1] | 462.0 | 583.0 | 531.4 | 373.4 | 96.9 | 107.5 |
| IPK 000 079 13 | 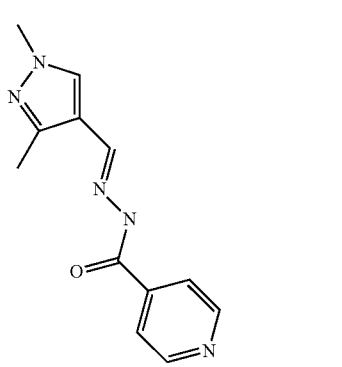 [SMILES: Cc1nn(C)cc1/C=N/NC(=O)c1ccncc1] | 294.0 | 528.5 | 493.6 | 217.9 | 69.6 | 101.6 |

TABLE 1-continued

| ID | Structure | | | | | | |
|---|---|---|---|---|---|---|---|
| IPK00007915 | (structure) | 383.3 | 470.9 | 477.4 | 274.6 | 82.4 | 97.9 |
| IPK00007988 | (structure) | 181.8 | 368.8 | 289.8 | 254.3 | −69.2 | 28.1 |
| IPK00008001 | (structure) | 409.8 | 469.1 | 387.1 | 360.5 | 14.3 | 56.6 |
| IPK00008024 | (structure) | 188.8 | 321.0 | 492.1 | 323.8 | 0.2 | 23.0 |
| IPK00008036 | (structure) | 79.8 | 251.4 | 559.6 | 514.4 | −91.1 | 26.0 |
| IPK00008037 | (structure) | 110.8 | 393.6 | 491.4 | 377.0 | −44.0 | 36.0 |

TABLE 1-continued

| ID | Structure | | | | | | |
|---|---|---|---|---|---|---|---|
| IPK 000 080 38 | (thiosemicarbazone of 2'-hydroxyacetophenone) | 307.5 | 371.6 | 337.3 | 264.9 | 21.0 | 3.4 |
| IPK 000 080 39 | (thiosemicarbazone of 4'-isobutylacetophenone) | 99.0 | 377.1 | 591.3 | 418.3 | 38.3 | 9.2 |
| IPK 000 080 69 | (Schiff base with 5-bromo-3-nitrosalicylaldehyde and 2-aminophenol) | 123.5 | 328.0 | 358.9 | 289.4 | −42.5 | 16.5 |
| IPK 000 080 81 | (isonicotinoyl hydrazone of 5-bromo-3-nitrosalicylaldehyde) | 363.3 | 482.0 | 559.0 | 405.8 | 94.7 | 99.5 |
| IPK 000 083 89 | (ethyl 2-methyl-5-oxo-7-phenyl-4-(3-hydroxyphenyl)-1,4,5,6,7,8-hexahydroquinoline-3-carboxylate) | 38.8 | 268.3 | 255.5 | 217.4 | 73.5 | 59.1 |
| IPK 000 085 99 | (propyl 2-methyl-5-oxo-7-phenyl-4-(3-hydroxyphenyl)-1,4,5,6,7,8-hexahydroquinoline-3-carboxylate) | 67.3 | 261.3 | 322.0 | 267.5 | 37.1 | 49.5 |

TABLE 1-continued

| ID | Structure | | | | | | |
|---|---|---|---|---|---|---|---|
| IPK 000 091 17 | 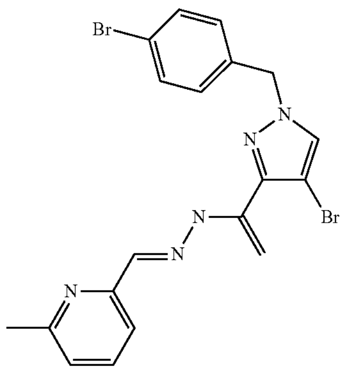 [SMILES: C=C(N/N=C/c1cccc(C)n1)c1nn(Cc2ccc(Br)cc2)cc1Br] | 191.5 | 276.8 | 254.8 | 319.9 | 75.6 | 75.7 |
| IPK 000 091 49 | 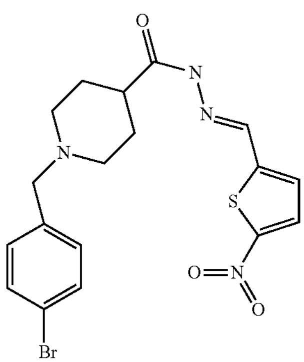 [SMILES: O=C(N/N=C/c1ccc([N+](=O)[O-])s1)C1CCN(Cc2ccc(Br)cc2)CC1] | 110.5 | 228.6 | 265.4 | 388.5 | 90.5 | 95.1 |
| IPK 000 094 38 | 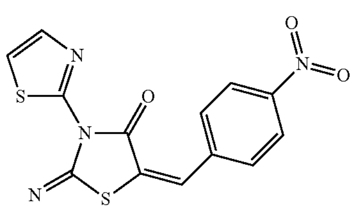 [SMILES: N=C1S/C(=C/c2ccc([N+](=O)[O-])cc2)C(=O)N1c1nccs1] | 126.3 | 367.8 | 286.9 | 271.6 | 46.0 | 6.0 |
| IPK 000 095 07 | 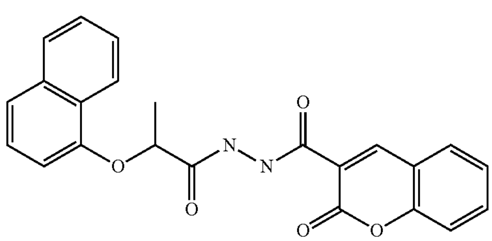 [SMILES: CC(Oc1cccc2ccccc12)C(=O)NNC(=O)c1cc2ccccc2oc1=O] | 388.3 | 551.8 | 348.6 | 377.4 | 70.9 | 75.8 |
| IPK 000 102 07 | 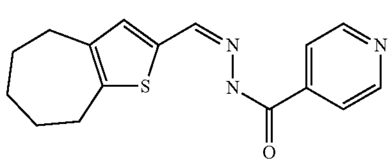 [SMILES: O=C(N/N=C\c1cc2c(s1)CCCCC2)c1ccncc1] | 116.0 | 124.8 | 516.3 | 476.1 | 94.7 | 84.7 |
| IPK 000 102 36 | 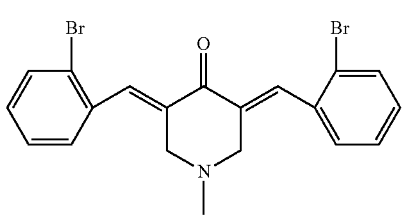 [SMILES: CN1C/C(=C\c2ccccc2Br)C(=O)/C(=C/c2ccccc2Br)C1] | 193.3 | 194.8 | 224.0 | 291.8 | 65.6 | 66.5 |

TABLE 1-continued
| | | | | | | | |
|---|---|---|---|---|---|---|---|
| IPK 000 102 52 | 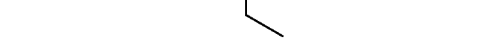 | 179.8 | 175.9 | 145.9 | 219.5 | 70.4 | 68.1 |
| IPK 000 103 28 |  | 134.3 | 164.6 | 419.5 | 263.8 | 71.1 | 71.3 |
| IPK 000 103 76 |  | 47.8 | 122.4 | 109.5 | 143.1 | 85.7 | 74.5 |
| IPK 000 103 78 |  | 263.5 | 409.1 | 244.8 | 236.5 | 94.6 | 98.0 |
| IPK 000 104 07 | 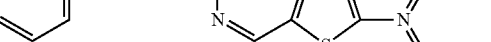 | 243.5 | 222.5 | 575.9 | 330.4 | 82.3 | 80.2 |
| IPK 000 104 11 |  | 203.8 | 370.3 | 278.4 | 240.4 | 89.7 | 83.3 |
| IPK 000 104 13 | 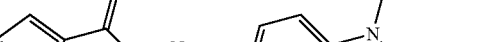 | 115.8 | 446.5 | 313.3 | 260.6 | 68.8 | 89.6 |

TABLE 1-continued
| | | | | | | | | |
|---|---|---|---|---|---|---|---|---|
| IPK 00010420 | 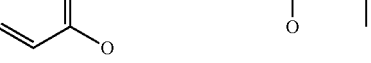 | 29.5 | 81.9 | 153.1 | 230.0 | 65.2 | 34.6 |
| IPK 00010467 | 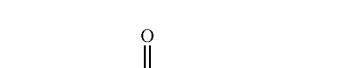 | 183.0 | 211.4 | 332.9 | 283.1 | 33.8 | 73.7 |
| IPK 00010519 | 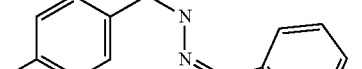 | 374.3 | 425.6 | 566.4 | 521.1 | 98.7 | 105.8 |
| IPK 00010520 | 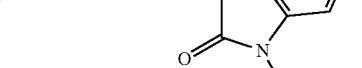 | 316.5 | 397.9 | 547.6 | 482.3 | 97.1 | 96.4 |
| IPK 00010547 | 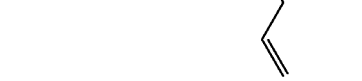 | 125.8 | 172.4 | 468.0 | 270.4 | 60.1 | 50.7 |
| IPK 00010555 |  | 181.3 | 538.8 | 402.4 | 272.8 | 89.3 | 91.5 |

TABLE 1-continued
| | | | | | | | |
|---|---|---|---|---|---|---|---|
| IPK00010556 | 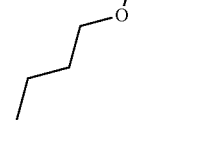 | 225.0 | 169.6 | 442.0 | 371.5 | 65.7 | 86.9 |
| IPK00010570 | 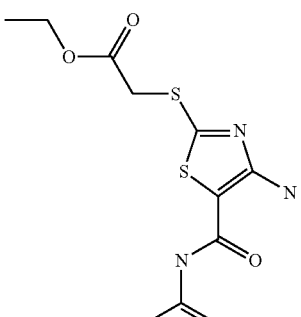 | 315.5 | 573.6 | 226.4 | 237.8 | 61.2 | 84.6 |
| IPK00010630 | 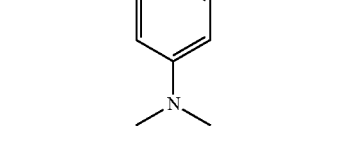 | 146.5 | 171.3 | 409.1 | 233.5 | 65.7 | 67.2 |
| IPK00010790 | 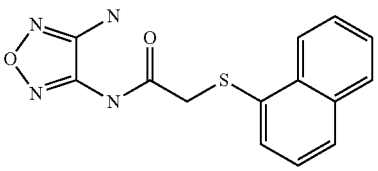 [SMILES: Nc1nonc1NC(=O)CSc1cccc2ccccc12] | 494.3 | 577.5 | 498.0 | 339.3 | 79.3 | 89.6 |
| IPK00010827 | 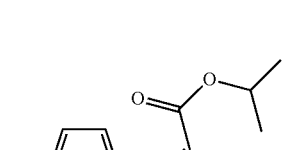 | 171.0 | 369.9 | 332.0 | 321.6 | 54.7 | 44.1 |
| IPK00010878 | 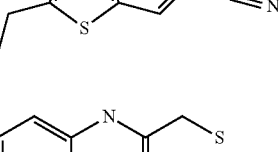 | 200.3 | 287.6 | 400.0 | 339.8 | 78.8 | 68.8 |

TABLE 1-continued

| ID | Structure | | | | | | |
|---|---|---|---|---|---|---|---|
| IPK00010900 | (structure) | 87.8 | 171.8 | 348.5 | 312.4 | −7.8 | 8.2 |
| IPK00010999 | (structure) | 183.0 | 170.0 | 174.3 | 332.1 | 8.5 | 28.1 |
| IPK00011016 | (structure) | 179.5 | 204.9 | 224.6 | 288.0 | 59.0 | 86.0 |
| IPK00011017 | (structure) | 155.5 | 173.4 | 221.5 | 292.3 | 55.6 | 71.6 |
| IPK00011079 | (structure) | 462.3 | 459.5 | 260.1 | 337.0 | 72.9 | 83.4 |
| IPK00011267 | (structure) | 250.8 | 383.9 | 356.4 | 188.8 | −36.5 | 32.6 |

TABLE 1-continued
| | | | | | | | |
|---|---|---|---|---|---|---|---|
| IPK 00011280 | 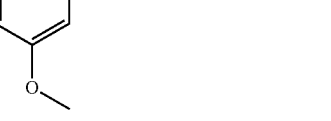 | 152.0 | 183.0 | 189.0 | 279.9 | 41.1 | 55.6 |
| IPK 00011305 | 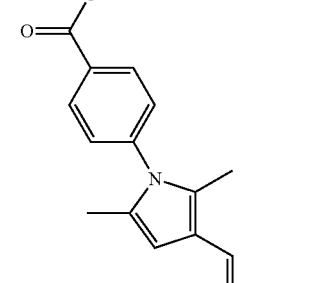 | 162.0 | 107.9 | 309.0 | 264.5 | 55.4 | 56.4 |
| IPK 00011377 | 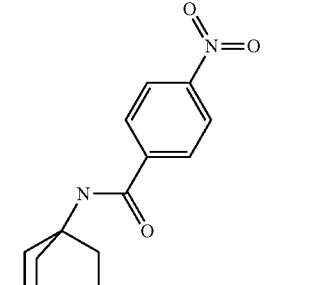 | 319.8 | 523.4 | 437.4 | 319.8 | 60.9 | 74.3 |
| IPK 00011401 | 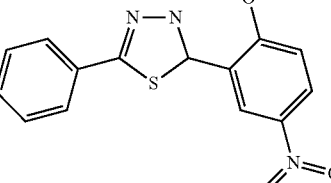 | 163.5 | 236.9 | 198.4 | 233.3 | 3.2 | −1.5 |
| IPK 00011705 | 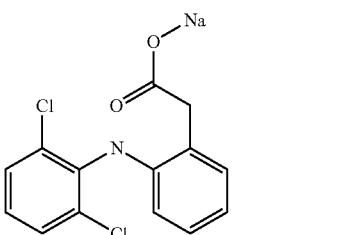 | 656.5 | 578.0 | 540.9 | 503.5 | 79.8 | 80.5 |

TABLE 1-continued
| ID | Structure | | | | | | |
|---|---|---|---|---|---|---|---|
| IPK 000 117 14 | 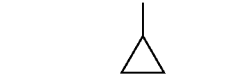 | 546.0 | 548.6 | 349.0 | 329.5 | 69.1 | 66.5 |
| IPK 000 122 62 | 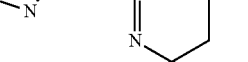 | 131.5 | 92.6 | 328.4 | 254.9 | 62.8 | 65.1 |
| IPK 000 123 02 | 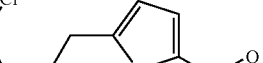 | 411.8 | 347.8 | 427.0 | 270.5 | 76.8 | 78.2 |
| IPK 000 123 03 | 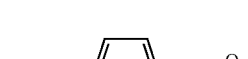 | 540.8 | 467.6 | 319.6 | 234.1 | 78.3 | 72.1 |
| IPK 000 123 30 | 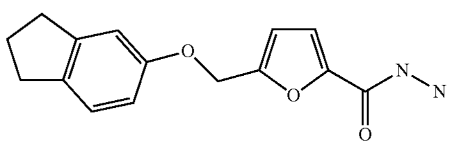 [SMILES: NNC(=O)c1ccc(COc2ccc3c(c2)CCC3)o1] | 296.8 | 390.9 | 495.6 | 263.1 | 77.2 | 64.1 |
| IPK 000 123 90 | 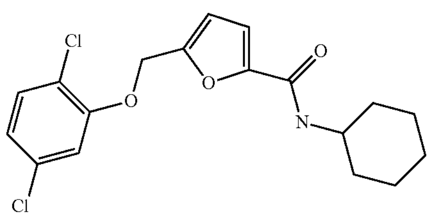 [SMILES: O=C(NC1CCCCC1)c1ccc(COc2cc(Cl)ccc2Cl)o1] | 205.0 | 226.5 | 374.3 | 230.8 | 73.1 | 87.7 |
| IPK 000 123 92 | 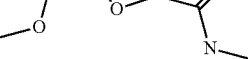 | 135.8 | 127.8 | 409.8 | 277.3 | 45.3 | 15.4 |
| IPK 000 124 43 | 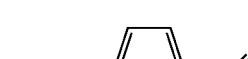 | 168.3 | 110.6 | 305.5 | 279.0 | 35.6 | 64.7 |

TABLE 1-continued

| ID | Structure | | | | | | |
|---|---|---|---|---|---|---|---|
| IPK000 12454 | (4-chlorophenoxy)methyl-furan-N-thiazolyl carboxamide | 503.3 | 591.0 | 268.3 | 320.1 | 75.5 | 75.0 |
| IPK000 12464 | (2-bromophenoxy)methyl-furan carbohydrazide | 501.5 | 421.5 | 343.1 | 256.5 | 79.9 | 78.2 |
| IPK000 12465 | (4-fluorophenoxy)methyl-furan carbohydrazide | 490.8 | 577.0 | 416.9 | 267.0 | 77.1 | 94.3 |
| IPK000 12508 | N-(2,4-dimethylphenyl)-4-((3-(methylthio)-1,2,4-thiadiazol-5-ylthio)methyl)benzamide | 261.5 | 254.5 | 476.3 | 388.9 | 72.8 | 65.1 |
| IPK000 12515 | N-(2,4-dimethylphenyl)-4-((4,5-dihydrothiazol-2-ylthio)methyl)benzamide | 233.8 | 153.1 | 186.4 | 237.5 | 87.1 | 88.7 |
| IPK000 12522 | N-(2,4-dimethylphenyl)-4-((pyridin-2-ylthio)methyl)benzamide | 265.5 | 254.5 | 194.1 | 274.0 | 75.4 | 82.0 |
| IPK000 12561 | 2-(4-(2-(pyrrolidin-1-yl)acetamido)phenyl)-6-methylbenzothiazole | 55.5 | 112.0 | 293.5 | 280.8 | 44.1 | 85.8 |

TABLE 1-continued

| ID | Structure | | | | | | |
|---|---|---|---|---|---|---|---|
| IPK00012633 | (structure) | 123.3 | 86.8 | 126.8 | 270.9 | 80.7 | 73.4 |
| IPK00012673 | (structure) | 524.3 | 271.6 | 149.0 | 225.6 | 85.7 | 60.8 |
| IPK00012837 | (structure) | 519.8 | 402.6 | 312.4 | 274.4 | 43.8 | 26.5 |
| IPK00012972 | (structure) | 479.5 | 540.9 | 272.3 | 289.8 | 61.8 | 75.4 |
| IPK00012991 | (structure) | 436.3 | 477.9 | 426.5 | 372.0 | −36.0 | 38.2 |
| IPK00013026 | (structure) | 476.8 | 385.9 | 270.4 | 340.1 | 66.3 | 29.9 |

TABLE 1-continued

| ID | Structure | | | | | | |
|---|---|---|---|---|---|---|---|
| IPK 000 130 54 | (4-chlorophenyl ketone with 3-methoxyphenyl and dicyanomethyl substituents) | 539.5 | 507.4 | 515.3 | 384.9 | 66.7 | 65.8 |
| IPK 000 133 02 | (N-thiazol-2-yl 3-methoxynaphthalene-2-carboxamide) | 194.8 | 255.4 | 472.4 | 360.5 | −44.8 | 37.2 |
| IPK 000 133 46 | (N-(3-fluorophenyl)-N'-(2-cyclohexenylethyl)oxalamide) | 473.3 | 534.5 | 397.5 | 243.9 | 69.6 | 94.4 |
| IPK 000 134 50 | (3-ethyl-5-hydroxy-5-trifluoromethyl-1-isonicotinoyl-pyrazoline) | 560.0 | 526.9 | 490.5 | 255.9 | 99.7 | 100.7 |
| IPK 000 134 51 | (3-trifluoromethyl-5-hydroxy-5-(4-ethylphenyl)-1-isonicotinoyl-pyrazoline) | 415.5 | 559.0 | 545.1 | 423.9 | 90.2 | 101.5 |
| IPK 000 134 62 | (3-(4-bromophenyl)-5-methylsulfonyl-1,2,4-triazole) | 207.8 | 406.9 | 296.6 | 308.6 | −56.1 | 25.5 |
| IPK 000 134 63 | (3-(4-chlorophenyl)-5-methylsulfonyl-1,2,4-triazole) | 275.3 | 294.1 | 416.9 | 316.6 | −18.3 | 12.6 |

TABLE 1-continued
| ID | Structure | | | | | | |
|---|---|---|---|---|---|---|---|
| IPK00013528 | 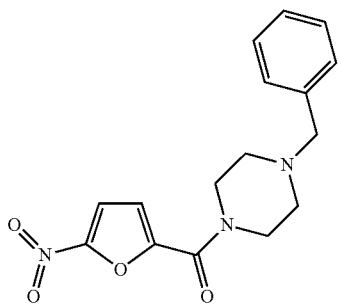 [SMILES: O=C(c1ccc([N+](=O)[O-])o1)N1CCN(Cc2ccccc2)CC1] | 337.5 | 255.6 | 223.4 | 219.5 | 53.3 | 26.6 |
| IPK00013812 | 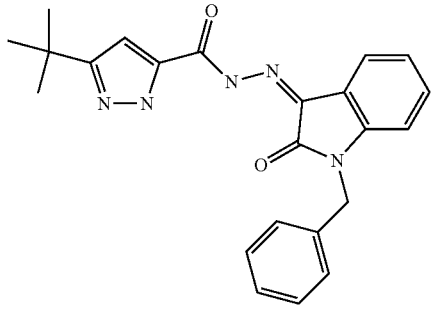 [SMILES: CC(C)(C)c1cc(C(=O)N/N=C2\C(=O)N(Cc3ccccc3)c3ccccc32)[nH]n1] | 480.8 | 501.4 | 420.9 | 343.8 | 96.8 | 104.7 |
| IPK00013840 | 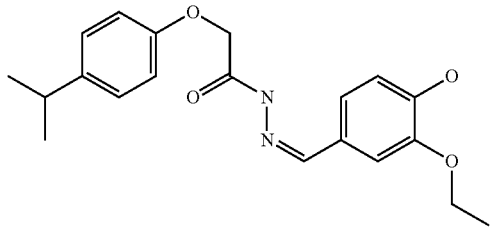 [SMILES: CCOc1cc(/C=N\NC(=O)COc2ccc(C(C)C)cc2)ccc1O] | 569.8 | 575.8 | 285.0 | 230.3 | 75.0 | 86.4 |
| IPK00013843 | 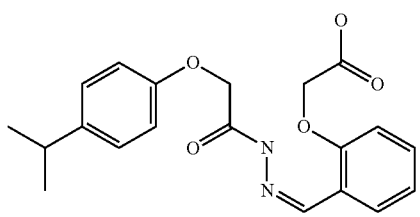 [SMILES: CC(C)c1ccc(OCC(=O)N/N=C\c2ccccc2OCC(=O)O)cc1] | 514.0 | 521.3 | 361.5 | 276.6 | 76.3 | 78.9 |
| IPK00013917 | 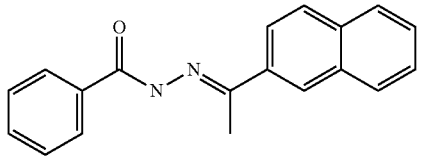 [SMILES: C/C(=N\NC(=O)c1ccccc1)c1ccc2ccccc2c1] | 199.8 | 195.3 | 414.0 | 411.5 | 72.9 | 65.8 |
| IPK00014081 | 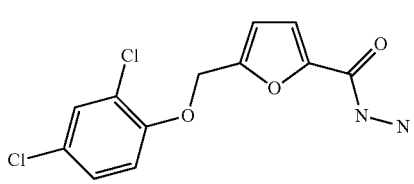 [SMILES: NNC(=O)c1ccc(COc2ccc(Cl)cc2Cl)o1] | 208.5 | 384.4 | 460.8 | 276.8 | 94.6 | 91.8 |
| IPK00014087 | 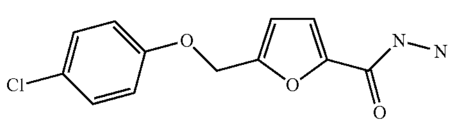 [SMILES: NNC(=O)c1ccc(COc2ccc(Cl)cc2)o1] | 269.5 | 421.0 | 551.0 | 245.0 | 92.2 | 91.1 |

TABLE 1-continued
| | | | | | | | |
|---|---|---|---|---|---|---|---|
| IPK00014108 |  | 529.8 | 625.5 | 270.9 | 200.4 | 67.5 | 84.0 |
| IPK00014158 | 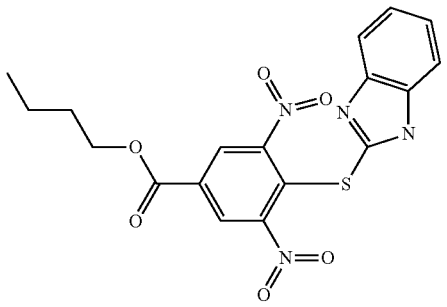 [SMILES: CCCCOC(=O)c1cc([N+](=O)[O-])c(Sc2nc3ccccc3[nH]2)c([N+](=O)[O-])c1] | 191.5 | 167.0 | 239.1 | 184.0 | 58.2 | 59.2 |
| IPK00014161 | 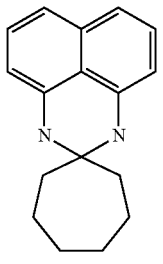 | 308.3 | 337.6 | 378.3 | 225.5 | 4.2 | 50.8 |
| IPK00014217 | 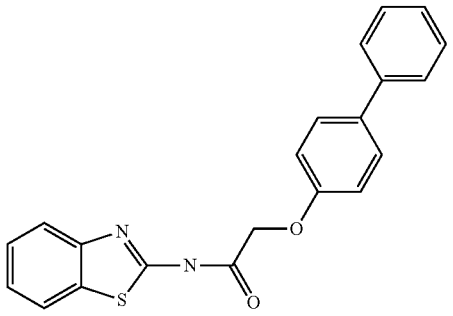 [SMILES: O=C(COc1ccc(-c2ccccc2)cc1)Nc1nc2ccccc2s1] | 635.8 | 581.1 | 361.8 | 340.4 | 84.3 | 82.3 |
| IPK00014218 | 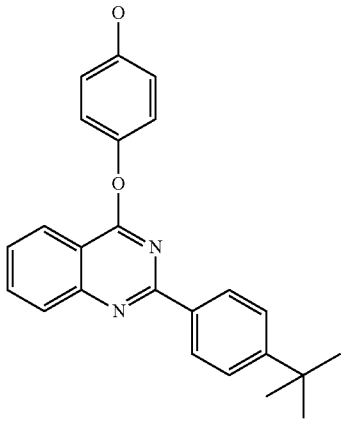 [SMILES: CC(C)(C)c1ccc(-c2nc(Oc3ccc(O)cc3)c3ccccc3n2)cc1] | 167.8 | 132.6 | 372.4 | 234.3 | 73.2 | 79.4 |

TABLE 1-continued

| ID | Structure | | | | | | |
|---|---|---|---|---|---|---|---|
| IPK 000 143 45 | phenyl 2-hydroxy-5-tert-butylbenzoate | 581.8 | 625.4 | 467.4 | 282.6 | 81.2 | 83.5 |
| IPK 000 144 22 | 4-(4-methoxyphenyl)-2-(pyridin-3-yl)thiazole | 262.5 | 377.4 | 452.9 | 318.4 | −9.8 | 30.0 |
| IPK 000 146 91 | 1-(3-fluorophenyl)-3-(4-(trifluoromethyl)phenyl)urea | 167.5 | 132.9 | 201.1 | 229.5 | 57.0 | 70.0 |
| IPK 000 146 98 | 1-(4-chlorophenyl)-3-(4-(trifluoromethyl)phenyl)urea | 101.3 | 167.8 | 283.5 | 264.0 | 55.8 | 26.5 |
| IPK 000 147 17 | 1-(4-fluorophenyl)-3-(4-(trifluoromethyl)phenyl)urea | 81.0 | 177.6 | 186.5 | 330.8 | 11.9 | 40.8 |

TABLE 1-continued

| ID | Structure | | | | | | |
|---|---|---|---|---|---|---|---|
| IPK00014754 | (3-chlorophenyl)-[4-(trifluoromethyl)phenyl]urea | 45.3 | 388.4 | 316.0 | 364.1 | −10.9 | 10.1 |
| IPK00014798 | N'-[(5-nitrofuran-2-yl)methylidene]-2-(3-chlorophenoxy)acetohydrazide | 67.5 | 82.4 | 375.9 | 250.9 | 6.3 | 72.3 |
| IPK00014804 | 2-(4-fluorophenoxy)-N'-[(5-nitrofuran-2-yl)methylidene]acetohydrazide | 48.0 | 63.8 | 313.4 | 317.6 | 21.8 | 59.3 |
| IPK00014811 | 2-[4-(pentan-2-yl)phenoxy]-N'-(thiophen-3-ylmethylidene)acetohydrazide | 333.0 | 577.0 | 347.5 | 341.8 | 65.4 | 86.6 |

TABLE 1-continued

| ID | Structure | | | | | | |
|---|---|---|---|---|---|---|---|
| IPK00014844 | (allyl-methoxyphenoxy-acetohydrazide-nitrofuran) | 58.8 | 364.3 | 268.6 | 264.9 | −15.1 | 8.2 |
| IPK00014864 | (trifluoromethylphenyl-pentanamide-dihydrothiophene) | 379.3 | 516.6 | 427.3 | 261.9 | 72.5 | 71.4 |
| IPK00014865 | (nitrofuran-hydrazide-ethoxypyridine carboxamide) | 47.8 | 73.8 | 338.0 | 247.8 | 41.2 | 29.1 |
| IPK00014902 | (quinolinyl-thio-uracil) | 97.0 | 406.3 | 130.0 | 250.3 | 23.5 | 19.1 |
| IPK00014944 | (dinitrobenzoyl-hydrazide-benzoyl-indanyloxymethyl) | 259.5 | 465.9 | 298.1 | 200.1 | 57.6 | 47.1 |

TABLE 1-continued
| ID | Structure | | | | | | |
|---|---|---|---|---|---|---|---|
| IPK 000 149 78 | 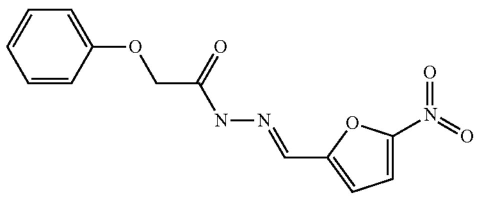 [SMILES: O=C(COc1ccccc1)N/N=C/c1ccc([N+](=O)[O-])o1] | 36.0 | 328.1 | 331.9 | 289.0 | 15.2 | 3.6 |
| IPK 000 150 41 | 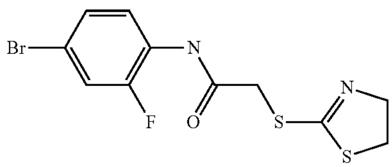 [SMILES: O=C(CSC1=NCCS1)Nc1ccc(Br)cc1F] | 373.8 | 539.6 | 366.1 | 285.3 | 78.3 | 83.3 |
| IPK 000 150 48 | 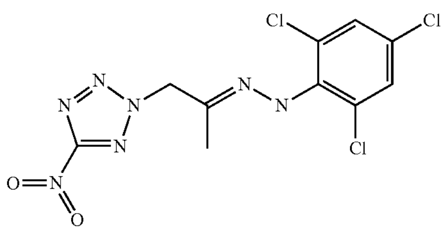 [SMILES: C/C(Cn1nnc([N+](=O)[O-])n1)=N\Nc1c(Cl)cc(Cl)cc1Cl] | 61.0 | 333.6 | 209.5 | 349.3 | −96.3 | 16.1 |
| IPK 000 150 85 | 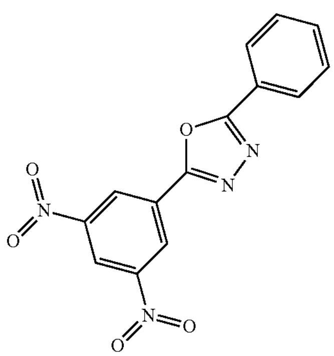 [SMILES: O=[N+]([O-])c1cc(-c2nnc(-c3ccccc3)o2)cc([N+](=O)[O-])c1] | 416.3 | 397.3 | 299.6 | 230.3 | 72.3 | 72.2 |
| IPK 000 155 36 | 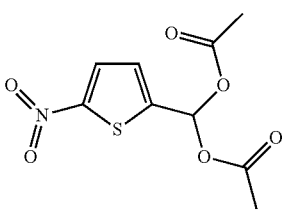 [SMILES: CC(=O)OC(OC(C)=O)c1ccc([N+](=O)[O-])s1] | 183.8 | 182.1 | 201.4 | 232.0 | 67.8 | 74.0 |
| IPK 000 157 51 | 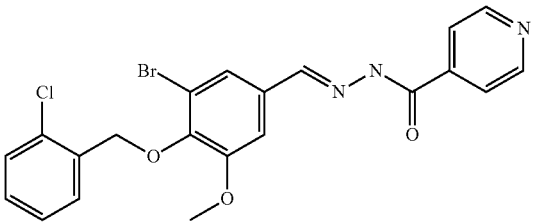 [SMILES: COc1cc(/C=N/NC(=O)c2ccncc2)cc(Br)c1OCc1ccccc1Cl] | 321.3 | 227.9 | 377.4 | 393.8 | 96.0 | 46.2 |

TABLE 1-continued
| | | | | | | | |
|---|---|---|---|---|---|---|---|
| IPK 00015755 | 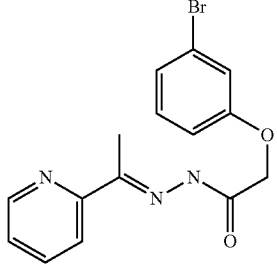 | 108.3 | 277.0 | 278.0 | 396.4 | 22.0 | 19.9 |
| IPK 00015849 | 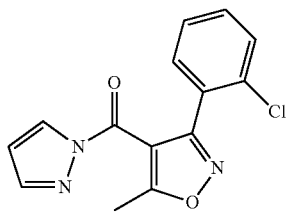 [SMILES: Cc1onc(-c2ccccc2Cl)c1C(=O)n1cccn1] | 96.0 | 266.6 | 168.3 | 248.6 | −3.0 | 4.8 |
| IPK 00016045 | 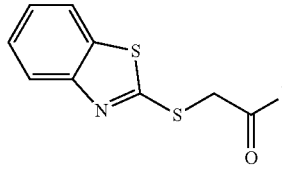 | 436.3 | 371.4 | 285.5 | 296.5 | 66.0 | 70.7 |
| IPK 00016132 | 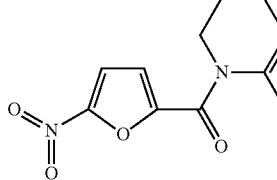 | 100.3 | 65.1 | 194.0 | 245.4 | −37.9 | 17.8 |
| IPK 00016327 | 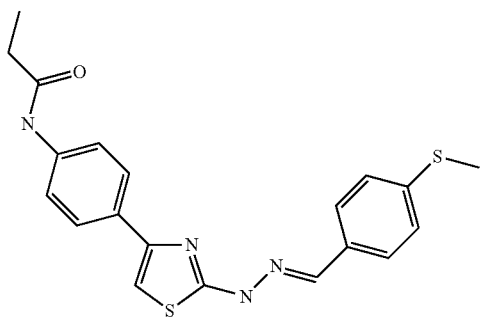 [SMILES: CCC(=O)Nc1ccc(-c2csc(N/N=C/c3ccc(SC)cc3)n2)cc1] | 534.3 | 263.4 | 474.9 | 393.4 | 69.5 | 17.9 |
| IPK 00016351 | 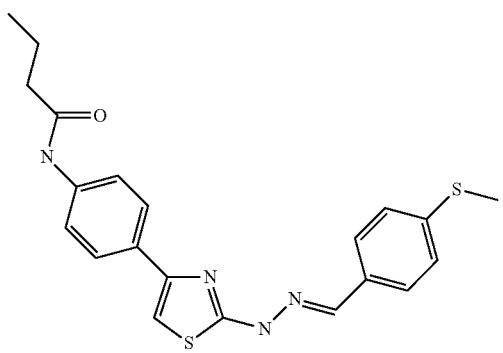 [SMILES: CCCC(=O)Nc1ccc(-c2csc(N/N=C/c3ccc(SC)cc3)n2)cc1] | 447.5 | 377.5 | 491.4 | 335.8 | 89.4 | 50.0 |

TABLE 1-continued

| ID | Structure | | | | | | |
|---|---|---|---|---|---|---|---|
| IPK 00016352 | 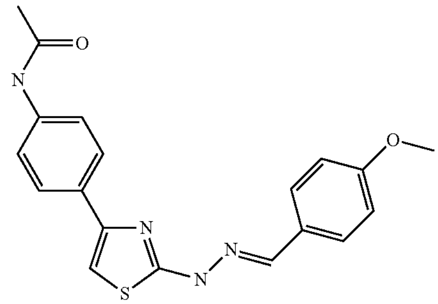 [SMILES: COc1ccc(/C=N/Nc2nc(-c3ccc(NC(C)=O)cc3)cs2)cc1] | 446.5 | 473.3 | 447.6 | 428.4 | 86.2 | 70.7 |
| IPK 00016362 | 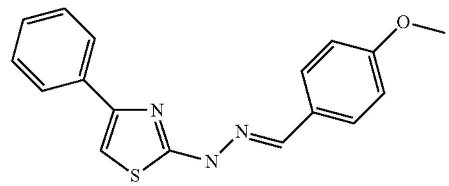 [SMILES: COc1ccc(/C=N/Nc2nc(-c3ccccc3)cs2)cc1] | 246.5 | 599.8 | 485.8 | 451.9 | 81.3 | 107.2 |
| IPK 00016364 | 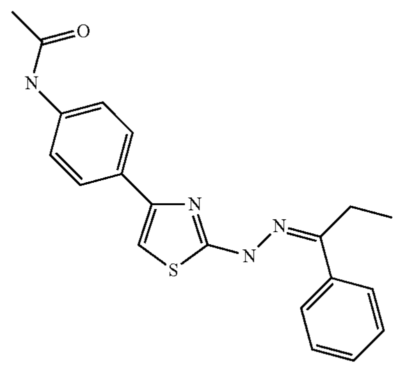 [SMILES: CC/C(=N/Nc1nc(-c2ccc(NC(C)=O)cc2)cs1)c1ccccc1] | 486.3 | 576.1 | 394.9 | 302.8 | 74.9 | 74.2 |
| IPK 00016367 | 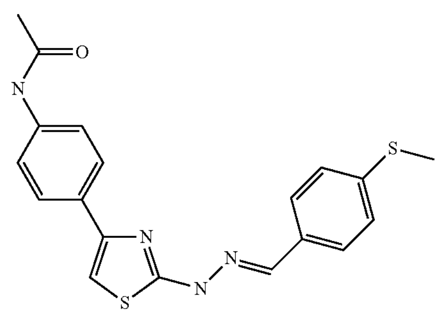 | 517.5 | 481.6 | 520.1 | 340.0 | 68.1 | 99.5 |
| IPK 00016393 | 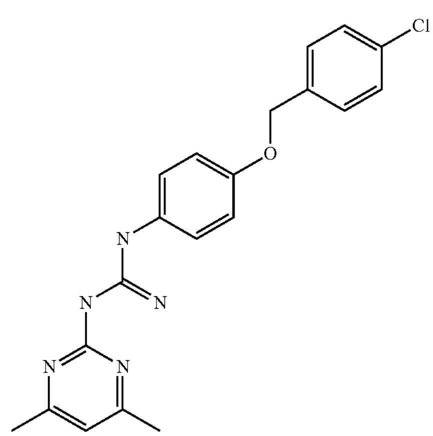 [SMILES: Cc1cc(C)nc(NC(=N)Nc2ccc(OCc3ccc(Cl)cc3)cc2)n1] | 74.0 | 123.6 | 249.4 | 339.0 | 66.7 | 89.9 |

TABLE 1-continued

| ID | Structure | | | | | | |
|---|---|---|---|---|---|---|---|
| IPK 000 164 52 | (4-nitro-2-(5-(1,1,2,2-tetrafluoroethyl)-1H-pyrazol-3-yl)phenol) | 202.3 | 171.8 | 204.8 | 286.8 | 64.7 | 80.0 |
| IPK 000 167 54 | (N-(3-chloro-2-methylphenyl)-1-(5-nitrofuran-2-yl)methanimine) | 60.3 | 117.3 | 184.8 | 248.0 | 19.5 | 16.5 |
| IPK 000 168 10 | ((1E,4E)-1,5-diphenylpenta-1,4-dien-3-one oxime) | 106.5 | 185.3 | 137.1 | 294.4 | 38.0 | 65.6 |
| IPK 000 168 31 | (3-methyl-5-oxo-4-(2-(p-tolyl)hydrazono)-4,5-dihydro-1H-pyrazole-1-carbothioamide) | 178.8 | 254.9 | 159.9 | 256.1 | 83.9 | 78.1 |
| IPK 000 168 32 | (3-methyl-5-oxo-4-(2-(o-tolyl)hydrazono)-4,5-dihydro-1H-pyrazole-1-carbothioamide) | 167.5 | 254.9 | 352.9 | 312.6 | 75.7 | 81.9 |
| IPK 000 169 30 | (N'-(3,5-dinitrobenzoyl)-2-methylbenzohydrazide) | 220.0 | 291.1 | 313.0 | 269.3 | 56.2 | 73.7 |
| IPK 000 169 42 | (N-(4-bromo-3-chlorophenyl)thiophene-2-carboxamide) | 106.0 | 218.3 | 410.4 | 361.9 | −64.0 | 76.9 |

TABLE 1-continued
| | | | | | | | |
|---|---|---|---|---|---|---|---|
| IPK 00016968 | 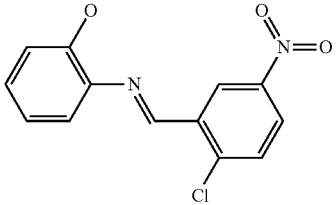 | 97.8 | 114.9 | 183.8 | 289.1 | −5.0 | −5.3 |
| IPK 00016976 | 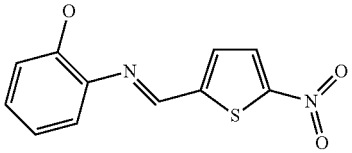 [SMILES: O=[N+]([O-])c1ccc(/C=N/c2ccccc2O)s1] | 62.0 | 137.6 | 188.0 | 301.6 | −71.9 | 16.7 |
| IPK 00016986 | 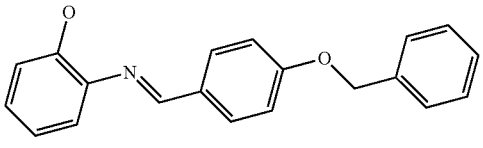 [SMILES: Oc1ccccc1/N=C/c1ccc(OCc2ccccc2)cc1] | 119.3 | 174.4 | 191.5 | 359.9 | 0.5 | 13.0 |
| IPK 00016996 | 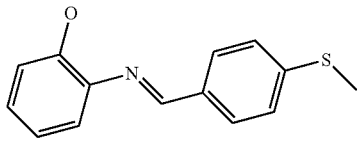 [SMILES: CSc1ccc(/C=N/c2ccccc2O)cc1] | 64.8 | 140.4 | 134.5 | 193.4 | −50.2 | 14.7 |
| IPK 00017027 | 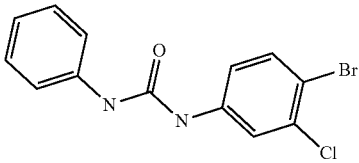 | 59.0 | 118.9 | 319.5 | 499.9 | −72.4 | 18.9 |
| IPK 00017033 | 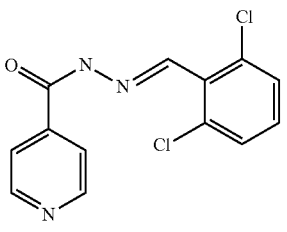 [SMILES: O=C(N/N=C/c1c(Cl)cccc1Cl)c1ccncc1] | 143.0 | 353.9 | 525.0 | 501.1 | 49.5 | 96.3 |
| IPK 00017072 | 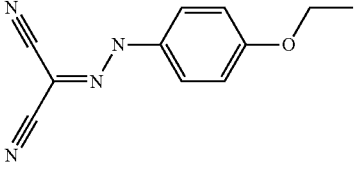 [SMILES: CCOc1ccc(NN=C(C#N)C#N)cc1] | 67.0 | 72.1 | 321.0 | 275.8 | −29.5 | −21.3 |
| IPK 00017127 | 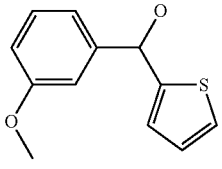 | 283.3 | 176.9 | 201.4 | 276.8 | 95.2 | 95.2 |
| IPK 00017146 | 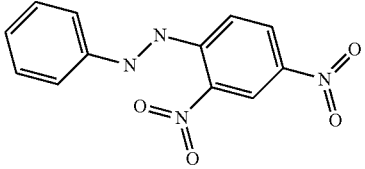 [SMILES: O=[N+]([O-])c1ccc(NNc2ccccc2)c([N+](=O)[O-])c1] | 55.0 | 108.5 | 82.0 | 236.5 | 24.3 | 72.1 |

TABLE 1-continued
| | | | | | | | |
|---|---|---|---|---|---|---|---|
| IPK00017184 | 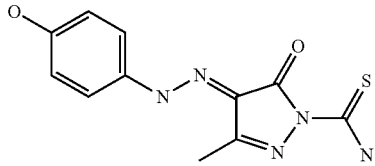 [SMILES: CC1=NN(C(N)=S)C(=O)/C1=N/Nc1ccc(O)cc1] | 30.0 | 93.9 | 129.5 | 298.4 | −79.6 | 13.3 |
| IPK00017234 | 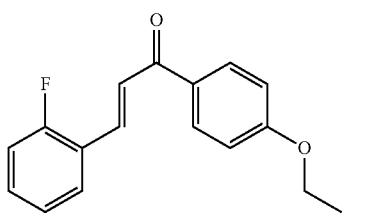 [SMILES: CCOc1ccc(C(=O)/C=C/c2ccccc2F)cc1] | 40.8 | 69.5 | 158.4 | 298.4 | −82.4 | 12.5 |
| IPK00017235 | 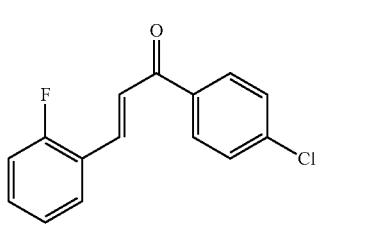 [SMILES: O=C(/C=C/c1ccccc1F)c1ccc(Cl)cc1] | 104.3 | 185.4 | 470.5 | 345.6 | 0.9 | 59.9 |
| IPK00017254 | 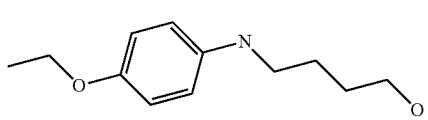 | 92.0 | 221.3 | 190.0 | 226.6 | 4.1 | 40.4 |
| IPK00017306 | 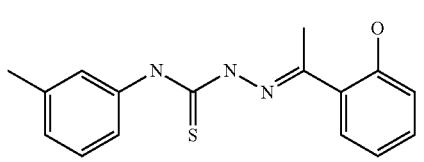 [SMILES: C/C(=N\NC(=S)Nc1cccc(C)c1)c1ccccc1O] | 54.3 | 314.4 | 224.9 | 308.4 | 44.0 | 15.8 |
| IPK00017345 | 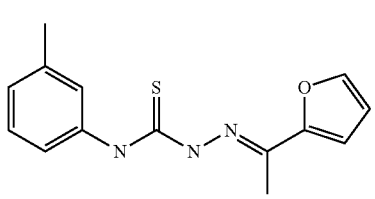 [SMILES: C/C(=N\NC(=S)Nc1cccc(C)c1)c1ccco1] | 113.0 | 304.0 | 305.5 | 292.8 | 14.9 | 19.2 |
| IPK00017527 | 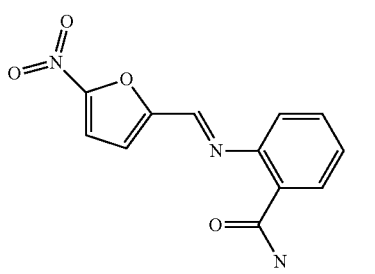 [SMILES: NC(=O)c1ccccc1/N=C/c1ccc([N+](=O)[O-])o1] | 44.3 | 177.0 | 131.8 | 302.8 | −69.7 | 25.8 |
| IPK00017824 | 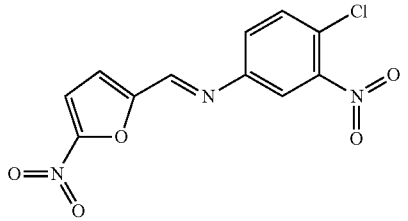 [SMILES: O=[N+]([O-])c1ccc(/C=N/c2ccc(Cl)c([N+](=O)[O-])c2)o1] | 111.8 | 140.4 | 158.6 | 199.5 | −26.4 | −4.1 |

TABLE 1-continued

| ID | Structure | | | | | | |
|---|---|---|---|---|---|---|---|
| IPK 000 179 05 | 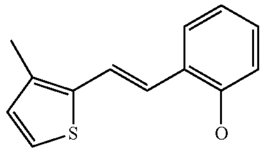 | 124.3 | 190.0 | 194.5 | 352.4 | −31.7 | 16.6 |
| IPK 000 179 49 | 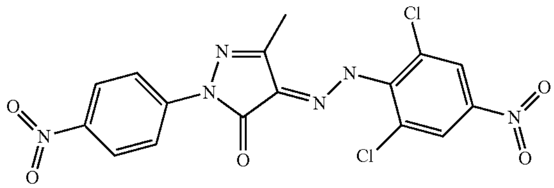 [SMILES: CC1=NN(c2ccc([N+](=O)[O-])cc2)C(=O)/C1=N/Nc1c(Cl)cc([N+](=O)[O-])cc1Cl] | 187.0 | 257.9 | 163.8 | 300.4 | 65.7 | 78.5 |
| IPK 000 180 11 | 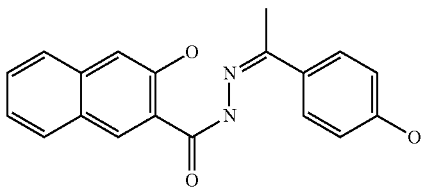 [SMILES: C/C(=N/NC(=O)c1cc2ccccc2cc1O)c1ccc(O)cc1] | 447.8 | 451.5 | 309.9 | 309.1 | 68.2 | 69.7 |
| IPK 000 180 16 | 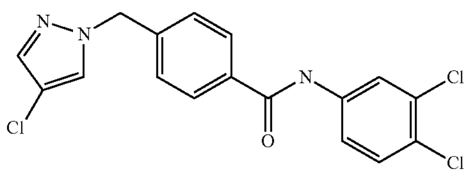 [SMILES: O=C(Nc1ccc(Cl)c(Cl)c1)c1ccc(Cn2cc(Cl)cn2)cc1] | 217.0 | 234.4 | 323.8 | 332.3 | 46.1 | 69.8 |
| IPK 000 180 17 | 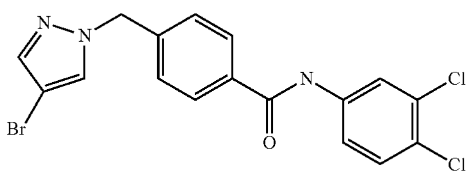 | 199.3 | 229.5 | 377.5 | 265.0 | 63.2 | 34.5 |
| IPK 000 180 76 | 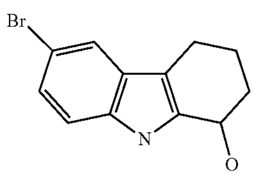 [SMILES: OC1CCCc2c1[nH]c1ccc(Br)cc21] | 467.8 | 565.3 | 289.9 | 347.6 | 70.6 | 92.1 |
| IPK 000 184 56 | 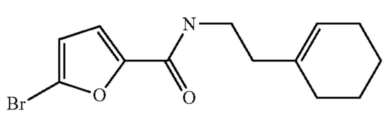 [SMILES: O=C(NCCC1=CCCCC1)c1ccc(Br)o1] | 256.3 | 215.1 | 391.5 | 342.5 | 85.1 | 72.7 |
| IPK 000 192 45 | 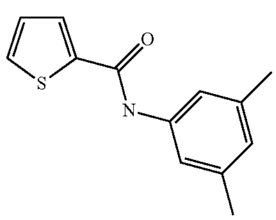 [SMILES: Cc1cc(C)cc(NC(=O)c2cccs2)c1] | 219.8 | 386.4 | 376.8 | 334.0 | 88.8 | 65.4 |
| IPK 000 192 59 | 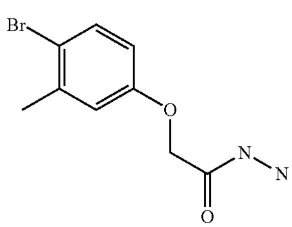 | 470.5 | 551.3 | 344.4 | 246.3 | 65.3 | 81.1 |

TABLE 1-continued

| ID | Structure | | | | | | |
|---|---|---|---|---|---|---|---|
| IPK 000 193 76 | (pyridine-C(O)-NH-N=CH-3-methylfuran) | 355.5 | 420.4 | 497.1 | 520.4 | 81.4 | 97.4 |
| IPK 000 195 99 | (pyridine-C(O)-NH-N=CH-C6H4-N(Et)2) | 305.0 | 488.8 | 537.1 | 477.8 | 79.1 | 69.5 |
| IPK 000 198 53 | (fluorene derivative with dimethylaminophenyl and piperidinyl pentanone) | 129.5 | 217.9 | 192.3 | 210.1 | 58.5 | 41.9 |
| IPK 000 198 54 | (fluorene derivative with 3,4-dimethoxyphenyl and piperidinyl pentanone) | 153.0 | 189.3 | 394.4 | 309.5 | 38.6 | 77.9 |
| IPK 000 198 56 | (fluorene derivative with 4-methoxyphenyl and piperidinyl pentanone) | 131.5 | 278.1 | 272.5 | 276.0 | 15.1 | 64.7 |
| IPK 000 199 70 | (thiophene-C(O)-NH-C6H4-NH-C(O)-pyridine) | 227.5 | 256.5 | 301.6 | 345.8 | 70.5 | 69.6 |

TABLE 1-continued

| ID | Structure | | | | | | |
|---|---|---|---|---|---|---|---|
| IPK 000 200 16 | 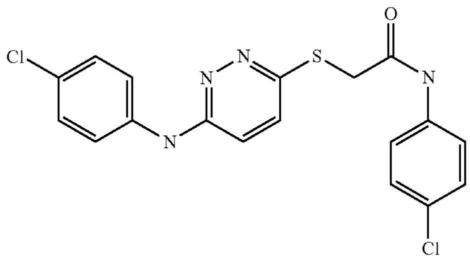 [SMILES: O=C(CSc1ccc(Nc2ccc(Cl)cc2)nn1)Nc1ccc(Cl)cc1] | 265.0 | 430.5 | 238.4 | 235.3 | 73.3 | 76.8 |
| IPK 000 200 47 | 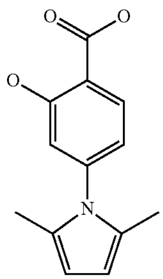 [SMILES: Cc1ccc(C)n1-c1ccc(C(=O)O)c(O)c1] | 146.0 | 309.6 | 294.9 | 370.5 | 6.3 | 19.1 |
| IPK 000 202 08 | 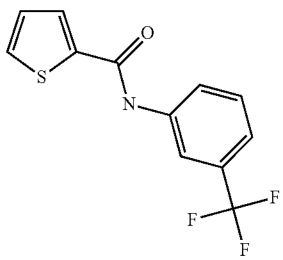 [SMILES: O=C(Nc1cccc(C(F)(F)F)c1)c1cccs1] | 283.0 | 279.9 | 354.1 | 396.1 | 65.7 | 67.4 |
| IPK 000 205 22 | 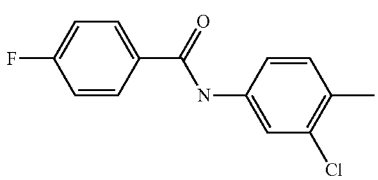 [SMILES: Cc1ccc(NC(=O)c2ccc(F)cc2)cc1Cl] | 280.0 | 319.8 | 414.0 | 313.6 | 85.1 | 69.7 |
| IPK 000 205 42 | 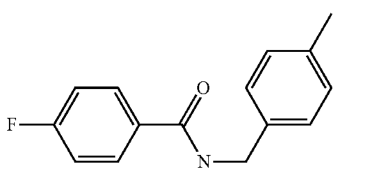 [SMILES: Cc1ccc(CNC(=O)c2ccc(F)cc2)cc1] | 205.3 | 314.8 | 430.8 | 330.6 | 71.5 | 69.3 |
| IPK 000 208 53 | 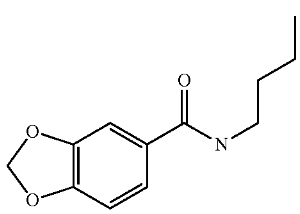 [SMILES: CCCCNC(=O)c1ccc2c(c1)OCO2] | 166.8 | 232.5 | 319.1 | 275.9 | 71.6 | 23.3 |
| IPK 000 210 74 | 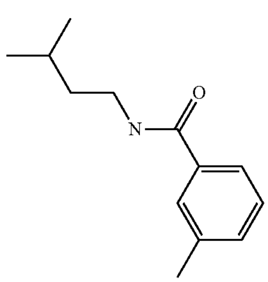 | 191.8 | 304.9 | 425.6 | 344.3 | 76.4 | 20.2 |

TABLE 1-continued

| ID | Structure | | | | | | |
|---|---|---|---|---|---|---|---|
| IPK00021079 | (3-chloro-N-isopentylbenzamide) | 273.8 | 255.0 | 350.9 | 353.6 | 77.2 | 28.7 |
| IPK00021083 | (4-ethoxy-N-isopentylbenzamide) | 200.8 | 190.5 | 320.4 | 213.9 | 70.4 | 48.2 |
| IPK00021926 | (N'-((5-methylfuran-2-yl)methylene)isonicotinohydrazide) | 548.0 | 218.4 | 476.1 | 435.6 | 91.1 | 51.4 |
| IPK00021927 | (N'-benzylideneisonicotinohydrazide) | 586.3 | 384.6 | 513.9 | 443.3 | 96.9 | 57.4 |
| IPK00021928 | (N'-(4-methoxybenzylidene)isonicotinohydrazide) | 623.3 | 240.8 | 480.5 | 433.8 | 106.5 | 46.2 |
| IPK00021929 | (N'-(1-(4-methoxyphenyl)ethylidene)isonicotinohydrazide) | 623.5 | 423.8 | 502.5 | 221.3 | 107.4 | 67.6 |

TABLE 1-continued

| ID | Structure | | | | | | |
|---|---|---|---|---|---|---|---|
| IPK00021930 | 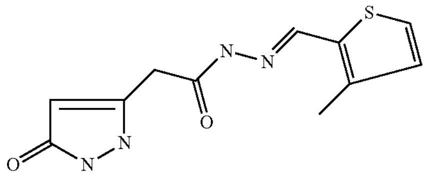 [SMILES: Cc1ccsc1/C=N/NC(=O)Cc1cc(=O)[nH][nH]1] | 700.8 | 300.0 | 564.3 | 356.9 | 103.5 | 93.0 |
| IPK00022200 | 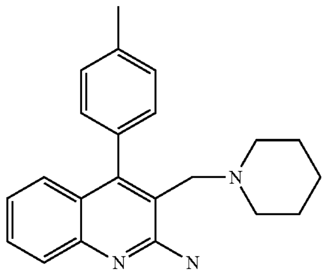 [SMILES: Cc1ccc(-c2c(CN3CCCCC3)c(N)nc3ccccc23)cc1] | 148.3 | 279.5 | 218.5 | 282.6 | 74.4 | 86.2 |
| IPK00022204 | 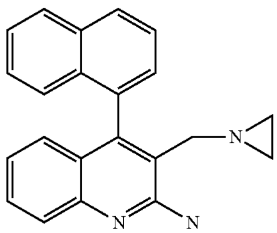 [SMILES: Nc1nc2ccccc2c(-c2cccc3ccccc23)c1CN1CC1] | 181.3 | 124.9 | 210.8 | 261.9 | 65.4 | 85.8 |
| IPK00022232 | 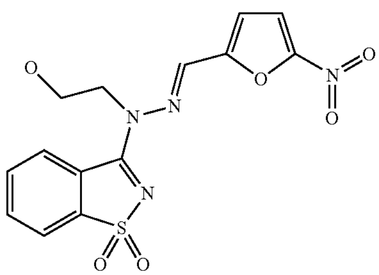 [SMILES: O=[N+]([O-])c1ccc(/C=N/N(CCO)C2=NS(=O)(=O)c3ccccc32)o1] | 124.8 | 114.3 | 227.8 | 294.8 | 16.2 | 63.2 |
| IPK00022459 | 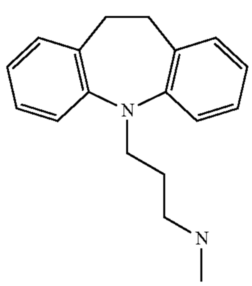 [SMILES: CNCCCN1c2ccccc2CCc2ccccc21] | 60.3 | 95.1 | 248.2 | 333.3 | 72.9 | 86.2 |
| IPK00022846 | 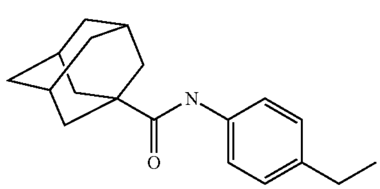 [SMILES: CCc1ccc(NC(=O)C23CC4CC(CC(C4)C2)C3)cc1] | 492.8 | 261.5 | 431.4 | 376.6 | 22.5 | 37.8 |
| IPK00022950 | 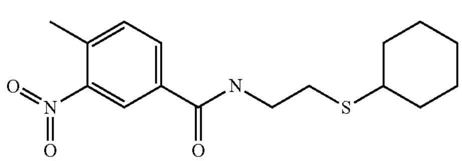 [SMILES: Cc1ccc(C(=O)NCCSC2CCCCC2)cc1[N+](=O)[O-]] | 488.0 | 322.5 | 352.8 | 412.9 | 60.1 | 83.6 |

TABLE 1-continued

| ID | Structure | | | | | | |
|---|---|---|---|---|---|---|---|
| IPK00022972 | 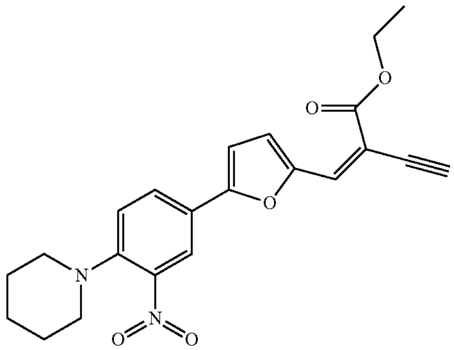 [SMILES: C#C/C(=C/c1ccc(-c2ccc(N3CCCCC3)c([N+](=O)[O-])c2)o1)C(=O)OCC] | 300.3 | 386.8 | 483.6 | 322.8 | 69.4 | 90.7 |
| IPK00023002 | 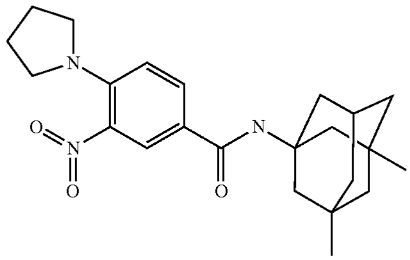 [SMILES: CC12CC3CC(C)(C1)CC(NC(=O)c1ccc(N4CCCC4)c([N+](=O)[O-])c1)(C3)C2] | 223.5 | 277.6 | 453.1 | 388.4 | -7.7 | 40.5 |
| IPK00023461 | 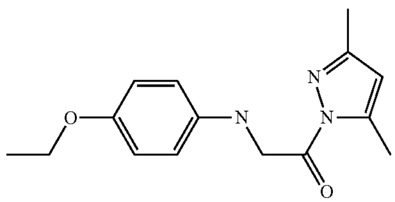 [SMILES: CCOc1ccc(NCC(=O)n2nc(C)cc2C)cc1] | 156.8 | 207.9 | 209.1 | 292.6 | -61.0 | -1.6 |
| IPK00023509 | 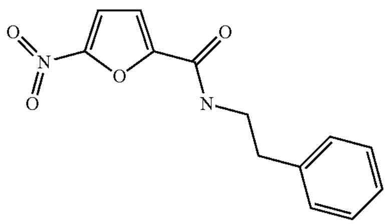 [SMILES: O=C(NCCc1ccccc1)c1ccc([N+](=O)[O-])o1] | 91.8 | 251.8 | 346.0 | 276.6 | 46.2 | 36.4 |
| IPK00023512 | 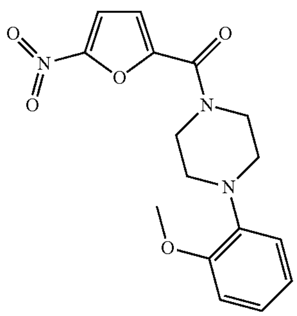 [SMILES: COc1ccccc1N1CCN(C(=O)c2ccc([N+](=O)[O-])o2)CC1] | 39.8 | 254.0 | 325.5 | 333.5 | -67.9 | 26.9 |
| IPK00023891 | 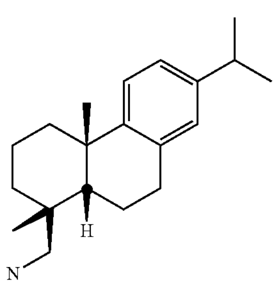 | 379.0 | 382.4 | 145.6 | 202.6 | 99.3 | 27.8 |

TABLE 1-continued
| ID | Structure | | | | | | |
|---|---|---|---|---|---|---|---|
| IPK 000 240 37 | 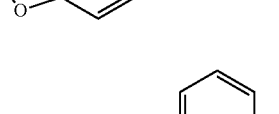 | 132.8 | 156.5 | 116.5 | 213.9 | 17.0 | 67.5 |
| IPK 000 241 72 | 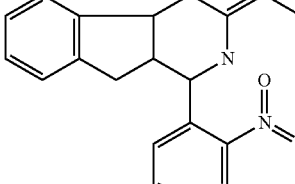 | 175.3 | 102.4 | 487.5 | 421.1 | −43.3 | 28.0 |
| IPK 000 244 12 | 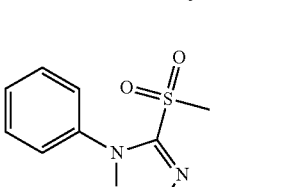 | 136.0 | 257.8 | 249.4 | 270.0 | 29.9 | 11.8 |
| IPK 000 247 44 | 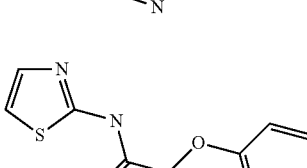 | 584.0 | 332.8 | 158.6 | 174.5 | 89.1 | 97.1 |
| IPK 000 248 71 | 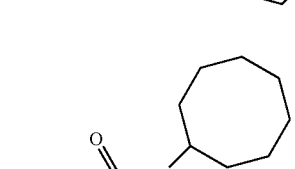 | 150.8 | 256.0 | 486.9 | 334.6 | 79.5 | 79.0 |
| IPK 000 249 12 | 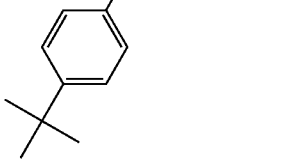 | 130.8 | 124.3 | 138.9 | 172.9 | 23.6 | 53.2 |
| IPK 000 249 14 | 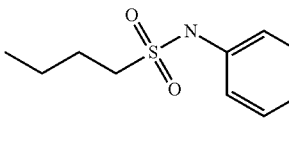 | 404.3 | 211.3 | 407.6 | 332.9 | 45.0 | 68.6 |

TABLE 1-continued
| | | | | | | | |
|---|---|---|---|---|---|---|---|
| IPK 000 249 84 | 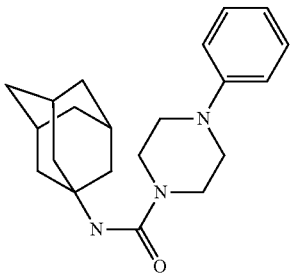 [SMILES: O=C(NC12CC3CC(CC(C3)C1)C2)N1CCN(c2ccccc2)CC1] | 163.3 | 173.8 | 295.4 | 325.3 | 78.2 | 80.9 |
| IPK 000 251 49 | 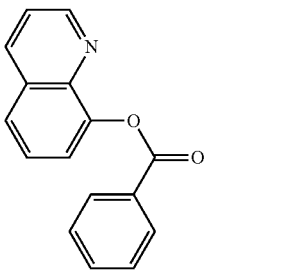 [SMILES: O=C(Oc1cccc2cccnc12)c1ccccc1] | 162.5 | 282.1 | 327.6 | 285.9 | 27.0 | 15.0 |
| IPK 000 251 80 | 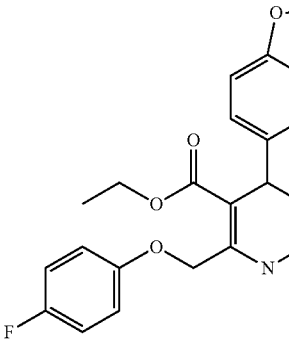 | 321.0 | 322.1 | 217.8 | 294.5 | 25.5 | 38.2 |
| IPK 000 254 12 | 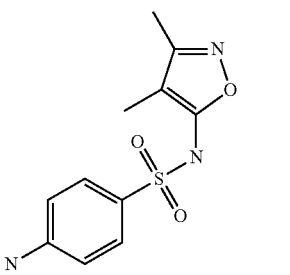 [SMILES: Cc1noc(NS(=O)(=O)c2ccc(N)cc2)c1C] | 179.8 | 351.4 | 306.5 | 225.3 | 30.3 | 13.2 |
| IPK 000 254 25 | 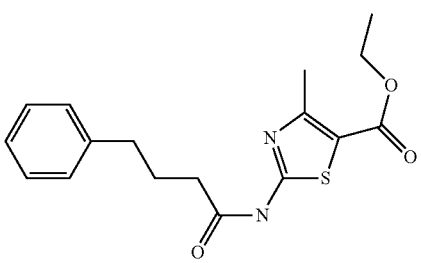 [SMILES: CCOC(=O)c1sc(NC(=O)CCCc2ccccc2)nc1C] | 243.3 | 367.0 | 356.3 | 356.9 | 32.5 | 18.5 |

TABLE 1-continued

| ID | Structure | | | | | | |
|---|---|---|---|---|---|---|---|
| IPK 000 255 46 | (ethyl 2-(3-cyclohexylpropanamido)-4-methylthiazole-5-carboxylate) | 192.3 | 279.6 | 499.5 | 408.3 | 25.0 | 53.1 |
| IPK 000 257 61 | (N-(3-ethylphenyl)thiophene-2-carboxamide) | 285.0 | 226.9 | 381.8 | 314.1 | 71.5 | 79.9 |
| IPK 000 258 07 | (1-cyclohexyl-5-((4-nitrobenzyl)thio)-1H-tetrazole) | 142.3 | 174.8 | 380.6 | 240.9 | 49.9 | 72.7 |
| IPK 000 259 35 | (3-(1H-benzo[d]imidazol-2-yl(phenyl)methylene)indolin-2-one) | 64.5 | 78.8 | 262.1 | 335.9 | 66.0 | 68.8 |
| IPK 000 259 78 | (1-(2,3-difluoro-6-nitrophenoxy)propan-2-one) | 115.8 | 194.3 | 271.1 | 292.8 | 4.9 | 58.8 |

| ID | Structure | | | | | | |
|---|---|---|---|---|---|---|---|
| IPK 000 262 07 | (structure) | 242.0 | 309.8 | 461.8 | 383.3 | 80.3 | 7.9 |
| IPK 000 262 39 | (structure) | 93.3 | 273.3 | 164.5 | 349.1 | 2.1 | 29.5 |

| ID | Structure | QIM Confirm % Inhibition 2 uM | QIM Confirm % Inhibition 0.2 uM | Primary QUM % Inhibition | QUM Confirm % Inhibition 20 uM | QUM Confirm % Inhibition 2 uM | QUM Confirm % Inhibition 0.2 uM |
|---|---|---|---|---|---|---|---|
| IPK 000 001 32 | (structure) | 0.2 | 10.3 | 99.9 | 89.1 | 41.2 | 43.9 |
| IPK 000 001 90 | (structure) | 13.2 | 12.7 | 2.9 | 42.3 | 29.4 | 34.6 |
| IPK 000 002 03 | (structure) | 7.7 | −2.0 | 99.7 | 69.7 | 52.4 | 32.5 |

TABLE 1-continued
| | | | | | | | | |
|---|---|---|---|---|---|---|---|---|
| IPK000 00217 | 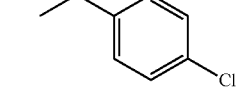 | | 70.4 | 54.5 | 98.9 | 49.7 | 67.4 | 56.9 |
| IPK000 00287 |  | | −1.3 | 11.4 | −13.8 | 36.4 | 36.1 | 45.9 |
| IPK000 00301 |  | | 77.1 | 4.7 | 98.7 | 43.0 | 82.8 | 46.4 |
| IPK000 00389 |  | | 86.6 | 20.1 | 100.3 | 67.0 | 76.5 | 44.0 |
| IPK000 00390 | 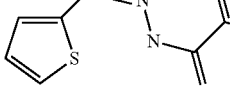 | | 43.2 | 2.2 | 99.7 | 72.7 | 68.8 | 44.0 |
| IPK000 00391 |  | | 36.8 | 2.9 | 99.6 | 76.7 | 41.4 | 46.6 |

TABLE 1-continued

| ID | Structure | | | | | | |
|---|---|---|---|---|---|---|---|
| IPK 000 006 35 | 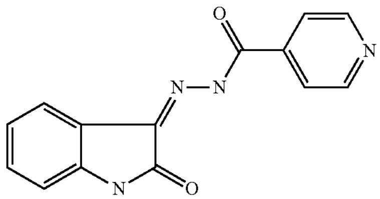 [SMILES: O=C1Nc2ccccc2/C1=N/NC(=O)c1ccncc1] | 22.8 | 17.7 | 42.0 | 43.4 | 41.9 | 23.7 |
| IPK 000 007 31 | 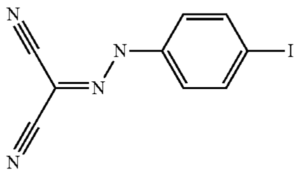 [SMILES: N#CC(C#N)=NNc1ccc(I)cc1] | 14.7 | 45.7 | 76.6 | 80.8 | 33.0 | 41.0 |
| IPK 000 008 02 | 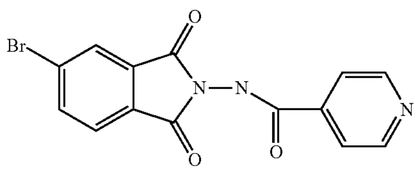 [SMILES: O=C(NN1C(=O)c2ccc(Br)cc2C1=O)c1ccncc1] | 9.3 | 0.7 | 34.8 | 98.2 | 31.9 | 36.4 |
| IPK 000 008 12 | 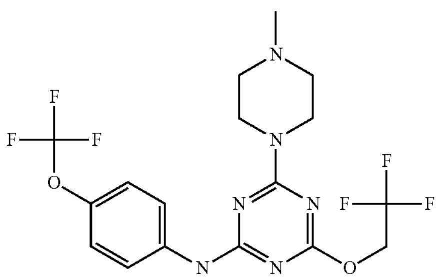 [SMILES: CN1CCN(c2nc(Nc3ccc(OC(F)(F)F)cc3)nc(OCC(F)(F)F)n2)CC1] | 18.9 | 2.7 | 97.2 | 48.0 | 39.7 | 36.5 |
| IPK 000 009 33 | 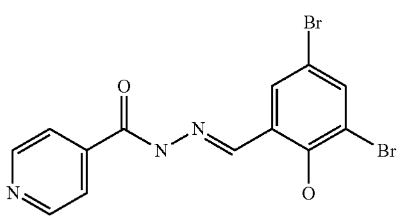 [SMILES: O=C(N/N=C/c1cc(Br)cc(Br)c1O)c1ccncc1] | 92.5 | 8.5 | 30.3 | 69.8 | 44.5 | 31.8 |
| IPK 000 009 41 | 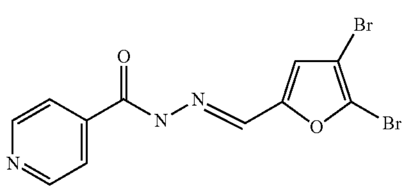 [SMILES: O=C(N/N=C/c1cc(Br)c(Br)o1)c1ccncc1] | 92.8 | 19.6 | 97.7 | 99.4 | 59.6 | 28.3 |
| IPK 000 009 42 | 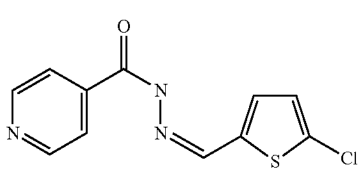 [SMILES: O=C(N/N=C\c1ccc(Cl)s1)c1ccncc1] | 92.3 | 21.3 | 92.6 | 100.0 | 50.3 | 28.8 |
| IPK 000 009 78 | 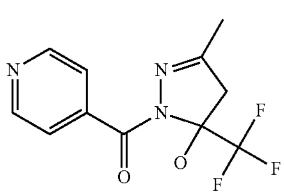 [SMILES: CC1=NN(C(=O)c2ccncc2)C(O)(C(F)(F)F)C1] | 50.2 | 17.0 | 39.5 | 100.1 | 61.1 | 30.0 |

TABLE 1-continued

| ID | Structure | | | | | | |
|---|---|---|---|---|---|---|---|
| IPK 000 010 06 | 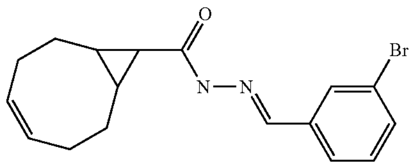 [SMILES: O=C(N/N=C/c1cccc(Br)c1)C1C2CC/C=C\CCC21] | 18.0 | 17.1 | 98.4 | 39.2 | 43.1 | 39.5 |
| IPK 000 011 19 | 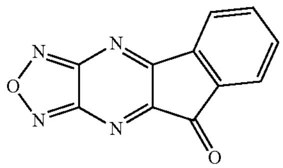 [SMILES: O=C1c2ccccc2-c2nc3nonc3nc21] | 31.6 | 9.7 | 90.5 | 43.1 | 93.2 | 67.2 |
| IPK 000 011 65 | 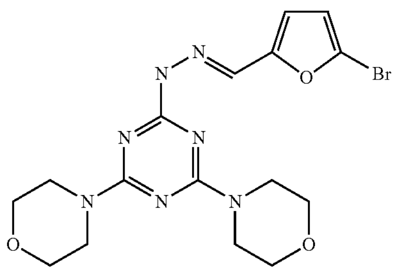 [SMILES: Brc1ccc(/C=N/Nc2nc(N3CCOCC3)nc(N3CCOCC3)n2)o1] | 23.4 | 4.7 | 100.0 | 96.3 | 40.6 | 39.8 |
| IPK 000 013 67 | 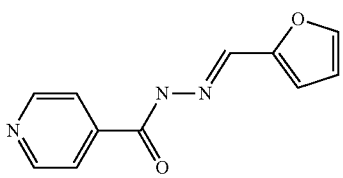 [SMILES: O=C(N/N=C/c1ccco1)c1ccncc1] | 102.1 | 84.1 | 98.7 | 69.7 | 90.2 | 49.4 |
| IPK 000 013 68 | 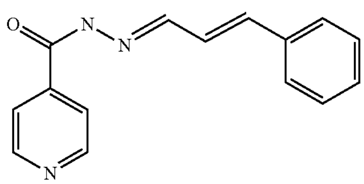 [SMILES: O=C(N/N=C/C=C/c1ccccc1)c1ccncc1] | 101.8 | 50.9 | 98.9 | 77.6 | 77.1 | 50.4 |
| IPK 000 013 69 | 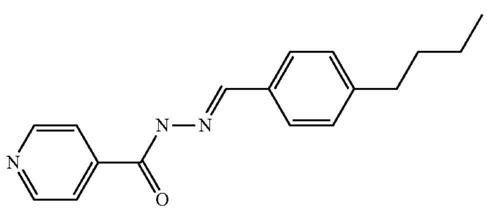 [SMILES: CCCCc1ccc(/C=N/NC(=O)c2ccncc2)cc1] | 104.9 | 68.9 | 99.2 | 62.4 | 79.1 | 51.2 |
| IPK 000 013 70 | 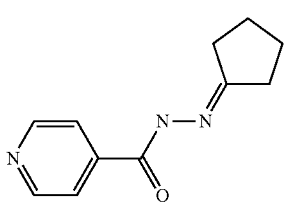 [SMILES: O=C(NN=C1CCCC1)c1ccncc1] | 98.1 | 50.5 | 98.4 | 67.6 | 79.4 | 46.3 |
| IPK 000 013 71 | 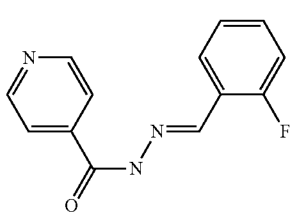 [SMILES: O=C(N/N=C/c1ccccc1F)c1ccncc1] | 105.2 | 86.3 | 99.4 | 68.4 | 92.2 | 51.6 |

TABLE 1-continued

| ID | Structure | | | | | | |
|---|---|---|---|---|---|---|---|
| IPK000 01372 | (structure) | 103.7 | 63.2 | 100.0 | 98.0 | 73.9 | 57.7 |
| IPK000 01536 | (structure) | −4.8 | 15.8 | 100.3 | 79.5 | 59.4 | 41.9 |
| IPK000 01600 | (structure) | 19.4 | 3.2 | 90.5 | 68.0 | 48.6 | 47.1 |
| IPK000 01605 | (structure) | 0.8 | −2.2 | 98.7 | 70.0 | 42.5 | 36.6 |
| IPK000 01865 | (structure) | 14.0 | 28.0 | 99.9 | 99.0 | 54.0 | 36.4 |
| IPK000 01866 | (structure) | 0.4 | 8.6 | 100.6 | 99.6 | 72.0 | 39.3 |

TABLE 1-continued

| ID | Structure | | | | | | |
|---|---|---|---|---|---|---|---|
| IPK000 01882 | 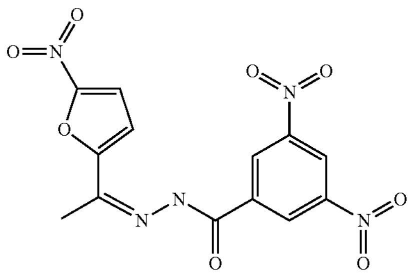 [SMILES: C/C(=N/NC(=O)c1cc([N+](=O)[O-])cc([N+](=O)[O-])c1)c1ccc([N+](=O)[O-])o1] | 17.6 | 42.7 | 99.3 | 67.6 | 41.9 | 41.1 |
| IPK000 01897 | 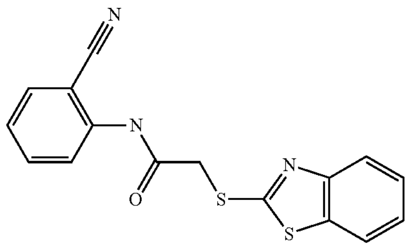 [SMILES: N#Cc1ccccc1NC(=O)CSc1nc2ccccc2s1] | 20.0 | 7.3 | 10.3 | 36.1 | 33.9 | 40.5 |
| IPK000 01984 | 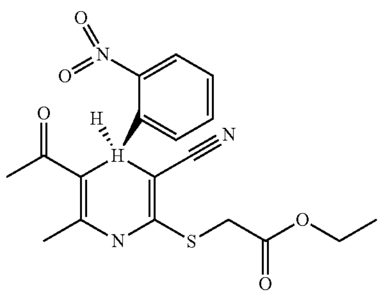 | 2.2 | 7.8 | −10.5 | 43.7 | 36.8 | 46.7 |
| IPK000 02187 | 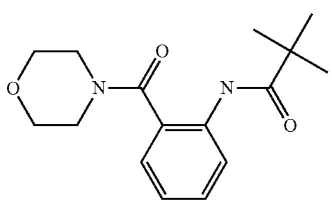 [SMILES: CC(C)(C)C(=O)Nc1ccccc1C(=O)N1CCOCC1] | 29.8 | 15.4 | 2.7 | 41.9 | 42.9 | 49.1 |
| IPK000 02233 | 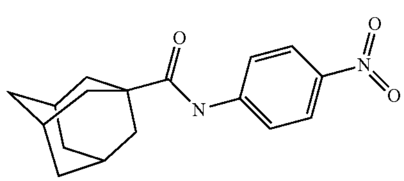 [SMILES: O=C(Nc1ccc([N+](=O)[O-])cc1)C12CC3CC(CC(C3)C1)C2] | 33.5 | 30.3 | 96.0 | 74.2 | 45.4 | 35.7 |
| IPK000 02443 | 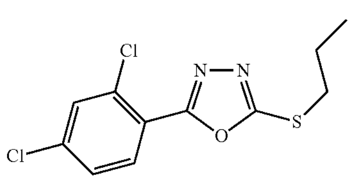 [SMILES: CCCSc1nnc(-c2ccc(Cl)cc2Cl)o1] | 58.3 | 50.4 | 75.8 | 67.7 | 40.1 | 34.7 |

TABLE 1-continued
| IPK 000 027 72 | 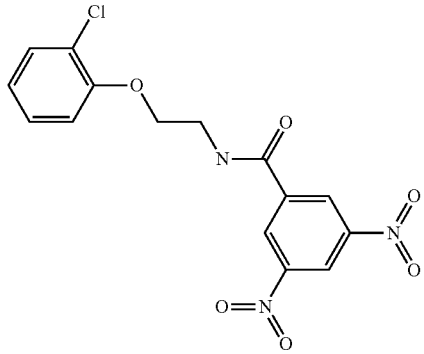 [SMILES: O=C(NCCOc1ccccc1Cl)c1cc([N+](=O)[O-])cc([N+](=O)[O-])c1] | 77.7 | 29.3 | 100.0 | 100.9 | 97.6 | 35.1 |
| --- | --- | --- | --- | --- | --- | --- | --- |
| IPK 000 027 74 | 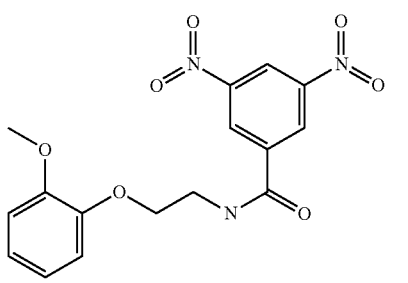 [SMILES: COc1ccccc1OCCNC(=O)c1cc([N+](=O)[O-])cc([N+](=O)[O-])c1] | 83.3 | −2.7 | 98.8 | 100.4 | 97.5 | 43.5 |
| IPK 000 027 77 | 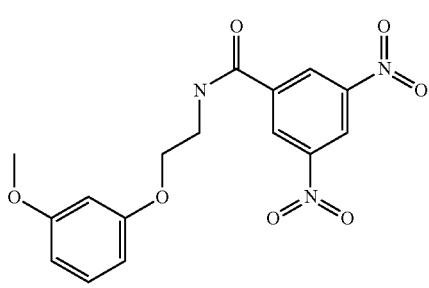 [SMILES: COc1cccc(OCCNC(=O)c2cc([N+](=O)[O-])cc([N+](=O)[O-])c2)c1] | 47.7 | −12.6 | 99.6 | 100.4 | 96.8 | 40.2 |
| IPK 000 027 78 | 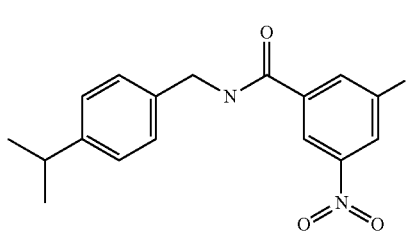 | 99.3 | 33.0 | 98.8 | 78.2 | 97.5 | 71.7 |
| IPK 000 027 85 | 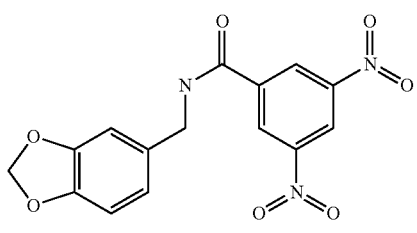 [SMILES: O=C(NCc1ccc2c(c1)OCO2)c1cc([N+](=O)[O-])cc([N+](=O)[O-])c1] | 99.4 | 83.0 | 99.6 | 71.7 | 97.9 | 97.2 |
| IPK 000 027 91 | 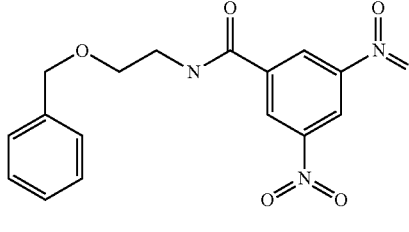 | 98.5 | 14.2 | 99.3 | 75.0 | 97.6 | 65.8 |

TABLE 1-continued

| ID | Structure | | | | | | |
|---|---|---|---|---|---|---|---|
| IPK000 02835 | 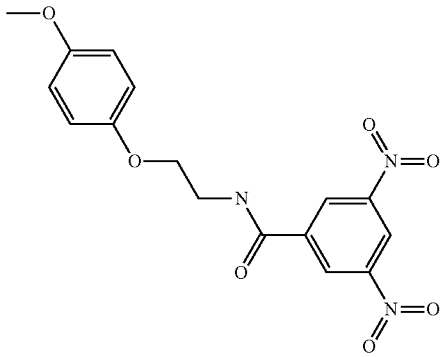 [SMILES: COc1ccc(OCCNC(=O)c2cc([N+](=O)[O-])cc([N+](=O)[O-])c2)cc1] | 102.4 | 64.5 | 99.8 | 48.3 | 98.1 | 94.0 |
| IPK000 03316 | 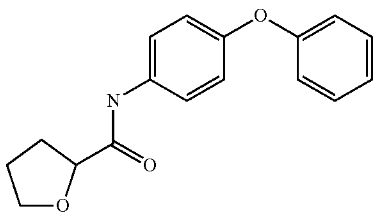 [SMILES: O=C(Nc1ccc(Oc2ccccc2)cc1)C1CCCO1] | 69.6 | 5.0 | 43.4 | 61.3 | 42.0 | 34.1 |
| IPK000 03361 | 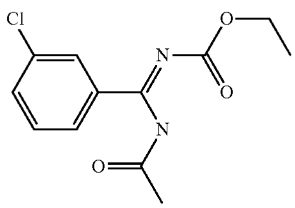 [SMILES: CCOC(=O)/N=C(\NC(C)=O)c1cccc(Cl)c1] | 13.8 | 16.2 | 94.9 | 67.1 | 37.6 | 51.6 |
| IPK000 03556 | 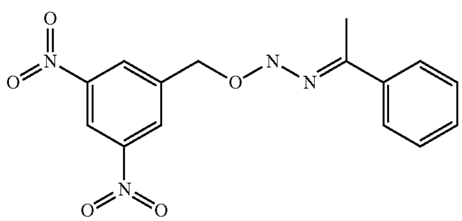 [SMILES: C/C(=N\NOCc1cc([N+](=O)[O-])cc([N+](=O)[O-])c1)c1ccccc1] | 18.8 | 9.1 | 71.9 | 65.6 | 39.6 | 41.5 |
| IPK000 03558 | 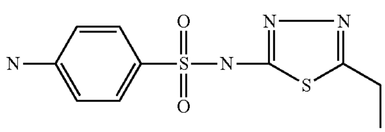 [SMILES: CCc1nnc(NS(=O)(=O)c2ccc(N)cc2)s1] | 34.4 | 5.1 | 87.2 | 65.3 | 46.4 | 45.1 |
| IPK000 03607 | 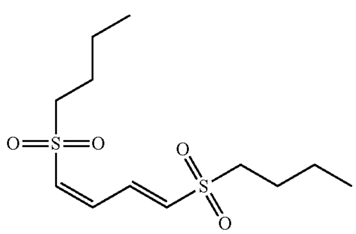 [SMILES: CCCCS(=O)(=O)/C=C\C=C\S(=O)(=O)CCCC] | 32.0 | 17.2 | 96.4 | 70.6 | 47.9 | 42.3 |
| IPK000 04014 | 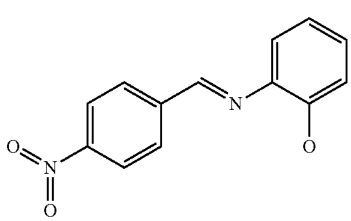 [SMILES: O=[N+]([O-])c1ccc(/C=N/c2ccccc2O)cc1] | 15.6 | 20.4 | 97.7 | 68.4 | 46.8 | 38.7 |

TABLE 1-continued

| | | | | | | | |
|---|---|---|---|---|---|---|---|
| IPK 000 041 45 | *[structure: salicylaldehyde isonicotinoyl hydrazone]* | 103.2 | 56.7 | 44.7 | 100.5 | 47.4 | 38.4 |
| IPK 000 041 46 | *[structure: naphthalene-1-carbaldehyde isonicotinoyl hydrazone]* | 101.2 | 41.8 | 98.3 | 57.9 | 81.4 | 41.1 |
| IPK 000 041 47 | *[structure: 3-nitrobenzaldehyde isonicotinoyl hydrazone]* | 101.8 | 74.5 | 91.8 | 99.5 | 82.3 | 43.8 |
| IPK 000 041 48 | *[structure: 4-nitrobenzaldehyde isonicotinoyl hydrazone]* | 97.5 | 55.9 | 96.4 | 38.6 | 84.5 | 43.7 |
| IPK 000 041 49 | *[structure: 4-ethoxybenzaldehyde isonicotinoyl hydrazone]* | 102.3 | 56.4 | 98.9 | 39.4 | 85.5 | 44.4 |

TABLE 1-continued
| | | | | | | | |
|---|---|---|---|---|---|---|---|
| IPK 000 041 50 | 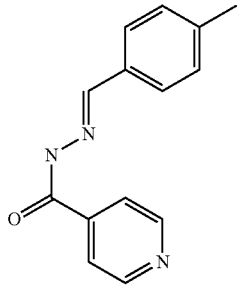 [SMILES: Cc1ccc(/C=N/NC(=O)c2ccncc2)cc1] | 102.2 | 66.3 | 99.2 | 77.7 | 94.3 | 52.0 |
| IPK 000 041 51 | 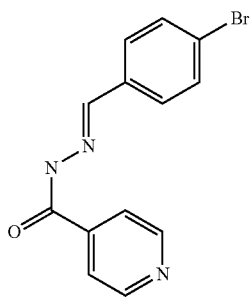 [SMILES: O=C(N/N=C/c1ccc(Br)cc1)c1ccncc1] | 102.9 | 55.1 | 98.4 | 70.9 | 85.2 | 40.8 |
| IPK 000 041 52 | 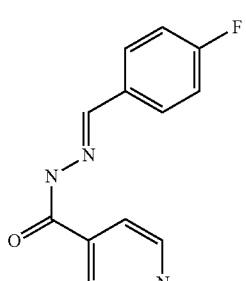 | 103.2 | 89.7 | 99.0 | 56.0 | 93.0 | 53.1 |
| IPK 000 041 53 | 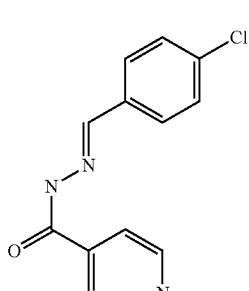 | 98.1 | 18.8 | 96.9 | 44.4 | 82.2 | 15.1 |
| IPK 000 042 07 | 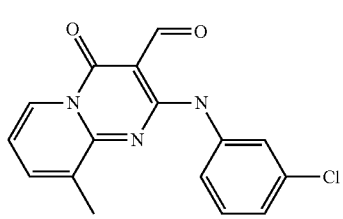 [SMILES: Cc1cccn2c(=O)c(C=O)c(Nc3cccc(Cl)c3)nc12] | 104.0 | 12.4 | 93.4 | 98.0 | 96.5 | 70.8 |

TABLE 1-continued

| ID | Structure | | | | | | |
|---|---|---|---|---|---|---|---|
| IPK000 04230 | 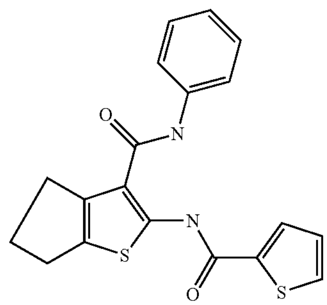 [SMILES: O=C(Nc1sc2c(c1C(=O)Nc1ccccc1)CCC2)c1cccs1] | 75.2 | 11.0 | 85.2 | 95.8 | 62.9 | 39.1 |
| IPK000 04272 | 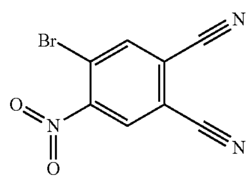 [SMILES: N#Cc1cc(Br)c([N+](=O)[O-])cc1C#N] | −1.9 | 2.5 | 82.5 | 67.7 | 43.7 | 39.6 |
| IPK000 04277 | 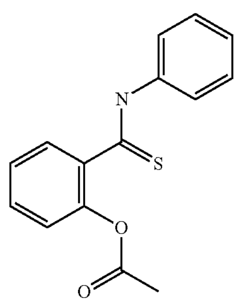 [SMILES: CC(=O)Oc1ccccc1C(=S)Nc1ccccc1] | 7.7 | 22.4 | 99.2 | 67.1 | 51.3 | 33.5 |
| IPK000 04278 | 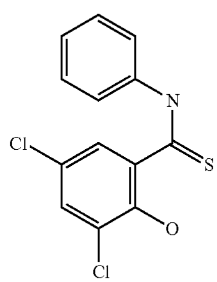 [SMILES: Oc1c(Cl)cc(Cl)cc1C(=S)Nc1ccccc1] | 33.0 | 25.8 | 98.7 | 67.1 | 56.4 | 42.9 |
| IPK000 04293 | 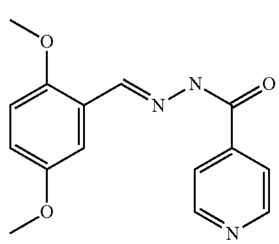 [SMILES: COc1ccc(OC)c(/C=N/NC(=O)c2ccncc2)c1] | 105.1 | 49.3 | 96.6 | 98.5 | 76.0 | 44.3 |
| IPK000 04295 | 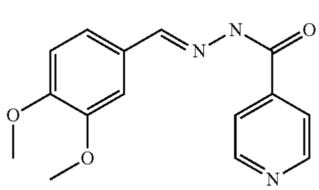 [SMILES: COc1cc(/C=N/NC(=O)c2ccncc2)ccc1O] | 106.0 | 70.4 | 96.6 | 53.1 | 82.0 | 42.2 |

TABLE 1-continued

| ID | Structure | | | | | | |
|---|---|---|---|---|---|---|---|
| IPK00004296 | (4-dimethylamino-benzylidene isonicotinohydrazide) | 101.1 | 77.4 | 94.3 | 97.2 | 83.3 | 43.3 |
| IPK00004297 | (3-methoxy-4-hydroxy-benzylidene isonicotinohydrazide) | 99.2 | 19.2 | 97.0 | 98.8 | 73.9 | 40.1 |
| IPK00004298 | (2-hydroxy-5-nitro-benzylidene isonicotinohydrazide) | 95.3 | 19.0 | 30.3 | 82.9 | 48.5 | 31.8 |
| IPK00004299 | (3-ethoxy-4-hydroxy-benzylidene isonicotinohydrazide) | 104.1 | 43.4 | 97.9 | 97.1 | 79.3 | 51.8 |
| IPK00004300 | (2,4-dimethoxy-benzylidene isonicotinohydrazide) | 101.4 | 37.5 | 98.3 | 98.6 | 70.6 | 51.0 |
| IPK00004301 | (2-methoxy-benzylidene isonicotinohydrazide) | 103.6 | 56.3 | 98.6 | 98.8 | 74.2 | 47.4 |
| IPK00004302 | (2,3-dimethoxy-benzylidene isonicotinohydrazide) | 98.7 | 71.3 | 98.4 | 98.2 | 82.6 | 48.4 |

TABLE 1-continued

| ID | Structure | | | | | | |
|---|---|---|---|---|---|---|---|
| IPK00004305 | 2-Cl-benzylidene isonicotinohydrazide | 101.6 | 80.2 | 99.4 | 98.8 | 94.4 | 51.4 |
| IPK00004306 | 4-butoxy-benzylidene isonicotinohydrazide | 98.1 | -0.4 | 99.8 | 98.5 | 75.2 | 38.5 |
| IPK00004307 | 4-hydroxy-benzylidene isonicotinohydrazide | 102.5 | 68.4 | 99.7 | 98.9 | 79.2 | 44.8 |
| IPK00004308 | 3-methoxy-2-hydroxy-benzylidene isonicotinohydrazide | 102.7 | 72.9 | 77.2 | 63.9 | 63.5 | 39.8 |
| IPK00004309 | 3-Br-benzylidene isonicotinohydrazide | 100.5 | 59.3 | 99.5 | 98.4 | 80.1 | 49.1 |

TABLE 1-continued

| ID | Structure | | | | | | |
|---|---|---|---|---|---|---|---|
| IPK 00004310 | 2,3-dichlorobenzaldehyde isonicotinoyl hydrazone | 92.7 | 28.5 | 98.7 | 66.9 | 73.1 | 46.5 |
| IPK 00004311 | 4-hydroxy-3-nitrobenzaldehyde isonicotinoyl hydrazone | 99.5 | 40.3 | 97.5 | 70.9 | 76.7 | 43.5 |
| IPK 00004312 | indole-2-carbaldehyde isonicotinoyl hydrazone | 104.6 | 56.5 | 98.5 | 69.8 | 84.5 | 48.9 |
| IPK 00004313 | 2,4-dichlorobenzaldehyde isonicotinoyl hydrazone | 101.6 | 17.8 | 98.7 | 98.5 | 75.0 | 48.9 |
| IPK 00004226 | 3-methylbenzaldehyde isonicotinoyl hydrazone | 102.2 | 72.4 | 99.5 | 98.6 | 89.6 | 52.7 |

TABLE 1-continued

| ID | Structure | | | | | | |
|---|---|---|---|---|---|---|---|
| IPK 000 043 27 | (isonicotinoyl hydrazone of 2-ethoxybenzaldehyde) | 105.2 | 87.8 | 99.2 | 98.8 | 86.3 | 67.0 |
| IPK 000 043 28 | (isonicotinoyl hydrazone of 2,4-dihydroxybenzaldehyde) | 87.1 | 11.2 | 12.2 | 69.7 | 38.8 | 43.0 |
| IPK 000 043 29 | (isonicotinoyl hydrazone of 2-methylbenzaldehyde) | 105.2 | 71.9 | 98.3 | 98.6 | 76.8 | 51.3 |
| IPK 000 043 30 | (isonicotinoyl hydrazone of 4-nitrocinnamaldehyde) | 100.8 | −5.6 | 98.0 | 97.9 | 69.7 | 32.8 |
| IPK 000 043 31 | (isonicotinoyl hydrazone of 4-ethylbenzaldehyde) | 101.5 | 43.8 | 98.7 | 52.7 | 69.8 | 24.0 |
| IPK 000 043 32 | (isonicotinoyl hydrazone of 4-isopropylbenzaldehyde) | 94.5 | 72.0 | 98.9 | 99.1 | 78.1 | 37.0 |

TABLE 1-continued

| ID | Structure | | | | | | |
|---|---|---|---|---|---|---|---|
| IPK00004333 | (N'-(thiophen-2-ylmethylene)isonicotinohydrazide) | 94.5 | 31.3 | 98.4 | 98.8 | 59.3 | 34.8 |
| IPK00004335 | (N'-(2-nitrobenzylidene)isonicotinohydrazide) | 94.4 | 31.6 | 96.1 | 67.1 | 75.7 | 39.9 |
| IPK00004362 | (N'-((2-ethoxynaphthalen-1-yl)methylene)isonicotinohydrazide) | 98.8 | 63.7 | 99.4 | 98.3 | 71.0 | 42.9 |
| IPK00004383 | (5-bromo-2-hydroxy-N-(2-hydroxyphenyl)benzylideneamine) | 17.1 | 22.6 | 99.7 | 99.2 | 50.6 | 34.2 |
| IPK00004420 | (2-hydroxy-N-(2-hydroxyphenyl)-5-nitrobenzylideneamine) | 6.3 | 24.5 | 99.6 | 98.5 | 52.4 | 40.3 |
| IPK00004441 | (3,5-dibromo-2-hydroxy-N-(2-hydroxyphenyl)benzylideneamine) | 34.0 | 18.0 | 98.6 | 84.0 | 41.4 | 37.1 |

TABLE 1-continued
| IPK 000 045 01 | 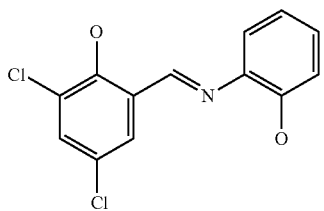 [SMILES: Oc1ccccc1/N=C/c1cc(Cl)cc(Cl)c1O] | 24.3 | 19.3 | 99.3 | 66.8 | 57.6 | 41.3 |
| --- | --- | --- | --- | --- | --- | --- | --- |
| IPK 000 046 78 | 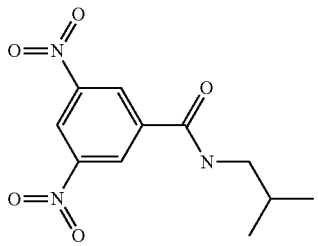 [SMILES: CC(C)CNC(=O)c1cc([N+](=O)[O-])cc([N+](=O)[O-])c1] | 36.5 | 13.9 | 100.8 | 99.1 | 65.2 | 36.5 |
| IPK 000 046 80 | 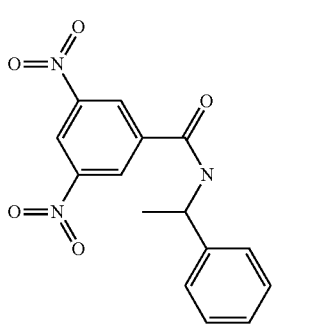 [SMILES: CC(NC(=O)c1cc([N+](=O)[O-])cc([N+](=O)[O-])c1)c1ccccc1] | 3.1 | 38.6 | 99.2 | 73.5 | 41.8 | 44.4 |
| IPK 000 046 83 | 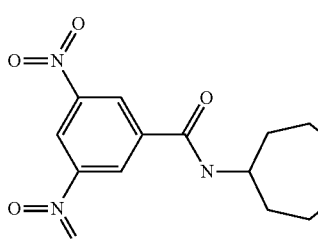 | 91.7 | 37.2 | 100.1 | 69.6 | 97.1 | 44.3 |
| IPK 000 046 86 | 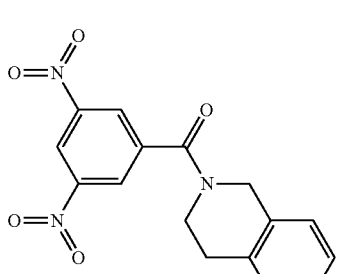 | 15.0 | 17.3 | 100.2 | 70.3 | 41.2 | 38.3 |
| IPK 000 046 87 | 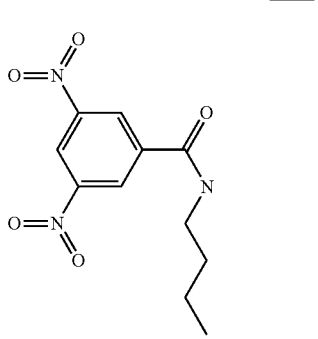 | 61.3 | 14.4 | 99.2 | 62.5 | 70.4 | 44.2 |

TABLE 1-continued

| | | | | | | | |
|---|---|---|---|---|---|---|---|
| IPK 00004692 | (structure) | 8.1 | 31.2 | 17.0 | 53.1 | 38.4 | 42.2 |
| IPK 00004706 | (structure) | 17.6 | 35.0 | 97.4 | 76.4 | 41.9 | 41.1 |
| IPK 00004715 | (structure) | 61.1 | 13.3 | 99.3 | 97.7 | 36.4 | 36.8 |
| IPK 00004716 | (structure) | 77.9 | 6.0 | 100.4 | 98.3 | 39.0 | 32.0 |
| IPK 00004717 | (structure) | 69.7 | 46.5 | 99.3 | 98.6 | 36.5 | 37.7 |
| IPK 00004849 | (structure) | 41.7 | 25.8 | 32.6 | 57.7 | 34.3 | 40.3 |
| IPK 00004871 | (structure) | 22.6 | 4.5 | 85.2 | 72.7 | 44.3 | 39.8 |

TABLE 1-continued

| ID | Structure | | | | | | |
|---|---|---|---|---|---|---|---|
| IPK 000 048 99 | (structure) | 40.3 | 8.6 | 84.7 | 72.0 | 36.4 | 43.6 |
| IPK 000 049 00 | (structure) | 72.2 | 24.4 | 86.2 | 73.9 | 38.7 | 48.1 |
| IPK 000 049 03 | (structure) | 56.0 | 23.4 | 94.5 | 69.1 | 43.7 | 41.3 |
| IPK 000 049 20 | (structure) | 54.8 | 36.9 | 28.3 | 27.0 | 31.5 | 36.0 |
| IPK 000 052 50 | (structure) | 10.8 | 33.8 | 101.0 | 70.4 | 28.8 | 30.9 |
| IPK 000 052 75 | (structure) | 13.3 | 14.7 | 85.6 | 66.9 | 43.8 | 43.3 |

TABLE 1-continued

| ID | Structure | | | | | | |
|---|---|---|---|---|---|---|---|
| IPK00005778 | 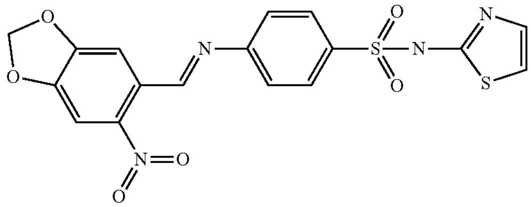 [SMILES: O=[N+]([O-])c1cc2c(cc1/C=N/c1ccc(S(=O)(=O)Nc3nccs3)cc1)OCO2] | 12.6 | 4.5 | 93.9 | 86.2 | 39.0 | 43.7 |
| IPK00005792 | 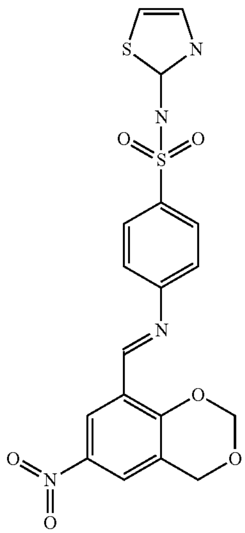 [SMILES: O=[N+]([O-])c1cc(/C=N/c2ccc(S(=O)(=O)NC3NC=CS3)cc2)c2c(c1)COCO2] | 23.0 | 26.2 | 89.8 | 81.6 | 29.1 | 33.5 |
| IPK00005820 | 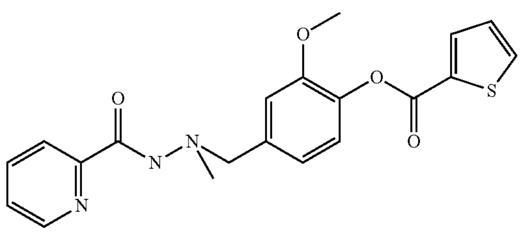 [SMILES: COc1cc(CN(C)NC(=O)c2ccccn2)ccc1OC(=O)c1cccs1] | 66.6 | 13.3 | 55.8 | 68.0 | 57.9 | 42.5 |
| IPK00005821 | 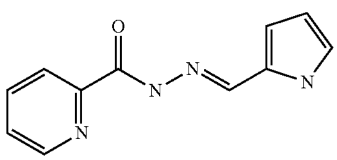 [SMILES: O=C(N/N=C/c1ccc[nH]1)c1ccccn1] | 75.7 | 24.8 | 52.3 | 41.2 | 54.6 | 47.6 |
| IPK00005829 | 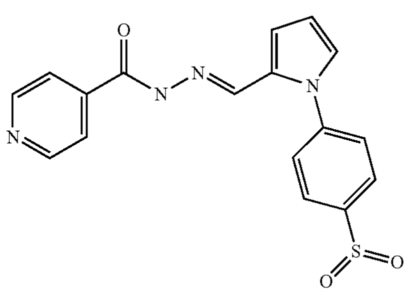 | 103.7 | 77.6 | 99.2 | 47.5 | 93.4 | 52.2 |
| IPK00005830 | 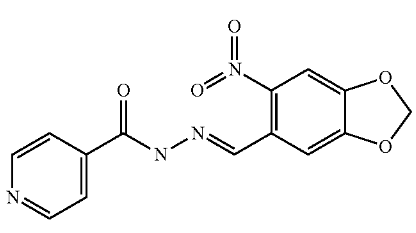 [SMILES: O=C(N/N=C/c1cc2c(cc1[N+](=O)[O-])OCO2)c1ccncc1] | 98.3 | 21.0 | 84.5 | 48.8 | 72.8 | 47.0 |

TABLE 1-continued
| | | | | | | | |
|---|---|---|---|---|---|---|---|
| IPK 000 063 24 | 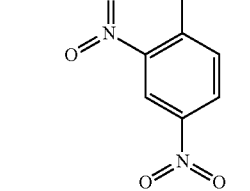 | 16.7 | 17.4 | 96.2 | 74.8 | 38.1 | 37.1 |
| IPK 000 065 03 | 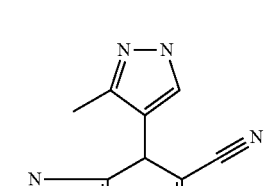 | 1.1 | 14.7 | −16.3 | 38.1 | 35.2 | 29.1 |
| IPK 000 067 51 | 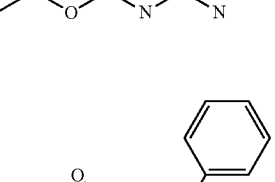 | 17.9 | 11.0 | 37.4 | 59.5 | 39.9 | 39.0 |
| IPK 000 067 60 | 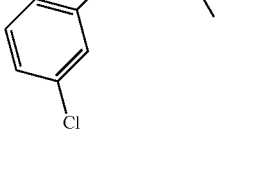 | 25.8 | 17.7 | 99.7 | 65.3 | 46.4 | 40.8 |
| IPK 000 067 61 | 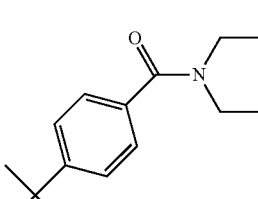 | 28.2 | 14.3 | 99.3 | 70.6 | 44.5 | 39.6 |

TABLE 1-continued
| | | | | | | | |
|---|---|---|---|---|---|---|---|
| IPK 000 006 887 |  | −12.0 | −0.6 | 92.9 | 79.3 | 31.0 | 38.1 |
| IPK 000 073 11 | 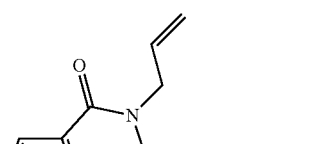 | −10.5 | 6.4 | 84.0 | 67.2 | 33.5 | 42.2 |
| IPK 000 073 29 | 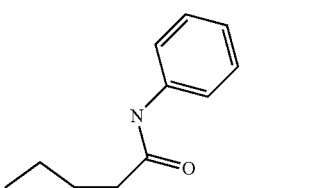 | 55.1 | 1.3 | 94.1 | 74.9 | 73.9 | 50.0 |
| IPK 000 073 68 | 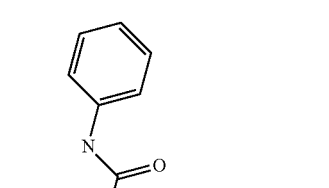 | 74.7 | 16.9 | 94.9 | 73.4 | 69.2 | 53.5 |

TABLE 1-continued

| ID | Structure | | | | | | |
|---|---|---|---|---|---|---|---|
| IPK00007369 | (4-methylphenyl carboxamide, 2-chlorobenzamide cyclopenta-thiophene) | 14.0 | 21.8 | 80.9 | 72.9 | 44.3 | 37.2 |
| IPK00007370 | (3-methylphenyl carboxamide, 2-chlorobenzamide cyclopenta-thiophene) | 56.7 | 17.8 | 96.3 | 74.9 | 68.1 | 49.8 |
| IPK00007371 | (2-methylphenyl carboxamide, 2-chlorobenzamide cyclopenta-thiophene) | 29.8 | −4.5 | 8.3 | 45.3 | 59.6 | 44.5 |
| IPK00007722 | (2,4-dimethylphenyl carboxamide, trifluoroacetamide cyclopenta-thiophene) | 33.3 | 35.6 | 95.4 | 68.6 | 45.7 | 45.0 |

TABLE 1-continued

| ID | Structure | | | | | | |
|---|---|---|---|---|---|---|---|
| IPK00007830 | (structure) | 97.0 | 8.2 | 96.6 | 69.7 | 62.0 | 39.2 |
| IPK00007853 | (structure) | 95.6 | 17.6 | 98.3 | 68.4 | 73.8 | 39.3 |
| IPK00007886 | (structure) | 88.3 | 32.7 | 98.5 | 68.0 | 74.5 | 37.9 |
| IPK00007913 | (structure) | 97.8 | 8.4 | 97.0 | 97.8 | 68.5 | 36.6 |

TABLE 1-continued

| ID | Structure | | | | | | |
|---|---|---|---|---|---|---|---|
| IPK00007915 | (structure) | 90.5 | 13.4 | 97.1 | 98.6 | 72.6 | 41.5 |
| IPK00007988 | (structure) | 7.5 | 0.9 | 92.2 | 88.3 | 34.9 | 39.3 |
| IPK00008001 | (structure) | 27.4 | 20.1 | 96.1 | 70.4 | 47.4 | 39.5 |
| IPK00008024 | (structure) | 67.6 | 13.0 | 99.5 | 73.0 | 62.4 | 45.3 |
| IPK00008036 | (structure) | 75.8 | 70.0 | 98.9 | 71.9 | 68.7 | 59.7 |
| IPK00008037 | (structure) | 62.1 | 55.4 | 99.6 | 78.6 | 80.6 | 63.1 |

TABLE 1-continued

| ID | Structure | | | | | | |
|---|---|---|---|---|---|---|---|
| IPK00008038 | (thiosemicarbazone of 2'-hydroxyacetophenone) | 32.1 | 13.3 | 98.2 | 73.8 | 58.7 | 52.3 |
| IPK00008039 | (thiosemicarbazone of 4'-isobutylacetophenone) | 73.0 | 51.8 | 96.3 | 68.2 | 66.6 | 54.7 |
| IPK00008069 | (Schiff base of 2-aminophenol and 5-bromo-3-nitrosalicylaldehyde) | 37.6 | 27.5 | 99.1 | 71.8 | 47.6 | 46.9 |
| IPK00008081 | (isonicotinohydrazide of 5-bromo-3-nitrosalicylaldehyde) | 104.9 | 66.3 | 55.0 | 69.5 | 48.4 | 50.8 |
| IPK00008389 | (ethyl 4-(3-hydroxyphenyl)-2-methyl-5-oxo-7-phenyl-1,4,5,6,7,8-hexahydroquinoline-3-carboxylate) | 19.5 | 2.6 | 98.7 | 72.9 | 48.1 | 46.3 |
| IPK00008599 | (propyl 4-(3-hydroxyphenyl)-2-methyl-5-oxo-7-phenyl-1,4,5,6,7,8-hexahydroquinoline-3-carboxylate) | 4.5 | 2.2 | 84.3 | 72.0 | 47.7 | 49.5 |

TABLE 1-continued
| | | | | | | | |
|---|---|---|---|---|---|---|---|
| IPK 000 0091 17 | 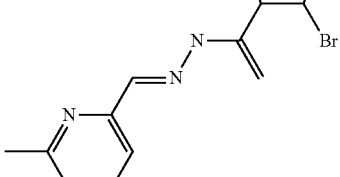 | 35.4 | 50.6 | -11.9 | 22.4 | 38.8 | 42.6 |
| IPK 000 0091 49 | 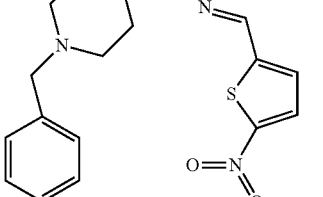 | 9.3 | 30.6 | 94.1 | 65.5 | 33.4 | 37.3 |
| IPK 000 0094 38 | 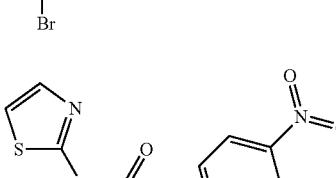 | 13.6 | -9.3 | 97.2 | 68.6 | 54.6 | 41.3 |
| IPK 000 0095 07 | 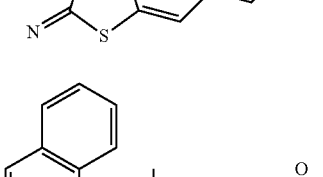 | 8.0 | 19.2 | -3.7 | 39.6 | 46.1 | 45.0 |
| IPK 000 0102 07 | 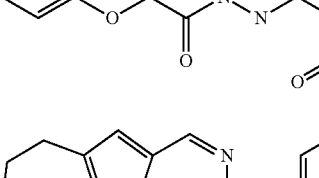 | 99.5 | 79.6 | 99.2 | 100.1 | 84.3 | 77.4 |
| IPK 000 0102 36 | 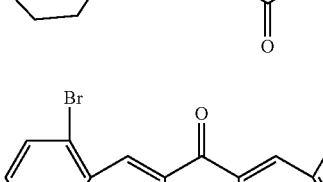 | 4.4 | 13.2 | -1.6 | 16.8 | 32.7 | 36.3 |

TABLE 1-continued
| | | | | | | | |
|---|---|---|---|---|---|---|---|
| IPK 000 102 52 | 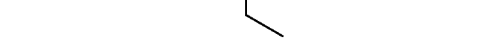 | −7.0 | 12.6 | 18.3 | 19.1 | 40.8 | 36.7 |
| IPK 000 103 28 |  | 49.5 | 11.6 | 5.0 | 48.2 | 47.6 | 39.8 |
| IPK 000 103 76 |  | −1.7 | −13.2 | 45.6 | 50.2 | 50.0 | 39.0 |
| IPK 000 103 78 |  | 3.5 | −3.9 | 90.8 | 94.0 | 34.8 | 31.6 |
| IPK 000 104 07 | 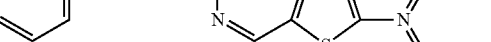 | 65.1 | 37.5 | 35.1 | 58.0 | 45.1 | 42.5 |
| IPK 000 104 11 |  | 19.9 | 10.2 | 36.1 | 52.8 | 42.4 | 26.9 |
| IPK 000 104 13 | 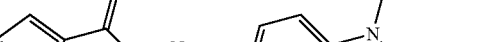 | 25.2 | 10.1 | 3.7 | 37.9 | 29.0 | 44.7 |

TABLE 1-continued

| ID | Structure | | | | | | |
|---|---|---|---|---|---|---|---|
| IPK 00010420 | (2-hydroxybenzoyl hydrazone of 5-chloro-2-hydroxy-3-methoxybenzaldehyde) | −2.9 | 5.3 | 67.1 | 90.6 | 56.2 | 40.4 |
| IPK 00010467 | (4-fluorobenzoyl hydrazone of 1-allyl-isatin) | 16.1 | 11.9 | 67.7 | 86.2 | 34.2 | 36.4 |
| IPK 00010519 | (isonicotinoyl hydrazone of 2-(carboxymethoxy)benzaldehyde) | 104.1 | 88.5 | 98.7 | 66.4 | 93.6 | 70.3 |
| IPK 00010520 | (isonicotinoyl hydrazone of 2-phenylpropanal) | 103.8 | 83.8 | 99.6 | 66.0 | 96.0 | 66.6 |
| IPK 00010547 | (N-(5-bromopyridin-2-yl)-4-butylbenzamide) | 68.1 | 13.0 | 75.5 | 95.5 | 54.7 | 47.3 |
| IPK 00010555 | (ethyl 9H-fluorene-9-carboxylate) | 55.5 | 13.0 | 29.2 | 62.2 | 35.1 | 18.8 |

TABLE 1-continued

| ID | Structure | | | | | | |
|---|---|---|---|---|---|---|---|
| IPK 000 105 56 | 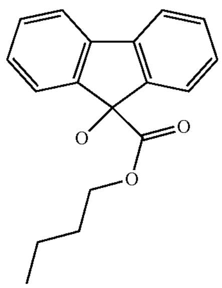 [SMILES: CCCCOC(=O)C1(O)c2ccccc2-c2ccccc21] | 79.9 | 28.0 | 36.1 | 68.0 | 39.5 | 36.4 |
| IPK 000 105 70 | 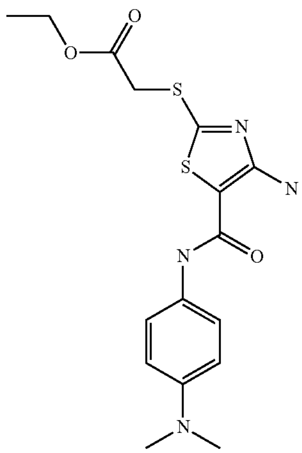 [SMILES: CCOC(=O)CSc1nc(N)c(C(=O)Nc2ccc(N(C)C)cc2)s1] | 4.7 | 16.8 | 70.7 | 80.7 | 53.8 | 41.8 |
| IPK 000 106 30 | 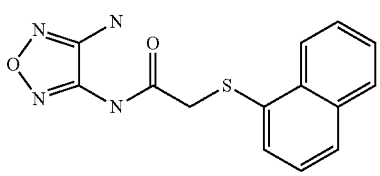 [SMILES: Nc1nonc1NC(=O)CSc1cccc2ccccc12] | 28.5 | 9.3 | 19.1 | 61.2 | 36.4 | 17.1 |
| IPK 000 107 90 | 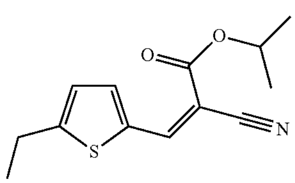 [SMILES: CCc1ccc(/C=C(/C#N)C(=O)OC(C)C)s1] | 52.8 | 23.7 | 7.0 | 42.6 | 39.6 | 37.4 |
| IPK 000 108 27 | 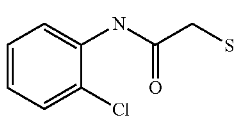 [SMILES: O=C(CS)Nc1ccccc1Cl] | 19.0 | 14.1 | 95.0 | 71.0 | 47.6 | 49.0 |
| IPK 000 108 78 | 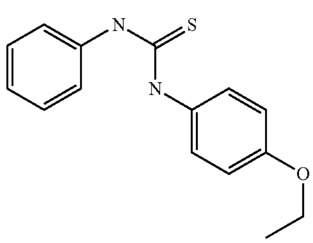 [SMILES: CCOc1ccc(NC(=S)Nc2ccccc2)cc1] | 38.3 | 28.2 | 20.9 | 43.1 | 39.2 | 38.4 |

TABLE 1-continued

| ID | Structure | | | | | | |
|---|---|---|---|---|---|---|---|
| IPK 00010900 | 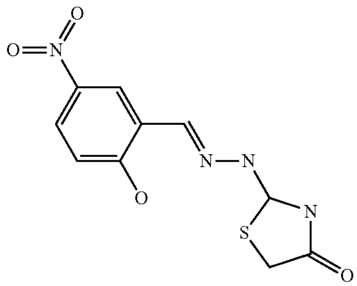 [SMILES: O=C1CSC(N/N=C/c2cc([N+](=O)[O-])ccc2O)N1] | 23.8 | 15.6 | 98.4 | 72.2 | 55.2 | 47.6 |
| IPK 00010999 | 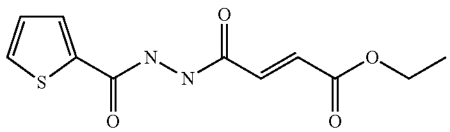 [SMILES: CCOC(=O)/C=C/C(=O)NNC(=O)c1cccs1] | 20.3 | 22.6 | 101.3 | 99.5 | 90.5 | 29.6 |
| IPK 00011016 | 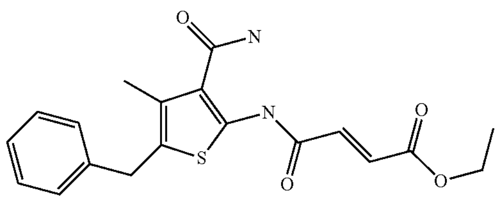 [SMILES: CCOC(=O)/C=C/C(=O)Nc1sc(Cc2ccccc2)c(C)c1C(N)=O] | 6.0 | 8.1 | 99.4 | 96.3 | 36.7 | 44.2 |
| IPK 00011017 | 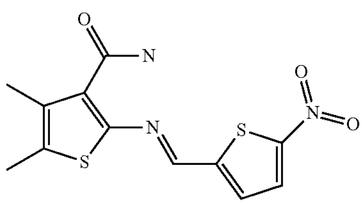 [SMILES: Cc1sc(/N=C/c2ccc([N+](=O)[O-])s2)c(C(N)=O)c1C] | 12.9 | 23.9 | 92.6 | 97.3 | 47.2 | 44.1 |
| IPK 00011079 | 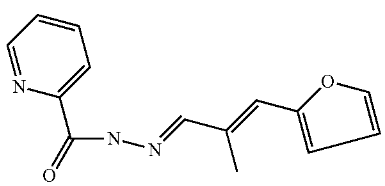 [SMILES: CC(/C=N/NC(=O)c1ccccn1)=C\c1ccco1] | 22.8 | 44.6 | 19.7 | 49.5 | 32.4 | 34.0 |
| IPK 00011267 | 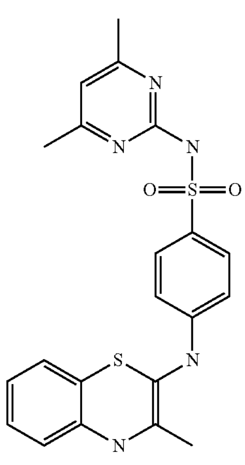 [SMILES: CC1=C(Nc2ccc(S(=O)(=O)Nc3nc(C)cc(C)n3)cc2)Sc2ccccc2N1] | 27.6 | 8.2 | 91.3 | 68.9 | 59.6 | 43.8 |

TABLE 1-continued
| | | | | | | | |
|---|---|---|---|---|---|---|---|
| IPK000 11280 |  | 10.7 | 7.7 | 98.3 | 72.1 | 32.5 | 35.9 |
| IPK000 11305 | 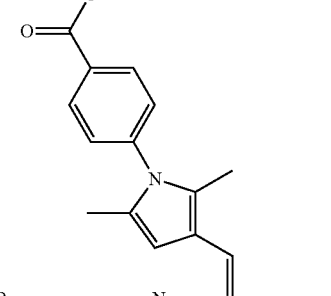 | 31.6 | 10.0 | 74.9 | 67.9 | 45.3 | 41.6 |
| IPK000 11377 | 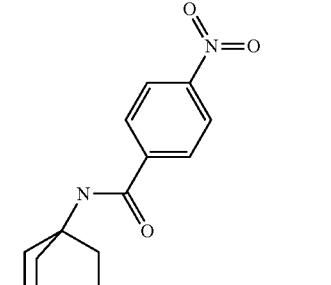 | 48.4 | 26.6 | 66.7 | 82.9 | 59.5 | 45.0 |
| IPK000 11401 | 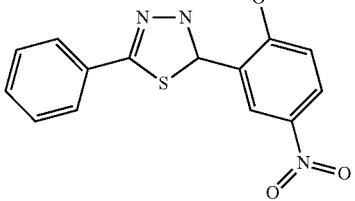 | 7.3 | 18.3 | 73.9 | 71.1 | 51.4 | 53.6 |
| IPK000 11705 | 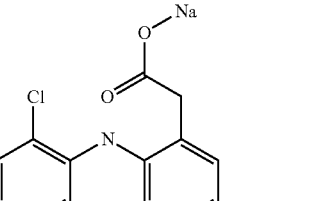 | 45.4 | 49.9 | 12.9 | 46.3 | 44.5 | 39.6 |

TABLE 1-continued
| ID | Structure | | | | | | |
|---|---|---|---|---|---|---|---|
| IPK 000 117 14 | 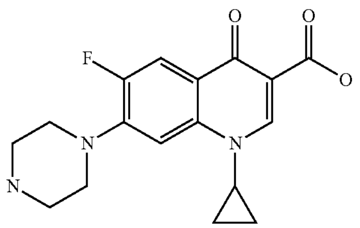 [SMILES: O=C(O)c1cn(C2CC2)c2cc(N3CCNCC3)c(F)cc2c1=O] | 15.6 | 11.2 | 100.8 | 98.6 | 82.8 | 33.9 |
| IPK 000 122 62 | 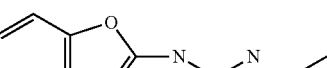 | 26.2 | 13.0 | 90.7 | 67.9 | 37.7 | 26.4 |
| IPK 000 123 02 | 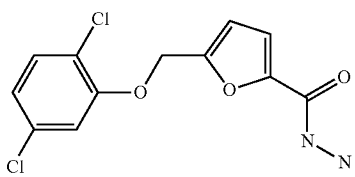 [SMILES: NNC(=O)c1ccc(COc2cc(Cl)ccc2Cl)o1] | 45.3 | 24.6 | 23.9 | 32.0 | 38.2 | 42.1 |
| IPK 000 123 03 | 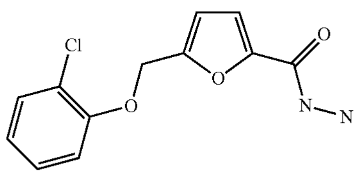 [SMILES: NNC(=O)c1ccc(COc2ccccc2Cl)o1] | 12.0 | −8.6 | 21.2 | 34.7 | 35.8 | 36.5 |
| IPK 000 123 30 | 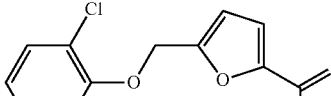 | 72.5 | 22.6 | 20.9 | 37.0 | 36.6 | 38.0 |
| IPK 000 123 90 | 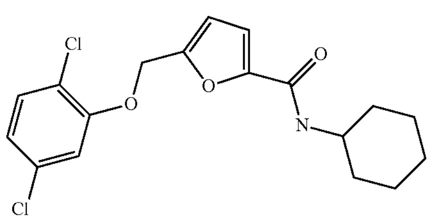 [SMILES: O=C(NC1CCCCC1)c1ccc(COc2cc(Cl)ccc2Cl)o1] | 26.7 | −6.0 | 35.1 | 49.4 | 43.2 | 40.5 |
| IPK 000 123 92 | 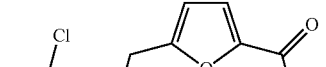 | 32.3 | 12.0 | 96.4 | 77.0 | 46.7 | 31.5 |
| IPK 000 124 43 | 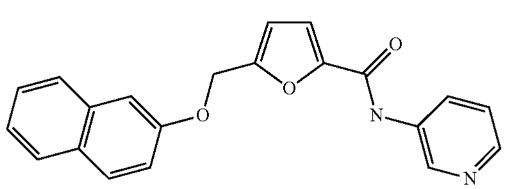 [SMILES: O=C(Nc1cccnc1)c1ccc(COc2ccc3ccccc3c2)o1] | 26.2 | 15.5 | 96.6 | 66.0 | 42.2 | 44.0 |

TABLE 1-continued
| | | | | | | | |
|---|---|---|---|---|---|---|---|
| IPK 000 124 54 | 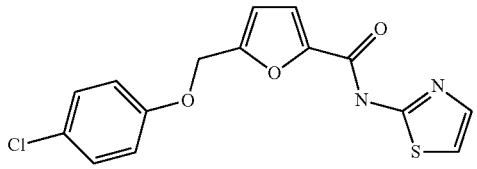 [SMILES: O=C(Nc1nccs1)c1ccc(COc2ccc(Cl)cc2)o1] | 16.4 | 21.3 | 22.7 | 38.9 | 37.0 | 34.8 |
| IPK 000 124 64 | 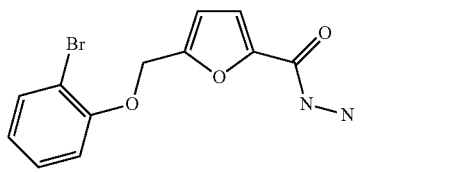 [SMILES: NNC(=O)c1ccc(COc2ccccc2Br)o1] | 54.7 | 22.6 | −0.6 | 25.1 | 31.1 | 33.9 |
| IPK 000 124 65 | 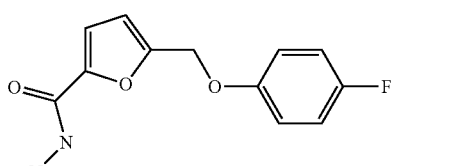 | 45.0 | 7.2 | 5.2 | 38.6 | 38.6 | 36.9 |
| IPK 000 125 08 | 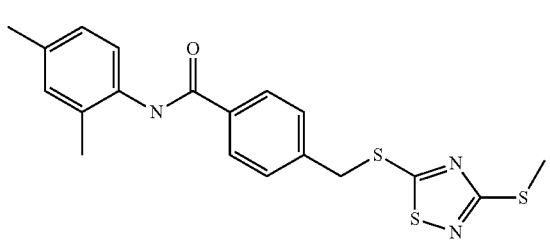 | 46.9 | 28.2 | 74.4 | 65.1 | 32.8 | 36.9 |
| IPK 000 125 15 | 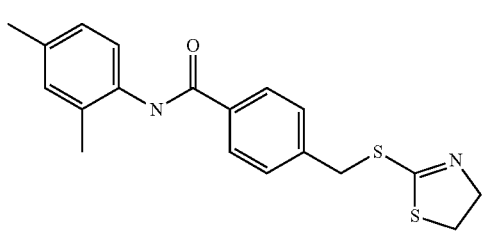 [SMILES: Cc1ccc(NC(=O)c2ccc(CSC3=NCCS3)cc2)c(C)c1] | 4.0 | 4.4 | 95.2 | 55.2 | 40.3 | 40.9 |
| IPK 000 125 22 | 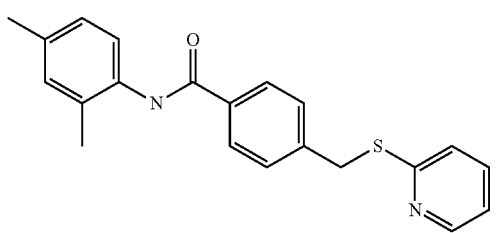 [SMILES: Cc1ccc(NC(=O)c2ccc(CSc3ccccn3)cc2)c(C)c1] | −11.9 | 3.1 | 81.0 | 73.2 | 40.0 | 38.5 |
| IPK 000 125 61 | 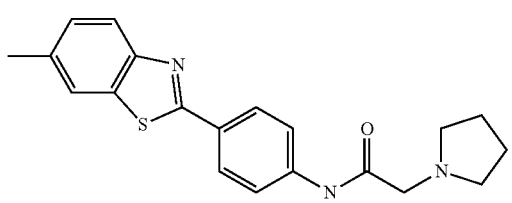 [SMILES: Cc1ccc2nc(-c3ccc(NC(=O)CN4CCCC4)cc3)sc2c1] | 15.7 | 2.8 | 89.0 | 25.3 | 26.3 | 31.2 |

TABLE 1-continued

| ID | Structure | | | | | | |
|---|---|---|---|---|---|---|---|
| IPK 000 126 33 | 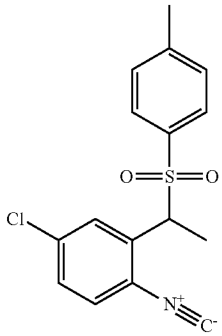 [SMILES: [C-]#[N+]c1ccc(Cl)cc1C(C)S(=O)(=O)c1ccc(C)cc1] | 12.5 | 24.9 | 98.7 | 99.6 | 66.8 | 41.4 |
| IPK 000 126 73 | 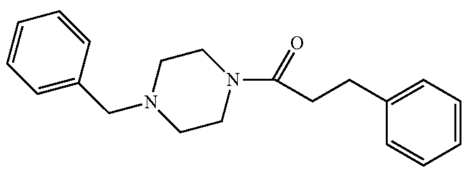 [SMILES: O=C(CCc1ccccc1)N1CCN(Cc2ccccc2)CC1] | 5.7 | 3.3 | 78.1 | 76.0 | 55.4 | 35.5 |
| IPK 000 128 37 | 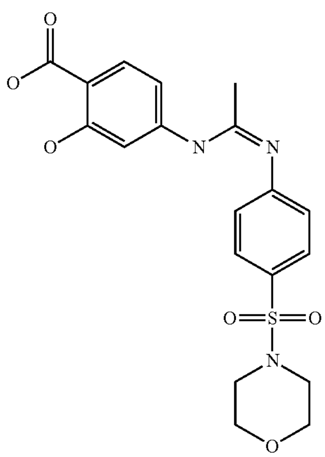 [SMILES: C/C(=N/c1ccc(S(=O)(=O)N2CCOCC2)cc1)Nc1ccc(C(=O)O)c(O)c1] | 8.4 | 6.5 | 90.9 | 71.8 | 95.9 | 90.6 |
| IPK 000 129 72 | 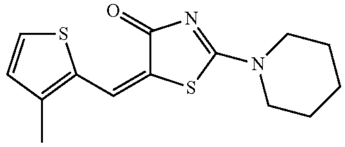 [SMILES: Cc1ccsc1/C=C1/SC(N2CCCCC2)=NC1=O] | 16.8 | 14.1 | 98.1 | 69.4 | 44.9 | 46.3 |
| IPK 000 129 91 | 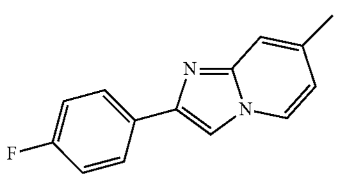 [SMILES: Cc1ccn2cc(-c3ccc(F)cc3)nc2c1] | 25.4 | 25.1 | 69.3 | 74.8 | 51.4 | 52.1 |
| IPK 000 130 26 | 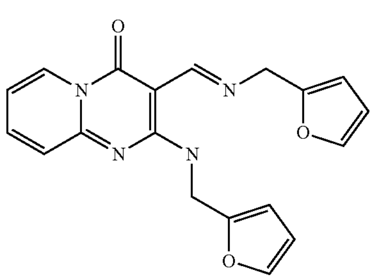 [SMILES: O=c1c(/C=N/Cc2ccco2)c(NCc2ccco2)nc2ccccn12] | 14.5 | 17.8 | 100.0 | 70.1 | 79.7 | 53.0 |

TABLE 1-continued

| ID | Structure | | | | | | |
|---|---|---|---|---|---|---|---|
| IPK 00013054 | (4-chlorophenyl ketone with methoxyphenyl and dicyano substituents) | 45.8 | 25.3 | 34.8 | 45.1 | 56.7 | 46.5 |
| IPK 00013302 | (3-methoxy-N-(thiazol-2-yl)naphthalene-2-carboxamide) | 27.6 | 18.1 | 90.2 | 68.1 | 49.0 | 35.7 |
| IPK 00013346 | (N-(3-fluorophenyl)-N'-(2-(cyclohex-1-en-1-yl)ethyl)oxalamide) | 45.3 | 22.5 | 40.1 | 57.0 | 38.3 | 40.2 |
| IPK 00013450 | (3-ethyl-5-hydroxy-5-(trifluoromethyl)-1-(isonicotinoyl)-4,5-dihydro-1H-pyrazole) | 70.4 | 0.1 | 95.1 | 64.5 | 71.7 | 34.1 |
| IPK 00013451 | (3-(trifluoromethyl)-5-hydroxy-5-(4-ethylphenyl)-1-(isonicotinoyl)-4,5-dihydro-1H-pyrazole) | 66.7 | 34.9 | 84.3 | 48.7 | 56.3 | 51.4 |
| IPK 00013462 | (3-(4-bromophenyl)-5-(methylsulfonyl)-1,2,4-triazole) | 11.5 | 13.0 | 89.8 | 68.6 | 44.8 | 46.8 |
| IPK 00013463 | (3-(4-chlorophenyl)-5-(methylsulfonyl)-1,2,4-triazole) | 23.9 | 33.9 | 94.1 | 67.3 | 54.0 | 49.9 |

TABLE 1-continued

| ID | Structure | | | | | | |
|---|---|---|---|---|---|---|---|
| IPK00013528 | 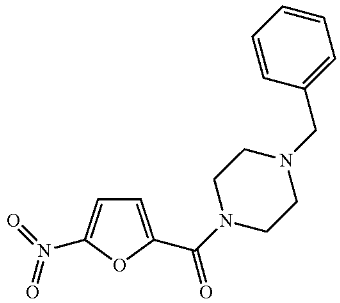 [SMILES: O=C(c1ccc([N+](=O)[O-])o1)N1CCN(Cc2ccccc2)CC1] | 17.5 | 2.9 | 99.0 | 73.2 | 56.9 | 46.4 |
| IPK00013812 | 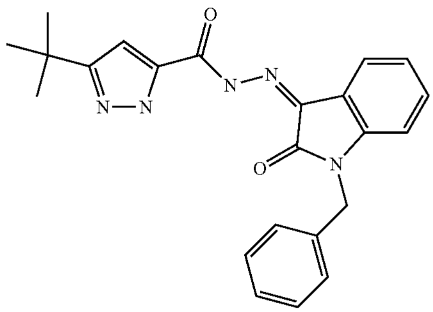 [SMILES: CC(C)(C)c1cc(C(=O)N/N=C2\C(=O)N(Cc3ccccc3)c3ccccc32)[nH]n1] | 92.8 | 16.4 | 98.8 | 67.5 | 90.8 | 37.7 |
| IPK00013840 | 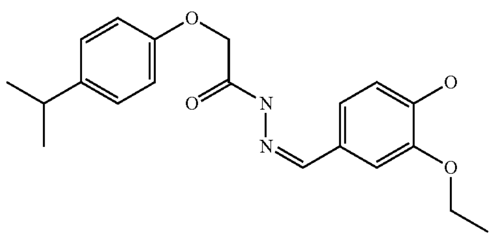 [SMILES: CCOc1cc(/C=N\NC(=O)COc2ccc(C(C)C)cc2)ccc1O] | 35.4 | 2.8 | −1.0 | 52.4 | 47.7 | 44.6 |
| IPK00013843 | 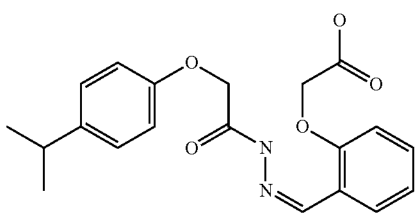 [SMILES: CC(C)c1ccc(OCC(=O)N/N=C\c2ccccc2OCC(=O)O)cc1] | 25.3 | 6.6 | 16.0 | 47.9 | 22.9 | 48.3 |
| IPK00013917 | 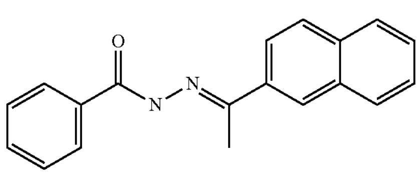 [SMILES: C/C(=N\NC(=O)c1ccccc1)c1ccc2ccccc2c1] | 38.1 | 40.8 | 33.8 | 70.4 | 54.4 | 52.3 |
| IPK00014081 | 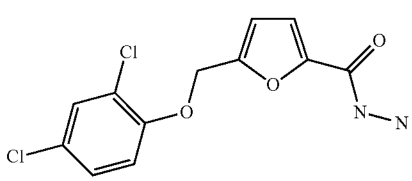 [SMILES: NNC(=O)c1ccc(COc2ccc(Cl)cc2Cl)o1] | 51.8 | 11.0 | 12.0 | 37.9 | 35.4 | 35.4 |
| IPK00014087 | 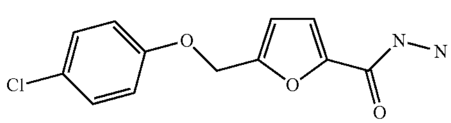 [SMILES: NNC(=O)c1ccc(COc2ccc(Cl)cc2)o1] | 71.8 | 5.9 | 17.0 | 41.7 | 41.3 | 30.4 |

TABLE 1-continued
| ID | Structure | | | | | | |
|---|---|---|---|---|---|---|---|
| IPK 00014108 | 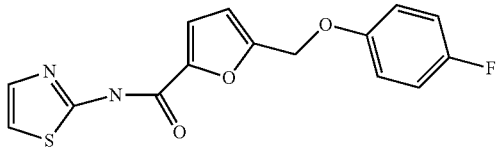 [SMILES: O=C(Nc1nccs1)c1ccc(COc2ccc(F)cc2)o1] | 11.7 | 4.6 | 13.8 | 34.5 | 47.8 | 41.3 |
| IPK 00014158 | 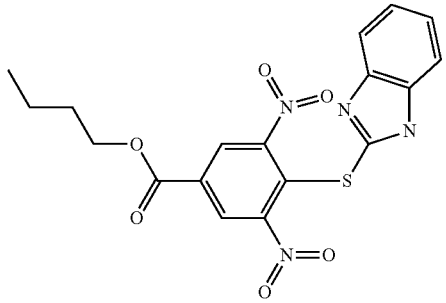 [SMILES: CCCCOC(=O)c1cc([N+](=O)[O-])c(Sc2nc3ccccc3[nH]2)c([N+](=O)[O-])c1] | −2.2 | −14.1 | 92.7 | 95.9 | 45.3 | 42.9 |
| IPK 00014161 | 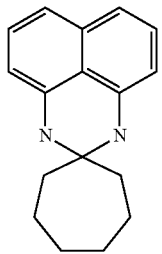 | 23.0 | 10.3 | 87.4 | 83.4 | 46.7 | 45.5 |
| IPK 00014217 | 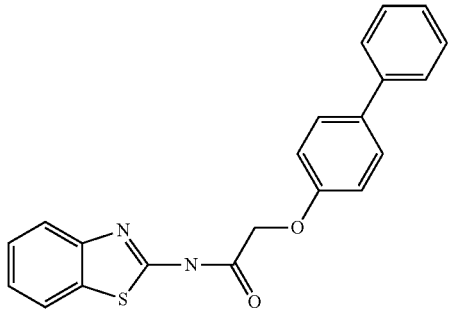 [SMILES: O=C(COc1ccc(-c2ccccc2)cc1)Nc1nc2ccccc2s1] | 18.5 | 28.7 | 14.6 | 54.3 | 35.1 | 42.9 |
| IPK 00014218 | 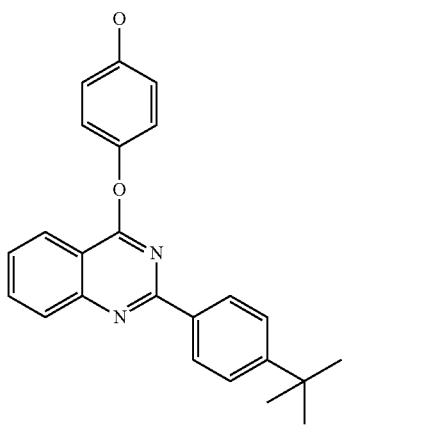 [SMILES: CC(C)(C)c1ccc(-c2nc(Oc3ccc(O)cc3)c3ccccc3n2)cc1] | 20.6 | 0.5 | −1.3 | 38.3 | 39.8 | 39.4 |

TABLE 1-continued

| ID | Structure | | | | | | |
|---|---|---|---|---|---|---|---|
| IPK 000 143 45 | phenyl 5-tert-butyl-2-hydroxybenzoate | 60.3 | 14.4 | 11.5 | 72.5 | 50.0 | 38.3 |
| IPK 000 144 22 | 4-(4-methoxyphenyl)-2-(pyridin-3-yl)thiazole | 38.5 | 16.6 | 72.1 | 82.4 | 38.7 | 35.9 |
| IPK 000 146 91 | 1-(3-fluorophenyl)-3-(4-(trifluoromethyl)phenyl)urea | 57.2 | 4.4 | 99.5 | 100.7 | 40.9 | 40.7 |
| IPK 000 146 98 | 1-(4-chlorophenyl)-3-(4-(trifluoromethyl)phenyl)urea | 26.2 | −2.8 | 100.3 | 70.3 | 35.1 | 37.6 |
| IPK 000 147 17 | 1-(4-fluorophenyl)-3-(4-(trifluoromethyl)phenyl)urea | 47.2 | 22.9 | 98.7 | 74.3 | 40.4 | 45.1 |

TABLE 1-continued

| ID | Structure | | | | | | |
|---|---|---|---|---|---|---|---|
| IPK00014754 | (3-chlorophenyl)-(4-trifluoromethylphenyl)urea | 13.0 | 26.0 | 92.6 | 66.8 | 48.9 | 42.9 |
| IPK00014798 | 2-(3-chlorophenoxy)-N'-[(5-nitrofuran-2-yl)methylene]acetohydrazide | 40.7 | 15.4 | 99.3 | 98.1 | 37.2 | 39.9 |
| IPK00014804 | 2-(4-fluorophenoxy)-N'-[(5-nitrofuran-2-yl)methylene]acetohydrazide | 26.8 | 17.7 | 98.0 | 67.6 | 46.8 | 48.9 |
| IPK00014811 | 2-[4-(pentan-2-yl)phenoxy]-N'-[(thiophen-3-yl)methylene]acetohydrazide | 25.3 | 31.9 | 14.0 | 36.6 | 43.7 | 49.4 |

TABLE 1-continued
| | | | | | | | |
|---|---|---|---|---|---|---|---|
| IPK 000 148 44 | 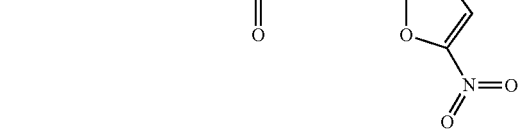 | 14.9 | 11.0 | 98.4 | 67.1 | 43.4 | 41.7 |
| IPK 000 148 64 | 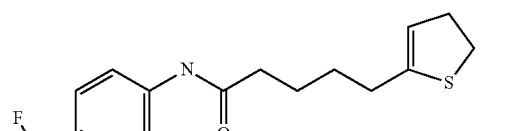 | 40.3 | 3.7 | 29.2 | 42.0 | 35.3 | 46.5 |
| IPK 000 148 65 |  | 17.1 | 6.4 | 99.1 | 65.1 | 43.4 | 43.1 |
| IPK 000 149 02 | 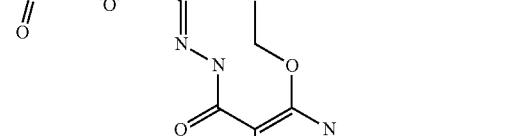 | 49.7 | 13.5 | 99.1 | 66.8 | 69.8 | 45.8 |
| IPK 000 149 44 | 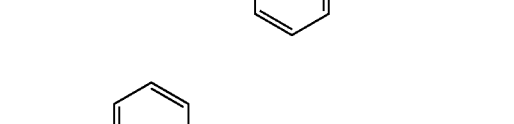 | 21.2 | −10.4 | 100.0 | 70.4 | 43.0 | 27.1 |

TABLE 1-continued

| ID | Structure | | | | | | |
|---|---|---|---|---|---|---|---|
| IPK 000 149 78 | (phenoxyacetohydrazide N'-[(5-nitrofuran-2-yl)methylene]) | 12.3 | 9.6 | 99.6 | 74.4 | 56.2 | 49.9 |
| IPK 000 150 41 | (N-(4-bromo-2-fluorophenyl)-2-(4,5-dihydro-1,3-thiazol-2-ylsulfanyl)acetamide) | 24.2 | 5.2 | 31.8 | 44.6 | 46.3 | 35.9 |
| IPK 000 150 48 | (5-nitro-2H-tetrazol-2-yl propan-2-one (2,4,6-trichlorophenyl)hydrazone) | −2.3 | 26.4 | 95.6 | 69.8 | 46.4 | 52.3 |
| IPK 000 150 85 | (2-(3,5-dinitrophenyl)-5-phenyl-1,3,4-oxadiazole) | 33.8 | 5.1 | 23.0 | 93.2 | 58.8 | 40.4 |
| IPK 000 155 36 | ((5-nitrothiophen-2-yl)methanediyl diacetate) | 43.7 | −8.6 | 88.3 | 68.3 | 29.0 | 33.2 |
| IPK 000 157 51 | (N'-[(3-bromo-4-(2-chlorobenzyloxy)-5-methoxyphenyl)methylene]isonicotinohydrazide) | 100.9 | 39.7 | 99.3 | 47.4 | 82.2 | 47.2 |

TABLE 1-continued
| | | | | | | | |
|---|---|---|---|---|---|---|---|
| IPK 00015755 | 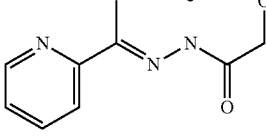 | 77.5 | 39.0 | 97.6 | 77.0 | 55.2 | 45.1 |
| IPK 00015849 | 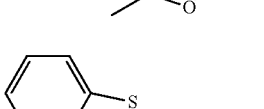 | −0.8 | 8.4 | 66.6 | 69.1 | 44.3 | 43.2 |
| IPK 00016045 | 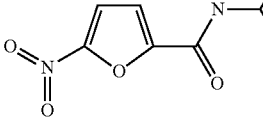 | 43.2 | 31.7 | 17.6 | 25.1 | 30.9 | 45.0 |
| IPK 00016132 | 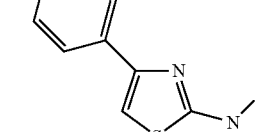 | 25.1 | 9.4 | 99.1 | 63.7 | 95.8 | 52.1 |
| IPK 00016327 | 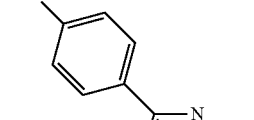 | 71.8 | 33.5 | 86.4 | 45.6 | 55.6 | 47.7 |
| IPK 00016351 | 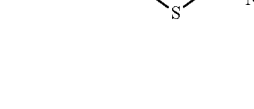 | 82.7 | 40.8 | 92.9 | 68.6 | 57.2 | 52.8 |

TABLE 1-continued
| | | | | | | | |
|---|---|---|---|---|---|---|---|
| IPK 00016352 | 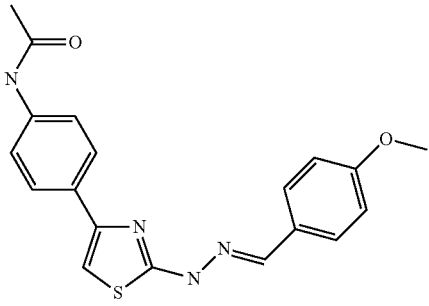 [SMILES: COc1ccc(/C=N/Nc2nc(-c3ccc(NC(C)=O)cc3)cs2)cc1] | 61.4 | 43.7 | 83.0 | 64.6 | 46.4 | 44.3 |
| IPK 00016362 | 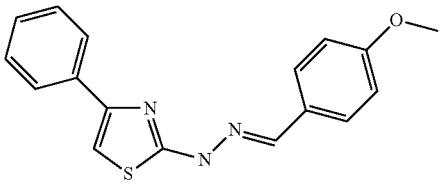 [SMILES: COc1ccc(/C=N/Nc2nc(-c3ccccc3)cs2)cc1] | 59.4 | 49.8 | 95.9 | 68.1 | 54.8 | 47.8 |
| IPK 00016364 | 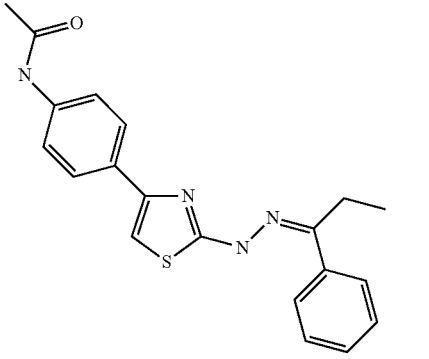 [SMILES: CC/C(=N/Nc1nc(-c2ccc(NC(C)=O)cc2)cs1)c1ccccc1] | 26.7 | 14.7 | 20.8 | 63.3 | 47.4 | 49.9 |
| IPK 00016367 | 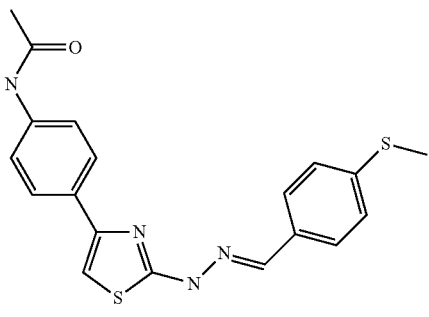 | 70.7 | 27.4 | 76.2 | 65.3 | 44.7 | 47.9 |
| IPK 00016393 | 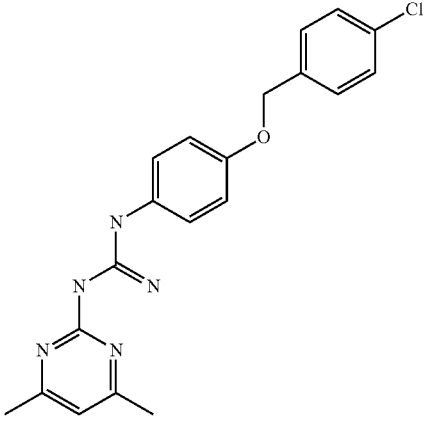 [SMILES: Cc1cc(C)nc(NC(=N)Nc2ccc(OCc3ccc(Cl)cc3)cc2)n1] | 36.3 | 45.5 | 30.4 | 50.1 | 34.2 | 31.3 |

TABLE 1-continued
| | | | | | | | |
|---|---|---|---|---|---|---|---|
| IPK 000 164 52 | 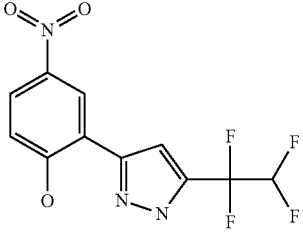 [SMILES: O=[N+]([O-])c1ccc(O)c(-c2cc(C(F)(F)C(F)F)[nH]n2)c1] | -2.2 | 0.1 | 91.8 | 86.8 | 36.5 | 38.7 |
| IPK 000 167 54 | 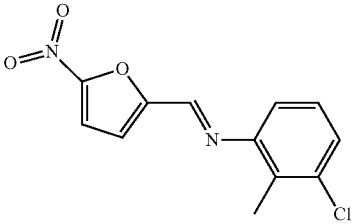 [SMILES: Cc1c(Cl)cccc1/N=C/c1ccc([N+](=O)[O-])o1] | 27.7 | 23.2 | 74.3 | 98.3 | 34.3 | 33.3 |
| IPK 000 168 10 | 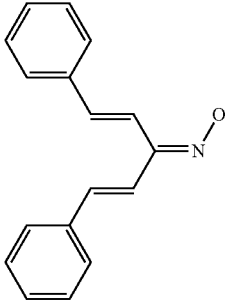 [SMILES: ON=C(/C=C/c1ccccc1)/C=C/c1ccccc1] | 17.9 | 8.2 | 100.2 | 54.4 | 38.1 | 43.5 |
| IPK 000 168 31 | 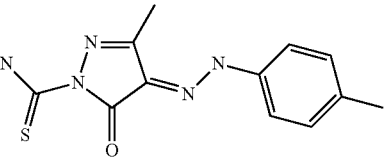 [SMILES: CC1=NN(C(N)=S)C(=O)/C1=N/Nc1ccc(C)cc1] | 20.6 | 15.7 | 15.9 | 29.3 | 38.8 | 32.3 |
| IPK 000 168 32 | 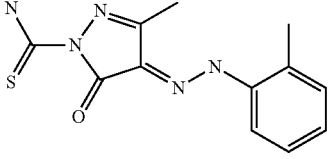 [SMILES: CC1=NN(C(N)=S)C(=O)/C1=N/Nc1ccccc1C] | 37.2 | 18.3 | 50.5 | 29.5 | 31.5 | 35.6 |
| IPK 000 169 30 | 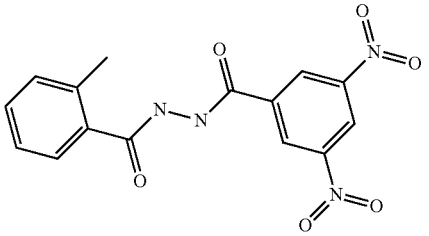 [SMILES: Cc1ccccc1C(=O)NNC(=O)c1cc([N+](=O)[O-])cc([N+](=O)[O-])c1] | 12.4 | 8.8 | 99.3 | 99.4 | 62.8 | 42.8 |
| IPK 000 169 42 | 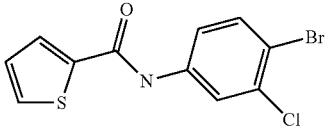 [SMILES: O=C(Nc1ccc(Br)c(Cl)c1)c1cccs1] | 32.9 | 8.5 | 95.2 | 45.0 | 44.0 | 44.8 |

TABLE 1-continued

| ID | Structure | | | | | | |
|---|---|---|---|---|---|---|---|
| IPK00016968 | 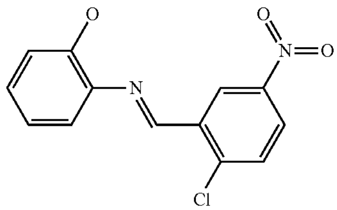 [SMILES: O=[N+]([O-])c1ccc(Cl)c(/C=N/c2ccccc2O)c1] | -5.9 | 16.8 | 99.1 | 65.3 | 43.9 | 45.5 |
| IPK00016976 | 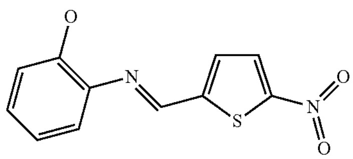 [SMILES: O=[N+]([O-])c1ccc(/C=N/c2ccccc2O)s1] | 2.1 | 16.4 | 99.6 | 100.3 | 31.4 | 30.7 |
| IPK00016986 | 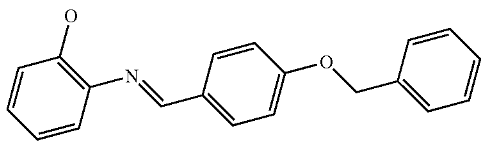 [SMILES: Oc1ccccc1/N=C/c1ccc(OCc2ccccc2)cc1] | 14.4 | 31.1 | 100.9 | 100.3 | 43.7 | 34.8 |
| IPK00016996 | 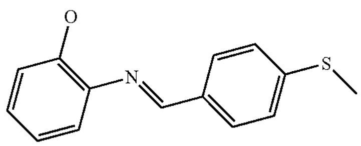 [SMILES: CSc1ccc(/C=N/c2ccccc2O)cc1] | 27.5 | 17.0 | 103.8 | 100.6 | 68.8 | 34.4 |
| IPK00017027 | 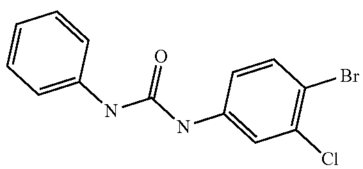 [SMILES: O=C(Nc1ccccc1)Nc1ccc(Br)c(Cl)c1] | 8.1 | 46.9 | 80.7 | 76.3 | 34.0 | 33.5 |
| IPK00017033 | 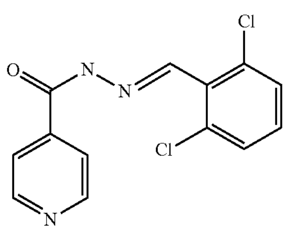 [SMILES: O=C(N/N=C/c1c(Cl)cccc1Cl)c1ccncc1] | 102.5 | 92.7 | 103.5 | 100.2 | 97.4 | 75.7 |
| IPK00017072 | 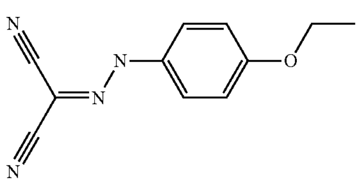 [SMILES: CCOc1ccc(NN=C(C#N)C#N)cc1] | 27.0 | 17.4 | 76.0 | 82.7 | 30.3 | 5.9 |
| IPK00017127 | 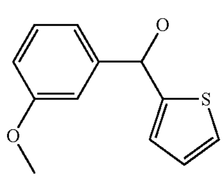 | -1.5 | 9.0 | 99.2 | 82.5 | 59.9 | 40.9 |
| IPK00017146 | 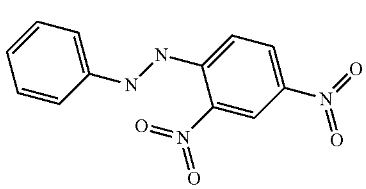 [SMILES: O=[N+]([O-])c1ccc(NNc2ccccc2)c([N+](=O)[O-])c1] | 0.9 | 11.0 | 100.0 | 59.5 | 73.5 | 39.6 |

TABLE 1-continued
| ID | Structure | | | | | | |
|---|---|---|---|---|---|---|---|
| IPK00017184 | 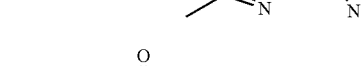 | 29.4 | 16.9 | 99.0 | 98.8 | 46.1 | 31.0 |
| IPK00017234 | 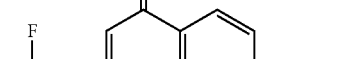 | 18.2 | 7.7 | 98.2 | 69.9 | 45.1 | 37.8 |
| IPK00017235 | 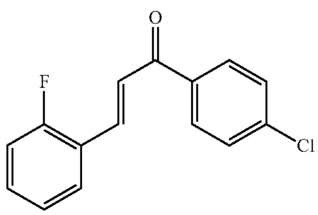 [SMILES: O=C(/C=C/c1ccccc1F)c1ccc(Cl)cc1] | 55.2 | 28.5 | 101.4 | 81.2 | 53.6 | 41.1 |
| IPK00017254 | 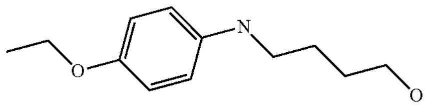 | 14.5 | 11.4 | 82.1 | 92.0 | 40.3 | 36.2 |
| IPK00017306 | 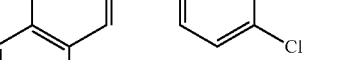 | 9.2 | 26.9 | 74.8 | 73.6 | 58.5 | 44.2 |
| IPK00017345 | 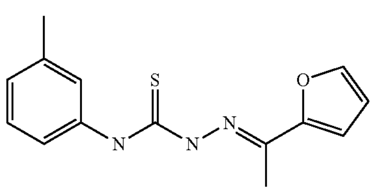 [SMILES: C/C(=N\NC(=S)Nc1cccc(C)c1)c1ccco1] | 25.3 | 24.8 | 103.7 | 71.5 | 72.0 | 46.7 |
| IPK00017527 | 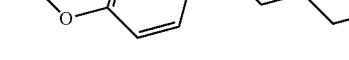 | −3.3 | 25.1 | 95.8 | 70.7 | 46.5 | 39.9 |
| IPK00017824 | 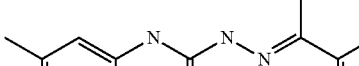 | 6.9 | 1.3 | 74.0 | 97.0 | 37.9 | 34.0 |

TABLE 1-continued
| ID | Structure | | | | | | |
|---|---|---|---|---|---|---|---|
| IPK 000 179 05 | 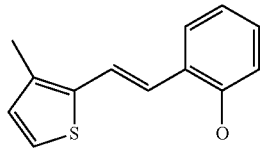 | 30.0 | 27.5 | 101.0 | 100.6 | 81.6 | 24.9 |
| IPK 000 179 49 | 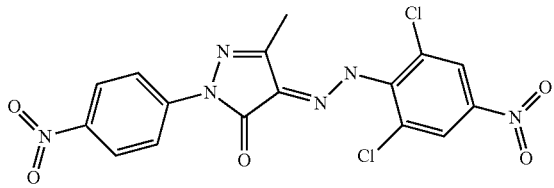 [SMILES: CC1=NN(c2ccc([N+](=O)[O-])cc2)C(=O)/C1=N/Nc1c(Cl)cc([N+](=O)[O-])cc1Cl] | −8.9 | 17.6 | 16.2 | 54.5 | 44.4 | 48.0 |
| IPK 000 180 11 | 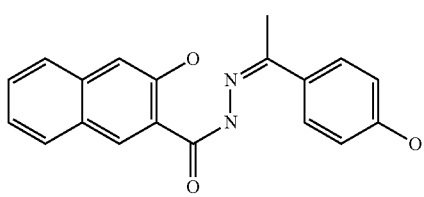 | 26.0 | 9.7 | 14.8 | 28.9 | 40.6 | 44.8 |
| IPK 000 180 16 | 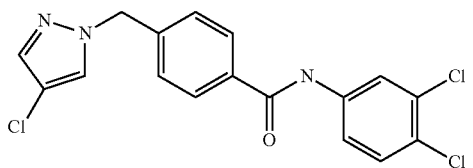 [SMILES: O=C(Nc1ccc(Cl)c(Cl)c1)c1ccc(Cn2cc(Cl)cn2)cc1] | 12.6 | 13.5 | 93.8 | 68.9 | 41.3 | 43.5 |
| IPK 000 180 17 | 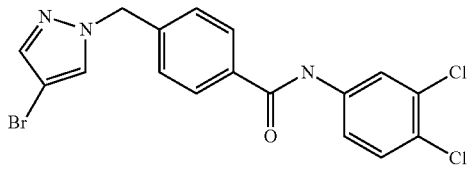 | 20.2 | 8.6 | 93.8 | 72.0 | 29.6 | 50.6 |
| IPK 000 180 76 | 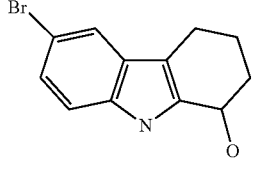 [SMILES: OC1CCCc2c1[nH]c1ccc(Br)cc21] | 37.5 | 43.8 | 90.0 | 63.8 | 40.8 | 32.9 |
| IPK 000 184 56 | 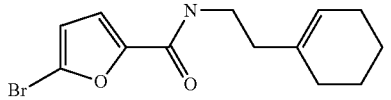 [SMILES: O=C(NCCC1=CCCCC1)c1ccc(Br)o1] | 45.0 | 34.4 | 63.3 | 67.3 | 46.9 | 46.5 |
| IPK 000 192 45 | 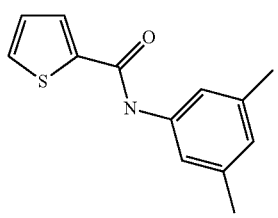 | 22.0 | 16.2 | −9.0 | 42.7 | 43.3 | 42.7 |
| IPK 000 192 59 | 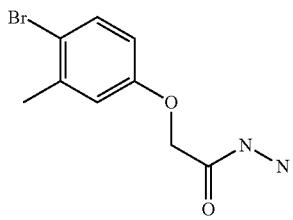 | 30.1 | 10.8 | −8.7 | 41.9 | 31.7 | 42.7 |

TABLE 1-continued
| | | | | | | | |
|---|---|---|---|---|---|---|---|
| IPK 00019376 | 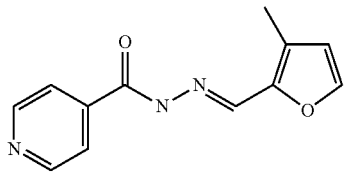 [SMILES: Cc1ccoc1/C=N/NC(=O)c1ccncc1] | 100.4 | 91.9 | 98.6 | 68.4 | 85.6 | 63.9 |
| IPK 00019599 | 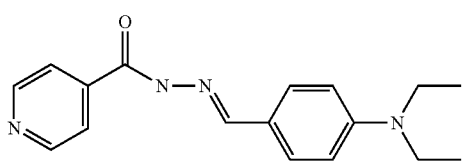 [SMILES: CCN(CC)c1ccc(/C=N/NC(=O)c2ccncc2)cc1] | 105.7 | 96.1 | 98.8 | 74.2 | 97.1 | 70.8 |
| IPK 00019853 | 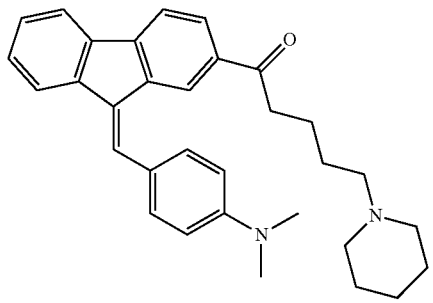 [SMILES: CN(C)c1ccc(/C=C2/c3ccccc3-c3ccc(C(=O)CCCCN4CCCCC4)cc32)cc1] | 10.2 | 1.8 | 97.3 | 66.2 | 29.5 | 34.9 |
| IPK 00019854 | 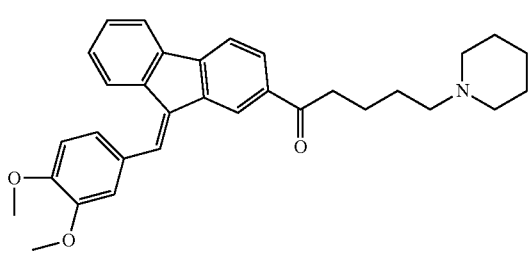 [SMILES: COc1ccc(/C=C2\c3ccccc3-c3ccc(C(=O)CCCCN4CCCCC4)cc32)cc1OC] | 27.3 | 20.3 | 88.8 | 55.5 | 44.6 | 31.6 |
| IPK 00019856 | 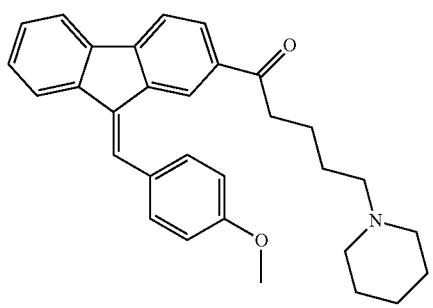 [SMILES: COc1ccc(/C=C2/c3ccccc3-c3ccc(C(=O)CCCCN4CCCCC4)cc32)cc1] | 28.7 | 21.2 | 95.9 | 68.3 | 39.0 | 34.3 |
| IPK 00019970 | 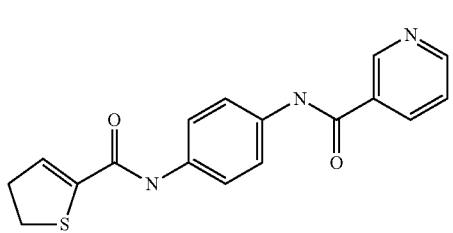 [SMILES: O=C(Nc1ccc(NC(=O)c2cccnc2)cc1)C1=CCCS1] | 11.2 | 23.0 | −8.2 | 39.8 | 43.5 | 49.3 |

TABLE 1-continued

| ID | Structure | | | | | | |
|---|---|---|---|---|---|---|---|
| IPK 000 200 16 | (4-chlorophenyl pyridazine thioacetamide structure) | 2.7 | 1.6 | −16.9 | 50.3 | 42.3 | 40.2 |
| IPK 000 200 47 | (dimethylpyrrole salicylate structure) | 3.5 | 15.8 | 90.3 | 95.0 | 58.9 | 37.1 |
| IPK 000 202 08 | (thiophene carboxamide trifluoromethylphenyl structure) | 18.1 | 23.7 | 4.6 | 28.7 | 38.5 | 39.4 |
| IPK 000 205 22 | (4-fluorobenzamide chloromethylphenyl structure) | 33.2 | 6.2 | 38.2 | 47.4 | 50.0 | 45.5 |
| IPK 000 205 42 | (4-fluorobenzamide methylbenzyl structure) | 58.7 | 19.9 | 44.7 | 47.0 | 65.1 | 51.8 |
| IPK 000 208 53 | (benzodioxole butylcarboxamide structure) | 65.1 | −4.0 | 46.0 | 56.4 | 57.3 | 44.0 |
| IPK 000 210 74 | (isopentyl methylbenzamide structure) | 88.9 | 32.6 | 49.9 | 43.9 | 66.8 | 50.0 |

TABLE 1-continued
| | | | | | | | |
|---|---|---|---|---|---|---|---|
| IPK 000 210 79 | 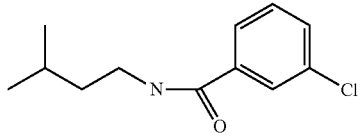 | 71.5 | 25.1 | 43.5 | 48.6 | 58.2 | 49.2 |
| IPK 000 210 83 | 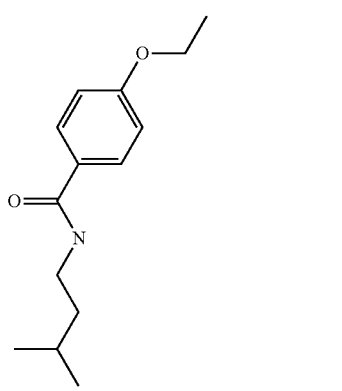 [SMILES: CCOc1ccc(C(=O)NCCC(C)C)cc1] | 71.4 | −5.0 | 49.8 | 52.8 | 62.8 | 50.6 |
| IPK 000 219 26 | 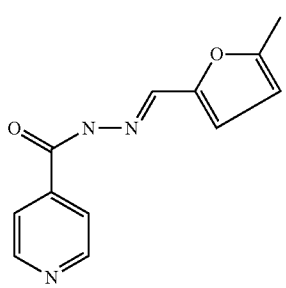 [SMILES: Cc1ccc(/C=N/NC(=O)c2ccncc2)o1] | 98.6 | 63.8 | 98.6 | 46.0 | 84.5 | 45.3 |
| IPK 000 219 27 | 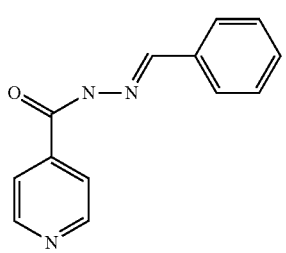 [SMILES: O=C(N/N=C/c1ccccc1)c1ccncc1] | 104.8 | 78.1 | 98.7 | 70.3 | 85.0 | 47.6 |
| IPK 000 219 28 | 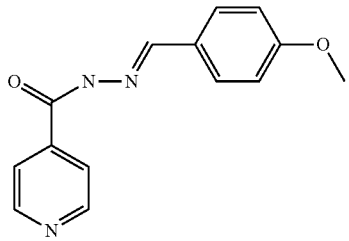 [SMILES: COc1ccc(/C=N/NC(=O)c2ccncc2)cc1] | 98.1 | 57.6 | 98.0 | 40.9 | 83.1 | 42.4 |
| IPK 000 219 29 | 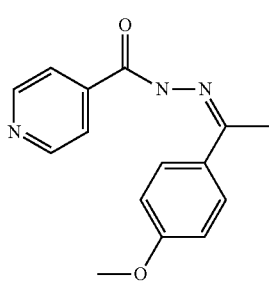 [SMILES: COc1ccc(/C(C)=N\NC(=O)c2ccncc2)cc1] | 95.1 | 18.5 | 99.3 | 32.9 | 84.5 | 46.5 |

TABLE 1-continued
| | | | | | | | |
|---|---|---|---|---|---|---|---|
| IPK 000 219 30 | 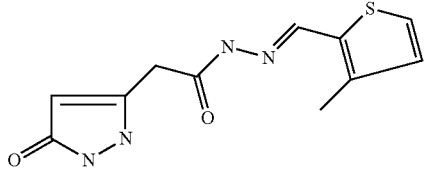 [SMILES: Cc1ccsc1/C=N/NC(=O)Cc1cc(=O)[nH][nH]1] | 101.1 | 13.0 | 99.5 | 99.7 | 82.9 | 44.9 |
| IPK 000 222 00 | 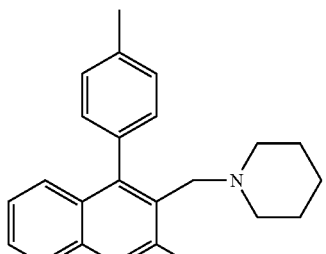 | 29.9 | 3.6 | 82.3 | 19.7 | 26.8 | 30.8 |
| IPK 000 222 04 | 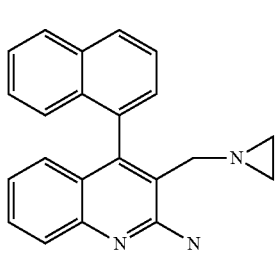 [SMILES: Nc1nc2ccccc2c(-c2cccc3ccccc23)c1CN1CC1] | 69.0 | 40.1 | 54.9 | 78.1 | 21.1 | 30.0 |
| IPK 000 222 32 | 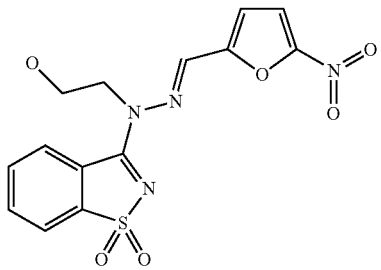 [SMILES: O=[N+]([O-])c1ccc(/C=N/N(CCO)C2=NS(=O)(=O)c3ccccc32)o1] | 53.1 | 14.4 | 102.4 | 96.7 | 47.9 | 40.7 |
| IPK 000 224 59 | 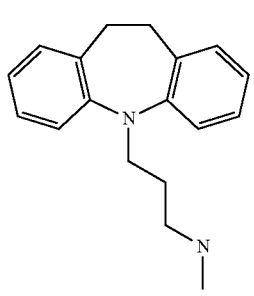 [SMILES: CNCCCN1c2ccccc2CCc2ccccc21] | 41.8 | 14.9 | 30.0 | 31.5 | 37.7 | 45.7 |
| IPK 000 228 46 | 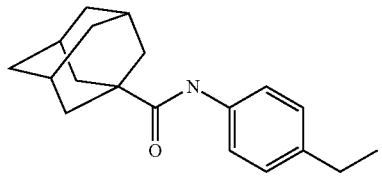 [SMILES: CCc1ccc(NC(=O)C23CC4CC(CC(C4)C2)C3)cc1] | 67.1 | 38.9 | 97.5 | 41.0 | 47.1 | 25.0 |
| IPK 000 229 50 | 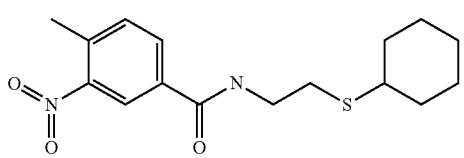 [SMILES: Cc1ccc(C(=O)NCCSC2CCCCC2)cc1[N+](=O)[O-]] | 21.6 | 24.6 | 99.6 | 28.1 | 39.7 | 36.6 |

TABLE 1-continued
| | | | | | | | |
|---|---|---|---|---|---|---|---|
| IPK 00022972 | 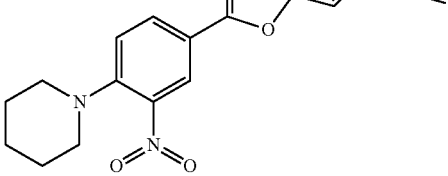 | 83.2 | 19.6 | 16.9 | 30.0 | 45.7 | 27.1 |
| IPK 00023002 | 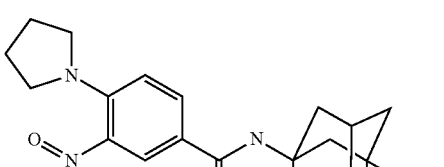 | 78.8 | 19.0 | 95.7 | 41.9 | 44.6 | 40.5 |
| IPK 00023461 | 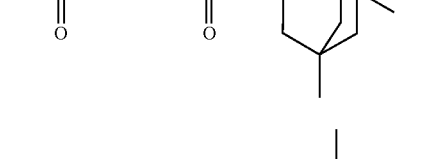 | −5.8 | 14.6 | 67.9 | 76.3 | 42.7 | 37.4 |
| IPK 00023509 | 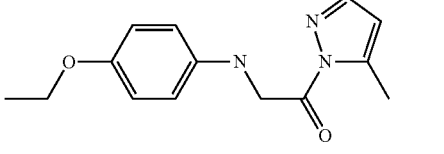 | 32.6 | 3.9 | 98.8 | 45.4 | 70.1 | 22.4 |
| IPK 00023512 | 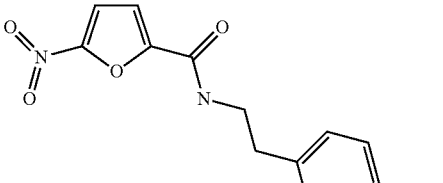 | 31.9 | 34.9 | 99.4 | 71.1 | 48.7 | 40.9 |
| IPK 00023891 | 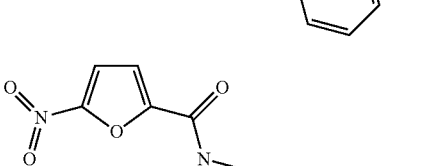 | 78.4 | −6.0 | 96.7 | 70.1 | 43.2 | 28.6 |

TABLE 1-continued

| ID | Structure | | | | | | |
|---|---|---|---|---|---|---|---|
| IPK 000 240 37 | 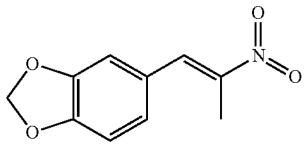 | 11.6 | −10.9 | 104.1 | 76.2 | 37.9 | 30.6 |
| IPK 000 241 72 | 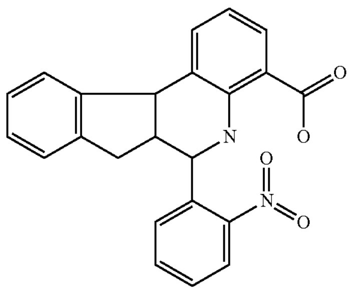 [SMILES: O=C(O)c1cccc2c1NC(c1ccccc1[N+](=O)[O-])C1Cc3ccccc3C21] | 67.1 | 53.6 | 100.4 | 97.2 | 92.6 | 68.9 |
| IPK 000 244 12 | 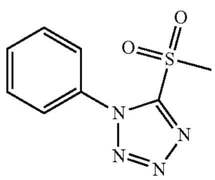 | 60.1 | 0.5 | 98.4 | 75.7 | 66.8 | 42.3 |
| IPK 000 247 44 | 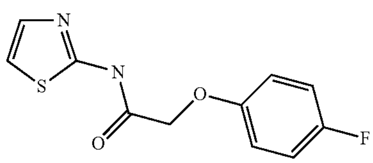 [SMILES: O=C(COc1ccc(F)cc1)Nc1nccs1] | 17.5 | 12.3 | −12.2 | 23.8 | 30.8 | 34.7 |
| IPK 000 248 71 | 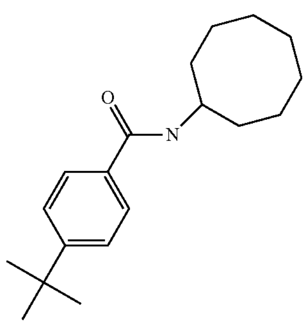 [SMILES: CC(C)(C)c1ccc(C(=O)NC2CCCCCCC2)cc1] | 73.4 | 21.5 | 99.2 | 41.6 | 70.4 | 40.5 |
| IPK 000 249 12 | 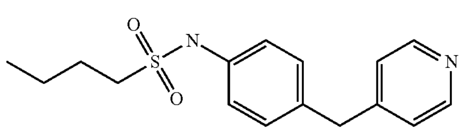 [SMILES: CCCCS(=O)(=O)Nc1ccc(Cc2ccncc2)cc1] | 41.8 | 7.8 | 94.3 | 86.2 | 56.8 | 41.7 |
| IPK 000 249 14 | 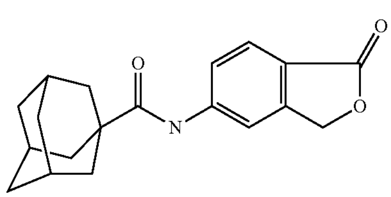 [SMILES: O=C1OCc2cc(NC(=O)C34CC5CC(CC(C5)C3)C4)ccc21] | 41.9 | 21.0 | 96.3 | 37.4 | 40.3 | 43.3 |

TABLE 1-continued
| | | | | | | | |
|---|---|---|---|---|---|---|---|
| IPK 000 249 84 | 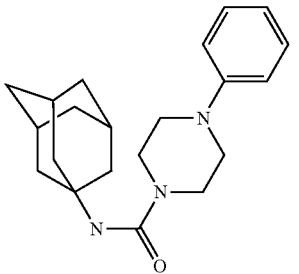 [SMILES: O=C(NC12CC3CC(CC(C3)C1)C2)N1CCN(c2ccccc2)CC1] | −4.9 | 21.4 | 86.0 | 64.6 | 46.3 | 45.8 |
| IPK 000 251 49 | 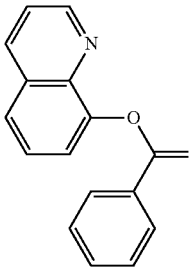 | 18.0 | 0.8 | 92.6 | 65.1 | 55.1 | 44.5 |
| IPK 000 251 80 | 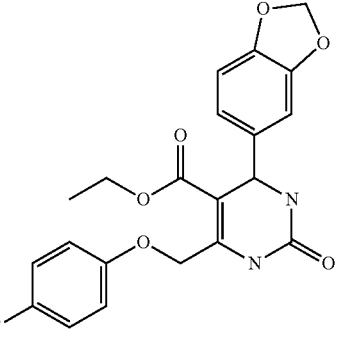 | 9.2 | 3.9 | 77.6 | 69.2 | 64.3 | 48.0 |
| IPK 000 254 12 | 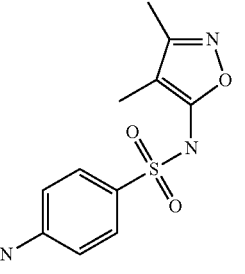 | 13.1 | −11.6 | 90.9 | 66.4 | 43.8 | 43.0 |
| IPK 000 254 25 | 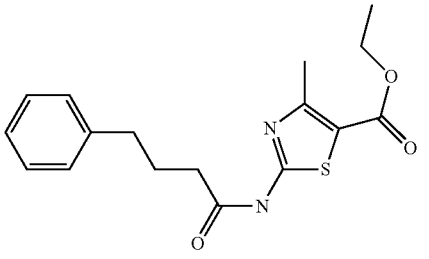 [SMILES: CCOC(=O)c1sc(NC(=O)CCCc2ccccc2)nc1C] | 20.0 | 20.5 | 100.5 | 75.6 | 53.2 | 49.1 |

TABLE 1-continued

| ID | Structure | | | | | | |
|---|---|---|---|---|---|---|---|
| IPK 000 255 46 | (ethyl 2-(3-cyclohexylpropanamido)-4-methylthiazole-5-carboxylate) | 54.7 | 32.6 | 96.3 | 68.7 | 64.7 | 31.8 |
| IPK 000 257 61 | (N-(3-ethylphenyl)thiophene-2-carboxamide) | 42.1 | 15.8 | 31.8 | 60.5 | 28.1 | 33.2 |
| IPK 000 258 07 | (1-cyclohexyl-5-((4-nitrobenzyl)thio)-1H-tetrazole) | 26.2 | 9.4 | 98.4 | 47.9 | 36.8 | 37.0 |
| IPK 000 259 35 | (3-(phenyl(1H-benzimidazol-2-yl)methylene)indolin-2-one) | 12.0 | 5.3 | 10.9 | 28.4 | 42.5 | 40.2 |
| IPK 000 259 78 | (1-(2,3-difluoro-6-nitrophenoxy)propan-2-one) | 11.0 | 14.9 | 91.4 | 83.6 | 25.0 | 30.2 |

TABLE 1-continued

| | | | | | | | |
|---|---|---|---|---|---|---|---|
| IPK 00026207 | | 89.0 | 40.1 | 99.0 | 34.3 | 61.4 | 45.9 |
| IPK 00026239 | | 48.7 | 20.4 | 98.5 | 75.4 | 60.0 | 43.8 |

TABLE 3

| Scaffold Name | Scaffold Coding | Number of Compounds | Scaffold Structure |
|---|---|---|---|
| Isonicotinohydrazides | I | 69 | |
| Benzamides | II | 19 | |
| Thiazolhydrazides | III | 6 | |
| Hydrazinecarbothioamides | IV | 5 | |

TABLE 3-continued
| Scaffold Name | Scaffold Coding | Number of Compounds | Scaffold Structure |
| --- | --- | --- | --- |
| Furancarbohydrazides | V | 4 | 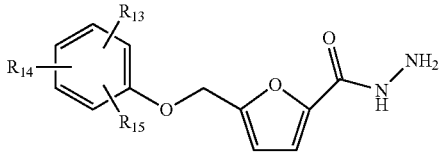 |
| Thiophenes | VI | 3 | 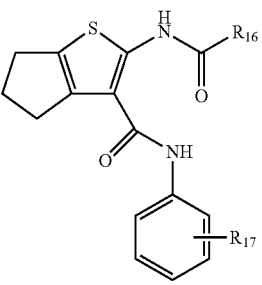 |
| Pyrazole-pyridines | VII | 2 | 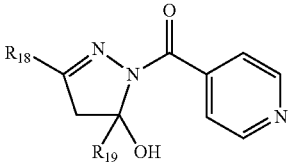 |
| Pyridopyrimidinone | VIII | 1 | 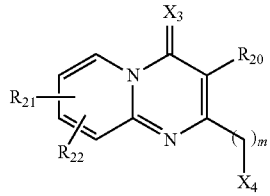 |
| One hit compound | IX | 1 | 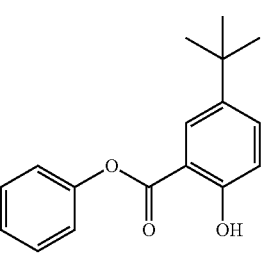 [SMILES: CC(C)(C)c1ccc(O)c(C(=O)Oc2ccccc2)c1] |
| One hit compound | X | 1 | 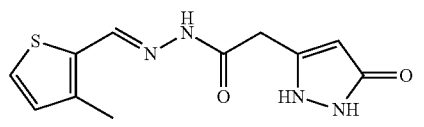 [SMILES: Cc1ccsc1/C=N/NC(=O)Cc1cc(=O)[nH][nH]1] |

TABLE 3-continued

| Scaffold Name | Scaffold Coding | Number of Compounds | Scaffold Structure |
|---|---|---|---|
| One hit compound | XI | 1 | |
| One hit compound | XII | 1 | |
| One hit compound | XIII | 1 | |
| One hit compound | XIV | 1 | |
| One hit compound | XV | 1 | |
| One hit compound | XVI | 1 | |

TABLE 3-continued

| Scaffold Name | Scaffold Coding | Number of Compounds | Scaffold Structure |
|---|---|---|---|
| One hit compound | XVII | 1 | |
| One hit compound | XVIII | 1 | |
| One hit compound | XIX | 1 | |
| One hit compound | XX | 1 | |

TABLE 4

| Compound | QIM (µM) | QUM (µM) |
|---|---|---|
| 1 | +++ | +++ |
| 2 | ++ | +++ |

TABLE 4-continued
| Compound | QIM (μM) | QUM (μM) |
|---|---|---|
| 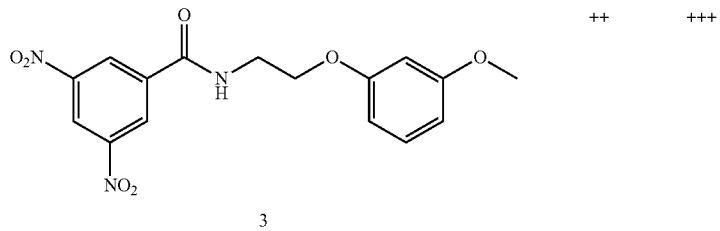 3 | ++ | +++ |
| 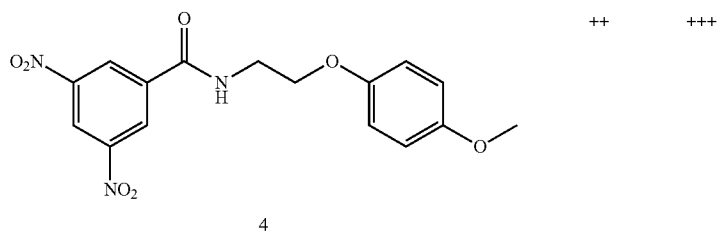 4 | ++ | +++ |
| 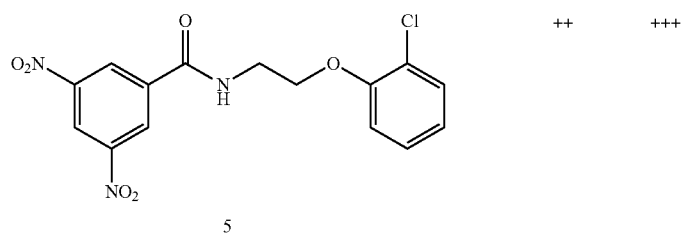 5 | ++ | +++ |
| 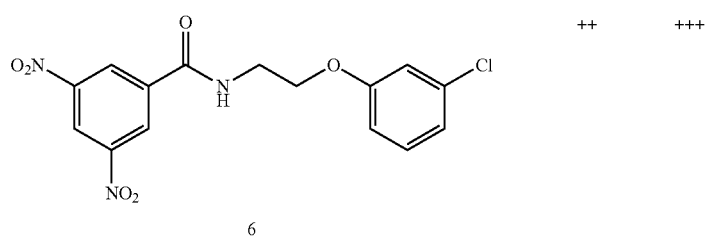 6 | ++ | +++ |
| 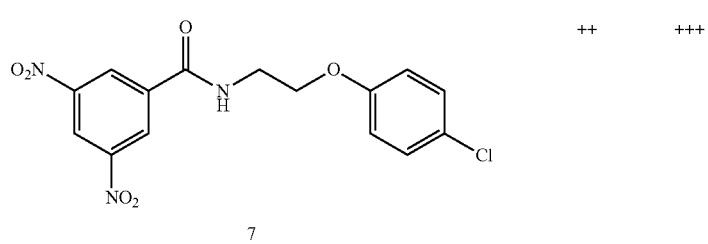 7 | ++ | +++ |
| 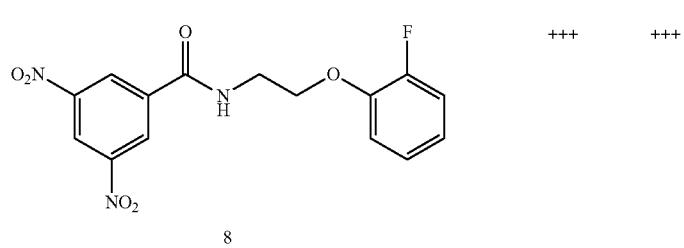 8 | +++ | +++ |

TABLE 4-continued
| Compound | QIM (μM) | QUM (μM) |
|---|---|---|
| 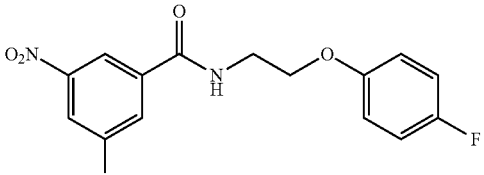 9 | ++ | +++ |
| 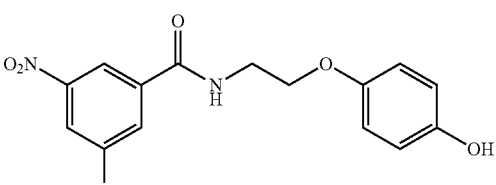 10 | ++ | +++ |
| 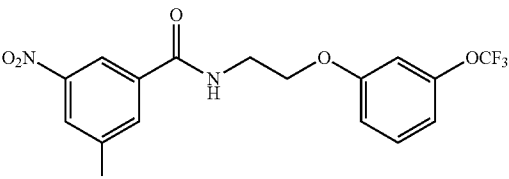 11 | +++ | +++ |
| 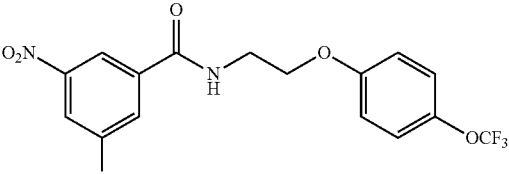 12 | +++ | +++ |
| 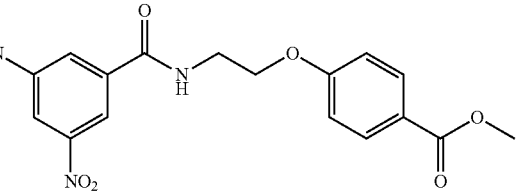 13 | ++ | +++ |
| 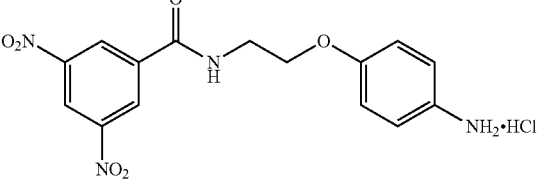 14 | ++ | ++ |

TABLE 4-continued

| Compound | QIM (μM) | QUM (μM) |
|---|---|---|
| 15 | ++ | +++ |
| 16 | + | + |
| 17 | + | + |
| 18 | + | + |
| 19 | + | ++ |
| 20 | + | + |

TABLE 4-continued
| Compound | QIM (μM) | QUM (μM) |
|---|---|---|
| 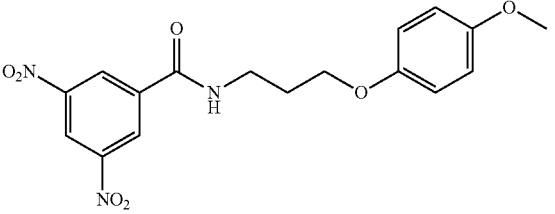 21 | ++ | +++ |
| 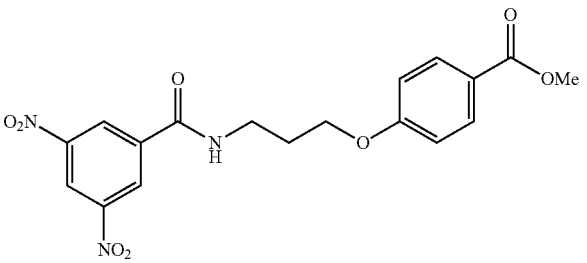 22 | ++ | +++ |
| 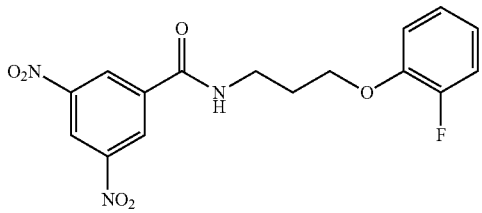 23 | +++ | +++ |
| 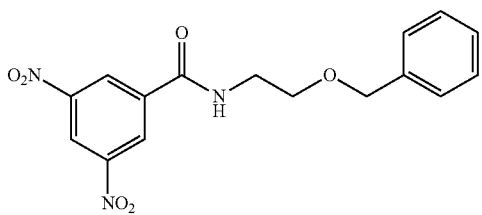 24 | +++ | +++ |
| 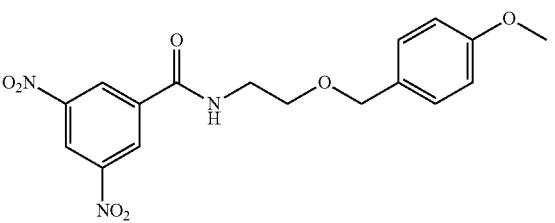 26 | ++ | +++ |
| 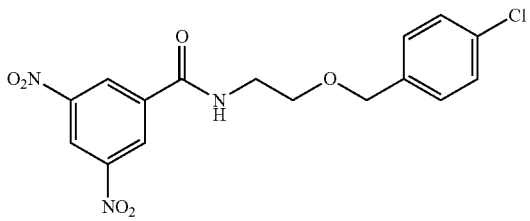 27 | +++ | +++ |

TABLE 4-continued
| Compound | QIM (μM) | QUM (μM) |
|---|---|---|
| 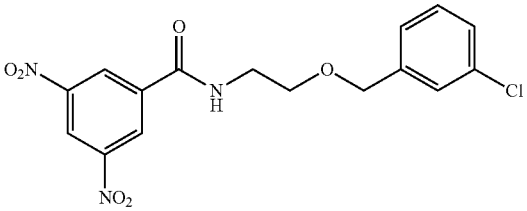 28 | +++ | +++ |
| 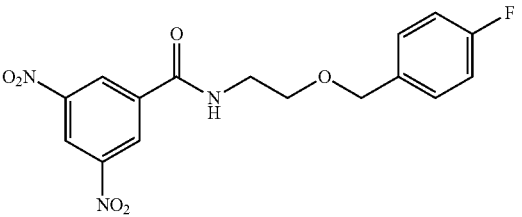 29 | +++ | +++ |
| 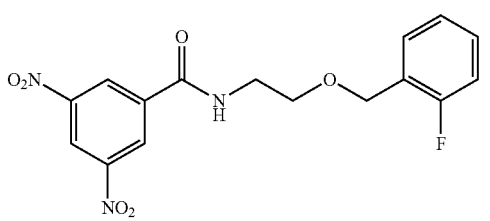 30 | +++ | +++ |
| 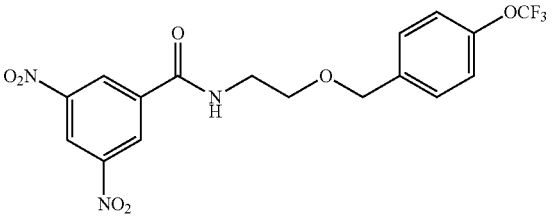 31 | +++ | +++ |
| 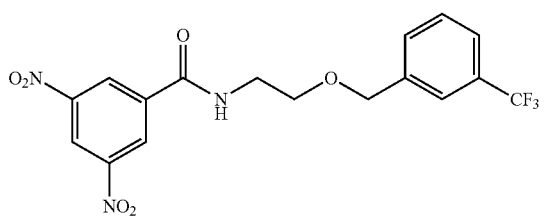 32 | +++ | +++ |
| 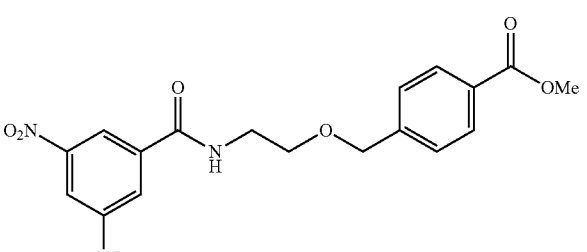 33 | ++ | +++ |

TABLE 4-continued
| Compound | QIM (μM) | QUM (μM) |
|---|---|---|
| 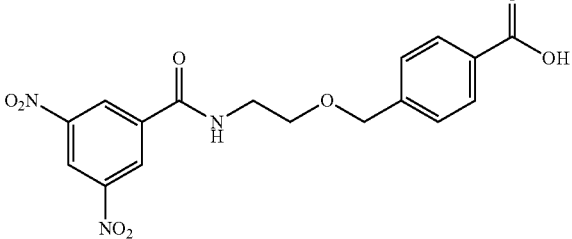 34 | + | + |
| 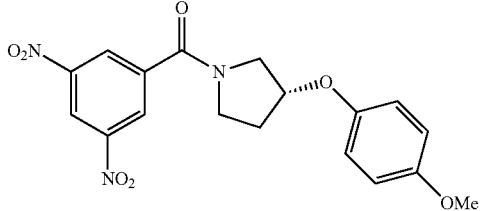 54 | ++ | +++ |
| 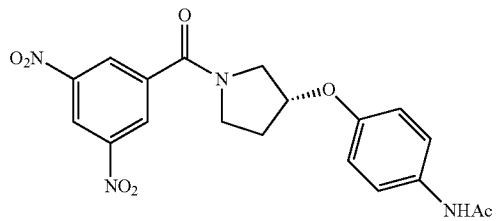 56 | + | ++ |
| 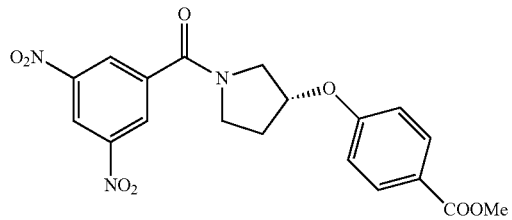 58 | + | +++ |
| 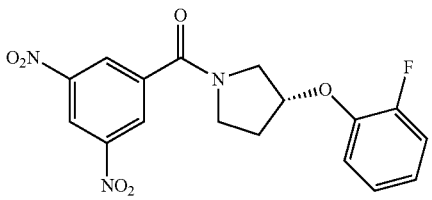 59 | ++ | +++ |
| 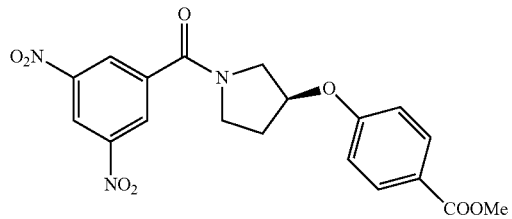 60 | + | +++ |

TABLE 4-continued

| Compound | QIM (μM) | QUM (μM) |
|---|---|---|
| 61 | + | +++ |
| 63 | + | ++ |
| 64 | ++ | +++ |
| 67 | + | + |
| 90 | + | + |
| 91 | ++ | +++ |

TABLE 4-continued
| Compound | QIM (μM) | QUM (μM) |
|---|---|---|
| 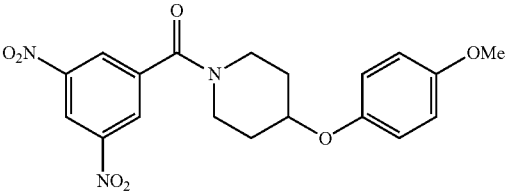<br>92 | + | +++ |
| 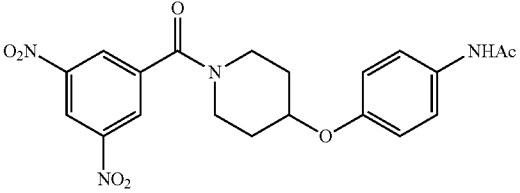<br>93 | + | ++ |
| 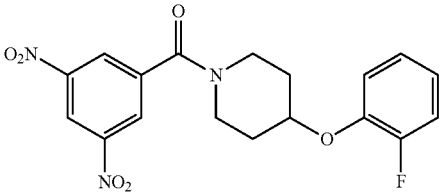<br>94 | ++ | +++ |
| 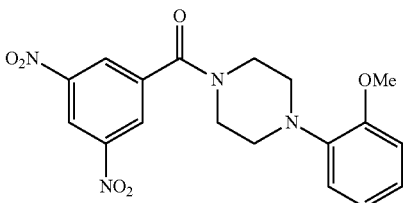<br>95 | + | ++ |
| 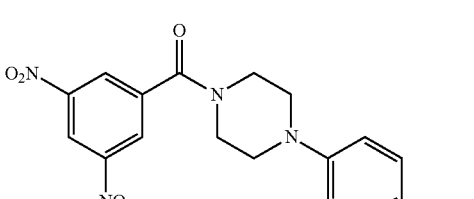<br>96 | ++ | ++ |
| 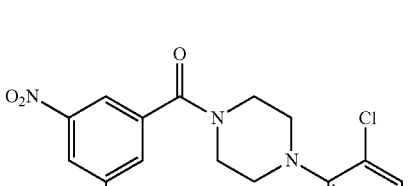<br>97 | + | +++ |

TABLE 4-continued
| Compound | QIM (μM) | QUM (μM) |
|---|---|---|
| 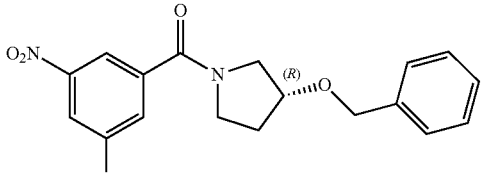 98 | + | ++ |
| 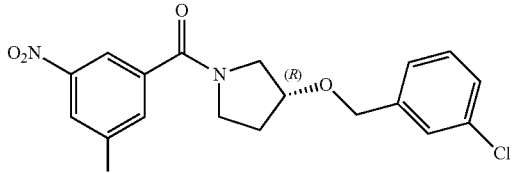 99 | + | ++ |
| 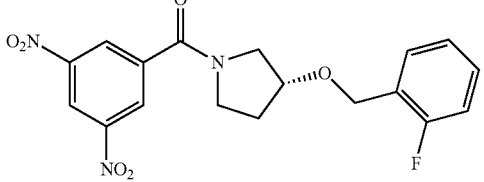 100 | + | +++ |
| 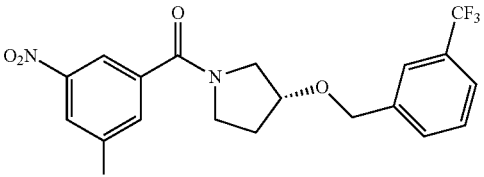 101 | + | ++ |
| 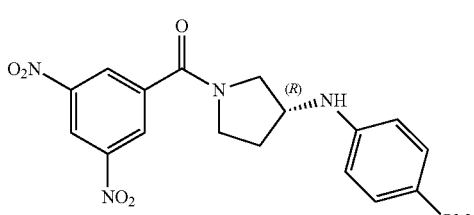 103 | ++ | +++ |
| 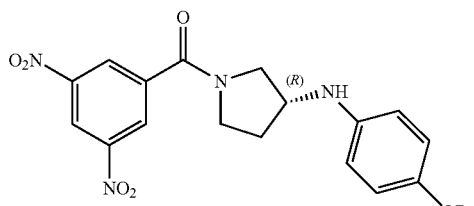 104 | ++ | +++ |

TABLE 4-continued
| Compound | QIM (μM) | QUM (μM) |
|---|---|---|
| 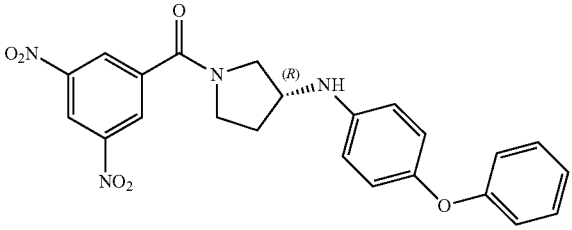 105 | +++ | ++ |
| 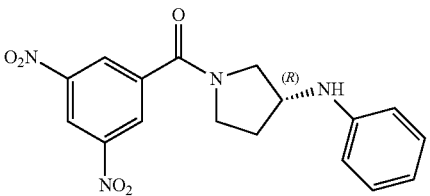 107 | ++ | +++ |
| 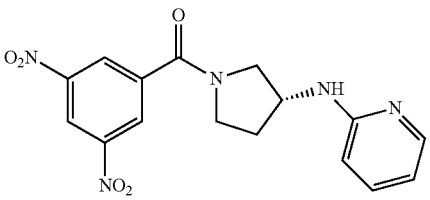 108 | ++ | +++ |
| 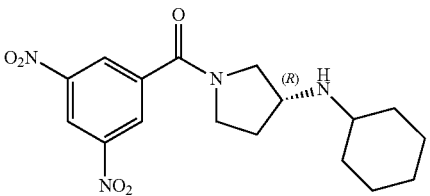 109 | + | + |
| 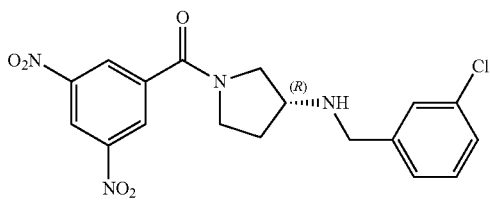 112 | + | ++ |
| 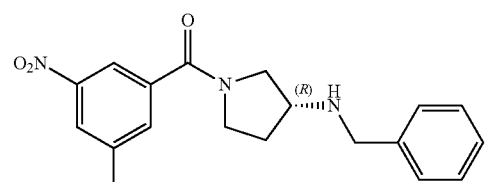 114 | + | ++ |

TABLE 4-continued
| Compound | QIM (μM) | QUM (μM) |
|---|---|---|
| 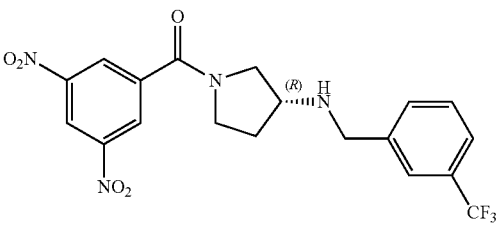 115 | + | ++ |
| 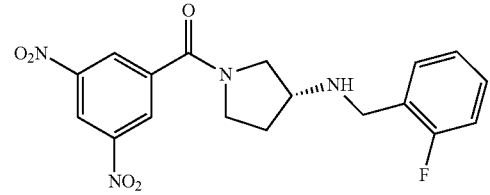 116 | + | ++ |
| 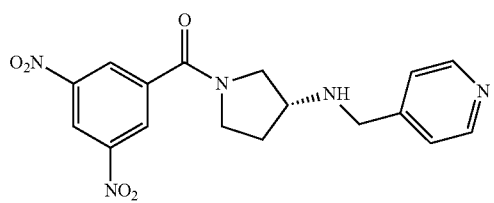 118 | + | ++ |
| 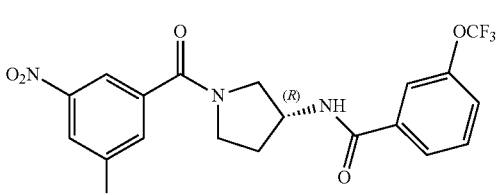 119 | + | +++ |
| 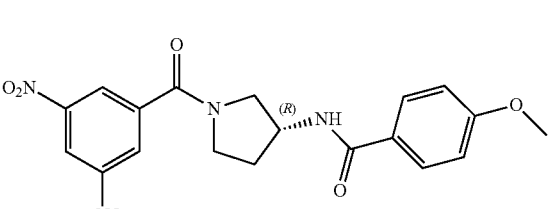 120 | + | +++ |
| 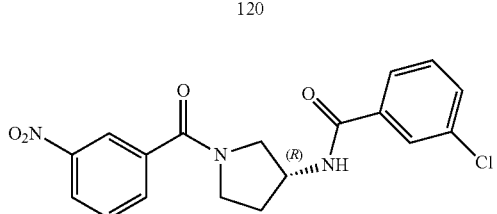 121 | + | ++ |

TABLE 4-continued

| Compound | QIM (μM) | QUM (μM) |
|---|---|---|
| 132 | + | ++ |
| 133 | ++ | +++ |
| 134 | + | ++ |
| 135 | + | ++ |
| 137 | + | + |

TABLE 4-continued
| Compound | QIM (μM) | QUM (μM) |
|---|---|---|
| 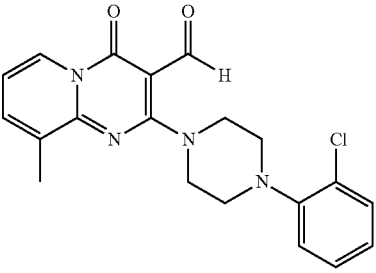<br>139 | + | + |
| 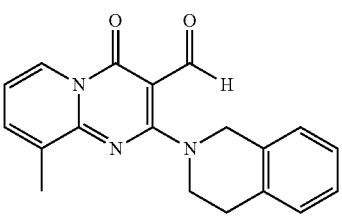<br>140 | + | + |
| 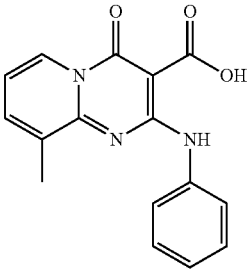<br>147 | + | + |
| 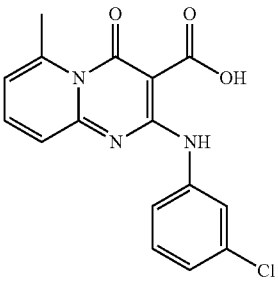<br>151 | ++ | + |
| 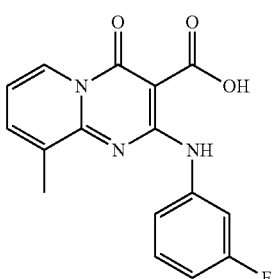<br>152 | + | + |

TABLE 4-continued
| Compound | QIM (μM) | QUM (μM) |
|---|---|---|
| 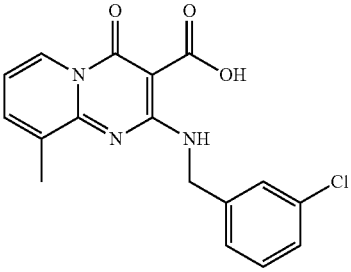 160 | + | + |
| 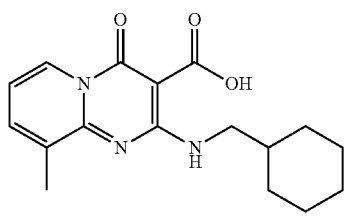 163 | + | + |
| 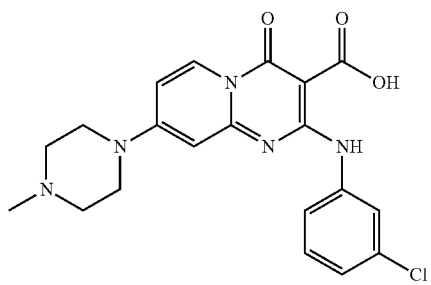 173 | + | + |
| 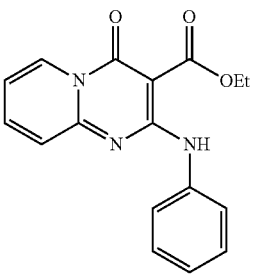 180 | + | + |
| 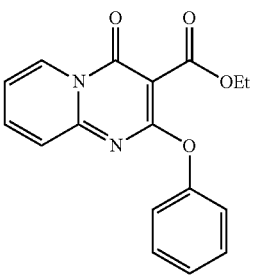 184 | + | + |

TABLE 4-continued

| Compound | QIM (μM) | QUM (μM) |
|---|---|---|
| 185 | + | ++ |
| 193 | + | + |
| 195 | + | + |
| 199 | + | ++ |
| 200 | + | + |

TABLE 4-continued
| Compound | QIM (μM) | QUM (μM) |
|---|---|---|
| 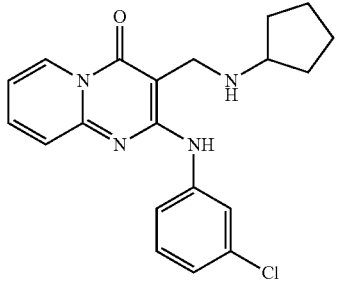 201 | + | + |
| 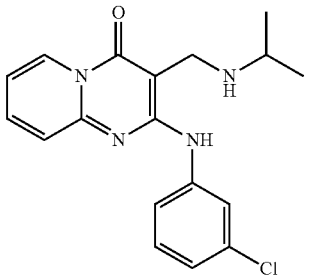 204 | + | + |
| 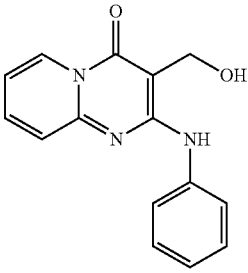 206 | +++ | +++ |
| 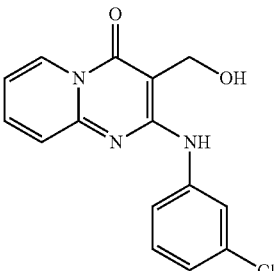 207 | +++ | +++ |
| 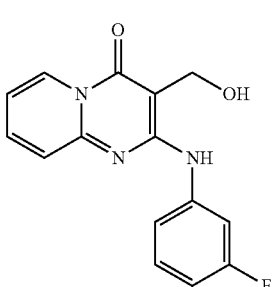 208 | +++ | +++ |

TABLE 4-continued
| Compound | QIM (μM) | QUM (μM) |
|---|---|---|
| 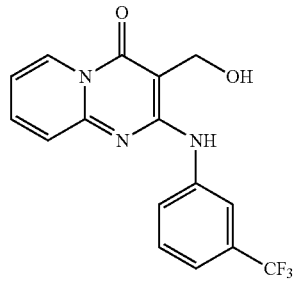 209 | +++ | +++ |
| 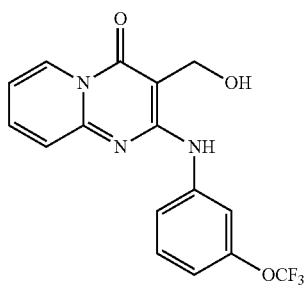 210 | +++ | +++ |
| 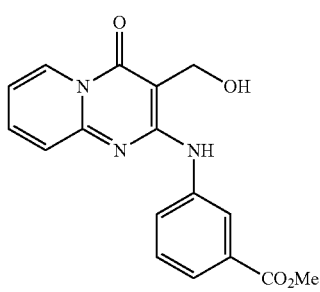 211 | + | +++ |
| 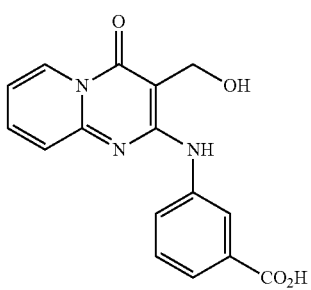 212 | + | + |

TABLE 4-continued

| Compound | QIM (μM) | QUM (μM) |
|---|---|---|
| 213 | + | +++ |
| 214 | + | ++ |
| 215 | + | + |
| 216 | + | + |

TABLE 4-continued
| Compound | QIM (μM) | QUM (μM) |
|---|---|---|
| 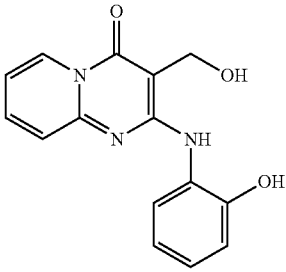 217 | + | +++ |
| 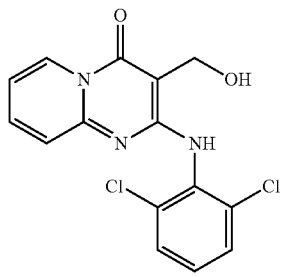 218 | + | + |
| 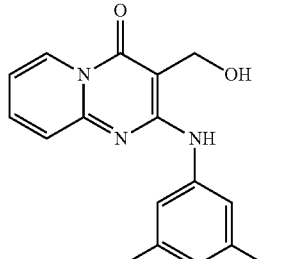 219 | + | + |
| 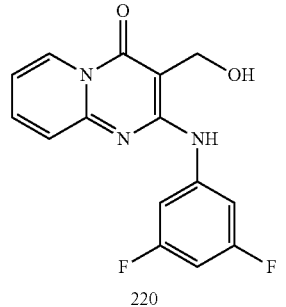 220 | ++ | +++ |
| 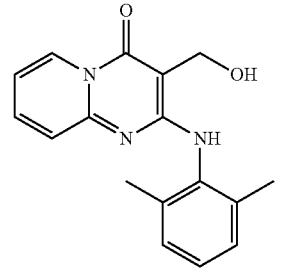 221 | + | + |

TABLE 4-continued

| Compound | QIM (μM) | QUM (μM) |
|---|---|---|
| 222 | + | + |
| 224 | + | + |
| 226 | + | + |
| 229 | + | + |
| 231 | +++ | +++ |

TABLE 4-continued

| Compound | QIM (μM) | QUM (μM) |
|---|---|---|
| 232 | +++ | ++ |
| 233 | + | + |
| 234 | + | + |
| 235 | +++ | +++ |
| 236 | ++ | +++ |

TABLE 4-continued
| Compound | QIM (μM) | QUM (μM) |
|---|---|---|
| 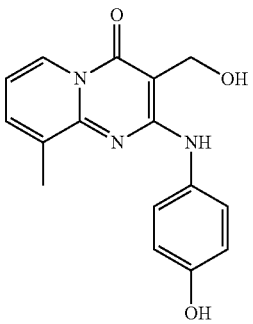 237 | + | +++ |
| 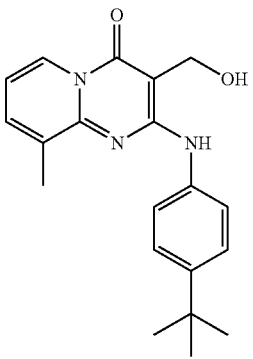 238 | + | + |
| 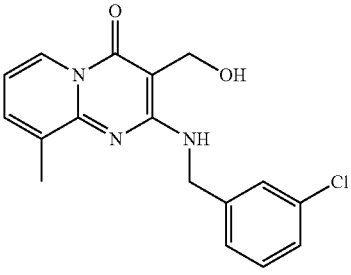 239 | + | + |
| 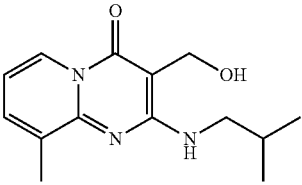 240 | ++ | ++ |
| 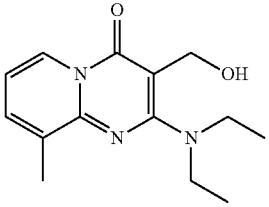 241 | + | + |

TABLE 4-continued
| Compound | QIM (µM) | QUM (µM) |
|---|---|---|
| 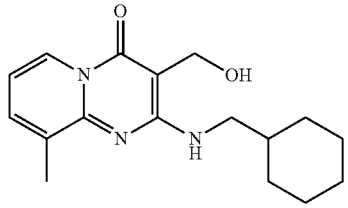 242 | + | + |
| 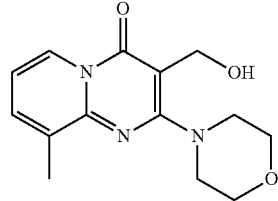 243 | + | + |
| 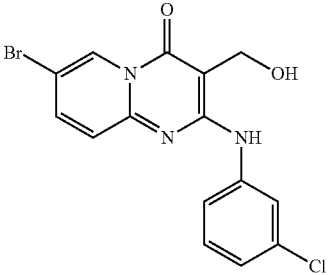 245 | + | ++ |
| 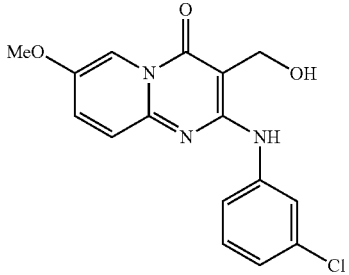 246 | + | + |
| 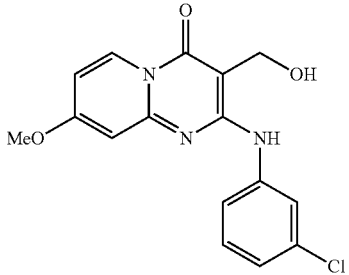 247 | + | +++ |

TABLE 4-continued
| Compound | QIM (μM) | QUM (μM) |
|---|---|---|
| 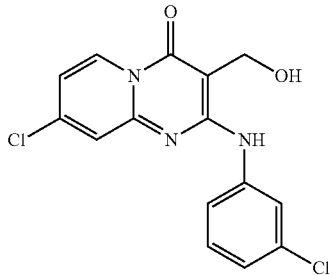 248 | + | +++ |
| 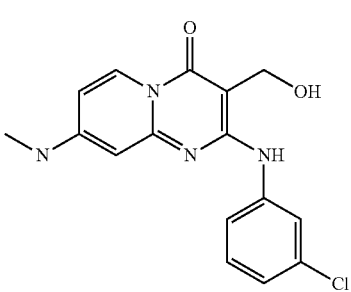 249 | + | + |
| 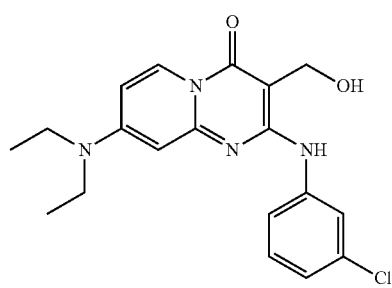 250 | + | + |
| 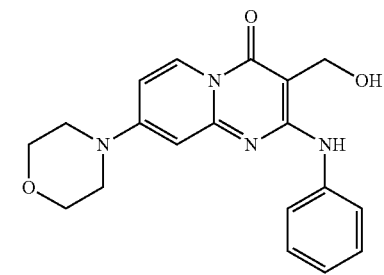 251 | + | + |
| 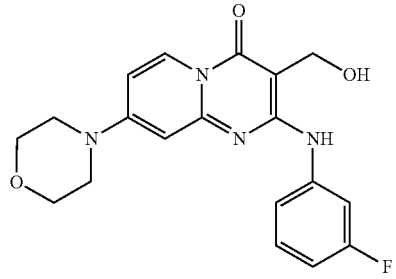 252 | + | + |

TABLE 4-continued
| Compound | QIM (μM) | QUM (μM) |
|---|---|---|
| 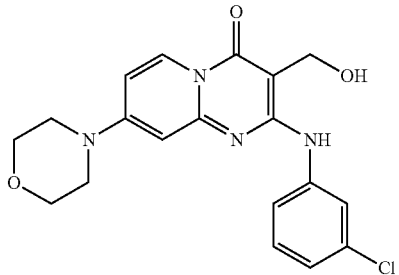 253 | + | + |
| 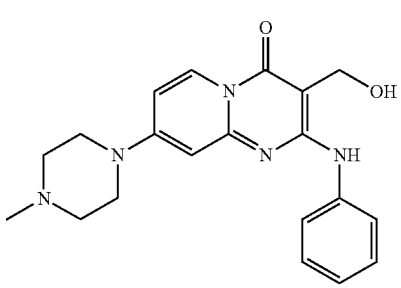 254 | + | + |
| 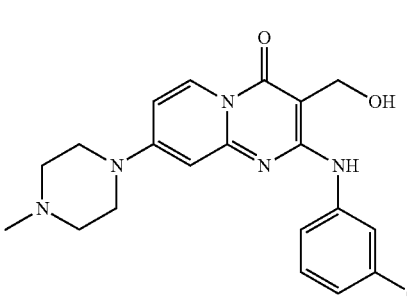 255 | + | + |
| 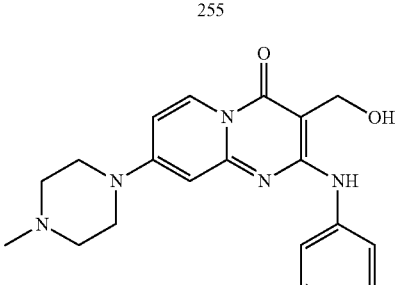 256 | + | + |
| 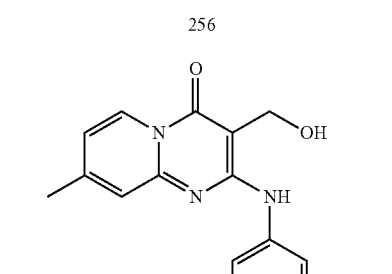 257 | +++ | +++ |

TABLE 4-continued
| Compound | QIM (μM) | QUM (μM) |
|---|---|---|
| 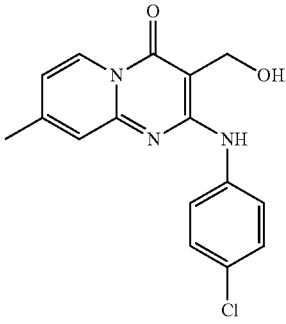 258 | +++ | +++ |
| 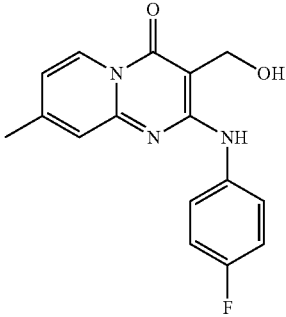 259 | ++ | +++ |
| 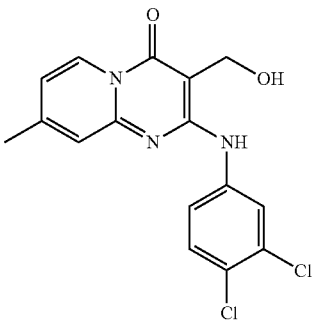 260 | + | ++ |
| 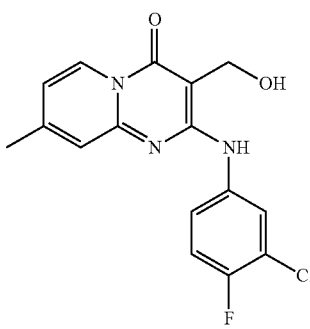 261 | +++ | +++ |

TABLE 4-continued
| Compound | QIM (μM) | QUM (μM) |
|---|---|---|
| 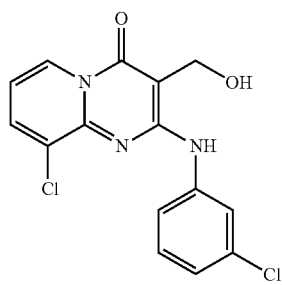<br>262 | + | + |
| 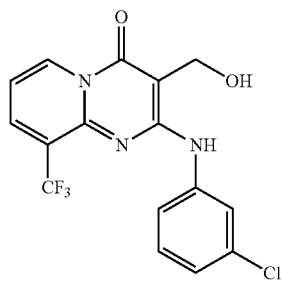<br>263 | + | + |
| 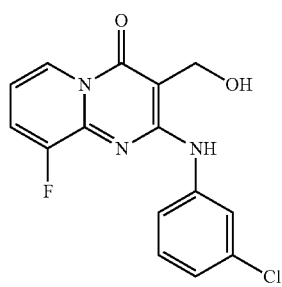<br>264 | ++ | +++ |
| 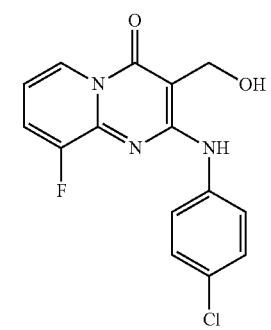<br>265 | +++ | +++ |

TABLE 4-continued
| Compound | QIM (μM) | QUM (μM) |
|---|---|---|
| 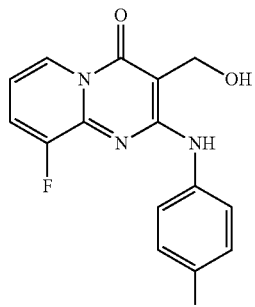 [SMILES: Cc1cccn2c(=O)c(CO)c(Nc3ccccc3)nc12 ; "231"] 266 | + | +++ |
| 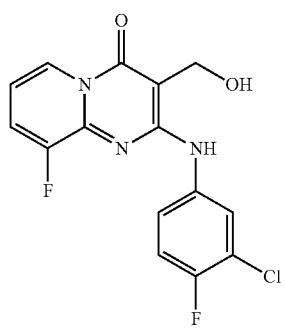 267 | +++ | +++ |
| 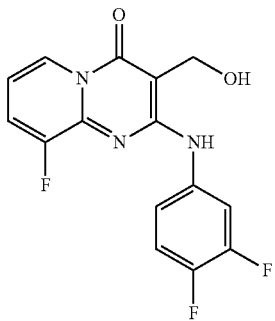 268 | + | ++ |
| 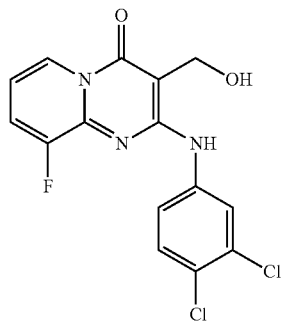 269 | ++ | ++ |

TABLE 4-continued
| Compound | QIM (μM) | QUM (μM) |
|---|---|---|
| 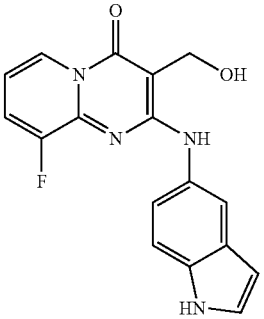 270 | +++ | +++ |
| 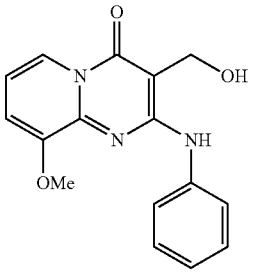 271 | + | +++ |
| 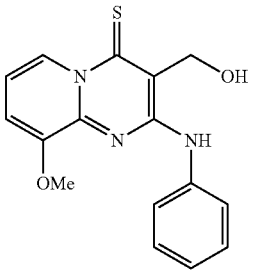 272 | + | + |
| 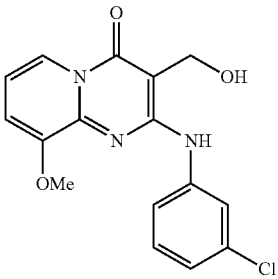 273 | +++ | +++ |

TABLE 4-continued
| Compound | QIM (μM) | QUM (μM) |
|---|---|---|
| 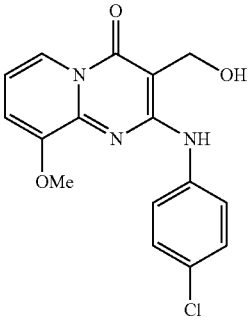 274 | + | +++ |
| 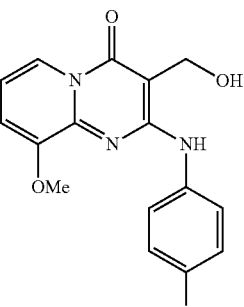 275 | + | +++ |
| 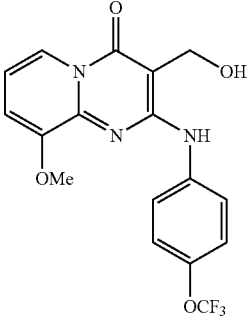 276 | + | ++ |
| 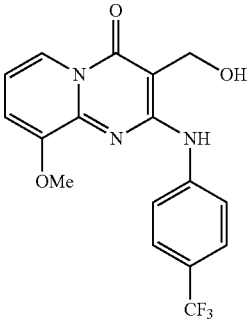 277 | + | ++ |

TABLE 4-continued
| Compound | QIM (μM) | QUM (μM) |
|---|---|---|
| 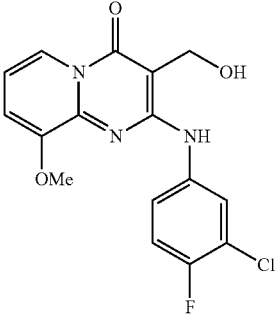278 | +++ | +++ |
| 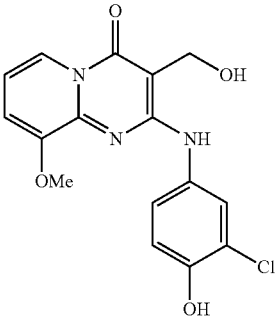280 | + | +++ |
| 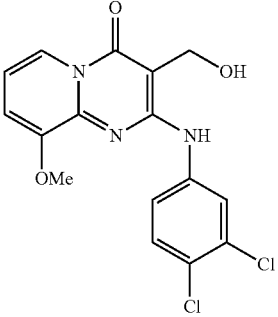281 | + | +++ |
| 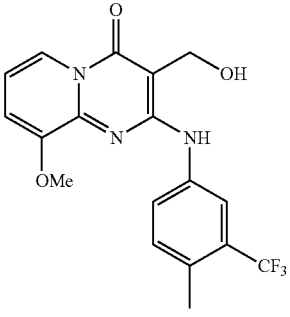282 | + | + |

TABLE 4-continued
| Compound | QIM (μM) | QUM (μM) |
|---|---|---|
| 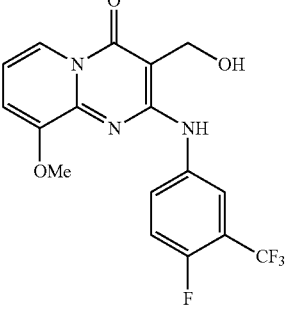 283 | + | + |
| 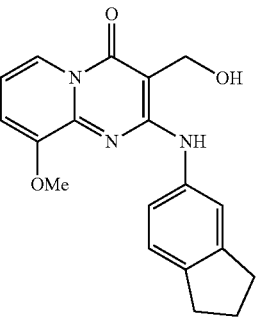 284 | + | +++ |
| 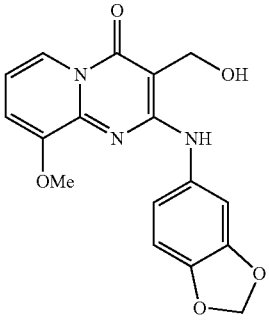 285 | + | +++ |
| 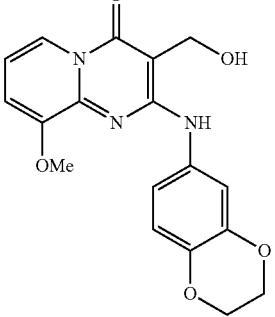 286 | + | +++ |

TABLE 4-continued
| Compound | QIM (μM) | QUM (μM) |
|---|---|---|
| 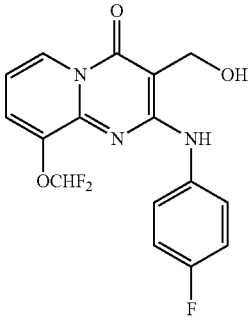<br>290 | + | + |
| 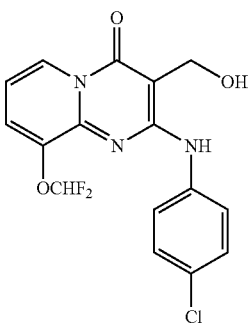<br>291 | + | + |
| 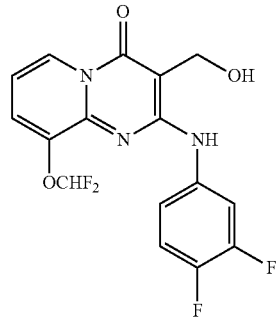<br>292 | + | + |
| 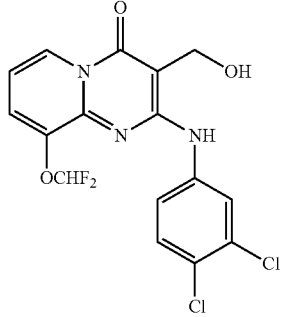<br>293 | + | + |

TABLE 4-continued
| Compound | QIM (μM) | QUM (μM) |
|---|---|---|
| 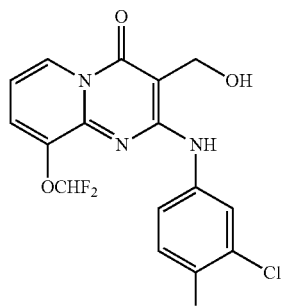 294 | + | + |
| 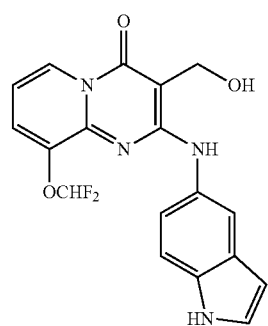 295 | ++ | +++ |
| 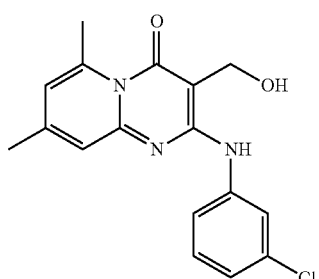 296 | + | + |
| 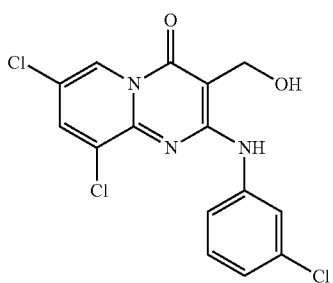 297 | + | + |

TABLE 4-continued
| Compound | QIM (μM) | QUM (μM) |
|---|---|---|
| 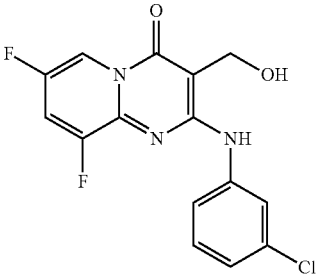 298 | + | + |
| 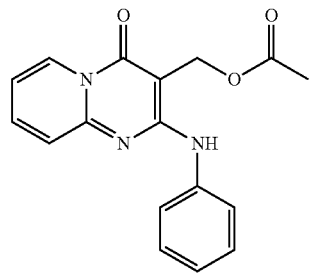 299 | ++ | +++ |
| 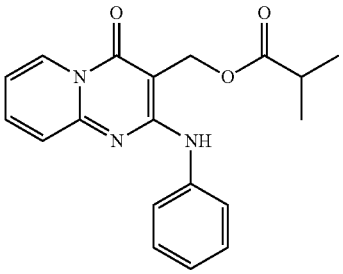 300 | ++ | +++ |
| 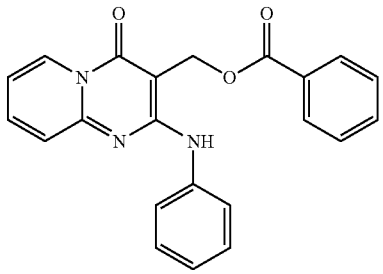 301 | ++ | +++ |
Activity range: +++ indicates <5 uM, ++ indicates between 5-20 uM, + indicates >20 uM
TABLE 5
| | Cytotoxicity | |
|---|---|---|
| Compounds | 4 | 24 |
| Host Cells | Range of MTC$_{50}$ (μM) | |
| SK-N-SH-Brain | >100 | >100 |
| HepG2-Hepatocytes | >100 | >100 |
| MRC5-Lung | >100 | >100 |
| BJ-Skin | >100 | >100 |
| HEK293-Kidney | >100 | >100 |

TABLE 5-continued

Antibacterial activity & Specificity

| Mycobacterium Strains/Isolates | Type | Origin | Number | Range of MICs for multiple strains (μM) | |
|---|---|---|---|---|---|
| M. tuberculosis clinical isolates[1] | Drug Sensitive | Tissue | 1 | 0.38 | 0.31 |
| | RIF[R] | Sputum | 2 | 0.05 | 0.08 |
| | | Tissue | 2 | 0.02-0.05 | 0.08 |
| | INH[R] RIF[R] Strep[R] | Sputum | 1 | 0.1 | 0.08 |
| | | Tissue | 3 | 0.05-0.1 | 0.04-0.08 |
| | XDR | Sputum | 5 | 0.02-0.05 | 0.04-0.08 |
| | | Tissue | 0 | 0.05-0.1 | 0.08 |
| | MDR | Sputum | 3 | 0.05-0.1 | 0.04-0.08 |
| | | Tissue | 5 | 0.05-0.1 | 0.04-0.08 |
| M. tuberculosis laboratory strains | H37Rv | | | 0.6 | 0.6 |
| | H37Ra | | | 1.2 | 1.3 |
| | Beijing 1237 | | | 0.3 | 0.1 |
| M. bovis BCG | BCG Tokyo | | | 1.2 | 0.6 |
| | BCG Pasteur | | | 1.2 | 1.2 |
| M. smegmatis | mc$^2$ 155 | | | 1.2 | 0.6 |

| Gram-negative | | |
|---|---|---|
| Acinetobacter baumannii, Escherichia coli, Enterobacter cloacae, E. aerogenes, Klebsiella oxytoca, Pseudomonas aeruginosa, Salmonella enteridis, Vibrio mimicus | >250 | >250 |

| Gram-positive | | |
|---|---|---|
| Staphylococcus aureus, S. epidermis, S. capitis, S. xylosus, Micrococcus luteus, Listeria innocua, Lactobacillus gallinarum, group G Streptococcus, Streptococcus agalactiae, S. pyogenes, Enterococcus faecalis, E. faecium, E. gallinarum, Bacillus pumilus Corynebacterium | >250 | >250 |
| C. striatum | 27 | 27 |
| C. jeikeium | 2.7 | 2.7 |

| Fungi | | |
|---|---|---|
| Candida albicans, C. glabrata, C. parapsilosis | >250 | >250 |

INH: Isoniazid,
RIF: Rifampin,
Strep: Streptomycin,
[R]resistant.

[1]The clinical isolates were isolated either from resected lung tissue or sputum specimen, which were collected from active tuberculosis in-patients from the National Masan Tuberculosis Hospital during October 2003 to March 2007.

TABLE 6

Cytotoxicity

| Compounds Host Cells | 133 Range of MTC$_{50}$ (μM) |
|---|---|
| SK-N-SH-Brain | >100 |
| HepG2-Hepatocytes | >100 |
| MRC5-Lung | >100 |
| BJ-Skin | >100 |
| HEK293-Kidney | >100 |
| Jurkat-T-cell | >100 |
| THP-1-Monocytes | >100 |
| Primary BMDM | >100 |
| Primary human macrophages | >100 |

Antibacterial activity & Specificity

| Mycobacterium Strains/Isolates | Type | Origin | Number | Range of MICs for multiple strains (μM) |
|---|---|---|---|---|
| M. tuberculosis clinical isolates[1] | Drug Sensitive | Sputum | 2 | 5->20 |
| | | Tissue | 2 | 2.5-5 |
| | RIF[R] | Sputum | 1 | 2.5 |
| | | Tissue | 1 | 1.2 |
| | INH[R] RIF[R] Strep[R] | Sputum | 3 | 0.3-1.2 |
| | | Tissue | 1 | 1.2 |
| | XDR | Sputum | 4 | 0.6-2.5 |
| | | Tissue | 5 | 0.3-5 |

TABLE 6-continued

| | | | | |
|---|---|---|---|---|
| | MDR | Sputum | 3 | 0.3–1.2 |
| | | Tissue | 1 | 1.2 |
| M. tuberculosis | H37Rv | | | 2 |
| laboratory strains | H37Ra | | | 2 |
| | BCG Pasteur-Tokyo | | | 2 |
| M. smegmatis | mc² 155 | | | >100 |

| | |
|---|---|
| Gram-negative | |
| Acinetobacter baumannii, Escherichia coli, Enterobacter cloacae, E. aerogenes, Klebsiella oxytoca, Pseudomonas aeruginosa, Salmonella enteridis, Vibrio mimicus | NE |
| Gram-positive | |
| Staphylococcus aureus, S. epidermis, S. capitis, S. xylosus, Micrococcus luteus, Listeria innocua, Lactobacillus gallinarum, group G Streptococcus, Streptococcus agalactiae, S. pyogenes, Enterococcus faecalis, E. faecium, E. gallinarum, Bacillus pumilus Corynebacterium | NE |
| C. striatum C. jeikeium Fungi | NE |
| Candida albicans, C. glabrata, C. parapsilosis | NE |

INH: Isoniazid,
RIF: Rifampin,
Strep: Streptomycin,
$^R$resistant.
[1]The clinical isolates were isolated either from resected lung tissue or sputum specimen, which were collected from active tuberculosis in-patients from the National Masan Tuberculosis Hospital during October 2003 to March 2007.
NE: No effect up to 100 μg/mL equivalent to 320 μM. The antimicrobial spectrum was performed on clinical isolates from CHU d'Angers, France.

TABLE 7

| Compound | Concentration (μg/ml) | Bacteria inoculum (CFU) | | | | Frequency of resistance |
|---|---|---|---|---|---|---|
| | | $10^5$ | $10^6$ | $10^7$ | $10^8$ | |
| 4 | 0.2 | — | — | 12 | >100 | $1 \times 10^{-6}$ |
| | 0.8 | — | — | — | <100 | |
| | 1.6 | — | — | — | <100 | |
| | 3.2 | — | — | — | 1 | $1 \times 10^{-8}$ |
| 24 | 0.2 | — | — | 7 | >100 | $7 \times 10^{-7}$ |
| | 0.8 | — | — | — | <100 | |
| | 1.6 | — | — | — | >100 | |
| | 3.2 | — | — | — | 1 | $1 \times 10^{-8}$ |
| INH-control | 10 | ND | ND | 33 | ND | $3 \times 10^{-6}$ |

| Compound | Concentration (μg/ml) | Bacteria inoculum (CFU) | | | Frequency of resistance |
|---|---|---|---|---|---|
| | | $10^6$ | $10^7$ | $10^8$ | |
| 264 | 0.4 | — | 37 | 306 | $3.4 \times 10^{-6}$ |
| | 0.8 | — | 5 | 117 | $8 \times 10^{-6}$ |
| | 1.6 | — | — | 22 | $2 \times 10^{-8}$ |
| | 3.2 | — | — | 2 | $2 \times 10^{-8}$ |
| INH-control | 10 | — | 4 | 18 | $2.9 \times 10^{-6}$ |

ND: not done;
—: no colonies

The invention claimed is:

1. A compound having the general formula VIIIa:

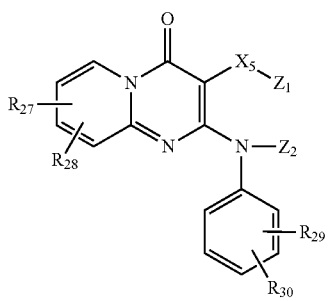

wherein $X_5$ is selected from the group consisting of $CH_2$ and C=O;

$Z_1$ is selected from the group consisting of alkoxy, alkylamino, alkylether, alkylthio, alkynyl, amido, amino, aryl, arylalkoxy, arylamino, arylthio, carboxy, cyano, cycloalkyl, ester, halo, haloalkoxy, haloalkyl, heteroaryl, heteroarylamino, heterocycloalkyl, and hydroxyl, any of which is optionally substituted;

$Z_2$ is selected from the group consisting of alkoxy, alkyl, alkylamino, alkylether, alkylthio, alkynyl, amido, amino, aryl, arylalkoxy, arylamino, arylthio, carboxy, cyano, cycloalkyl, ester, halo, haloalkoxy, haloalkyl, heteroaryl, heteroarylamino, heterocycloalkyl, hydroxyl, and hydrogen, any of which is optionally substituted;

$R_{27}$ and $R_{28}$ are each independently selected from the group consisting of alkoxy, alkyl, alkyl amino, alkeny, alkylether, alkylthio, alkynyl, amido, amino, aryl, arylether, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thiol, sulfonate, sulfonyl and sulfonylamino, any of which is optionally substituted; and $R_{29}$ and $R_{30}$ are each independently selected from the group consisting of alkoxy, alkyl, alkylamino, alkenyl, alkylether, alkylthio, alkynyl, amido, amino, aryl, arylether, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thiol, sulfonate, sulfonyl and sulfonylamino, or two groups are connected to each other to make five or six membered cyclic, heterocyclic, aryl, and heteroaryl rings, any of which is optionally substituted, wherein $Z_1$ and $Z_2$ may be connected to each other to make five or six membered cyclic, heterocyclic and heteroaryl rings, any of which is optionally substituted.

2. The compound according to claim 1, having a formula selected from the group consisting of the following formulae 147-159, 173, 180-183, 188, 189, 198-221, 225-238, and 245-301:

9-Methyl-4-oxo-2-(phenylamino)-4H-pyrido[1,2-a]pyrimidine-3-carboxylic acid (147)

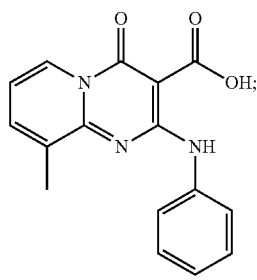 [SMILES: Cc1cccn2c(=O)c(C(=O)O)c(Nc3ccccc3)nc12]

2-(3-Chlorophenylamino)-9-methyl-4-oxo-4H-pyrido[1,2-a]pyrimidine-3-carboxylic acid (148)

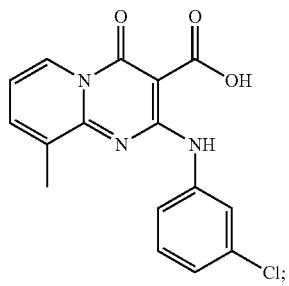

2-(3-Chlorophenylamino)-8-methyl-4-oxo-4H-pyrido[1,2-a]pyrimidine-3-carboxylic acid (149)

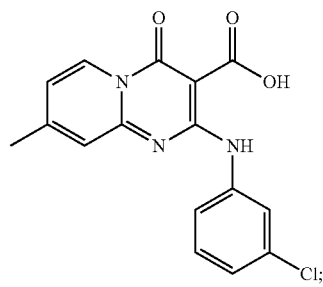 [SMILES: Cc1ccn2c(=O)c(C(=O)O)c(Nc3cccc(Cl)c3)nc2c1]

2-(3-Chlorophenylamino)-7-methyl-4-oxo-4H-pyrido[1,2-a]pyrimidine-3-carboxylic acid (150)

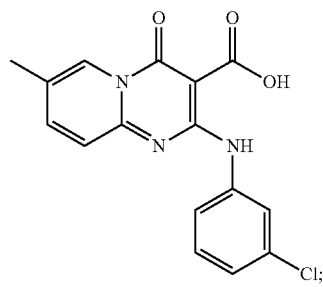

2-(3-Chlorophenylamino)-6-methyl-4-oxo-4H-pyrido[1,2-a]pyrimidine-3-carboxylic acid (151)

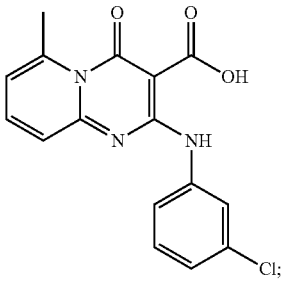 [SMILES: Cc1cccc2nc(Nc3cccc(Cl)c3)c(C(=O)O)c(=O)n12]

2-(3-Fluorophenylamino)-9-methyl-4-oxo-4H-pyrido[1,2-a]pyrimidine-3-carboxylic acid (152)

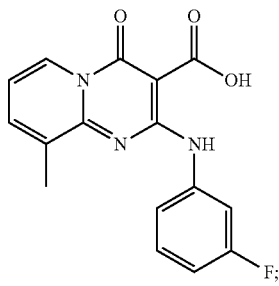 [SMILES: Cc1cccn2c(=O)c(C(=O)O)c(Nc3cccc(F)c3)nc12]

9-Methyl-4-oxo-2-(3-(trifluoromethyl)phenylamino)-4H-pyrido[1,2-a]pyrimidine-3-carboxylic acid (153)

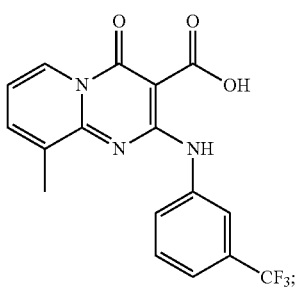 [SMILES: Cc1cccn2c(=O)c(C(=O)O)c(Nc3cccc(C(F)(F)F)c3)nc12]

9-Methyl-4-oxo-2-(3-(trifluoromethoxy)phenylamino)-4H-pyrido[1,2-a]pyrimidine-3-carboxylic acid (154)

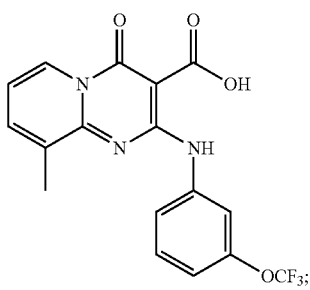

9-Methyl-2-(3-nitrophenylamino)-4-oxo-4H-pyrido[1,2-a]pyrimidine-3-carboxylic acid (155)

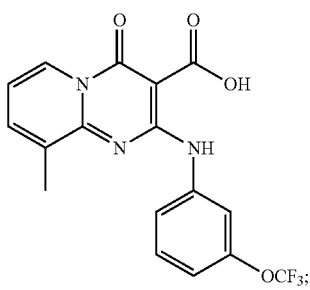

2-(3-(Methoxycarbonyl)phenylamino)-9-methyl-4-oxo-4H-pyrido[1,2-a]pyrimidine-3-carboxylic acid (156)

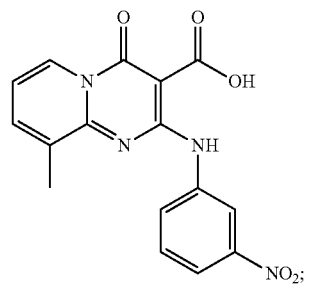 [SMILES: Cc1cccn2c(=O)c(C(=O)O)c(Nc3cccc([N+](=O)[O-])c3)nc12]

2-(3-Hydroxyphenylamino)-9-methyl-4-oxo-4H-pyrido[1,2-a]pyrimidine-3-carboxylic acid (157)

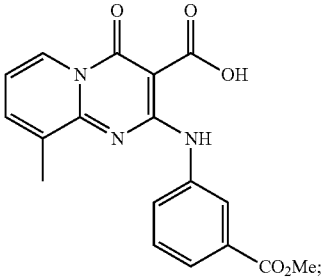 [SMILES: COC(=O)c1cccc(Nc2nc3c(C)cccn3c(=O)c2C(=O)O)c1]

2-(4-Hydroxyphenylamino)-9-methyl-4-oxo-4H-pyrido[1,2-a]pyrimidine-3-carboxylic acid (158)

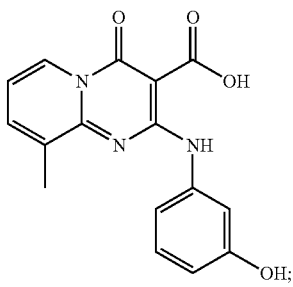 [SMILES: Cc1cccn2c(=O)c(C(=O)O)c(Nc3cccc(O)c3)nc12]

2-(4-tert-Butylphenylamino)-9-methyl-4-oxo-4H-pyrido[1,2-a]pyrimidine-3-carboxylic acid (159)

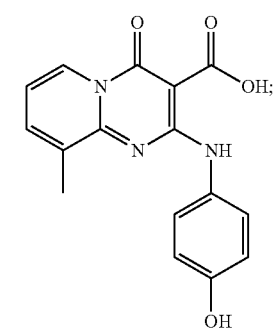 [SMILES: Cc1cccn2c(=O)c(C(=O)O)c(Nc3ccc(O)cc3)nc12]

2-(3-Chlorophenylamino)-8-(4-methylpiperazin-1-yl)-4-oxo-4H-pyrido[1,2-a]pyrimidine-3-carboxylic acid (173)

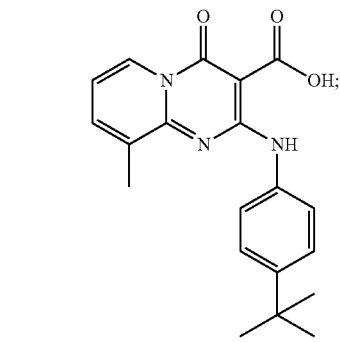 [SMILES: Cc1cccn2c(=O)c(C(=O)O)c(Nc3ccc(C(C)(C)C)cc3)nc12]

Ethyl 4-oxo-2-(phenylamino)-4H-pyrido[1,2-a]pyrimidine-3-carboxylate (180)

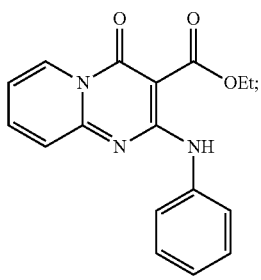 [SMILES: CCOC(=O)c1c(Nc2ccccc2)nc2ccccn2c1=O]

Ethyl 2-(3-hydroxyphenylamino)-4-oxo-4H-pyrido[1,2-a]pyrimidine-3-carboxylate (181)

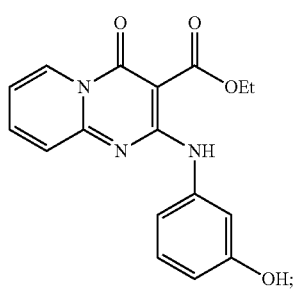 [SMILES: CCOC(=O)c1c(Nc2cccc(O)c2)nc2ccccn2c1=O]

Ethyl 2-(2-hydroxyphenylamino)-4-oxo-4H-pyrido[1,2-a]pyrimidine-3-carboxylate (182)

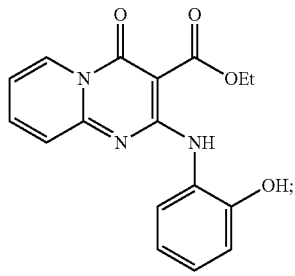 [SMILES: CCOC(=O)c1c(Nc2ccccc2O)nc2ccccn2c1=O]

Ethyl 2-(3-nitrophenylamino)-4-oxo-4H-pyrido[1,2-a]pyrimidine-3-carboxylate (183)

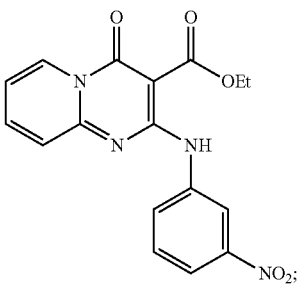 [SMILES: CCOC(=O)c1c(Nc2cccc([N+](=O)[O-])c2)nc2ccccn2c1=O]

Methyl 2-(3-chlorophenylamino)-9-methyl-4-oxo-4H-pyrido[1,2-a]pyrimidine-3-carboxylate (188)

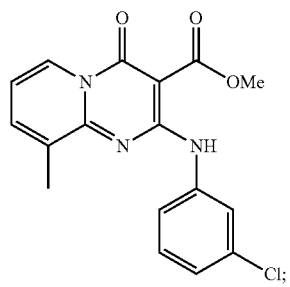 [SMILES: COC(=O)c1c(Nc2cccc(Cl)c2)nc2c(C)cccn2c1=O]

Methyl 2-(3-chlorobenzylamino)-9-methyl-4-oxo-4H-pyrido[1,2-a]pyrimidine-3-carboxylate (189)

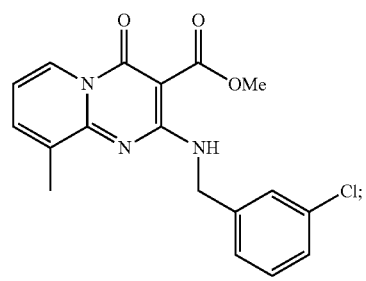 [SMILES: COC(=O)c1c(NCc2cccc(Cl)c2)nc2c(C)cccn2c1=O]

2-(3-Chloro-4-fluorophenylamino)-9-methoxy-N-methyl-4-oxo-4H-pyrido[1,2-a]pyrimidine-3-carboxamide (198)

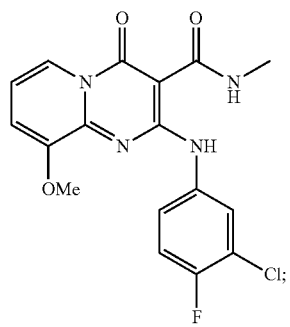 [SMILES: CNC(=O)c1c(Nc2ccc(F)c(Cl)c2)nc2c(OC)cccn2c1=O]

2-(3-Chlorophenylamino)-3-((cyclopentylamino)methyl)-4H-pyrido[1,2-a]pyrimidin-4-one (201)

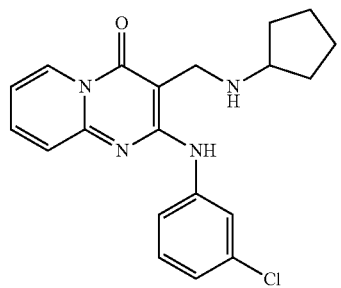

2-(3-Chlorophenylamino)-3-((cyclohexylamino)methyl)-4H-pyrido[1,2-a]pyrimidin-4-one (202)

453

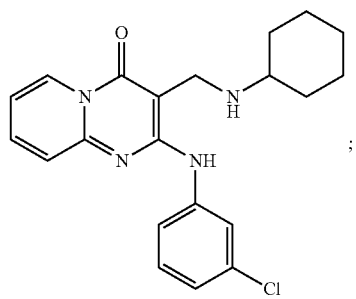 [SMILES: O=c1c(CNC2CCCCC2)c(Nc2cccc(Cl)c2)nc2ccccn12]

2-(3-Chlorophenylamino)-3-((cycloheptylamino)methyl)-4H-pyrido[1,2-a]pyrimidin-4-one (203)

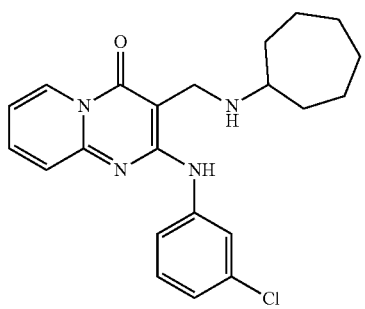

2-(3-Chlorophenylamino)-3-((isopropylamino)methyl)-4H-pyrido[1,2-a]pyrimidin-4-one (204)

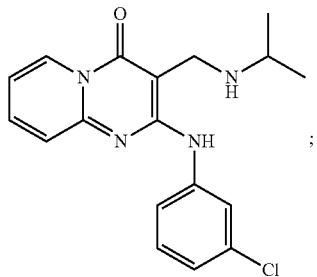 [SMILES: CC(C)NCc1c(Nc2cccc(Cl)c2)nc2ccccn2c1=O]

2-(3-Chlorophenylamino)-3-((cyclohexylamino)methyl)-8-(4-methylpiperazin-1-yl)-4H-pyrido[1,2-a]pyrimidin-4-one (205)

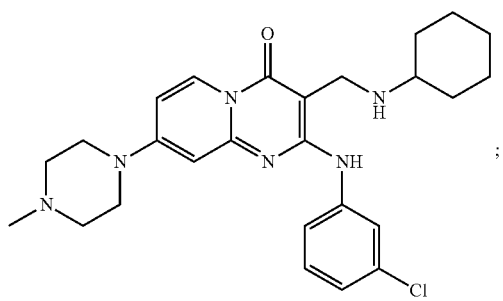 [SMILES: CN1CCN(c2ccn3c(=O)c(CNC4CCCCC4)c(Nc4cccc(Cl)c4)nc3c2)CC1]

3-(Hydroxymethyl)-2-(phenylamino)-4H-pyrido[1,2-a]pyrimidin-4-one (206)

454

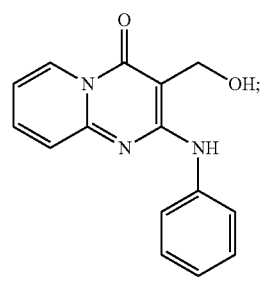 [SMILES: O=c1c(CO)c(Nc2ccccc2)nc2ccccn12]

2-(3-Chlorophenylamino)-3-(hydroxy methyl)-4H-pyrido-[1,2-a]pyrimidin-4-one (207)

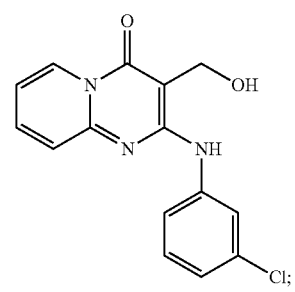 [SMILES: O=c1c(CO)c(Nc2cccc(Cl)c2)nc2ccccn12]

2-(3-Fluorophenylamino)-3-(hydroxymethyl)-4H-pyrido[1,2-a]pyrimidine-3-carbaldehyde (208)

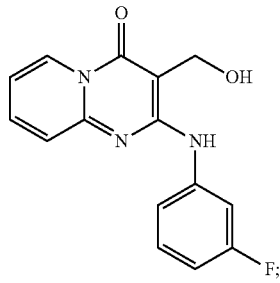

3-(Hydroxymethyl)-2-(3-(trifluoromethyl)phenylamino)-4H-pyrido[1,2-a]pyrimidin-4-one (209)

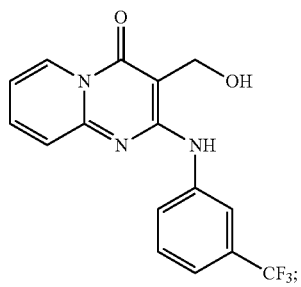 [SMILES: O=c1c(CO)c(Nc2cccc(C(F)(F)F)c2)nc2ccccn12]

3-(Hydroxymethyl)-2-(3-(trifluoromethoxy)phenylamino)-4H-pyrido[1,2-a]pyrimidin-4-one (210)

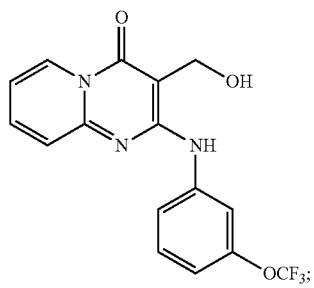

Methyl 3-(3-(hydroxymethyl)-4-oxo-4H-pyrido[1,2-a]pyrimidin-2-ylamino)benzoate (211)

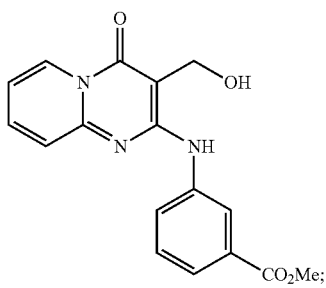 [SMILES: COC(=O)c1cccc(Nc2nc3ccccn3c(=O)c2CO)c1]

3-(3-(hydroxymethyl)-4-oxo-4H-pyrido[1,2-a]pyrimidin-2-ylamino)benzoic acid (212)

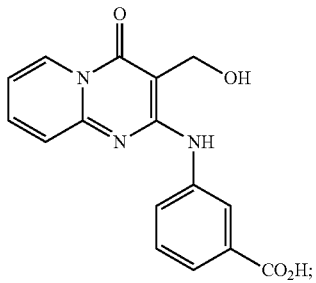 [SMILES: O=C(O)c1cccc(Nc2nc3ccccn3c(=O)c2CO)c1]

2-(4-Chlorophenylamino)-3-(hydroxymethyl)-4H-pyrido[1,2-a]pyrimidin-4-one (213)

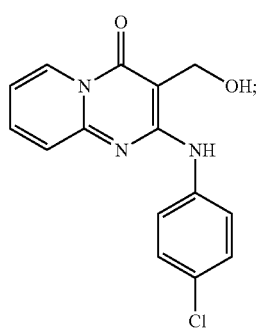 [SMILES: O=c1c(CO)c(Nc2ccc(Cl)cc2)nc2ccccn12]

2-(2-Chlorophenylamino)-3-(hydroxymethyl)-4H-pyrido[1,2-a]pyrimidin-4-one (214)

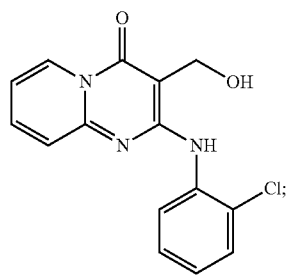 [SMILES: O=c1c(CO)c(Nc2ccccc2Cl)nc2ccccn12]

3-(Hydroxymethyl)-2-(3-hydroxyphenylamino)-4H-pyrido[1,2-a]pyrimidin-4-one (215)

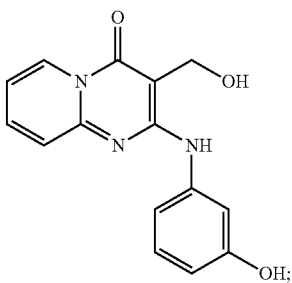 [SMILES: O=c1c(CO)c(Nc2cccc(O)c2)nc2ccccn12]

3-(Hydroxymethyl)-2-(4-hydroxyphenylamino)-4H-pyrido[1,2-a]pyrimidin-4-one (216)

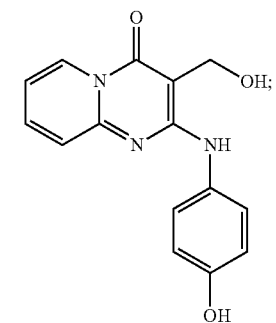

3-(Hydroxymethyl)-2-(2-hydroxyphenylamino)-4H-pyrido[1,2-a]pyrimidin-4-one (217)

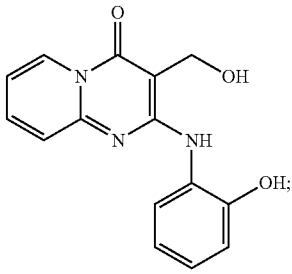 [SMILES: O=c1c(CO)c(Nc2ccccc2O)nc2ccccn12]

2-(2,6-Dichlorophenylamino)-3-(hydroxymethyl)-4H-pyrido[1,2-a]pyrimidin-4-one (218)

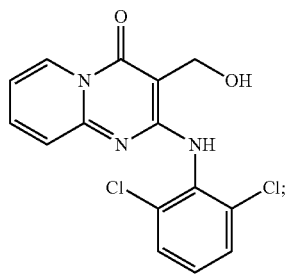 [SMILES: O=c1c(CO)c(Nc2c(Cl)cccc2Cl)nc2ccccn12]

2-(3,5-Dichlorophenylamino)-3-(hydroxymethyl)-4H-pyrido[1,2-a]pyrimidin-4-one (219)

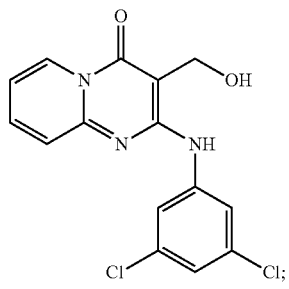 [SMILES: O=c1c(CO)c(Nc2cc(Cl)cc(Cl)c2)nc2ccccn12]

2-(3,5-Difluorophenylamino)-3-(hydroxymethyl)-4H-pyrido[1,2-a]pyrimidin-4-one (220)

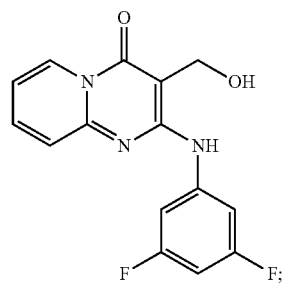 [SMILES: O=c1c(CO)c(Nc2cc(F)cc(F)c2)nc2ccccn12]

2-(2,6-Dimethylphenylamino)-3-(hydroxymethyl)-4H-pyrido[1,2-a]pyrimidin-4-one (221)

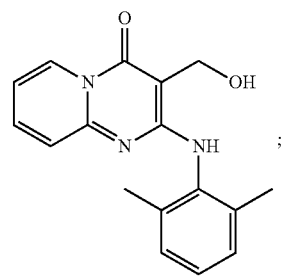 [SMILES: Cc1cccc(C)c1Nc1nc2ccccn2c(=O)c1CO]

3-(Hydroxymethyl)-9-methyl-2-(phenylamino)-4H-pyrido[1,2-a]pyrimidin-4-one (231)

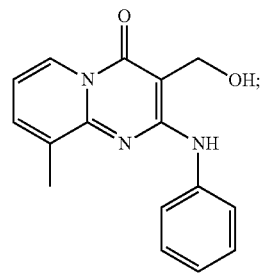 [SMILES: Cc1cccn2c(=O)c(CO)c(Nc3ccccc3)nc12]

2-(3-Chlorophenylamino)-3-(hydroxymethyl)-9-methyl-4H-pyrido[1,2-a]pyrimidin-4-one (232)

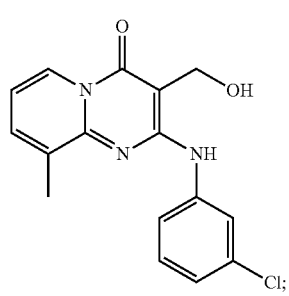

2-((3-Chlorophenyl)(methyl)amino)-3-(hydroxymethyl)-9-methyl-4H-pyrido[1,2-a]pyrimidin-4-one (233)

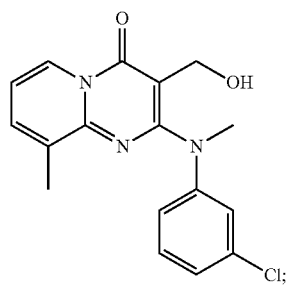 [SMILES: Cc1cccn2c(=O)c(CO)c(N(C)c3cccc(Cl)c3)nc12]

2-((3-Chlorophenyl)(methyl)amino)-3-(methoxymethyl)-9-methyl-4H-pyrido[1,2-a]pyrimidin-4-one (234)

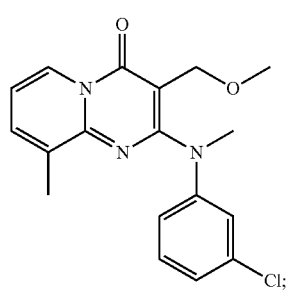

3-(Hydroxymethyl)-9-methyl-2-(3-(trifluoromethoxy)phenylamino)-4H-pyrido[1,2-a]pyrimidin-4-one (235)

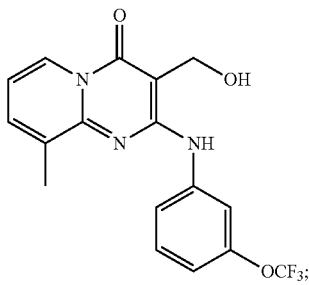 [SMILES: Cc1cccn2c(=O)c(CO)c(Nc3cccc(OC(F)(F)F)c3)nc12]

3-(Hydroxymethyl)-2-(3-hydroxyphenylamino)-9-methyl-4H-pyrido[1,2-a]pyrimidin-4-one (236)

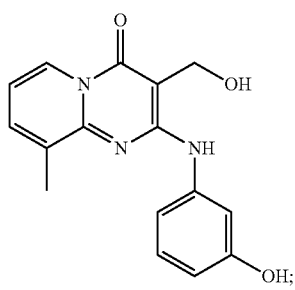

3-(Hydroxymethyl)-2-(4-hydroxyphenylamino)-9-methyl-4H-pyrido[1,2-a]pyrimidin-4-one (237)

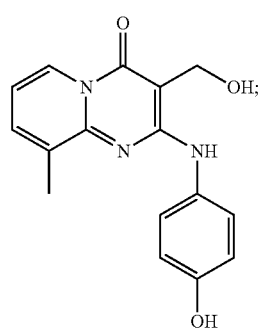

2-(4-tert-Butylphenylamino)-3-(hydroxymethyl)-9-methyl-4H-pyrido[1,2-a]pyrimidin-4-one (238)

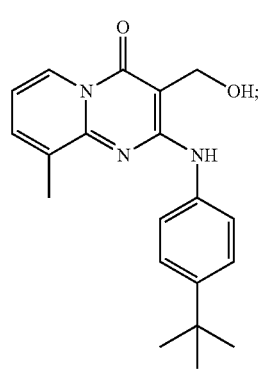 [SMILES: Cc1cccn2c(=O)c(CO)c(Nc3ccc(C(C)(C)C)cc3)nc12]

7-Bromo-2-(3-chlorophenylamino)-3-(hydroxymethyl)-4H-pyrido[1,2-a]pyrimidin-4-one (245)

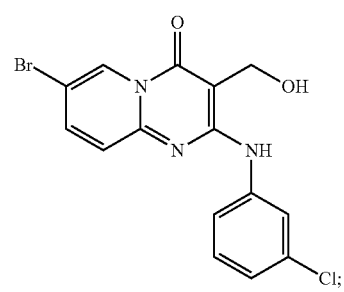

2-(3-Chlorophenylamino)-3-(hydroxymethyl)-7-methoxy-4H-pyrido[1,2-a]pyrimidin-4-one (246)

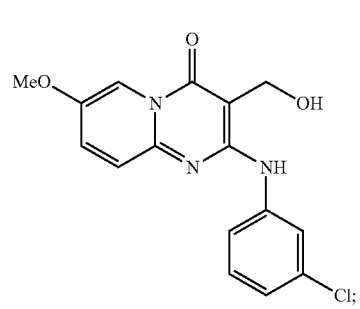 [SMILES: COc1ccc2nc(Nc3cccc(Cl)c3)c(CO)c(=O)n2c1]

2-(3-Chlorophenylamino)-3-(hydroxymethyl)-8-methoxy-4H-pyrido[1,2-a]pyrimidin-4-one (247)

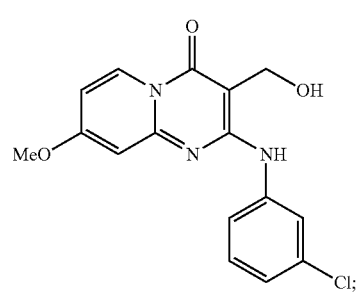 [SMILES: COc1ccn2c(=O)c(CO)c(Nc3cccc(Cl)c3)nc2c1]

8-Chloro-2-(3-chlorophenylamino)-3-(hydroxymethyl)-4H-pyrido[1,2-a]pyrimidin-4-one (248)

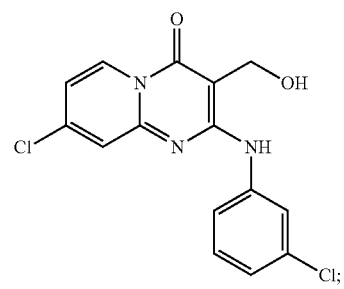 [SMILES: O=c1c(CO)c(Nc2cccc(Cl)c2)nc2cc(Cl)ccn12]

2-(3-Chlorophenylamino)-3-(hydroxymethyl)-8-(methylamino)-4H-pyrido[1,2-a]pyrimidin-4-one (249)

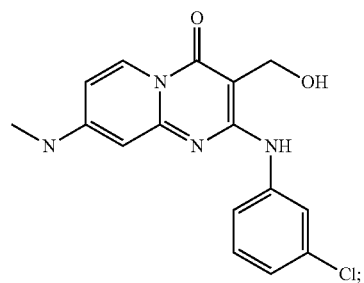 [SMILES: CNc1ccn2c(=O)c(CO)c(Nc3cccc(Cl)c3)nc2c1]

2-(3-Chlorophenylamino)-8-(diethylamino)-3-(hydroxymethyl)-4H-pyrido[1,2-a]pyrimidin-4-one (250)

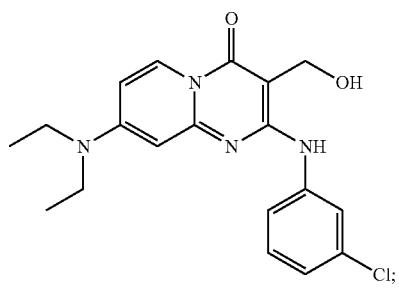 [SMILES: CCN(CC)c1ccn2c(=O)c(CO)c(Nc3cccc(Cl)c3)nc2c1]

3-(Hydroxymethyl)-8-morpholino-2-(phenylamino)-4H-pyrido[1,2-a]pyrimidin-4-one (251)

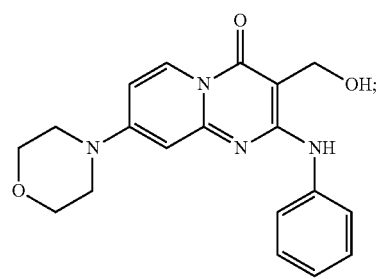 [SMILES: O=c1c(CO)c(Nc2ccccc2)nc2cc(N3CCOCC3)ccn12]

2-(3-Fluorophenylamino)-3-(hydroxymethyl)-8-morpholino-4H-pyrido[1,2-a]pyrimidin-4-one (252)

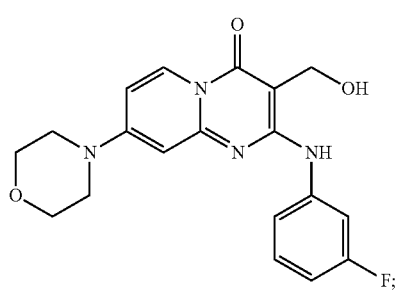 [SMILES: O=c1c(CO)c(Nc2cccc(F)c2)nc2cc(N3CCOCC3)ccn12]

2-(3-Chlorophenylamino)-3-(hydroxymethyl)-8-morpholino-4H-pyrido[1,2-a]pyrimidin-4-one (253)

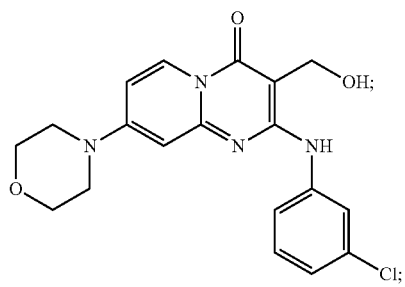 [SMILES: O=c1c(CO)c(Nc2cccc(Cl)c2)nc2cc(N3CCOCC3)ccn12]

3-(Hydroxymethyl)-8-(4-methylpiperazin-1-yl)-2-(phenylamino)-4H-pyrido[1,2-a]pyrimidin-4-one (254)

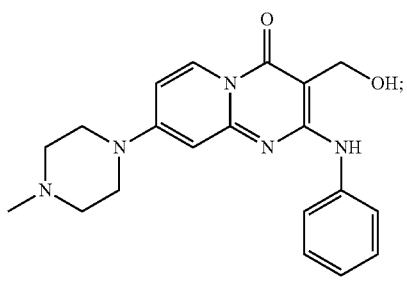 [SMILES: CN1CCN(c2ccn3c(=O)c(CO)c(Nc4ccccc4)nc3c2)CC1]

2-(3-Chlorophenylamino)-3-(hydroxymethyl)-8-(4-methylpiperazin-1-yl)-4H-pyrido[1,2-a]pyrimidin-4-one (255)

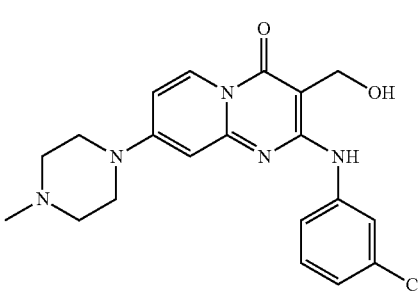

2-(3-Fluorophenylamino)-3-(hydroxymethyl)-8-(4-methylpiperazin-1-yl)-4H-pyrido[1,2-a]pyrimidin-4-one (256)

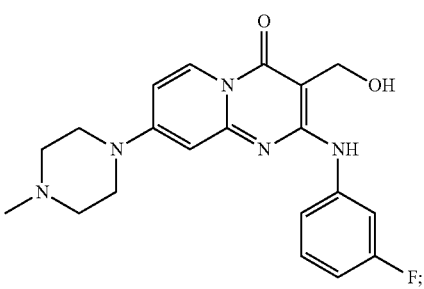

2-(3-Chlorophenylamino)-3-(hydroxymethyl)-8-methyl-4H-pyrido[1,2-a]pyrimidin-4-one (257)

463

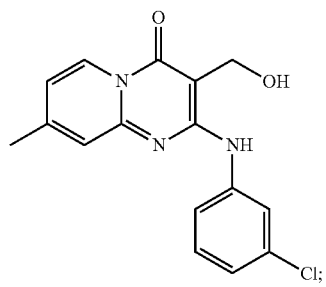 [SMILES: Cc1ccn2c(=O)c(CO)c(Nc3cccc(Cl)c3)nc2c1]

2-(4-Chlorophenylamino)-3-(hydroxymethyl)-8-methyl-
4H-pyrido[1,2-a]pyrimidin-4-one (258)

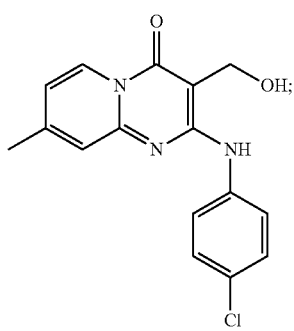

2-(4-Fluorophenylamino)-3-(hydroxymethyl)-8-methyl-
4H-pyrido[1,2-a]pyrimidin-4-one (259)

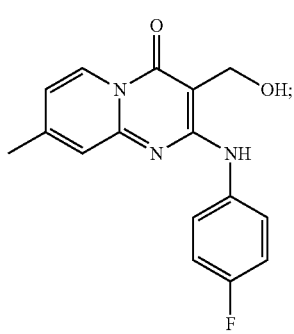 [SMILES: Cc1ccn2c(=O)c(CO)c(Nc3ccc(F)cc3)nc2c1]

2-(3,4-Dichlorophenylamino)-3-(hydroxymethyl)-8-me-
thyl-4H-pyrido[1,2-a]pyrimidin-4-one (260)

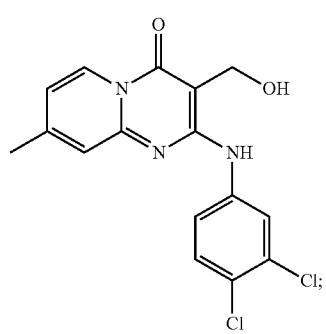 [SMILES: Cc1ccn2c(=O)c(CO)c(Nc3ccc(Cl)c(Cl)c3)nc2c1]

2-(3-Chloro-4-fluorophenylamino)-3-(hydroxymethyl)-
8-methyl-4H-pyrido[1,2-a]pyrimidin-4-one (261)

464

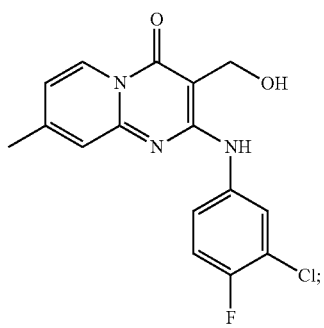

9-Chloro-2-(3-chlorophenylamino)-3-(hydroxymethyl)-
4H-pyrido[1,2-a]pyrimidin-4-one (262)

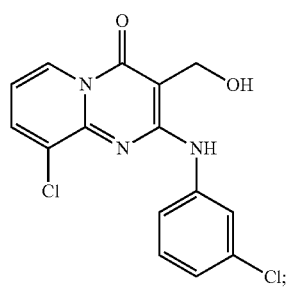

2-(3-Chlorophenylamino)-3-(hydroxymethyl)-9-(trifluo-
romethyl)-4H-pyrido[1,2-a]pyrimidin-4-one (263)

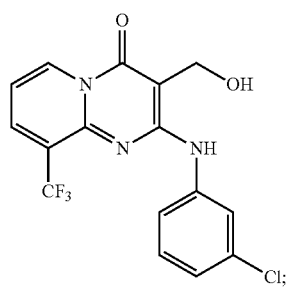

2-(3-Chlorophenylamino)-9-fluoro-3-(hydroxymethyl)-
4H-pyrido[1,2-a]pyrimidin-4-one (264)

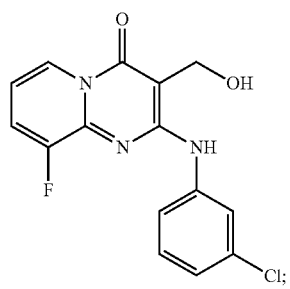

2-(4-Chlorophenylamino)-9-fluoro-3-(hydroxymethyl)-
4H-pyrido[1,2-a]pyrimidin-4-one (265)

465

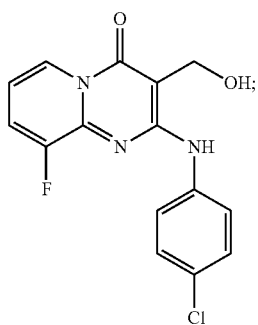 [SMILES: O=c1c(CO)c(Nc2ccc(Cl)cc2)nc2c(F)cccn12]

9-Fluoro-2-(4-fluorophenylamino)-3-(hydroxymethyl)-4H-pyrido[1,2-a]pyrimidin-4-one (266)

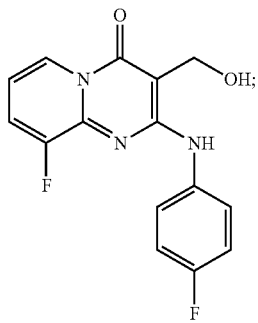

2-(3-Chloro-4-fluorophenylamino)-9-fluoro-3-(hydroxymethyl)-4H-pyrido[1,2-a]pyrimidin-4-one (267)

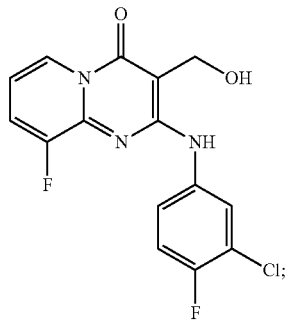 [SMILES: O=c1c(CO)c(Nc2ccc(F)c(Cl)c2)nc2c(F)cccn12]

2-(3,4-Difluorophenylamino)-9-fluoro-3-(hydroxymethyl)-4H-pyrido[1,2-a]pyrimidin-4-one (268)

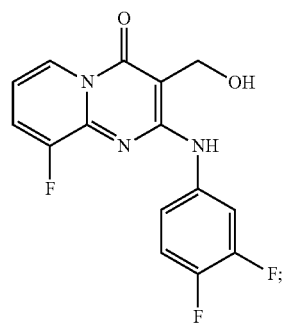 [SMILES: O=c1c(CO)c(Nc2ccc(F)c(F)c2)nc2c(F)cccn12]

466

2-(3,4-Dichlorophenylamino)-9-fluoro-3-(hydroxymethyl)-4H-pyrido[1,2-a]pyrimidin-4-one (269)

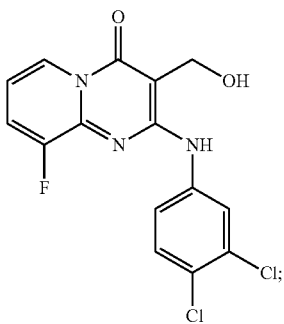 [SMILES: O=c1c(CO)c(Nc2ccc(Cl)c(Cl)c2)nc2c(F)cccn12]

2-(1H-Indol-5-ylamino)-9-fluoro-3-(hydroxymethyl)-4,1-pyrido[1,2-a]pyrimidin-4-one (270)

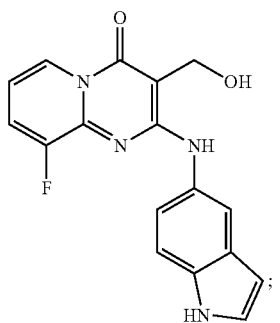 [SMILES: O=c1c(CO)c(Nc2ccc3[nH]ccc3c2)nc2c(F)cccn12]

3-(Hydroxymethyl)-9-methoxy-2-(phenylamino)-4H-pyrido[1,2-a]pyrimidin-4-one (271)

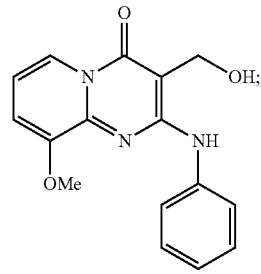 [SMILES: COc1cccn2c(=O)c(CO)c(Nc3ccccc3)nc12]

2-(3-Chlorophenylamino)-3-(hydroxymethyl)-9-methoxy-4H-pyrido[1,2-a]pyrimidin-4-one (273)

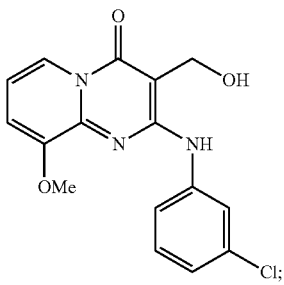 [SMILES: COc1cccn2c(=O)c(CO)c(Nc3cccc(Cl)c3)nc12]

2-(4-Chlorophenylamino)-3-(hydroxymethyl)-9-methoxy-4H-pyrido[1,2-a]pyrimidin-4-one (274)

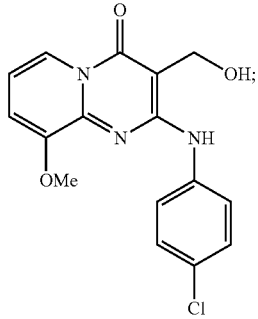 [SMILES: COc1cccn2c(=O)c(CO)c(Nc3ccc(Cl)cc3)nc12]

2-(4-Fluorophenylamino)-3-(hydroxymethyl)-9-methoxy-4H-pyrido[1,2-a]pyrimidin-4-one (275)

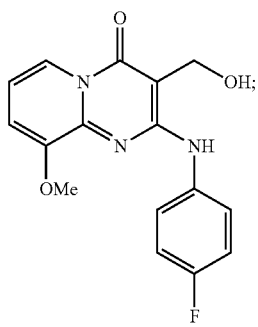 [SMILES: COc1cccn2c(=O)c(CO)c(Nc3ccc(F)cc3)nc12]

3-(Hydroxymethyl)-9-methoxy-2-(4-(trifluoromethoxy)phenylamino)-4H-pyrido[1,2-a]pyrimidin-4-one (276)

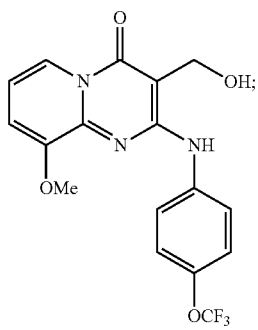 [SMILES: COc1cccn2c(=O)c(CO)c(Nc3ccc(OC(F)(F)F)cc3)nc12]

3-(Hydroxymethyl)-9-methoxy-2-(4-(trifluoromethyl)phenyl amino)-4H-pyrido one (277)

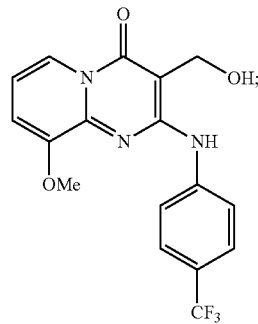 [SMILES: COc1cccn2c(=O)c(CO)c(Nc3ccc(C(F)(F)F)cc3)nc12]

2-(3-Chloro-4-fluorophenylamino)-3-(hydroxymethyl)-9-methoxy-4H-pyrido[1,2-a]pyrimidin-4-one (278)

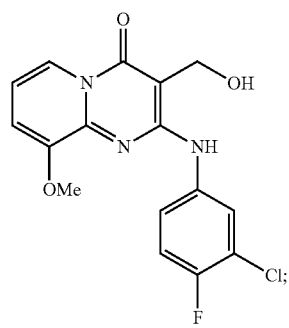 [SMILES: COc1cccn2c(=O)c(CO)c(Nc3ccc(F)c(Cl)c3)nc12]

2-(3,4-Difluorophenylamino)-3-(hydroxymethyl)-9-methoxy-4H-pyrido[1,2-a]pyrimidin-4-one (279)

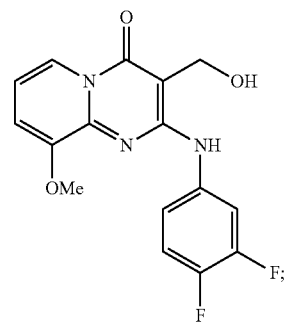 [SMILES: COc1cccn2c(=O)c(CO)c(Nc3ccc(F)c(F)c3)nc12]

2-(3-Chloro-4-hydroxyphenylamino)-3-(hydroxymethyl)-9-methoxy-4H-pyrido one (280)

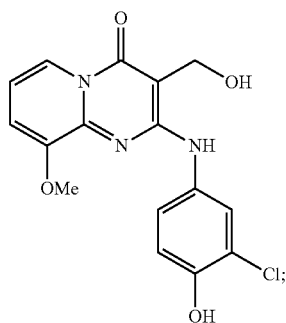 [SMILES: COc1cccn2c(=O)c(CO)c(Nc3ccc(O)c(Cl)c3)nc12]

2-(3,4-Dichlorophenylamino)-3-(hydroxymethyl)-9-methoxy-4H-pyrido[1,2-a]pyrimidin-4-one (281)

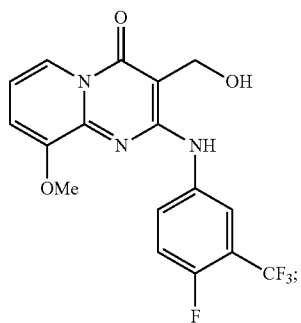

2-(2,3-Dihydro-1H-inden-5-ylamino)-3-(hydroxymethyl)-9-methoxy-4H-pyrido[1,2-a]pyrimidin-4-one (284)

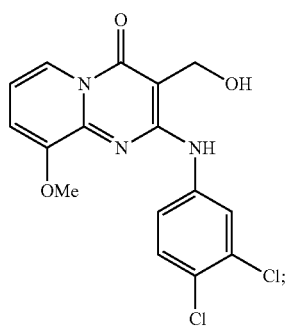 [SMILES: COc1cccn2c(=O)c(CO)c(Nc3ccc(Cl)c(Cl)c3)nc12]

3-(Hydroxymethyl)-9-methoxy-2-(4-methyl-3-(trifluoromethyl)phenylamino)-4H-pyrido[1,2-a]pyrimidin-4-one (282)

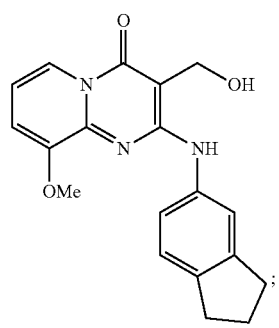

2-(Benzo[d][1,3]dioxol-5-ylamino)-3-(hydroxymethyl)-9-methoxy-4H-pyrido[1,2-a]pyrimidin-4-one (285)

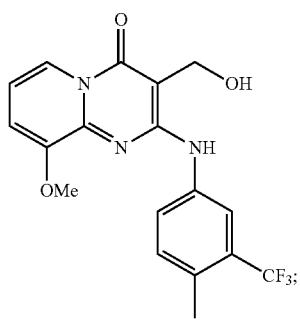 [SMILES: COc1cccn2c(=O)c(CO)c(Nc3ccc(C)c(C(F)(F)F)c3)nc12]

2-(4-Fluoro-3-(trifluoromethyl)phenylamino)-3-(hydroxymethyl)-9-methoxy-4H-pyrido[1,2-a]pyrimidin-4-one (283)

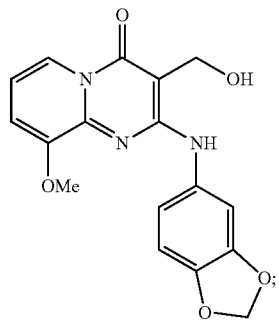 [SMILES: COc1cccn2c(=O)c(CO)c(Nc3ccc4c(c3)OCO4)nc12]

2-(2,3-Dihydrobenzo[b][1,4]dioxin-6-ylamino)-3-(hydroxymethyl)-9-methoxy-4H-pyrido[1,2-a]pyrimidin-4-one (286)

| 471 | 472 |
|---|---|
| 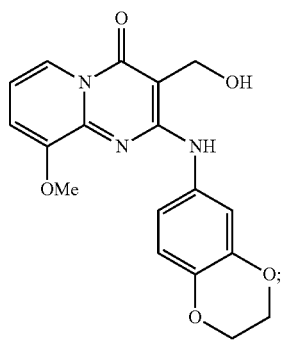 [SMILES: COc1cccn2c(=O)c(CO)c(Nc3ccc4c(c3)OCCO4)nc12] | 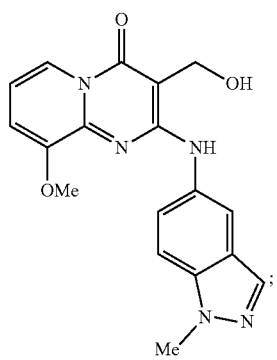 |
| 3-(Hydroxymethyl)-9-methoxy-2-(1-methyl-1H-indol-5-ylamino)-4H-pyrido[1,2-a]pyrimidin-4-one (287) | 9-(Difluoromethoxy)-2-(4-fluorophenylamino)-3-(hydroxymethyl)-4H-pyrido[1,2-a]pyrimidin-4-one (290) |
| 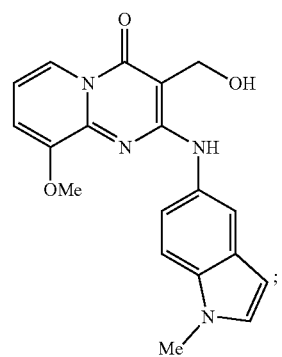 [SMILES: COc1cccn2c(=O)c(CO)c(Nc3ccc4c(ccn4C)c3)nc12] | 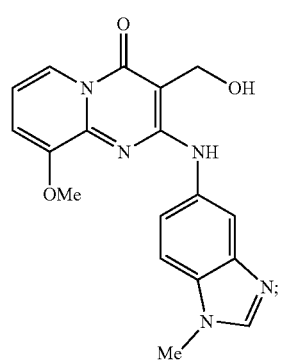 [SMILES: COc1cccn2c(=O)c(CO)c(Nc3ccc4c(c3)ncn4C)nc12] |
| 3-(Hydroxymethyl)-9-methoxy-2-(1-methyl-1H-benzo[d]imidazol-5-ylamino)-4H-pyrido[1,2-a]pyrimidin-4-one (288) | 2-(4-Chlorophenylamino)-9-(difluoromethoxy)-3-(hydroxymethyl)-4H-pyrido[1,2-a]pyrimidin-4-one (291) |
| 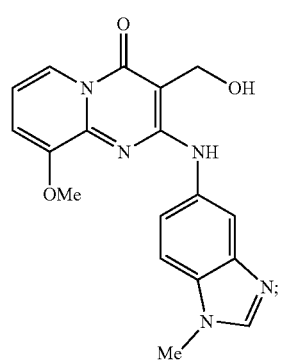 [SMILES: COc1cccn2c(=O)c(CO)c(Nc3ccc4c(c3)ncn4C)nc12] | 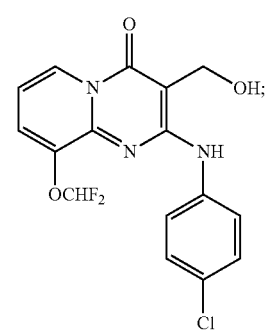 [SMILES: O=c1c(CO)c(Nc2ccc(Cl)cc2)nc2c(OC(F)F)cccn12] |
| 3-(Hydroxymethyl)-9-methoxy-2-(1-methyl-1H-indazol-5-ylamino)-4H-pyrido[1,2-a]pyrimidin-4-one (289) | 9-(Difluoromethoxy)-2-(3,4-difluorophenylamino)-3-(hydroxymethyl)-4H-pyrido[1,2-a]pyrimidin-4-one (292) |

473

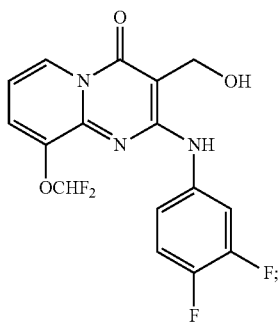 [SMILES: O=c1c(CO)c(Nc2ccc(F)c(F)c2)nc2c(OC(F)F)cccn12]

2-(3,4-Dichlorophenylamino)-9-(difluoromethoxy)-3-(hydroxymethyl)-4H-pyrido[1,2-a]pyrimidin-4-one (293)

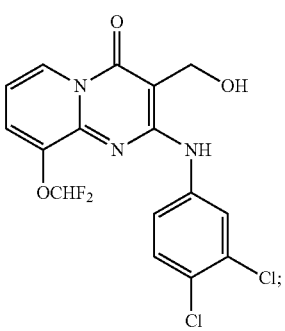 [SMILES: O=c1c(CO)c(Nc2ccc(Cl)c(Cl)c2)nc2c(OC(F)F)cccn12]

2-(3-Chloro-4-fluorophenylamino)-9-(difluoromethoxy)-3-(hydroxymethyl)-4H-pyrido[1,2-a]pyrimidin-4-one (294)

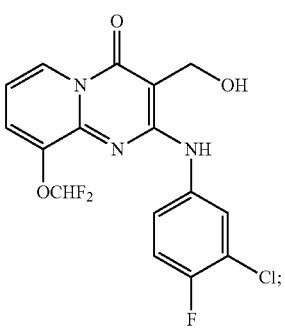 [SMILES: O=c1c(CO)c(Nc2ccc(F)c(Cl)c2)nc2c(OC(F)F)cccn12]

2-(1H-Indol-5-ylamino)-9-(difluoromethoxy)-3-(hydroxymethyl)-4H-pyrido[1,2-a]pyrimidin-4-one (295)

474

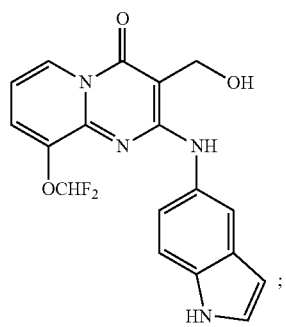 [SMILES: O=c1c(CO)c(Nc2ccc3[nH]ccc3c2)nc2c(OC(F)F)cccn12]

2-(3-chlorophenylamino)-3-(hydroxymethyl)-6,8-dimethyl-4H-pyrido[1,2-a]pyrimidin-4-one (296)

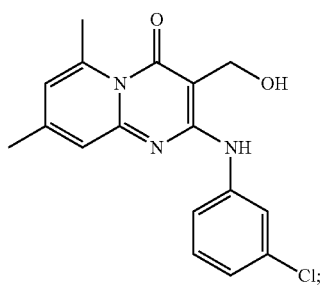 [SMILES: Cc1cc(C)n2c(=O)c(CO)c(Nc3cccc(Cl)c3)nc2c1]

7,9-Dichloro-2-(3-chlorophenylamino)-3-(hydroxymethyl)-4H-pyrido[1,2-a]pyrimidin-4-one (297)

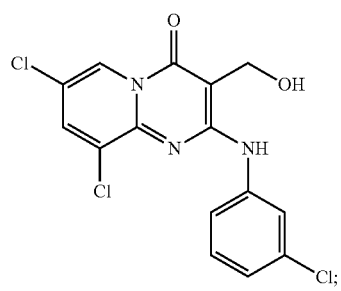 [SMILES: O=c1c(CO)c(Nc2cccc(Cl)c2)nc2c(Cl)cc(Cl)cn12]

2-(3-Chlorophenylamino)-7,9-difluoro-3-(hydroxymethyl)-4H-pyrido[1,2-a]pyrimidin-4-one (298)

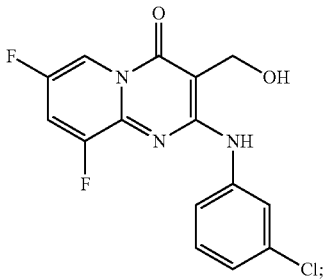

(4-Oxo-2-(phenylamino)-4H-pyrido[1,2-a]pyrimidin-3-yl)methyl benzoate (299)

475

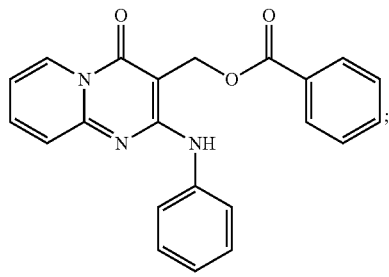 [SMILES: O=C(OCc1c(Nc2ccccc2)nc2ccccn2c1=O)c1ccccc1]

(4-Oxo-2-(phenylamino)-4H-pyrido[1,2-a]pyrimidin-3-yl)methyl acetate (300)

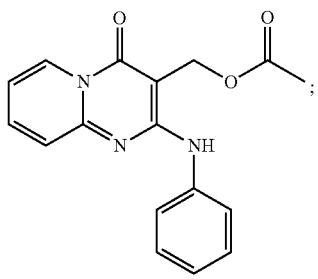 [SMILES: CC(=O)OCc1c(Nc2ccccc2)nc2ccccn2c1=O]

and
(4-Oxo-2-(phenylamino)-4H-pyrido[1,2-a]pyrimidin-3-yl)methyl isobutyrate (301)

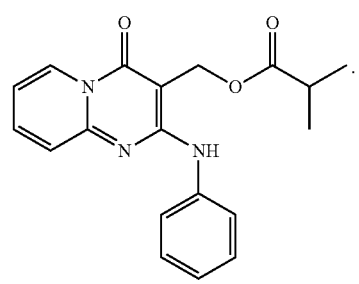 [SMILES: CC(C)C(=O)OCc1c(Nc2ccccc2)nc2ccccn2c1=O]

3. The compound, according to claim 2, having a formula selected from the group consisting of the following formulae 180, 199-201, 204, 206-221, 226, 229, 231-238, 245-278, 280-286 and 290-301:

Ethyl 4-oxo-2-(phenylamino)-4H-pyrido[1,2-a]pyrimidine-3-carboxylate (180)

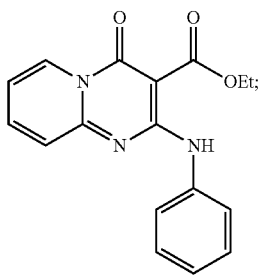 [SMILES: CCOC(=O)c1c(Nc2ccccc2)nc2ccccn2c1=O]

2-(3-Chlorophenylamino)-3-((cyclopentylamino)methyl)-4H-pyrido[1,2-a]pyrimidin-4-one (201)

476

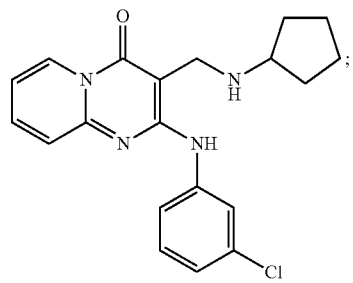 [SMILES: O=c1c(CNC2CCCC2)c(Nc2cccc(Cl)c2)nc2ccccn12]

2-(3-Chlorophenylamino)-3-((isopropylamino)methyl)-4H-pyrido[1,2-a]pyrimidin-4-one (204)

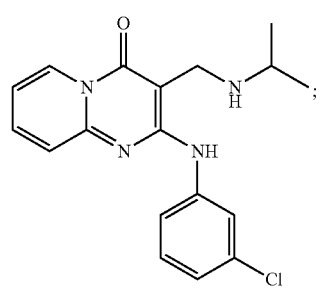 [SMILES: CC(C)NCc1c(Nc2cccc(Cl)c2)nc2ccccn2c1=O]

3-(Hydroxymethyl)-2-(phenylamino)-4H-pyrido[1,2-a]pyrimidin-4-one (206)

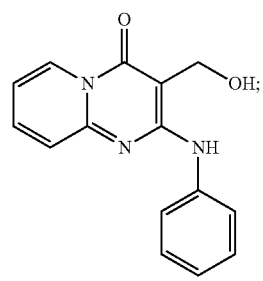 [SMILES: O=c1c(CO)c(Nc2ccccc2)nc2ccccn12]

2-(3-Chlorophenylamino)-3-(hydroxymethyl)-4H-pyrido-[1,2-a]pyrimidin-4-one (207)

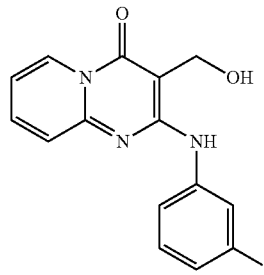

2-(3-Fluorophenylamino)-3-(hydroxymethyl)-4H-pyrido[1,2-a]pyrimidine-3-carbaldehyde (208)

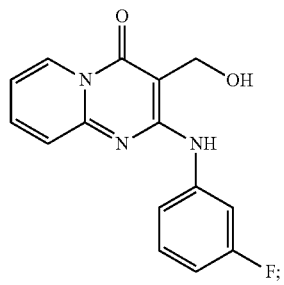 [SMILES: O=c1c(CO)c(Nc2cccc(F)c2)nc2ccccn12]

3-(Hydroxymethyl)-2-(3-(trifluoromethyl)phenylamino)-4H-pyrido[1,2-a]pyrimidin-4-one (209)

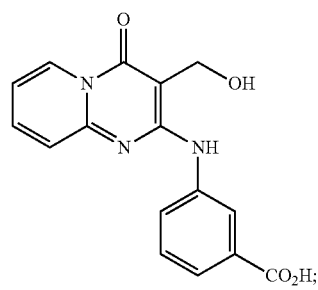 [SMILES: O=C(O)c1cccc(Nc2nc3ccccn3c(=O)c2CO)c1]

2-(4-Chlorophenylamino)-3-(hydroxymethyl)-4H-pyrido[1,2-a]pyrimidin-4-one (213)

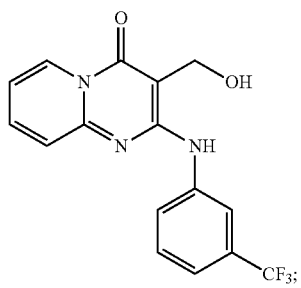

3-(Hydroxymethyl)-2-(3-(trifluoromethoxy)phenylamino)-4H-pyrido[1,2-a]pyrimidin-4-one (210)

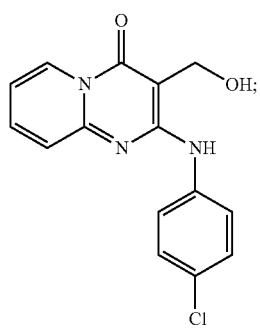 [SMILES: O=c1c(CO)c(Nc2ccc(Cl)cc2)nc2ccccn12]

2-(2-Chlorophenylamino)-3-(hydroxymethyl)-4H-pyrido[1,2-a]pyrimidin-4-one (214)

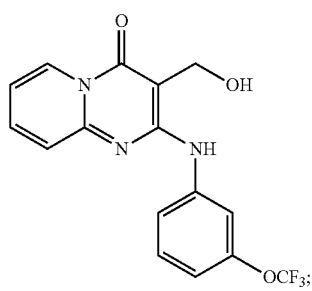

Methyl 3-(3-(hydroxymethyl)-4-oxo-4H-pyrido[1,2-a]pyrimidin-2-ylamino)benzoate (211)

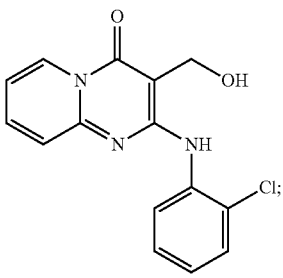 [SMILES: O=c1c(CO)c(Nc2ccccc2Cl)nc2ccccn12]

3-(Hydroxymethyl)-2-(3-hydroxyphenylamino)-4H-pyrido[1,2-a]pyrimidin-4-one (215)

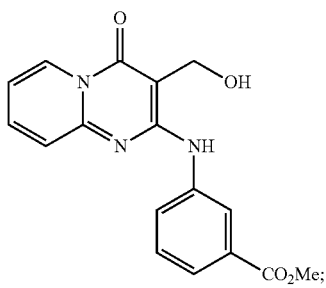

3-(3-(hydroxymethyl)-4-oxo-4H-pyrido[1,2-a]pyrimidin-2-ylamino)benzoic acid (212)

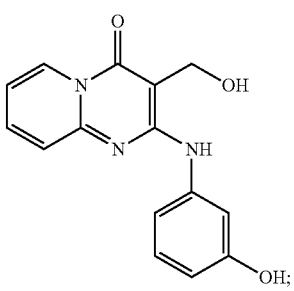 [SMILES: O=c1c(CO)c(Nc2cccc(O)c2)nc2ccccn12]

3-(Hydroxymethyl)-2-(4-hydroxyphenylamino)-4H-pyrido[1,2-a]pyrimidin-4-one (216)

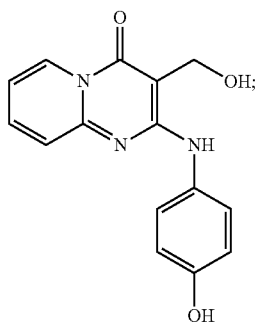 [SMILES: O=c1c(CO)c(Nc2ccc(O)cc2)nc2ccccn12]

3-(Hydroxymethyl)-2-(2-hydroxyphenylamino)-4H-pyrido[1,2-a]pyrimidin-4-one (217)

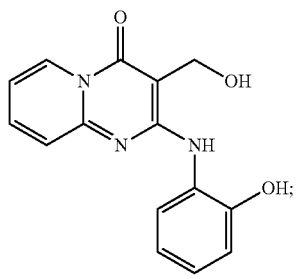 [SMILES: O=c1c(CO)c(Nc2ccccc2O)nc2ccccn12]

2-(2,6-Dichlorophenylamino)-3-(hydroxymethyl)-4H-pyrido[1,2-a]pyrimidin-4-one (218)

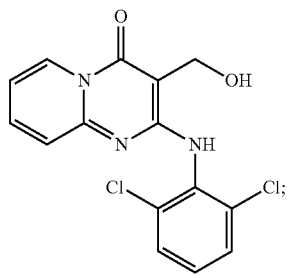 [SMILES: O=c1c(CO)c(Nc2c(Cl)cccc2Cl)nc2ccccn12]

2-(3,5-Dichlorophenylamino)-3-(hydroxymethyl)-4H-pyrido[1,2-a]pyrimidin-4-one (219)

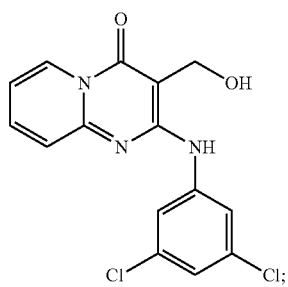 [SMILES: O=c1c(CO)c(Nc2cc(Cl)cc(Cl)c2)nc2ccccn12]

2-(3,5-Difluorophenylamino)-3-(hydroxymethyl)-4H-pyrido[1,2-a]pyrimidin-4-one (220)

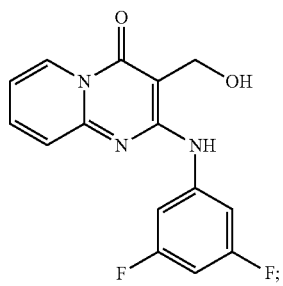

2-(2,6-Dimethylphenylamino)-3-(hydroxymethyl)-4H-pyrido[1,2-a]pyrimidin-4-one (221)

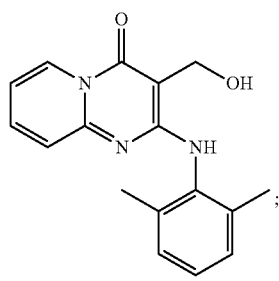 [SMILES: Cc1cccc(C)c1Nc1nc2ccccn2c(=O)c1CO]

3-(Hydroxymethyl)-9-methyl-2-(phenylamino)-4H-pyrido[1,2-a]pyrimidin-4-one (231)

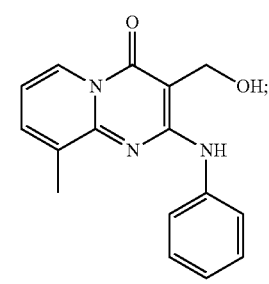 [SMILES: Cc1cccn2c(=O)c(CO)c(Nc3ccccc3)nc12]

2-(3-Chlorophenylamino)-3-(hydroxymethyl)-9-methyl-4H-pyrido[1,2-a]pyrimidin-4-one (232)

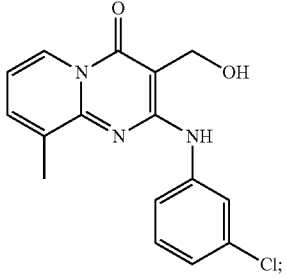

2-((3-Chlorophenyl)(methyl)amino)-3-(hydroxymethyl)-9-methyl-4H-pyrido[1,2-a]pyrimidin-4-one (233)

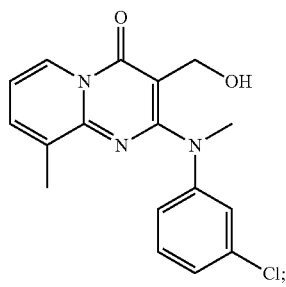 [SMILES: Cc1cccn2c(=O)c(CO)c(N(C)c3cccc(Cl)c3)nc12]

2-((3-Chlorophenyl)(methyl)amino)-3-(methoxymethyl)-
9-methyl-4H-pyrido[1,2-a]pyrimidin-4-one (234)

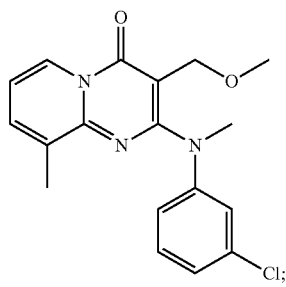 [SMILES: COCc1c(N(C)c2cccc(Cl)c2)nc2c(C)cccn2c1=O]

3-(Hydroxymethyl)-9-methyl-2-(3-(trifluoromethoxy)
phenylamino)-4H-pyrido[1,2-a]pyrimidin-4-one (235)

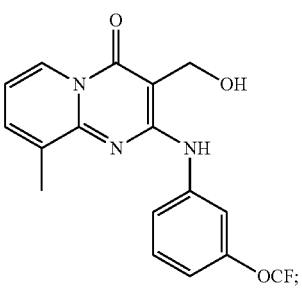

3-(Hydroxymethyl)-2-(3-hydroxyphenylamino)-9-me-
thyl-4H-pyrido[1,2-a]pyrimidin-4-one (236)

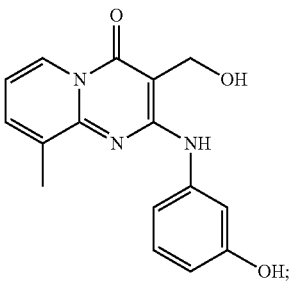

3-(Hydroxymethyl)-2-(4-hydroxyphenylamino)-9-me-
thyl-4H-pyrido[1,2-a]pyrimidin-4-one (237)

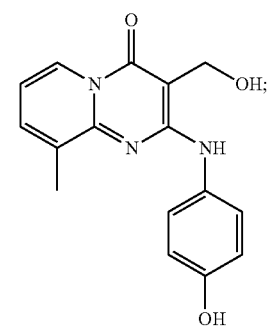

2-(4-tert-Butylphenylamino)-3-(hydroxymethyl)-9-me-
thyl-4H-pyrido[1,2-a]pyrimidin-4-one (238)

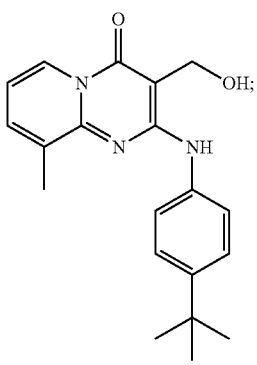 [SMILES: Cc1cccn2c(=O)c(CO)c(Nc3ccc(C(C)(C)C)cc3)nc12]

7-Bromo-2-(3-chlorophenylamino)-3-(hydroxymethyl)-
4H-pyrido[1,2-a]pyrimidin-4-one (245)

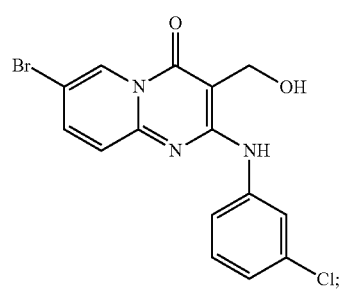

2-(3-Chlorophenylamino)-3-(hydroxymethyl)-7-meth-
oxy-4H-pyrido[1,2-a]pyrimidin-4-one (246)

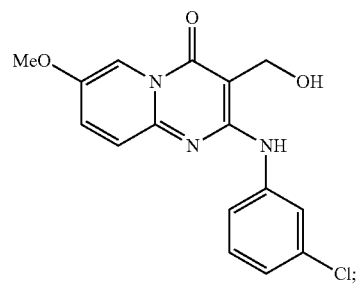 [SMILES: COc1ccc2nc(Nc3cccc(Cl)c3)c(CO)c(=O)n2c1]

2-(3-Chlorophenylamino)-3-(hydroxymethyl)-8-meth-
oxy-4H-pyrido[1,2-a]pyrimidin-4-one (247)

| 483 | 484 |
|---|---|
| 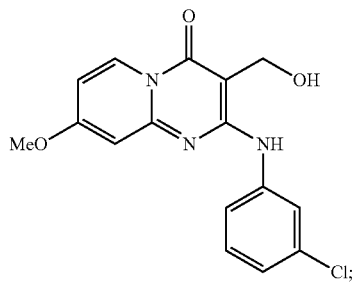 [SMILES: COc1ccn2c(=O)c(CO)c(Nc3cccc(Cl)c3)nc2c1] 8-Chloro-2-(3-chlorophenylamino)-3-(hydroxymethyl)-4H-pyrido[1,2-a]pyrimidin-4-one (248) | 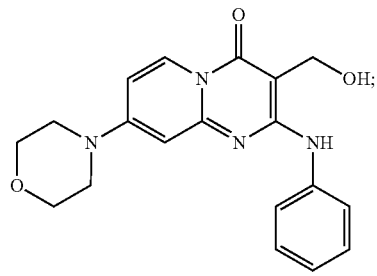 2-(3-Fluorophenylamino)-3-(hydroxymethyl)-8-morpholino-4H-pyrido[1,2-a]pyrimidin-4-one (252) |
| 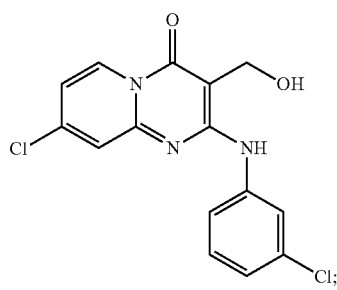 [SMILES: O=c1c(CO)c(Nc2cccc(Cl)c2)nc2cc(Cl)ccn12] 2-(3-Chlorophenylamino)-3-(hydroxymethyl)-8-(methylamino)-4H-pyrido[1,2-a]pyrimidin-4-one (249) | 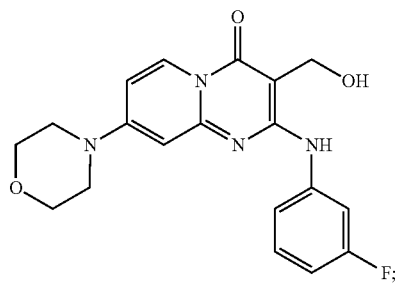 [SMILES: O=c1c(CO)c(Nc2cccc(F)c2)nc2cc(N3CCOCC3)ccn12] 2-(3-Chlorophenylamino)-3-(hydroxymethyl)-8-morpholino-4H-pyrido[1,2-a]pyrimidin-4-one (253) |
| 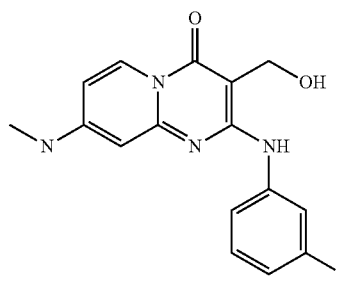 2-(3-Chlorophenylamino)-8-(diethylamino)-3-(hydroxymethyl)-4H-pyrido[1,2-a]pyrimidin-4-one (250) | 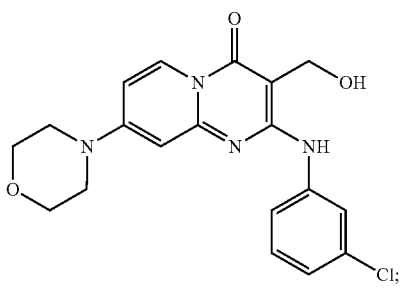 [SMILES: O=c1c(CO)c(Nc2cccc(Cl)c2)nc2cc(N3CCOCC3)ccn12] 3-(Hydroxymethyl)-8-(4-methylpiperazin-1-yl)-2-(phenylamino)-4H-pyrido[1,2-a]pyrimidin-4-one (254) |
| 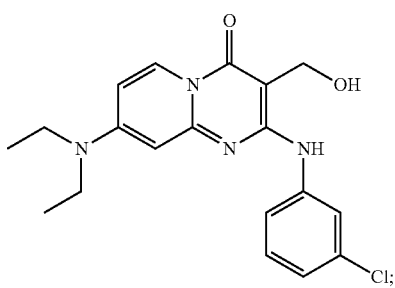 3-(Hydroxymethyl)-8-morpholino-2-(phenylamino)-4H-pyrido[1,2-a]pyrimidin-4-one (251) | 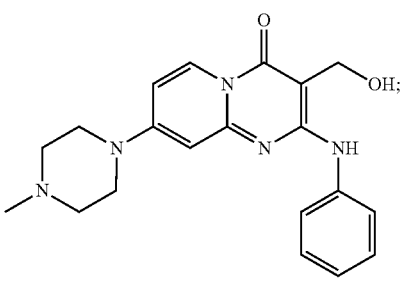 [SMILES: CN1CCN(c2ccn3c(=O)c(CO)c(Nc4ccccc4)nc3c2)CC1] 2-(3-Chlorophenylamino)-3-(hydroxymethyl)-8-(4-methylpiperazin-1-yl)-4H-pyrido[1,2-a]pyrimidin-4-one (255) |

485

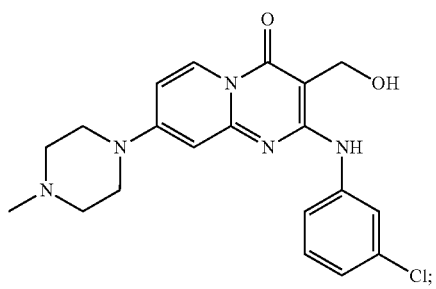 [SMILES: CN1CCN(c2ccn3c(=O)c(CO)c(Nc4cccc(Cl)c4)nc3c2)CC1]

2-(3-Fluorophenylamino)-3-(hydroxymethyl)-8-(4-methylpiperazin-1-yl)-4H-pyrido[1,2-a]pyrimidin-4-one (256)

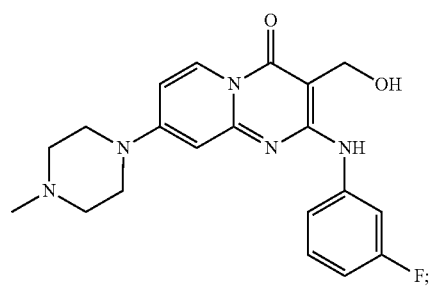 [SMILES: CN1CCN(c2ccn3c(=O)c(CO)c(Nc4cccc(F)c4)nc3c2)CC1]

2-(3-Chlorophenylamino)-3-(hydroxymethyl)-8-methyl-4H-pyrido[1,2-a]pyrimidin-4-one (257)

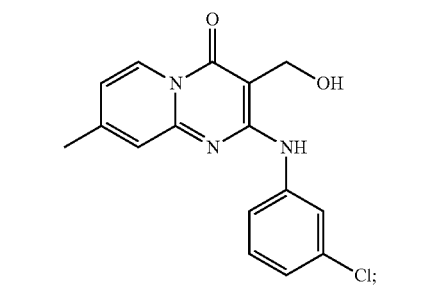

2-(4-Chlorophenylamino)-3-(hydroxymethyl)-8-methyl-4H-pyrido[1,2-a]pyrimidin-4-one (258)

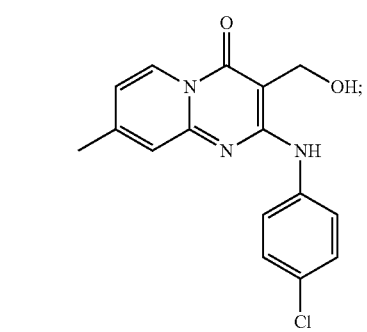 [SMILES: Cc1ccn2c(=O)c(CO)c(Nc3ccc(Cl)cc3)nc2c1]

2-(4-Fluorophenylamino)-3-(hydroxymethyl)-8-methyl-4H-pyrido[1,2-a]pyrimidin-4-one (259)

486

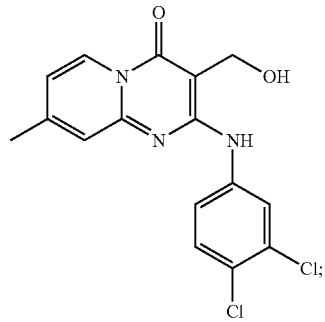

2-(3,4-Dichlorophenylamino)-3-(hydroxymethyl)-8-methyl-4H-pyrido[1,2-a]pyrimidin-4-one (260)

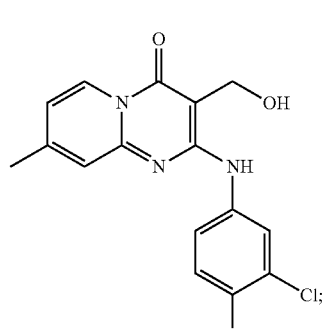

2-(3-Chloro-4-fluorophenylamino)-3-(hydroxymethyl)-8-methyl-4H-pyrido[1,2-a]pyrimidin-4-one (261)

9-Chloro-2-(3-chlorophenylamino)-3-(hydroxymethyl)-4H-pyrido[1,2-a]pyrimidin-4-one (262)

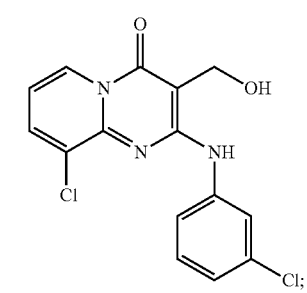

2-(3-Chlorophenylamino)-3-(hydroxymethyl)-9-(trifluoromethyl)-4H-pyrido[1,2-a]pyrimidin-4-one (263)

487

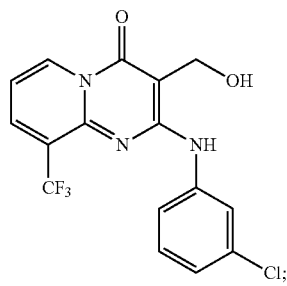 [SMILES: O=c1c(CO)c(Nc2cccc(Cl)c2)nc2c(C(F)(F)F)cccn12]

2-(3-Chlorophenylamino)-9-fluoro-3-(hydroxymethyl)-
4H-pyrido[1,2-a]pyrimidin-4-one (264)

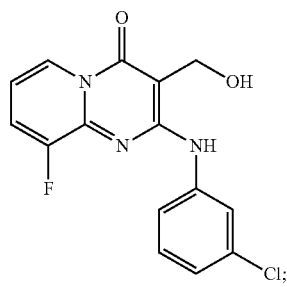 [SMILES: O=c1c(CO)c(Nc2cccc(Cl)c2)nc2c(F)cccn12]

2-(4-Chlorophenylamino)-9-fluoro-3-(hydroxymethyl)-
4H-pyrido[1,2-a]pyrimidin-4-one (265)

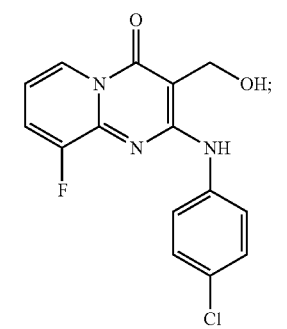

9-Fluoro-2-(4-fluorophenylamino)-3-(hydroxymethyl)-
4H-pyrido[1,2-a]pyrimidin-4-one (266)

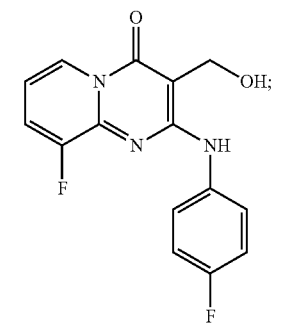

2-(3-Chloro-4-fluorophenylamino)-9-fluoro-3-(hydroxymethyl)-4H-pyrido[1,2-a]pyrimidin-4-one (267)

488

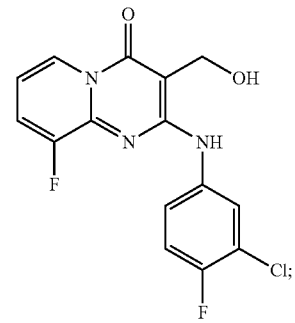 [SMILES: O=c1c(CO)c(Nc2ccc(F)c(Cl)c2)nc2c(F)cccn12]

2-(3,4-Difluorophenylamino)-9-fluoro-3-(hydroxymethyl)-4H-pyrido[1,2-a]pyrimidin-4-one (268)

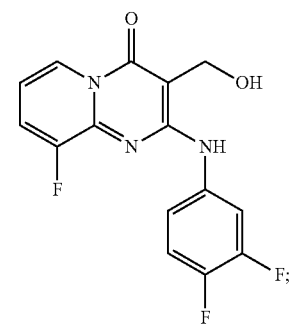 [SMILES: O=c1c(CO)c(Nc2ccc(F)c(F)c2)nc2c(F)cccn12]

2-(3,4-Dichlorophenylamino)-9-fluoro-3-(hydroxymethyl)-4H-pyrido[1,2-a]pyrimidin-4-one (269)

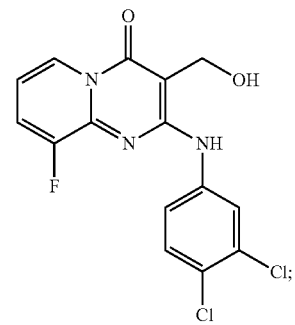 [SMILES: O=c1c(CO)c(Nc2ccc(Cl)c(Cl)c2)nc2c(F)cccn12]

2-(1H-Indol-5-ylamino)-9-fluoro-3-(hydroxymethyl)-
4H-pyrido[1,2-a]pyrimidin-4-one (270)

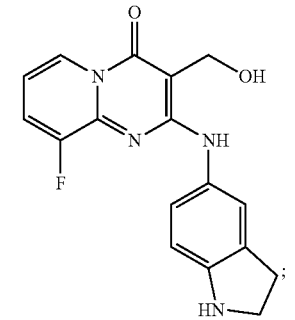 [SMILES: O=c1c(CO)c(Nc2ccc3c(c2)CCN3)nc2c(F)cccn12]

489

3-(Hydroxymethyl)-9-methoxy-2-(phenylamino)-4H-pyrido[1,2-a]pyrimidin-4-one (271)

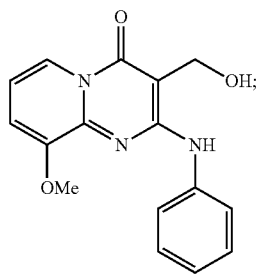 [SMILES: COc1cccn2c(=O)c(CO)c(Nc3ccccc3)nc12]

2-(3-Chlorophenylamino)-3-(hydroxymethyl)-9-methoxy-4H-pyrido[1,2-a]pyrimidin-4-one (273)

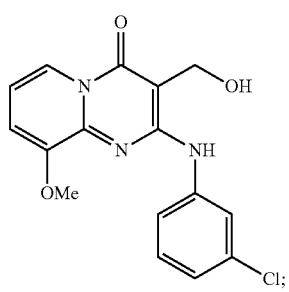 [SMILES: COc1cccn2c(=O)c(CO)c(Nc3cccc(Cl)c3)nc12]

2-(4-Chlorophenylamino)-3-(hydroxymethyl)-9-methoxy-4H-pyrido[1,2-a]pyrimidin-4-one (274)

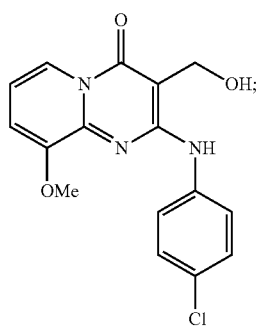 [SMILES: COc1cccn2c(=O)c(CO)c(Nc3ccc(Cl)cc3)nc12]

2-(4-Fluorophenylamino)-3-(hydroxymethyl)-9-methoxy-4H-pyrido[1,2-a]pyrimidin-4-one (275)

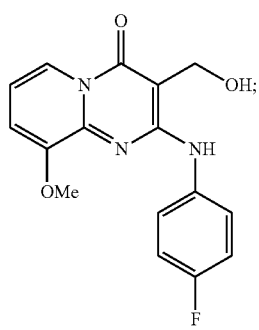 [SMILES: COc1cccn2c(=O)c(CO)c(Nc3ccc(F)cc3)nc12]

490

3-(Hydroxymethyl)-9-methoxy-2-(4-(trifluoromethoxy)phenylamino)-4H-pyrido[1,2-a]pyrimidin-4-one (276)

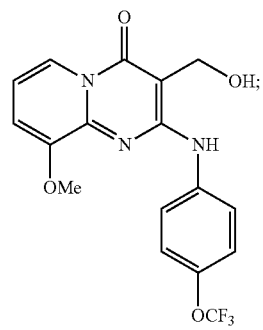 [SMILES: COc1cccn2c(=O)c(CO)c(Nc3ccc(OC(F)(F)F)cc3)nc12]

3-(Hydroxymethyl)-9-methoxy-2-(4-(trifluoromethyl)phenylamino)-4H-pyrido[1,2-a]pyrimidin-4-one (277)

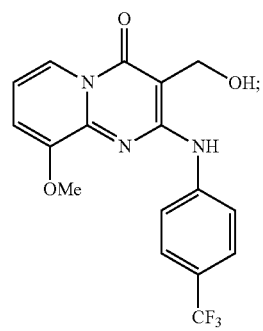 [SMILES: COc1cccn2c(=O)c(CO)c(Nc3ccc(C(F)(F)F)cc3)nc12]

2-(3-Chloro-4-fluorophenylamino)-3-(hydroxymethyl)-9-methoxy-4H-pyrido[1,2-a]pyrimidin-4-one (278)

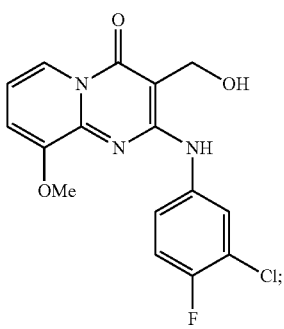 [SMILES: COc1cccn2c(=O)c(CO)c(Nc3ccc(F)c(Cl)c3)nc12]

2-(3-Chloro-4-hydroxyphenylamino)-3-(hydroxymethyl)-9-methoxy-4H-pyrido[1,2-a]pyrimidin-4-one (280)

491

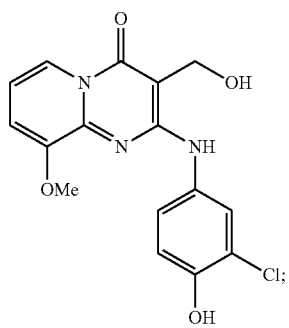 [SMILES: COc1cccn2c(=O)c(CO)c(Nc3ccc(O)c(Cl)c3)nc12]

2-(3,4-Dichlorophenylamino)-3-(hydroxymethyl)-9-methoxy-4H-pyrido[1,2-a]pyrimidin-4-one (281)

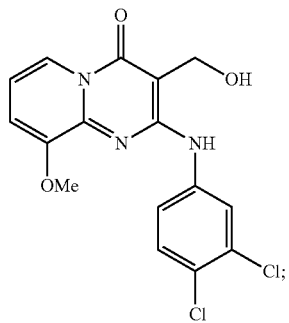 [SMILES: COc1cccn2c(=O)c(CO)c(Nc3ccc(Cl)c(Cl)c3)nc12]

3-(Hydroxymethyl)-9-methoxy-2-(4-methyl-3-(trifluoromethyl)phenylamino)-4H-pyrido[1,2-a]pyrimidin-4-one (282)

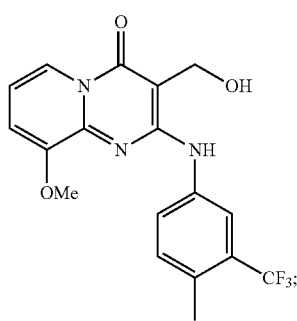 [SMILES: COc1cccn2c(=O)c(CO)c(Nc3ccc(C)c(C(F)(F)F)c3)nc12]

2-(4-Fluoro-3-(trifluoromethyl)phenylamino)-3-(hydroxymethyl)-9-methoxy-4H-pyrido[1,2-a]pyrimidin-4-one (283)

492

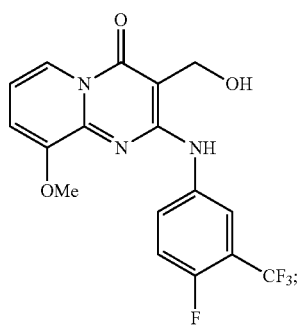 [SMILES: COc1cccn2c(=O)c(CO)c(Nc3ccc(F)c(C(F)(F)F)c3)nc12]

2-(2,3-Dihydro-1H-inden-5-ylamino)-3-(hydroxymethyl)-9-methoxy-4H-pyrido[1,2-a]pyrimidin-4-one (284)

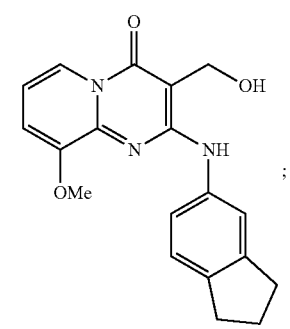 [SMILES: COc1cccn2c(=O)c(CO)c(Nc3ccc4c(c3)CCC4)nc12]

2-(Benzo[d][1,3]dioxol-5-ylamino)-3-(hydroxymethyl)-9-methoxy-4H-pyrido[1,2-a]pyrimidin-4-one (285)

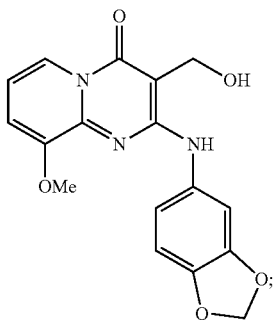 [SMILES: COc1cccn2c(=O)c(CO)c(Nc3ccc4c(c3)OCO4)nc12]

2-(2,3-Dihydrobenzo[b][1,4]dioxin-6-ylamino)-3-(hydroxymethyl)-9-methoxy-4H-pyrido[1,2-a]pyrimidin-4-one (286)

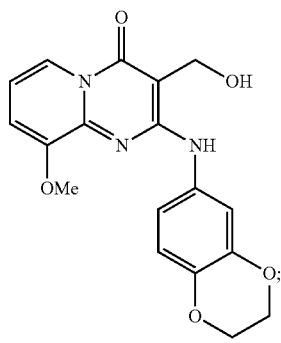 [SMILES: COc1cccn2c(=O)c(CO)c(Nc3ccc4c(c3)OCCO4)nc12]

9-(Difluoromethoxy)-2-(4-fluorophenylamino)-3-(hydroxymethyl)-4H-pyrido[1,2-a]pyrimidin-4-one (290)

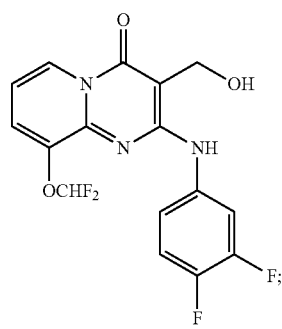

2-(3,4-Dichlorophenylamino)-9-(difluoromethoxy)-3-(hydroxymethyl)-4H-pyrido[1,2-a]pyrimidin-4-one (293)

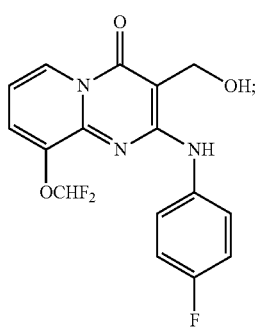 [SMILES: O=c1c(CO)c(Nc2ccc(F)cc2)nc2c(OC(F)F)cccn12]

2-(4-Chlorophenylamino)-9-(difluoromethoxy)-3-(hydroxymethyl)-4H-pyrido[1,2-a]pyrimidin-4-one (291)

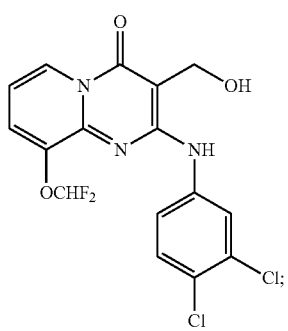

2-(3-Chloro-4-fluorophenylamino)-9-(difluoromethoxy)-3-(hydroxymethyl)-4H-pyrido[1,2-a]pyrimidin-4-one (294)

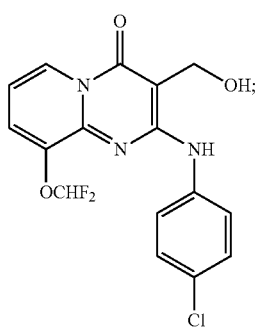 [SMILES: O=c1c(CO)c(Nc2ccc(Cl)cc2)nc2c(OC(F)F)cccn12]

9-(Difluoromethoxy)-2-(3,4-difluorophenylamino)-3-(hydroxymethyl)-4H-pyrido[1,2-a]pyrimidin-4-one (292)

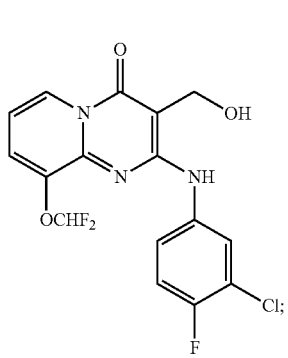 [SMILES: O=c1c(CO)c(Nc2ccc(F)c(Cl)c2)nc2c(OC(F)F)cccn12]

2-(1H-Indol-5-ylamino)-9-(difluoromethoxy)-3-(hydroxymethyl)-4H-pyrido[1,2-a]pyrimidin-4-one (295)

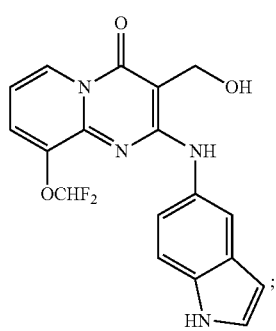 [SMILES: O=c1c(CO)c(Nc2ccc3[nH]ccc3c2)nc2c(OC(F)F)cccn12]

2-(3-chlorophenylamino)-3-(hydroxymethyl)-6,8-dimethyl-4H-pyrido[1,2-a]pyrimidin-4-one (296)

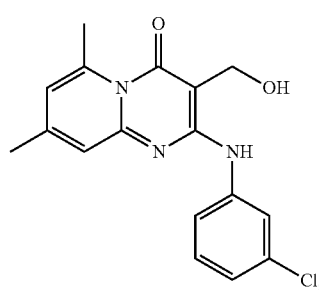

7,9-Dichloro-2-(3-chlorophenylamino)-3-(hydroxymethyl)-4H-pyrido[1,2-a]pyrimidin-4-one (297)

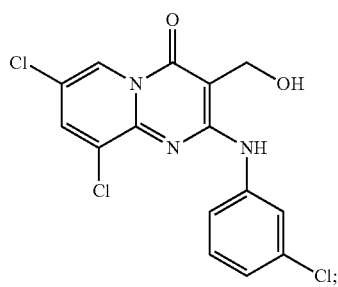 [SMILES: O=c1c(CO)c(Nc2cccc(Cl)c2)nc2c(Cl)cc(Cl)cn12]

2-(3-Chlorophenylamino)-7,9-difluoro-3-(hydroxymethyl)-4H-pyrido[1,2-a]pyrimidin-4-one (298)

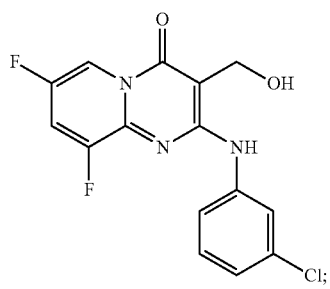 [SMILES: O=c1c(CO)c(Nc2cccc(Cl)c2)nc2c(F)cc(F)cn12]

(4-Oxo-2-(phenylamino)-4H-pyrido[1,2-a]pyrimidin-3-yl)methyl benzoate (299)

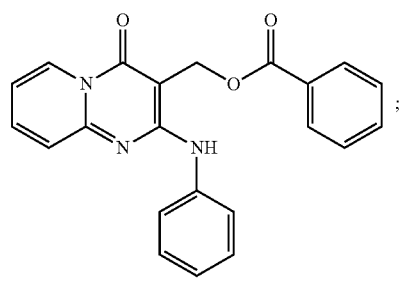 [SMILES: O=C(OCc1c(Nc2ccccc2)nc2ccccn2c1=O)c1ccccc1]

(4-Oxo-2-(phenylamino)-4H-pyrido[1,2-a]pyrimidin-3-yl)methyl acetate (300)

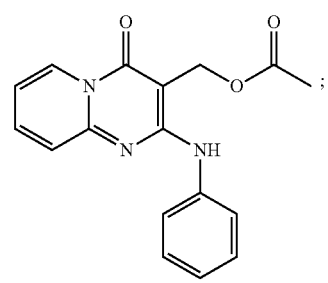 [SMILES: CC(=O)OCc1c(Nc2ccccc2)nc2ccccn2c1=O]

and (4-Oxo-2-(phenylamino)-4H-pyrido[1,2-a]pyrimidin-3-yl)methyl isobutyrate (301)

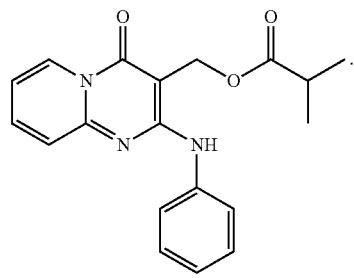 [SMILES: CC(C)C(=O)OCc1c(Nc2ccccc2)nc2ccccn2c1=O]

4. A compound having a formula selected from the group consisting of the following formulae 125, 126, and 132-143:

2-Hydroxy-9-methyl-4H-pyrido[1,2-a]pyrimidin-4-one (125)

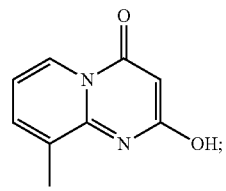

2-Hydroxy-8-methyl-4H-pyrido[1,2-a]pyrimidin-4-one (126)

497

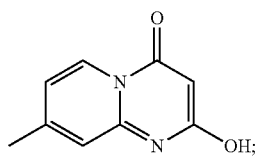

9-Methyl-4-oxo-2-(phenylamino)-4H-pyrido[1,2-a]pyrimidine-3-carbaldehyde (132)

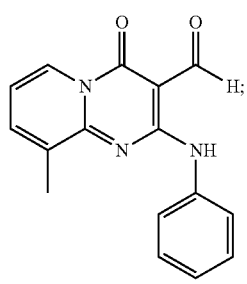

2-(3-Chlorophenylamino)-9-methyl-4-oxo-4H-pyrido[1,2-a]pyrimidine-3-carbaldehyde (133)

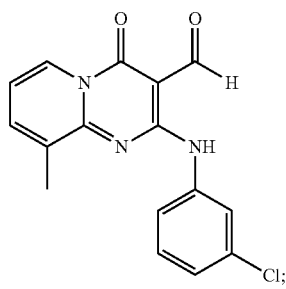 [SMILES: Cc1cccn2c(=O)c(C=O)c(Nc3cccc(Cl)c3)nc12]

9-Methyl-4-oxo-2-(3-(trifluoromethoxy)phenylamino)-4H-pyrido[1,2-a]pyrimidine-3-carbaldehyde (134)

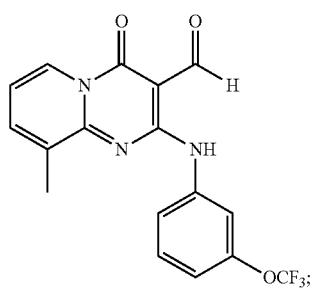 [SMILES: Cc1cccn2c(=O)c(C=O)c(Nc3cccc(OC(F)(F)F)c3)nc12]

9-Methyl-4-oxo-2-(3-(trifluoromethyl)phenylamino)-4H-pyrido[1,2-a]pyrimidine-3-carbaldehyde (135)

498

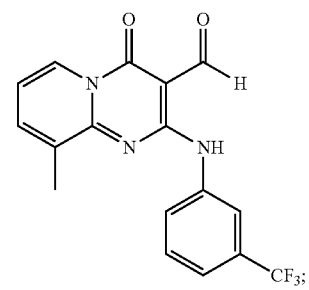 [SMILES: Cc1cccn2c(=O)c(C=O)c(Nc3cccc(C(F)(F)F)c3)nc12]

2-(4-tert-Butylphenylamino)-9-methyl-4-oxo-4H-pyrido[1,2-a]pyrimidine-3-carbaldehyde (136)

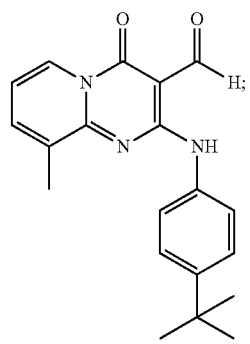

2-(3-Chlorobenzylamino)-9-methyl-4-oxo-4H-pyrido[1,2-a]pyrimidine-3-carbaldehyde (137)

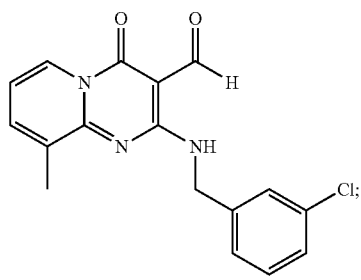 [SMILES: Cc1cccn2c(=O)c(C=O)c(NCc3cccc(Cl)c3)nc12]

9-Methyl-2-morpholino-4-oxo-4H-pyrido[1,2-a]pyrimidine-3-carbaldehyde (138)

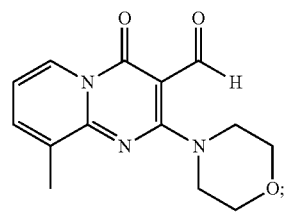 [SMILES: Cc1cccn2c(=O)c(C=O)c(N3CCOCC3)nc12]

2-(4-(2-Chlorophenyl)piperazin-1-yl)-9-methyl-4-oxo-4H-pyrido[1,2-a]pyrimidine-3-carbaldehyde (139)

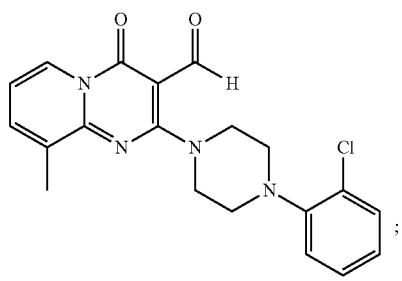 [SMILES: Cc1cccn2c(=O)c(C=O)c(N3CCN(c4ccccc4Cl)CC3)nc12]

2-(3,4-Dihydroisoquinolin-2(1H)-yl)-9-methyl-4-oxo-4H-pyrido[1,2-a]pyrimidine-3-carbaldehyde (140)

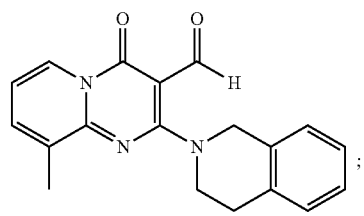 [SMILES: Cc1cccn2c(=O)c(C=O)c(N3CCc4ccccc4C3)nc12]

2-(Isobutylamino)-9-methyl-4-oxo-4H-pyrimidine-3-carbaldehyde (141)

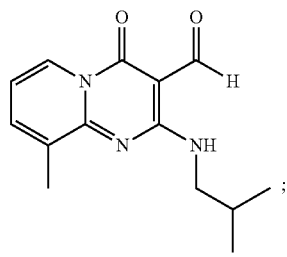 [SMILES: Cc1cccn2c(=O)c(C=O)c(NCC(C)C)nc12]

2-(Diethylamino)-9-methyl-4-oxo-4H-pyrido[1,2-a]pyrimidine-3-carbaldehyde (142)

and

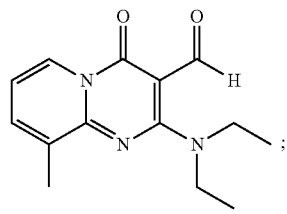 [SMILES: CCN(CC)c1nc2c(C)cccn2c(=O)c1C=O]

2-(Cyclohexylmethylamino)-9-methyl-4-oxo-4H-pyrido[1,2-a]pyrimidine-3-carbaldehyde (143)

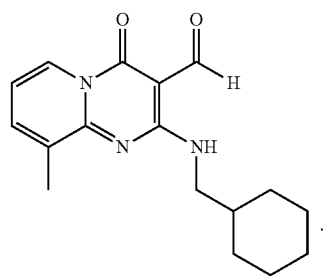

5. A compound having a formula selected from the group consisting of the following formulae 147-173, 188-189, 198, 205 and 231-298:

9-Methyl-4-oxo-2-(phenylamino)-4H-pyrido[1,2-a]pyrimidine-3-carboxylic acid (147)

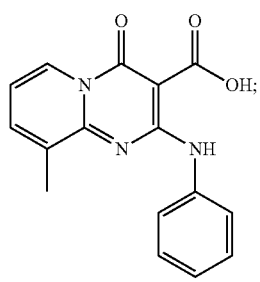

2-(3-Chlorophenylamino)-9-methyl-4-oxo-4H-pyrido[1,2-a]pyrimidine-3-carboxylic acid (148)

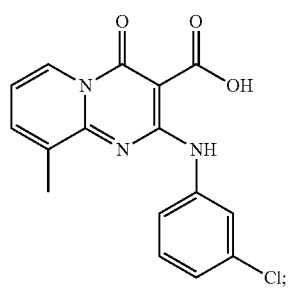 [SMILES: Cc1cccn2c(=O)c(C(=O)O)c(Nc3cccc(Cl)c3)nc12]

2-(3-Chlorophenylamino)-8-methyl-4-oxo-4H-pyrido[1,2-a]pyrimidine-3-carboxylic acid (149)

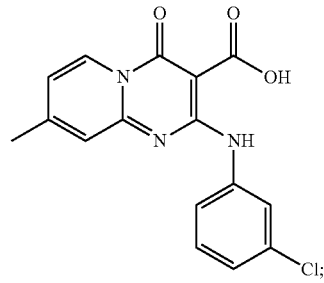 [SMILES: Cc1ccn2c(=O)c(C(=O)O)c(Nc3cccc(Cl)c3)nc2c1]

2-(3-Chlorophenylamino)-7-methyl-4-oxo-4H-pyrido[1,2-a]pyrimidine-3-carboxylic acid (150)

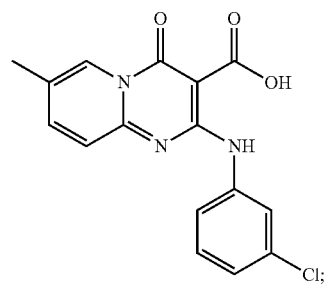 [SMILES: Cc1ccc2nc(Nc3cccc(Cl)c3)c(C(=O)O)c(=O)n2c1]

2-(3-Chlorophenylamino)-6-methyl-4-oxo-4H-pyrido[1,
2-a]pyrimidine-3-carboxylic acid (151)

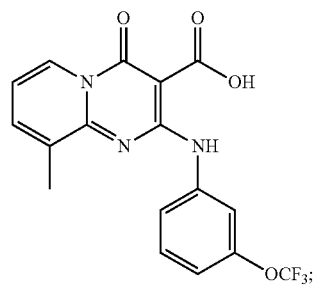

9-Methyl-2-(3-nitrophenylamino)-4-oxo-4H-pyrido[1,2-
a]pyrimidine-3-carboxylic acid (155)

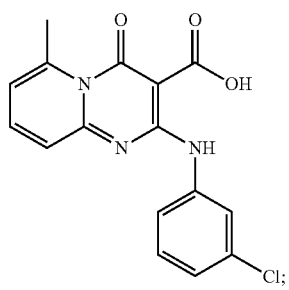 [SMILES: Cc1cccc2nc(Nc3cccc(Cl)c3)c(C(=O)O)c(=O)n12]

2-(3-Fluorophenylamino)-9-methyl-4-oxo-4H-pyrido[1,
2-a]pyrimidine-3-carboxylic acid (152)

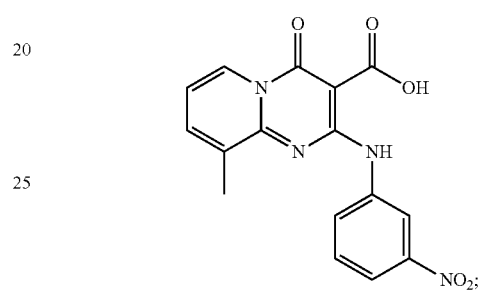

2-(3-(Methoxycarbonyl)phenylamino)-9-methyl-4-oxo-
4H-pyrido[1,2-a]pyrimidine-3-carboxylic acid (156)

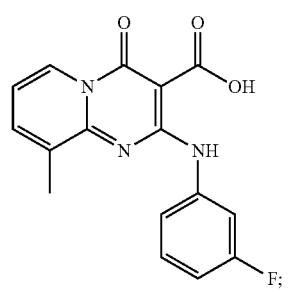 [SMILES: Cc1cccn2c(=O)c(C(=O)O)c(Nc3cccc(F)c3)nc12]

9-Methyl-4-oxo-2-(3-(trifluoromethyl)phenylamino)-4H-
pyrido[1,2-a]pyrimidine-3-carboxylic acid (153)

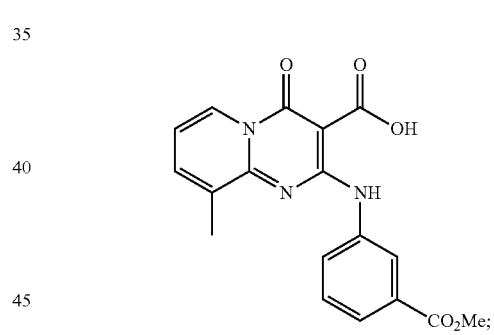

2-(3-Hydroxyphenylamino)-9-methyl-4-oxo-4H-pyrido
[1,2-a]pyrimidine-3-carboxylic acid (157)

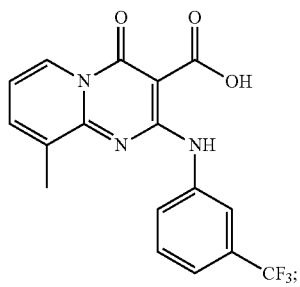 [SMILES: Cc1cccn2c(=O)c(C(=O)O)c(Nc3cccc(C(F)(F)F)c3)nc12]

9-Methyl-4-oxo-2-(3-(trifluoromethoxy)phenylamino)-
4H-pyrido[1,2-a]pyrimidine-3-carboxylic acid (154)

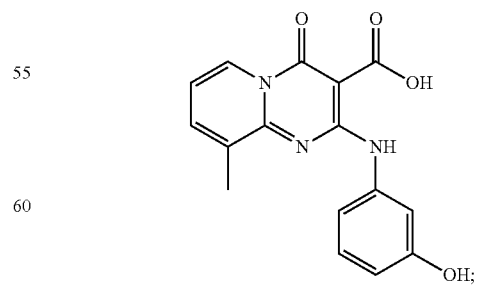

2-(4-Hydroxyphenylamino)-9-methyl-4-oxo-4H-pyrido
[1,2-a]pyrimidine-3-carboxylic acid (158)

503

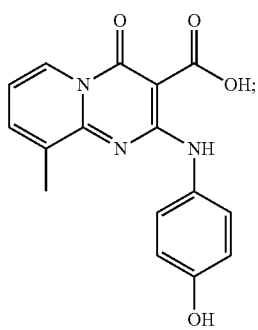 [SMILES: Cc1cccn2c(=O)c(C(=O)O)c(Nc3ccc(O)cc3)nc12]

2-(4-tert-Butylphenylamino)-9-methyl-4-oxo-4H-pyrido
[1,2-a]pyrimidine-3-carboxylic acid (159)

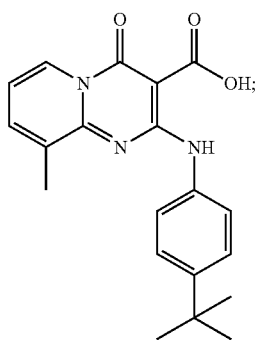 [SMILES: Cc1cccn2c(=O)c(C(=O)O)c(Nc3ccc(C(C)(C)C)cc3)nc12]

2-(3-Chlorobenzylamino)-9-methyl-4-oxo-4H-pyrido[1,
2-a]pyrimidine-3-carboxylic acid (160)

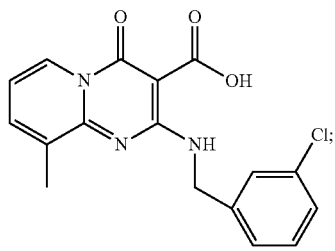 [SMILES: Cc1cccn2c(=O)c(C(=O)O)c(NCc3cccc(Cl)c3)nc12]

2-(Diethylamino)-9-methyl-4-oxo-4H-pyrido[1,2-a]pyrimidine-3-carboxylic acid (161)

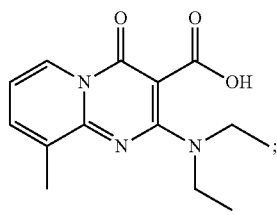 [SMILES: CCN(CC)c1nc2c(C)cccn2c(=O)c1C(=O)O]

2-(Isobutylamino)-9-methyl-4-oxo-4H-pyrido[1,2-a]pyrimidine-3-carboxylic acid (162)

504

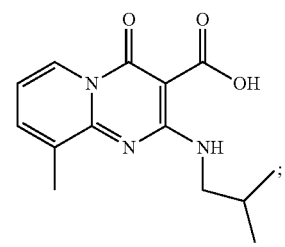 [SMILES: Cc1cccn2c(=O)c(C(=O)O)c(NCC(C)C)nc12]

2-(Cyclohexylmethylamino)-9-methyl-4-oxo-4H-pyrido
[1,2-a]pyrimidine-3-carboxylic acid (163)

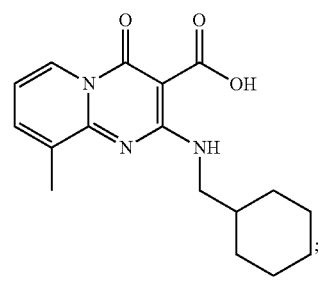 [SMILES: Cc1cccn2c(=O)c(C(=O)O)c(NCC3CCCCC3)nc12]

2-(Cyclohexylamino)-9-methyl-4-oxo-4H-pyrido[1,2-a]
pyrimidine-3-carboxylic acid (164)

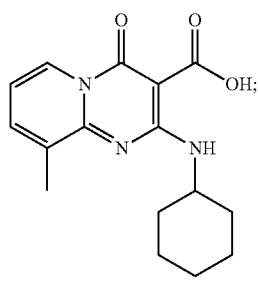 [SMILES: Cc1cccn2c(=O)c(C(=O)O)c(NC3CCCCC3)nc12]

2-(Cyclopentylamino)-9-methyl-4-oxo-4H-pyrido[1,2-a]
pyrimidine-3-carboxylic acid (165)

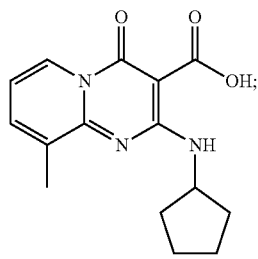 [SMILES: Cc1cccn2c(=O)c(C(=O)O)c(NC3CCCC3)nc12]

2-(Cycloheptylamino)-9-methyl-4-oxo-4H-pyrido[1,2-a]
pyrimidine-3-carboxylic acid (166)

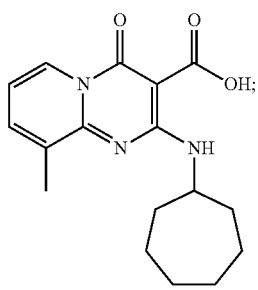 [SMILES: Cc1cccn2c(=O)c(C(=O)O)c(NC3CCCCCC3)nc12]

2-(1-(tert-Butoxycarbonyl)piperidin-4-ylamino)-9-methyl-4-oxo-4H-pyrido[1,2-a]pyrimidine-3-carboxylic acid (167)

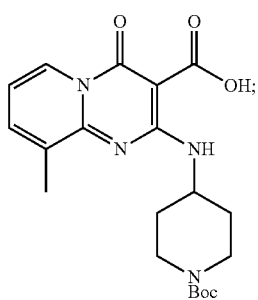 [SMILES: Cc1cccn2c(=O)c(C(=O)O)c(NC3CCN(C(=O)OC(C)(C)C)CC3)nc12]

2-(2-(4-Fluorophenoxy)ethylamino)-9-methyl-4-oxo-4H-pyrido[1,2-a]pyrimidine-3-carboxylic acid (168)

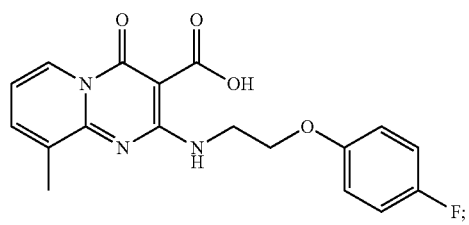 [SMILES: Cc1cccn2c(=O)c(C(=O)O)c(NCCOc3ccc(F)cc3)nc12]

9-Methyl-4-oxo-2-(2-(4-(trifluoromethoxy)phenoxy)ethylamino)-4H-pyrido[1,2-a]pyrimidine-3-carboxylic acid (169)

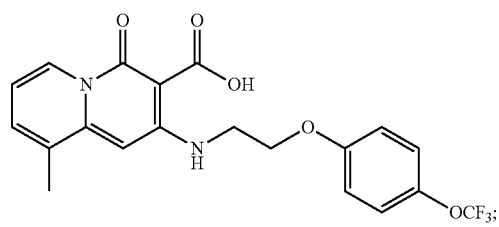 [SMILES: Cc1cccn2c(=O)c(C(=O)O)c(NCCOc3ccc(OC(F)(F)F)cc3)cc12]

9-Methyl-2-morpholino-4-oxo-4H-pyrido[1,2-a]pyrimidine-3-carboxylic acid (170)

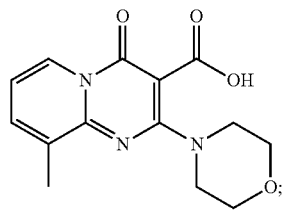 [SMILES: Cc1cccn2c(=O)c(C(=O)O)c(N3CCOCC3)nc12]

2-(3,4-Dihydroisoquinolin-2(1H)-yl)-9-methyl-4-oxo-4H-pyrido[1,2-a]pyrimidine-3-carboxylic acid (171)

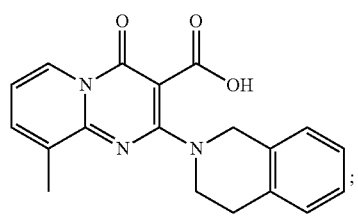 [SMILES: Cc1cccn2c(=O)c(C(=O)O)c(N3CCc4ccccc4C3)nc12]

2-(4-(2-Chlorophenyl)piperazin-1-yl)-9-methyl-4-oxo-4H-pyrido[1,2-a]pyrimidine-3-carboxylic acid (172)

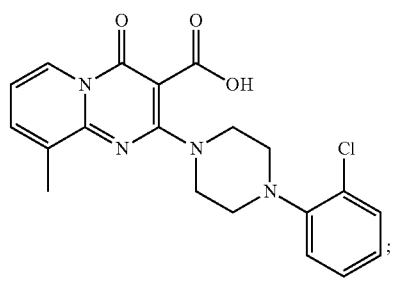 [SMILES: Cc1cccn2c(=O)c(C(=O)O)c(N3CCN(c4ccccc4Cl)CC3)nc12]

2-(3-Chlorophenylamino)-8-(4-methylpiperazin-1-yl)-4-oxo-4H-pyrido[1,2-a]pyrimidine-3-carboxylic acid (173)

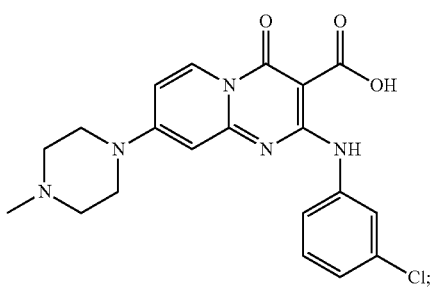 [SMILES: CN1CCN(c2ccn3c(=O)c(C(=O)O)c(Nc4cccc(Cl)c4)nc3c2)CC1]

Methyl 2-(3-chlorophenylamino)-9-methyl-4-oxo-4H-pyrido[1,2-a]pyrimidine-3-carboxylate (188)

507 508

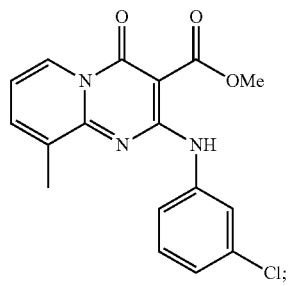 [SMILES: COC(=O)c1c(Nc2cccc(Cl)c2)nc2c(C)cccn2c1=O]

Methyl 2-(3-chlorobenzylamino)-9-methyl-4-oxo-4H-pyrido[1,2-a]pyrimidine-3-carboxylate (189)

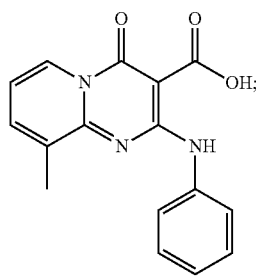

2-(3-Chlorophenylamino)-3-(hydroxymethyl)-9-methyl-4H-pyrido[1,2-a]pyrimidin-4-one (232)

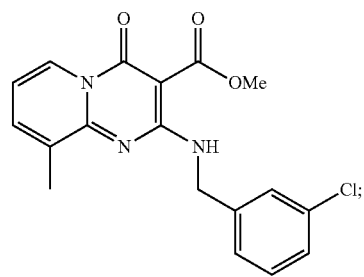 [SMILES: COC(=O)c1c(NCc2cccc(Cl)c2)nc2c(C)cccn2c1=O]

2-(3-Chloro-4-fluorophenylamino)-9-methoxy-N-methyl-4-oxo-4H-pyrido[1,2-a]pyrimidine-3-carboxamide (198)

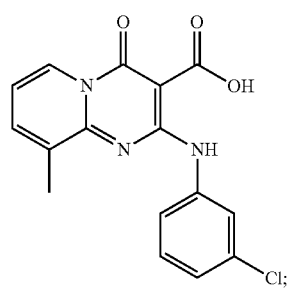

2-((3-Chlorophenyl)(methyl)amino)-3-(hydroxymethyl)-9-methyl-4H-pyrido[1,2-a]pyrimidin-4-one (233)

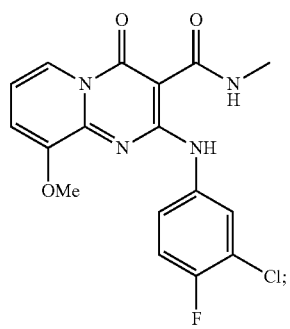 [SMILES: CNC(=O)c1c(Nc2ccc(F)c(Cl)c2)nc2c(OC)cccn2c1=O]

2-(3-Chlorophenylamino)-3-((cyclohexylamino)methyl)-8-(4-methylpiperazin-1-yl)-4H-pyrido[1,2-a]pyrimidin-4-one (205)

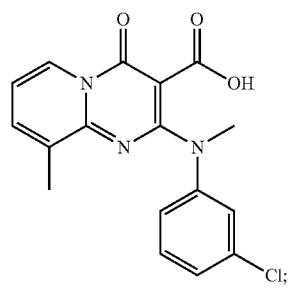

2-((3-Chlorophenyl)(methyl)amino)-3-(methoxymethyl)-9-methyl-4H-pyrido[1,2-a]pyrimidin-4-one (234)

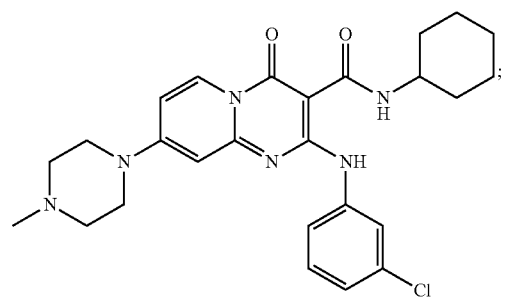 [SMILES: CN1CCN(c2ccn3c(=O)c(C(=O)NC4CCCCC4)c(Nc4cccc(Cl)c4)nc3c2)CC1]

3-(Hydroxymethyl)-9-methyl-2-(phenylamino)-4H-pyrido[1,2-a]pyrimidin-4-one (231)

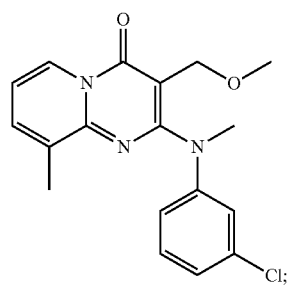 [SMILES: COCc1c(N(C)c2cccc(Cl)c2)nc2c(C)cccn2c1=O]

3-(Hydroxymethyl)-9-methyl-2-(3-(trifluoromethoxy)phenylamino)-4H-pyrido[1,2-a]pyrimidin-4-one (235)

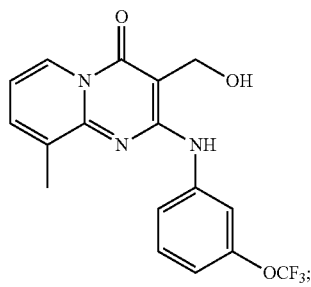 [SMILES: Cc1cccn2c(=O)c(CO)c(Nc3cccc(OC(F)(F)F)c3)nc12]

3-(Hydroxymethyl)-2-(3-hydroxyphenylamino)-9-methyl-4H-pyrido[1,2-a]pyrimidin-4-one (236)

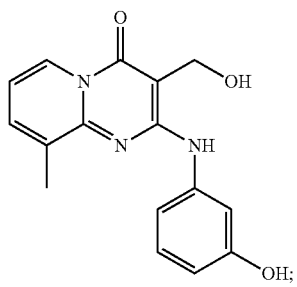 [SMILES: Cc1cccn2c(=O)c(CO)c(Nc3cccc(O)c3)nc12]

3-(Hydroxymethyl)-2-(4-hydroxyphenylamino)-9-methyl-4H-pyrido[1,2-a]pyrimidin-4-one (237)

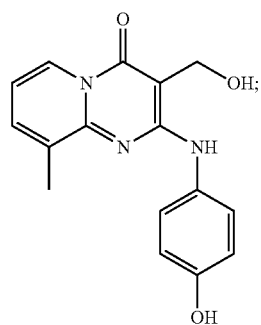 [SMILES: Cc1cccn2c(=O)c(CO)c(Nc3ccc(O)cc3)nc12]

2-(4-tert-Butylphenylamino)-3-(hydroxymethyl)-9-methyl-4H-pyrido[1,2-a]pyrimidin-4-one (238)

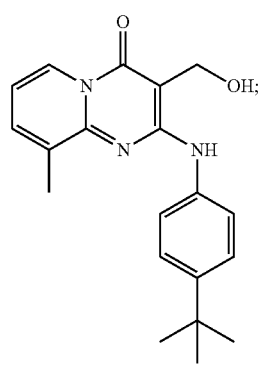 [SMILES: Cc1cccn2c(=O)c(CO)c(Nc3ccc(C(C)(C)C)cc3)nc12]

2-(3-Chlorobenzylamino)-3-(hydroxymethyl)-9-methyl-4H-pyrido[1,2-a]pyrimidin-4-one (239)

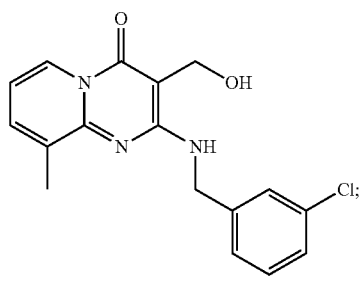 [SMILES: Cc1cccn2c(=O)c(CO)c(NCc3cccc(Cl)c3)nc12]

3-(Hydroxymethyl)-2-(isobutylamino)-9-methyl-4H-pyrido[1,2-a]pyrimidin-4-one (240)

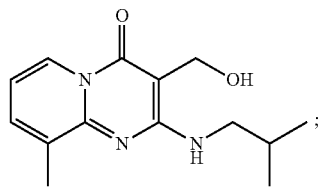 [SMILES: Cc1cccn2c(=O)c(CO)c(NCC(C)C)nc12]

2-(Diethylamino)-3-(hydroxymethyl)-9-methyl-4H-pyrido[1,2-a]pyrimidin-4-one (241)

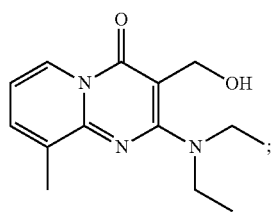

2-(Cyclohexylmethylamino)-3-(hydroxymethyl)-9-methyl-4H-pyrido[1,2-a]pyrimidin-4-one (242)

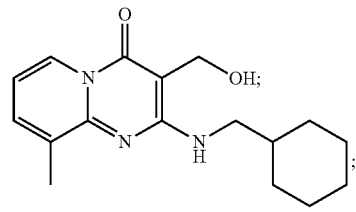 [SMILES: Cc1cccn2c(=O)c(CO)c(NCC3CCCCC3)nc12]

3-(Hydroxymethyl)-9-methyl-2-morpholino-4H-pyrido[1,2-a]pyrimidin-4-one (243)

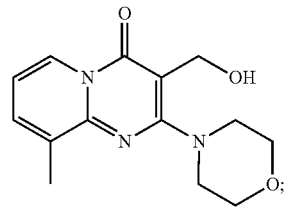 [SMILES: Cc1cccn2c(=O)c(CO)c(N3CCOCC3)nc12]

3-(Hydroxymethyl)-9-methyl-2-morpholino-4H-pyrido[1,2-a]pyrimidin-4-one hydrochloride (244)

511    512

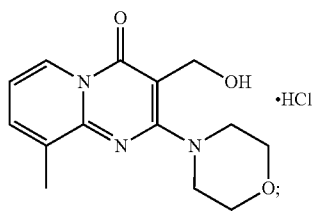 [SMILES: Cc1cccn2c(=O)c(CO)c(N3CCOCC3)nc12 ; Cl] ·HCl

7-Bromo-2-(3-chlorophenylamino)-3-(hydroxymethyl)-4H-pyrido[1,2-a]pyrimidin-4-one (245)

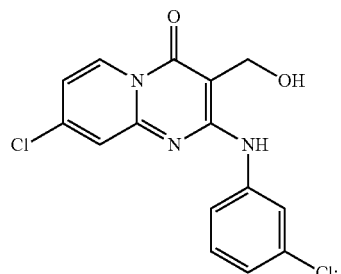

2-(3-Chlorophenylamino)-3-(hydroxymethyl)-8-(methylamino)-4H-pyrido[1,2-a]pyrimidin-4-one (249)

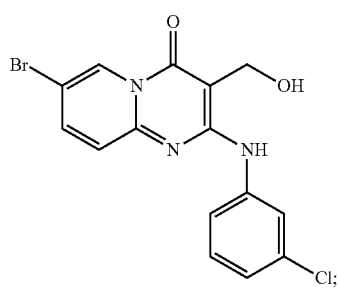 [SMILES: O=c1c(CO)c(Nc2cccc(Cl)c2)nc2ccc(Br)cn12]

2-(3-Chlorophenylamino)-3-(hydroxymethyl)-7-methoxy-4H-pyrido[1,2-a]pyrimidin-4-one (246)

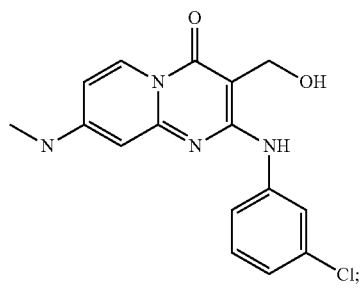

2-(3-Chlorophenylamino)-8-(diethylamino)-3-(hydroxymethyl)-4H-pyrido[1,2-a]pyrimidin-4-one (250)

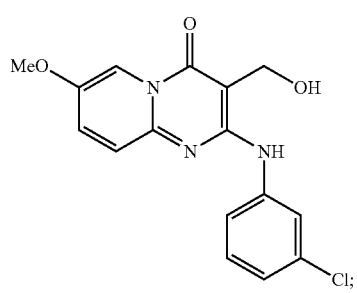 [SMILES: COc1ccc2nc(Nc3cccc(Cl)c3)c(CO)c(=O)n2c1]

2-(3-Chlorophenylamino)-3-(hydroxymethyl)-8-methoxy-4H-pyrido[1,2-a]pyrimidin-4-one (247)

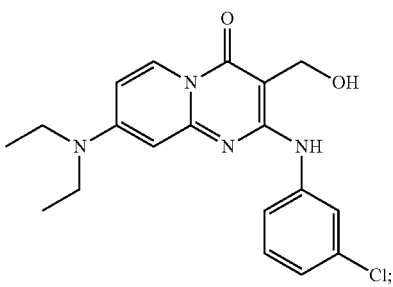

3-(Hydroxymethyl)-8-morpholino-2-(phenylamino)-4H-pyrido[1,2-a]pyrimidin-4-one (251)

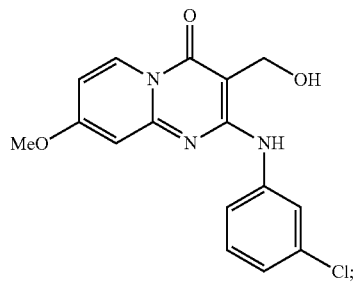 [SMILES: COc1ccn2c(=O)c(CO)c(Nc3cccc(Cl)c3)nc2c1]

8-Chloro-2-(3-chlorophenylamino)-3-(hydroxymethyl)-4H-pyrido[1,2-a]pyrimidin-4-one (248)

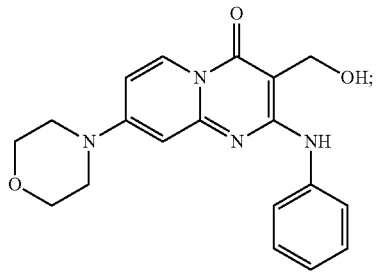 [SMILES: O=c1c(CO)c(Nc2ccccc2)nc2cc(N3CCOCC3)ccn12]

2-(3-Fluorophenylamino)-3-(hydroxymethyl)-8-morpholino-4H-pyrido[1,2-a]pyrimidin-4-one (252)

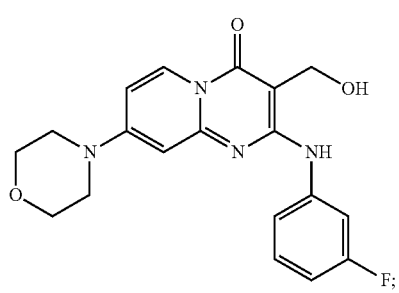

2-(3-Chlorophenylamino)-3-(hydroxymethyl)-8-morpholino-4H-pyrido[1,2-a]pyrimidin-4-one (253)

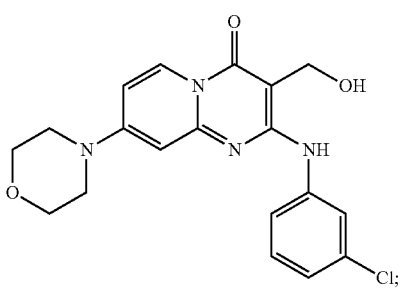

3-(Hydroxymethyl)-8-(4-methylpiperazin-1-yl)-2-(phenylamino)-4H-pyrido[1,2-a]pyrimidin-4-one (254)

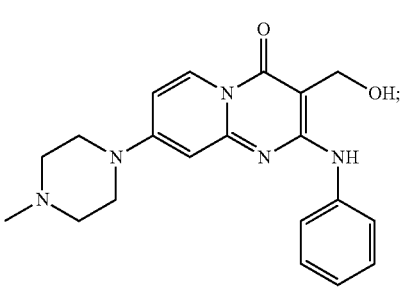 [SMILES: CN1CCN(c2ccn3c(=O)c(CO)c(Nc4ccccc4)nc3c2)CC1]

2-(3-Chlorophenylamino)-3-(hydroxymethyl)-8-(4-methylpiperazin-1-yl)-4H-pyrido[1,2-a]pyrimidin-4-one (255)

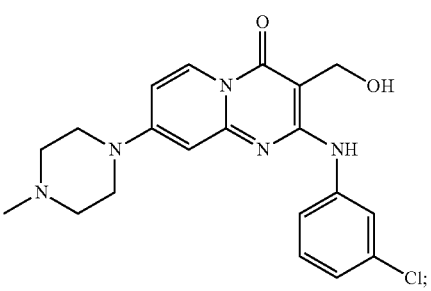 [SMILES: CN1CCN(c2ccn3c(=O)c(CO)c(Nc4cccc(Cl)c4)nc3c2)CC1]

2-(3-Fluorophenylamino)-3-(hydroxymethyl)-8-(4-methylpiperazin-1-yl)-4H-pyrido[1,2-a]pyrimidin-4-one (256)

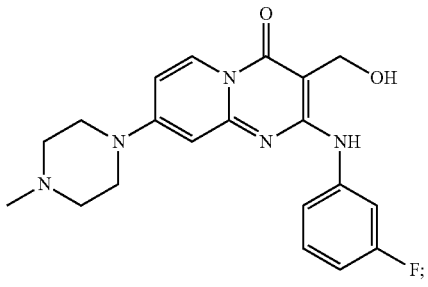 [SMILES: CN1CCN(c2ccn3c(=O)c(CO)c(Nc4cccc(F)c4)nc3c2)CC1]

2-(3-Chlorophenylamino)-3-(hydroxymethyl)-8-methyl-4H-pyrido[1,2-a]pyrimidin-4-one (257)

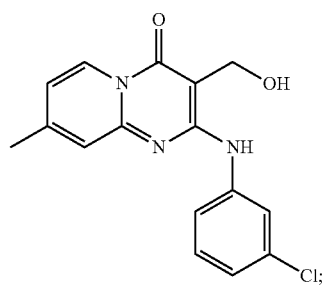 [SMILES: Cc1ccn2c(=O)c(CO)c(Nc3cccc(Cl)c3)nc2c1]

2-(4-Chlorophenylamino)-3-(hydroxymethyl)-8-methyl-4H-pyrido[1,2-a]pyrimidin-4-one (258)

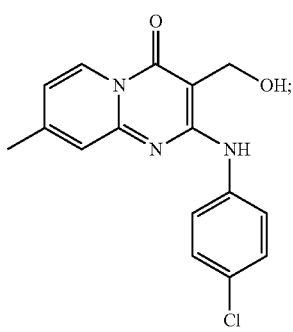 [SMILES: Cc1ccn2c(=O)c(CO)c(Nc3ccc(Cl)cc3)nc2c1]

2-(4-Fluorophenylamino)-3-(hydroxymethyl)-8-methyl-4H-pyrido[1,2-a]pyrimidin-4-one (259)

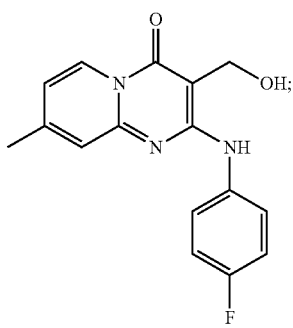 [SMILES: Cc1ccn2c(=O)c(CO)c(Nc3ccc(F)cc3)nc2c1]

2-(3,4-Dichlorophenylamino)-3-(hydroxymethyl)-8-methyl-4H-pyrido[1,2-a]pyrimidin-4-one (260)

515

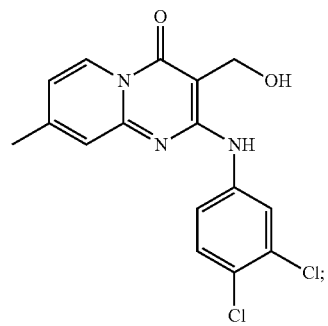 [SMILES: Cc1ccn2c(=O)c(CO)c(Nc3ccc(Cl)c(Cl)c3)nc2c1]

2-(3-Chloro-4-fluorophenylamino)-3-(hydroxymethyl)-
8-methyl-4H-pyrido[1,2-a]pyrimidin-4-one (261)

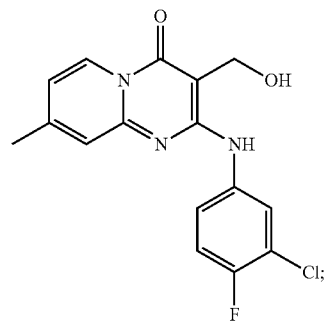 [SMILES: Cc1ccn2c(=O)c(CO)c(Nc3ccc(F)c(Cl)c3)nc2c1]

9-Chloro-2-(3-chlorophenylamino)-3-(hydroxymethyl)-
4H-pyrido[1,2-a]pyrimidin-4-one (262)

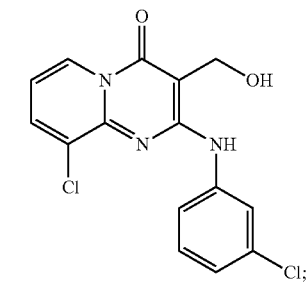 [SMILES: O=c1c(CO)c(Nc2cccc(Cl)c2)nc2c(Cl)cccn12]

2-(3-Chlorophenylamino)-3-(hydroxymethyl)-9-(trifluo-
romethyl)-4H-pyrido[1,2-a]pyrimidin-4-one (263)

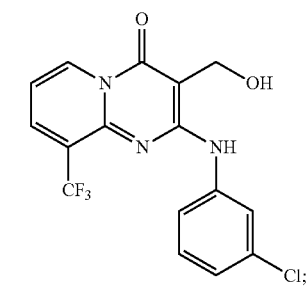 [SMILES: O=c1c(CO)c(Nc2cccc(Cl)c2)nc2c(C(F)(F)F)cccn12]

2-(3-Chlorophenylamino)-9-fluoro-3-(hydroxymethyl)-
4H-pyrido[1,2-a]pyrimidin-4-one (264)

516

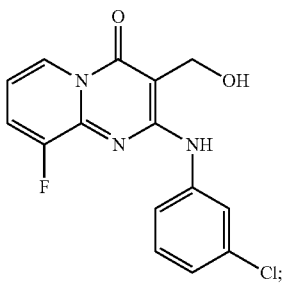 [SMILES: O=c1c(CO)c(Nc2cccc(Cl)c2)nc2c(F)cccn12]

2-(4-Chlorophenylamino)-9-fluoro-3-(hydroxymethyl)-
4H-pyrido[1,2-a]pyrimidin-4-one (265)

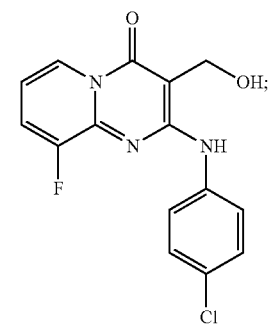 [SMILES: O=c1c(CO)c(Nc2ccc(Cl)cc2)nc2c(F)cccn12]

9-Fluoro-2-(4-fluorophenylamino)-3-(hydroxymethyl)-
4H-pyrido[1,2-a]pyrimidin-4-one (266)

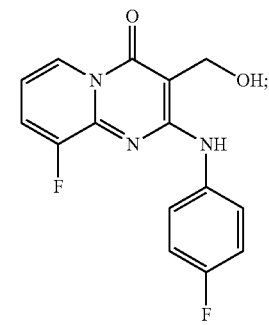 [SMILES: O=c1c(CO)c(Nc2ccc(F)cc2)nc2c(F)cccn12]

2-(3-Chloro-4-fluorophenylamino)-9-fluoro-3-(hy-
droxymethyl)-4H-pyrido[1,2-a]pyrimidin-4-one (267)

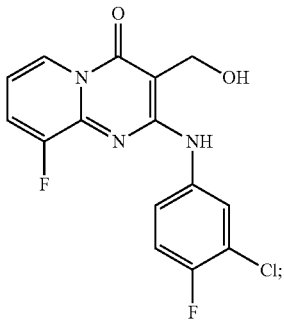 [SMILES: O=c1c(CO)c(Nc2ccc(F)c(Cl)c2)nc2c(F)cccn12]

2-(3,4-Difluorophenylamino)-9-fluoro-3-(hydroxym-
ethyl)-4H-pyrido[1,2-a]pyrimidin-4-one (268)

517

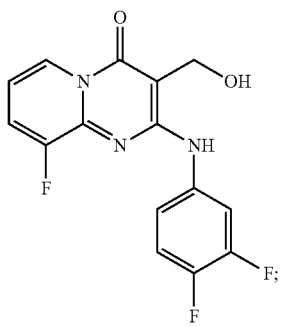 [SMILES: O=c1c(CO)c(Nc2ccc(F)c(F)c2)nc2c(F)cccn12]

2-(3,4-Dichlorophenylamino)-9-fluoro-3-(hydroxymethyl)-4H-pyrido[1,2-a]pyrimidin-4-one (269)

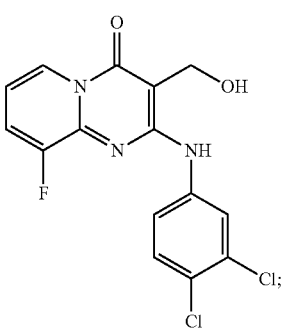 [SMILES: O=c1c(CO)c(Nc2ccc(Cl)c(Cl)c2)nc2c(F)cccn12]

2-(1H-Indol-5-ylamino)-9-fluoro-3-(hydroxymethyl)-4H-pyrido[1,2-a]pyrimidin-4-one (270)

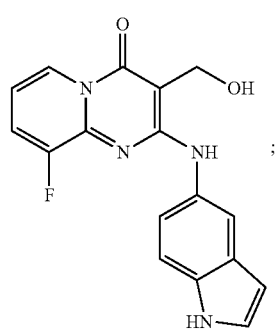 [SMILES: O=c1c(CO)c(Nc2ccc3[nH]ccc3c2)nc2c(F)cccn12]

3-(Hydroxymethyl)-9-methoxy-2-(phenylamino)-4H-pyrido[1,2-a]pyrimidin-4-one (271)

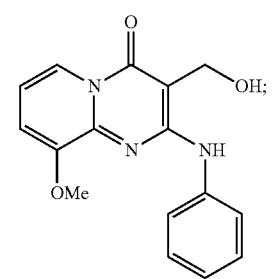 [SMILES: COc1cccn2c(=O)c(CO)c(Nc3ccccc3)nc12]

2-(3-Chlorophenylamino)-3-(hydroxymethyl)-9-methoxy-4H-pyrido[1,2-a]pyrimidin-4-one (273)

518

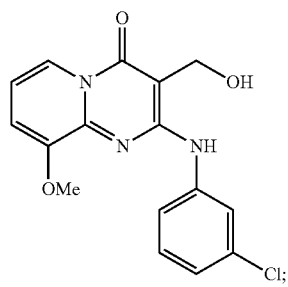 [SMILES: COc1cccn2c(=O)c(CO)c(Nc3cccc(Cl)c3)nc12]

2-(4-Chlorophenylamino)-3-(hydroxymethyl)-9-methoxy-4H-pyrido[1,2-a]pyrimidin-4-one (274)

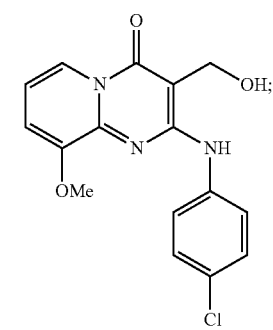

2-(4-Fluorophenylamino)-3-(hydroxymethyl)-9-methoxy-4H-pyrido[1,2-a]pyrimidin-4-one (275)

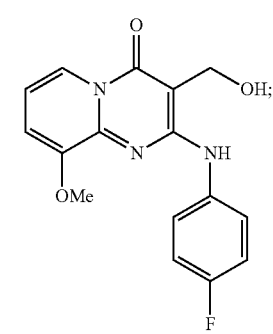 [SMILES: COc1cccn2c(=O)c(CO)c(Nc3ccc(F)cc3)nc12]

3-(Hydroxymethyl)-9-methoxy-2-(4-(trifluoromethoxy)phenylamino)-4H-pyrido[1,2-a]pyrimidin-4-one (276)

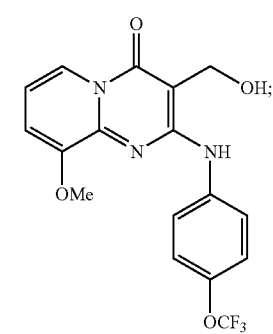 [SMILES: COc1cccn2c(=O)c(CO)c(Nc3ccc(OC(F)(F)F)cc3)nc12]

3-(Hydroxymethyl)-9-methoxy-2-(4-(trifluoromethyl)phenylamino)-4H-pyrido[1,2-a]pyrimidin-4-one (277)

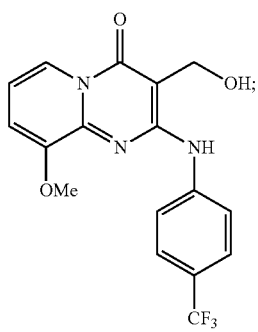 [SMILES: COc1cccn2c(=O)c(CO)c(Nc3ccc(C(F)(F)F)cc3)nc12]

2-(3-Chloro-4-fluorophenylamino)-3-(hydroxymethyl)-9-methoxy-4H-pyrido[1,2-a]pyrimidin-4-one (278)

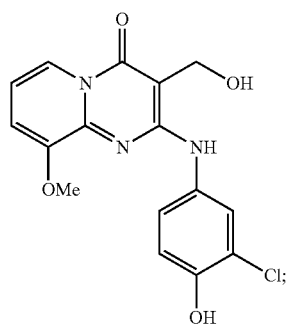

2-(3,4-Dichlorophenylamino)-3-(hydroxymethyl)-9-methoxy-4H-pyrido[1,2-a]pyrimidin-4-one (281)

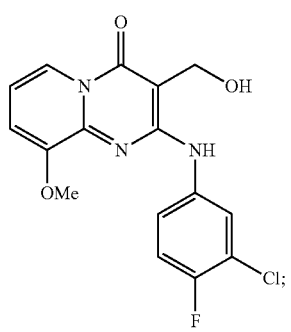 [SMILES: COc1cccn2c(=O)c(CO)c(Nc3ccc(F)c(Cl)c3)nc12]

2-(3,4-Difluorophenylamino)-3-(hydroxymethyl)-9-methoxy-4H-pyrido[1,2-a]pyrimidin-4-one (279)

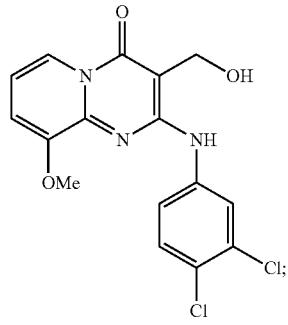

3-(Hydroxymethyl)-9-methoxy-2-(4-methyl-3-(trifluoromethyl)phenylamino)-4H-pyrido[1,2-a]pyrimidin-4-one (282)

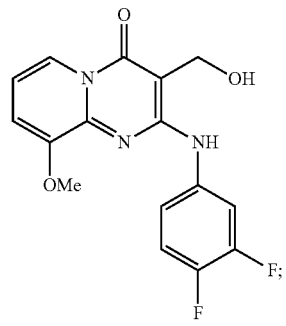 [SMILES: COc1cccn2c(=O)c(CO)c(Nc3ccc(F)c(F)c3)nc12]

2-(3-Chloro-4-hydroxyphenylamino)-3-(hydroxymethyl)-9-methoxy-4H-pyrido[1,2-a]pyrimidin-4-one (280)

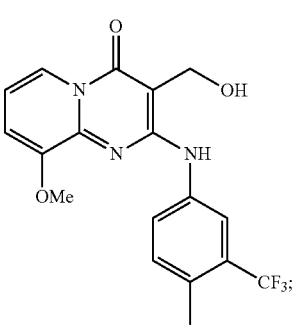 [SMILES: COc1cccn2c(=O)c(CO)c(Nc3ccc(C)c(C(F)(F)F)c3)nc12]

2-(4-Fluoro-3-(trifluoromethyl)phenylamino)-3-(hydroxymethyl)-9-methoxy-4H-pyrido[1,2-a]pyrimidin-4-one (283)

| 521 | 522 |
|---|---|
| 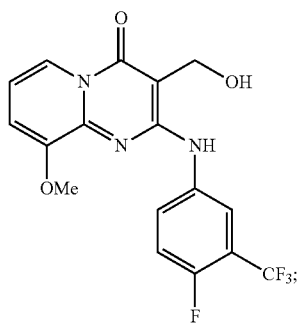 [SMILES: COc1cccn2c(=O)c(CO)c(Nc3ccc(F)c(C(F)(F)F)c3)nc12] | 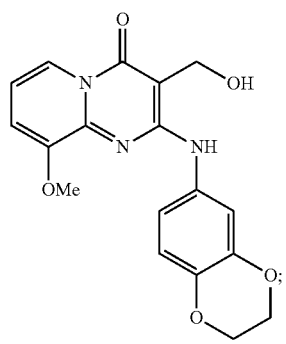 |
| 2-(2,3-Dihydro-1H-inden-5-ylamino)-3-(hydroxymethyl)-9-methoxy-4H-pyrido[1,2-a]pyrimidin-4-one (284) | 3-(Hydroxymethyl)-9-methoxy-2-(1-methyl-1H-indol-5-ylamino)-4H-pyrido[1,2-a]pyrimidin-4-one (287) |
| 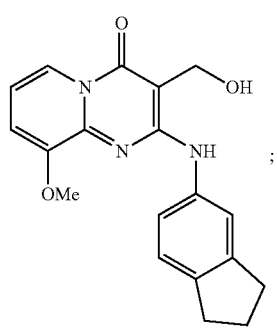 [SMILES: COc1cccn2c(=O)c(CO)c(Nc3ccc4c(c3)CCC4)nc12] | 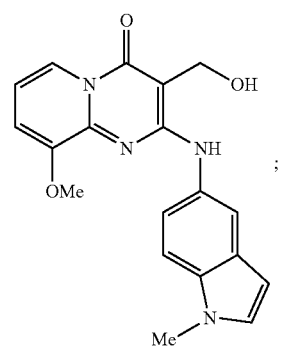 |
| 2-(Benzo[d][1,3]dioxol-5-ylamino)-3-(hydroxymethyl)-9-methoxy-4H-pyrido[1,2-a]pyrimidin-4-one (285) | 3-(Hydroxymethyl)-9-methoxy-2-(1-methyl-1H-benzo[d]imidazol-5-ylamino)-4H-pyrido[1,2-a]pyrimidin-4-one (288) |
| 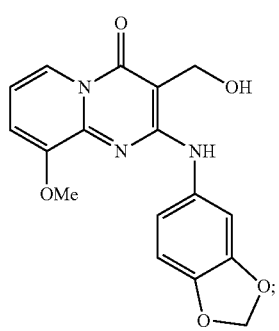 [SMILES: COc1cccn2c(=O)c(CO)c(Nc3ccc4c(c3)OCO4)nc12] | 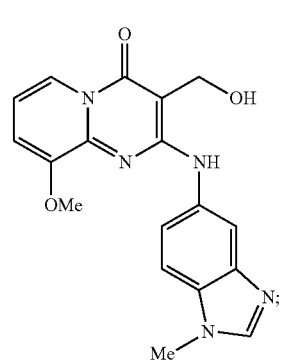 [SMILES: COc1cccn2c(=O)c(CO)c(Nc3ccc4c(c3)ncn4C)nc12] |
| 2-(2,3-Dihydrobenzo[b][1,4]dioxin-6-ylamino)-3-(hydroxymethyl)-9-methoxy-4H-pyrido[1,2-a]pyrimidin-4-one (286) | 3-(Hydroxymethyl)-9-methoxy-2-(1-methyl-1H-indazol-5-ylamino)-4H-pyrido[1,2-a]pyrimidin-4-one (289) |

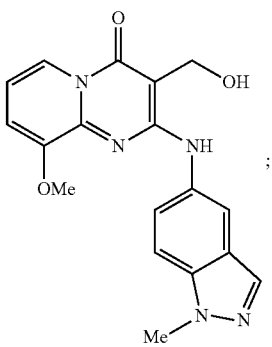 [SMILES: COc1cccn2c(=O)c(CO)c(Nc3ccc4c(cnn4C)c3)nc12]

9-(Difluoromethoxy)-2-(4-fluorophenylamino)-3-(hydroxymethyl)-4H-pyrido[1,2-a]pyrimidin-4-one (290)

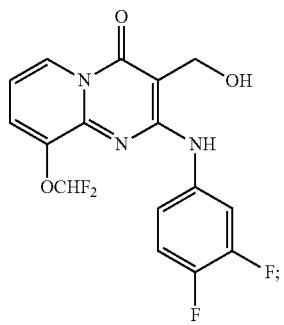

2-(3,4-Dichlorophenylamino)-9-(difluoromethoxy)-3-(hydroxymethyl)-4H-pyrido[1,2-a]pyrimidin-4-one (293)

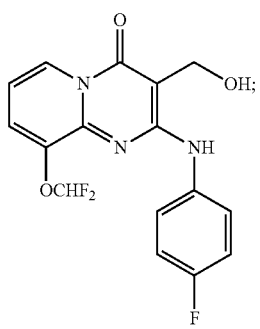 [SMILES: O=c1c(CO)c(Nc2ccc(F)cc2)nc2c(OC(F)F)cccn12]

2-(4-Chlorophenylamino)-9-(difluoromethoxy)-3-(hydroxymethyl)-4H-pyrido[1,2-a]pyrimidin-4-one (291)

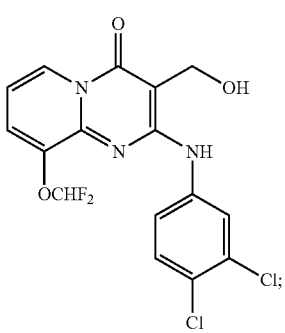

2-(3-Chloro-4-fluorophenylamino)-9-(difluoromethoxy)-3-(hydroxymethyl)-4H-pyrido[1,2-a]pyrimidin-4-one (294)

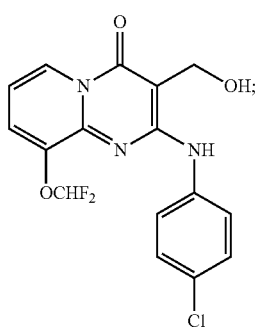 [SMILES: O=c1c(CO)c(Nc2ccc(Cl)cc2)nc2c(OC(F)F)cccn12]

9-(Difluoromethoxy)-2-(3,4-difluorophenylamino)-3-(hydroxymethyl)-4H-pyrido[1,2-a]pyrimidin-4-one (292)

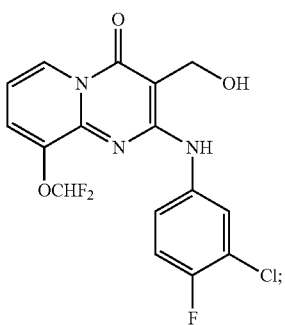

2-(1H-Indol-5-ylamino)-9-(difluoromethoxy)-3-(hydroxymethyl)-4H-pyrido[1,2-a]pyrimidin-4-one (295)

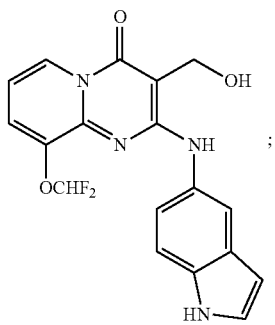 [SMILES: O=c1c(CO)c(Nc2ccc3[nH]ccc3c2)nc2c(OC(F)F)cccn12]

2-(3-chlorophenylamino)-3-(hydroxymethyl)-6,8-dimethyl-4H-pyrido[1,2-a]pyrimidin-4-one (296)

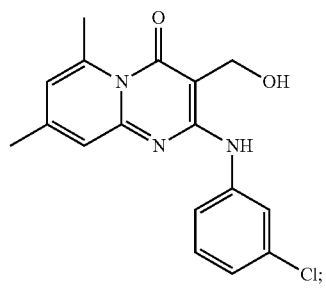 [SMILES: Cc1cc(C)n2c(=O)c(CO)c(Nc3cccc(Cl)c3)nc2c1]

7,9-Dichloro-2-(3-chlorophenylamino)-3-(hydroxymethyl)-4H-pyrido[1,2-a]pyrimidin-4-one (297)

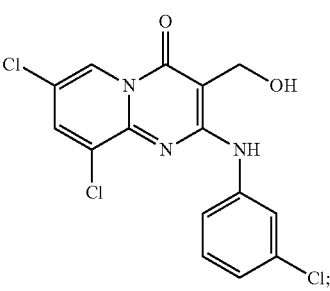 [SMILES: O=c1c(CO)c(Nc2cccc(Cl)c2)nc2c(Cl)cc(Cl)cn12]

and
2-(3-Chlorophenylamino)-7,9-difluoro-3-(hydroxymethyl)-4H-pyrido[1,2-a]pyrimidin-4-one (298)

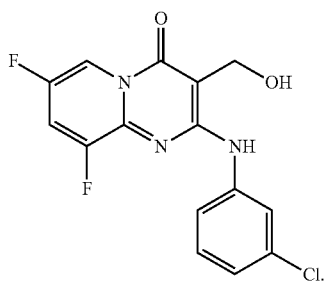

6. A compound having a formula selected from the group consisting of the following formulae 132-135, 137, 139-140, 147, 151-152, 160, 163, and 173:

9-Methyl-4-oxo-2-(phenylamino)-4H-pyrido[1,2-a]pyrimidine-3-carbaldehyde (132)

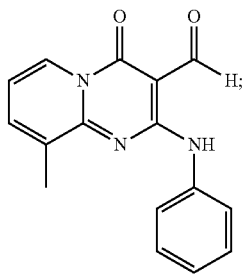

2-(3-Chlorophenylamino)-9-methyl-4-oxo-4H-pyrido[1,2-a]pyrimidine-3-carbaldehyde (133)

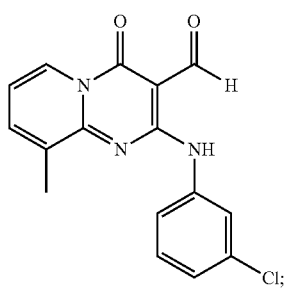 [SMILES: Cc1cccn2c(=O)c(C=O)c(Nc3cccc(Cl)c3)nc12]

9-Methyl-4-oxo-2-(3-(trifluoromethoxy)phenylamino)-4H-pyrido[1,2-a]pyrimidine-3-carbaldehyde (134)

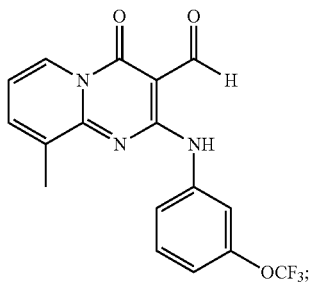 [SMILES: Cc1cccn2c(=O)c(C=O)c(Nc3cccc(OC(F)(F)F)c3)nc12]

9-Methyl-4-oxo-2-(3-(trifluoromethyl)phenylamino)-4H-pyrido[1,2-a]pyrimidine-3-carbaldehyde (135)

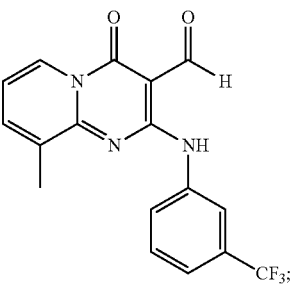 [SMILES: Cc1cccn2c(=O)c(C=O)c(Nc3cccc(C(F)(F)F)c3)nc12]

2-(3-Chlorobenzylamino)-9-methyl-4-oxo-4H-pyrido[1,2-a]pyrimidine-3-carbaldehyde (137)

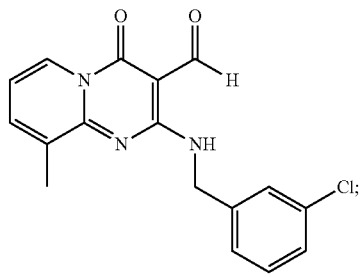 [SMILES: Cc1cccn2c(=O)c(C=O)c(NCc3cccc(Cl)c3)nc12]

2-(4-(2-Chlorophenyl)piperazin-1-yl)-9-methyl-4-oxo-4H-pyrido[1,2-a]pyrimidine-3-carbaldehyde (139)

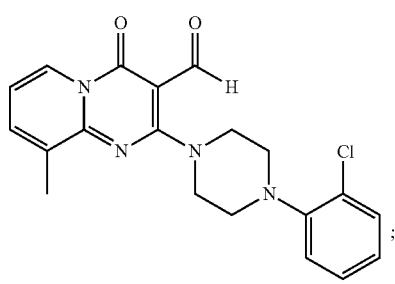 [SMILES: Cc1cccn2c(=O)c(C=O)c(N3CCN(c4ccccc4Cl)CC3)nc12]

2-(3,4-Dihydroisoquinolin-2(1H)-yl)-9-methyl-4-oxo-4H-pyrido[1,2-a]pyrimidine-3-carbaldehyde (140)

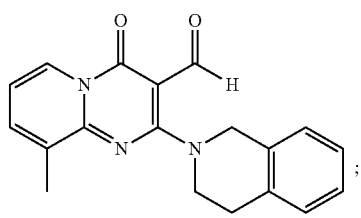 [SMILES: Cc1cccn2c(=O)c(C=O)c(N3CCc4ccccc4C3)nc12]

9-Methyl-4-oxo-2-(phenylamino)-4H-pyrido[1,2-a]pyrimidine-3-carboxylic acid (147)

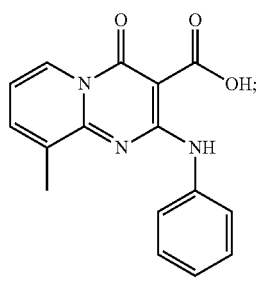 [SMILES: Cc1cccn2c(=O)c(C(=O)O)c(Nc3ccccc3)nc12]

2-(3-Chlorophenylamino)-6-methyl-4-oxo-4H-pyrido[1,2-a]pyrimidine-3-carboxylic acid (151)

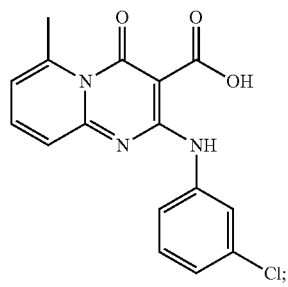 [SMILES: Cc1cccc2nc(Nc3cccc(Cl)c3)c(C(=O)O)c(=O)n12]

2-(3-Fluorophenylamino)-9-methyl-4-oxo-4H-pyrido[1,2-a]pyrimidine-3-carboxylic acid (152)

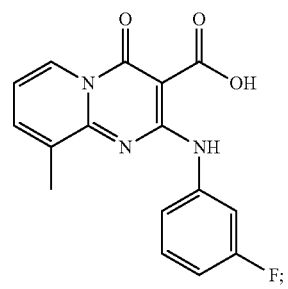 [SMILES: Cc1cccn2c(=O)c(C(=O)O)c(Nc3cccc(F)c3)nc12]

2-(3-Chlorobenzylamino)-9-methyl-4-oxo-4H-pyrido[1,2-a]pyrimidine-3-carboxylic acid (160)

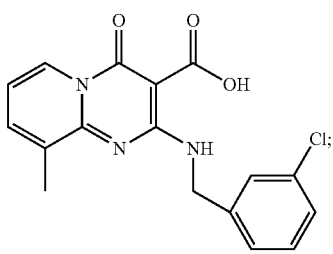 [SMILES: Cc1cccn2c(=O)c(C(=O)O)c(NCc3cccc(Cl)c3)nc12]

2-(Cyclohexylmethylamino)-9-methyl-4-oxo-4H-pyrido[1,2-a]pyrimidine-3-carboxylic acid (163)

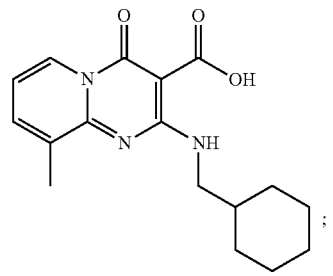 [SMILES: Cc1cccn2c(=O)c(C(=O)O)c(NCC3CCCCC3)nc12]

and 2-(3-Chlorophenylamino)-8-(4-methylpiperazin-1-yl)-4-oxo-4H-pyrido[1,2-a]pyrimidine-3-carboxylic acid (173)

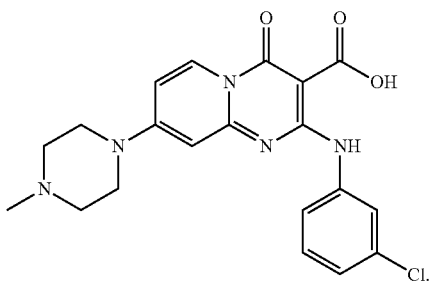 [SMILES: CN1CCN(c2ccn3c(=O)c(C(=O)O)c(Nc4cccc(Cl)c4)nc3c2)CC1]

7. A compound having a formula selected from the group consisting of the following formulae 129-131, 144-146, 174-177 and 187:

2-Chloro-8-methyl-4-oxo-4H-pyrido[1,2-a]pyrimidine-3-carbaldehyde (129)

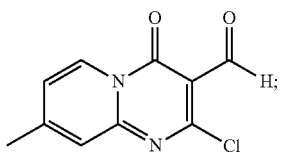

2-Chloro-7-methyl-4-oxo-4H-pyrido[1,2-a]pyrimidine-3-carbaldehyde (130)

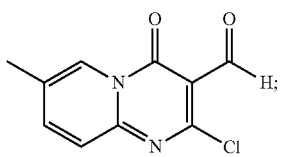

2-Chloro-6-methyl-4-oxo-4H-pyrido[1,2-a]pyrimidine-3-carbaldehyde (131)

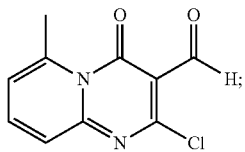

2-Chloro-9-methyl-4-oxo-4H-pyrido[1,2-a]pyrimidine-3-carboxylic acid (144)

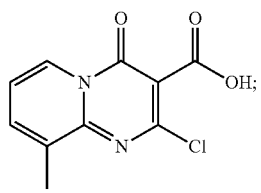 [SMILES: Cc1cccn2c(=O)c(C(=O)O)c(Cl)nc12]

2-Chloro-7-methyl-4-oxo-4H-pyrido[1,2-a]pyrimidine-3-carboxylic acid (145)

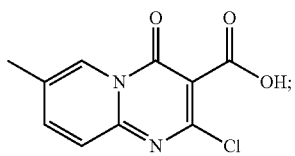 [SMILES: Cc1ccc2nc(Cl)c(C(=O)O)c(=O)n2c1]

2-Chloro-6-methyl-4-oxo-4H-pyrido[1,2-a]pyrimidine-3-carboxylic acid (146)

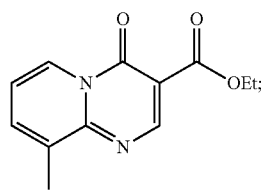 [SMILES: CCOC(=O)c1cnc2c(C)cccn2c1=O]

Ethyl 9-methyl-4-oxo-4H-pyrido[1,2-a]pyrimidine-3-carboxylate (174)

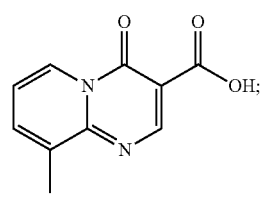

9-Methyl-4-oxo-4H-pyrido[1,2-a]pyrimidine-3-carboxylic acid (175)

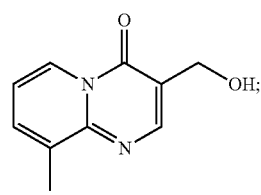

3-(Hydroxymethyl)-9-methyl-4H-pyrido[1,2-a]pyrimidin-4-one (176)

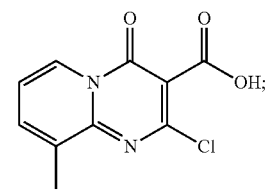

9-Methyl-4-oxo-4H-pyrido[1,2-a]pyrimidine-3-carbaldehyde (177)

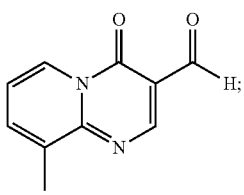

and

Methyl 2-chloro-9-methyl-4-oxo-4H-pyrido[1,2-a]pyrimidine-3-carboxylate (187)

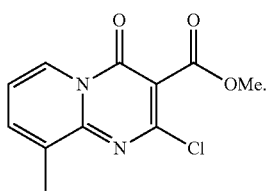 [SMILES: COC(=O)c1c(Cl)nc2c(C)cccn2c1=O]

8. A compound having the general formula VIIIa:

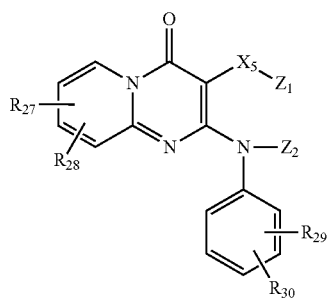

VIIIa wherein
$X_5$ is C=O;
$Z_1$ and $Z_2$ are each independently selected from the group consisting of alkoxy, alkyl, alkylamino, alkenyl, alkylether, alkylthio, alkynyl, amido, amino, aryl, arylalkoxy, arylamino, arylthio, carboxy, cyano, cycloalkyl, ester, halo, haloalkoxy, haloalkyl, heteroaryl, heteroarylamino, heterocycloalkyl, hydroxyl, and hydrogen, or any two groups are connected to each other to make five or six membered cyclic, heterocyclic and heteroaryl rings, any of which is optionally substituted;
$R_{27}$ is selected from the group consisting of alkoxy, alkyl, alkyl amino, alkenyl, alkylether, alkylthio, alkynyl, amido, amino, aryl, arylether, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thiol, sulfonate, sulfonyl and sulfonylamino, any of which is optionally substituted;
$R_{28}$ is selected from the group consisting of alkoxy, alkyl, alkylamino, alkenyl, alkylether, alkylthio, alkynyl, amido, amino, aryl, arylether, arylalkoxy, arylamino, arylthio, carboxy, cyano, cycloalkyl, ester, halo, haloalkoxy, haloalkyl, heteroaryl, heteroarylamino, heterocycloalkyl, hydroxyl, nitro, thiol, sulfonate, sulfonyl and sulfonylamino, any of which is optionally substituted; and $R_{29}$ and $R_{30}$ are each independently selected from the group consisting of alkoxy, alkyl, alkylamino, alkenyl, alkylether, alkylthio, alkynyl, amido, amino, aryl, arylether, arylalkoxy, arylamino, arylthio, carboxy, cyano, cycloalkyl, ester, halo, haloalkoxy, haloalkyl, heteroaryl, heteroarylamino, heterocycloalkyl, hydroxyl, hydrogen, nitro, thiol, sulfonate, sulfonyl and sulfonylamino, or two groups are connected to each other to make five or six membered cyclic, heterocyclic, aryl, and heteroaryl rings, any of which is optionally substituted.

9. The compound according to claim 8, having a formula selected from the group consisting of the following formulae 132-136:

9-Methyl-4-oxo-2-(phenylamino)-4H-pyrido[1,2-a]pyrimidine-3-carbaldehyde (132)

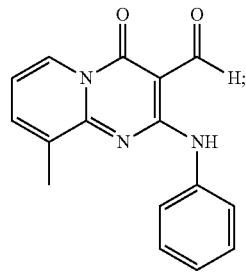

2-(3-Chlorophenylamino)-9-methyl-4-oxo-4H-pyrido[1,2-a]pyrimidine-3-carbaldehyde (133)

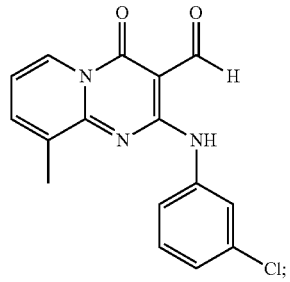 [SMILES: Cc1cccn2c(=O)c(C=O)c(Nc3cccc(Cl)c3)nc12]

9-Methyl-4-oxo-2-(3-(trifluoromethoxy)phenylamino)-4H-pyrido[1,2-a]pyrimidine-3-carbaldehyde (134)

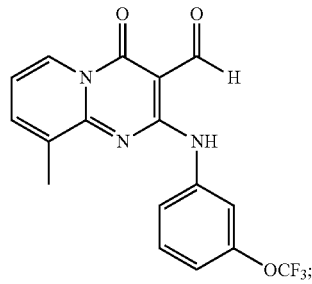 [SMILES: Cc1cccn2c(=O)c(C=O)c(Nc3cccc(OC(F)(F)F)c3)nc12]

9-Methyl-4-oxo-2-(3-(trifluoromethyl)phenylamino)-4H-pyrido[1,2-a]pyrimidine-3-carbaldehyde (135)

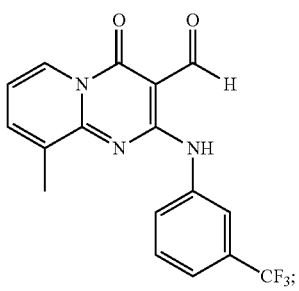 [SMILES: Cc1cccn2c(=O)c(C=O)c(Nc3cccc(C(F)(F)F)c3)nc12]

and 2-(4-tert-Butylphenylamino)-9-methyl-4-oxo-4H-pyrido[1,2-a]pyrimidine-3-carbaldehyde (136)

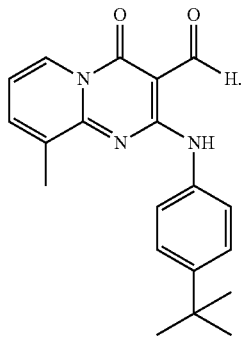

10. A pharmaceutical composition comprising a compound of claim 2 and a carrier.

11. A pharmaceutical composition comprising a compound of claim 1 and a carrier.

12. A pharmaceutical composition comprising a compound of claim 3 and a carrier.

13. A pharmaceutical composition comprising a compound of claim 4 and a carrier.

14. A pharmaceutical composition comprising a compound of claim 5 and a carrier.

15. A pharmaceutical composition comprising a compound of claim 6 and a carrier.

16. A pharmaceutical composition comprising a compound of claim 7 and a carrier.

17. A pharmaceutical composition comprising a compound of claim 8 and a carrier.

18. A pharmaceutical composition comprising a compound of claim 9 and a carrier.

19. A method for treating a bacterial infection wherein said method comprises administering a compound of claim 1, wherein the bacterial infection is tuberculosis.

20. A method for treating a bacterial infection wherein said method comprises administering a compound of claim 2, wherein the bacterial infection is tuberculosis.

21. A method for treating a bacterial infection wherein said method comprises administering a compound of claim 3, wherein the bacterial infection is tuberculosis.

22. A method for treating a bacterial infection wherein said method comprises administering a compound of claim 4, wherein the bacterial infection is tuberculosis.

23. A method for treating a bacterial infection wherein said method comprises administering a compound of claim 5, wherein the bacterial infection is tuberculosis.

24. A method for treating a bacterial infection wherein said method comprises administering a compound of claim 6, wherein the bacterial infection is tuberculosis.

25. A method for treating a bacterial infection wherein said method comprises administering a compound of claim 7, wherein the bacterial infection is tuberculosis.

26. A method for treating a bacterial infection wherein said method comprises administering a compound of claim 8, wherein the bacterial infection is tuberculosis.

27. A method for treating a bacterial infection wherein said method comprises administering a compound of claim 9, wherein the bacterial infection is tuberculosis.

\* \* \* \* \*

UNITED STATES PATENT AND TRADEMARK OFFICE
CERTIFICATE OF CORRECTION

| | | |
|---|---|---|
| PATENT NO. | : 8,785,452 B2 | |
| APPLICATION NO. | : 12/999095 | |
| DATED | : July 22, 2014 | |
| INVENTOR(S) | : Priscille Brodin et al. | |

It is certified that error appears in the above-identified patent and that said Letters Patent is hereby corrected as shown below:

In the Specification,

Column 4,
Line 15, "5OR$_{32}$," should read --SOR$_{32}$,--.

Column 35,
Line 59, "(m, 41-1)," should read --(m, 4H),--.

Column 39,
Line 1, "δ:4 ratio" should read --6:4 ratio--.

Column 39,
Line 34, "5 22.1," should read --δ 22.1,--.

Column 57,
Lines 63-64, "-120 D;" should read -- -120°;--.

Column 59,
Line 44, "CD$_3$ OD) 0.99 - 1.35" should read --CD$_3$ OD) δ 0.99 - 1.35--.

Column 65,
Lines 23-24, "138 - 140 µl;" should read --138 - 140°;--.

Column 87,
Line 1, before the formula insert --Scheme 9--.

Column 111,
Line 36, "614.3, 22.2," should read --δ14.3, 22.2,--.

Signed and Sealed this
Twenty-fourth Day of March, 2015

Michelle K. Lee
*Director of the United States Patent and Trademark Office*

CERTIFICATE OF CORRECTION (continued)
U.S. Pat. No. 8,785,452 B2

Column 121,
Line 43, "$^1$H NMR H (400" should read --$^1$H NMR (400--.

Column 135,
Line 50, "330 [M+H]." should read --330 [M+H]$^+$.--.

Column 156,
Line 35, "266.0" should read --226.0--.

Column 183,

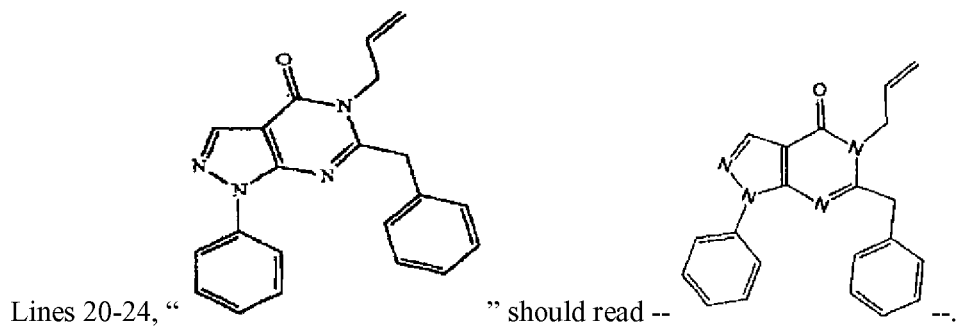

Lines 20-24, " " should read -- --.

Column 201,

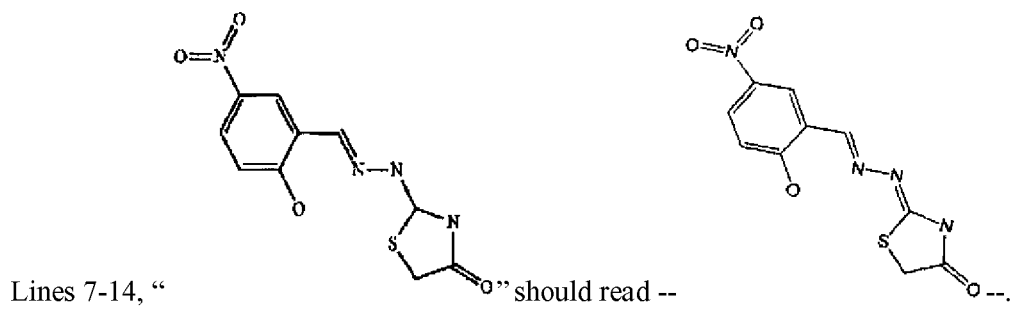

Lines 7-14, " " should read -- --.

Column 235,

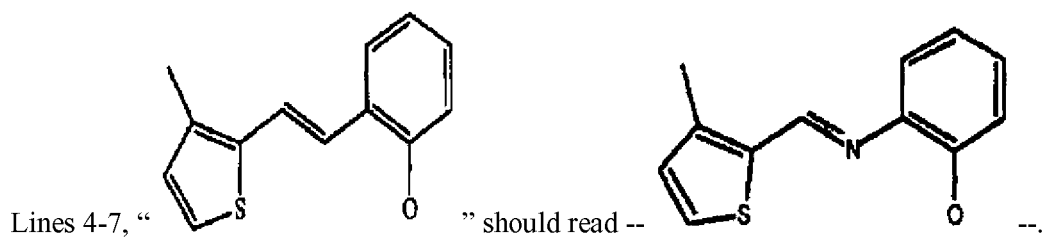

Lines 4-7, " " should read -- --.

Column 249,

Lines 14-19, " 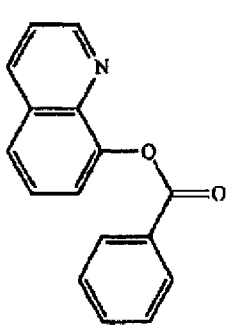 " should read -- 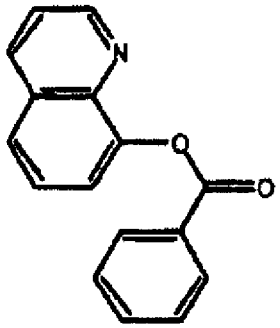 --.

Column 294,
Line 56, "28.2" should read --29.2--.

Column 310,
Line 20, "96.0    66.6" should read --98.0    68.6--.

In the Claims,

Column 446,
Line 65, "alkeny" should read --alkenyl--.

Column 447,
Line 25, "198-221, 225-238," should read --198, 201-221, 231-238,--.

Column 447,
Line 26, "245-301:" should read --245-271, and 273-301:--.

Column 466,
Lines 19-20, "-4,1-pyrido[1,2-a]" should read -- -4H-pyrido[1,2-a]--.

Column 467,
Line 67, "pyrido one (277)" should read -- pyrido[1,2-a]pyrimidin-4-one (277)--.

Column 468,
Line 67, "pyrido one (280)" should read --pyrido[1,2-a]pyrimidin-4-one (280)--.

Column 475,
Line 48, "199-201, 204, 206-221, 226, 229, 231-238, 245-278, 280-286 and 290-301:" should read --201, 204, 206-221, 231-238, 245-271, 273-278, 280-286, and 290-301:--.

Column 481,
Lines 43-45, " 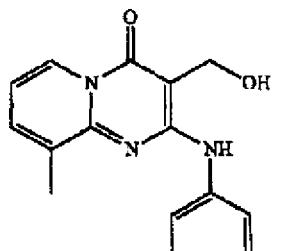 " should read -- 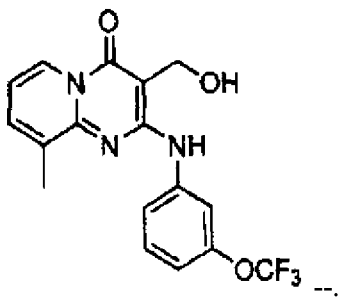 --.
Column 488,
Lines 63-66, " 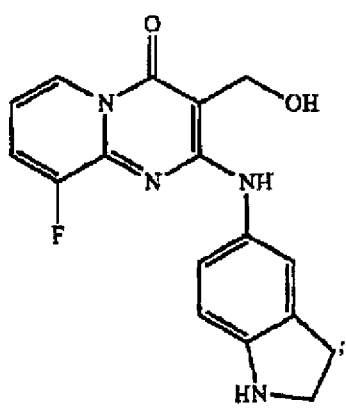 " should read -- 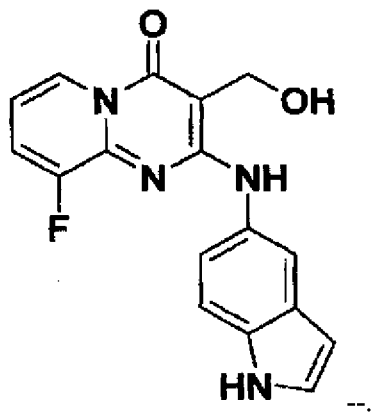 --.
Column 500,
Line 16, "205 and 231-298;" should read --205, 231-271, 273-298;--.
Column 505,
Lines 59-61, " 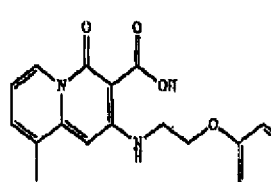 " should read -- 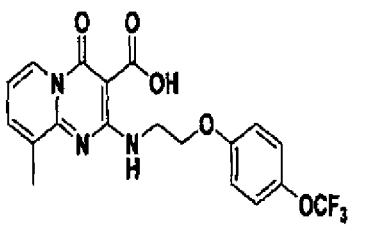 --.
Column 507,
Lines 53-57, " 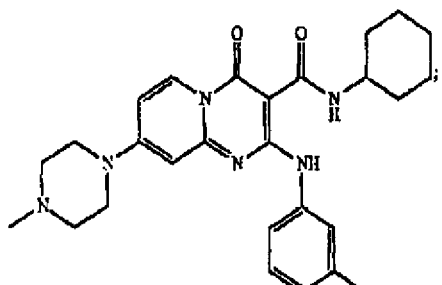 " should CERTIFICATE OF CORRECTION (continued) Page 5 of 5
U.S. Pat. No. 8,785,452 B2 read -- 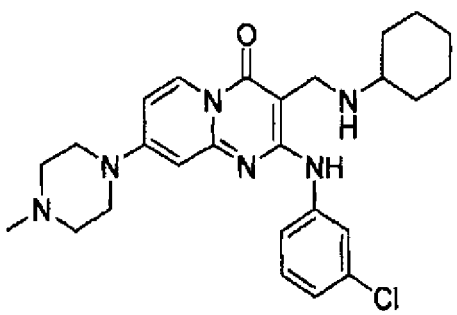 --.

Column 508,

Lines 2-5, " 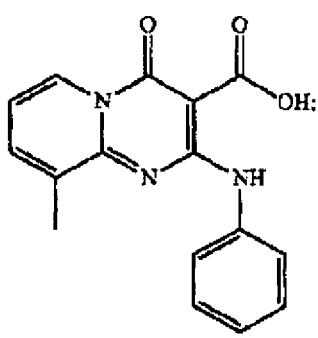 " should read -- 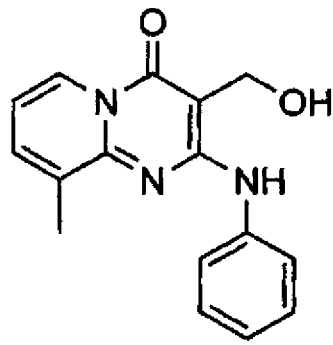 --.

Column 508,

Lines 18-22, " 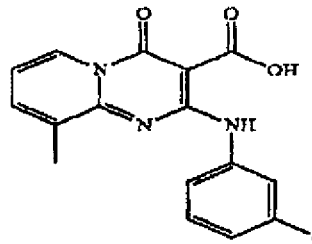 " should read -- 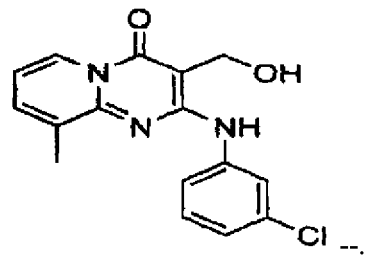 --.

Column 508,

Lines 37-39, " 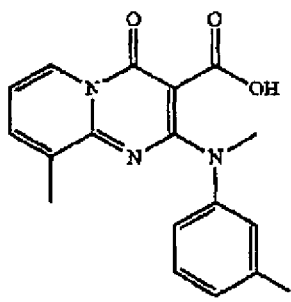 " should read -- 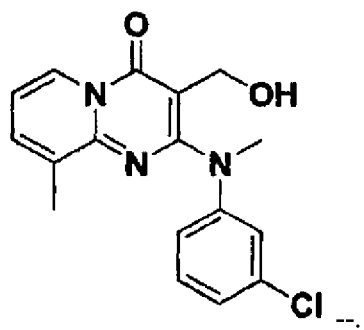 --.